(12) United States Patent
Bezencon et al.

(10) Patent No.: US 7,427,613 B2
(45) Date of Patent: Sep. 23, 2008

(54) 7-ARYL-3,9-DIAZABICYCLO(3.3.1)NON-6-ENE DERIVATIVES AND THEIR USE AS RENIN INHIBITORS IN THE TREATMENT OF HYPERTENSION, CARDIOVASCULAR OR RENAL DISEASES

(75) Inventors: Olivier Bezencon, Allschwil (CH); Daniel Bur, Therwil (CH); Walter Fischli, Allschwil (CH); Lubos Remen, Allschwil (CH); Sylvia Richard-Bildstein, Rixheim (FR); Hans-Peter Weber, Hochwald (CH); Thomas Weller, Binningen (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 463 days.

(21) Appl. No.: 10/513,103

(22) PCT Filed: Apr. 8, 2003

(86) PCT No.: PCT/EP03/03721

§ 371 (c)(1),
(2), (4) Date: Oct. 29, 2004

(87) PCT Pub. No.: WO03/093267

PCT Pub. Date: Nov. 13, 2003

(65) Prior Publication Data

US 2005/0176700 A1  Aug. 11, 2005

(30) Foreign Application Priority Data

Apr. 29, 2002 (WO) .................. PCT/EP02/04705

(51) Int. Cl.
- *A61K 31/55* (2006.01)
- *A01N 43/62* (2006.01)
- *C07D 245/00* (2006.01)
- *C07D 487/00* (2006.01)
- *C07D 243/00* (2006.01)
- *C07D 487/02* (2006.01)

(52) U.S. Cl. .................. 514/221; 540/472; 540/567
(58) Field of Classification Search .................. 544/403
See application file for complete search history.

(56) References Cited

U.S. PATENT DOCUMENTS

2006/0223795 A1 * 10/2006 Bezencon et al. ......... 514/220
2007/0111989 A1 *  5/2007 Bezencon et al. ......... 514/221

FOREIGN PATENT DOCUMENTS

| WO | WO 92/05174 | 4/1992 |
| WO | WO 97/09311 | 3/1997 |
| WO | WO 98/39328 | 9/1998 |

OTHER PUBLICATIONS

U.S. Appl. No. 10/575,794, filed Apr. 2006, Benzecon et al.*
U.S. Appl. No. 10/581,824, filed Jun. 2006, Benzecon et al.*
Chawla et. al.; CRIPS vol. 5, No. 1, p. 9-12.*
Newman et. al.; DDT vol. 8, No. 19, p. 898-905.*
Vippagunta, et. al., Advanced Drug Delivery Reviews; 48, (2001) 3-26.*
B.K. Blount et al., J. Chem. Soc., pp. 2485-2487 (1932).
Neale et al., J. Org. Chem., vol. 30, pp. 3683-3688 (1965).
Brabander et al., J. Org. Chem., pp. 4053-4055 (1967).
Dallacker et al., Chem. Ber., vol. 104, pp. 2517-2525 (1971).
Jacques et al., Tetrahedron, vol. 33, pp. 581-588 (1977).
Meyers et al., J. Am. Chem. Soc., vol. 104, pp. 877-879 (1982).
Jerry March, "Reactions, Mechanisms, and Structure", Advanced Organic Chemistry, published by John Wiley & Sons (1929).
Kihara et al., Heterocycles, vol. 29, pp. 957-965 (1989).
Glover et al., Tetrahedron, vol. 46, pp. 7247-7262 (1990).
Fuji et al., Tetrahedron Letters, vol. 31, pp. 6553-6556 (1990).
Ishihara et al., Chem. Pharm. Bull., vol. 39, pp. 3225-3235 (1991).
Neutel, M.D. et al., American Heart Journal, vol. 122, pp. 1094-1100 (1991).
Zhuangyu et al., Synthesis, pp. 539-542 (1991).
Israili, Ph.D. et al., Annals of Internal Medicine, vol. 117, pp. 234-242 (1992).
Pfeffer, M.D, Ph.D., et al., The New England Journal of Medicine, vol. 327, No. 10, pp. 669-677 (1992).
Michael A. Weber et al., American Journal of Hypertension, Inc., vol. 5, pp. 247S-251S (1992).
Qi-dong et al., Chemical Research in Chinese Universities, vol. 8, No. 4, pp. 468-472 (1992).
Ahsan Husain, Journal of Hypertension, vol. 11, pp. 1155-1159 (1993).

(Continued)

*Primary Examiner*—James O. Wilson
*Assistant Examiner*—Jeffrey H Murray
(74) *Attorney, Agent, or Firm*—Dickstein Shapiro LLP

(57) ABSTRACT

The invention relates to novel 3,9-diazabicyclo[3.3.1]nonene derivatives of formula (I) and related compounds and their use as active ingredients in the preparation of pharmaceutical compositions. The invention also concerns related aspects including processes for the preparation of the compounds, pharmaceutical compositions containing one or more of those compounds and especially their use as inhibitors or renin.

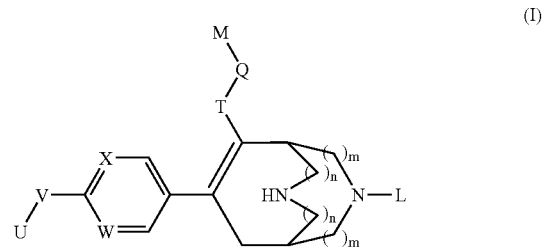

10 Claims, No Drawings

OTHER PUBLICATIONS

Dale O. Kiesewetter et al., Tetrahedron:Asymmetry, vol. 4, pp. 2183-2198 (1993).
Aziz et al., Journal of Hypertension, vol. 12, pp. 419-427 (1994).
Breyer et al., Kidney International, vol. 45—Supplemental 45, pp. S156-S160 (1994).
Rosenberg et al., Kidney International, vol. 45, pp. 403-410 (1994).
Vaughan et al., Cardiovascular Research, vol. 28, pp. 159-165 (1994).
Hollis D. Kleinert, Cardiovascular Drugs and Theraphy, vol. 9, pp. 645-655 (1995).
Lavastre et al., Bull. Soc. Chim. Fr., vol. 132, pp. 188-195 (1995).
Majewski et al., J. Org. Chem., vol. 60, pp. 5825-5830 (1995).
Waeber et al., Handbook of Hypertension, vol. 8: Pathophysiology of Hypertension—Regulatory Mechanisms, pp. 489-519 (1986).
Ho et al., Tetrahedron Letters, vol. 38, pp. 2799-2802 (1997).
Smith et al., J. Med. Chem., vol. 41, pp. 787-797 (1998).
Oefner et al., Chemistry & Biology, vol. 6, pp. 127-131 (1999).
Vieira et al., Bioorganic & Medicinal Chemistry Letters, vol. 9, pp. 1397-1402 (1999).
Bellier et al., J. Med. Chem., vol. 43, pp. 3614-3623 (2000).
Loeppky et al., J. Org. Chem., vol. 65, pp. 96-103 (2000).
Morita et al., Heterocycles, vol. 52, pp. 1163-1169 (2000).
Rahuel et al., Chemistry & Biology, vol. 7, pp. 493-504 (2000).
Blass et al., Tetrahedron Letters, vol. 42, pp. 1611-1613 (2001).
Marki et al., II Farmaco, vol. 56, pp. 21-27 (2001).
Aliskiren Fumarate, Drugs of the Future, vol. 26, pp. 1139-1148 (2001).
Melnyk et al., J. Org. Chem., vol. 66, pp. 4153-4160 (2001).
Ross et al., J. Org. Chem., vol. 31, pp. 133-137 (1966).
Fouad-Tarazi, M.D. et al., The American Journal of Medicine, vol. 84—Supplemental 3A, pp. 83-86 (1988).
Cossy et al., Tetrahedron Letters, vol. 41, pp. 2097-2099 (2000).

* cited by examiner

7-ARYL-3,9-DIAZABICYCLO(3.3.1)NON-6-ENE DERIVATIVES AND THEIR USE AS RENIN INHIBITORS IN THE TREATMENT OF HYPERTENSION, CARDIOVASCULAR OR RENAL DISEASES

The invention relates to novel compounds of the general formula I. The invention also concerns related aspects including processes for the preparation of the compounds, pharmaceutical compositions containing one or more compounds of formula I and especially their use as renin inhibitors in cardiovascular events and renal insufficiency. Furthermore, these compounds can be regarded as inhibitors of other aspartyl proteases and might therefore be useful as inhibitors of plasmepsins to treat malaria and as inhibitors of *Candida albicans* secreted aspartyl proteases to treat fungal infections.

In the renin-angiotensin system (RAS) the biologically active angiotensin II (Ang II) is generated by a two-step mechanism. The highly specific enzyme renin cleaves angiotensinogen to angiotensin I (Ang I), which is then further processed to Ang II by the less specific angiotensin-converting enzyme (ACE). Ang I is known to work on at least two receptor subtypes called $AT_1$ and $AT_2$. Whereas $AT_1$ seems to transmit most of the known functions of Ang II, the role of $AT_2$ is still unknown.

Modulation of the RAS represents a major advance in the treatment of cardiovascular diseases. ACE inhibitors and $AT_1$ blockers have been accepted to treat hypertension (Waeber B. et al., "The renin-angiotensin system: role in experimental and human hypertension", in Berkenhager W. H., Reid J. L. (eds): *Hypertension*, Amsterdam, Elsevier Science Publishing Co, 1996, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (Suppl. 3A), 83) and myocardial infarction (Pfeffer M. A. et al., *N. Engl. J. Med.*, 1992, 327, 669).

The rationale to develop renin inhibitors is the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be by-passed by chymase, a serine protease (Husain A., *J. Hypertens.*, 1993, 11, 1155). In patients inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the $AT_1$ receptor (e.g. by losartan) on the other hand overexposes other AT-receptor subtypes to Ang II, whose concentration is dramatically increased by the blockade of $AT_1$ receptors. This may raise serious questions regarding the safety and efficacy profile of $AT_1$ receptor antagonists. In summary, renin inhibitors are not only expected to be different from ACE inhibitors and $AT_1$ blockers with regard to safety, but more importantly also with regard to their efficacy to block the RAS.

Only limited clinical experience (Azizi M. et al., *J. Hypertens.*, 1994, 12, 419; Neutel J. M. et al., *Am. Heart*, 1991, 122, 1094) has been created with renin inhibitors because of their insufficient oral activity due to their peptidomimetic character (Kleinert H. D., *Cardiovasc. Drugs*, 1995, 9, 645). The clinical development of several compounds has been stopped because of this problem together with the high cost of goods. Only one compound containing four chiral centers has entered clinical trials (Rahuel J. et al, *Chem. Biol.*, 2000, 7, 493; Mealy N. E., *Drugs of the Future*, 2001, 26, 1139). Thus, metabolically stable, orally bioavailable and sufficiently soluble renin inhibitors that can be prepared on a large scale are missing and sought. Recently, the first non-peptide renin inhibitors were described which show high in vitro activity (Oefuer C. et al., *Chem. Biol.*, 1999, 6, 127; Patent Application WO97/09311; Märki H. P. et al., *Il Farmaco*, 2001, 56, 21). However, the development status of these compounds is not known.

The present invention relates to the identification of renin inhibitors of a non-peptidic nature and of low molecular weight. Orally active renin inhibitors of long duration of action which are active in indications beyond blood pressure regulation where the tissular renin-chymase system may be activated leading to pathophysiologically altered local functions such as renal, cardiac and vascular remodeling, atherosclerosis, and possibly restenosis are described.

The present invention describes non-peptidic renin inhibitors.

In particular, the present invention relates to novel compounds of the general formula I,

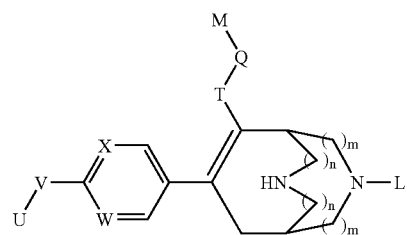

Formula I wherein

X and W represent independently a nitrogen atom or a —CH— group;

V represents —$(CH_2)_r$—; -A-$(CH_2)_s$—; —$CH_2$-A-$(CH_2)_t$—; —$(CH_2)_s$-A-; —$(CH_2)_2$-A-$(CH_2)_u$—; -A-$(CH_2)_v$—B—; —$CH_2$—$CH_2$—$CH_2$-A-$CH_2$—; -A-$CH_2$—$CH_2$—B—$CH_2$—; —$CH_2$-A-$CH_2$—$CH_2$—B—; —$CH_2$—$CH_2$—$CH_2$-A-$CH_2$—$CH_2$—; —$CH_2$—$CH_2$—$CH_2$—$CH_2$-A-$CH_2$—; -A-$CH_2$—$CH_2$—B—$CH_2$—$CH_2$—; —$CH_2$-A-$CH_2$—$CH_2$—B—$CH_2$—; —$CH_2$-A-$CH_2$—$CH_2$—B—; or —$CH_2$—$CH_2$-A-$CH_2$—$CH_2$—B—;

A and B independently represent —O—; —S—; —SO—; —$SO_2$—;

U represents aryl; heteroaryl;

T represents —$CONR^1$—; —$(CH_2)_pOCO$—; —$(CH_2)_pN(R^1)CO$—; —$(CH_2)_pN(R^1)SO_2$—; or —COO—;

Q represents lower alkylene; lower alkenylene;

M represents hydrogen; cycloalkyl; aryl; heterocyclyl; heteroaryl;

L represents —$R^3$; —$COR^3$; —$COOR^3$; —$CONR^2R^3$; —$SO_2R^3$; —$SO_2NR^2R^3$; —$COCH(Aryl)_2$;

$R^1$ represents hydrogen; lower alkyl; lower alkenyl; lower alkinyl; cycloalcyl; aryl; cycloalkyl-lower alkyl;

$R^2$ and $R^{2'}$ independently represent hydrogen; lower alkyl; lower alkenyl; cycloalkyl; cycloalkyl-lower alkyl;

$R^3$ represents hydrogen; lower alkyl; lower alkenyl; cycloalkyl; aryl; heteroaryl; heterocyclyl; cycloalkyl-lower alkyl; aryl-lower alkyl; heteroaryl-lower alkyl; heterocyclyl-lower alkyl; aryloxy-lower alkyl; heteroaryloxy-lower alkyl, whereby these groups may be unsubstituted or mono-, di- or trisubstituted with hydroxy, —OCOR$^2$, —COOR$^2$, lower alkoxy, cyano, —CONR$^2$R$^{2'}$, CO-morpholin-4-yl, CO-((4loweralkyl)piperazin-1-yl), —NH(NH)NH$^2$, —NR$^4$R$^{4'}$ or lower alkyl, with the proviso that a carbon atom is attached at the most to one heteroatom in case this carbon atom is sp3-hybridized;

R$^4$ and R$^{4'}$ independently represent hydrogen; lower alkyl; cycloalkyl; cycloalkyl—lower alkyl; hydroxy-lower alkyl; —COOR$^2$; —CONH$_2$;

m and n represent the integer 0 or 1, with the proviso that in case m represents the integer 1, n is the integer 0, and in case n represents the integer 1, m is the integer 0;

p is the integer 1, 2, 3 or 4;

r is the integer 3, 4, 5, or 6;

s is the integer 2, 3, 4, or 5;

t is the integer 1, 2, 3, or 4;

u is the integer 1, 2, or 3;

v is the integer 2, 3, or 4;

and optically pure enantiomers, mixtures of enantiomers such as racemates, diastereomers, mixtures of diastereomers, diastereomeric racemates, mixtures of diastereomeric racemates, and the meso-form; as well as pharmaceutically acceptable salts, solvent complexes and morphological forms.

In the definitions of general formula I—if not otherwise stated—the term lower alkyl alone or in combination with other groups, means saturated, straight and branched chain groups with one to seven carbon atoms, preferably one to four carbon atoms that can be optionally substituted by halogens. Examples of lower alkyl groups are methyl, ethyl, n-propyl, iso-propyl, n-butyl, iso-butyl, sec-butyl, tert-butyl, pentyl, hexyl and heptyl. The methyl, ethyl nad isopropyl groups are preferred.

The term lower alkoxy refers to a R—O group, wherein R is a lower alkyl. Examples of lower alkoxy groups are methoxy, ethoxy, propoxy, iso-propoxy, iso-butoxy, sec-butoxy and tert-butoxy.

The term lower alkenyl, alone or in combination with other groups, means straight and branched chain groups comprising an olefinic bond and consisting of two to seven carbon atoms, preferably two to four carbon atoms, that can be optionally substituted by halogens. Examples of lower alkenyl are vinyl propenyl or butenyl.

The term lower alkinyl, alone or in combination with other groups, means straight and branched chain groups comprising a triple bond and consisting of two to seven carbon atoms, preferably two to four carbon atoms, that can be optionally substituted by halogens. Examples of lower alkinyl are ethinyl, propinyl or butinyl.

The term lower alkylene, alone or in combination with other groups, means straight and branched divalent chain groups with one to seven carbon atoms, preferably one to four carbon atoms, that can be optionally substituted by halogens. Examples of lower alkylene are ethylene, propylene or butylene.

The term lower alkenylene, alone or in combination with other groups, means straight and branched divalent chain groups comprising an olefinic bond and consisting of two to seven carbon atoms, preferably two to four carbon atoms, that can be optionally substituted by halogens. Examples of lower alkenylene are vinylene, propenylene and butenylene.

The term lower alkylenedioxy, refers to a lower alkylene substituted at each end by an oxygen atom. Examples of lower alkylenedioxy groups are preferably methylenedioxy and ethylenedioxy.

The term lower alkylenoxy refers to a lower alkylene substituted at one end by an oxygen atom. Examples of lower alkylenoxy groups are preferably methylenoxy, ethylenoxy and propylenoxy.

The term halogen means fluorine, chlorine, bromine or iodine, preferably fluorine, chlorine and bromine.

The term cycloalkyl alone or in combination, means a saturated cyclic hydrocarbon ring system with 3 to 7 carbon atoms, e.g. cyclopropyl, cyclobutyl, cyclopentyl, cyclohexyl and cycloheptyl, which can be optionally mono- or multisubstituted by lower alkyl, lower alkenyl, lower alkenylene, lower alkoxy, lower alkylenoxy, lower alkylenedioxy, hydroxy, halogen, —CF$_3$, —NR$^1$R$^{1'}$, —NR$^1$C(O)R$^{1'}$, —NR$^1$S(O$_2$)R1', —C(O)NR$^1$R$^{1'}$, lower alkylcarbonyl, —COOR$^1$, —SR$^1$, —SOR$^1$, —SO$_2$R$^1$, —SO$_2$NR$^1$R$^{1'}$ whereby R$^{1'}$ represents hydrogen; lower alkyl; lower alkenyl; lower alkinyl; cycloalkyl; aryl; cycloalkyl-lower alkyl. The cyclopropyl group is a preferred group.

The term aryl, alone or in combination, relates to the phenyl, the naphthyl or the indanyl group, preferably the phenyl group, which can be optionally mono- or multisubstituted by lower alkyl, lower alkenyl, lower alkinyl, lower alkenylene or lower alkylene forming with the aryl ring a five- or six-membered ring, lower alkoxy, lower alkylenedioxy, lower alkylenoxy, hydroxy, hydroxy-lower alkyl, halogen, cyano, —CF$_3$, —OCF$_3$, —NR$^1$R$^{1'}$, —NR$^1$R$^{1'}$-lower alkyl, —NR$^1$C(O)R$^{1'}$, —NR$_1$S(O$_2$)R$^1$, —C(O)NR$^1$R$^{1'}$, —NO$_2$, lower alkylcarbonyl, —COOR$^1$, —SR$^1$, —SOR$^1$, —SO$_2$R$^1$, —SO$_2$NR$^1$R$^{1'}$, benzyloxy, whereby R$^{1'}$ has the meaning given above. Preferred substituents are halogen, lower alkoxy, lower alkyl, CF$_3$, OCF$_3$.

The term aryloxy refers to an Ar—O group, wherein Ar is an aryl. An example of a lower aryloxy group is phenoxy.

The term heterocyclyl, alone or in combination, means saturated or unsaturated (but not aromatic) five-, six- or seven-membered rings containing one or two nitrogen, oxygen or sulfur atoms which may be the same or different and which rings can be optionally substituted with lower alkyl, hydroxy, lower alkoxy and halogen. The nitrogen atoms, if present, can be substituted by a —COOR$^2$ group. Examples of such rings are piperidinyl, morpholinyl, thiomorpholinyl, piperazinyl, tetrahydropyranyl, dihydropyranyl, 1,4-dioxanyl, pyrrolidinyl, tetrahydrofuranyl, dihydropyrrolyl, imidazolidinyl, dihydropyrazolyl, pyrazolidinyl, dihydroquinolinyl, tetrahydroquinolinyl, tetrahydroisoquinolinyl.

The term heteroaryl, alone or in combination, means six-membered aromatic rings containing one to four nitrogen atoms; benzofused six-membered aromatic rings containing one to three nitrogen atoms; five-membered aromatic rings containing one oxygen, one nitrogen or one sulfur atom; benzofused five-membered aromatic rings containing one oxygen, one nitrogen or one sulfur atom; five-membered aromatic rings containing one oxygen and one nitrogen atom and benzofused derivatives thereof; five-membered aromatic rings containing a sulfur and a nitrogen or an oxygen atom and benzofused derivatives thereof; five-membered aromatic rings containing two nitrogen atoms and benzofused derivatives thereof; five-membered aromatic rings containing three nitrogen atoms and benzofused derivatives thereof, or a tetrazolyl ring. Examples of such ring systems are furanyl, thiophenyl, pyrrolyl, pyridinyl, pyrimidinyl, indolyl, quinolinyl, isoquinolinyl, imidazolyl, triazinyl, thiazinyl, thiazolyl, isothiazolyl, pyridazinyl, pyrazolyl, oxazolyl, isoxazolyl, coumarinyl, benzothiophenyl, quinazolinyl, quinoxalinyl. Such rings may be adequately substituted with lower alkyl, lower alkenyl, lower alkinyl, lower alkylene, lower alkenylene, lower alkylenedioxy, lower alkyleneoxy, hydroxy-lower alkyl, lower alkoxy, hydroxy, halogen, cyano, —CF$_3$, —OCF$_3$, —NR$^1$R$^{1"}$, —NR$^1$R$^{1"}$-lower alkyl, —N(R$^1$)COR$^1$, —N(R$^1$)SO$_2$R$^1$, —CONR$^1$R$^{1"}$, —NO$_2$, lower alkylcarbonyl, —COOR$^1$, —SR$^1$, —SOR$^1$, —SO$_2$R$^1$, —SO$_2$NR$^1$R$^{1"}$, another aryl, another heteroaryl or another heterocyclyl and the like, whereby R$^{1"}$ has the meaning given above.

The term heteroaryloxy refers to a Het-O group, wherein Het is a heteroaryl.

The term sp3-hybridized refers to a carbon atom and means that this carbon atom forms four bonds to four substituents placed in a tetragonal fashion around this carbon atom.

The expression pharmaceutically acceptable salts encompasses either salts with inorganic acids or organic acids like hydrochloric or hydrobromic acid, sulfuric acid, phosphoric acid, citric acid, formic acid, acetic acid, maleic acid, tartaric acid, benzoic acid, methanesulfonic acid, p-toluenesulfonic acid, and the like that are non toxic to living organisms or in case the compound of formula I is acidic in nature with an inorganic base like an alkali or earth alkali base, e.g. sodium hydroxide, potassium hydroxide, calcium hydroxide and the like.

The compounds of the general formula I can contain two or more asymmetric carbon atoms and may be prepared in form of optically pure enantiomers, mixtures of enantiomers such as racemates, diastereomers, mixtures of diastereomers, diastereomeric racemates, mixtures of diastereomeric racemates, and the meso-form and pharmaceutically acceptable salts thereof.

The present invention encompasses all these forms. Mixtures may be separated in a manner known per se, i.e. by, column chromatography, thin layer chromatography, HPLC or crystallization.

A group of preferred compounds are compounds of general formula I wherein X, W, V, U, T, Q, L, and M are as defined in general formula I above and wherein
n is 0 and
m is 1.

Another group of preferred compounds of general formula I are those wherein X, W, V, U, T, Q, M, m, and n are as defined in general formula I above and
L represents H; —COR$^{3"}$; —COOR$^{3"}$; —CONR$^{2"}$R$^{3"}$;
  whereby R$^{2"}$ and R$^{3"}$ represent independently lower alkyl, lower cycloalkyl-lower alkyl, which lower alkyl and lower cycloalkyl-lower alkyl groups are unsubstituted or monosubstituted with halogen, cyano, hydroxy, —OCOCH$_3$, —CONH$_2$, —COOH, —NH$_2$, with the proviso that a carbon atom is attached at the most to one heteroatom in case this carbon atom is sp3-hybridized.

Another group of preferred compounds of general formula I above are those wherein X, W, V, U, L, m, and n are as defined in general formula I and
T is —CONR$^1$;
Q is methylene;
M is hydrogen; aryl; or heteroaryl.

Another group of even more preferred compounds of general formula I are those wherein X, W, U, L, T, Q, M, m, and n are as defined in general formula I above and
V is —CH$_2$CH$_2$O—; —CH$_2$CH$_2$CH$_2$O—; —OCH$_2$CH$_2$O—;——.

Another group of also more preferred compounds of general formula I are those wherein V, U, T, Q, M, L, m, and n are as defined in general formula I above and
X and W represent —CH—.

Another group of also more preferred compounds of general formula I are those wherein X, W, V, Q, T. M, L, m, and n are as defined in general formula I above and U is a mono-, di-, or trisubstituted phenyl wherein the substituents are halogen; lower alkyl or lower alkoxy.

Especially preferred compounds of general formula I are those selected from the group consisting of:
(rac.)-(1R*,5S*)-3-acetyl-7-{4-[2-(2,3-dichlorophenoxy) ethyl]phenyl}-3,9-diazabicyclo[3.3.1]non-6-ene-6-carboxylic acid methylphenethylamide;
(rac.)-(1R*,5S*)-3-acetyl-7-{4-[3-(2-chloro-5-methylphenoxy)propyl]phenyl}-3,9-diazabicyclo[3.3.1]non-6-ene-6-carboxylic acid methylphenethylamide;
(rac.)-(2-methoxyphenyl)acetic acid (1R*,5S*)-3-acetyl-7-{4-[3-(2-chlorophenoxy)propyl]phenyl}-3,9-diazabicyclo[3.3.1]non-6-en-6-ylmethyl ester;
(rac.)-(1R*,5S*)-3-acetyl-7-{4-[2-(4-bromo-3-methylphenoxy)ethyl]phenyl}-3,9-diazabicyclo[3.3.1]non-6-ene-6-carboxylic acid methylphenethylamide;
(rac.)-(2-methoxyphenyl)acetic acid (1R*,5S*)-3-acetyl-7-{4-[3-(2-chlorophenoxy)propoxy]phenyl}-3,9-diazabicyclo[3.3.1]non-6-en-6-ylmethyl ester;
(rac.)-(1R*,5S*)-3-acetyl-7-{4-[3-(2,4-dimethylphenoxy) propyl]phenyl}-3,9-diazabicyclo[3.3.1]non-6-ene-6-carboxylic acid methylphenethylamide;
(rac.)-(1R*,5S*)-3-acetyl-7-{4-[3-(4-bromo-3-methylphenoxy)propyl]phenyl}-3,9-diazabicyclo[3.3.1]non-6-ene-6-carboxylic acid methylphenethylamide;
(rac.)-(1R*,5S*)-3-acetyl-7-{4-[2-(2-acetylphenoxy)ethyl] phenyl}-3,9-diazabicyclo[3.3.1 ]non-6-ene-6-carboxylic acid methylphenethylamide;
(rac.)-(1R*,5S*)-3-acetyl-7-{4-[2-(2-ethylphenoxy)ethyl] phenyl}-3,9-diazabicyclo[3.3.1]non-6-ene-6-carboxylic acid methylphenethylamide;
(rac.)-(1R*,5S*)-3-acetyl-7-{4-[2-(3,5-dichlorophenoxy) ethyl]phenyl}-3,9-diazabicyclo[3.3.1]non-6-ene-6-carboxylic acid methylphenethylamide;
(rac.)-(1R*,5S*)-3-acetyl-7-{4-[3-(3,4-dichlorophenoxy) propyl]phenyl}-3,9-diazabicyclo[3.3.1]non-6-ene-6-carboxylic acid methylphenethylamide;
(rac.)-(1R*,5S*)-3-acetyl-7-{4-[2-(2,4-dimethylphenoxy) ethyl]phenyl}-3,9-diazabicyclo[3.3.1]non-6-ene-6-carboxylic acid methylphenethylamide;
(rac.)-(1R*,5S*)-3-acetyl-7-[4-(3-o-tolyloxypropyl)phenyl]-3,9-diazabicyclo[3.3.1]non-6-ene-6-carboxylic acid methylphenethylamide;
(rac.)-(2-methoxyphenyl)acetic acid (1R*,5S*)-3-acetyl-7-{6-[3-(2-methoxybenzyloxy)propoxy]pyridin-3-yl}-3,9-diazabicyclo[3.3.1]non-6-en-6-ylmethyl ester;
(rac.)-(1R*,5S*)-3-acetyl-7-{4-[2-(2-chlorophenoxy) ethoxy]phenyl}-3,9-diazabicyclo[3.3.1]non-6-ene-6-carboxylic acid methylphenethylamide;
(rac.)-(1R*,5S*)-3-Acetyl-7-[4(2-m-tolyloxyethyl)phenyl]-3,9-diazabicyclo-[3.3.1]non-6-ene-6-carboxylic acid methylphenethylamide;
(rac.)-(1R*,5S*)-3-acetyl-7-{4-[2-(3-methoxyphenoxy) ethyl]phenyl}-3,9-diazabicyclo[3.3.1]non-6-ene-6-carboxylic acid methylphenethylamide;
(rac.)-(1R*,5S*)-3-acetyl-7-{4-[2-(2-chloro-3-trifluoromethylphenoxy)ethyl]phenyl}-3,9-diazabicyclo[3.3.1]non-6-ene-6-carboxylic acid methylphenethylamide;
(rac.)-(1R*,5S*)-3-acetyl-7-{4[2-(4tert-butyl-2-methylphenoxy)ethyl]phenyl}-3,9-diazabicyclo[3.3.1]non-6-ene-6-carboxylic acid methylphenethylamide;
(rac.)-(2-methoxyphenyl)acetic acid (1R*,5S*)-3-acetyl-7-{4-[3-(2-bromophenoxy)propyl]phenyl}-3,9-diazabicyclo[3.3.1]non-6-en-6-ylmethyl ester;
(rac.)-(1R*,5S*)-3-acetyl-7-{4-[3-(3-chlorophenoxy)propyl]phenyl}-3,9-diazabicyclo[3.3.1]non-6-ene-6-carboxylic acid methylphenethylamide;

(rac.)-(1R*,5S*)-3-acetyl-7-{4-[3-(2-isopropylphenoxy)propyl]phenyl}-3,9-diazabicyclo[3.3.1]non-6-ene-6-carboxylic acid methylphenethylamide;
(rac.)-(1R*,5S*)-3-acetyl-7-{4-[2-(3-bromophenoxy)ethyl]phenyl}-3,9-diazabicyclo[3.3.1]non-6-ene-6-carboxylic acid methylphenethylamide;
(rac.)-(1R*,5S*)-3-acetyl-7-{4-[3-(2-bromophenoxy)propyl]phenyl}-3,9-diazabicyclo[3.3.1]non-6-ene-6-carboxylic acid methylphenethylamide;
(rac.)-(2-methoxyphenyl)acetic acid (1R*,5S*)-3-acetyl-7-[4-(3-o-tolyloxy-propyl)phenyl]-3,9-diazabicyclo[3.3.1]non-6-en-6-ylmethyl ester;
(rac.)-(1R*,5S*)-3-acetyl-7-{4-[2-(3,4-dichlorophenoxy)ethyl]phenyl}-3,9-diazabicyclo[3.3.1]non-6-ene-6-carboxylic acid methylphenethylamide;
(rac.)-(1R*,5S*)-3-Acetyl-7-{4-[3-(2-tert-butylphenoxy)propyl]phenyl}-3,9-diazabicyclo[3.3.1]non-6-ene-6-carboxylic acid methylphenethylamide;
(rac.)-(1R*,5S*)-3-acetyl-7-{4-[2-(3-chlorophenoxy)ethyl]phenyl}-3,9-diazabicyclo[3.3.1]non-6-ene-6-carboxylic acid methylphenethylamide;
(rac.)-(1R*,5S*)-3-acetyl-7-{4-[3-(2-ethylphenoxy)propyl]phenyl}-3,9-diazabicyclo[3.3.1]non-6-ene-6-carboxylic acid methylphenethylamide;
(rac.)-(1R*,5S*)-3-acetyl-7-{4-[3-(2,3-dimethylphenoxy)propyl]phenyl}-3,9-diazabicyclo[3.3.1]non-6-ene-6-carboxylic acid methylphenethylamide;
(rac.)-(1R*,5S*)-3-acetyl-7-{4-[2-(3-trifluoromethoxyphenoxy)ethyl]phenyl}-3,9-diazabicyclo[3.3.1]non-6-ene-6-carboxylic acid methylphenethylamide;
(rac.)-(1R*,5S*)-3-acetyl-7-{4-[3-(3,4-dimethylphenoxy)propyl]phenyl}-3,9-diazabicyclo[3.3.1]non-6-ene-6-carboxylic acid methylphenethylamide;
(rac.)-(1R*,5S*)-3-acetyl-7-{4-[3-(2-chloro-4,5-dimethylphenoxy)propyl]phenyl}-3,9-diazabicyclo[3.3.1]non-6-ene-6-carboxylic acid methylphenethylamide;
(rac.)-(1R*,5S*)-3-acetyl-7-{4-[2-(2-chlorophenyl)ethoxy]phenyl}-3,9-diazabicyclo[3.3.1]non-6-ene-6-carboxylic acid methylphenethylamide;
(rac.)-(2-methoxyphenyl)acetic acid (1R*,5S*)-3-[2-(4-chlorophenyl)ethyl]-7-{4-[3-(2-methoxybenzyloxy)propoxy]phenyl}-3,9-diazabicyclo[3.3.1]non-6-en-6-yl methyl ester;
(rac.)-(1R*,5S*)-3-acetyl-7-{4-[3-(2-chloro-3-trifluoromethylphenoxy)propyl]-phenyl}-3,9-diazabicyclo[3.3.1]non-6-ene-6-carboxylic acid methylphenethylamide;
(rac.)-(2-methoxyphenyl)acetic acid (1R*,5S*)-3-acetyl-7-{4-[2-(3-chlorophenoxy)ethyl]phenyl}-3,9-diazabicyclo[3.3.1]non-6-en-6-ylmethyl ester;
(rac.)-(1R*,5S*)-3-acetyl-7-[4-(2-m-tolyloxyethoxy)phenyl]-3,9-diazabicyclo[3.3.1]non-6-ene-6-carboxylic acid methylphenethylamide;
(rac.)-(1R*,5S*)-3-acetyl-7-{4-[3-(2,4-dichlorophenoxy)propyl]-phenyl}-3,9-diazabicyclo[3.3.1]non-6-ene-6-carboxylic acid methylphenethylamide;
(rac.)-(1R*,5S*)-3-acetyl-7-{4-[3-(2,5-dimethylphenoxy)propyl]phenyl}-3,9-diazabicyclo[3.3.1]non-6-ene-6-carboxylic acid methylphenethylamide;
(rac.)-(1R*,5S*)-3-acetyl-7-{4-[2-(3,5-dimethylphenoxy)ethyl]phenyl}-3,9-diazabicyclo[3.3.1]non-6-ene-6-carboxylic acid methylphenethylamide;
(rac.)-(1R*,5S*)-3-acetyl-7-{4-[2-(2-ethoxyphenoxy)ethyl]phenyl}-3,9-diazabicyclo[3.3.1]non-6-ene-6-carboxylic acid methylphenethylamide;
(rac.)-(2-methoxyphenyl)acetic acid (1R*,5S*)-3-acetyl-7-{4-[3-(3-chlorophenoxy)propyl]phenyl}-3,9-diazabicyclo[3.3.1]non-6-en-6-ylmethyl ester;
(rac.)-(1R*,5S*)-3-acetyl-7-{4-[3-(3,5-dimethylphenoxy)propyl]phenyl}-3,9-diazabicyclo[3.3.1]non-6-ene-6-carboxylic acid methylphenethylamide;
(rac.)-(1R*,5S*)-3-acetyl-7-{4-[3-(2-fluorophenoxy)propyl]phenyl}-3,9-diazabicyclo[3.3.1]non-6-ene-6-carboxylic acid methylphenethylamide;
(rac.)-(2-methoxyphenyl)acetic acid (1R*,5S*)-3-acetyl-7-{4-[2-(2-chlorophenoxy)ethyl]phenyl}-3,9-diazabicyclo[3.3.1]non-6-en-6-ylmethyl ester;
(rac.)-(1R*,5S*)-3-acetyl-7-{4-[2-(2,5-dichlorophenoxy)ethyl]phenyl}-3,9-diazabicyclo[3.3.1]non-6-ene-6-carboxylic acid methylphenethylamide;
(rac.)-(1R*,5S*)-3-acetyl-7-{4-[3-(2,3,5-trimethylphenoxy)propyl]-phenyl}-3,9-diazabicyclo[3.3.1]non-6-ene-6-carboxylic acid methylphenethylamide;
(rac.)-(1R*,5S*)-3-acetyl-7-{4-[2-(3-chlorophenyl)ethoxy]phenyl}-3,9-diazabicyclo[3.3.1]non-6-ene-6-carboxylic acid methylphenethylamide;
(rac.)-(1R*,5S*)-3-acetyl-7-{4-[2-(2,3-difluorophenoxy)ethyl]phenyl}-3,9-diazabicyclo[3.3.1]non-6-ene-6-carboxylic acid methylphenethylamide;
(rac.)-(1R*,5S*)-3-acetyl-7-{4-[2-(2-chlorophenoxy)ethyl]phenyl}-3,9-diazabicyclo[3.3.1]non-6-ene-6-carboxylic acid methylphenethylamide;
(rac.)-(1R*,5S*)-3-acetyl-7-{4-[2-(2,4-dichlorophenoxy)ethyl]phenyl}-3,9-diazabicyclo[3.3.1]non-6-ene-6-carboxylic acid methylphenethylamide;
(rac.)-(1R*,5S*)-3-acetyl-7-{4-[2-(2,3,6-trifluorophenoxy)ethyl]phenyl}-3,9-diazabicyclo[3.3.1]non-6-ene-6-carboxylic acid methylphenethylamide;
(rac.)-(2-methoxyphenyl)acetic acid (1R*,5S*)-3-acetyl-7-{4-[3-(2-trifluoromethylphenoxy)propyl]phenyl}-3,9-diazabicyclo[3.3.1]non-6-en-6-ylmethyl ester;
(rac.)-(1R*,5S*)-3-acetyl-7-{4-[2-(3-trifluoromethylphenoxy)ethyl]phenyl}-3,9-diazabicyclo[3.3.1]non-6-ene-6-carboxylic acid methylphenethylamide,
(rac.)-(1R*,5S*)-3-acetyl-7-{4-[3-(3,5-dichlorophenoxy)propyl]phenyl}-3,9-diazabicyclo[3.3.1]non-6-ene-6-carboxylic acid methylphenethylamide;
(rac.)-(1R*,5S*)-3-acetyl-7-{4-[3-(m-tolyloxy)propyl]phenyl}-3,9-diazabicyclo[3.3.1]non-6-ene-6-carboxylic acid methylphenethylamide;
(rac.)-(1R*,5S*)-3-acetyl-7-{4-[2-(2-methoxyphenyl)ethoxy]phenyl}-3,9-diazabicyclo[3.3.1]non-6-ene-6-carboxylic acid methylphenethylamide;
(rac.)-(1R*,5S*)-3-acetyl-7-{4-[3-(4-fluorophenoxy)propyl]phenyl}-3,9-diazabicyclo[3.3.1]non-6-ene-6-carboxylic acid methylphenethylamide;
(rac.)-(1R*,5S*)-3-acetyl-7-{4-[2-(3,4-dimethylphenoxy)ethyl]phenyl}-3,9-diazabicyclo[3.3.1]non-6-ene-6-carboxylic acid methylphenethylamide;
(rac.)-(2-methoxyphenyl)acetic acid (1R*,5S*)-3-acetyl-7-{4-[3-(3-fluorophenoxy)propyl]phenyl}-3,9-diazabicyclo[3.3.1]non-6-en-6-ylmethyl ester;
(rac.)-(1R*,5S*)-3-acetyl-7-{4-[3-(2-methoxybenzyloxy)propoxy]phenyl}-3,9-diazabicyclo[3.3.1]non-6-ene-6-carboxylic acid phenethylamide;
(rac.)-(2-methoxyphenyl)acetic acid (1R*,5S*)-3-acetyl-7-[4-(3-phenoxypropyl)-phenyl]-3,9-diazabicyclo[3.3.1]non-6-en-6-ylmethyl ester;
(rac.)-(1R*,5S*)-3-acetyl-7-{4-[3-(2-acetyl-5-fluorophenoxy)propyl]phenyl}-3,9-diazabicyclo[3.3.1]non-6-ene-6-carboxylic acid methylphenethylamide;
(rac.)-(1R*,5S*)-7-{4-[3-(2-methoxybenzyloxy)propoxy]phenyl}-6-[2-(2-methoxyphenyl)acetoxymethyl]-3,9-diazabicyclo[3.3.1]non-6-ene-9-carboxylic acid 2,2,2-trichloro-1,1-dimethylethyl ester;

(rac.)-(1R*,5S*)-3-acetyl-7-{4-[3-(2-chlorophenoxy)propyl]phenyl}-3,9-diazabicyclo[3.3.1]non-6-ene-6-carboxylic acid methylphenethylamide;

(rac.)-(1R*,5S*)-3-acetyl-7-{4-[3-(2,3-difluorophenoxy)propyl]phenyl}-3,9-diazabicyclo[3.3.1]non-6-ene-6-carboxylic acid methylphenethylamide;

(rac.)-(1R*,5S*)-3-acetyl-7-{4-[2-(2-tert-butylphenoxy)ethyl]phenyl}-3,9-diazabicyclo[3.3.1]non-6-ene-6-carboxylic acid methylphenethylamide;

(rac.)-(1R*,5S*)-3-acetyl-7-{4-[2-(2-propionylphenoxy)ethyl]phenyl}-3,9-diazabicyclo[3.3.1]non-6-ene-6-carboxylic acid methylphenethylamide;

1:1 mixture of (2R)- and (2S)-N-((1R*,5S*)-3-acetyl-7-{4-[3-(2-methoxybenzyloxy)propoxy]phenyl}-3,9-diazabicyclo[3.3.1]non-6-en-6-ylmethyl)-N-methyl-2-phenyl-propionamide;

(rac.)-(1R*,5S*)-3-acetyl-7-{4-[3-(2-tert-butyl-4-methylphenoxy)propyl]phenyl}-3,9-diazabicyclo[3.3.1]non-6-ene-6-carboxylic acid methylphenethylamide;

(rac.)-(1R*,5S*)-3-acetyl-7-{4-[3-(2-tert-butyl-6-methylphenoxy)propyl]phenyl}-3,9-diazabicyclo[3.3.1]non-6-ene-6-carboxylic acid methylphenethylamide;

(rac.)-(1R*,5S*)-3-acetyl-7-{4-[3-(4-chloro-2-methoxyphenoxy)propyl]phenyl}-3,9-diazabicyclo[3.3.1]non-6-ene-6-carboxylic acid methylphenethylamide;

(rac.)-(1R*,5S*)-3-acetyl-7-{4-[2-(2-methoxy-5-methylphenoxy)ethyl]phenyl}-3,9-diazabicyclo[3.3.1]non-6-ene-6-carboxylic acid methylphenethylamide;

(rac.)-(1R*,5S*)-3-acetyl-7-{4-[3-(3-methoxyphenoxy)propyl]phenyl}-3,9-diazabicyclo[3.3.1]non-6-ene-6-carboxylic acid methylphenethylamide;

(rac.)-(1R*,5S*)-3-acetyl-7-{4-[3-(4-tert-butyl-2-methylphenoxy)propyl]phenyl}-3,9-diazabicyclo[3.3.1]non-6-ene-6-carboxylic acid methylphenethylamide;

(rac.)-(1R*,5S*)-3-acetyl-7-{4-[2-(3,5-dimethoxyphenoxy)ethyl]phenyl}-3,9-diazabicyclo[3.3.1]non-6-ene-6-carboxylic acid methylphenethylamide;

(rac.)-(1R*,5S*)-3-acetyl-7-{4-[2-(2-iso-propylphenoxy)ethyl]phenyl}-3,9-diazabicyclo[3.3.1]non-6-ene-6-carboxylic acid methylphenethylamide;

(rac.)-(1R*,5S*)-3-acetyl-7-{4-[3-(2-methoxybenzyloxy)propoxy]phenyl}-3,9-diazabicyclo[3.3.1]non-6-ene-6-carboxylic acid [2-(2-methoxyphenyl)ethyl]amide;

(rac.)-(1R*,5S*)-3-acetyl-7-{4-[3-(3-bromophenoxy)propyl]phenyl}-3,9-diazabicyclo[3.3.1]non-6-ene-6-carboxylic acid methylphenethylamide;

(rac.)-(2-methoxyphenyl)acetic acid (1R*,5S)-3-acetyl-7-[4-(3-p-tolyloxypropyl)phenyl]-3,9-diazabicyclo[3.3.1]non-6-en-6-ylmethyl ester;

(rac.)-acetic acid 2-((1R*,5S*)-7-{4-[3-(2-chlorophenoxy)propyl]phenyl}-6-{[2-(2-chlorophenyl)ethyl]methylcarbamoyl}-3,9-diazabicyclo[3.3.1]non-6-en-3-yl)-2-oxoethyl ester;

(rac.)-(1R*,5S*)-7-{4-[3-(2-chlorophenoxy)propyl]phenyl}-3-(2-cyanoacetyl)-3,9-diazabicyclo[3.3.1]non-6-ene-6-carboxylic acid [2-(2-chlorophenyl)ethyl]-methylamide;

(rac.)-(1R*,5S*)-3-(2-acetylaminoacetyl)-7-{4-[3-(2-chlorophenoxy)propyl]phenyl}-3,9-diazabicyclo[3.3.1]non-6-ene-6-carboxylic acid [2-(2-chlorophenyl)-ethyl]methylamide;

1:1 mixture of (1R,5S)-3-((4R)-2-acetylamino-4-methylpentanoyl)-7-{4-[3-(2-chlorophenoxy)propyl]phenyl}-3,9-diazabicyclo[3.3.1]non-6-ene-6-carboxylic acid [2-(2-chlorophenyl)ethyl]methylamide and (1S,5R)-3-((4R)-2-acetylamino-4-methylpentanoyl)-7-{4-[3-(2-chlorophenoxy)propyl]phenyl}-3,9-diazabicyclo-[3.3.1]non-6-ene-6-carboxylic acid [2-(2-chlorophenyl)ethyl]methylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid [2-(2-chlorophenyl)ethyl]methylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid (2-hydroxybenzyl)methylamide;

1:1 mixture of (rac.)-(1R*,5S*)-3-acetyl-7-{4-[3-(2-chlorophenoxy)propyl]-phenyl}-3,9-diazabicyclo[3.3.1]non-6-ene-6-carboxylic acid [(3R*)-3-(2-chlorophenyl)butyl]methylamide and (rac.)-(1R*,5S*)-3-acetyl-7-{4-[3-(2-chlorophenoxy)propyl]phenyl}-3,9-diazabicyclo[3.3.1]non-6-ene-6-carboxylic acid [(3S*)-3-(2-chlorophenyl)butyl]methylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid methyl-(4-phenylbutyl)amide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid methyl-(3-phenoxypropyl)amide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid methyl-(4-phenylpentyl)amide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid (3-benzo[1,3]dioxol-5-ylpropyl)methylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid [2-(4-methoxyphenoxy)ethyl]methylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid [2-(4-chlorophenoxy)ethyl]methylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid methyl-(2-p-tolyloxyethyl)amide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid diethylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid methyl-(2-pyridin-2-ylethyl)amide;

(rac.)-(1R*,5S*)-3-acetyl-7-{4-[3-(2-bromo-5-fluorophenoxy)ethyl]phenyl}-3,9-diazabicyclo[3.3.1]non-6-ene-6-carboxylic acid (2-chlorobenzyl)cyclopropylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid (2-chlorobenzyl)cyclopropylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid [2-(4-methoxyphenoxy)ethyl]methylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid methyl-(3-trifluoromethylbenzyl)amide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid [2-(3,4-dimethylphenoxy)ethyl]methylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid (3,5-dimethoxybenzyl)methylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid (2-chlorobenzyl)methylamide;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid methylphenethylamide;

(rac.)-(1R*,5S*)-3-acetyl-7-{4-[2-(3,4-dichlorophenoxy)ethoxy]phenyl}-3,9-diazabicyclo[3.3.1]non-6-ene-6-carboxylic acid methylphenethylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid (2-chlorobenzyl)ethylamide;

(rac.)-(1R*,5S*)-3-acetyl-7-{4-[3-(2,3,6-trichlorophenoxy)ethyl]phenyl}-3,9-diazabicyclo[3.3.1]non-6-ene-6-carboxylic acid methylphenethylamide;

(rac.)-(1R*,5S*)-3-acetyl-7-{4-[3-(3-fluorophenoxy)propyl]phenyl}-3,9-diazabicyclo[3.3.1]non-6-ene-6-carboxylic acid (2-chlorobenzyl)cyclopropyl-amide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid (2-chlorobenzyl)isopropylamide;

(rac.)-(1R*,5S*)-5-[7-{4-([2-(2-bromo-5-fluorophenoxy)ethyl]phenyl}-6-(methylphenethylcarbamoyl)-3,9-diazabicyclo[3.3.1]non-6-en-3-yl]-2,2-dimethyl-5-oxopentanoic acid;

(1S,5R)-3-acetyl-7-{4-[2-(2,3,6-trifluorophenoxy)ethyl]phenyl}-3,9-diazabicyclo[3.3.1]non-6-ene-6-carboxylic acid methylphenethylamide;

1:1-mixture of (rac.)-(1R*,5S*)-3-acetyl-7-({4-[3-(2-bromo-5-fluorophenoxy)-propyl]phenyl}-3,9-diazabicyclo[3.3.1]non-6-ene-6-carboxylic acid cyclopropyl-[2-((2R*)-2,3-dihydroxypropyl)benzyl]amide and (rac.)-(1R*,5S*)-3-acetyl-7-{4-[3-(2-bromo-5-fluorophenoxy)-propyl]phenyl}-3,9-diazabicyclo[3.3.1]non-6-ene-6-carboxylic acid cyclopropyl-[2-((2S*)-2,3-dihydroxypropyl)benzyl]amide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid cyclopropyl-[2-(2-hydroxyethyl)benzyl]amide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid benzylcyclopropylamide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid (2-chlorobenzyl)ethylamide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid cyclopropyl-(2-fluorobenzyl)amide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid cyclopropyl-(2-methylbenzyl)amide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid cyclopropyl-[2(4-methoxyphenoxy)ethyl)amide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid cyclopropyl-(2-m-tolyloxyethyl)amide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid cyclopropyl-[2-(3,4-dimethylphenoxy)ethyl]amide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid cyclopropylphenethylamide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid [2-(2-chlorophenyl)ethyl]-cyclopropylamide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid cyclopropyl-[2-(2,3-difluorophenyl)ethyl]amide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid cyclopropyl-[2-(4-fluorophenyl)ethyl]amide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid cyclopropyl-(2-o-tolylethyl)amide;

1:1-mixture of (rac.)-(1R*,5S*)-3-acetyl-7-{4-[3-(2-bromo-5-fluorophenoxy)-propyl]phenyl}-3,9-diazabicyclo[3.3.1]non-6-ene-6-carboxylic acid ((2R*)-2-hydroxy-2-phenylethyl)methylamide and (rac.)-(1R*,5S*)-3-acetyl-7-{4-[3-(2-bromo-5-fluorophenoxy)-propyl]phenyl}-3,9-diazabicyclo[3.3.1]non-6-ene-6-carboxylic acid ((2S*)-2-hydroxy-2-phenylethyl)methylamide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid cyclopropyl-(3-trifluoromethylbenzyl)amide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(2-o-tolylethyl)amide;

(rac.)-(1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester;

(rac.)-(1R*,5S*)-6-[(2-fluorobenzyl)cyclopropylcarbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester;

(rac.)-(1R*,5S*)-6-[(2-methylbenzyl)cyclopropylcarbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester;

(rac.)-(1R*,5S*)-6-[cyclopropyl-(2-o-tolylethyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester;

(rac.)-(1R*,5S*)-6-[cyclopropyl-(2-p-tolylethyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester;

(rac.)-(1R*,5S*)-6-[cyclopropyl-(3,5-dimethoxybenzyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-[2-(4-methoxyphenoxy)ethyl]amide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-[2-(3-methoxyphenoxy)ethyl]amide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(2-m-tolyloxyethyl)amide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-[2-(3,4-dimethylphenoxy)ethyl]amide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-[2-(2,3-difluorophenyl)ethyl]amide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-[2-(4-fluorophenyl)ethyl]amide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(2-o-tolylethyl)amide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(2-p-tolylethyl)amide;

1:1-mixture of (1R,5S)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid benzylcyclopropylamide and (1S,5R)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid benzylcyclopropylamide;

1:1-mixture of (1R,5S)-3-((1S,4R)-4-hydroxypyrrolidine-2-carbonyl)-7-{4-[3-(2,3,6-trifluorophenoxy)propylphenyl}-3,9-diazabicyclo[3.3.1]non-6-ene-6-carboxylic acid (2-chlorobenzyl)ethylamide and (1S,5R)-3-((1S,4R)-4-hydroxypyrrolidine-2-carbonyl)-7-{4-[3-(2,3,6-trifluorophenoxy)propylphenyl}-3,9-diazabicyclo[3.3.1]non-6-ene-6-carboxylic acid (2-chlorobenzyl)ethylamide;

1:1-mixture of (1R,5S)-3-(1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-fluorobenzyl)amide and (1S,5R)-3-((1S,4R)-4-hydroxypyrrolidine-2-carbonyl)-7-{4-[3-(2,3,6-trifluorophenoxy)propyl]phenyl}-3,9-diazabicyclo-[3.3.1]non-6-ene-6-carboxylic acid cyclopropyl-(2-fluorobenzyl)amide;

1:1-mixture of (1R,5S)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(3-trifluoromethylbenzyl)amide and (1S,5R)-3-((1S,4R)-4-hydroxypyrrolidine-2-carbonyl)-7-{4-[3-(2,3,6-trifluorophenoxy)propyl]-phenyl}-3,9-diazabicyclo[3.3.1]non-ene-6-carboxylic acid cyclopropyl-(3-trifluoromethylbenzyl)amide;

1:1-mixture of (1R,5S)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-methylbenzyl)amide and (1S,5R)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-methylenzyl)amide;

1:1-mixture of (1R,5S)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-m-tolyloxyethyl)amide and (1S,5R)-3-((1R4S)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-m-tolyloxyethyl)amide;

1:1-mixture of (1R,5S)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-3,5-dimethoxybenzyl)amide and (1S,5R)-3-((1S,4R)-4-hydroxypyrrolidine-2-carbonyl)-7-{4-[3-(2,3,6-trifluorophenoxy)propyl]-phenyl}-3,9-diazabicyclo[3.3.1]non-6-ene-6-carboxylic acid cyclopropyl-(3,5-dimethoxybenzyl)amide;

1:1-mixture of (1R,5S)-3-((1S,4R)-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-p-tolylethyl)amide and (1S,5R)-3-((1S,4R)-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-p-tolylethyl)amide;

1:1-mixture of (rac.)-(3R*)-5-(1R*,5S*)-6-{cyclopropyl-[2-(3-methoxy-phenoxy)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid and (rac.)-(3S*)-5-((1R*,5S*)-6-{cyclopropyl-[2-(3-methoxyphenoxy)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid;

1:1-mixture of (rac.)-(3R*)-5-(1R*,5S*)-6-{cyclopropyl-[2-(3,4-dimethyl-phenoxy)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid and (rac.)-(3S*)-5-((1R*,5S*)-6-{cyclopropyl-[2-(3,4-dimethylphenoxy)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid;

1:1-mixture of (rac.)-(3R*)-5-((1R*,5S*)-(6-(cyclopropylphenethylcarbamoyl)-7-{4-[3-(2,3,6-trifluorophenoxy)propyl]phenyl}-3,9-diazabicyclo[3.3.1]non-6-en-3-yl)-3-hydroxy-5-oxopentanoic acid and (rac.)-(3S*)-5-((1R*,5S*)-(6-(cyclopropylphenethylcarbamoyl)-7-{4-[3-(2,3,6-trifluorophenoxy)propyl]-phenyl}-3,9-diazabicyclo-[3.3.1]non-6-en-3-yl)-3-hydroxy-5-oxopentanoic acid;

1:1-mixture of (rac.)-(3R*)-5-((1R*,5S*)-6-{cyclopropyl-[2-(2,3-difluorophenyl)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid and (rac.)-(3S*)-5-((1R*,5*S)-6-{cyclopropyl-[2-(2,3-difluorophenyl)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid;

1:1-mixture of (rac.)-(3R*)-5-((1R*,5S*)-6-{cyclopropyl-[2-(4-fluorophenyl)-ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid and (rac.)-(3S*)-5-((1R*,5S*)-6-{cyclopropyl-[2-(4-fluorophenyl)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid;

1:1-mixture of (rac.)-(3R*)-5-((1R*,5S*)-6-[cyclopropyl-(2-o-tolylethyl)-carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid and (rac.)-(3S*)-5-((1R*, 5S*)-6-[cyclopropyl-(2-o-tolylethyl)carbamoyl]-7-{4-[3-(2,3,6-trifluorophenoxy)-propyl]phenyl}-3,9-diazabicyclo-[3.3.1]non-6-en-3-yl)-3-hydroxy-5-oxopentanoic acid;

1:1-mixture of (rac.)-(3R*)-5-((1R*,5S*)-6-[cyclopropyl-(2-p-tolylethyl)-carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid and (rac.)-(3R*)-5-((1R*, 5S*)-6-[cyclopropyl-(2-p-tolylethyl)carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid benzylcyclopropylamide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(2-fluorobenzyl)amide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(2-methylbenzyl)amide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-[2-(4-methoxyphenoxy)ethyl]amide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-[2-(3-methoxyphenoxy)ethyl]amide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-[2-(3-methyl-phenoxy)ethyl]amide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropylphenethylamide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl(2-p-tolylethyl)amide;

(rac.)-5-((1R*,5S*)-6-{cyclopropyl-[2-(4-methoxyphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-{cyclopropyl-[2-(3-methoxyphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-{cyclopropyl[2-(3-methylphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-{cyclopropyl-[2-(3,4-dimethylphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-(cyclopropylphenethylcarbamoyl)-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5*S)-6-{cyclopropyl-[2-(2,3-trifluorophenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-{cyclopropyl-[2-(4-fluorophenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-{cyclopropyl-[2-(2-methylphenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-(benzylcyclopropylcarbamoyl)-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-[cyclopropyl-(3-trifluoromethylbenzyl)carbamoyl]-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-[cyclopropyl-(2-methymethylbenzyl)carbamoyl]-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-{cyclopropyl-[2-(4-methoxyphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-{cyclopropyl-[2-(3-methoxyphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-{cyclopropyl-[2-(3-methylphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-{cyclopropyl-[2-(3,4-dimethylphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-(cyclopropylphenethylcarbamoyl)-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-{[2-(2-chlorophenyl)ethyl]cyclopropylcarbamoyl}-7-{4-[4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-{cyclopropyl-[2-(2,3-difluorophenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-{cyclopropyl-[2-(4-fluorophenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-{cyclopropyl-[2-(2-methylphenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-{cyclopropyl-[2-(4-methylphenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-(benzylcyclopropylcarbamoyl)-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-[cyclopropyl-(3-trifluoromethylbenzyl)carbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-{cyclopropyl-[2-(4-methoxyphenoxy)ethyl]carbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-{cyclopropyl-[2-(3-methoxyphenoxy)ethyl]carbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-{cyclopropyl-[2-(3-methylphenoxy)ethyl]carbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-{cyclopropyl-[2-(3,4-dimethylphenoxy)ethyl]carbamoyl}-7-{4-[3-(2,3,6-trifluorophenoxy)

propyl]phenyl}-3,9-diazabicyclo[3.3.1]non-6-en-3-yl)-2,2-dimethyl-5-oxopentanoic acid;

(rac.)-5-(1R*,5S*)-6-(cyclopropylphenethylcarbamoyl)-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-(1R*,5S*)-6-{[2-(2-chlorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-{[2-(2,3-difluorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-{[2-(4-fluorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-{[2-(2-methylphenyl)ethyl]cyclopropylcarbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-{[2-(4-methylphenyl)ethyl]cyclopropylcarbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid;

1:1-mixture of (rac.)-(2R*,3S*)-4-((1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-en-3-yl)-2,3-dihydroxy-4-oxobutyric acid and (rac.)-(2S*,3R*)-4-((1R*,5S*)-6-[(2-chlorobenzyl)ethylcarbamoyl]-7-{4-[3-(2,3,6-trifluorophenoxy)propyl]phenyl}-3,9-diazabicyclo-[3.3.1]non-6-en-3-yl)-2,3-dihydroxy-4-oxobutyric acid;

1:1-mixture of (rac.)-(2R*,3S*)-4-((1R*,5S*)-6-[cyclopropyl-(2-fluorobenzyl)-carbamoyl]-7-{4-[3-(2,3,6-trifluorophenoxy)propyl]phenyl}-3,9-diazabicyclo[3.3.1]non-6-en-3-yl)-2,3-dihydroxy-4-oxobutyric acid and (rac.)-(2S*,3R*)-4-((1R*,5S*)-6-[cyclopropyl-(2-fluorobenzyl)carbamoyl]-7-{4-[3-(2,3,6-trifluorophenoxy)propyl]phenyl}-3,9-diazabicyclo-[3.3.1]non-6-en-3-yl)-2,3-dihydroxy-4-oxobutyric acid;

1:1-mixture of (rac.)-(2R*,3S*)-4-((1R*,5S*)-6-[cyclopropyl-(3-trifluoromethylbenzyl)carbamoyl]-7-{4-[3-(2,3,6-trifluorophenoxy)propyl]phenyl}-3,9-diazabicyclo[3.3.1]non-6-en-3-yl)-2,3dihydroxy-4-oxobutyric acid and (rac.)-(2S*,3R*)-4-((1R*,5S*)-6-[cyclopropyl-(3-trifluoromethylbenzyl)carbamoyl]-7-{4-[3-(2,3,6-trifluorophenoxy)propyl]phenyl}-3,9-diazabicyclo-[3.3.1]non-6-en-3-yl)-2,3-dihydroxy-4-oxobutyric acid;

1:1-mixture of (rac.)-(2R*,3S*)-4-((1R*,5S*)-6-{cyclopropyl-[2-(2,3-difluorophenyl)ethyl]carbamoyl}-7-{4-[3-(2,3,6-trifluorophenoxy)propyl]phenyl}-3,9-diazabicyclo[3.3.1]non-6-en-3-yl)-2,3-dihydroxy-4-oxobutyric acid and (rac.)-(2S*,3R*)-4-((1R*,5S*)-6-{cyclopropyl-[2-(2,3-difluorophenyl)ethyl]-carbamoyl}-7-{4-[3-(2,3,6-trifluorophenoxy)propyl]phenyl}-3,9-diazabicyclo[3.3.1]non-6-en-3-yl)-2,3-dihydroxyoxobutyric acid;

1:1-mixture of (rac.)-(2R*,3S*)-4-((1R*,5S*)-6-{cyclopropyl-[2-(2-methyl-phenyl)ethyl]carbamoyl}-7-{4-[3-(2,3,6-trifluorophenoxy)propyl]phenyl}-3,9-diazabicyclo[3.3.1]non-6-en-3-yl)-2,3-dihydroxy-4-oxobutyric acid and (rac.)-(2S*,3R*)-4-((1R*,5S*)-6-{cyclopropyl-[2-(2-methylphenyl)ethyl]carbamoyl}-7-{4-[3-(2,3,6-trifluorophenoxy)propyl]phenyl}-3,9-diazabicyclo-[3.3.1]non-6-en-3-yl)-2,3-dihydroxy-4-oxobutyric acid;

1:1-mixture of (rac.)-(2R*,3S*)-4-((1R*,5S*)-6-[cyclopropyl-(3,5-dimethoxy-benzyl)carbamoyl]-7-{4-[3-(2,3,6-trifluorophenoxy)propyl]phenyl}-3,9-diazabicyclo[3.3.1]non-6-en-3-yl)-2,3-dihydroxy-4-oxobutyric acid and (rac.)-(2S*,3R*)-4-((1R*,5S*)-6-[cyclopropyl-(3,5-dimethoxybenzyl)carbamoyl]-7-{4-[3-(2,3,6-trifluorophenoxy)propyl]phenyl}-3,9-diazabicyclo[3.3.1]non-6-en-3-yl)-2,3-dihydroxy-4-oxobutyric acid;

1:1-mixture of (rac.)-(2R*,3S*)-4-((1R*,5S*)-6-{cyclopropyl-[2-(4-methylphenyl)ethyl]carbamoyl}-7-{4-[3-(2,3,6-trifluorophenoxy)propyl]phenyl}-3,9-diazabicyclo[3.3.1]non-6-en-3-yl)-2,3-dihydroxy-4-oxobutyric acid and (rac.)-(2S*,3R*)-4-((1R*,5S*)-6-{cyclopropyl-[2-(4-methylphenyl)ethyl]carbamoyl}-7-{4-[3-(2,3,6-trifluorophenoxy)propyl]phenyl}-3,9-diazabicyclo-[3.3.1]non-6-en-3-yl)-2,3-dihydroxy-4-oxobutyric acid;

1:1-mixture of (rac.)-(3R*)-5-((1R*,5S*)-6-[(2-chlorobenzyl)cyclopropylcarbamoyl]-7-{4-[3-(2,3,5-trimethylphenoxy)ethyl]phenyl}-3,9-diazabicyclo-[3.3.1]non-6-en-3-yl)-3-hydroxy-5-oxopentanoic acid and (rac.)-(3S*)-5-((1R*, 5S*)-6-[(2-chlorobenzyl)cyclopropylcarbamoyl]-7-{4-[3-(2,3,5-trimethylphenoxy)ethyl]phenyl}-3,9-diazabicyclo-[3.3.1]non-6-en-3-yl)-3-hydroxy-5-oxopentanoic acid;

1:1-mixture of (rac.)-(3R*)-5-((1R*,5S*)-6-[(2-chlorobenzyl)ethylcarbamoyl]-7-{4-[3-(2,3,5-trimethylphenoxy)ethyl]phenyl}-3,9-diazabicyclo[3.3.1]non-6-en-3-yl)-3-hydroxy-5-oxopentanoic acid and (rac.)-(3S*)-5-((1R*,5S*)-6-[(2-chlorobenzyl)ethylcarbamoyl]-7-{4-[3-(2,3,5-trimethylphenoxy)ethyl]phenyl}-3,9-diazabicyclo[3.3.1]non-6-en-3-yl)-3-hydroxy-5-oxopentanoic acid;

(rac.)-5-((1R*,5S*)-7-{4-[3-(2-bromo-5-fluorophenoxy)propyl]phenyl}-6-{cyclopropyl-[2-(2-hydroxyethyl)benzyl]carbamoyl}-3,9-diazabicyclo[3.3.1]non-6-en-3-yl)-5-oxopentanoic acid;

(rac.)-5-((1R*,5S*)-7-{4-[3-(2-bromo-5-fluorophenoxy)propyl]phenyl}-6-{cyclopropyl-[2-(2-hydroxyethyl)benzyl]carbamoyl}-3,9-diazabicyclo[3.3.1]non-6-en-3-yl)-5-oxopentanoic acid methyl ester;

(rac.)-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid cyclopropyl-[2-(2-hydroxyethyl)benzyl]amide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-[2-(2-hydroxyethyl)benzyl]amide;

(rac.)-5-((1R*,5S*)-4-{cyclopropyl-[2-(2-hydroxyethyl)benzyl]carbamoyl}-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-{cyclopropyl-[2-(2-hydroxyethyl)benzyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-{cyclopropyl-[2-(2-hydroxyethyl)benzyl]carbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-(1R*,5S*)-3-(4-carbamoylbutyryl)-7-{([3-(2,3,6-trifluorophenoxy)-propyl]phenyl}-3,9-diazabicyclo[3.3.1]non-6-ene-6-carboxylic acid cyclopropyl-[2-(2-hydroxyethyl)benzyl]amide;

(rac.)-5-{(1R*,5S*)-7-{4-[3-(2-bromo-5-fluorophenoxy)propyl]phenyl}-6-[(2-chlorobenzyl)ethylcarbamoyl]-3,9-diazabicyclo[3.3.1]non-6-en-3-yl}-5-oxopentanoic acid;

(rac.)-5-{(1R*,5S*)-7-{4-[3-(2-bromo-5-fluorophenoxy)propyl]phenyl}-6-[cyclopropyl-(3-trifluoromethylbenzyl)carbamoyl]-3,9-diazabicyclo[3.3.1]non-6-en-3-yl}-5-oxopentanoic acid;

(rac.)-5-{(1R*,5S*)-7-{4-[3-(2-bromo-5-fluorophenoxy)propyl]phenyl}-6-[cyclopropyl-(2-methylbenzyl)carbamoyl]-3,9-diazabicyclo[3.3.1]non-6-en-3-yl}-5-oxopentanoic acid;

(rac.)-5-{(1R*,5S*)-7-{4-[3-(2-bromo-5-fluorophenoxy)propyl]phenyl}-6-{cyclopropyl-[2-(4-methoxyphenoxy)ethyl]carbamoyl}-3,9-diazabicyclo[3.3.1]-non-6-en-3-yl}-5-oxopentanoic acid;

(rac.)-5-{(1R*,5S*)-7-{4-[3-(2-bromo-5-fluorophenoxy)propyl]phenyl}-6-{cyclopropyl-[2-(3,4-dimethylphenoxy)ethyl]carbamoyl}-3,9-diazabicyclo[3.3.1]-non-6-en-3-yl}-5-oxopentanoic acid;

(rac.)-5-((1R*,5S*)-7-{4-[3-(2-bromo-5-fluorophenoxy)propyl]phenyl}-6-{[2-(4-fluorophenyl)ethyl]cyclopropylcarbamoyl}-3,9-diazabicyclo[3.3.1]non-6-en-3-yl)-5-oxopentanoic acid;

(rac.)-5-{(1R*,5S*)-7-{4-[3-(2-bromo-5-fluorophenoxy)propyl]phenyl}-6-[(2-chlorobenzyl)ethylcarbamoyl]-3,9-diazabicyclo[3.3.1]non-6-en-3-yl}-5-oxopentanoic acid methyl ester;

(rac.)-5-{(1R*,5S*)-7-{4-[3-(2-bromo-5-fluorophenoxy)propyl]phenyl}-6-[cyclopropyl-(2-fluorobenzyl)carbamoyl]-3,9-diazabicyclo[3.3.1]non-6-en-3-yl}-5-oxopentanoic acid methyl ester;

(rac.)-5-{(1R*,5S*)-7-{4-[3-(2-bromo-5-fluorophenoxy)propyl]phenyl}-6-[cyclopropyl-(3-trifluoromethylbenzyl)carbamoyl]-3,9-diazabicyclo[3.3.1]non-6-en-3-yl}-5-oxopentanoic acid methyl ester;

(rac.)-5-{(1R*,5S*)-7-{4-[3-(2-bromo-5-fluorophenoxy)propyl]phenyl}-6-[cyclopropyl-(2-methylbenzyl)carbamoyl]-3,9-diazabicyclo[3.3.1]non-6-en-3-yl}-5-oxopentanoic acid methyl ester;

(rac.)-5-((1R*,5S*)-7-{4-[3-(2-bromo-5-fluorophenoxy)propyl]phenyl}-6-{cyclopropyl-[2-(4-methoxyphenoxy)ethyl]carbamoyl}-3,9-diazabicyclo[3.3.1]-non-6-en-3-yl)-5-oxopentanoic acid methyl ester;

(rac.)-5-((1R*,5S*)-7-{4-[3-(2-bromo-5-fluorophenoxy)propyl]phenyl}-6-{cyclopropyl-[2-(3-methylphenoxy)ethyl]carbamoyl}-3,9-diazabicyclo[3.3.1]non-6-en-3-yl)-5-oxopentanoic acid methyl ester;

(rac.)-5-((1R*,5S*)-7-{4-[3-(2-bromo-5-fluorophenoxy)propyl]phenyl}-6-{cyclopropyl-[2-(3,4-dimethylphenoxy)ethyl]carbamoyl}-3,9-diazabicyclo[3.3.1]-non-6-en-3-yl)-5-oxopentanoic acid methyl ester;

(rac.)-5-[(1R*,5S*)-7-{4-[3-(2-bromo-5-fluorophenoxy)propyl]phenyl}-6-(cyclopropylphenethylcarbamoyl)-3,9-diazabicyclo[3.3.1]non-6-en-3-yl]-5-oxopentanoic acid methyl ester;

(rac.)-5-((1R*,5S*)-7-{4-[3-(2-bromo-5-fluorophenoxy)propyl]phenyl}-6-{[2-(2-chlorophenyl)ethyl]cyclopropylcarbamoyl}-3,9-diazabicyclo[3.3.1]non-6-en-3-yl)-5-oxopentanoic acid methyl ester;

(rac.)-5-((1R*,5S*)-7-{4-[3-(2-bromo-5-fluorophenoxy)propyl]phenyl}-6-{[2-2,3-difluorophenyl)ethyl]cyclopropylcarbamoyl}-3,9-diazabicyclo[3.3.1]non-6-en-3-yl)-5-oxopentanoic acid methyl ester;

(rac.)-5-((1R*,5S*)-7-{4-[3-(2-bromo-5-fluorophenoxy)propyl]phenyl}-6-{[2-(4-fluorophenyl)ethyl]cyclopropylcarbamoyl}-3,9-diazabicyclo[3.3.1]non-6-en-3-yl)-5-oxopentanoic acid methyl ester;

(rac.)-5-((1R*,5S*)-7-{4-[3-(2-bromo-5-fluorophenoxy)propyl]phenyl}-6-{[2-(2-methylphenyl)ethyl]cyclopropylcarbamoyl}-3,9-diazabicyclo[3.3.1]non-6-en-3-yl)-5-oxopentanoic acid methyl ester;

(rac.)-5-((1R*,5S*)-7-{4-[3-(2-bromo-5-fluorophenoxy)propyl]phenyl}-6-{[2-(2-methylphenyl)ethyl]cyclopropylcarbamoyl}-3,9-diazabicyclo[3.3.1]non-6-en-3-yl)-5-oxopentanoic acid methyl ester;

(rac.)-5-{(1R*,5S*)-7-{4-[3-(2-bromo-5-fluorophenoxy)propyl]phenyl}-6-[(2-chlorobenzyl)ethylcarbamoyl]-3,9-diazabicyclo[3.3.1]non-6-en-3-yl}-2,2-dimethyl-5-oxopentanoic acid;

(rac.)-5-{(1R*,5S*)-7-{4-[3-(2-bromo-5-fluorophenoxy)propyl]phenyl}-6-[cyclopropyl-(3-trifluoromethylbenzyl)carbamoyl]-3,9-diazabicyclo[3.3.1]non-6-en-3-yl}-2,2-dimethyl-5-oxopentanoic acid;

(rac.)-5-((1R*,5S*)-7-{4-[3-(2-bromo-5-fluorophenoxy)propyl]phenyl}-6-{cyclopropyl-[2-(4-methoxyphenoxy)ethyl]carbamoyl}-3,9-diazabicyclo[3.3.1]-non-6-en-3-yl)-2,2-dimethyl-5-oxopentanoic acid;

(rac.)-5-((1R*,5S*)-7-{4-[3-(2-bromo-5-fluorophenoxy)propyl]phenyl}-6-{cyclopropyl-[2-(3-methylphenoxy)ethyl]carbamoyl}-3,9-diazabicyclo[3.3.1]-non-6-en-3-yl)-2,2-dimethyl-5-oxopentanoic acid;

(rac.)-5-((1R*,5S*)-7-{4-[3-(2-bromo-5-fluorophenoxy)propyl]phenyl}-6-{cyclopropyl-[2-(3,4-dimethylphenoxy)ethyl]carbamoyl}-3,9-diazabicyclo-[3.3.1]non-6-en-3-yl)-2,2-dimethyl-5-oxopentanoic acid;

(rac.)-5-((1R*,5S*)-7-{4-[3-(2-bromo-5-fluorophenoxy)propyl]phenyl}-6-{[2-[2-chlorophenyl)ethyl]cyclopropylcarbamoyl}-3,9-diazabicyclo[3.3.1]non-6-en-3-yl)-2,2-dimethyl-5-oxopentanoic acid;

(rac.)-5-((1R*,5S*)-7-{4-[3-(2-bromo-5-fluorophenoxy)propyl]phenyl}-6-{[2-(2,3-difluorophenyl)ethyl]cyclopropylcarbamoyl}-3,9-diazabicyclo[3.3.1]non-6-en-3-yl)-2,2-dimethyl-5-oxopentanoic acid;

(rac.)-5-((1R*,5S*)-7-{4-[3-(2-bromo-5-fluorophenoxy)propyl]phenyl}-6-{[2-(4-fluorophenyl)ethyl]cyclopropylcarbamoyl}-3,9-diazabicyclo[3.3.1]non-6-en-3-yl)-2,2-dimethyl-5-oxopentanoic acid;

(rac.)-5-(1R*,5S*)-7-{4-[3-(2-bromo-5-fluorophenoxy)propyl]phenyl}-6-{[2-(2-methylphenyl)ethyl]cyclopropylcarbamoyl}-3,9-diazabicyclo[3.3.1]non-6-en-3-yl)-2,2-dimethyl-5-oxopentanoic acid;

1:1-mixture of (rac.)-(2R*,3S*)-4-{(1R*,5S*)-7-{4-[3-(2-bromo-5-fluorophenoxy)propyl]phenyl}-6-[(2-chlorobenzyl)ethylcarbamoyl]-3,9-diazabicyclo-[3.3.1]non-6-en-3-yl}-2,3-dihydroxy-4-oxobutyric acid and (rac.)-(2S*,3R*)-4-{(1R*,5S*)-7-{4-[3-(2-bromo-5-fluorophenoxy)propyl]phenyl}-6-[(2-chlorobenzyl)ethylcarbamoyl]-3,9-diazabicyclo-[3.3.1]non-6-en-3-yl}-2,3-dihydroxy-4-oxobutyric acid;

1:1-mixture of (rac.)-(2R*,3S*)-4-{(1R*,5S*)-7-{4-[3-(2-bromo-5-flurophenoxy)propyl]phenyl}-6-[cyclopropyl-(2-fluorobenzyl)carbamoyl]-3,9-diazabicyclo[3.3.1]non-6-en-3-yl}-2,3-dihydroxy-4-oxobutyric acid and (rac.)-(2S*,3R*)-4-{(1R*,5S*)-7-{4-[3-(2-bromo-5-fluorophenoxy)propyl]phenyl}-6-[cyclopropyl-(2-fluorobenzyl)carbamoyl]-3,9-diazabicyclo[3.3.1]non-6-en-3-yl}-2,3-dihydroxy-4-oxobutyric acid;

1:1-mixture of (rac.)-(2R*,3S*)-4-{(1R*,5S*)-7-{4-[3-(2-bromo-5-fluorophenoxy)propyl]phenyl}-6-[cyclopropyl-(3-trifluoromethylbenzyl)carbamoyl]-3,9-diazabicyclo[3.3.1]non-6-en-3-yl}-2,3-dihydroxy-4-oxobutyric acid and (rac.)-(2S*,3R*)-4-{(1R*,5S*)-7-{4-[3-(2-bromo-5-fluorophenoxy)propyl]-phenyl}-6-[cyclopropyl-(3-trifluoromethylbenzyl)carbamoyl]-3,9-diazabicyclo-[3.3.1]non-6-en-3-yl}-2,3-dihydroxy-4-oxobutyric acid;

1:1-mixture of (rac.)-(2R*,3S*)-4-{(1R*,5S*)-7-{4-[3-(2-bromo-5-fluorophenoxy)propyl]phenyl}-6-[cyclopropyl-(2-methylbenzyl)carbamoyl]-3,9-diazabicyclo[3.3.1]non-6-en-3-yl}-2,3-dihydroxy-4-oxobutyric acid and (rac.)-(2S*,3R*)-4-{(1R*,5S*)-7-{4-[3-(2-bromo-5-fluorophenoxy)propyl]-phenyl}-6-[cyclopropyl-(2-methylbenzyl)carbamoyl]-3,9-diazabicyclo-[3.3.1]non-6-en-3-yl}-2,3-dihydroxy-4-oxobutyric acid;

1:1-mixture of (rac.)-(2R*,3S*)-4-((1R*,5S*)-7-{4-[3-(2-bromo-5-fluorophenoxy)propyl]phenyl}-6-{cyclopropyl-[2-(4-methoxyphenoxy)ethyl]-carbamoyl}-3,9-diazabicyclo[3.3.1]non-6-3-yl)-2,3-dihydroxy-4-oxobutyric acid and (rac.)-(2S*,3R*)-4-((1R*,5S*)-7-{4-[3-(2-bromo-5-fluorophenoxy)propyl]phenyl}-6-{cyclopropyl-[2-(4-methoxyphenoxy)ethyl]-carbamoyl}-3,9-diazabicyclo[3.3.1]non-6-en-3-yl)-2,3-dihydroxy-4-oxobutyric acid;

1:1-mixture of (rac.)-(2R*,3S*)-4-((1R*,5S*)-7-{4-[3-(2-bromo-5-fluorophenoxy)propyl]phenyl}-6-{cyclopropyl-[2-(3-methylphenoxy)ethyl]carbamoyl}-3,9-diazabicyclo[3.3.1]non-6-en-3-yl)-2,3-dihydroxy-4-oxobutyric acid and (rac.)-(2S*,3R*)-4-((1R*,5S*)-7-{4-[3-(2-bromo-5-fluorophenoxy)propyl]-phenyl}-6-{cyclopropyl-[2-(3-methylphenoxy)ethyl]carbamoyl}-3,9-diazabicyclo[3.3.1]non-6-en-3-yl)-2,3-dihydroxy-4-oxobutyric acid;

1:1-mixture of (rac.)-(2R*,3S*)-4-((1R*,5S*)-7-{4-[3-(2-bromo-5-fluorophenoxy)propyl]phenyl}-6-{cyclopropyl-[2-(3,4-dimethylphenoxy)ethyl]-carbamoyl}-3,9-diazabicyclo[3.3.1]non-6-en-3-yl)-2,3-dihydroxy-4-oxobutyric acid and (rac.)-(2S*,3R*)-4-((1R*,5S*)-7-{4-[3-(2-bromo-5-fluorophenoxy)-propyl]phenyl}-6-{cyclopropyl-[2-(3,4-dimethylphenoxy)ethyl]carbamoyl}-3,9-diazabicyclo[3.3.1]non-6-en-3-yl)-2,3-dihydroxy-4-oxobutyric acid;

1:1-mixture of (rac.)-(2R*,3S*)-4-[(1R*,5S*)-7-{4-[3-(2-bromo-5-fluorophenoxy)propyl]phenyl}-6-(cyclopropylphenethylcarbamoyl)-3,9-diazabicyclo-[3.3.1]non-6-en-3-yl]-2,3-dihydroxy-4-oxobutyric acid and (rac.)-(2S*,3R*)-4-[(1R*,5S*)-7-{4-[3-(2-bromo-5-fluorophenoxy)propyl]phenyl}-6-(cyclopropylphenethylcarbamoyl)-3,9-diazabicyclo-[3.3.1]non-6-en-3-yl]-2,3-dihydroxy-4-oxobutyric acid;

1:1-mixture of (rac.)-(2R*,3S*)-4-((1R*,5S*)-7-{4-[3-(2-bromo-5-fluorophenoxy)propyl]phenyl}-6-{[2-(2-chlorophenyl)ethyl]cyclopropylcarbamoyl}-3,9-diazabicyclo[3.3.1]non-6-en-3-yl)-2,3-dihydroxy-4-oxobutyric acid and
(rac.)-(2S*,3R*)-4-((1R*,5S*)-7-{4-[3-(2-bromo-5-fluorophenoxy)propyl]-phenyl}-6-{[2-(2-chlorophenyl)ethyl]cyclopropylcarbamoyl}-3,9-diazabicyclo[3.3.1]non-6-en-3-yl)-2,3-dihydroxy-4-oxobutyric acid;

1:1-mixture of (rac.)-(2R*,3S*)-4-((1R*,5S*)-7-{4-[3-(2-bromo-5-fluorophenoxy)propyl]phenyl}6-{[2-(4-fluorophenyl)ethyl]cyclopropylcarbamoyl}-3,9-diazabicyclo[3.3.1]non-6-en-3-yl)-2,3-dihydroxy-4-oxobutyric acid and (rac.)-(2S*,3R*)-4-((1R*,5S*)-7-{4-[3-(2-bromo-5-fluorophenoxy)propyl]-phenyl}-6-{[2-(4-fluorophenyl)ethyl]cyclopropylcarbamoyl}-3,9-diazabicyclo-[3.3.1]non-6-en-3-yl)-2,3-dihydroxy-4-oxobutyric acid;

1:1-mixture of (rac.)-(2R*,3S*)-4-((1R*,5S*)-7-{4-[3-(2-bromo-5-fluorophenoxy)propyl]phenyl}-6-{[2-(2-methylphenyl)ethyl]cyclopropylcarbamoyl}-3,9-diazabicyclo[3.3.1]non-6-en-3-yl)-2,3-dihydroxy-4-oxobutyric acid and (rac.)-(2S*,3R*)-4-((1R*,5S*)-7-{4-[3-(2-bromo-5-fluorophenoxy)propyl]-phenyl}-6-{[2-(2-methylphenyl)ethyl]cyclopropylcarbamoyl}-3,9-diazabicyclo-[3.3.1]non-6-en-3-yl)-2,3-dihydroxy-4-oxobutyric acid;

1:1-mixture of (rac.)-(2R*,3S*)-4-((1R*,5S*)-7-{4-[3-(2-bromo-5-fluorophenoxy)propyl]phenyl}-6-{[2-(4-methylphenyl)ethyl]cyclopropylcarbamoyl}-3,9-diazabicyclo[3.3.1]non-6-en-3-yl)-2,3-dihydroxy acid and (rac.)-(2S*,3R*)-4-(1R*,5S*)-7-{4-[3-(2-bromo-5-fluorophenoxy)propyl]-phenyl}-6-{[2-(4-methylphenyl)ethyl]cyclopropylcarbamoyl}-3,9-diazabicyclo-[3.3.1]non-6-en-3-yl)-2,3-dihydroxyoxobutyric acid;

(rac.)-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid (2- chlorobenzyl)ethylamide;

(rac.)(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid cyclopropyl-(2-fluorobenzyl)amide;

(rac.)-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid cyclopropyl-(2-methylbenzyl)amide;

(rac.)-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid cyclopropyl-[2-(4-methoxyphenoxy)ethyl]amide;

(rac.)-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid cyclopropyl-[2-(3,4-dimethylphenoxy)ethyl]amide;

(rac.)-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid [2-(2-chlorophenyl)ethyl]cyclopropylamide;

(rac.)-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid [2-(2,3-difluorophenyl)ethyl]cyclopropylamide;

(rac.)-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid [2-(4-fluorophenyl)ethyl]cyclopropylamide;

(rac.)-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid [2-(2-methylphenyl)ethyl]cyclopropylamide;

(rac )-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid [2-(4-methylphenyl)ethyl]cyclopropylamide;

(rac.)-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid Cyclopropyl-(3,5-dimethoxybenzyl)amide;

1:1-mixture of (rac.)-(3R*)-5-{1R*,5S*)-7-{4-[3-(2-bromo-5-fluorophenoxy)-propyl]phenyl}-6-[(2-chlorobenzyl)ethylcarbamoyl]-3,9-diazabicyclo[3.3.1]non-6-en-3-yl}-3-hydroxy-5-oxopentanoic acid and (rac.)-(3S*)-5-{(1R*,5S*)-7-{4-[3-(2-bromo-5-fluorophenoxy)propyl]phenyl}-6-[(2-chlorobenzyl)ethylcarbamoyl]-3,9-diazabicyclo[3.3.1]non-6-en-3-yl}-3-hydroxy-5-oxopentanoic acid;

1:1-mixture of (rac.)-(3R*)-5-{(1R*,5S*)-7-{4-[3-(2-bromo-5-fluorophenoxy)-propyl]phenyl}-6-[cyclopropyl-(2-fluorobenzyl)carbamoyl]-3,9-diazabicyclo-[3.3.1]non-6-en-3-yl}-3-hydroxy-5-oxopentanoic acid and (rac.)-(3S*)-5-{(1R*,5S*)-7-{4-[3-(2-bromo-5-fluorophenoxy)propyl]phenyl}-6-[cyclopropyl-(2-fluorobenzyl)carbamoyl]-3,9-diazabicyclo[3.3.1]non-6-en-3-yl}-3-hydroxy-5- oxopentanoic acid;

1:1-mixture of (rac.)-(3R*)-5-{(1R*,5S*)-7-{4-[3-(2-bromo-5-fluorophenoxy)-propyl]phenyl}-6-[cyclopropyl-(3-trifluoromethylbenzyl)carbamoyl]-3,9-diazabicyclo[3.3.1]non-6-en-3-yl}-3-hydroxy-5-oxopentanoic acid and (rac.)-(3S*)-5-{(1R*,5S*)-7-{4-[3-(2-bromo-5-fluorophenoxy)propyl]phenyl}-6-[cyclopropyl-(3-trifluoromethylbenzyl)carbamoyl]-3,9-diazabicyclo[3.3.1]non-6-en-3-yl}-3-hydroxy-5-oxopentanoic acid;

1:1-mixture of (rac.)-(3R*)-5-{(1R*,5S*)-7-{4-[3-(2-bromo-5-fluorophenoxy)-propyl]phenyl}-6-[cyclopropyl-(2-methylbenzyl)carbamoyl]-3,9-diazabicyclo[3.3.1]non-6-en-3-yl}-3-hydroxy-5-oxopentanoic acid and (rac.)-(3S*)-5-{(1R*,5S*)-7-{4-[3-(2-bromo-5-fluorophenoxy)propyl]phenyl}-6-[cyclopropyl-(2-methylbenzyl)carbamoyl]-3,9-diazabicyclo[3.3.1]non-6-en-3-yl}-3-hydroxy-5-oxopentanoic acid;

1:1-mixture of (rac.)-(3R*)-5-(1R*,5S*)-7-{4-[3-(2-bromo-5-fluorophenoxy)-propyl]phenyl}-6-{cyclopropyl-[2-(4-methoxyphenoxy)ethyl]carbamoyl}-3,9-diazabicyclo[3.3.1]non-6-en-3-yl)-3-hydroxy-5-oxopentanoic acid and (rac.)-(3S*)-5-((1R*,5S*)-7-{4-[3-(2-bromo-5-fluorophenoxy)propyl]phenyl}-6-{cyclopropyl-[2-(4-methoxyphenoxy)ethyl]carbamoyl}-3,9-diazabicyclo[3.3.1]-non-6-en-3-yl)-3-hydroxy-5-oxopentanoic acid;

1:1-mixture of (rac.)-(3R*)-5-((1R*,5S*)-7-{4-[3-(2-bromo-5-fluorophenoxy)-propyl]phenyl}-6-{cyclopropyl-[2-(3-methylphenoxy)ethyl]carbamoyl}-3,9-diazabicyclo[3.3.1]non-6-en-3-yl)-3-hydroxy-5-oxopentanoic acid and (rac.)-(3S*)-5-((1R*,5S*)-7-{4-[3-(2-bromo-5-fluorophenoxy)propyl]phenyl}-6-{cyclopropyl-[2-(3-methylphenoxy)ethyl]carbamoyl}-3,9-diazabicyclo[3.3.1]non-6-en-3-yl)-3-hydroxy-5-oxopentanoic acid;

1:1-mixture of (rac.)-(3R*)-5-((1R*,5S*)-7-({4-[3-(2-bromo-5-fluorophenoxy)-propyl]phenyl}-6-{cyclopropyl-[2-(3,4-dimethylphenoxy)ethyl]carbamoyl}-3,9-diazabicyclo[3.3.1]non-6-en-3-yl)-3-hydroxy-5-oxopentanoic acid and (rac.)-(3S*)-5-((1R*,5S*)-7-{4-[3-(2-bromo-5-fluorophenoxy)propyl]phenyl}-6-{cyclopropyl-[2-(3,4-dimethylphenoxy)ethyl]carbamoyl}-3,9-diazabicyclo[3.3.1]-non-6-en-3-yl)-3-hydroxy-5-oxopentanoic acid;

1:1-mixture of (rac.)-(3R*)-5-[(1R*,5S*)-7-{4-[3-(2-bromo-5-fluorophenoxy)-propyl]phenyl}-6-(cyclopropylphenethylcarbamoyl)-3,9-diazabicyclo[3.3.1]non-6-en-3-yl]-3-hydroxy-5-oxopentanoic acid and (rac.)-(3R*)-5-[(1R*,5S*)-7-{4-[3-(2-bromo-5-fluorophenoxy)propyl]phenyl}-6-(cyclopropylphenethylcarbamoyl)-3,9-diazabicyclo[3.3.1]non-6-en-3-yl]-3-hydroxy-5-oxopentanoic acid;

1:1-mixture of (rac.)-(3R*)-5-((1R*,5S*)-7-{4-[3-(2-bromo-5-fluorophenoxy)-propyl]phenyl}-6-{[2-(2-chlorophenyl)ethyl]cyclopropylcarbamoyl}-3,9-diazabicyclo[3.3.1]non-6-en-3-yl)-3-hydroxy-5-oxopentanoic acid and (rac.)-(3R*)-5-((1R*,5S*)-7-{4-[3-(2-bromo-5-fluorophenoxy)propyl]phenyl}-6-{[2-(2-chlorophenyl)ethyl]cyclopropylcarbamoyl}-3,9-diazabicyclo[3.3.1]non-6-en-3-yl)-3-hydroxy-5oxopentanoic acid;

1:1-mixture of (rac.)-(3R*)-5-((1R*,5S*)-7-{4-[3-(2-bromo-5-fluorophenoxy)-propyl]phenyl}-6-{[2-(2,3-difluorophenyl)ethyl]cyclopropylcarbamoyl}-3,9-diazabicyclo[3.3.1]non-6-en-3-yl)-3-hydroxy-5-oxopentanoic acid and (rac.)-(3R*)-5-((1R*,5S*)-7-{4-[3-(2-bromo-5-fluorophenoxy)propyl]phenyl}-6-{[2-(2,3-difluorophenyl)ethyl]cyclopropylcarbamoyl}-3,9-diazabicyclo[3.3.1]-non-6-en-3-yl)-3-hydroxy-5-oxopentanoic acid;

1:1-mixture of (rac.)-(3R*)-5-(1R*,5S*)-7-{4-[3-(2-bromo-5-fluorophenoxy)-propyl]phenyl}-6-{[2-(4-fluorophenyl)ethyl]cyclopropylcarbamoyl}-3,9-diazabicyclo[3.3.1]non-6-en-3-yl)-3-hydroxy-5-oxopentanoic acid and (rac.)-(3R*)-5-((1R*,5S*)-7-{4-[3-(2-bromo-5-fluorophenoxy)propyl]phenyl}-6-{[2-(4-phenyl)ethyl]cyclopropylcarbamoyl}-3,9-diazabicyclo[3.3.1]non-6-en-3-yl)-3-hydroxy-5-oxopentanoic acid;

1:1-mixture of (rac.)-(3R*)-5-((1R*,5S*)-7-{4-[3-(2-bromo-5-fluorophenoxy)-propyl]phenyl}-6-{[2-(2-methylphenyl)ethyl]cyclopropylcarbamoyl}-3,9-diazabicyclo[3.3.1]non-6-en-3-yl)-3-hydroxy-5-oxopentanoic acid and (rac.)-(3R*)-5-((1R*,5S*)-7-{4-[3-(2-bromo-5-fluorophenoxy)propyl]phenyl}-6-{[2-(2-methylphenyl)ethyl]cyclopropylcarbamoyl}-3,9-diazabicyclo[3.3.1]non-6-en-3-yl)-3-hydroxy-5-oxopentanoic acid;

1:1-mixture of (rac.)-(3R*)-5-((1R*,5S*)-7-{4-[3-(2-bromo-5-fluorophenoxy)-propyl]phenyl}-6-{[2-(4-methylphenyl)ethyl]cyclopropylcarbamoyl}-3,9-diazabicyclo[3.3.1]non-6-en-3-yl)-3-hydroxy-5-oxopentanoic acid and (rac.)-(3R*)-5-((1R*,5S*)-7-{4-[3-(2-bromo-5-fluorophenoxy)propyl]phenyl}-6-{[2-(4-methylphenyl)ethyl]cyclopropylcarbamoyl}-3,9-diazabicyclo[3.3.1]non-6-en-3-yl)-3-hydroxy-5-oxopentanoic acid;

1:1-mixture of (rac.)-(3R*)-5-{(1R*,5S*)-7-{4-[3-(2-bromo-5-fluorophenoxy)-propyl]phenyl}-6-[cyclopropyl-(3,5-dimethoxybenzyl)carbamoyl]-3,9-diazabicyclo[3.3.1]non-6-en-3-yl}-3-hydroxy-5-oxopentanoic acid and (rac.)-(3S*)-5-{(1R*,5S*)-7-{4-[3-(2-bromo-5-fluorophenoxy)propyl]phenyl}-6-[cyclopropyl-(3,5-dimethoxybenzyl)carbamoyl]-3,9-diazabicyclo[3.3.1]non-6-en-3-yl}-3-hydroxy-5-oxopentanoic acid;

1:1-mixture of (rac.)-(3R*)-5-(1R*,5S*)-6-{cyclopropyl-[2-(2-hydroxyethyl)benzyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid and (rac.)-(3S*)-5-((1R*,5S*)-6-{cyclopropyl-[2-(2-hydroxyethyl)benzyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid;

(rac.)-(1R*,5S*)-3-acetyl-7-{4-[2-(2,3,5-trimethylphenoxy)ethyl]phenyl}-3,9-diazabicyclo[3.3.1]non-6-ene-6-carboxylic acid (2-chlorobenzyl)cyclopropylamide;

(rac.)-(1R*,5S*)-3-acetyl-7-{4-[2-(2,3,5-trimethylphenoxy)ethyl]phenyl}-3,9-diazabicyclo[3.3.1]non-6-ene-6-carboxylic acid (2-chlorobenzyl)ethylamide;

(rac.)-(1R*,5S*)-3-acetyl-7-{4-[2-(2,3,5-trimethylphenoxy)ethyl]phenyl}-3,9-diazabicyclo[3.3.1]non-6-ene-6-carboxylic acid (2-fluorobenzyl)cyclopropylamide;

(rac.)-(1R*,5S*)-3-acetyl-7-{4-[2-(2,3,5-trimethylphenoxy)ethyl]phenyl}-3,9-diazabicyclo[3.3.1]non-6-ene-6-carboxylic acid (3-trifluoromethylbenzyl)-cyclopropylamide;

(rac.)-(1R*,5S*)-3-acetyl-7-{4-[2-(2,3,5-trimethylphenoxy)ethyl]phenyl}-3,9-diazabicyclo[3.3.1]non-6-ene-6-carboxylic acid (2-methylbenzyl)cyclopropylamide;

(rac.)-(1R*,5S*)-3-acetyl-7-{4-[2-(2,3,5-trimethylphenoxy)ethyl]phenyl}-3,9-diazabicyclo[3.3.1]non-6-ene-6-carboxylic acid cyclopropyl-[2-(4-methoxyphenoxy)ethyl]amide;

(rac.)-5-(1R*,5S*)-6-(benzylcyclopropylcarbamoyl)-7-{4-[2-(2,3,5-trimethylphenoxy)ethyl]phenyl}-3,9-diazabicyclo[3.3.1]non-6-en-3-yl)-5-oxopentanoic acid;

(rac.)-5-((1R*,5S*)-6-[(2-chlorobenzyl)ethylcarbamoyl]-7-{4-[2-(2,3,5-trimethylphenoxy)ethyl]phenyl}-3,9-diazabicyclo[3.3.1]non-6-en-3-yl)-5-oxopentanoic acid;

(rac.)-5-((1R*,5S*)-6-[(2-fluorobenzyl)cyclopropylcarbamoyl]-7-{4-[2-(2,3,5-trimethylphenoxy)ethyl]phenyl}-3,9-diazabicyclo[3.3.1]non-6-en-3-yl)-5-oxopentanoic acid;

(rac.)-5-((1R*,5S*)-6-{cyclopropyl-[2-(4-methoxyphenoxy)ethyl]carbamoyl}-7-{4-[2-(2,3,5-trimethylphenoxy)ethyl]phenyl}-3,9-diazabicyclo[3.3.1]non-6-en-3-yl)-5-oxopentanoic acid;

(rac.)-5-((1R*,5S*)-6-{cyclopropyl-[2-(3-methoxyphenoxy)ethyl]carbamoyl}-7-{4-[2-(2,3,5-trimethylphenoxy)ethyl]phenyl}-3,9-diazabicyclo[3.3.1]non-6-en-3-yl)-5-oxopentanoic acid;

(rac.)-5-((1R*,5S*)-6-{cyclopropyl-[2-(3-methylphenoxy)ethyl]carbamoyl}-7-{4-[2-(2,3,5-trimethylphenoxy)ethyl]phenyl}-3,9-diazabicyclo[3.3.1]non-6-en-3-yl)-5-oxopentanoic acid;

(rac.)-5-((1R*,5S*)-6-[(2-chlorobenzyl)ethylcarbamoyl]-7-{4-[2-(2,3,5-trimethylphenoxy)ethyl]phenyl}-3,9-diazabicyclo[3.3.1]non-6-en-3-yl)-5-oxopentanoic acid methyl ester;

(rac.)-5-((1R*,5S*)-6-[cyclopropyl-(2-fluorobenzyl)carbamoyl]-7-{[2-(2,3,5-trimethylphenoxy)ethyl]phenyl}-3,9-diazabicyclo[3.3.1]non-6-en-3-yl)-5-oxopentanoic acid methyl ester;

(rac.)-5-((1R*,5S*)-6-[cyclopropyl-(2-methylbenzyl)carbamoyl]-7-{4-[2-(2,3,5-trimethylphenoxy)ethyl]phenyl}-3,9-diazabicyclo[3.3.1]non-6-en-3-yl)-5-oxopentanoic acid methyl ester;

(rac.)-5-((1R*,5S*)-6-[(2-chlorobenzyl)cyclopropylcarbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid;

(rac.)-5-((1R*,5S*)-6-(benzylcyclopropylcarbamoyl)-7-{4-[2-(2,3,5-trimethylphenoxy)ethyl]phenyl}-3,9-diazabicyclo[3.3.1]non-6-en-3-yl)-2,2-dimethyl-5-oxopentanoic acid;

(rac.)-5-((1R*,5S*)-6-[cyclopropyl-(2-methylbenzyl)carbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid;

1:1-mixture of (rac.)-(3R*)-4-((1R*,5S*)-6-[cyclopropyl(2-methylbenzyl)-carbamoyl]-7-{4-[2-(2,3,5-trimethylphenoxy)ethyl]phenyl}-3,9-diazabicyclo-[3.3.1]non-6-en-3-yl)-2,3-dihydroxy-4-oxobutyric acid and (rac.)-(3S*)-4-((1R*,5S*)-6-[cyclopropyl-(2-methylbenzyl)carbamoyl]-7-{4-[2-(2,3,5-trimethylphenoxy)ethyl]phenyl}-3,9-diazabicyclo-[3.3.1]non-6-en-3-yl)-2,3-dihydroxy-4-oxobutyric acid;

(rac.)-(1R*,5S*)-3-(4-carbamoylbutyryl)-7-{4-[2-(2,3,5-trimethylphenoxy)-ethyl]phenyl}-3,9-diazabicyclo[3.3.1]non-6-ene-6-carboxylic acid benzylcyclopropylamide;

(rac.)-(1R*,5S*)-3-(4-carbamoylbutyryl)-7-{4-[2-(2,3,5-trimethylphenoxy)-ethyl]phenyl}-3,9-diazabicyclo[3.3.1]non-6-ene-6-carboxylic acid (2-chlorobenzyl)ethylamide;

(rac.)-(1R*,5S*)-3-(4-carbamoylbutyryl)-7-{4-[2-(2,3,5-trimethylphenoxy)-ethyl]phenyl}-3,9-diazabicyclo[3.3.1]non-6-ene-6-carboxylic acid cyclopropyl-(2-fluorobenzyl)amide;

1:1-mixture of (1R,5S)-7-({4-[3-(2-bromo-5-fluorophenoxy)propyl]phenyl}-3-((2S,4R)-4-hydroxypyrrolidine-2-carbonyl)-3,9-diazabicyclo[3.3.1]non-6-ene-6-carboxylic acid cyclopropyl-(3,5-dimethoxybenzyl)amide and (1S,5R)-7-{4-[3-(2-bromo-5-fluorophenoxy)propyl]phenyl}-3-(2S,4R)-4-hydroxypyrrolidine-2-carbonyl)-3,9-diazabicyclo[3.3.1]non-6-ene-6-carboxylic acid cyclopropyl-(3,5-dimethoxybenzyl)amide;

(rac.)-5-{(1R*,5S*)-7-{4-[3-(2-bromo-5-fluorophenoxy)propyl]phenyl}-6-[(2-chlorobenzyl)cyclopropylcarbamoyl]-3,9-diazabicyclo[3.3.1]non-6-en-3-yl}-5-oxopentanoic acid methyl ester;

1:1-mixture of (rac.)-(3R*)-4-{(1R*,4S*)-7-{4-[3-(2-bromo-5-fluorophenoxy)-propyl]phenyl}-6-[(2-chlorobenzyl)cyclopropylcarbamoyl]-3,9-diazabicyclo-[3.3.1]non-6-en-3-yl}-2,3-dihydroxy-4-oxobutyric acid and (rac.)-(3S*)-4-{(1R*,5S*)-7-{4-[3-(2-bromo-5-fluorophenoxy)propyl]phenyl}-6-[(2-chlorobenzyl)-cyclopropylcarbamoyl]-3,9-diazabicyclo-[3.3.1]non-6-en-3-yl}-2,3-dihydroxy-4-oxobutyric acid;

(rac.)-5-((1R*,5S*)-6-(benzylcyclopropylcarbamoyl)-7-{4-[3-(2-bromo-5-fluorophenoxy)propyl]phenyl}-3,9-diazabicyclo[3.3.1]non-6-en-3-yl)-5-oxopentanoic acid;

1:1-mixture of (rac.)-(2R*,3S*)-4-((1R*,5S*)-6-(benzylcyclopropylcarbamoyl)-7-{([3-(2-bromo-5-fluorophenoxy)propyl]phenyl}-3,9-diazabicyclo[3.3.1]non-6-en-3-yl)-2,3-dihydroxy-4-oxobutyric acid and (rac.)-(2S*,3R*)-4-((1R*,5S*)-6-(benzylcyclopropylcarbamoyl)-7-{4-[3-(2-bromo-5-fluorophenoxy)propyl]-phenyl}-3,9-diazabicyclo[3.3.1]non-6-en-3-yl)-2,3-dihydroxy-4-oxobutyric acid;

(rac.)-(1R*,5S*)-7-{4-[3-(2-bromo-5-fluorophenoxy)propyl]phenyl}-3-(4-carbamoylbutyryl)-3,9-diazabicyclo[3.3.1]non-6-ene-6-carboxylic acid benzylcyclopropylamide;

1:1-mixture of (rac.)-5-{(1R*,5S*)-7-{4-[3-(2-bromo-5-fluorophenoxy)propyl]-phenyl}-6-[((2R*)-2-hydroxy-2-phenylethyl)methylcarbamoyl]-3,9-diazabicyclo-[3.3.1]non-6-en-3-yl}-5-oxopentanoic acid and (rac.)-5-{(5R*,5S*)-7-{4-[3-(2-bromo-5-fluorophenoxy)propylphenyl}-6-[((2S*)-2-hydroxy-2-phenylethyl)-methylcarbamoyl]-3,9-diazabicyclo-[3.3.1]non-6-en-3-yl}-5-oxopentanoic acid;

1:1-mixture of (rac.)-5-{(1R*,5S*)-7-{4-[3-(2-bromo-5-fluorophenoxy)propyl]-phenyl}-6-[((2R*)-2-hydroxy-2-phenylethyl)methylcarbamoyl]-3,9-diazabicyclo-[3.3.1]non-6-en-3-yl}-5-oxopentanoic acid methyl ester and (rac.)-5-((1R*,5S*)-7-{4-[3-(2-bromo-5-fluorophenoxy)propyl]phenyl}-6-[((2S*)-2-hydroxy-2-phenylethyl)methylcarbamoyl]-3,9-diazabicyclo-[3.3.1]non-6-en-3-yl}-5-oxopentanoic acid methyl ester;

1:1-mixture of (rac.)-5-{(1R*,5S*)-7-{4-[3-(2-bromo-5-fluorophenoxy)propyl]-phenyl}-6-[((2R*)-2-hydroxy-2-phenylethyl)methylcarbamoyl]-3,9-diazabicyclo-[3.3.3]non-6-en-3-yl}-2,2-dimethyl-5-oxopentanoic acid and (rac.)-5-{(1R*,5S*)-7-{4-[3-(2-bromo-5-fluorophenoxy)propyl]phenyl}-6-[((2S*)-2-hydroxy-2-phenylethyl)methylcarbamoyl]-3,9-diazabicyclo-[3.3.1]non-6-en-3-yl}-2,2-dimethyl-5-oxopentanoic acid;

1:1-mixture of (rac.)-(1R*,5S*)-7-{4-[3-(2-bromo-5-fluorophenoxy)propyl]-phenyl}-3-(4-carbamoylbutyryl)-3,9-diazabicyclo[3.3.1]non-6-ene-6-carboxylic acid ((2R*)-2-hydroxy-2-phenylethyl)methylamide and (rac.)-(1R*,5S*)-7-{4-[3-(2-bromo-5-fluorophenoxy)propyl]-phenyl}-3-(4-carbamoylbutyryl)-3,9-diazabicyclo[3.3.1]non-6-ene-6-carboxylic acid ((2R*)-2-hydroxy-2-phenylethyl)-methylamide;

1:1-mixture of (rac.)-(3R*)-5-{(1R*,5S*)-7-{4-[3-(2-bromo-5-fluorophenoxy)-propyl]phenyl}-6-[(2-chlorobenzyl)cyclopropylcarbamoyl]-3,9-diazabicyclo-[3.3.1]non-6-en-3-yl}-3-hydroxy-5-oxopentanoic acid and (rac.)-(3S*)-5-{(1R*,5S*)-7-{4-[3-(2-bromo-5-fluorophenoxy)propyl]phenyl}-6-[(2-chlorobenzyl)-cyclopropylcarbamoyl]-3,9-diazabicyclo[3.3.1]non-6-en-3-yl}-3-hydroxy-5-oxopentanoic acid;

1:1-mixture of (rac.)-(3R*)-5-((1R*,5S*)-6-(benzylcyclopropylcarbamoyl)-7-{4-[3-(2-bromo-5-fluorophenoxy)propyl]phenyl}-3,9-diazabicyclo[3.3.1]non-6-en-3-yl)-3-hydroxy-5-oxopentanoic acid and (rac.)-(3S*)-5-((1R*, 5S*)-6-(benzylcyclopropylcarbamoyl)-7-{4-[3-(2-bromo-5-fluorophenoxy)propyl]-phenyl}-3,9-diazabicyclo[3.3.1]non-6-en-3-yl)-3-hydroxy-5-oxopentanoic acid;

(rac.)-(1R*,5S*)-7-{4-[2-(2-chloro-4,5-dimethylphenoxy)ethoxy]phenyl}-3,9-diazabicyclo[3.3.1]non-6-ene-6-carboxylic acid [2-(2-chlorophenyl)ethyl]-cyclopropylamide;

(rac.)-(1R*,5S*)-7-{4-[2-(2-chloro-4,5-dimethylphenoxy)ethoxy]phenyl}-3,9-diazabicyclo[3.3.1]non-6-ene-6-carboxylic acid cyclopropyl-(3,5-dimethoxybenzyl)amide;

(rac.)-(1R*,5S*)-7-{4-[2-(2-chloro-4,5-dimethylphenoxy)ethoxy]phenyl}-3,9-diazabicyclo[3.3.1]non-6-ene-6-carboxylic acid cyclopropyl-(p-toluyl-ethyl)amide;

(rac.)-(1R*,5S*)-3-acetyl-7-{4-[2-(4-bromophenoxy)ethoxy]phenyl}-3,9-diazabicyclo[3.3.1]non-6-ene-6-carboxylic acid (2-chlorobenzyl)cyclopropylamide;

(rac.)-(1R*,5S*)-3-acetyl-7-{4-[2-(4-bromophenoxy)ethoxy]phenyl}-3,9-diazabicyclo[3.3.1]non-6-ene-6-carboxylic acid cyclopropyl-(3,5-dimethoxybenzyl)amide;

(rac.)-5-{(1R*,5S*)-7-{4-[2-(4-bromophenoxy)ethoxy]phenyl}-6-[(2-chlorobenzyl)cyclopropylcarbamoyl]-3,9-diazabicyclo[3.3.1]non-6-en-3-yl}-5-oxopentanoic acid;

(rac.)-5-((1R*,5S*)-6-(benzylcyclopropylcarbamoyl)-7-{4-[2-(4-bromophenoxy)-ethoxy]phenyl}-3,9-diazabicyclo[3.3.1]non-6-en-3-yl)-5-oxopentanoic acid;

(rac.)-5-{(1R*,5S*)-7-{4-[2-(4-bromophenoxy)ethoxy]phenyl}-6-[cyclopropyl-(2-fluorobenzyl)carbamoyl]-3,9-diazabicyclo[3.3.1]non-6-en-3-yl}-5-oxopentanoic acid;

(rac.)-5-{(1R*,5S*)-7-{4-[2-(4-bromophenoxy)ethoxy]phenyl}-6-[cyclopropyl-(3-trifluoromethylbenzyl)carbamoyl]-3,9-diazabicyclo[3.3.1]non-6-en-3-yl}-5-oxopentanoic acid;

(rac.)-5-{(1R*,5S*)-7-{4-[2-(4-bromophenoxy)ethoxy]phenyl}-6-[cyclopropyl-(2-methylbenzyl)carbamoyl]-3,9-diazabicyclo[3.3.1]non-6-en-3-yl}-5-oxopentanoic acid;

(rac.)-5-{(1R*,5S*)-7-{4-[2-(4-bromophenoxy)ethoxy]phenyl}-6-{cyclopropyl-[2-(3,4-dimethylphenoxy)ethyl]carbamoyl}-3,9-diazabicyclo[3.3.1]non-6-en-3-yl}-5-oxopentanoic acid;

(rac.)-5-{(1R*,5S*)-7-{4-[2-(4-bromophenoxy)ethoxy]phenyl}-6-{[2-(2-chlorophenyl)ethyl]cyclopropylcarbamoyl}-3,9-diazabicyclo[3.3.1]non-6-en-3-yl}-5-oxopentanoic acid;

(rac.)-5-{(1R*,5S*)-7-{4-[2-(4-bromophenoxy)ethoxy]phenyl}-6-{cyclopropyl-[2-(4-fluorophenyl)ethyl]carbamoyl}-3,9-diazabicyclo[3.3.1]non-6-en-3-yl}-5-oxopentanoic acid;

(rac.)-5-{(1R*,5S*)-7-{4-[2-(4-bromophenoxy)ethoxy]phenyl}-6-{cyclopropyl-[2-(2-methylphenyl)ethyl]carbamoyl}-3,9-diazabicyclo[3.3.1]non-6-en-3-yl}-5-oxopentanoic acid;

(rac.)-5-{(1R*,5S*)-7-{4-[2-(4-bromophenoxy)ethoxy]phenyl}-6-{cyclopropyl-[2-(4-methylphenyl)ethyl]carbamoyl}-3,9-diazabicyclo[3.3.1]non-6-en-3-yl}-5-oxopentanoic acid;

(rac.)-5-{(1R*,5S*)-7-{4-[2-(4-bromophenoxy)ethoxy]phenyl}-6-[cyclopropyl-(3,5-dimethoxybenzyl)carbamoyl]-3,9-diazabicyclo[3.3.1]non-6-en-3-yl}-5-oxopentanoic acid;

(rac.)-5-{(1R*,5S*)-7-{4-[2-(4-bromophenoxy)ethoxy]phenyl}-6-[cyclopropyl-(2-fluorobenzyl)carbamoyl]-3,9-diazabicyclo[3.3.1]non-6-en-3-yl}-2,2-dimethyl-5-oxopentanoic acid;

(rac.)-5-((1R*,5S*)-7-{4-[2-(4-bromophenoxy)ethoxy]phenyl}-6-{[2-chlorophenyl)ethyl]cyclopropylcarbamoyl}-3,9-diazabicyclo[3.3.1]non-6-en-3-yl)-2,2-dimethyl-5-oxopentanoic acid;

(rac.)-5-((1R*,5S*)-7-{4-[2-(4-bromophenoxy)ethoxy]phenyl}-6-{cyclopropyl-[2-(2,3-difluorophenyl)ethyl]carbamoyl}-3,9-diazabicyclo[3.3.1]non-6-en-3-yl)-2,2-dimethyl-5-oxopentanoic acid;

(rac.)-5-((1R*,5S*)-7-{4-[2-(4-bromophenoxy)ethoxy]phenyl}-6-{cyclopropyl-[2-(2-methylphenyl)ethyl]carbamoyl}-3,9-diazabicyclo[3.3.1]non-6-en-3-yl)-2,2-dimethyl-5-oxopentanoic acid;

(rac.)-5(1R*,5S*)-7-{4-[2-(4-bromophenoxy)ethoxy]phenyl}-6-{cyclopropyl-[2-(4-methylphenyl)ethyl]carbamoyl}-3,9-diazabicyclo[3.3.1]non-6-en-3-yl)-2,2-dimethyl-5-oxopentanoic acid;

(rac.)-5-{(1R*,5S*)-7-{4-[2-(4-bromophenoxy)ethoxy]phenyl}-6[cyclopropyl-(3,5-dimethoxybenzyl)carbamoyl]-3,9-diazabicyclo[3.3.1]non-6-en-3-yl}-2,2-dimethyl-5-oxopentanoic acid;

(rac.)-(1R*,5S*)-7-{4-[2-(4-bromophenoxy)ethoxy]phenyl}-3-(4-carbamoylbutyryl)-3,9-diazabicyclo[3.3.1]non-6-ene-6-carboxylic acid benzylcyclopropylamide;

(rac.)-(1R*,5S*)-7-{4-[2-(4-bromophenoxy)ethoxy]phenyl}-3-(4-carbamoylbutyryl)-3,9-diazabicyclo[3.3.1]non-6-ene-6-carboxylic acid (2-chlorobenzyl)-ethylamide;

(rac.)-(1R*,5S*)-7-{4-[2-(4-bromophenoxy)ethoxy]phenyl}-3-(4-carbamoylbutyryl)-3,9-diazabicyclo[3.3.1]non-6-ene-6-carboxylic acid cyclopropyl-(2-fluorobenzyl)amide;

(rac.)-(1R*,5S*)-7-{4-[2-(4-bromophenoxy)ethoxy]phenyl}-3-(4-carbamoylbutyryl)-3,9-diazabicyclo[3.3.1]non-6-ene-6-carboxylic acid cyclopropyl-[2-(4-methoxyphenoxy)ethyl]amide;

(rac.)-(1R*,5S*)-7-{4-[2-(4-bromophenoxy)ethoxy]phenyl}-3-(4-carbamoylbutyryl)-3,9-diazabicyclo[3.3.1]non-6-ene-6-carboxylic acid [2-(2-chlorophenyl)-ethyl]cyclopropylamide;

(rac.)-(1R*,5S*)-7-{4-[2-(4-bromophenoxy)ethoxy]phenyl}-3-(4-carbamoylbutyryl)-3,9-diazabicyclo[3.3.1]non-6-ene-6-carboxylic acid cyclopropyl-(3,5-dimethoxybenzyl)amide;

(rac.)-(1R*,5S*)-7-{4-[2-(4-bromophenoxy)ethoxy]phenyl}-3-(4-carbamoylbutyryl)-3,9-diazabicyclo[3.3.1]non-6-ene-6-carboxylic acid cyclopropyl-[2-(2-hydroxyethyl)benzyl]amide;

(rac.)-(1R*,5S*)-7-{4-[2-(2-chloro-4,5-dimethylphenoxy)ethoxy]phenyl}-3-formyl-3,9-diazabicyclo[3.3.1]non-6-ene-6-carboxylic acid (2-chlorobenzyl)-ethylamide;

(rac.)-(1R*,5S*)-7-{4-[2-(2-chloro-4,5-dimethylphenoxy)ethoxy]phenyl}-3-formyl-3,9-diazabicyclo[3.3.1]non-6-ene-6-carboxylic acid cyclopropyl-(2-o-tolylethyl)amide;

(rac.)-(1R*,5S*)-7-{4-[2-(2-chloro-4,5-dimethylphenoxy)ethoxy]phenyl}-3-formyl-3,9-diazabicyclo[3.3.1]non-6-ene-6-carboxylic acid cyclopropyl-(3,5-dimethoxybenzyl)amide;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid (2-chlorobenzyl)-ethylamide;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(2-fluorobenzyl)amide;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(2-methylbenzyl) amide;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(3,5-dimethoxybenzyl)amide;

(rac.)-(1R*,5S*)-3-acetyl-7-{4-[2-(2-chloro-4,5-diethylphenoxy)ethoxy]-phenyl}-3,9-diazabicyclo[3.3.1]non-6-ene-6-carboxylic acid cyclopropyl-(2-p-tolylethyl)amide;

(rac.)-5-((1R*,5)-6-[(2-chlorobenzyl)ethylcarbamoyl]-7-{4-[2-(2-chloro-4,5-dimethylphenoxy)ethoxy]phenyl}-3,9-diazabicyclo[3.3.1]non-6-en-3-yl)-5-oxopentanoic acid;

(rac.)-5-{(1R*,5S*)-7-{4-[2-(2-chloro-4,5-dimethylphenoxy)ethoxy]phenyl}-6-[cyclopropyl-(2-fluorobenzyl)carbamoyl]-3,9-diazabicyclo[3.3.1]non-6-en-3-yl}-5-oxopentanoic acid;

(rac.)-5-{(1R*,5S*)-7-{4-[2-(2-chloro-4,5-dimethylphenoxy)ethoxy]phenyl}-6-[cyclopropyl-(3-trifluoromethylbenzyl)carbamoyl]-3,9-diazabicyclo[3.3.1]non-6-en-3-yl}-5-oxopentanoic acid;

(rac.)-5-((1R*,5S*)-7-{4-[2-(2-chloro-4,5-dimethylphenoxy)ethoxy]phenyl}-6-{cyclopropyl-[2-(4-methoxyphenoxy)ethyl]carbamoyl}-3,9-diazabicyclo[3.3.1]-non-6-en-3-yl)-5-oxopentanoic acid;

(rac.)-5-((1R*,5S*)-7-{4-[2-(2-chloro-4,5-dimethylphenoxy)ethoxy]phenyl}-6-{cyclopropyl-[2-(3-methoxyphenoxy)ethyl]carbamoyl}-3,9-diazabicyclo[3.3.1]-non-6-en-3-yl)-5-oxopentanoic acid;

(rac.)-5-((1R*,5S*)-7-{4-[2-(2-chloro-4,5-dimethylphenoxy)ethoxy]phenyl}-6-{cyclopropyl-[2-(3-methylphenoxy)ethyl]carbamoyl}-3,9-diazabicyclo[3.3.1]-non-6-en-3-yl)-5-oxopentanoic acid;

(rac.)-5-[(1R*,5S*)-7-{4-[2-(2-chloro-4,5-dimethylphenoxy)ethoxy]phenyl}-6-(cyclopropylphenethylcarbamoyl)-3,9-diazabicyclo[3.3.1]non-6-en-3-yl]-5-oxopentanoic acid;

(rac.)-5-((1R*,5S*)-7-{4-[2-(2-chloro-4,5-dimethylphenoxy)ethoxy]phenyl}-6-{[2-(2-chlorophenyl)ethyl]cyclopropylcarbamoyl}-3,9-diazabicyclo[3.3.1]non-6-en-3-yl)-5-oxopentanoic acid;

(rac.)-5-((1R*,5S*)-7-{4-[2-(2-chloro-4,5-dimethylphenoxy)ethoxy]phenyl}-6-{cyclopropyl-[2-(2,3-difluorophenyl)ethyl]carbamoyl}-3,9-diazabicyclo[3.3.1]-non-6-en-3-yl)-5-oxopentanoic acid;

(rac.)-5-((1R*,5S*)-7-{4-[2-(2-chloro-4,5-dimethylphenoxy)ethoxy]phenyl}-6-{cyclopropyl-[2-(4-fluorophenyl)ethyl]carbamoyl}-3,9-diazabicyclo[3.3.1]-non-6-en-3-yl)-5-oxopentanoic acid;

(rac.)-5-((1R*,5S*)-7-{4-[2-(2-chloro-4,5-dimethylphenoxy)ethoxy]phenyl}-6-{cyclopropyl-[2-(2-methylphenyl)ethyl]carbamoyl}-3,9-diazabicyclo[3.3.1]-non-6-en-3-yl)-5-oxopentanoic acid;

(rac.)-5-((1R*,5S*)-7-{4-[2-(2-chloro-4,5-dimethylphenoxy)ethoxy]phenyl}-6-{cyclopropyl-[2-(4-methylphenyl)ethyl]carbamoyl}-3,9-diazabicyclo[3.3.1]-non-6-en-3-yl)-5-oxopentanoic acid;

(rac.)-5-((1R*,5S*)-6-[(2-chlorobenzyl)cyclopropylcarbamoyl]-7-{4-[2-(2-chloro-4,5-dimethylphenoxy)ethoxy]phenyl}-3,9-diazabicyclo[3.3.1]non-6-en-3-yl)-5-oxopentanoic acid methyl ester;

(rac.)-5-((1R*,5S*)-6-[(2-chlorobenzyl)ethylcarbamoyl]-7-{4-[2-(2-chloro-4,5-dimethylphenoxy)ethoxy]phenyl}-3,9-diazabicyclo[3.3.1]non-6-en-3-yl)-5-oxopentanoic acid methyl ester;

(rac.)-5-{(1R*,5S*)-7-{4-[2-(2-chloro-4,5-dimethylphenoxy)ethoxy]phenyl}-6-[cyclopropyl-(2-fluorobenzyl)carbamoyl]-3,9-diazabicyclo[3.3.1]non-6-en-3-yl}-7-oxopentanoic acid methyl ester;

(rac.)-5-{(1R*,5S*)-7-{4-[2-(2-chloro-4,5-dimethylphenoxy)ethoxy]phenyl}-6-[cyclopropyl-(2-methylbenzyl)carbamoyl]-3,9-diazabicyclo[3.3.1]non-6-en-3-yl}-5-oxopentanoic acid methyl ester;

(rac.)-5-{(1R*,5S*)-7-{4-[2-(2-chloro-4,5-dimethylphenoxy)ethoxy]phenyl}-6-[cyclopropyl-(3-trifluoromethylbenzyl)carbamoyl]-3,9-diazabicyclo[3.3.1]non-6-en-3-yl}-5-oxopentanoic acid methyl ester;

(rac.)-5-[(1R*,5S*)-7-{4-[2-(2-chloro-4,5-dimethylphenoxy)ethoxy]phenyl}-6-(cyclopropylphenethylcarbamoyl)-3,9-diazabicyclo[3.3.1]non-6-en-3-yl]-5-oxopentanoic acid methyl ester;

(rac.)-5-((1R*,5S*)-7-{4-[2-(2-chloro-4,5-dimethylphenoxy)ethoxy]phenyl}-6-{[2-(2-chlorophenyl)ethyl]cyclopropylcarbamoyl}-3,9-diazabicyclo[3.3.1]non-6-en-3-yl)-5-oxopentanoic acid methyl ester;

(rac.)-5-((1R*,5S*)-7-{4-[2-(2-chloro-4,5-dimethylphenoxy)ethoxy]phenyl}-6-{[2-(2,3-difluorophenyl)ethyl]cyclopropylcarbamoyl}-3,9-diazabicyclo[3.3.1]non-6-en-3-yl)-5-oxopentanoic acid methyl ester;

(rac.)-5-((1R*,5S*)-7-{4-[2-(2-chloro-4,5-dimethylphenoxy)ethoxy]phenyl}-6-{[2-(4-fluorophenyl)ethyl]cyclopropylcarbamoyl}-3,9-diazabicyclo[3.3.1]non-6-en-3-yl)-5-oxopentanoic acid methyl ester;

(rac.)-5-((1R*,5S*)-7-{4-[2-(2-chloro-4,5-dimethylphenoxy)ethoxy]phenyl}-6-{[2-(2-methylphenyl)ethyl]cyclopropylcarbamoyl}-3,9-diazabicyclo[3.3.1]non-6-en-3-yl)-5-oxopentanoic acid methyl ester;

(rac.)-5-((1R*,5S*)-7-{4-[2-(2-chloro-4,5-dimethylphenoxy)ethoxy]phenyl}-6-{[2-(4-methylphenyl)ethyl]cyclopropylcarbamoyl}-3,9-diazabicyclo[3.3.1]non-6-en-3-yl)-5-oxopentanoic acid methyl ester;

(rac.)-5-{(1R*,5S*)-7-{4-[2-(2-chloro-4,5-dimethylphenoxy)ethoxy]phenyl}-6-[cyclopropyl-(3,5-dimethoxybenzyl)carbamoyl]-3,9-diazabicyclo[3.3.1]non-6-en-3-yl}-5-oxopentanoic acid methyl ester;

(rac.)-5-((1R*,5S*)-6-(benzylcyclopropylcarbamoyl)-7-{4-[2-(2-chloro-4,5-dimethylphenoxy)ethoxy]phenyl}-3,9-diazabicyclo[3.3.1]non-6-en-3-yl)-2,2-dimethyl-5-oxopentanoic acid;

(rac.)-5-{(1R*,5S*)-7-{4-[2-(2-chloro-4,5-dimethylphenoxy)ethoxy]phenyl}-6-[cyclopropyl-(2-methylbenzyl)carbamoyl]-3,9-diazabicyclo[3.3.1]non-6-en-3-yl}-2,2-dimethyl-5-oxopentanoic acid;

(rac.)-5-((1R*,5S*)-7-{4-[2-(2-chloro-4,5-dimethylphenoxy)ethoxy]phenyl}-6-{cyclopropyl-[2-(3,4-dimethylphenoxy)ethyl]carbamoyl}-3,9-diazabicyclo[3.3.1]-non-6-en-3-yl)-2,2-dimethyl-5-oxopentanoic acid;

(rac.)-5-[(1R*,5S*)-7-{4-[2-(2-chloro-4,5-dimethylphenoxy)ethoxy]phenyl}-6-(cyclopropylphenethylcarbamoyl)-3,9-diazabicyclo[3.3.1]non-6-en-3-yl]-2,2-dimethyl-5-oxopentanoic acid;

(rac.)-5-((1R*,5S*)-7-{4-[2-(2-chloro-4,5-dimethylphenoxy)ethoxy]phenyl}-6-{[2-(2-chlorophenyl)ethyl]cyclopropylcarbamoyl}-3,9-diazabicyclo[3.3.1]non-6-en-3-yl)-2,2-dimethyl-5-oxopentanoic acid;

(rac.)-5-((1R*,5S*)-7-{4-[2-(2-chloro-4,5-dimethylphenoxy)ethoxy]phenyl}-6-{[2-(2,3-difluorophenyl)ethyl]cyclopropylcarbamoyl}-3,9-diazabicyclo[3.3.1]non-6-en-3-yl)-2,2-dimethyl-5-oxopentanoic acid;

(rac.)-5-((1R*,5S*)-7-{4-[2-(2-chloro-4,5-dimethylphenoxy)ethoxy]phenyl}-6-{[2-(4-fluorophenyl)ethyl]cyclopropylcarbamoyl}-3,9-diazabicyclo[3.3.1]non-6-en-3-yl)-2,2-dimethyl-5-oxopentanoic acid;

(rac.)-5-((1R*,5S*)-7-{4-[2-(2-chloro-4,5-dimethylphenoxy)ethoxy]phenyl}-6-{[2-(2-methylphenyl)ethyl]cyclopropylcarbamoyl}-3,9-diazabicyclo[3.3.1]non-6-en-3-yl)-2,2-dimethyl-5-oxopentanoic acid;

(rac.)-5-((1R*,5S*)-7-{4-[2-(2-chloro-4,5-dimethylphenoxy)ethoxy]phenyl}-6-{[2-(4-methylphenyl)ethyl]cyclopropylcarbamoyl}-3,9-diazabicyclo[3.3.1]non-6-en-3-yl)-2,2-dimethyl-5-oxopentanoic acid;

(rac.)-5-{(1R*,5S*)-7-{4-[2-(2-chloro-4,5-dimethylphenoxy)ethoxy]phenyl}-6-[cyclopropyl-(3,5-dimethoxybenzyl)carbamoyl]-3,9-diazabicyclo[3.3.1]non-6-en-3-yl}-2,2-dimethyl-5-oxopentanoic acid;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-carboxylic acid (2-chlorobenzyl)cyclopropylamide;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-carboxylic acid benzylcyclopropylamide;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-carboxylic acid (2-chlorobenzyl)ethylamide;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-(2-fluorobenzyl)amide;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-(3-trifluoromethylbenzyl)amide;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-caxboxylic acid cyclopropyl-(2-methylbenzyl)amide;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-[2-(4-methoxyphenoxy)ethyl]amide;

(rac.)-(1R*,5S*)-3-(4-carbamoylbutyryl)-7-{4-[2-(2-chloro-4,5-dimethylphenoxy)ethoxy]phenyl)-3,9-diazabicyclo[3.3.1]non-6-ene-6-carboxylic acid cyclopropylphenethylamide;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-carboxylic acid [2-(2-chlorophenyl)ethyl]cyclopropylamide;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-[2-(2,3-difluorophenyl)ethyl]amide;

(rac.)-(1R*,5S*)-3-(4-carbamoylbutyryl)-7-{([2-(2-chloro-4,5-dimethylphenoxy)ethoxy]phenyl}-3,9-diazabicyclo[3.3.1]non-6-ene-6-carboxylic acid cyclopropyl-[2-(4-fluorophenyl)ethylamide;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-(2-o-tolylethyl)amide;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-(2-p-tolylethyl)amide;

(rac.)-(1R*,5S*)-3-(4-carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-(3,5-dimethoxybenzyl)amide;

1:1-mixture of (rac.)-(3R*)-5-((1R*,5S*)-6-[(2-chlorobenzyl)cyclopropylcarbamoyl]-7-{[2-(2-chloro-4,5-dimethylphenoxy)ethoxy]phenyl}-3,9-diazabicyclo[3.3.1]non-6-en-3-yl)-3-hydroxy-5-oxopentanoic acid and (rac.)-(3S*)-5-((1R*,5S*)-6-[(2-chlorobenzyl)cyclopropylcarbamoyl]-7-{4-[2-(2-chloro-4,5-dimethylphenoxy)ethoxy]phenyl}-3,9-diazabicyclo[3.3.1]non-6-en-3-yl)-3-hydroxy-5-oxopentanoic acid;

1:1-mixture of (rac.)-(3R*)-5-((1R*,5S*)-6-[(2-chlorobenzyl)ethylcarbamoyl]-7-{4-[2-(2-chloro-4,5-dimethylphenoxy)ethoxy]phenyl}-3,9-diazabicyclo[3.3.1]-non-6-en-3-yl)-3-hydroxy-5-oxopentanoic acid and (rac.)-(3S*)-5-((1R*,5S*)-6-[(2-chlorobenzyl)ethylcarbamoyl]-7-{4-[2-(2-chloro-4,5-dimethylphenoxy)-ethoxy]phenyl}-3,9-diazabicyclo[3.3.1]-non-6-en-3-yl)-3-hydroxy-5-oxopentanoic acid;

1:1-mixture of (rac.)-(3R*)-5-{(1R*,5S*)-7-{4-[2-(2-chloro-4,5-dimethylphenoxy)ethoxy]phenyl}-6-[cyclopropyl-(2-fluorobenzyl)carbamoyl]-3,9-diazabicyclo[3.3.1]non-6-en-3-yl}-3-hydroxy-5-oxopentanoic acid and (rac.)-(3S*)-5-{(1R*,5S*)-7-{4-[2-(2-chloro-4,5-dimethylphenoxy)ethoxy]phenyl}-6-[cyclopropyl-(2-fluorobenzyl)carbamoyl]-3,9-diazabicyclo[3.3.1]non-6-en-3-yl}-3-hydroxy-5-oxopentanoic acid;

1:1-mixture of (rac.)-(3R*)-5-((1R*,5S*)-7-{4-[2-(2-chloro-4,5-dimethylphenoxy)ethoxy]phenyl}-6-[cyclopropyl-(3-trifluoromethylbenzyl)carbamoyl]-3,9-diazabicyclo[3.3.1]non-6-en-3-yl}-3-hydroxy-5-oxopentanoic acid and (rac.)-(3S*)-5-{(1R*,5S*)-7-{4-[2-(2-chloro-4,5-dimethylphenoxy)ethoxy]-phenyl}-6-[cyclopropyl-(3-trifluormethylobenzyl)carbamoyl]-3,9-diazabicycl-o[3.3.1]non-6-en-3-yl}-3-hydroxy-5-oxopentanoic acid;

1:1-mixture of (rac.)-(3R*)-5-((1R*,5S*)-7-{4-[2-(2-chloro-4,5-dimethylphenoxy)ethoxy]phenyl}-6-{cyclopropyl-[2-(4-methoxyphenoxy)ethyl]-carbamoyl]-3,9-diazabicyclo[3.3.1]non-6-en-3-yl}3-hydroxy-5-oxopentanoic acid and (rac.)-(3S*)-5-((1R*,5S*)-7-{4-[2-(2-chloro-4,5-dimethylphenoxy)-ethoxy]phenyl}-6-{cyclopropyl-[2-(4-methoxyphenoxy)ethyl]carbamoyl}-3,9-diazabicyclo[3.3.1]non-6-en-3-yl)-3-hydroxy-5-oxopentanoic acid;

1:1-mixture of (rac.)-(3R*)-5-[(1R*,5S*)-7-{4-[2-(2-chloro-4,5-dimethylphenoxy)ethoxy]phenyl}-6-(cyclopropylphenethylcarbamoyl)-3,9-diazabicyclo-[3.3.1]non-6-en-3-yl]-3-hydroxy-5-oxopentanoic acid and (rac.)-(3S*)-5-[(1R*,5S*)-7-{4-[2-(2-chloro-4,5-dimethylphenoxy)ethoxy]phenyl}-6-(cyclopropylphenethylcarbamoyl)-3,9-diazabicyclo-[3.3.1]non-6-en-3-yl]-3-hydroxy-5-oxopentanoic acid;

1:1-mixture of (rac.)-(3R*)-5-((1R*,5S*)-7-{4-[2-(2-chloro-4,5-dimethylphenoxy)ethoxy]phenyl}-6-{[2-(2-chlorophenyl)ethyl]cyclopropylcarbamoyl}-3,9-diazabicyclo[3.3.1]non-6-en-3-yl)-3-hydroxy-5-oxopentanoic acid and (rac.)-(3R*)-5-((1R*,5S*)-7-{4-[2-(2-chloro-4,5-dimethylphenoxy)ethoxy]phenyl}-6-{[2-(2-chlorophenyl)ethyl]cyclopropylcarbamoyl}-3,9-diazabicyclo[3.3.1]non-6-en-3-yl)-3-hydroxy-5-oxopentanoic acid;

1:1-mixture of (rac.)-(3R*)-5-((1R*,5S*)-7-{4-[2-(2-chloro-4,5-dimethylphenoxy)ethoxy]phenyl}-6-{cyclopropyl-[2-(2,3-difluorophenyl)ethyl]-carbamoyl}-3,9-diazabicyclo[3.3.1]non-6-en-3-yl)-3-hydroxy-5-oxopentanoic acid and (rac.)-(3S*)-5-((1R*,5S*)-7-{4-[2-(2-chloro-4,5-dimethylphenoxy)-ethoxy]phenyl}-6-{cyclopropyl-[2-(2, 3-difluorophenyl)ethyl]carbamoyl}-3,9-diazabicyclo [3.3.1]non-6-en-3-yl)-3-hydroxy-5-oxopentanoic acid;
1:1-mixture of (rac.)-(3R*)-5-((1R*,5S*)-7-{4-[2-(2-chloro-4,5-dimethylphenoxy)ethoxy]phenyl}-6-{cyclopropyl-[2-(4-fluorophenyl)ethyl]carbamoyl}-3,9-diazabicyclo [3.3.1]non-6-en-3-yl)-3-hydroxy-5-oxopentanoic acid and (rac.)-(3S*)-5-((1R*,5S*)-7-{4-[2-(2-chloro-4,5-dimethylphenoxy)ethoxy]phenyl}-6-{cyclopropyl-[2-(4-fluorophenyl)ethyl]carbamoyl}-3,9-diazabicyclo[3.3.1] non-6-en-3-yl)-3-hydroxy-5-oxopentanoic acid;
1:1-mixture of (rac.)-(3R*)-5-{(1R*,5S*)-7-{4-[2-(2-chloro-4,5-dimethylphenoxy)ethoxy]phenyl}-6-[cyclopropyl(2-o-tolylethyl)carbamoyl]-3,9-diazabicyclo[3.3.1] non-6-en-3-yl}-3-hydroxy-5-oxopentanoic acid and (rac.)-(3S*)-5-{(1R*,5S*)-7-{4-[2-(2-chloro-4,5-dimethylphenoxy)ethoxy]phenyl}-6-[cyclopropyl(2-o-tolylethyl)carbamoyl]-3,9-diazabicyclo[3.3.1]non-6-en-3-yl}-3-hydroxy-5-oxopentanoic acid;
1:1-mixture of (rac.)-(3R*)-5-{((1R*,5S*)-7-{4-[2-(2-chloro-4,5-diethylphenoxy)ethoxy]phenyl}-6-[cyclopropyl(2-p-tolylethyl)carbamoyl]-3,9-diazabicyclo[3.3.1] non-6-en-3-yl)-3-hydroxy-5-oxopentanoic acid and (rac.)-(3S*)-5-{(1R*,5S*)-7-{4-[2-(2-chloro-4,5-dimethylphenoxy)ethoxy]phenyl}-6-[cyclopropyl(2-p-tolylethyl)carbamoyl]-3,9-diazabicyclo[3.3.1]non-6-en-3-yl}-3-hydroxy-5-oxopentanoic acid;
1:1-mixture of (rac.)-(3R*)-5-{(1R*,5S*)-7-{4-[2-(2-chloro-4,5-dimethylphenoxy)ethoxy]phenyl}-6-[cyclopropyl-(3,5-dimethoxybenzyl)carbamoyl]-3,9-diazabicyclo[3.3.1]non-6-en-3-yl}-3-hydroxy-5-oxopentanoic acid and (rac.)-(3S*)-5-{(1R*,5S*)-7-{4-[2-(2-chloro-4,5-dimethyl-phenoxy)ethoxy]phenyl}-6-[cyclopropyl-(3,5-dimethoxybenzyl)carbamoyl]-3,9-diazabicyclo[3.3.1] non-6-en-3-yl}-3-hydroxy-5-oxopentanoic acid;
1:1-mixture of (1R,5)-7-{4-[2-(2-chloro-4,5-dimethylphenoxy)ethoxy]phenyl}-3-(2S,4R)-4-hydroxypyrrolidine-2-carbonyl)-3,9-diazabicyclo[3.3.1]non-6-ene-6-carboxylic acid (2-chlorobenzyl)cyclopropylamide and (1S,5R)-7-{4-[2-(2-chloro-4,5-dimethylphenoxy)ethoxy]phenyl}-3-((2S,4R)-4-hydroxypyrrolidine-2-carbonyl)-3,9-diazabicyclo[3.3.1]non-6-ene-6-carboxylic acid (2-chlorobenzyl) cyclopropylamide;
1:1-mixture of (1R,5S)-7-{4-[2-(2-chloro-4,5-diethylphenoxy)ethoxy]phenyl}-3-((2S,4R)-4-hydroxypyrrolidine-2-carbonyl)-3,9-diazabicyclo[3.3.1]non-6-ene-6-carboxylic acid cyclopropyl-(2-methylbenzyl)amide and (1S, 5R)-7-{4-[2-(2-chloro-4,5-dimethylphenoxy)ethoxy] phenyl}-3-((2S,4R)-4-hydroxypyrrolidine-2-carbonyl)-3, 9-diazabicyclo[3.3.1]non-6-ene-6-carboxylic acid cyclopropyl-(2-methylbenzyl)amide;
(rac.)-(1R*,5S*)-3-acetyl-7-{4-[2-(2,3,5-trimethylphenoxy) ethyl]phenyl}-3,9-diazabicyclo[3.3.1]non-6-ene-6-carboxylic acid [2-(2-chlorophenyl)ethyl]-cyclopropylamide;
(rac.)-(1R*,5S*)-3-acetyl-7-{4-[2-(2,3,5-trimethylphenoxy) ethyl]phenyl}-3,9-diazabicyclo[3.3.1]non-6-ene-6-carboxylic acid cyclopropylphenethylamide;
(rac.)-(1R*,5S*)-3-acetyl-7-{4-[2-(2,3,5-trimethylphenoxy) ethyl]phenyl}-3,9-diazabicyclo[3.3.1]non-6-ene-6-carboxylic acid cyclopropyl-[2-(2,3-difluorophenyl)ethyl] amide;
(rac.)-(1R*,5S*)-3-acetyl-7-{4-[2-(2,3,5-trimethylphenoxy) ethyl]phenyl}-3,9-diazabicyclo[3.3.1]non-6-ene-6-carboxylic acid cyclopropyl-(3,5-dimethoxybenzyl)amide;
(rac.)-(1R*,5S*)-3-acetyl-7-{[2-(2,3,5-trimethylphenoxy) ethyl]phenyl}-3,9-diazabicyclo[3.3.1]non-6-ene-6-carboxylic acid cyclopropyl-(2-p-tolylethyl)amide;
(rac.)-(1R*,5S*)-3-acetyl-7-{4-[2-(2,3,5-trimethylphenoxy) ethyl]phenyl}-3,9-diazabicyclo[3.3.1]non-6-ene-6-carboxylic acid cyclopropyl-[2-(2-hydroxyethyl)benzyl] amide;
(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid cyclopropyl-[2-(2-hydroxyethyl) benzyl]amide;
(rac.)-5-((1R*,5S*)-6-(cyclopropylphenethylcarbamoyl)-7-{4-[2-(2,3,5-trimethylphenoxy)ethyl]phenyl}-3,9-diazabicyclo[3.3.1]non-6-en-3-yl)-5-oxopentanoic acid;
(rac.)-5-((1R*,5S*)-6-{[2-(2-chlorophenyl)ethyl]cyclopropylcarbamoyl}-7-{4-[2-(2,3,5-trimethylphenoxy)ethyl] phenyl}-3,9-diazabicyclo[3.3.1]non-6-en-3-yl)-2,2-dimethyl-5-oxopentanoic acid;
(rac.)-5-((1R*,5S*)-6-{cyclopropyl-[2-(2,3-difluorophenyl) ethyl]carbamoyl}-7-{4-[2-(2,3,5-trimethylphenoxy) ethyl]phenyl}-3,9-diazabicyclo[3.3.1]non-6-en-3-yl)-5-oxopentanoic acid;
(rac.)-5-((1R*,5S*)-6-{cyclopropyl-[2-(4-fluorophenyl) ethyl]carbamoyl}-7-{4-[2-(2,3,5-trimethyl-phenoxy) ethyl]phenyl}-3,9-diazabicyclo[3.3.1]non-6-en-3-yl)-5-oxopentanoic acid;
(rac.)-5-((1R*,5S*)-6-[cyclopropyl-(2-o-tolylethyl)carbamoyl-7-{4-[2-(2,3,5-trimethylphenoxy)ethyl]phenyl}-3,9-diazabicyclo[3.3.1]non-6-en-3-yl)-5-oxopentanoic acid;
1:1-mixture of (rac.)-5-((1R*,5S*)-6-[cyclopropyl-((2R*)-2-hydroxy-2-phenylethyl)carbamoyl]-7-{4-[2-(2,3,5-trirnethylphenoxy)ethyl]phenyl}-3,9-diazabicyclo[3.3.1] non-6-en-3-yl)-5-oxopentanoic acid and (rac.)-5-((1R*, 5S*)-6-[cyclopropyl-((2S*)-2-hydroxy-2-phenylethyl) carbamoyll-7-{4-[2-(2,3,5-trimethylphenoxy)ethyl] phenyl}-3,9-diazabicyclo-[3.3.1]non-6-en-3-yl)-5-oxopentanoic acid;
(rac.)-5-(1R*,5S*)-6-{cyclopropyl-[2-(2-hydroxyethyl)benzyl]carbamoyl}-7-{4-[2-(2,3,5-trimethylphenoxy)ethyl] phenyl}-3,9-diazabicyclo[3.3.1]-non-6-en-3-yl)-5-oxopentanoic acid;
(rac.)-5-((1R*,5S*)-7-{4-[3-(2-bromo-5-fluorophenoxy) propyl]phenyl}-6-{cyclopropyl-[2-(3-methoxyphenoxy) ethyl]carbamoyl}-3,9-diazabicyclo[3.3.1]-non-6-en-3-yl)-5-oxopentanoic acid;
(rac.)-5-((1R*,5S*)-6-{[2-(2-chlorophenyl)ethylcyclopropylcarbamoyl}-7-{4-[2-(2,3,5-trimethylphenoxy)ethyl] phenyl}-3,9-diazabicyclo[3.3.1]non-6-en-3-yl)-2,2-dimethyl-5-oxopentanoic acid;
(rac.)-5-((1R*,5S*)-6-{cyclopropyl-[2-(2,3-difluorophenyl) ethyl]carbamoyl}-7-{4-[2-(2,3,5-triethylphenoxy)ethyl] phenyl}-3,9-diazabicyclo[3.3.1]non-6-en-3-yl)-2,2-dimethyl-5-oxopentanoic acid;
(rac.)-5-((1R*,5S*)-6-{cyclopropyl-[2-(4-fluorophenyl) ethyl]carbamoyl}-7-{4-[2-(2,3,5-trimethylphenoxy) ethyl]phenyl}-3,9-diazabicyclo[3.3.1]non-6-en-3-yl)-2,2 ethyl-5-oxopentanoic acid;
(rac.)-5-((1R*,5S*)-6-[cyclopropyl-(2-o-tolylethyl)carbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid;
(rac.)-5-((1R*,5S*)-6-[cyclopropyl-(2-p-tolylethyl)carbamoyl]-7-{[2-(2,3,5-trimethylphenoxy)ethyl]phenyl}-3,9-diazabicyclo[3.3.1]non-6-en-3-yl)-2,2-dimethyl-5-oxopentanoic acid;
(rac.)-5-((1R*,5S*)-6-[cyclopropyl-(3,5-dimethoxybenzyl) carbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid;

(rac.)-5-((1R*,5S*)-7-{4-[2-(2-chloro-4,5-dimethylphe-noxy)ethoxy]phenyl}-6-{cyclopropyl-[2-(2-hydroxy-ethyl)benzyl]carbamoyl}-3,9-diazabicyclo[3.3.1]non-6-en-3-yl)-2,2-dimethyl-5-oxopentanoic acid;
(rac.)-(1R*,5S*)-3-(4-carbamoylbutyryl)-7-{4-[2-(2,3,5-trimethylphenoxy)ethyl]phenyl}-3,9-diazabicyclo[3.3.1]non-6-ene-6-carboxylic acid cyclopropylphenethylamide;
(rac.)-(1R*,5S*)-3-(4-carbamoylbutyryl)-7-{4-[2-(2,3,5-trimethylphenoxy)ethyl]-phenyl}-3,9-diazabicyclo[3.3.1]non-6-ene-6-carboxylic acid [2-(2-chlorophenyl)ethyl]cyclopropylamide;
(rac.)-(1R*,5S*)-3-(4-carbamoylbutyryl)-7-{4-[2-(2,3,5-trimethylphenoxy)ethyl]phenyl}-3,9-diazabicyclo[3.3.1]non-6-ene-6-carboxylic acid cyclopropyl-[2-(2,3-difluorophenyl)ethyl]amide;
(rac.)-(1R*,5S*)-3-(4-carbamoylbutyryl)-7-{4-[2-(2,3,5-trimethylphenoxy)ethyl]phenyl}-3,9-diazabicyclo[3.3.1]non-6-ene-6-carboxylic acid cyclopropyl-[2-(4-fluorophenyl)ethyl]amide;
(rac.)-(1R*,5S*)-3-(4-carbamoylbutyryl)-7-{4-[2-(2,3,5-trimethylphenoxy)ethyl]phenyl}-3,9-diazabicyclo[3.3.1]non-6-ene-6-carboxylic acid cyclopropyl-(3,5-dimethoxybenzyl)amide;
(rac.)-(1R*,5S*)-3-(4-carbamoylbutyryl)-7-{4-[2-(2,3,5-trimethylphenoxy)ethyl]phenyl}-3,9-diazabicyclo[3.3.1]non-6-ene-6-carboxylic acid cyclopropyl-(2-p-tolylethyl)amide;
(rac.)-(1R*,5S*)-3-(4-carbamoylbutyryl)-7-{4-[2-(2,3,5-trimethylphenoxy)ethyl]phenyl}-3,9-diazabicyclo[3.3.1]non-6-ene-6-carboxylic acid cyclopropyl-[2-(2-hydroxyethyl)benzyl]amide;
(rac.)-(1R*,5S*)-3-(4-carbamoylbutyryl)-7-{4-[2-(2-chloro-4,5-diethylphenoxy)ethoxy]phenyl}-3,9-diazabicyclo[3.3.1]non-6-ene-6-carboxylic acid cyclopropyl-[2-(2-hydroxyethyl)benzyl]amide;
(rac.)-acetic acid (1R*,5S*)-2-(2-{[(3-acetyl-7-{4-[2-(2,3,5-trimethylphenoxy)ethyl]phenyl}-3,9-diazabicyclo[3.3.1]non-6-ene-6-carbonyl)cyclopropylamino]-methyl}phenyl)ethyl ester;
(rac.)-acetic acid (1R*,5S*)-2-(2-{[(3-acetyl-7-{4-[2-(2-chloro-4,5-dimethylphenoxy)ethoxy]phenyl}-3,9-diazabicyclo[3.3.1]non-6-ene-6-carbonyl)cyclopropylamino]methyl}phenyl)ethyl ester;
(rac.)-(1R*,5S*)-7-{4-[2-(2,3,5-trimethylphenoxy)ethyl]phenyl}-3,9-diazabicyclo[3.3.1]non-6-ene-6-carboxylic acid cyclopropyl-[2-(4-fluorophenyl)ethyl]amide;
(rac.)-(1R*,5S*)-7-{4-[2-(2,3,5-trimethylphenoxy)ethyl]phenyl}-3,9-diazabicyclo[3.3.1]non-6-ene-6-carboxylic acid cyclopropyl-(3,5-dimethoxybenzyl)amide;
(rac.)-acetic acid (1R*,5S*)-2-(2-{[(3-acetyl-7-{4-[2-(4-bromophenoxy)ethoxy]phenyl}-3,9-diazabicyclo[3.3.1]non-6-ene-6-carbonyl)cyclopropylamino]methyl}phenyl)ethyl ester,
1:1 mixture of (rac.)-5-{(1R*,5S*)-7-{4-[2-(2-chloro-4,5-dimethylphenoxy)ethoxy]phenyl}-6-[((2R*)-2-hydroxy-2-phenylethyl)methylcarbamoyl]-3,9-diazabicyclo-[3.3.1]non-6-en-3-yl}-2,2-dimethyl-5-oxopentanoic acid and (rac.)-5-{(1R*,5S*)-7-{[2-(2-chloro-4,5-dimethylphenoxy)ethoxy]phenyl}-6-[((2S*)-2-hydroxy-2-phenylethyl)methylcarbamoyl]-3,9-diazabicyclo-[3.3.1]non-6-en-3-yl}-2,2-dimethyl-5-oxopentanoic acid;
(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid (2-chlorobenzyl)cyclopropylamide;
(rac.)-(1R*,5S*)-7-{4-[3-(2,3,6-trifluorophenoxy)propyl)phenyl}-3,9-diazabicyclo[3.3.1]non-6-ene-6-carboxylic acid benzylcyclopropylamide;
(rac.)-(1R*,5S*)-7-{4-[3-(2,3,6-trifluorophenoxy)propyl]phenyl}-3,9-diazabicyclo[3.3.1]non-6-ene-6-carboxylic acid cyclopropyl-(2-fluorobenzyl)amide;
(rac.)-(1R*,5S*)-7-{4-[3-(2,3,6-trifluorophenoxy)propyl]phenyl}-3,9-diazabicyclo[3.3.1]non-6-ene-6-carboxylic acid cyclopropyl-(3-trifluoromethylbenzyl)amide;
(rac.)-(1R*,5S*)-7-{4-[3-(2,3,6-trifluorophenoxy)propyl]phenyl}-3,9-diazabicyclo[3.3.1]non-6-ene-6-carboxylic acid cyclopropyl-(2-methylbenzyl)amide;
(rac.)-(1R*,5S*)-7-{4-[3-(2,3,6-trifluorophenoxy)propyl]phenyl}-3,9-diazabicyclo[3.3.1]non-6-ene-6-carboxylic acid cyclopropyl-[2-(4-methoxyphenoxy)ethyl]amide;
(rac.)-(1R*,5S*)-7-{4-[3-(2,3,6-trifluorophenoxy)propyl]phenyl}-3,9-diazabicyclo[3.3.1]non-6-ene-6-carboxylic acid [2-(2-chlorophenyl)ethyl]cyclopropylamide;
(rac.)-(1R*,5S*)-7-{4-[3-(2,3,6-trifluorophenoxy)propyl]phenyl}-3,9-diazabicyclo[3.3.1]non-6-ene-6-carboxylic acid cyclopropyl-[2-(2,3-difluorophenyl)ethyl]amide;
(rac.)-(1R*,5S*)-7-{4-[3-(2,3,6-trifluorophenoxy)propyl]phenyl}-3,9-diazabicyclo[3.3.1]non-6-ene-6-carboxylic acid cyclopropyl-(2-o-tolylethyl)amide;
(rac.)-(1R*,5S*)-3-7-{4-[3-(2,3,6-trifluorophenoxy)propyl]phenyl}-3,9-diazabicyclo[3.3.1]non-6-ene-6-carboxylic acid cyclopropyl-(2-p-tolylethyl)amide;
(rac.)-(1R*,5S*)-3-acetyl-7-{4-[3-(2,5-difluorophenoxy)propyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[3-(2,3-dichlorophenoxy)propyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[3-(2-chloro-5-fluorophenoxy)propyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[3-(3-cyanopyridin-2-yloxy)propyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[2-(2,3-dimethylphenoxy)ethyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[2-(2,5-dimethylphenoxy)ethyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[2-(2-chloro-4,5-dimethylphenoxy)ethyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[2-(2,4-dichlorophenoxy)ethyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[2-(2,3-dichlorophenoxy)ethyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[2-(2,6-difluorophenoxy)ethyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[2-(2,5-difluorophenoxy)ethyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[2-(3,5-dichlorophenoxy)ethyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[2-(2-chloro-5-methylphenoxy)ethyl]phenyl}-3,9-diazabicyclo[3.3.1]non-6-ene-6-carboxylic acid (2-chlorobenzyl)cyclopropylamide;
(rac.)-(1R*,5S*)-3-acetyl-7-{4-[2-(2-chloro-5-fluorophenoxy)ethyl]phenyl}-3,9-diazabicyclo[3.3.1]non-6-ene-6-carboxylic acid (2-chlorobenzyl)cyclopropylamide;

(rac.)-(1R*,5S*)-3-acetyl-7-{4-[2-(2,3,6-trichlorophenoxy)
ethyl]phenyl}-3,9-diazabicyclo[3.3.1]non-6-ene-6-carboxylic acid (2-chlorobenzyl)cyclopropylamide;

(rac.)-(1R*,5S*)-3-acetyl-7-{4-[3-(2,3,6-trifluorophenoxy)
propyl]phenyl}-3,9-diazabicyclo[3.3.1]non-6-ene-6-carboxylic acid cyclopropyl-(2-methoxybenzyl)amide;

(rac.)-(1R*,5S*)-3-acetyl-7-{4-[3-(2,3,6-trifluorophenoxy)
propyl]phenyl}-3,9-diazabicyclo[3.3.1]non-6-ene-6-carboxylic acid cyclopropyl-5-fluoro-2-methoxybenzyl)
amide;

(rac.)-(1R*,5S*)-3-acetyl-7-{4-[3-(2,3,6-trifluorophenoxy)
propyl]phenyl}-3,9-diazabicyclo[3.3.1]non-6-ene-6-carboxylic acid cyclopropyl-(2,6-difluorobenzyl)amide;

(rac.)-(1R*,5S*)-3-acetyl-7-{4-[3-(2,3,6-trifluorophenoxy)
propyl]phenyl}-3,9-diazabicyclo[3.3.1]non-6-ene-6-carboxylic acid cyclopropyl-(3-fluoro-2-methylbenzyl)
amide;

(rac.)-(1R*,5S*)-3-acetyl-7-{4-[3-(2,3,6-trifluorophenoxy)
propyl]phenyl}-3,9-diazabicyclo[3.3.1]non-6-ene-6-carboxylic acid (2-chloro-3,6-difluorobenzyl)cyclopropylamide;

(rac.)-(1R*,5S*)-3-acetyl-7-{4-[3-(2,3,6-trifluorophenoxy)
propyl]phenyl}-3,9-diazabicyclo[3.3.1]non-6-ene-6-carboxylic acid cyclopropyl-(2,3-difluorobenzyl)amide;

(rac.)-(1R*,5S*)-3-acetyl-7-{4-[3-(2,3,6-trifluorophenoxy)
propyl]phenyl}-3,9-diazabicyclo[3.3.1]non-6-ene-6-carboxylic acid cyclopropyl-(4-fluorobenzyl)amide;

(rac.)-(1R*,5S*)-7-{4-[3-(2-bromo-5-fluorophenoxy)propyl]phenyl}-3,9-diazabicyclo[3.3.1]non-6-ene-6-carboxylic acid (2-chlorobenzyl)ethylamide;

(rac.)-(1R*,5S*)-7-{4-[3-(2-bromo-5-fluorophenoxy)propyl]phenyl}-3,9-diazabicyclo[3.3.1]non-6-ene-6-carboxylic acid cyclopropyl-(3,5-dimethoxybenzyl)amide;

(rac.)-(1R*,5S*)-7-{4-[3-(2-bromo-5-fluorophenoxy)propyl]phenyl}-3,9-diazabicyclo[3.3.1]non-6-ene-6-carboxylic acid cyclopropyl-(2-methylbenzyl)amide;

(rac.)-(1R*,5S*)-7-{4-[3-(2-bromo-5-fluorophenoxy)propyl]phenyl}-3,9-diazabicyclo[3.3.1]non-6-ene-6-carboxylic acid cyclopropyl-[2-(4-methoxyphenoxy)ethyl]
amide;

(rac.)-(1R*,5S*)-3-methyl-7-{4-[3-(2,3,6-trifluorophenoxy)
propyl]phenyl}-3,9-diazabicyclo[3.3.1]non-6-ene-6-carboxylic acid (2-chlorobenzyl)cyclopropylamide;

(rac.)-(1R*,5S*)-3-ethyl-7-{4-[3-(2,3,6-trifluorophenoxy)
propyl]phenyl}-3,9-diazabicyclo[3.3.1]non-6-ene-6-carboxylic acid (2-chlorobenzyl)cyclopropylamide;

(rac.)-(1R*,5S*)-3-(2-aminoacetyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(rac.)-(1R*,5S*)-3-(3-aminopropionyl)-7-{4-[3-(2,3,6-trifluorophenoxy)-propyl]phenyl}-3,9-diazabicyclo[3.3.1]
non-6-ene-6-carboxylic acid (2-chlorobenzyl)cyclopropylamide;

(rac.)-(1R*,5S*)-3-acetyl-7-{4-[2-(2,4,5-trichlorophenoxy)
ethoxy]phenyl}-3,9-diazabicyclo[3.3.1]non-6-ene-6-carboxylic acid (2-chlorobenzyl)cyclopropylamide;

(rac.)-(1R*,5S*)-3-acetyl-7-{4-[2-(2-bromo-5-fluorophenoxy)ethoxy]phenyl}-3,9-diazabicyclo[3.3.1]non-6-ene-6-carboxylic acid (2-chloro-3-trifluoromethylbenzyl)cyclopropylamide;

(rac.)-(1R*,5S*)-3-acetyl-7-{4-[2-(2,4,5-trichlorophenoxy)
ethoxy]phenyl}-3,9-diazabicyclo-[3.3.1]non-6-ene-6-carboxylic acid (2-bromobenzyl)-cyclopropylamide;

(rac.)-(1R*,5S*)-3-acetyl-7-{4-[2-(2-bromo-5-fluorophenoxy)ethoxy]phenyl}-3,9-diazabicyclo[3.3.1]non-6-ene-6-carboxylic acid cyclopropyl-(2,3-dimethylbenzyl)
amide;

(rac.)-(1R*,5S*)-3-acetyl-7-{4-[2-(2,3-dichlorophenoxy)
ethoxy]phenyl}-3,9-diazabicyclo[3.3.1]non-6-ene-6-carboxylic acid (2-chloro-3-trifluoromethylbenzyl)cyclopropylamide;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid (3-chlorobenzyl)-cyclopropylamide;

(rac.)-(1R*,5S*)-3-acetyl-7-{4-[2-(2,4,5-trichlorophenoxy)
ethoxy]phenyl}-3,9-diazabicyclo[3.3.1]non-6-ene-6-carboxylic acid (2-chlorobenzyl)ethylamide;

(rac.)-(1R*,5S*)-3-acetyl-7-{4-[2-(2-chloro-5-fluorophenoxy)ethoxy]phenyl}-3,9-diazabicyclo[3.3.1]non-6-ene-6-carboxylic acid (2-bromobenzyl)cyclo-propylamide;

(rac.)-(1R*,5S*)-3-acetyl-7-{4-[2-(4-chloro-2-methylphenoxy)ethoxy]-phenyl}-3,9-diazabicyclo[3.3.1]non-6-ene-6-carboxylic acid cyclopropyl-(2,3-dichlorobenzyl)
amide;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(3-methoxybenzyl)
amide;

(rac.)-(1R*,5S*)-3-acetyl-7-{4-[2-(2-bromo-5-fluorophenoxy)ethoxy]-phenyl}-3,9-diazabicyclo[3.3.1]non-6-ene-6-carboxylic acid (2-bromobenzyl)-cyclopropylamide;

(rac.)-(1R*,5S*)-3-acetyl-7-{4-[2-(4chloro-2-methylphenoxy)ethoxy]-phenyl}-3,9-diazabicyclo[3.3.1]non-6-ene-6-carboxylic acid cyclopropyl-(2,3-dimethylbenzyl)
amide;

(rac.)-(1R*,5S*)-3-acetyl-7-{4-[2-(2,4,5-trichlorophenoxy)
ethoxy]phenyl}-3,9-diazabicyclo[3.3.1]non-6-ene-6-caxboxylic acid cyclopropyl-(3-methoxy-benzyl)amide;

(rac.)-(1R*,5S*)-3-acetyl-7-{4-[2-(2-chloro-4,5-diethylphenoxy)ethoxy]-phenyl}-3,9-diazabicyclo[3.3.1]non-6-ene-6-carboxylic acid cyclopropyl-(2-fluoro-5-methoxybenzyl)amide;

(rac.)-(1R*,5S*)-3-acetyl-7-{4-[2-(4-chloro-2-methylphenoxy)ethoxy]-phenyl}-3,9-diazabicyclo[3.3.1]non-6-ene-6-carboxylic acid (2-bromobenzyl)-cyclopropylamide;

(rac.)-(1R*,5S*)-3-acetyl-7-{4-[2-(2-chloro-5-fluorophenoxy)ethoxy]phenyl}-3,9-diazabicyclo[3.3.1]non-6-ene-6-carboxylic acid (2-chlorobenzyl)-cyclopropylamide;

(rac.)-(1R*,5S*)-3-Acetyl-7-{4-[$^2$-(2,4,5-trichlorophenoxy)
ethoxy]phenyl}-3,9-diazabicyclo[3.3.1]non-6-ene-6-carboxylic acid cyclopropyl-(3,5-dimethoxybenzyl)amide;

(rac.)-(1R*,5S*)-3-acetyl-7-{4-[2-(2,3-dichlorophenoxy)
ethoxy]phenyl}-3,9-diazabicyclo[3.3.1]non-6-ene-6-carboxylic acid (2-bromobenzyl)cyclopropylamide;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid (6-chlorobenzo[1,3]dioxol-5-ylmethyl)-cyclopropylamide;

(rac.)-(1R*,5S*)-3-acetyl-7-{4-[2-(2,3-dichlorophenoxy)
ethoxy]phenyl}-3,9-diazabicyclo[3.3.1]non-6-ene-6-carboxylic acid (2-chlorobenzyl)cyclopropyl-amide;

(rac.)-(1R*,5S*)-3-acetyl-7-{4-[2-(4-chloro-2-methylphenoxy)ethoxy]-phenyl}-3,9-diazabicyclo[3.3.1]non-6-ene-6-carboxylic acid (2-chloro-3-trifluoromethylbenzyl)cyclopropylamide;

(rac.)-1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(3-methylbenzyl)
amide;

(rac.)-(1R*,5S*)-3-acetyl-7-{4-[2-(2,3-dichlorophenoxy)
ethoxy]phenyl}-3,9-diazabicyclo[3.3.1]non-6-ene-6-carboxylic acid (2-chlorobenzyl)ethylamide;

(rac.)-(1R*,5S*)-3-acetyl-7-{4-[2-(2-chloro-5-fluorophenoxy)ethoxy]phenyl}-3,9-diazabicyclo[3.3.1]non-6-ene-6-carboxylic acid cyclopropyl-(2-fluoro-5-methoxybenzyl)amide;

(rac.)-(1R*,5S*)-3-acetyl-7-{4-[2-(4-chloro-2-methylphenoxy)ethoxy]-phenyl}-3,9-diazabicyclo[3.3.1]non-6-ene-6-carboxylic acid (2-chlorobenzyl)-cyclopropylamide;

(rac.)-(1R*,5S*)-3-acetyl-7-{4-[2-(2-bromo-5-fluorophenoxy)ethoxy]-phenyl}-3,9-diazabicyclo[3.3.1]non-6-ene-6-carboxylic acid cyclopropyl-(3,5-dimethoxybenzyl)amide;

(rac.)-(1R*,5S*)-3-acetyl-7-{4-[2-(2-chloro-5-fluorophenoxy)ethoxy]-phenyl}-3,9-diazabicyclo[3.3.1]non-6-ene-6-carboxylic acid cyclopropyl-(3-methoxybenzyl)amide;

(rac.)-(1R*,5S*)-3-acetyl-7-{4-[2-(2,4,5-trichlorophenoxy)ethoxy]phenyl}-3,9-diazabicyclo[3.3.1]non-6-ene-6-carboxylic acid (3-chlorobenzyl)-cyclopropylamide;

(rac.)-(1R*,5S*)-3-acetyl-7-{4-[2-(2,6-dichloro-4-methylphenoxy-ethoxy]-phenyl}-3,9-diazabicyclo[3.3.1]non-6-ene-6-carboxylic acid cyclopropyl-(3,5-difluorobenzyl)amide;

(rac.)-(1R*,5S*)-3-acetyl-7-{4-[2-(2,4,5-trichlorophenoxy)ethoxy]phenyl}-3,9-diazabicyclo[3.3.1]non-6-ene-6-carboxylic acid cyclopropyl-(2-fluoro-5-methoxybenzyl)amide;

(rac.)-(1R*,5S*)-3-acetyl-7-{4-[2-(2,4,5-trichlorophenoxy)ethoxy]phenyl}-3,9-diazabicyclo[3.3.1]non-6-ene-6-carboxylic acid cyclopropyl-(3,4-dimethoxybenzyl)amide;

(rac.)-1R*,5S*)-3-acetyl-7-{4-[2-(2-chloro-5-fluorophenoxy)ethoxy]phenyl}-3,9-diazabicyclo[3.3.1]non-6-ene-6-carboxylic acid (6-chloro-benzo[1,3]-dioxol-5-ylmethyl)cyclopropylamide;

(rac.)-1R*,5S*)-3-Acetyl-7-{4-[2-(2-bromo-5-fluorophenoxy)ethoxy]phenyl}-3,9-diazabicyclo[3.3.1]non-6-ene-6-carboxylic acid (3-chlorobenzyl)-cyclopropylamide;

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid cyclopropyl-(3,4-dimethoxy-benzyl)amide;

(rac.)-(1R*,5S*)-3-acetyl-7-{4-[2-(2-chloro-5-fluorophenoxy)ethoxy]phenyl}-3,9-diazabicyclo[3.3.1]non-6-ene-6-carboxylic acid (2-chlorobenzyl)-ethylamide;

(rac.)-1R*,5S*)-3-acetyl-7-{4-[2-(4-chloro-2-methylphenoxy)ethoxy]-phenyl}-3,9-diazabicyclo[3.3.1]non-6-ene-6-carboxylic acid cyclopropyl-(3,5-dimethoxybenzyl)amide;

(rac.)-(1R*,5S*)-3-acetyl-7-{4-[2-(2,4,5-trichlorophenoxy)ethoxy]phenyl}-3,9-diazabicyclo[3.3.1]non-6-ene-6-carboxylic acid cyclopropyl-(3-methylbenzyl)amide;

(rac.)-1R*,5S*)-3-acetyl-7-{4-[2-(2,3-dichlorophenoxy)ethoxy]phenyl}-3,9-diazabicyclo[3.3.1]non-6-ene-6-carboxylic acid cyclopropyl-(2-fluoro-5-methoxybenzyl)amide;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid cyclopropyl-3,5-difluorobenzyl)amide;

(rac.)-1R*,5S*)-3-acetyl-7-{4-[2-(2,3-dichlorophenoxy)ethoxy]phenyl}-3,9-diazabicyclo[3.3.1]non-6-ene-6-carboxylic acid cyclopropyl-(3,5-dimethoxy-benzyl)amide;

(rac.)-(1R*,5S*)-3-acetyl-7-{4-[2-(2-chloro-5-fluorophenoxy)ethoxy]-phenyl}-3,9-diazabicyclo[3.3.1]non-6-ene-6-carboxylic acid (2-chlorobenzyl)-cyclopropylamide;

(rac.)-(1R*,5S*)-3-acetyl-7-{4-[2-(2-bromo-5-fluorophenoxy)ethoxy]phenyl}-3,9-diazabicyclo[3.3.1]non-6-ene-6-carboxylic acid (2-chlorobenzyl)-cyclopropylamide;

(rac.}(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(3,4-dimethoxybenzyl)amide;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(3-trifluoromethoxybenzyl)amide;

(rac.)-(1R*,5S*)-3-acetyl-7-{4-[2-(2-chloro-5-fluorophenoxy)ethoxy]phenyl}-3,9-diazabicyclo[3.3.1]non-6-ene-6-carboxylic acid cyclopropyl-(3-methylbenzyl)amide;

(rac.)-(1R*,5S*)-3-acetyl-7-{4-[2-(2-chloro-5-fluorophenoxy)ethoxy]phenyl}-3,9-diazabicyclo[3.3.1]non-6-ene-6-carboxylic acid cyclopropyl-(3,5-dimethoxybenzyl)amide;

(rac.)-(1R*,5S*)-3-acetyl-7-{4-[2-(2,3-dichlorophenoxy)ethoxy]phenyl}-3,9-diazabicyclo[3.3.1]non-6-ene-6-carboxylic acid cyclopropyl-(3-methylbenzyl)amide;

(rac.)-(1R*,5S*)-3-acetyl-7-{4-[2-(2-bromo-5-fluorophenoxy)ethoxy]phenyl}-3,9-diazabicyclo[3.3.1]non-6-ene-6-carboxylic acid cyclopropyl-(2-fluoro-5-methoxybenzyl)amide;

(rac.)-(1R*,5S*)-3-acetyl-7-{4-[2-(2-bromo-5-fluorophenoxy)ethoxy]phenyl}-3,9-diazabicyclo[3.3.1]non-6-ene-6-carboxylic acid (2-chlorobenzyl)ethylamide;

(rac.)-(1R*,5S*)-3-acetyl-7-{4-[2-(2,3-dichlorophenoxy)ethoxy]phenyl}-3,9-diazabicyclo[3.3.1]non-6-ene-6-carboxylic acid (6-chlorobenzo[1,3]dioxol-5-ylmethyl)cyclopropylamide;

(rac.)-(1R*,5S*)-3-acetyl-7-{4-[2-(2,3-dichlorophenoxy)ethoxy]phenyl}-3,9-diazabicyclo[3.3.1]non-6-ene-6-carboxylic acid (3-chlorobenzyl)cyclopropylamide;

(rac.)-(1R*,5S*)-3-acetyl-7-{4-[2-(4-chloro-2-methylphenoxy)ethoxy]-phenyl}-3,9-diazabicyclo[3.3.1]non-6-ene-6-carboxylic acid (6-chloro-benzo[1,3]dioxol-5-ylmethyl)cyclopropylamide;

(rac.)-(1R*,5S*)-3-acetyl-7-{4-[2-(2-bromo-5-fluorophenoxy)ethoxyphenyl}-3,9-diazabicyclo[3.3.1]non-6-ene-6-carboxylic acid cyclopropyl-(3-methoxy-benzyl)amide;

(rac.)-1R*,5S*)-3-acetyl-7-{4-[2-(4-chloro-2-methylphenoxy)ethoxy]-phenyl}-3,9-diazabicyclo[3.3.1]non-6-ene-6-carboxylic acid (2-chlorobenzyl)ethylamide;

(rac.)-1R*,5S*)-3-acetyl-7-{4-[2-(4-chloro-2-methylphenoxy)ethoxy]-phenyl}-3,9-diazabicyclo[3.3.1]non-6-ene-6-carboxylic acid cyclopropyl-(3-methylbenzyl)amide;

(rac.)-1R*,5S*)-3-acetyl-7-{4-[2-(2,4,5-trichlorophenoxy)ethoxy]phenyl}-3,9-diazabicyclo[3.3.1]non-6-ene-6-carboxylic acid (6-chlorobenzo[1,3]dioxol-5-ylmethyl)cyclopropylamide;

(rac.)-(1R*,5S*)-3-acetyl-7-{4-[3-(2,6-dichloro-4-methylphenoxy)propyl]-phenyl}-3,9-diazabicyclo[3.3.1]non-6-ene-6-carboxylic acid (2-chlorobenzyl)-cyclopropylamide formate salt;

(rac.)-(1R*,5S*)-7-{4-[3-(2-bromo-5-fluorophenoxy)propyl]phenyl}-3,9-diazabicyclo[3.3.1]non-6-ene-6-carboxylic acid (2-chlorobenzyl)cyclopropylamide.

Most preferred compounds of general formula I are those selected from the group consisting of (rac.)-(2-methoxyphenyl)acetic acid (1R*,5S*)-7-{4-[3-(2-methoxybenzyloxy)-propoxy]phenyl}-3-(2-thiophen-2-ylacetyl)-3,9-diazabicyclo[3.3.1]non-6-en-6-ylmethyl ester;

(rac.)-(2-methoxyphenyl)acetic acid (1R*,5S*)-3-[2-(4-chlorophenyl)acetyl]-7-{4-[3-(2-methoxybenzyloxy)propoxy]phenyl}-3,9-diazabicyclo[3.3.1]non-6-en-6-ylmethyl ester;

(rac.)-(2-methoxyphenyl)acetic acid (1R*,5S*)-7-{4-[3-(2-methoxybenzyloxy)-propoxy]phenyl}-3-(quinoxaline-2-carbonyl)-3,9-diazabicyclo[3.3.1]non-6-en-6-ylmethyl ester;

(rac.)-(1R*,5S*)-3-acetyl-7-{4-[3-(2-methoxybenzyloxy) propoxy]phenyl}-3,9-diazabicyclo[3.3.1]non-6-ene-6-carboxylic acid[2-(2-chlorophenyl)ethyl]methylamide;

(rac.)-(2-methoxyphenyl)acetic acid (1R*,5S*)-3-(benzo[b]thiophene-3-carbonyl)-7-{4-[3-(2-methoxybenzyloxy) propoxy]phenyl}-3,9-diazabicyclo-[3.3.1]non-6-en-6-ylmethyl ester;

(rac.)-(2-methoxyphenyl)acetic acid (1R*,5S*)-3-acetyl-7-{4-[3-(2-methoxybenzyloxy)propoxy]phenyl}-3,9-diazabicyclo[3.3.1]non-6-en-6-ylmethyl ester;

(rac.)-(2-methoxyphenyl)acetic acid (1R*,5S*)-7-{4-[3-(2-methoxybenzyloxy)-propoxy]phenyl}-3-phenylmethanesulfonyl-3,9-diazabicyclo[3.3.1]non-6-en-6-ylmethyl ester;

(rac.)-(1R*,5S*)-3-acetyl-7-{4-[3-(2-methoxybenzyloxy) propoxy]phenyl}-3,9-diazabicyclo[3.3.1]non-6-ene-6-carboxylic acid [2-(4-methoxyphenyl)ethyl]-methylamide;

(rac.)-(1R*,5S*)-3-acetyl-7-{4-[2-(2-chloro-5-methylphenoxy)ethyl]phenyl}-3,9-diazabicyclo[3.3.1]non-6-ene-6-carboxylic acid methylphenethylamide;

(rac.)-(1R*,5S*)-3-acetyl-7-{4-[2-(2-bromo-5-fluorophenoxy)ethyl]phenyl}-3,9-diazabicyclo[3.3.1]non-6-ene-6-carboxylic acid methylphenethylamide;

(rac.)-(2-methoxyphenyl)acetic acid (1R*,5S*)-3-[2-(4-chlorophenyl)acetyl]-7-{6-[3-(2-methoxybenzyloxy)propoxy]pyridin-3-yl}-3,9-diazabicyclo[3.3.1]non-6-en-6-ylmethyl ester;

(rac.)-(1R*,5S*)-3-acetyl-7-{4-[2-(2,5-dimethylphenoxy)ethyl]phenyl}-3,9-diazabicyclo[3.3.1]non-6-ene-6-carboxylic acid methylphenethylanmide;

(rac.)-(1R*,5S*)-3-acetyl-7-{4-[3-(2-methoxybenzyloxy) propoxy]phenyl}-3,9-diazabicycloyclo[3.3.1]non-6-ene-6-carboxylic acid [2-(4-chlorophenyl)ethyl]methylamide;

(rac.)-(1R*,5S*)-3-acetyl-7-{4-[3-(2-methoxybenzyloxy) propoxy]phenyl}-3,9-diazabicyclo[3.3.1]non-6-ene-6-carboxylic acid [2-(3-chlorophenyl)ethyl]methylamide;

(rac.)-(1R*,5S*)-3-acetyl-7-{4-[3-(2-methoxybenzyloxy) propoxy]phenyl}-3,9-diazabicyclo[3.3.1]non-6-ene-6-carboxylic acid ethylphenethylamide;

(rac.)-(1R*,5S*)-3-acetyl-7-{4-[3-(2-methoxybenzyloxy) propoxy]phenyl}-3,9-diazabicyclo[3.3.1]non-6-ene-6-carboxylic acid [2-(3-methoxyphenyl)ethyl]methylamide;

(rac.)-(1R*,5S*)-3-acetyl-7-{4-[3-(2,3,6-trifluorophenoxy) propyl]phenyl}-3,9-diazabicyclo[3.1.1]non-6-ene-6-carboxylic acid methylphenethylamide;

(rac.)-(1R*,5S*)-3-acetyl-7-{4-[3-(2-methoxybenzyloxy) propoxy]phenyl}-3,9-diazabicyclo[3.3.1]non-6-ene-6-carboxylic acid methylphenethylamide;

(rac.)-(1R*,5S*)-3-acetyl-7-{4-[3-(2-bromo-5-fluorophenoxy)propyl]phenyl}-3,9-diazabicyclo[3.3.1]non-6-ene-6-carboxylic acid methylphenethylamide;

(rac.)-(2-methoxyphenyl)acetic acid (1R*,5S*)-7-{4-[3-(2-methoxybenzyloxy)-propoxy]phenyl}-3-methyl-3,9-diazabicyclo[3.3.1]non-6-en-6-ylmethyl ester;

(rac.)-(1R*,5S*)-3-acetyl-7-{4-[3-(2-methoxybenzyloxy) propoxy]phenyl}-3,9-diazabicyclo[3.3.1]non-6-ene-6-carboxylic acid [2-(3,4-dimethoxyphenyl)ethyl]-methylamide;

(rac.)-(1R*,5S*)-3-acetyl-7-{4-[2-{2,3,5-trimethylphenoxy)ethyl]phenyl}-3,9-diazabicyclo[3.3.1]non-6-ene-6-carboxylic acid methylphenethylamide;

(rac.)-(1R*,5S*)-3-acetyl-7-{4-[3-(2,5-dichlorophenoxy) propyl]phenyl}-3,9-diazabicyclo[3.3.1]non-6-ene-6-carboxylic acid methylphenethylamide;

(rac.)-(1R*,5S*)-3-acetyl-7-{4-[2-(2,3-dimethylphenoxy) ethyl]phenyl}-3,9-diazabicyclo[3.3.1]non-6-ene-6-carboxylic acid methylphenethylamide;

(rac.)-N-((1R*,5S*)-3-acetyl-7-{4-[2-(2-chloro-4,5-dimethylphenoxy)ethyl]phenyl}-3,9-diazabicyclo[3.3.1]non-6-ene-6-carboxylic acid methylphenethylamide;

(rac.)-(2-methoxyphenyl)acetic acid (1R*,5S*)-7-{4-[3-(2-methoxybenzyloxy)-propoxy]phenyl}-3,9-diazabicyclo[3.3.1]non-6-en-6-ylmethyl ester;

(rac.)-N-((1R*,5S*)-3-acetyl-7-{4-[3-(2-methoxybenzyloxy)propoxy]phenyl}-3,9-diazabicyclo[3.3.1]non-6-en-6-ylmethyl)-2-(2-methoxyphenyl)-N-methyl-acetamide;

(rac.)-N-((1R*,5S*)-3-acetyl-7-{4-[2-(2-tert-buty-4-methylphenoxy)ethyl]phenyl}-3,9-diazabicyclo[3.3.1]non-6-ene-6-carboxylic acid methylphenethylamide;

(rac.)-(1R*,5S*)-3-acetyl-7-{4-[2-(2,5-difluorophenoxy) ethyl]phenyl}-3,9-diazabicyclo[3.3.1]non-6-ene-6-carboxylic acid methylphenethylamide;

(rac.)-(1R*,5S*)-3-acetyl-7-{4-[3-(2-methoxybenzyloxy) propoxy]phenyl}-3,9-diazabicyclo[3.3.1]non-6-ene-6-carboxylic acid methyl-(3-phenylpropyl)amide;

(rac.)-(1R*,5S*)-3-acetyl-7-{4-[3-(2,3-dichlorophenoxy) propyl]phenyl}-3,9-diazabicyclo[3.3.1]non-6-ene-6-carboxylic acid methylphenethylamide;

(rac.)-(1R*,5S*)-3-acetyl-7-{4-[3-(2-acetylphenoxy)propyl]phenyl}-3,9-diazabicyclo[3.3.1]non-6-ene-6-carboxylic acid methylphenethylamide;

(rac.)-(1R*,5S*)-3-acetyl-7-{4-[3-(2-methoxybenzyloxy) propoxy]phenyl}-3,9-diazabicyclo[3.3.1]non-6-ene-6-carboxylic acid [2-(2-methoxyphenyl)ethyl]methylamide;

(rac.)-(1R*,5S*)-3-acetyl-7-{4-[3-(2-methoxybenzyloxy) propoxy]phenyl}-3,9-diazabicyclo[3.3.1]non-6-ene-6-carboxylic acid benzylmethylamide;

(rac.)-(1R*,5S*)-3-acetyl-7-{4-[3-(2,5-difluorophenoxy) propyl]phenyl}-3,9-diazabicyclo[3.3.1]non-6-ene-6-carboxylic acid methylphenethylamide;

(rac.)-(1R*,5S*)-3-acetyl-7-[4-(2-o-tolyloxyethyl)phenyl]-3,9-diazabicyclo-[3.3.1]non-6-ene-6-carboxylic acid methylphenethylamide;

(rac.)-(1R*,5S*)-3-acetyl-7-{4-[2-(3-isopropylphenoxy) ethyl]phenyl}-3,9-diazabicyclo[3.3.1]non-6-ene-6-carboxylic acid methylphenethylamide;

(rac.)-(1R*,5S*)-3-acetyl-7-{4-[3-(2-chlorophenoxy)propyl]phenyl}-3,9-diazabicyclo[3.3.1]non-6-ene-6-carboxylic acid (2-chlorobenzyl)cyclopropylamide;

(rac.)-(1R*,5S*)-5-[7-{4-[2-(2-bromo-5-fluorophenoxy) ethyl]phenyl}-6-(methyl-phenethylcarbamoyl)-3,9-diazabicyclo[3.3.1]non-6-en-3-yl]-5-oxopentanoic acid;

(rac.)-(1R*,5S*)-3-acetyl-7-{4-[3-(2,3,6-trifluorophenoxy) propyl]phenyl}-3,9-diazabicyclo[3.3.1]non-6-ene-6-carboxylic acid (2-chlorobenzyl)cyclopropyl-amide;

(rac.)-(1R*,5S*)-7-{4-[3-(2,3,6-trifluorophenoxy)propylphenyl}-3,9-diazabicyclo[3.3.1]non-6-ene-6-carboxylic acid (2-chlorobenzyl)cyclopropylamide;

(rac.)-5-((1R*,5S*)-6-[(2-chlorobenzyl)cyclopropylcarbamoyl]-7-{4-[3-(2,3,6-trifluorophenoxy)propylphenyl}-3,9-diazabicyclo[3.3.1]non-6-en-3-yl)-5-oxopentanoic acid;

(rac.)-(1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester;

(rac.)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-3-yl)-5-oxopentanoic acid methyl ester;

1:1-mixture of (1R,5S*)-3-(1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide and (1S,5R)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropyl-amide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid (2-chlorobenzyl)cyclopropylamide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid benzyl-cyclopropylamide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid (2-chlorobenzyl)ethylamide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(2-fluorobenzyl)amide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(3-trifluoromethylbenzyl)amide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(2-methylbenzyl)amide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropylphenethylamide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid [2-(2-chlorophenyl)ethyl]cyclopropylamide;

(rac.)-(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(3,5-dimethoxybenzyl)amide;

1:1-mixture of (rac.)-(3R*)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid and (rac.)-(3S*)-5-((1R*,5S*)-6-[(2-chlorobenzyl)cyclopropylcarbamoyl]-7-}4-[3-(2,3,6-trifluorophenoxy)propyl]phenyl}-3,9-diazabicyclo-[3.3.1]non-6-en-3-yl)-3-hydroxy-5-oxopentanoic acid;

1:1-mixture of (rac.)-(3R*)-5-(1R*,5S*)-6-(benzylcyclopropylcarbamoyl)-7-{4-[3-(2,3,6-trifluorophenoxy)propyl]phenyl}-3,9-diazabicyclo[3.3.1]non-6-en-3-yl)-3-hydroxy-5-oxopentanoic acid and (rac.)-(3S*)-5-((1R*,5S*)-6-(benzylcyclopropylcarbamoyl)-7-{4-[3-(2,3,6-trifluorophenoxy)propyl]phenyl}-3,9-diazabicyclo[3.3.1]non-6-en-3-yl)-3-hydroxy-5-oxopentanoic acid;

1:1-mixture of (rac.)-(3R*)-5-((1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid and (rac.)-(3S*)-5-((1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

1:1-mixture of (rac.)-(3R*)-5-((1R*,5S*)-6-[cyclopropyl-(2-fluorobenzyl)-carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid and (rac.)-(3S*)-5-((1R*,5S*)-6-[cyclopropyl-(2-fluorobenzyl)carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid;

1:1-mixture of (rac.)-(3R*)-5-((1R*,5S*)-6-[cyclopropyl-(3-trifluoromethylbenzyl)carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid and (rac.)-(3S*)-5-((1R*,5S*)-6-[cyclopropyl-(3-trifluoromethylbenzyl)carbamoyl]-7-{4-[3-(2,3,6-trifluorophenoxy)propyl]-phenyl}-3,9-diazabicyclo[3.3.1]non-6-en-3-yl)-3-hydroxy-5-oxopentanoic acid;

1:1-mixture of (rac.)-(3R*)-5-((1R*,5S*)-6-[cyclopropyl-(2-methylbenzyl)-carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid and (rac.)-(3S*)-5-((1R*,5S*)-6-[cyclopropyl-(2-methylbenzyl)carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

1:1-mixture of (rac.)-(3R*)-5-((1R*,5S*)-6-{cyclopropyl-[2-(4-methoxyphenoxy)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid and (rac.)-(3S*)-5-((1R*,5S*)-6-{cyclopropyl-[2-(4-methoxyphenoxy)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid;

1:1-mixture of (rac.)-(3R*)-5-((1R*,5S*)-6-[cyclopropyl-(2-m-tolyloxyethyl)-carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid and (rac.)-(3S*)-5-((1R*,5S*)-6-[cyclopropyl-(2-m-tolyloxyethyl)carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

1:1-mixture of (rac.)-(3R*)-5-((1R*,5S*)-6-{[2-(2-chlorophenyl)ethyl]-cyclopropylcarbamoyl}-7-{4-[3-(2,3,6-trifluorophenoxy)propylphenyl}-3,9-diazabicyclo[3.3.1]non-6-en-3-yl)-3-hydroxy-5-oxopentanoic acid and (rac.)-(3S*)-5-((1R*,5S*)-6-{[2-(2-chlorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid;

1:1-mixture of (rac.)-(3R*)-5-((1R*,5S*)-6-[cyclopropyl-(3,5-dimethoxybenzyl)carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid and (rac.)-(3S*)-5-((1R*,5S*)-6-[cyclopropyl-(3,5-dimethoxybenzyl)carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid (2-chlorobenzyl)ethylamide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(3,5-dimethoxybenzyl)amide;

(rac.)-5-((1R*,5S*)-6-(benzylcyclopropylcarbamoyl)-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-[cyclopropyl-(2-fluorobenzyl)carbamoyl]-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-[cyclopropyl-(3-trifluoromethylbenzyl)carbamoyl]-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-[cyclopropyl(2-methylbenzyl)carbamoyl]-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-{[2-(2-chlorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-[cyclopropyl(3,5-dimethoxybenzyl)carbamoyl]-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-[cyclopropyl(2-p-tolylethyl)carbamoyl]-7-{4-[3-(2,3,6-trifluorophenoxy)propyl]phenyl}-3,9-diazabicyclo[3.3.1]non-6-en-3-yl)-5-oxopentanoic acid;

(rac.)-5-((1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-[cyclopropyl-(2-fluorobenzyl)carbamoyl]-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-[cyclopropyl-(3,5-dimethoxybenzyl)carbamoyl]-7-{4-[3-(2,3,6-trifluorophenoxy)propyl]phenyl}-3,9-diazabicyclo[3.3.1]non-6-en-3-yl)-5-oxopentanoic acid methyl ester;

(rac.)-5-((1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-[cyclopropyl-(2-fluorobenzyl)carbamoyl)-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-[cyclopropyl-(2-methylbenzyl)carbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(rac.)-5-((1R*,5S*)-6-[cyclopropyl-(3,5-dimethoxybenzyl)carbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid;

1:1-mixture of (rac.)-(2R*,3S*)-4-((1R*,5S*)-6-[cyclopropyl-(2-methylbenzyl)-carbamoyl]-7-{4-[3-(2,3,6-trifluorophenoxy)propyl]phenyl}-3,9-diazabicyclo-[3.3.1]non-6-en-3-yl)-2,3-dihydroxy-4-oxobutyric acid and (rac.)-(2S*,3R*)-4-((1R*,5S*)-6-[cyclopropyl-(2-methylbenzyl)-carbamoyl]-7-{4-[3-(2,3,6-trifluorophenoxy)propyl]phenyl}-3,9-diazabicyclo-[3.3.1]non-6-en-3-yl)-2,3-dihydroxy-4-oxobutyric acid;

(rac.)-5-{(1R*,5S*)-7-{4-[3-(2-bromo-5-fluorophenoxy)propyl]phenyl}-6-[cyclopropyl-(2-fluorobenzyl)carbamoyl]-3,9-diazabicyclo[3.3.1]non-6-en-3-yl}-5-oxopentanoic acid;

(rac.)-5-{(1R*,5S*)-7-{4-[3-(2-bromo-5-fluorophenoxy)propyl]phenyl}-6-{cyclopropyl-[2-(3-methylphenoxy)ethyl]carbamoyl}-3,9-diazabicyclo[3.3.1]-non-6-en-3-yl)-5-oxopentanoic acid;

(rac.)-5-[(1R*,5S*)-7-{4-[3-(2-bromo-5-fluorophenoxy)propyl]phenyl}-6-(cyclopropylphenethylcarbamoyl)-3,9-diazabicyclo[3.3.1]non-6-en-3-yl]-5-oxopentanoic acid;

(rac.)-5-((1R*,5S*)-7-{4-[3-(2-bromo-5-fluorophenoxy)propyl]phenyl}-6-{[2-(2-chlorophenyl)ethyl]cyclopropylcarbamoyl}-3,9-diazabicyclo[3.3.1]non-6-en-3-yl)-5-oxopentanoic acid;

(rac.)-5-((1R*,5S*)-7-{4-[3-(2-bromo-5-fluorophenoxy)propyl]phenyl}-6-{[2-(2,3-difluorophenyl)ethyl]cyclopropylcarbamoyl}-3,9-diazabicyclo[3.3.1]non-6-en-3-yl)-5-oxopentanoic acid;

(rac.)-5-((1R*,5S*)-7-{4-[3-(2-bromo-5-fluorophenoxy)propyl]phenyl}-6-{[2-methylphenyl)ethyl]cyclopropylcarbamoyl}-3,9-diazabicyclo[3.3.1]non-6-en-3-yl)-5-oxopentanoic acid;

(rac.)-5-((1R*,5S*)-7-{4-[3-(2-bromo-5-fluorophenoxy)propyl]phenyl}-6-{[2-(4-methylphenyl)ethyl]cyclopropylcarbamoyl}-3,9-diazabicyclo[3.3.1]non-6-en-3-yl)-5-oxopentanoic acid;

(rac.)-5-{(1R*,5S*)-7-{4-[3-(2-bromo-5-fluorophenoxy)propyl]phenyl}-6-[cyclopropyl-(3,5-dimethoxybenzyl)carbamoyl]-3,9-diazabicyclo[3.3.1]non-6-en-3-yl}-5-oxopentanoic acid;

(rac.)-5-{(1R*,5S*)-7-{4-[3-(2-bromo-5-fluorophenoxy)propyl]phenyl}-6-[cyclopropyl-(3,5-dimethoxybenzyl)carbamoyl]-3,9-diazabicyclo[3.3.1]non-6-en-3-yl}-5-oxopentanoic acid methyl ester;

(rac.)-5-{(1R*,5S*)-7-{4-[3-(2-bromo-5-fluorophenoxy)propyl]phenyl}-6-[cyclopropyl-(2-fluorobenzyl)carbamoyl]-3,9-diazabicyclo[3.3.1]non-6-en-3-yl}-2,2-dimethyl-5-oxopentanoic acid;

(rac.)-5-{(1R*,5S*)-7-{4-[3-(2-bromo-5-fluorophenoxy)propyl]phenyl}-6-[cyclopropyl-(2-methylbenzyl)carbamoyl]-3,9-diazabicyclo[3.3.1]non-6-en-3-yl}-2,2-dimethyl-5-oxopentanoic acid;

(rac.)-5-[(1R*,5S*)-7-{4-[3-(2-bromo-5-fluorophenoxy)propyl]phenyl}-6-(cyclopropylphenethylcarbamoyl)-3,9-diazabicyclo[3.3.1]non-6-en-3-yl]-2,2-dimethyl-5-oxopentanoic acid;

(rac.)-5-((1R*,5S*)-7-{4-[3-(2-bromo-5-fluorophenoxy)propyl]phenyl}-6-{[2-(4-methylphenyl)ethyl]cyclopropylcarbamoyl}-3,9-diazabicyclo[3.3.1]non-6-en-3-yl)-2,2-dimethyl-5-oxopentanoic acid;

(rac.)-5-{(1R*,5S*)-7-{4-[3-(2-bromo-5-fluorophenoxy)propyl]phenyl}-6-[cyclopropyl-(3,5-diethoxybenzyl)carbamoyl]-3,9-diazabicyclo[3.3.1]non-6-en-3-yl}-2,2-dimethyl-5-oxopentanoic acid;

1:1-mixture of (rac.)-(2R*,3S*)-4-{(1R*,5S*)-7-{4-[3-(2-bromo-5-fluorophenoxy)propyl]phenyl}-6-[cyclopropyl(3,5-dimethoxybenzyl)carbamoyl]-3,9-diazabicyclo[3.3.1]non-6-en-3-yl}-2,3-dihydroxy-4-oxobutyric acid and (rac.)-(2S*,3R*)-4-{(1R*,5S*)-7-{4-[3-(2-bromo-5-fluorophenoxy)propyl]phenyl}-6-[cyclopropyl-(3,5-dimethoxybenzyl)carbamoyl]-3,9-diazabicyclo[3.3.1]non-6-en-3-yl}-2,3-dihydroxy-4-oxobutyric acid;

(rac.)-5-((1R*,5S*)-6-[(2-chlorobenzyl)cyclopropylcarbamoyl]-7-{4-[2-(2,3,5-trimethylphenoxy)ethyl]phenyl}-3,9-diazabicyclo[3.3.1]non-6-en-3-yl)-5-oxopentanoic acid;

(rac.)-5-((1R*,5S*)-6-[(3-trifluoromethylbenzyl)cyclopropylcarbamoyl]-7-{4-[2-(2,3,5-trimethylphenoxy)ethyl]phenyl}-3,9-diazabicyclo[3.3.1]non-6-en-3-yl)-5-oxopentanoic acid;

(rac.)-5-((1R*,5S*)-6-[(2-methylbenzyl)cyclopropylcarbamoyl]-7-{4-[2-(2,3,5-trimethylphenoxy)ethyl]phenyl}-3,9-diazabicyclo[3.3.1]non-6-en-3-yl)-5-oxopentanoic acid;

(rac.)-5-((1R*,5S*)-6-[(2-chlorobenzyl)ethylcarbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid;

(rac.)-5-((1R*,5S*)-6-[cyclopropyl-(2-fluorobenzyl)carbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid;

(rac.)-5-{(1R*,5S*)-7-{4-[3-(2-bromo-5-fluorophenoxy)propyl]phenyl}-6-[(2-chlorobenzyl)cyclopropylcarbamoyl]-3,9-diazabicyclo[3.3.1]non-6-en-3-yl}-5-oxopentanoic acid;

(rac.)-5-{(1R*,5S*)-7-{4-[3-(2-bromo-5-fluorophenoxy)propyl]phenyl}-6-[(2-chlorobenzyl)cyclopropylcarbamoyl]-3,9-diazabicyclo[3.3.1]non-6-en-3-yl}-2,2-dimethyl-5-oxopentanoic acid;

(rac.)-5-{(1R*,5S*)-4-[3-(2-bromo-5-fluorophenoxy)propyl]phenyl}-3-(4-carbamoylbutyryl)-3,9-diazabicyclo[3.3.1]non-6-ene-6-carboxylic acid (2-chlorobenzyl)cyclopropylamide;

(rac.)-5-((1R*,5S*)-6-(benzylcyclopropylcarbamoyl)-7-{4-[3-(2-bromo-5-fluorophenoxy)propyl]phenyl}-3,9-diazabicyclo[3.3.1]non-6-en-3-yl)-5-oxopentanoic acid methyl ester;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid (2-chlorobenzyl)-cyclopropylamide;

(rac.)-5-((1R*,5S*)-6-[(2-chlorobenzyl)cyclopropylcarbamoyl]-7-{4-[2-(2-chloro-4,5-dimethylphenoxy)ethoxy]phenyl}-3,9-diazabicyclo[3.3.1]non-6-en-3-yl)-5-oxopentanoic acid;

(rac.)-5-{(1R*,5S*)-7-{4-[2-(2-chloro-4,5-dimethylphenoxy)ethoxy]phenyl}-6-[cyclopropyl-(2-methylbenzyl)carbamoyl]-3,9-diazabicyclo[3.3.1]non-6-en-3-yl}-5-oxopentanoic acid;

(rac.)-5-{(1R*,5S*)-7-{4-[2-(2-chloro-4,5-dimethylphenoxy)ethoxy]phenyl}-6-[cyclopropyl-(3,5-dimethoxybenzyl)carbamoyl]-3,9-diazabicyclo[3.3.1]non-6-en-3-yl}-5-oxopentanoic acid;

(rac.)-5-((1R*,5S*)-6-[(2-chlorobenzyl)cyclopropylcarbamoyl]-7-{4-[2-(2-chloro-4,5-dimethylphenoxy)ethoxy]phenyl}-3,9-diazabicyclo[3.3.1]non-6-en-3-yl)-2,2-dimethyl-5-oxopentanoic acid;

(rac.)-5-((1R*,5S*)-6-[(2-chlorobenzyl)ethylcarbamoyl]-7-{4-[2-(2-chloro-4,5-dimethylphenoxy)ethoxy]phenyl}-3,9-diazabicyclo[3.3.1]non-6-en-3-yl)-2,2-dimethyl-5-oxopentanoic acid;

(rac.)-5-}(1R*,5S*)-7-{4-[2-(2-chloro-4,5-dimethylphenoxy)ethoxy]phenyl}-6-[cyclopropyl-(2-fluorobenzyl)carbamoyl]-3,9-diazabicyclo[3.3.1]non-6-en-3-yl}-2,2-dimethyl-5-oxopentanoic acid;

(rac.)-5-((1R*,5S*)-6-[cyclopropyl-(3,5-dimethoxybenzyl)carbamoyl]-7-{4-[2-(2,3,5-trimethylphenoxy)ethyl]phenyl}-3,9-diazabicyclo[3.3.1]non-6-en-3-yl)-5-oxopentanoic acid;

(rac.)-5-((1R*,5S*)-6-[cyclopropyl-(2-p-tolylethyl)carbamoyl-7-{4-[2-(2,3,5-triethylphenoxy)ethyl]phenyl}-3,9-diazabicyclo[3.3.1]non-6-en-3-yl)-5-oxopentanoic acid;

(rac.)-5-((1R*,5S*)-7-{4-[2-(2-chloro-4,5-dimethylphenoxy)ethoxy]phenyl}-6-{cyclopropyl-[2-(2-hydroxyethyl)benzyl]carbamoyl}-3,9-diazabicyclo[3.3.1]non-6-en-3-yl)-5-oxopentanoic acid;

(rac.)-5-((1R*,5S*)-6-(cyclopropylphenethylcarbamoyl)-7-{4-[2-(2,3,5-trimethylphenoxy)ethyl]phenyl}-3,9-diazabicyclo[3.3.1]non-6-en-3-yl)-2,2-dimethyl-5-oxopentanoic acid;

(rac.)-(1R*,5S*)-7-{4-[3-(2,3,6-trifluorophenoxy)propyl]phenyl}-3,9-diazabicyclo[3.3.1]non-6-ene-6-carboxylic acid (2-chlorobenzyl)ethylamide;

(rac.)-(1R*,5S*)-7-{4-[3-(2,3,6-trifluorophenoxy)propyl]phenyl}-3,9-diazabicyclo[3.3.1]non-6-ene-3,6-dicarboxylic acid 6-[(2-chlorobenzyl)cyclopropyl-amide]3-dimethylamide;

(rac.)-(1R*,5S*)-7-{4-[3-(2,3,6-trifluorophenoxy)propyl]phenyl}-3,9-diazabicyclo[3.3.1]non-6-ene-3,6-dicarboxylic acid 6-[(2-chlorobenzyl)cyclopropyl-amide]3-diethylamide;

(rac.)-(1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-3-carboxylic acid methyl ester;

(rac.)-(1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-3-carboxylic acid ethyl ester;

(rac.)-(1R*,5S*)-3-methanesulfonyl-7-{4-[3-(2,3,6-trifluorophenoxy)propyl]-phenyl}-3,9-diazabicyclo[3.3.1]non-6-ene-6-carboxylic acid (2-chlorobenzyl)-cyclopropylamide;

(rac.)-(1R*,5S*)-3-ethanesulfonyl-7-{4-[3-(2,3,6-trifluorophenoxy)propyl]-phenyl}-3,9-diazabicyclo[3.3.1]non-6-ene-6-carboxylic acid (2-chlorobenzyl)-cyclopropylamide;

(rac.)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-3-yl)-5-oxopentanoic acid ethyl ester;

(rac.)-4-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-3-yl)-4-oxo-butyric acid;

(rac.)-3-[((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-3-carbonyl)-amino]propionic acid ethyl ester, (rac.)4-[((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-3-carbonyl)-amino]butyric acid ethyl ester;

(rac.)-(1R*,5S*)-3-(3-carbamoylpropionyl)-7-{4-[3-(2,3,6-trifluorophenoxy)-propyl]phenyl}-3,9-diazabicyclo[3.3.1]non-6-ene-6-carboxylic acid(2-chloro-benzyl)cyclopropylamide;

(rac.)-(1R*,5S*)-3-(2-hydroxyacetyl)-7-{4-[3-(2,3,6-trifluorophenoxy)propyl]-phenyl}-3,9-diazabicyclo[3.3.1]non-6-ene-6-carboxylic acid(2-chlorobenzyl)-cyclopropylamide;

(1S,5R)-3-((3R)-3-hydroxybutyryl)-7-{4-[3-(2,3,6-trifluorophenoxy)propyl]-phenyl}-3,9-diazabicyclo[3.3.1]non-6-ene-6-carboxylic acid(2-chlorobenzyl)-cyclopropylamide;

1:1-mixture of (rac.)-(1R*,5S*)-3-((1R*,2S*)-2-hydroxycyclopentanecarbonyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide and (rac.)-(1R*,5S*)-3-((1S*,2R*)-2-hydroxycyclopentanecarbonyl)-7-{4-[3-(2,3,6-trifluorophenoxy)-propyl]phenyl}-3,9-diazabicyclo[3.3.1]non-6-ene-6-carboxylic acid (2-chloro-benzyl)cyclopropylamide;

(rac.)-(1R*,5S*)-9-acetyl-7-{4-[3-(2,3,6-trifluorophenoxy)propyl]phenyl}-3,9-diazabicyclo[3.3.1]non-6-ene-6-carboxylic acid (2-chlorobenzyl)cyclopropyl-amide;

(rac.)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-9-yl)-5-oxopentanoic acid;

(rac.)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-9-yl)-5-oxopentanoic acid ethyl ester;

(rac.)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-9-yl)-5-oxopentanoic acid methyl ester;

1:1-mixture of (rac.)-(3R*)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo-[3.3.1]non-6-en-9-yl)-3-hydroxy-5-oxopentanoic acid and (rac.)-(3S*)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo-[3.3.1]non-6-en-9-yl)-3-hydroxy-5-oxopentanoic acid;

(rac.)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-9-yl)-2,2-dimethyl-5-oxopentanoic acid;

(rac.)-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-9-yl)-4-oxo-butyric acid;

(rac.)-(1R*,5S*)-7-{4-[3-(2,3,6-trifluorophenoxy)propyl]phenyl}-3,9-diazabicyclo[3.3.1]non-6-ene-6,9-dicarboxylic acid 6-[(2-chlorobenzyl)cyclopropyl-amide]9-dimethylamide;

(rac.)-(1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-9-carboxylic acid methyl ester;

(rac.)-(1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-9-carboxylic acid ethyl ester;

(rac.)-3-[(1R*,5S*)-(6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-9-carbonyl)-amino]propionic acid ethyl ester;

(rac.)-4-[((1R*,5S*)-6-[(2-chlorobenzyl)cyclopropylcarbamoyl]-7-{4-[3-(2,3,6-trifuorophenoxy)propyl]phenyl}-3,9-diazabicyclo[3.3.1]non-6-ene-9-carbonyl)-amino]butyric acid ethyl ester;

(rac.)-(1R*,5S*)-3-formyl-7-{4-[3-(2,3,6-trifluorophenoxy)propyl]phenyl}-3,9-diazabicyclo[3.3.1]non-6-ene-6-carboxylic acid (2-chlorobenzyl)cyclopropyl-amide;

(rac.)-3-[((1R*,5S*)-[(2-chlorobenzyl)cyclopropylcarbamoyl]-7-{4-[3-(2,3,6-trifluorophenoxy)propyl]phenyl}-3,9-diazabicyclo[3.3.1]non-6-ene-3-carbonyl)-amino]propionic acid;

(rac.)-3-[((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-9-carbonyl)-amino]propionic acid;

(rac.)-4-[((1R*,5S*)-6-[(2chlorobenzyl)cyclopropylcarbamoyl]-7-{4-[3-(2,3,6-trifluorophenoxy)propyl]phenyl}-3,9-diazabicyclo[3.3.1]non-6-ene-9-carbonyl)-amino]butyric acid;

(rac.)-1R*,5S*)-3-acetyl-7-{4-[2-(2,3,6-trifluorophenoxy)ethyl]phenyl}-3,9-diazabicyclo[3.3.1]non-6-ene-6-carboxylic acid (2-chlorobenzyl)cyclopropyl-amide;

(rac.)-(1R*,5S*)-9-(4-carbamoylbutyryl)-7-{4-[2-(2,3,6-trifluorophenoxy)-propyl]phenyl}-3,9-diazabicyclo[3.3.1]non-6-ene-6-carboxylic acid (2-chlorobenzyl)cyclopropylamide;

(rac.)-(1R*,5S*)-9-(3-carbamoylpropionyl)-7-{4-[2-(2,3,6-trifluorophenoxy)-propyl]phenyl}-3,9-diazabicyclo[3.3.1]non-6-ene-6-carboxylic acid, (2-chloro-enzyl)cyclopropylamide;

(rac.)-(1R*,5S*)-9-(2-hydroxyacetyl)-7-{4-[2-(2,3,6-trifluorophenoxy)propyl]-phenyl}-3,9-diazabicyclo[3.3.1]non-6-ene-6-carboxylic acid (2-chlorobenzyl)-cyclopropylamide;

(1R,5S)-9-((3S)-3-hydroxybutyryl)-7-{4-[2-(2,3,6-trifluorophenoxy)propyl]-phenyl}-3,9-diazabicyclo[3.3.1]non-6-ene-6carboxylic acid (2-chlorobenzyl)-cyclopropylamide;

(rac.)-(1R*,5S*)-9-methanesulfonyl-7-{4-[2-(2,3,6-trifluorophenoxy)propyl]-phenyl}-3,9-diazabicyclo[3.3.1]non-6-ene-6-carboxylic acid (2-chlorobenzyl)-cyclopropylamide;

(rac.)-(1R*,5S*)-9-ethanesulfonyl-7-{4-[2-(2,3,6-trifluorophenoxy)propyl]-phenyl}-3,9-diazabicyclo[3.3.1]non-6-ene-6-carboxylic acid (2-chlorobenzyl)-cyclopropylamide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(2-fluoro-5-methoxy-benzyl) amide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(3-methoxybenzyl)-amide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(3,4dimethoxy-benzyl)amide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid (2-chloro-3-trifluoromethylbenzyl)cyclopropylamide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid benzo[1,3]dioxol-5-ylmethyl-cyclopropylamide;

(rac.)-(1R*,5S*)-3-acetyl-7-{4-[3-(2,3,6-trifluorophenoxy)propyl]phenyl}-3,9-diazabicyclo[3.3.1]non-6-ene-6-carboxylic acid (2-chloro-6-fluorobenzyl)-cyclopropylamide;

(rac.)-(1R*,5S*)-3-acetyl-7-{4-[3-(2,3,6-trifluorophenoxy) propyl]phenyl}-3,9-diazabicyclo[3.3.1]non-6-ene-6-carboxylic acid (2-bromobenzyl)cyclopropyl-amide;

(rac.)-1R*,5S*)-3-acetyl-7-{4-[3-(2,3,6-trifluorophenoxy) propyl]phenyl}-3,9-diazabicyclo[3.3.1]non-6-ene-6-carboxylic acid cyclopropyl-(2,3-dimethylbenzyl)amide;

(rac.)-1R*,5S*)-3-acetyl-7-{4-[3-(2,3,6-trifluorophenoxy) propyl]phenyl}-3,9-diazabicyclo[3.3.1]non-6-ene-6-carboxylic acid cyclopropyl-(3,5-difluorobenzyl)amide;

(rac.)-(1R*,5S*)-3-acetyl-7-{4-[3-(2,3,6-trifluorophenoxy) propyl]phenyl}-3,9-diazabicyclo[3.3.1]non-6ene-6-carboxylic acid cyclopropyl-(2,3-dichloro-benzyl)amide;

(rac.)-(1R*,5S*)-3-acetyl-7-{4-[3-(2,3,6-trifluorophenoxy) propyl]phenyl}-3,9-diazabicyclo[3.3.1]non-6-ene-6-carboxylic acid cyclopropyl-(3-trifluoromethoxy-benzyl) amide;

(rac.)-1R*,5S*)-3-acetyl-7-{4-[3-(2,3,6-trifluorophenoxy) propyl]phenyl}-3,9-diazabicyclo[3.3.1]non-6-ene-6-carboxylic acid cyclopropyl-(3-methylbenzyl)-amide;

(rac.)-1R*,5S*)-3-acetyl-7-{4-[3-(2,3,6-trifluorophenoxy) propyl]phenyl}-3,9-diazabicyclo[3.3.1]non-6-ene-6-carboxylic acid (3-chlorobenzyl)cyclopropyl-amide;

(rac.)-(1R*,5S*)-3-(5-morpholin-4-yl-5-oxopentanoyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(rac.)-(1R*,5S*)-3-(2-tetrazol-1-ylacetyl)-7-{4-[3-(2,3,6-trifluorophenoxy)-propyl]phenyl}-3,9-diazabicyclo[3.3.1]non-6ene-6-carboxylic acid (2-chloro-benzyl)cyclopropylamide;

(rac.)-(1R*,5S*)-3-(5-oxo-5-piperazin-1-ylpentanoyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

1:1-mixture of (1R,5S)-3-((2S)-2-amino-3-hydroxypropionyl)-7-{4-[3-(2,3,6-trifluorophenoxy)propyl]phenyl}-3, 9-diazabicyclo[3.3.1]non-6-ene-6-carboxylic acid (2-chlorobenzyl)cyclopropylamide and (1S,5R)-3-((2S)-2-amino-3-hydroxypropionyl)-7-{4-[3-(2,3,6-trifluorophenoxy)propyl]phenyl}-3,9-diazabicyclo[3.3.1]non-6-ene-6-carboxylic acid (2-chlorobenzyl) cyclopropylamide;

1:1-mixture of (1R,5S)-3-((2S)-2-aminopropionyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide and (1S,5R)-3-((2S)-2-aminopropionyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid cyclopropyl-(2,3-dichlorobenzyl)amide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid cyclopropyl-(2,3-dimethylbenzyl)amide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid (2-chloro-3-trifluoromethylbenzyl)cyclopropylamide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid (2-bromobenzyl)-cyclopropylamide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid (2-chlorobenzyl)-cyclopropylamide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid (2-chlorobenzyl)-ethylamide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid (6-chlorobenzo-[1,3]dioxol-5-ylmethyl)cyclopropylamide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid cyclopropyl-(3,5-dimethoxybenzyl)amide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid cyclopropyl-(3-methoxybenzyl)amide;

(rac.)-(1R*,5S*)-3-acetyl-7-{4-[2-(2-chloro-5-fluorophenoxy)ethoxy]phenyl}-3,9-diazabicyclo[3.3.1]non-6-ene-6-carboxylic acid cyclopropyl-(2,3-dichloro-benzyl)amide;

(rac.)-(1R*,5S*)-3-acetyl-7-{4-[2-(2-chloro-5-fluorophenoxy)ethoxy]phenyl}-3,9-diazabicyclo[3.3.1]non-6-ene-6-carboxylic acid (2-chloro-3-trifluoro-methylbenzyl)cyclopropylamide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid (3-chlorobenzyl)-cyclopropylamide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid cyclopropyl-(3-methylbenzyl) amide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid cyclopropyl-(2-fluoro-5-methoxybenzyl)amide;

(rac.)-(1R*,5S*)-3-acetyl-7-{4-[2-(2-chloro-4,5-dimethylphenoxy)-thoxy]phenyl}-3,9-diazabicyclo[3.3.1]non-6-ene-6-carboxylic acid cyclopropyl-(2,3-dichlorobenzyl) amide;

(rac.)-(1R*,5S*)-3-acetyl-7-{4-[3-(2-chloro-3,6-difluorophenoxy)propyl]-phenyl}-3,9-diazabicyclo[3.3.1]non-6-ene-6-carboxylic acid (2-chlorobenzyl)-cyclopropylamide;

(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid (2-chloro-3-trifluoromethylbenzyl)cyclopropylamide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid cyclopropyl-(3,4-dimethoxybenzyl)amide;

(rac.)-(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid cyclopropyl-(3-trifluoromethoxybenzyl)amide;

(rac.)-(1R*,5S*)-3-acetyl-7-{4-[2-(2,4,5-trichlorophenoxy)ethoxy]phenyl}-3,9-diazabicyclo[3.3.1]non-6-ene-6-carboxylic acid (2-chloro-3-trifluoro-methylbenzyl)cyclopropylamide;
(rac.)-(1R*,5S*)-3-acetyl-7-{4-[2-(2,4,5-trichlorophenoxy)ethoxy]phenyl}-3,9-diazabicyclo-[3.3.1]non-6-ene-6-carboxylic acid cyclopropyl-(2,3-dichlorobenzyl)amide;
(rac.)-(1R*,5S*)-3-acetyl-7-{4-[2-(2,3dichlorophenoxy)ethoxy]phenyl}-3,9-diazabicyclo[3.3.1]non-6-ene-6-carboxylic acid cyclopropyl-(2,3-dimethylbenzyl)amide;
(rac.)-(1R*,5S*)-3-acetyl-7-{4-[2-(2,4,5-trichlorophenoxy)ethoxy]phenyl}-3,9-diazabicyclo-[3.3.1]non-6-ene-6-carboxylic acid cyclopropyl-(2,3-dimethylbenzyl)amide;
(rac.)-(1R*,5S*)-3-acetyl-7-{4-[2-(2-chloro-4,5-dimethylphenoxy)ethoxyl-phenyl}-3,9-diazabicyclo[3.3.1]non-6-ene-6-carboxylic acid cyclopropyl-(2,3-dimethylbenzyl)amide;
(rac.)-(1R*,5S*)-3-acetyl-7-{4-[2-(2-bromo-5-fluorophenoxy)ethoxy]phenyl}-3,9-diazabicyclo[3.3.1]non-6-ene-6-carboxylic acid cyclopropyl-(2,3-dichlorobenzyl)amide;
(rac.)-(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid (2-bromobenzyl)-cyclopropylamide;
(rac.)-(1R*,5S*)-3-acetyl-7-{4-[2-(2,3-dichlorophenoxy)ethoxy]phenyl}-3,9-diazabicyclo[3.3.1]non-6-ene-6-carboxylic acid cyclopropyl-(2,3-dichlorobenzyl)amide;
(rac.)-(1R*,5S*)-3-acetyl-7-{4-[2-(2-chloro-5-fluorophenoxy)ethoxy]phenyl}-3,9-diazabicyclo[3.3.1]non-6-ene-6-carboxylic acid cyclopropyl-(2,3-dimethylbenzyl)amide;
(rac.)-(1R,5S)-7-{4-[3-(2,3,6-trifluorophenoxy)propylphenyl}-3,9-diazabicyclo-[3.3.1]non-6-ene-6-carboxylic acid (2-chlorobenzyl)cyclopropylamide;
(rac.)-(1S,5R)-7-{4-[3-(2,3,6-trifluorophenoxy)propylphenyl}-3,9-diazabicyclo-[3.3.1]non-6-ene-6-carboxylic acid (2-chlorobenzyl)cyclopropylamide.

The compounds of general formula I and their pharmaceutically acceptable salts may be used as therapeutics e.g. in form of pharmaceutical compositions. They may especially be used in the treatment and/or prophylaxis of cardiovascular and renal diseases. Examples of such diseases are hypertension, coronary diseases, cardiac insufficiency, renal insufficiency, renal and myocardial ischemia, and renal failure. They can also be used to prevent restenosis after balloon or stent angioplasty, to treat erectile dysfunction, glomerulonephritis, renal colic, and glaucoma Furthermore, they can be used in the therapy and the prophylaxis of diabetic complications, complications of vascular or cardiac surgery or after organ transplantation, complications of cyclosporin treatment, as well as other diseases presently known to be related to the RAS.

In another embodiment, the invention relates to a method for the treatment and/or prophylaxis of diseases which are related to the RAS such as hypertension, coronary diseases, cardiac insufficiency, renal insufficiency, renal and myocardial ischemia, and renal failure, which method comprises administrating a compound as defined above to a human being or animal.

The invention further relates to the use of compounds of general formula I as defined above for the treatment and/or prophylaxis of diseases which are associated with the RAS such as hypertension, coronary diseases, cardiac insufficiency, renal insufficiency, renal and myocardial ischemia, and renal failure.

In addition, the invention relates to the use of compounds as defined above for the preparation of medicaments for the treatment and/or prophylaxis of diseases which are associated with the RAS such as hypertension, coronary diseases, cardiac insufficiency, renal insufficiency, renal and myocardial ischemia, and renal failure.

The compounds of formula I may also be used in combination with one or more other therapeutically useful substances e. g. with other renin inhibitors, with ACE-inhibitors, with angiotensin-receptor antagonists, with diuretics, with calcium channel blockers, with endothelin receptors antagonists or with other drugs beneficial for the prevention or the treatment of cardiovascular events or renal insufficiency.

All forms of prodrugs leading to an active component comprised by general formula I above are included in the present invention.

The compounds of general formula I can be manufactured by the methods outlined below, by the methods described in the examples or by analogous methods.

Preparation of the Precursors:

Precursors are compounds which were prepared as key intermediates and/or building blocks and which were suitable for further transformations in parallel chemistry.

Bicyclononanone A was prepared from (4-benzyl-6-ethoxycarbonylmethyl-1-methylpiperazin-2-yl)acetic acid ethyl ester (Patent Application WO92/05174) as described in Scheme 1. Derivative A might also be present as enol form. In order to allow a coupling at the 7-position of bicyclononane A with aryl bromides, the vinyl triflate derivative B was prepared.

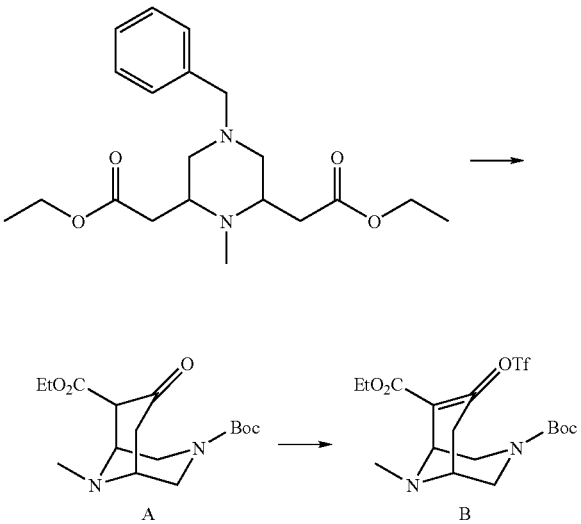

Scheme 1

The bromoaryl components can be prepared as described in Scheme 2. A Mitsunobu coupling (→compounds of type C) or the alkylation of an alcohol with a benzylic chloride (or bromide, →compounds of type D) are often the most convenient methods. Derivatives E and F were prepared in one step from 1-(3-chloropropoxymethyl)-2-methoxybenzene (Vieira E. et al., Bioorg. Med. Chem. Letters, 1999, 9, 1397) or 3-(5-bromopyridin-2-yloxy)propan-1-ol (Patent Application WO 98/39328) according to these methods. Other methods for the preparation of ethers or thioethers, like a Williamson synthesis, might be used as well (see e.g. March, J, "Advanced Organic Chemistry,", 3$^{rd}$ ed., John Wiley and sons, 1985).

related Pd(0)-complex in order to obtain bicyclononenes G (for details see the corresponding examples). Protective group manipulation would lead to the bicyclononenes H, which can finally be reduced to the alcohol derivatives J.

Scheme 2

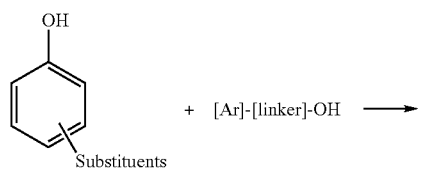

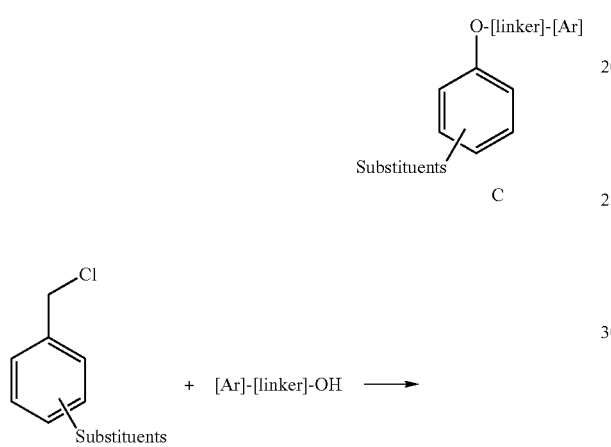

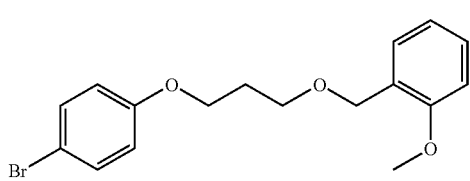

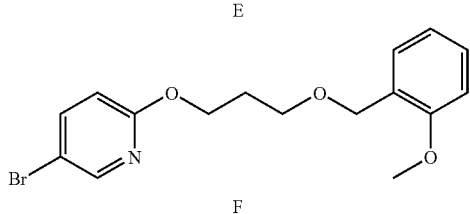

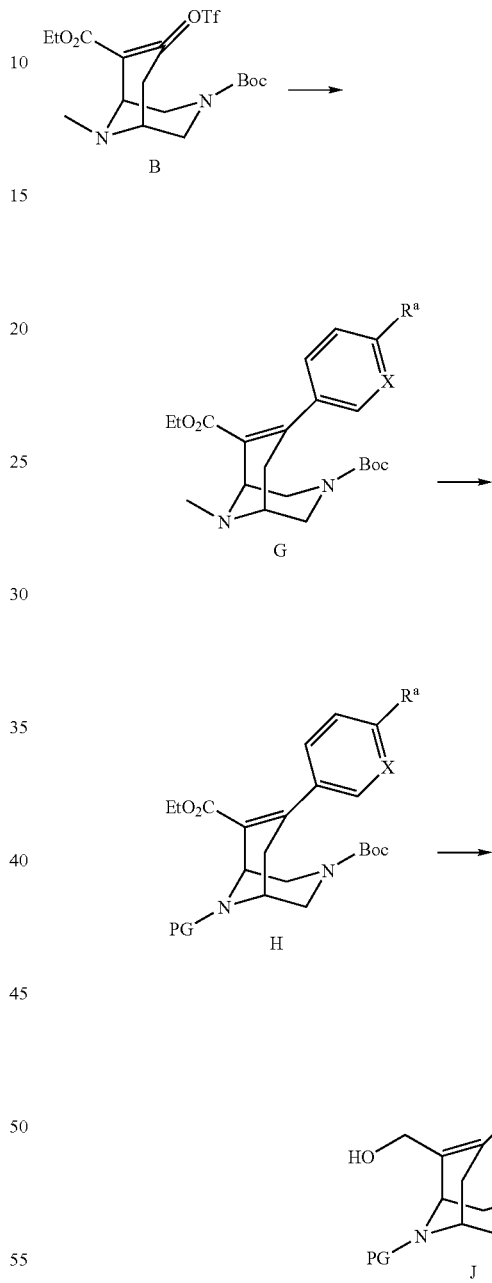

As shown in Scheme 3, these bromoaryl derivatives might then be coupled to triflate B in the presence of Pd(PPh$_3$)$_4$ or a If R$^a$ is O-SEM and X is CH, in compounds of type J, the SEM-protecting group can be cleaved under slightly acidic conditions, while the Boc-protecting group remains untouched as illustrated in Scheme 4. The phenolic moiety of bicyclononene K might then be alkylated to bicyclononene L. This alcohol intermediate would be transformed into the ester M, and the Boc-protecting group can finally be cleaved to yield precursor N.

Scheme 4
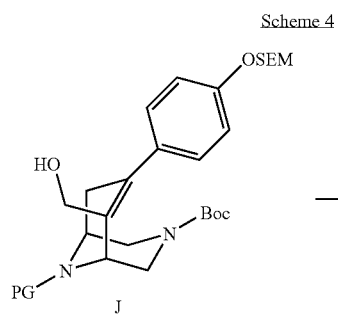
J
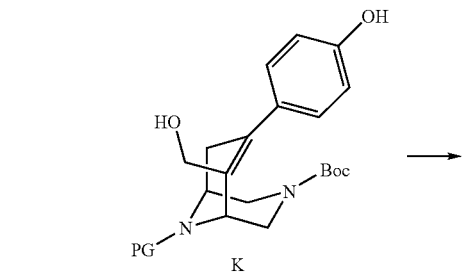
K
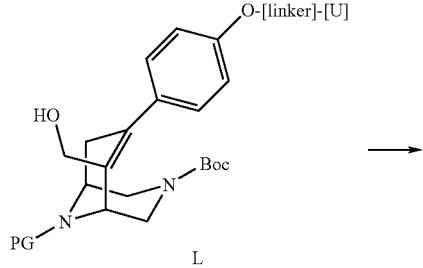
L
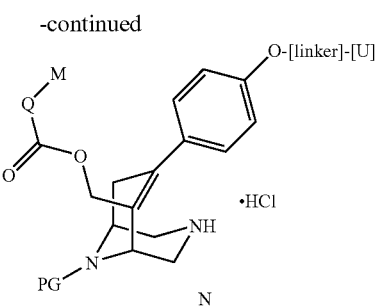
N
If X is N (Scheme 3), bicyclononenes of type J can be esterified to bicyclononenes O that can be deprotected to precursors P (Scheme 5).
Scheme 5
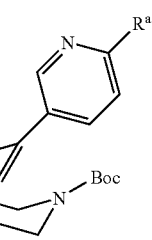
J
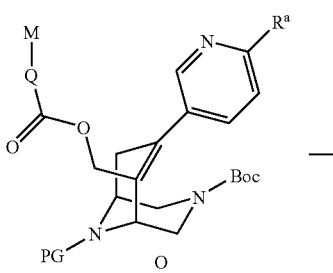
O
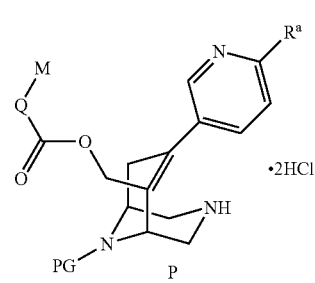
P
M If, in alkohols J, X is CH (Scheme 6) and, for instance, $R^a$ is $O(CH_2)_q OTBDMS$ or $(CH_2)_q OTBDMS$ (Scheme 3), an esterification might lead to bicyclononenes Q (Scheme 6). Under acidic conditions, both the Boc- and the TBDMS-groups would be cleaved and the secondary amine might be acylated, sulfonated, or alkylated to yield precursors R.

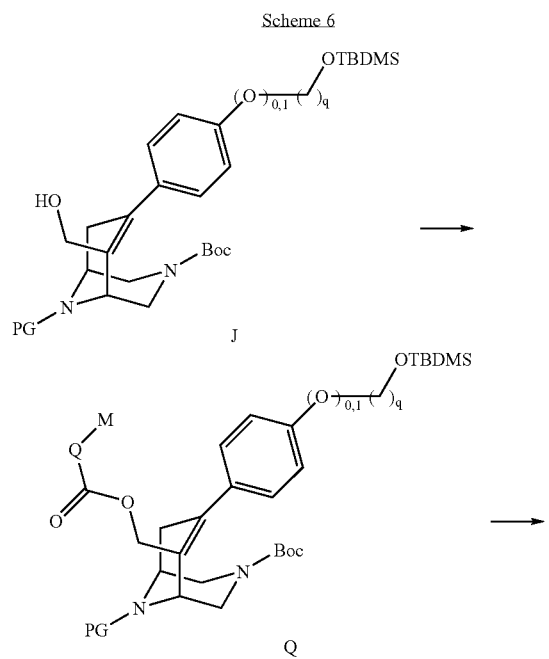

Scheme 6

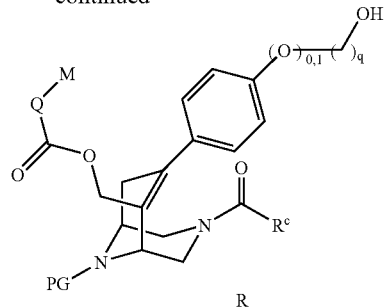

-continued

R

As illustrated in Scheme 7, the Boc-protecting group of bicyclononenes H might be cleaved and the resulting secondary amine acylated, sulfonated, or N-alkylated to bicyclononenes S. Saponification of the ester would lead to precursors T. If, for instance, $R^a$ is $O(CH_2)_n OTBDMS$ or $(CH_2)_n OTBDMS$, the silyl ether might be cleaved simultaneously during the cleavage of the Boc-protecting group or during the saponification. The acid might be transformed into an amide to lead to precursors U. Alternatively, amides U can be prepared from bicyclononenes H through the acids V, with simultaneous cleavage of the silyl ether. Reaction of the acids V with amines might give the amides W that can be transformed into precursors U. The amines can be prepared according to the literature or as described in the experimental part.

Scheme 7

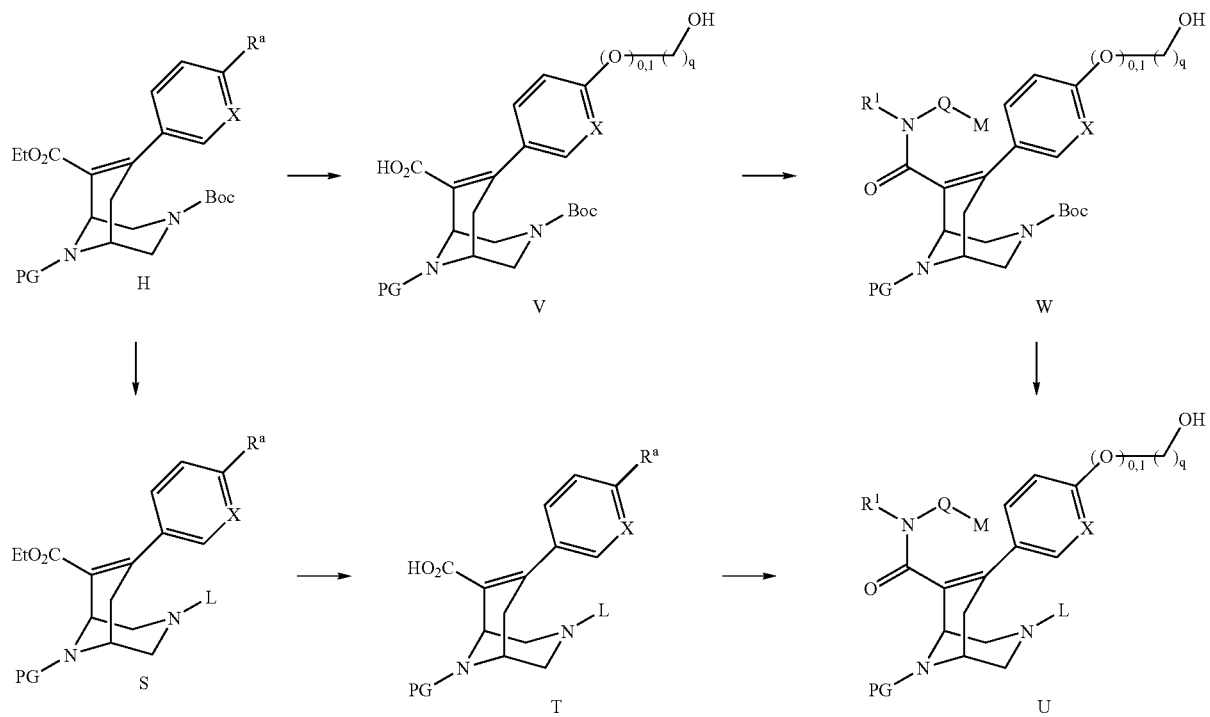

As illustrated in Scheme 8, the bicyclononenes S might be reduced to the corresponding alcohols X. The alcohol derivative X might then be oxidised to the aldehydes Y, which might transformed to the precursors Z by reductive amination.

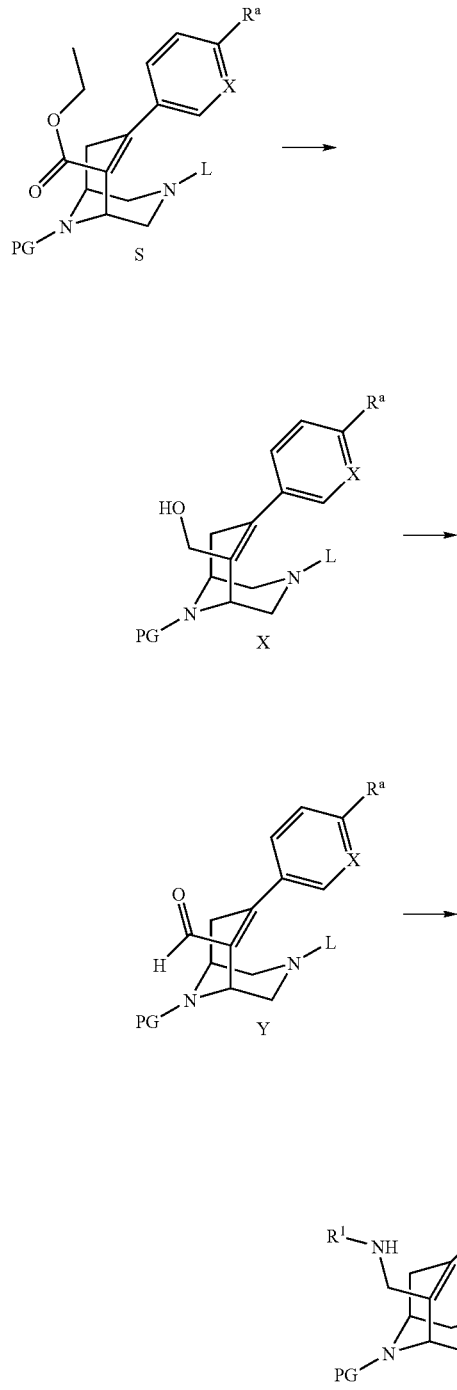

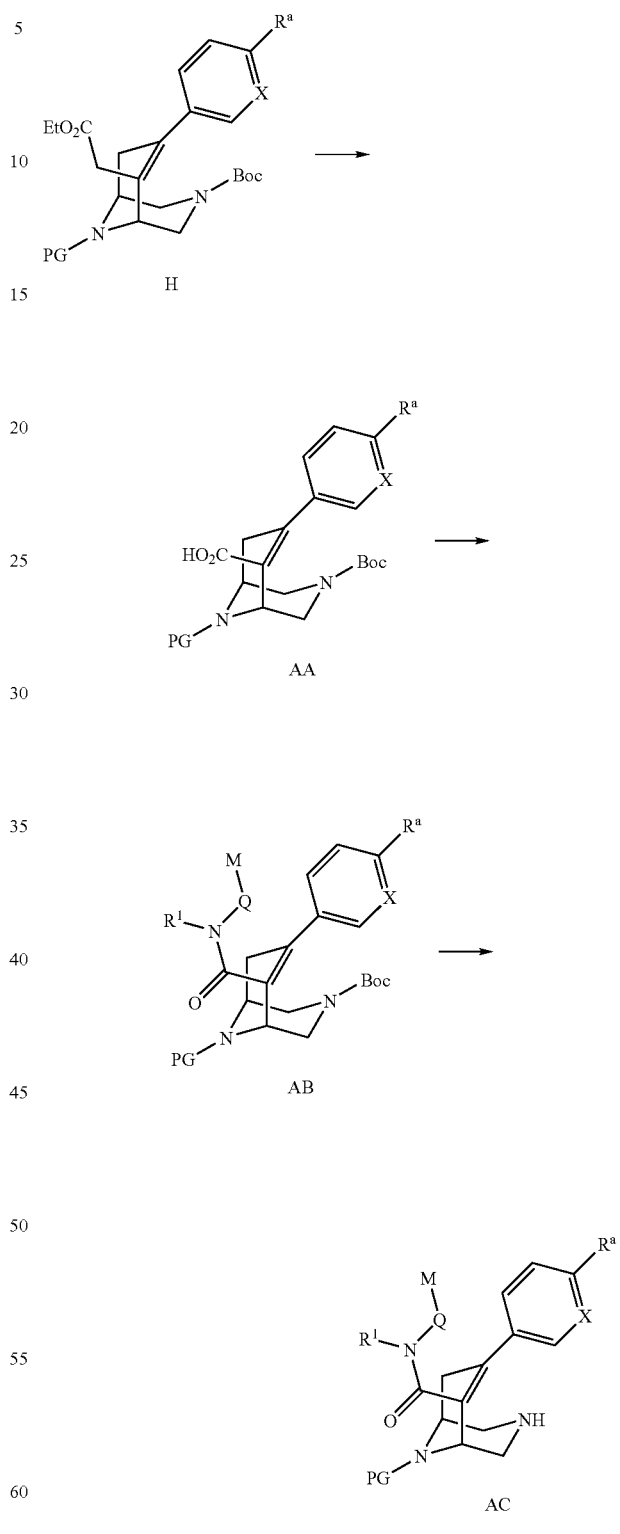

As shown in Scheme 9, a compound of type H might also be saponified to a compound of type AA After amide coupling to a derivative of type AB, removal of the Boc-group would yield a precursor of type AC.

As illustrated in Scheme 10, a compound of type S might also be transformed into a compound of type AH that in turn can be saponified to a precursor of type AJ.

Scheme 10
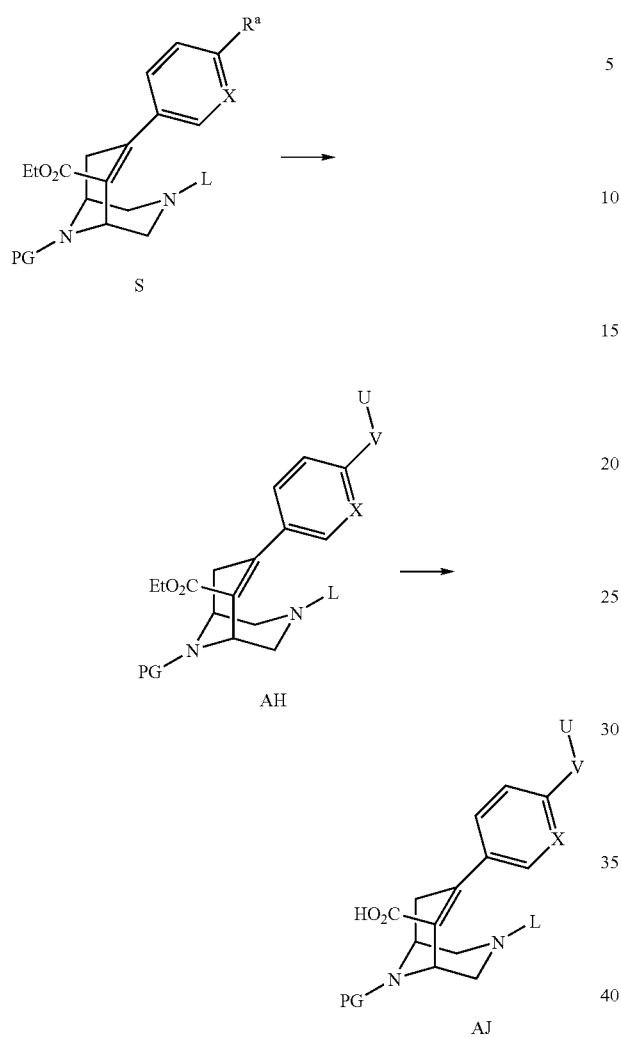
Alternatively precursors of type AJ might be prepared from bicyclononanone A, but using the benzyl ester instead of the ethyl ester, as illustrated in Scheme 11. After a tansesterification to compound AM similar reactions as described here above would lead to compounds AN, AO, AP, AQ, AR and finally AJ.
Scheme 11
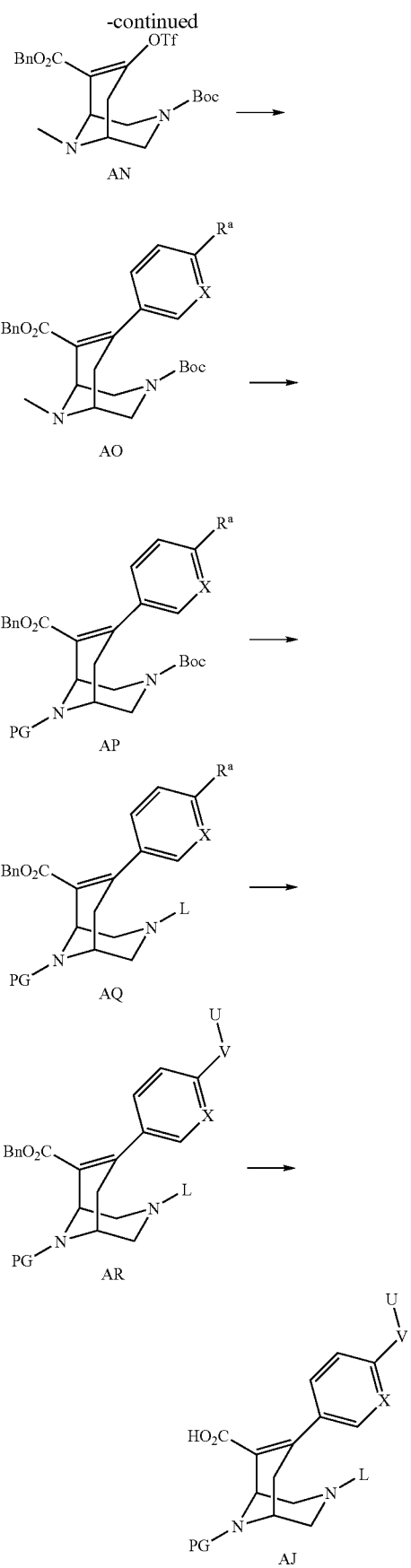

As shown in Scheme 12 a precursor of type AL might be prepared as well in two steps from a compound of type W.

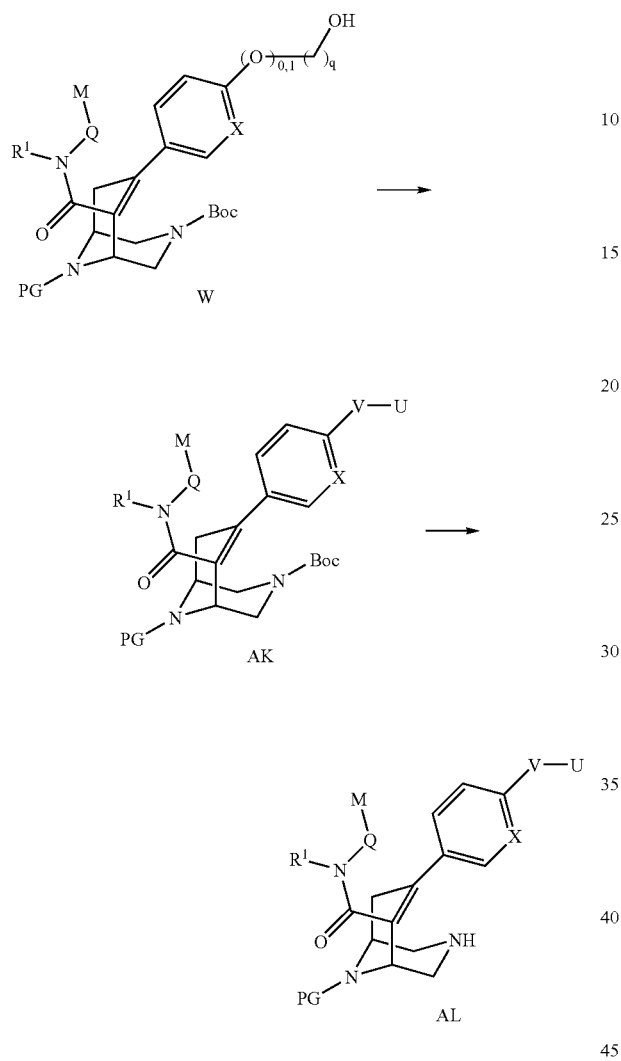

Sometimes it might be necessary to transform a substituent further after attaching it on the bicyclic template. For instance a compound of type AS, obtained by amide coupling from a compound of type AJ, might be transformed into a precursor of type AT, AU, or AV, as illustrated in Scheme 13.

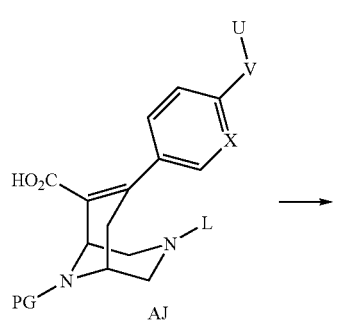

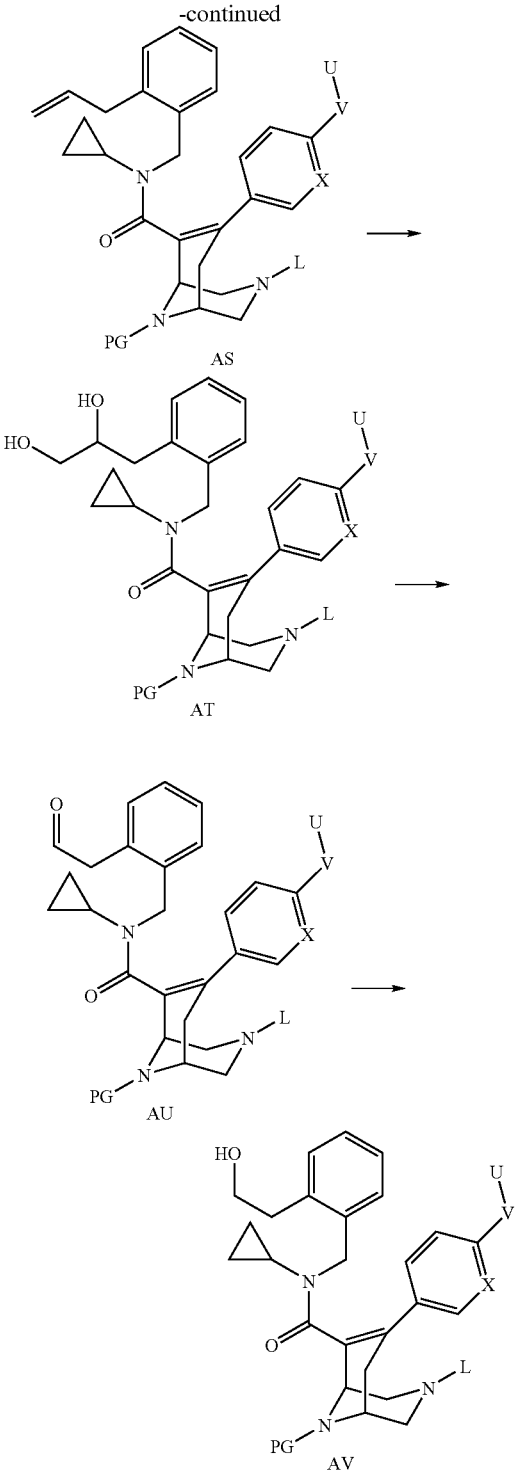

As illustrated in Scheme 14 compounds of type H might be deprotected into compounds of type AW. This type of compounds might be then transformed into compounds of type AX and finally into compounds of type AY. Compounds of type AY might also be prepared from compounds of type AP. Compounds of type AY might be transformed into compounds of type AK. Compounds of type AK might be finally transformed into precurosrs of type AL.

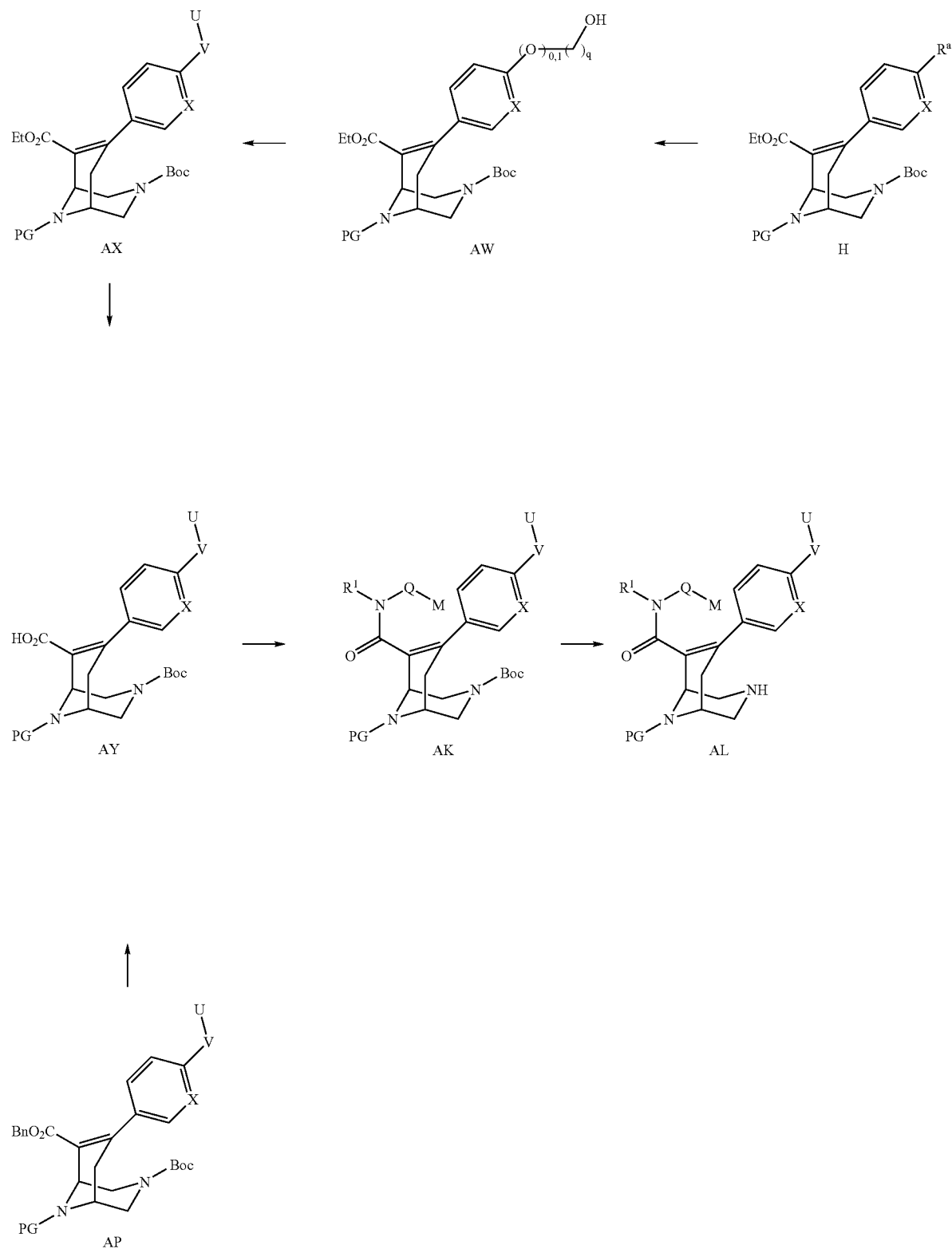
Scheme 14

Alternatively, as shown in Scheme 15, AX might be transformed into a compound of type BL, than might be then lead to a compound of type AJ.

Scheme 15

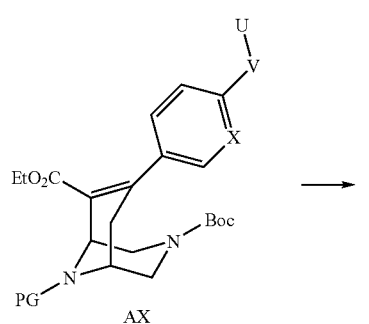

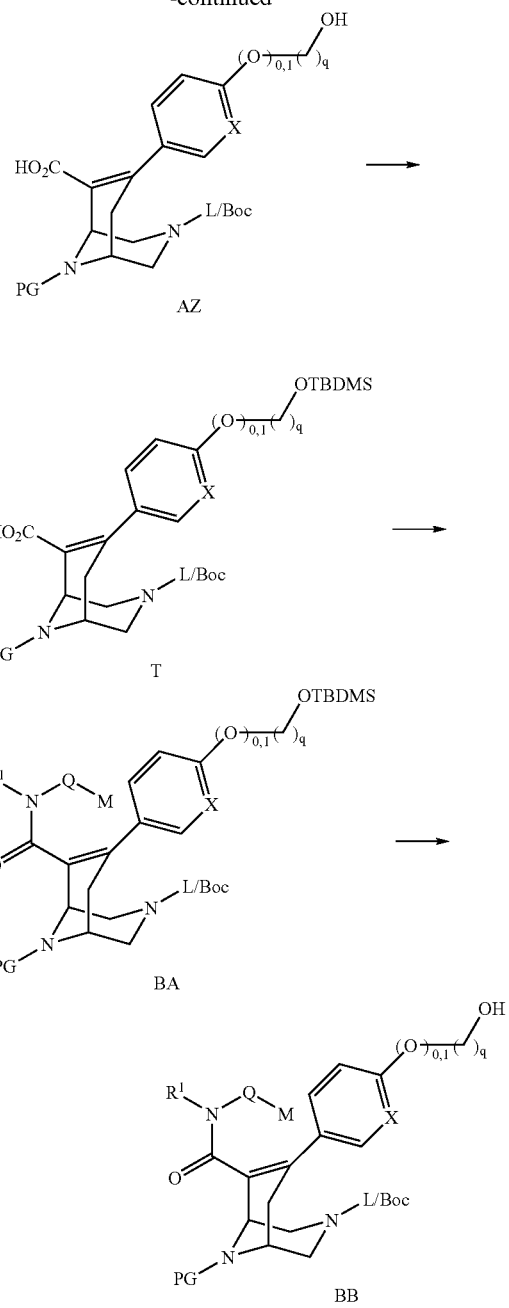

As shown in Scheme 16 compounds of type H or S might be transformed into compounds of type AZ (the substituent at the N(3) position be L or Boc). Then compounds of type T might be obtained that might be then transformed into compounds of type BA. Finally precursors of type BB might be prepared.

Scheme 16

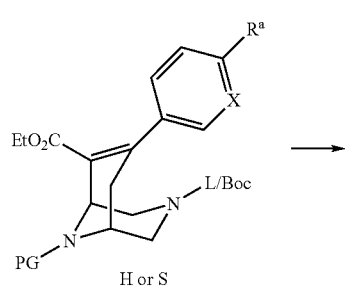

Also, as shown in Scheme 17, compounds of type AK might be transformed into precursors of type BC.

Scheme 17

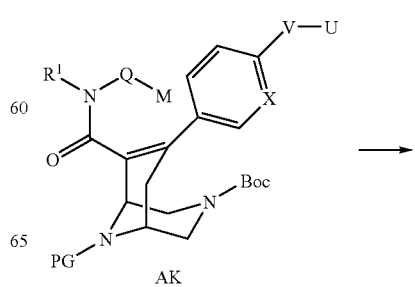

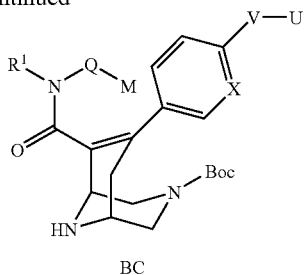

BC

Also, a compound of type S might be transformed into a compound of type BM, as shown in Scheme 18. A compound of type BM might be then saponified inot a precursor of type BN.

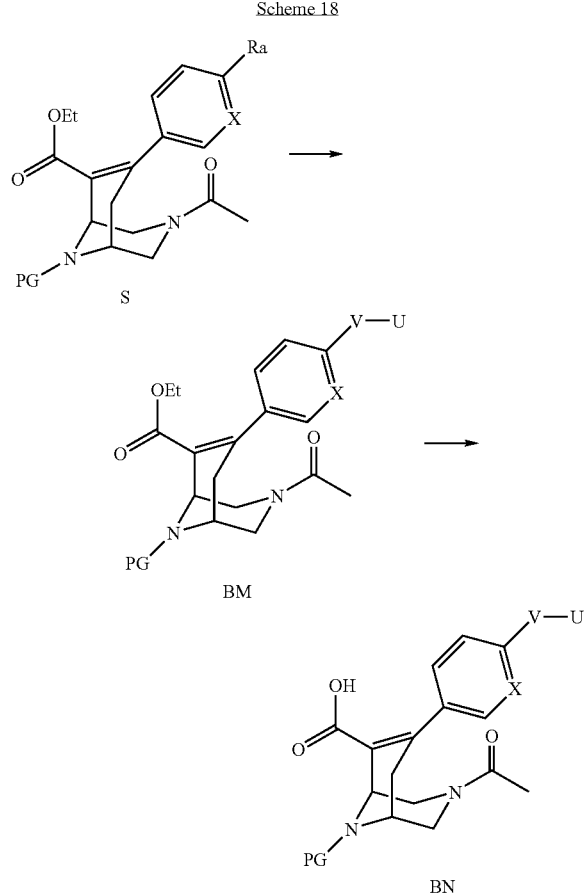

Preparation of the Secondary Amines

It might be necessary to prepare secondary amines as well. This might be done by reductive amination from the corresponding amine and aldehyde, or by amide coupling, from the corresponding amine and carboxylic acid, followed by reduction with LAH or borane. These standard procedures are well-described in the literature. (2-Allylphenyl)cyclopropylamine, necessary for instance in Scheme 13, might be prepared by allylation of 2-bromobenzaldehyde, protected as an acetal; subsequent deprotection to the 2-allylbenzaldehyde and reductive amination would lead to the desired amine.

Preparation of Final Compounds

From precursors prepared as described above, the final compounds can be prepared using parallel chemistry techniques. For the specific examples, see the experimental part.

Diazabicyclononenes of type of N can be acylated, or alkylated, or sulfonated, using standard procedures (Scheme 19), and then directly deprotected to yield the final compounds (for numbering, see specific examples). In each case, purification by preparative PLC might give the corresponding TFA salts or formate salts.

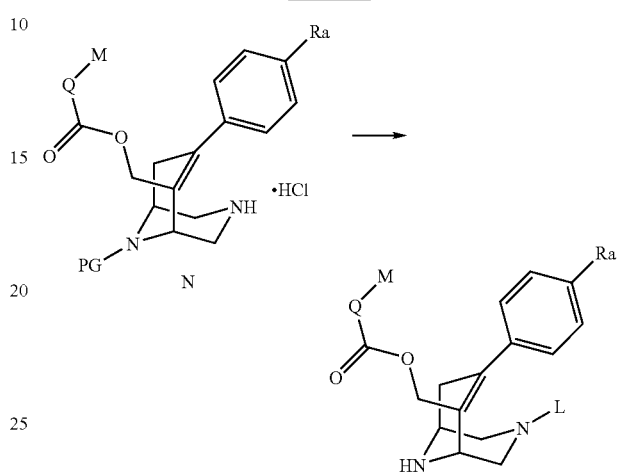

Precursors R, U or BB (with a L-substituent at the N(3)-position) might be transformed into the corresponding aryl ethers (Scheme 20), using the Mitsunobu reaction conditions. After deprotection, the final compounds are obtained.

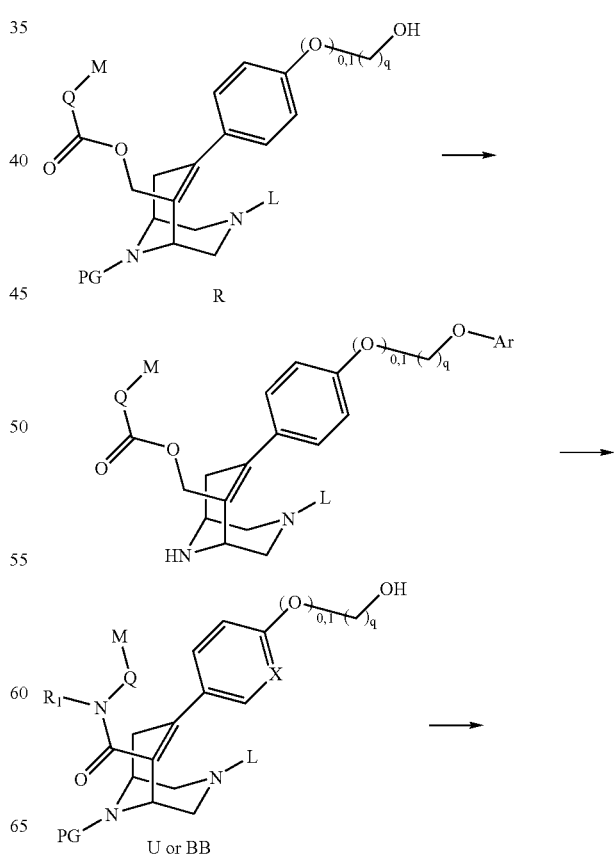

-continued

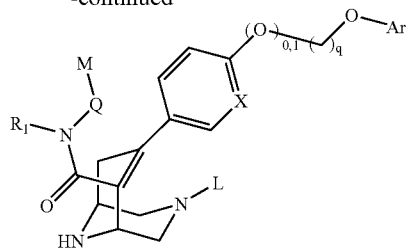

Precursors T, AJ or AV might be submitted to an amide coupling (Scheme 21). Deprotection would lead to the desired final compounds.

Scheme 21

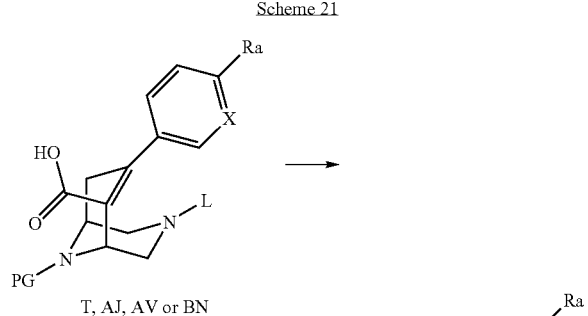

T, AJ, AV or BN

Compounds Z might be reacted with acylating (or sulfonating) reagents to lead to the corresponding amides (or sulfonamides) as well (Scheme 22). Deprotection would lead to the final compounds.

Scheme 22

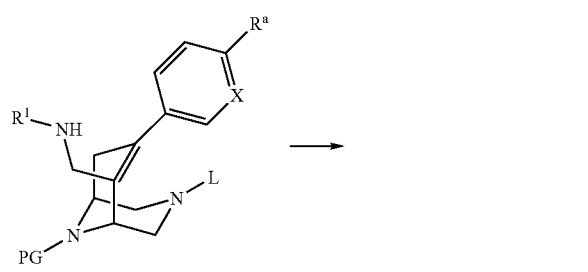

Z

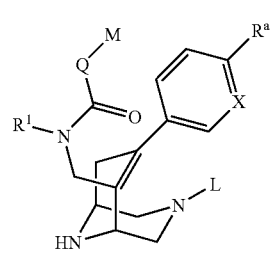

Compounds of type AC or AL can be reacted as well with acylating, sulfonating or alkylating reagents (Scheme 23). After deprotection, the final compounds would be obtained.

Scheme 23

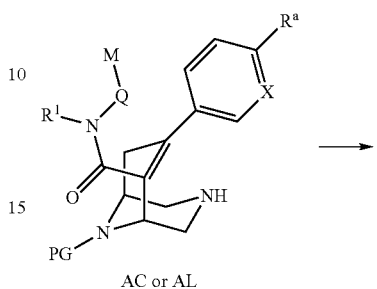

AC or AL

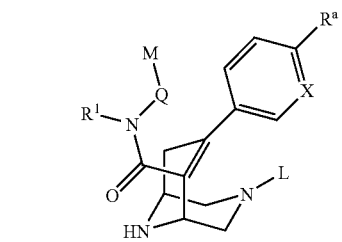

Precursors of type BC might also lead to final compounds as indicated in Scheme 24.

Scheme 24

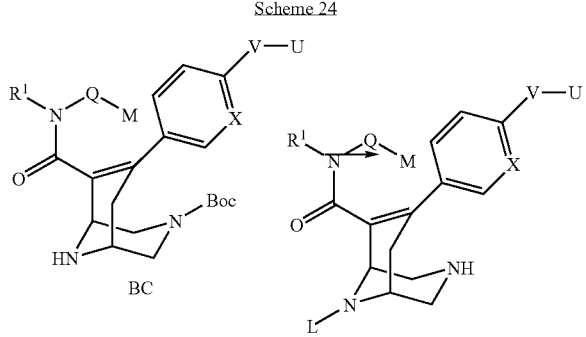

BC

Enantioselective Synthesis:

The compounds of the present invention contain at least two chiral centers which, however, are not independent from each other. The synthetic methods presented so far might lead to racemates. Both enantiomers might be prepared selectively starting from a meso-bicyclononane derivative, like compound AD (Blount B. K., Robinson, R, *J. Chem. Soc.*, 1932, 2485) or AE, prepared similarly to compound A with a subsequent decarboxylation (Scheme 25). For instance, compound AE might be stereoselectively acylated to bicyclononane derivatives AF or AG as already described elsewhere for similar compounds (Majewsli M., Lasny R., *J. Org. Chem.*, 1995, 60, 5825). Similarly, the other enantiomer might be prepared.

Scheme 25

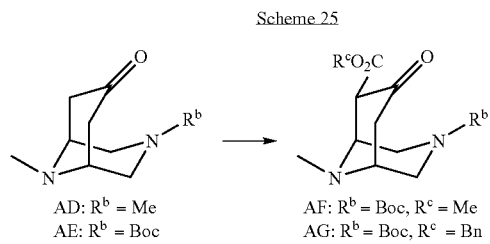

Finally precursor BK might be prepared as described in Scheme 26.

Scheme 26

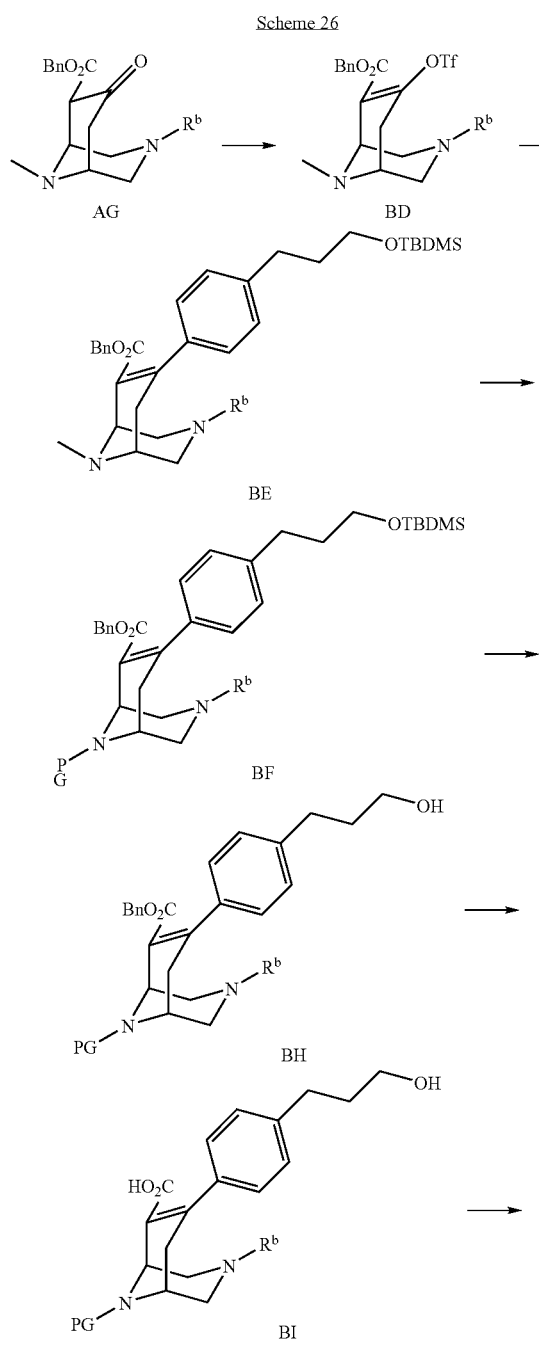

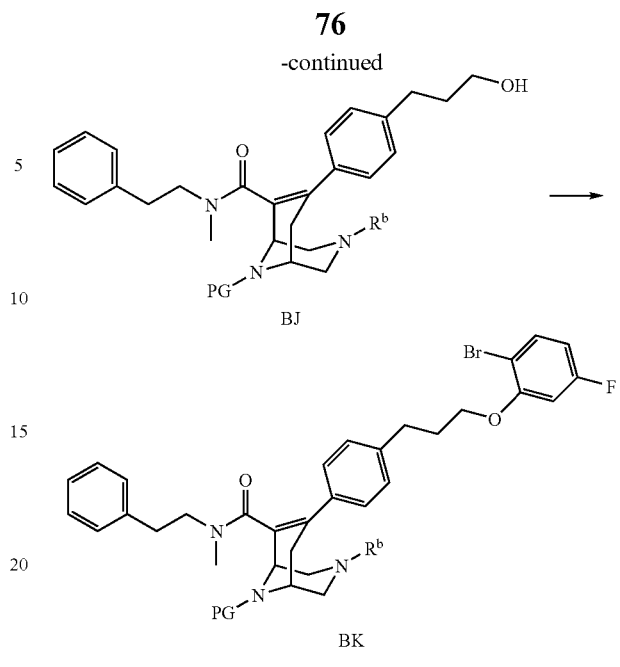

The compounds of formula I and their pharmaceutically acceptable acid addition salts can be used as medicaments, e. g. in the form of pharmaceutical preparations for enteral, parenteral, or topical administration. They can be administered, for example, perorally, e. g. in the form of tablets, coated tablets, drages, hard and soft gelatine capsules, solutions, emulsions or suspensions, rectally, e. g. in the form of suppositories, parenterally, e. g. in the form of injection solutions or infusion solutions, or topically, e. g. in the form of ointments, creams or oils.

The production of pharmaceutical preparations can be effected in a manner which will be familiar to any person skilled in the art by bringing the described compounds of formula I and their pharmaceutically acceptable acid addition salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid poyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injections are, for example, water, alcohols, polyols, glycerols and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifyg agents, consistency-improving agents, flavour-improving agents, salts for varying the osmotic pressure, buffer substances, solubilizers, colorants and masking agents and antioxidants come into consideration as pharmaceutical adjuvants.

The dosage of compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 50 mg to about 500 mg, comes into consideration.

The pharmaceutical preparations conveniently contain about 1-500 mg, preferably 5-200 mg of a compound of formula I.

The following examples serve to illustrate the present invention in more detail. They are, however, not intended to limit its scope in any manner.

EXAMPLES

General Remarks

The compounds were characterized at least by LC-MS and $^1$H-NMR. Only the LC-MS data are given here.

| Abbreviations | |
|---|---|
| AcCl | Acetyl chloride |
| ACE | Angiotensin Converting Enzyme |
| AcOH | Acetic acid |
| Ang | Angiotensin |
| aq. | aqueous |
| 9-BBN | 9-Borabicyclo[3.3.1]nonane |
| Bn | Benzyl |
| Boc | tert-Butyloxycarbonyl |
| BSA | Bovine serum albumine |
| BuLi | n-Butyllithium |
| CDI | 1,1-Carbonyldiimidazol |
| conc. | concentrated |
| DIBAL | Diisobutylaluminium hydride |
| DIPEA | Diisopropylethylamine |
| DMAP | 4-N,N-Dimethylaminopyridine |
| DMF | N,N-Dimethylformamide |
| DMSO | Dimethylsulfoxide |
| EDC•HCl | Ethyl-N,N-dimethylaminopropylcarbodiimide hydrochloride |
| EIA | Enzyme immunoassay |
| eq. | equivalent |
| Et | Ethyl |
| EtOAc | Ethyl acetate |
| FC | Flash Chromatography |
| HOBt | Hydroxybenzotriazol |
| KHMDS | Potassium hexamethyldisilazide |
| LAH | Lithium aluminium hydride |
| MeOH | Methanol |
| MPLC | Medium Pressure Liquid Chromatography |
| NMO | N-Methylmorpholine N-oxide |
| org. | organic |
| PG | protecting group |
| Ph | Phenyl |
| RAS | Renin Angiotensin System |
| RP18 | Reversed phase column, filled with $C_{18}$ hydrocarbon |
| rt | room temperature |
| SEM | Trimethylsilylethoxymethyl |
| sol. | Solution |
| TBAF | Tetra-n-butylammonium fluoride |
| TBDMS | tert-Butyldimethylsilyl |
| TBDPS | tert-Butyldiphenylsilyl |
| tBuOH | tert-Butanol |
| tBuOK | Potassium tert-butylate |
| Tf | Trifluoromethylsulfonyl |
| TFA | Trifluoroacetic acid |
| THF | Tetrahydrofuran |
| TLC | Thin Layer Chromatography |
| TMAD | N,N,N',N'-Tetramethylazodicarboxamide |

Preparation of the Precursors (rac.)-(1R*,5S*)-9-Methyl-7-oxo-3,9-diazabicyclo[3.3.1]nonane-3,6-dicarboxylic acid 3-tert-butyl ester 6-ethyl ester (A)

(4-Benzyl-6-ethoxycarbonylmethyl-1-methyl-piperazin-2-yl)acetic acid ethyl ester (Patent WO 92/05174) (71.0 g, 0.196 mol) was dissolved in MeOH (400 mL). TFA (77.8 mL, 1.02 mol) was added and the flask was purged with nitrogen. Pd/C (10%, 50% moisture, 3.6 g) was added. The flask was closed and purged with hydrogen (3×). After 1 day, the mixture was filtered through Celite and washed with MeOH. The solvents were removed under reduced pressure and the foamy residue (92.7 g) was dried under high vacuum. A sol. of tBuOK (117.2 g, 1.04 mol) in toluene (3.07 L) was heated to reflux. A sol. of the crude piperazine formerly obtained, dissolved in THF (300 mL), was added dropwise over 50 min. The black mixture was stirred for 10 further min. and allowed to cool to rt. The mixture was cooled to 0° C. and AcOH (36.6 mL, 0.635 mol) was added. The solvents were removed under reduced pressure. This crude material was suspended in $CH_2Cl_2$ (400 mL) and cooled to 0° C. DIPEA (19.1 mL, 112 mmol) was added. A sol. of $Boc_2O$ (24.3 g, 113 mmol) in $CH_2Cl_2$ (200 mL) was added dropwise. The mixture was stirred for 1 h at 0° C., then 1 h at rt. The mixture was washed with aq. 10% $Na_2CO_3$ (2×). The org. extracts were dried over $MgSO_4$, filtered and the solvents were evaporated under reduced pressure. The residue was purified by FC (EtOAc/heptane 1:1→EtOAc). The title compound was obtained as oil (24.5 g, 38%). $R_f$=0.05 (EtOAc/heptane 1:1) or 0.56 (MeOH/$CH_2Cl_2$ 1:9). LC-MS: $R_t$=2.94; ES+: 325.19.

(rac.)-(1R*,5S*)-9-Methyl-7-trifluoromethanesulfonyloxy-3,9-diazabicyclo-[3.3.1]non-6-ene-3,6-dicarboxylic acid 3-tert-butyl ester 6-ethyl ester (B)

A sol. of bicyclononanone A (2.22 g, 6.80 mmol) in THF (50 mL) was cooled to 0° C. and NaH (about 60% in mineral oil, 326 mg, about 8.2 mmol) was added. A gas evolution was observed. After 20 min, $Tf_2NPh$ (3.22 g, 9.00 mmol) was added. 10 min later, the ice bath was removed. After 3 h, the sol. was diluted with EtOAc and washed with brine (1×). The org. extracts were dried over $MgSO_4$, filtered, and the solvents were removed under reduced pressure. Purification by FC (EtOAc/heptane 3:1→EtOAc) yielded the title compound as an oil (2.50 g, 80%). $R_f$=0.15 (EtOAc/heptane 1:1). LC-MS: $R_t$=4.73; ES+: 458.95.

Compounds of Type C 3-(4Bromophenyl)prop-1-yl 2-chlorophenyl ether (C1)

To a sol. of 3-(4-bromophenyl)propan-1-ol (Glover S. A., et al.; *Tetrahearon*, 1990, 46, 7247; 24.5 g, 0.114 mol) in toluene (600 mL) under nitrogen were added 2-chlorophenol (17.4 mL, 0.171 mmol), diisopropyl azodicarboxylate (33.1 mL, 0.171 mol) and tri-n-butylphosphine (42.2 mL, 0.171 mol). The sol. was heated to reflux and stirred under reflux overnight. The sol. was allowed to cool to rt and the solvents were removed under reduced pressure. The residue was diluted in EtOAc and washed with aq. 1M HCl (1×) and aq. 1M NaOH (2×). The org. extracts were dried over $MgSO_4$, filtered and the solvents were removed under reduced pressure. Purification of the residue by FC (petroleum ether→$Et_2O$/petroleum ether 1:99→1:19) led to the tide compound (15.1 g, 41%). $R_f$=0.70 (EtOAc/heptane 1:3).

2-(4-Bromophenyl)eth-1-yl 2,3,5-trimethylphenyl ether (C2)

A mixture of 2-(4-bromophenyl)ethanol (20.0 mL, 143 mmol), 2,3,5-trimethylphenol (31.1 g, 229 mmol), azodicarboxylic dipiperidide (72.1 g, 286 mmol) and tributylphosphine (88 mL; 357 mmol) in toluene (2.00 L) was heated to reflux for 2 h. The mixture was allowed to cool to rt. The mixture was filtered, washed with toluene and the solvents were partially removed under reduced pressure. The residue was diluted with $Et_2O$ and washed with aq. 1M NaOH (2×). The org. extracts were dried over $MgSO_4$, filtered, and the solvents were removed under reduced pressure. Purification of the residue by FC (petroleum ether→$Et_2O$/petroleum ether 1:3) yielded the title compound (33.1 g, 73%). LC-MS: $R_t$=6.95.

1-Bromo-4-[3-(2-methoxybenzyl)propoxy]benzene (E)

4-Bromophenol (4.32 g, 25.0 mmol) and 1-(3chloropropoxymethyl)-2-methoxy-benzene (Vieira E., et al., *Bioorg. Med. Chem. Letters,* 1999, 9, 1397,4.88 g, 22.7 mmoL) were dissolved in DMF (150 mL). NaI (1.50 g, 0.10 mmol) and $Cs_2CO_3$ (16.3 g, 50.0 mmol) were added. The mixture was heated to 80° C. and stirred for 6 h, before it was allowed to cool to rt. After dilution with EtOAc (600 mL) the mixture was washed with water (1×), aq. 1M NaOH (1×). aq. 1M HCl (1×). The org. extracts were dried over $MgSO_4$ and filtered. The solvents were removed under reduced pressure. Purification of the residue by FC ($Et_2O$/petroleum ether 1:9→1:4) yielded the title compound (5.66 g, 71%). $R_f$=0.60 ($Et_2O$/heptane 1:1).

5-Bromo-2-[3-(2-methoxybenzyloxy)propoxy]pyridine (F)

3-(5-Bromopyridin-2-yloxy)propan-1-ol (Patent Application WO 98/39328, 1.05 g, 4.51 mmol) was diluted at rt in DMF (24 ml) and the sol. cooled to 0° C. NaH (55-65 weight % in mineral oil, 193 mg, 4.42-5.23 mmol) was added and the yellow mixture was stirred for 20 min. 2-Methoxybenzyl chloride (1.49 ml, 10.7 mmol) was added and the solution was allowed to warm to rt and was stirred for 4 h. The mixture was quenched with ice and diluted with EtOAc (20 ml), washed with brine and water, dried over $MgSO_4$ and filtered. The solvents were evaporated under reduced pressure. Purification of the residue by FC ($Et_2O$, heptane 1:39→1:19) yielded the title compound (627 mg, 40%) as an oil. $R_f$=0.07 ($Et_2O$/heptane, 1:3).

Compounds of Type G

(rac.)-(1R*,5S*)-9-Methyl-7-[4-(2-trimethylsilanylethoxymethoxy)phenyl]-3,9-diazabicyclo[3.3.1]non-6-ene-3,6-dicarboxylic acid 3-tert-butyl ester 6-ethyl ester (G1)

A sol. of [2-(4-bromophenoxymethoxy)ethyl]trimethylsilane (Blass B. E., et al., *Tetrahedron Lett.,* 2001, 42, 1611, 4.13 g, 13.6 mmol) in THF (30 mL) was cooled to −78° C. BuLi (1.6M in hexane, 9.1 mL, 14.6 mmol) was added. The sol. was stirred at −78° C. for 30 min. A sol. of $ZnCl_2$, prepared from $ZnCl_2$ (2.23 g, about 16.4 mmol) dried under high vacuum for 2 h at 140° C. and THF (35 mL), was added and the resulting sol. was allowed to warm up to rt. A sol. of bicyclononene B (2.50 g, 5.45 mmol) in THF (5 mL) and then $Pd(PPh_3)_4$ (157 mg, 0.136 mmol) were added. After 10 min, the reaction mixture was heated to reflux. After 90 min, the reaction mixture was allowed to cool to rt and quenched with aq. 1M HCl. The mixture was diluted with EtOAc and washed with aq. 10% $Na_2CO_3$ (1×). The org. extracts were dried over $MgSO_4$ and filtered. The solvents were removed under reduced pressure. Purification of the residue by FC (MeOH/$CH_2Cl_2$ 1:39→1:24→1:20) yielded the title compound as an oil (2.90 g, 99%). $R_f$=0.39 (MeOH/$CH_2Cl_2$ 1:9). LC-MS: $R_t$=4.35; ES+: 533.29.

(rac.)-(1R*,5S*)-7-{4-[2-(tert-Butldimethylsilanyloxy)ethyl]phenyl}-9-methyl-3,9-diazabicyclo[3.3.1]non-6-ene-3,6-dicarboxylic acid 3-tert-butyl ester 6-ethyl ester (G2)

A sol. of [2-(4-bromophenyl)ethoxy]-tert-butyldimethylsilane (Fuji K, et al., *Tetrahedron Lett.,* 1990, 31, 6553, 21.8 g, 69.1 mmol) in THF (250 mL) was cooled to −78° C. BuLi (1.55M in hexane, 44.6 mL, 69.1 mmol) was added. The sol. turned temporarily orange, then yellowish. After 30 min, $ZnCl_2$ (1M in THF, 70 mL, 70 mmol, prepared as described for G1) was added. The sol. was allowed to warm up to rt. Vinyl triflate B (12.91 g, 28.2 mmol) dissolved in THF (20 mL), and $Pd(PPh_3)_4$ (600 mg, 0.519 mmol) were added. The sol. was stirred at rt for 90 min and aq. 1M HCl (1 mL) was then added. The mixture was diluted in EtOAc and washed with aq. 1M NaOH (1×). The org. extracts were dried over $MgSO_4$, filtered, and the solvents were removed under reduced pressure. Purification of the residue by FC (MeOH/$CH_2Cl_2$ 1:49→1:24→3:47→2:25) yielded the title compound (10.91 g, 71%). $R_f$=0.65 (MeOH/$CH_2Cl_2$ 1:9). LC-MS: $R_t$=5.32, ES+: 545.49.

(rac.)-(1R*,5S*)-7-{4-[3-(tert-Butyldimethylsilanyloxy)propyl]phenyl}-9-methyl-3,9-diazabicyclo[3.3.1]non-6-ene-3,6-dicarboxylic acid 3-tert-butyl ester 6-ethyl ester (G3)

A sol. of [3-(4-bromophenyl)propoxy]-tert-butyldimethylsilane (Kiesewetter D. O., *Tetrahedron Asymmetry,* 1993, 4, 2183, 22.60 g, 68.6 mmol) in THF (250 mL) was cooled to −78° C. BuLi (1.55M in hexane, 44.3 mL, 68.6 mmol) was added. The sol. turned orange, then dark green. After 30 min, $ZnCl_2$ (1M in THF, 69 mL, 69 mmol, prepared as described for G2) was added, whereas the sol. turned deep yellow. The mixture was allowed to warm up to rt. Vinyl triflate B (12.91 g, 28.2 mmol) in THF (20 mL) and then $Pd(PPh_3)_4$ (600 mg, 0.519 mmol) were added. The mixture was stirred at rt for 90 min and aq. 1M HCl (1 mL) was added. The mixture was diluted with EtOAc and washed with aq. 1M NaOH (1×). The org. extracts were dried over $MgSO_4$, filtered and the solvents were removed under reduced pressure. Purification of the residue by FC (MeOH/$CH_2Cl_2$ 1:49→1:24→3:47→2:23) yielded the title product (10.76 g, 70%). $R_f$=0.60 (MeOH/$CH_2Cl_2$ 1:9). LC-MS: $R_t$=4.95; ES+: 559.51.

(rac.)-(1R*,5S*)-7-{6-[3-(2Methoxybenzyloxy)propoxy]pyridin-3-yl}-9-methyl-3,9-diazabicyclo[3.3.1]non-6-ene-3,6-dicarboxylic acid 3-tert-butyl ester 6-ethyl ester (G4)

A sol. of bromopyridinyl derivative F (300 mg, 852 µmol) in THF (10 ml) was cooled to −78° C. BuLi (1.55M in hexane, 0.580 ml, 889 µmol) was added and the mixture was stirred for 30 min. ZnCl$_2$ (1M in THF, 0.94 ml, 0.94 mmol, prepared as described for G2) was added and the reaction mixture was allowed to warm up to rt. Vinyl triflate B (259 mg, 596 µmol) in THF (1 ml), was added, followed by Pd(PPh$_3$)$_4$ (20.4 mg, 16.6 µmol). The mixture was refluxed for 2 h. The reaction was terminated upon addition of ice. After dilution with EtOAc (125 ml), the reaction mixture was washed with 10% aq. Na$_2$CO$_3$ and the org. extracts were dried over MgSO$_4$ and filtered. The solvents were evaporated under reduced pressure. Purification of the residue by FC (CH$_2$Cl$_2$/MeOH: 39:1→29:1→24:1→19:1→9:1) led to title compound (197 mg, 54%). R$_f$=0.35 (CH$_2$Cl$_2$/MeOH 9:1). LC-MS: R$_t$=4.06; ES+: 582.78.

(rac.)-(1R*,5S*)-7-{4-[3-(2-Methoxybenzyloxy)propoxy]phenyl}-9-methyl-3,9-diazabicyclo[3.3.1]non-6-ene-3,6-dicarboxylic acid 3-tert-butyl ester 6-ethyl ester (G5)

A sol. of bromophenyl derivative E (5.60 g, 15.9 mmol) in THF (50 mL) was cooled to −78° C. BuLi (1.55M in hexane, 10.3 mL, 15.9 mmol) was added. The sol. was stirred at −78° C. for 30 min and ZnCl$_2$ (1M in THF, 17.5 mL, 17.5 mmol, prepared as described for G2) was added. After warming up to rt, a sol. of vinyl triflate B (3.63 g, 7.90 mmol) in THF (5 mL), followed by Pd(PPh$_3$)$_4$ (205 mg, 0.177 mmol), were added. The mixture was heated to reflux while turning black. After 1 h, the reaction mixture was allowed to cool to rt. Ice was added and the mixture was diluted in EtOAc. The org. extracts were washed with aq. 1M NaOH (1×) and dried over MgSO$_4$. The solvents were removed under reduced pressure. Purification of the residue by FC (MeOH/CH$_2$Cl$_2$ 1:49→3:97→1:24→1:19→1:9) yielded the title compound (4.57 g, 99%). R$_f$=0.50 (MeOH/CH$_2$Cl$_2$ 1:9). LC-MS: R$_t$=4.17; ES+: 581.60.

(rac.)-(1R*,5S*)-7-{4-[3-(2-Chlorophenoxy)propyl]phenyl}-9-methyl-3,9-diazabicyclo[3.3.1]non-6-ene-3,6-dicarboxylic acid 3-tert-butyl ester 6-ethyl ester (G6)

A sol. of bromophenyl derivative C1 (16.0 g, 49.0 mmol) in THF (700 mL) was cooled to −78° C. BuLi (1.55M in hexane, 34.8 mL, 54.0 mmol) was added. The sol. was stirred at −78° C. for 30 min and ZnCl$_2$ (1M in THF, 54.0 mL, 54.0 mmol, prepared as described for G2) was added. After warming up to rt, a sol. of vinyl triflate B (15.0 g, 32.7 mmol) in THF (50 mL), followed by Pd(PPh$_3$)$_4$ (945 mg, 0.818 mmol), were added. The Sol. was heated to reflux. After 30 min, the reaction mixture was allowed to cool to rt. Ice was added and the mixture was diluted in EtOAc. The org. phase was washed with aq. 1M NaOH (1×) and dried over MgSO$_4$. The solvents were removed under reduced pressure. Purification of the residue by FC (MeOH/CH$_2$Cl$_2$ 1:49→3:97→1:24→1:19→1:9) yielded the title compound (10.5 g, 58%). LC-MS: R$_t$=4.41; ES+: 555.13.

(rac.)-(1R*,5S*)-7-{4-[2-(tert-Butydimethylsilanyloxy)ethoxy]phenyl}-9-methyl-3,9-diazabicyclo[3.3.1]non-6-ene-3,6-dicarboxylic acid 3-tert-butyl ester 6-ethyl ester (G7)

BuLi (1.6M in hexane, 218 mL, 350 mmol) was added to a sol. of [2-(4-bromophenoxy)ethoxy]-tert-butyldimethylsilane (Morita, C.; et al.; *Heterocycles*, 2000, 52, 1163; 129 g, 342 mmol) in THF (1.0 L) at −78° C. The mixture was stirred for 1 h at −78° C., and ZnCl$_2$ (1M in THF, 400 mL, 400 mmol, prepared as described for G2) was added. The mixture was allowed to warm up to rt. Bicyclononene B (78.4 g, 171 mmol) and Pd(PPh$_3$)$_4$ (4.94 g, 4.28 mmol) were added. The mixture was heated to reflux for 0.5 h, and was allowed to cool to rt. Aq. 1M HCl (2 mL) was added. The mixture was diluted with EtOAc (2 L) and washed with aq. 1M NaOH (750 mL). The aq. extracts were extracted back with EtOAc (1×). The combined org. extracts were dried over MgSO$_4$, filtered, and the solvents were removed under reduced pressure. Purification of the residue by FC (MeOH/CH$_2$Cl$_2$ 1:49→1:24→3:47→2:23) yielded the title compound (87.7 g, 91%). R$_f$=0.60 (MeOH/CH2Cl2 1:9). LC-MS: R$_t$=4.74; ES+: 561.41.

(rac.)-(1R*,5S*)-7-{4-[2-(tert-Butyldiphenylsilanyloxy)ethyl]phenyl}-9-methyl-3,9-diazabicyclo[3.3.1]non-6-ene-3,6-dicarboxylic acid 3-tert-butyl ester 6-ethyl ester (G8)

BuLi (1.5M in hexane, 13.4 mL, 20 mmol) was added to a sol. [2-(4bromophenyl)ethoxy]-tert-butyldiphenylsilane (8.79 g, 20.0 mmol, prepared from 2-(4-bromophenyl)ethanol, TBDPS-Cl and imidazol in DMF) in THF (40 mL) at −78° C. The mixture was stirred for 30 min at −78° C., and ZnCl$_2$ (1M in THF, 24 mL, 24 mmol, prepared as described for G2) was added. The mixture was allowed to warm up to rt. Bicyclononene B (3.67 g, 8.00 mmol) and Pd(PPh$_3$)$_4$ (231 mg, 0.20 mmol) were added. The mixture was heated to 40° C. for 40 min, and was allowed to cool to rt. Aq. 1M HCl (2 mL) was added. The mixture was diluted with EtOAc and washed with aq. 1M NaOH. The aq. extracts were extracted back with EtOAc (1×). The combined org. extracts were dried over MgSO$_4$, filtered, and the solvents were removed under reduced pressure. Purification of the residue by FC (MeOH/CH$_2$Cl$_2$ 1:49→1:24→3:47→2:23) yielded the title compound (4.32 g, 81%). LC-MS: R$_t$=1.06; ES+: 669.49.

Compounds of Type H

(rac.)-(1R*,5S*)-7-[4-(2-Trimethylsilanylethoxymethoxy)phenyl]-3,9-diazabicyclo[3.3.1]non-6-ene-3,6,9-tricarboxylic acid 3-tert-butyl ester 6-ethyl ester 9-(2,2,2-trichloro-1,1-dimethylethyl) ester (H1)

β,β,β-Trichloro-tert-butyl chloroformate (6.60 g, 27.5 mmol) was added to a sol. of bicyclononene G1 (2.93 g, 5.50 mmol) in 1,2dichloroethane (60 mL). The sol. was heated to reflux. After 3 h, the reaction mixture was allowed to cool to rt, and the solvents were removed under reduced pressure. Purification of the residue by FC (EtOAc/heptane 1:4→1:3→2:3→1:1) yielded the title compound as an oil (3.31 g, 83%). R$_f$=0.52 (EtOAc/heptane 1:1). LC-MS: R$_t$=7.40; ES+: 742.52.

(rac.)-(1R*,5S*)-7-{4-[2-(tert-Butyldimethylsilany-loxy)ethyl]phenyl}-3,9-diazabicyclo[3.3.1]non-6-ene-3,6,9-tricarboxylic acid 3-tert-butyl ester 6-ethyl ester 9-(2,2,2-trichloro-1,1-dimethylethyl) ester (H2)

As for the preparation of compound H1, from bicyclonon-ene G2 (10.91 g, 20.0 mmol), β,β,β-trichloro-tert-butyl chloroformate (24.0 g, 100 mmol), and 1,2-dichloroethane (210 mL). Purification of the residue FC (EtOAc/heptane 1:9→1:4→2:3) yielded the title compound (13.75 g, 94%). $R_f$=0.64 (EtOAc/heptane 1:1). LC-MS: $R_t$=7.66; ES+: 755.37.

(rac.)-(1R*,5S*)-7-{4-[3-(tert-Butyldimethylsilany-loxy)propyl]phenyl}-3,9-diazabicyclo[3.3.1]non4-ene-3,6,9-tricarboxylic acid 3-tert-butyl ester 6-ethyl ester 9-(2,2,2-trichloro-1,1-dimethylethyl) ester (H3)

As for the preparation of compound H1, from bicyclonon-ene G3 (10.96 g, 19.6 mmol), β,β,β-trichloro-tert-butyl chloroformate (23.5 g, 98.1 mmol), and 1,2-dichloroethane (210 mL). Purification of the residue by FC (EtOAc/heptane 1:9→1:4→2:3) yielded the title compound (13.50 g, 92%). $R_f$=0.58 (EtOAc/heptane 1:1). LC-MS: $R_t$=7.79; ES+: 769.49.

(rac.)-(1R*,5S*)-7-{6-[3-(2-Methoxybenzyloxy)propoxy]pyridin3-yl}-3,9-diazabicyclo[3.3.1]non-6-ene-3,6,9-tricarboxylic acid 3-tert-butyl ester 6-ethyl ester 9-(2,2,2-trichloro-1,1-dimethylethyl) ester (H4)

As for the preparation of compound H1, from bicyclonon-ene G4 (373 mg, 0.642 mmol), β,β,β-trichloro-tert-butyl chloroformate (770 mg, 3.11 mmol), and 1,2-dichloroethane (8 mL). Purification of the residue by FC (EtOAc/heptane 1:9→1:4→1:3) yielded the title compound (382 mg, 77%). $R_f$=0.47 (EtOAc/heptane 1:1). LC-MS: $R_t$=7.14; ES+: 770.50.

(rac.)-(1R*,5S*)-7-{4-[3-(2-Methoxybenzyloxy)propoxy]phenyl}-3,9-diazabicyclo[3.3.1]non-6-ene-3,6,9-tricarboxylic acid 3-tert-butyl ester 6-ethyl ester 9-(2,2,2-trichloro-1,1-dimethylethyl) ester (H5)

As for the preparation of compound H1, from bicyclonon-ene G5 (4.57 g, 7.87 mmol), β,β,β-trichloro-tert-butyl chloroformate (9.44 g, 39.4 mmol), and 1,2-dichloroethane (100 mL). Purification of the residue by FC (EtOAc/heptane 1:9→1:4→1:1) yielded the title compound (5.35 g, 88%). $R_f$=0.46 (EtOAc/heptane 1:1).

(rac.)-(1R*,5S*)-7-{4-[3-(2-Chlorophenoxy)propyl]phenyl}-3,9-diazabicyclo-[3.3.1]non-6-ene-3,6,9-tricarboxylic acid 3-tert-butyl ester 6-ethyl ester 9-(2,2,2-trichloro-1,1-dimethylethyl) ester (H6)

As for the preparation of compound H1, from bicyclonon-ene G6 (10.51 g, 18.9 mmol), β,β,β-trichloro-tert-butyl chloroformate (22.7 g, 94.7 mmol), and 1,2-dichloroethane (350 mL). Purification of the residue by FC (EtOAc/heptane 1:8→1:4→1:1) yielded the title compound (12.5 g, 88%).

(rac.)-(1R*,5S*)-7-{4-[2-(tert-Butyldimethylsilany-loxy)ethoxy]phenyl}-3,9-diazabicyclo[3.3.1]non-6-ene-3,6,9-tricarboxylic acid 3-tert-butyl ester 6-ethyl ester 9-(2,2,2-trichloro-1,1-dimethylethyl) ester (H7)

As for the preparation of compound H1, from bicyclonon-ene G7 (87.7 g, 156 mmol), β,β,β-trichloro-tert-butyl chloroformate (188 g, 784 mmol), and 1,2-dichloroethane (1.75 L). Purification of the residue by FC (EtOAc/heptane 1:19→1:3) yielded the title compound (111 g, 95%). $R_f$=0.75 (EtOAc/heptane 1:1). LC-MS: $R_t$=7.84.

(rac)-(1R*,5S*)-7-{4-[2-(tert-Butyldiphenylsilany-loxy)ethyl]phenyl}-3,9-diazabicyclo[3.3.1]non-6-ene-3,6,9-tricarboxylic acid 3-tert-butyl ester 6-ethyl ester 9-(2,2,2-trichloro-1,1-dimethylethyl) ester (H8)

As for the preparation of compound H1, from bicyclonon-ene G8 (4.32 g, 6.46 mmol), β,β,β-trichloro-tert-butyl chloroformate (7.75 g, 32.3 mmol), and 1,2-dichloroethane (100 mL). Purification of the residue by FC (EtOAc/heptane 1:19→1:3) yielded the title compound (4.97 g, 90%). $R_f$=0.75 (EtOAc/heptane 1:1). LC-MS: $R_t$=1.35.

Compounds of Type J (rac)-(1R*,5S*)-6-Hydroxymethyl-7-[4-(2-trimeth-ylsilanylethoxymethoxy)-phenyl]-3,9-diazabicyclo[3.3.1]non-6-ene-3,9-dicarboxylic acid 3-tert-butyl ester 9-(2,2,2-trichloro-1,1-dimethylethyl) ester (J1)

A sol. of bicyclononene H1 (3.31 g, 4.58 mmol) in $CH_2Cl_2$ (60 mL) was cooled to −78° C. DIBAL (1M in toluene, 10.1 mL, 10.1 mmol) was added. The sol. was stirred for 30 min at −78° C. and was then allowed to warm slowly. DIBAL (5 mL) was added again after 1.5 h (−65° C.). Later, DIBAL was added successively in 5 mL-portions until TLC displayed no more starting material. Ice and water were then added at −50° C. The cold bath was removed and the mixture warmed slowly to rt. More $CH_2Cl_2$ was added and the mixture was washed with aq. 1M HCl. The aq. phase was extracted with $CH_2Cl_2$ (1×) and the combined org. extracts were dried over $MgSO_4$. After filtration and evaporation of the solvents under reduced pressure, the residue was purified by FC (EtOAc/heptane 1:4→1:3→2:3) to yield the title compound as an oil (1.89 g, 60%). $R_f$=0.50 (EtOAc/heptane 1:1). LC-MS: $R_t$=7.08; ES+: 661.38, 702.83.

(rac.)-(1R*,5S*)-7-{4-2-(tert-Butyldimethylsilany-loxy)ethyl]phenyl}-6-hydroxymethyl-3,9-diazabicy-clo[3.3.1]non-6-ene-3,9-dicarboxylic acid 3-tert-butyl ester 9-(2,2,2-trichloro-1,1-dimethylethyl) ester (J2)

To a sol. of bicyclononene H2 (1.57 g, 2.32 mmol) in $CH_2Cl_2$ (40 mL) at −78° C. DIBAL (1M in toluene, 5.80 mL, 5.80 mmol) was added. The sol. was stirred at −78° C. for 1 h. Ice was added, and the mixture was allowed to warm up to rt. More $CH_2Cl_2$ was added and the org. extracts were washed with aq. 1M HCl (1×), dried over $MgSO_4$ and filtered. The solvents were removed under reduced pressure. Purification of the residue by FC (EtOAc/heptane 1:3) yielded the title compound (868 mg, 59%). LC-MS: $R_t$=7.38; ES+: 715.48.

(rac.)-(1R*,5S*)-7-{4-[3-(tert-Butyldimethylsilanyloxy)propyl]phenyl}-6-hydroxymethyl-3,9-diazabicyclo[3.3.1]non-6-ene-3,9-dicarboxylic acid 3-tert-butyl ester 9-(2,2,2-trichloro-1,1-dimethylethyl) ester (J3)

A sol. of bicyclononene H3 (2.39 g, 3.20 mmol) in $CH_2Cl_2$ (55 mL) was cooled to −78° C. DIBAL (1M in toluene, 8.00 mL, 8.00 mmol) was added and the mixture was stirred at −78° C. for 1 h Ice was added, and the mixture was allowed to warm up to rt. More $CH_2Cl_2$ was added and the org. extracts were washed with aq. 1M HCl (1×), dried over $MgSO_4$ and filtered. The solvents were removed under reduced pressure. Purification of the residue by FC (EtOAc/heptane 1:3) yielded the title compound (1.34 g, 59%). LC-MS: $R_t$=7.59; ES+: 727.54.

(rac.)-(1R*,5S*)-6-Hydroxymethyl-7-{6-[3-(2-methoxybenzyloxy)propoxy]-pyridin-3-yl}-3,9-diazabicyclo[3.3.1]non-6-ene-3,9-dicarboxylic acid 3-tert-butyl ester 9-(2,2,2-trichloro-1,1-dimethylethyl) ester (J4)

A sol. of bicyclononene H4 (345 mg, 0.447 mmol) in $CH_2Cl_2$ (10 mL) was cooled to −78° C. DIBAL (1M in toluene, 1.92 mL, 1.92 mmol) was added. The mixture was stirred at −78° C. for 1 h and again two portions of DIBAL (0.50 mL, 0.50 mmol) were added successively. After 2 h, ice was added. The mixture was allowed to warm up to rt and was diluted with more $CH_2Cl_2$. The org. extracts were washed with aq. 10% $Na_2CO_3$ (2×), dried over $MgSO_4$ and filtered. The solvents were removed under reduced pressure. Purification of the residue by FC (EtOAc/heptane 1:4→1:3→2:3→3:1) yielded the title compound (122 mg, 37%). $R_f$=0.36 (EtOAc/heptane 1:1). LC-MS: $R_t$=6.51; ES+: 728.49.

(rac.)-(1R*,5S*)-6-Hydroxymethyl-7-(4-hydroxyphenyl)-3,9-diazabicyclo-[3.3.1]non-6-ene-3,9-dicarboxylic acid 3-tert-butyl ester 9-(2,2,2-trichloro-1,1-dimethylethyl) ester (K)

To a sol. of bicyclononene J1 (1.89 g, 2.79 mmol) in THF/MeOH (1:1, 20 mL), a sol. of conc. $H_2SO_4$ (0.100 mL) in MeOH (10 mL) was added. The mixture was stirred for 3 h at rt. The reaction mixture was diluted with EtOAc, washed with brine (1×) and aq. sat. $NaHCO_3$ (1×). The org. extracts were dried over $MgSO_4$ and filtered. The solvents were removed under reduced pressure. Crystalliztion of the residue from EtOAc/heptane led to the title compound (1.03 g, 67%). $R_f$=0.14 (EtOAc/heptane 1:1). LC-MS: $R_t$=5.17; ES=: 547.06.

(rac.)-(1R*,5S*)-6-Hydroxymethyl-7-{4-[3-(2-methoxybenzyloxy)propoxy]-phenyl}-3,9-diazabicyclo[3.3.1]non-6-ene-3,9-dicarboxylic acid 3-tert-butyl ester 9-(2,2,2-trichloro-1,1-dimethylethyl) ester (L)

To a sol. of bicyclononene K (1.03 g, 1.87 mmol) in DMF (20 mL) were added NaI (280 mg, 1.87 mmol), $Cs_2CO_3$ (609 mg, 1.87 mmol) and then 1-(3-chloropropoxymethyl)-2-methoxybenzene (Vieira E., et al., *Bioorg. Med. Chem. Letters*, 1999, 9, 1397, 400 mg, 1.87 mmol). The mixture was stirred at 100° C. After 1.5 h, another portion of $Cs_2CO_3$ (609 mg, 1.87 mmol) and 1-(3-chloropropoxymethyl)-2-methoxybenzene chloride (400 mg, 1.87 mmol) were added to complete the reaction. After 1.5 h later, the mixture was allowed to cool to rt and diluted with EtOAc. The org. extracts were washed with brine (1×). The org. extracts were dried over $MgSO_4$ and filtered. The solvents were removed under reduced pressure. Purification of the residue by FC EtOAc/eptane 1:4→1:3→2:3) yielded the title compound (1.00 g, 73%). $R_f$=0.35 (EtOAc/heptane 1:1). LC-MS: $R_t$=6.54.

(rac.)-(1R*,5S*)-7-{4-[3-(2-Methoxybenzyloxy)propoxy]phenyl}-6-[2-(2-methoxyphenyl)acetoxymethyl]-3,9-diazabicyclo[3.3.1]non-6-ene-3,9-dicarboxylic acid 3-tert-butyl ester 9-(2,2,2-trichloro-1,1-dimethylethyl) ester (M)

To a sol. of bicyclononene L (500 mg, 0.687 mmol) in $CH_2Cl_2$ (10 mL) were added (2-methoxyphenyl)acetic acid (206 mg, 1.37 mmol), DMAP (cat. amount), DIPEA (0.230 mL, 1.34 mmol) and EDC.HCl (134 mg, 0.700 mmol). The sol. was stirred at rt for 90 min, when a second portion of DIPEA (0.100 mL, 0.584 mmol) was added. After 3 h, the reaction mixture was diluted in more $CH_2Cl_2$ and washed with water (1×). The org. extracts were dried over $MgSO_4$, filtered, and the solvents were removed under reduced pressure. Purification of the residue by FC (EtOAc/heptane 1:4→1:3→2:3) yielded the title compound (495 mg, 82%). $R_f$=0.42 (EtOAc/heptane 1:1). LC-MS: $R_t$=7.33; ES+: 897.33.

(rac.)-(1R*,5S*)-7-{4-[3-(2-Methoxybenzyloxy)propoxy]phenyl}-6-[2-(2-methoxyphenyl)acetoxymethyl]-3,9-diazabicyclo[3.3.1]non-6-ene-9-carboxylic acid 2,2,2-trichloro-1,1-dimethylethyl ester hydrochloride salt (N)

A mixture of $CH_2Cl_2$ (3 mL) and HCl/dioxane (4M, 1 mL) was slowly added to bicyclononene M (495 mg, 0.585 mmol) in an ice bath. The resulting sol. was stirred at 0° C. After 1 h, HCl/dioxane (4M, 0.5 mL) was added, and 1 h later the ice bath was removed. After 75 min, the solvents were removed under reduced pressure and the residue dried under high vacuum. The resulting foam was estimated to contain about 80% of the title compound according to LC-MS and was used without further purification. LC-MS: $R_t$=4.97; ES+: 774.97.

(rac.)-(1R*,5S*)-6-[2-(2-Methoxyphenyl)acetoxymethyl]-7-{6-[3-(2-methoxybenzyloxy)propoxy]pyridin-3-yl}-3,9-diazabicyclo[3.3.1]non-6-ene-3,9-dicarboxylic acid 3-tert-butyl ester 9-(2,2,2-trichloro-1,1-dimethylethyl) ester (O)

To a sol. of bicyclononene J4 (122 mg, 0.167 mmol) in $CH_2Cl_2$ (5 mL) were added (2-methoxyphenyl)acetic acid (50 mg, 0.328 mmol), DIPEA (0.126 mL, 0.740 mmol), DMAP (cat. amount) and EDC.HCl (34 mg, 0.173 mmol). The mixture was stirred at rt for 3 h, then diluted in $CH_2Cl_2$, and washed with washed with water (1×). The org. extracts were dried over $MgSO_4$ and filtered. The solvents were removed under reduced pressure. Purification of the residue by FC (EtOAc/heptane 1:4→1:3→2:3→1:1) yielded the title compound (108 mg, 74%). LC-MS: $R_t$=7.34; ES+: 876.54.

(rac.)-(1R*,5S*)-7-{6-[3-(2-Methoxybenzyloxy)propoxy]pyridin-3-yl}-6-[2-(2-methoxyphenyl)acetoxymethyl]-3,9-diazabicyclo[3.3.1]non-6-ene-9-carboxylic acid 2,2,2-trichloro-1,1-dimethylethyl ester dihydrochloride salt (P)

Bicyclononene O (114 mg, 0.130 mmol) was dissolved in $CH_2Cl_2$ (2 mL). The sol. was cooled to 40° C. and 4M HCl/

Compounds of Type Q (rac.)-(1R*,5S*)-7-{4-[2-(tert-Butyldimethylsilanyloxy)ethyl]phenyl}-6-[2-(2-methoxyphenyl)acetoxymethyl]-3,9-diazabicyclo[3.3.1]non-6-ene-3,9-dicarboxylic acid 3-tert-butyl ester 9-(2,2,2-trichloro-1,1-dimethylethyl) ester (Q1)

To a sol. of bicyclononene J2 (868 mg, 1.25 mmol) in $CH_2Cl_2$ (20 mL) were added (2-methoxyphenyl)acetic acid (343 mg, 2.06 mmol), DIPEA (0.652 mL, 3.81 mmol), DMAP (cat. amount), and EDC.HCl (201 mg, 1.05 mmol). The mixture was stirred at rt for 1 h and EDC.HCl (73 mg, 0.38 mmol) and DIPEA (0.163 mmol, 0.952 mmol) were added again. After 30 min. the reaction mixture was diluted with $CH_2Cl_2$, washed with aq. 1M HCl (1×), and aq. sat $NaHCO_3$ (1×). The org. extracts were dried over $MgSO_4$ and filtered. The solvents were removed under reduced pressure. Purification of the residue by FC (EtOAc/heptane 1:3) yielded the title compound (948 mg, 90%). LC-MS: $R_t$=7.98; ES+: 861.51.

(rac.)-(1R*,5S*)-7-{4-[3-(tert-Butyldimethylsilanyloxy)propyl]phenyl}-6-[2-(2-methoxyphenyl)acetoxymethyl]-3,9-diazabicyclo[3.3.1]non-6-ene-3,9-dicarboxylic acid 3-tert-butyl ester 9-(2,2,2-trichloro-1,1-dimethylethyl) ester (Q2)

To a sol. of bicyclononene J3 (1.34 g, 1.90 mmol) in $CH_2Cl_2$ (30 mL), were added 2-methoxyphenylacetic acid (633 mg, 3.81 mmol), DIPEA (0.652 mL, 3.81 mmol), DMAP (cat amount), and EDC.HCl (402 mg, 2.09 mmol). The sol. was stirred at rt for 1 h and EDC.HCl (73 mg, 0.38 mmol) and DIPEA (0.163 mmol, 0.952 mmol) were added again. After 30 min., the reaction mixture was diluted with $CH_2Cl_2$, washed with aq. 1M HCl (1×) and aq. sat. $NaHCO_3$ (1×). The org. extracts were dried over $MgSO_4$ and filtered. The solvents were removed under reduced pressure. Purification of the residue by FC (EtOAc/heptane 1:3) yielded the title compound (1.47 g, 90%). LC-MS: $R_t$=8.17; ES+: 875.53.

Compounds of Type R (rac.)-(1R*,5S*)-3-Acetyl-7-[4(2-hydroxyethyl)phenyl]-6-[2-(2-methoxyphenyl)acetoxymethyl]-3,9-diazabicyclo[3.3.1]non-6-ene-9-carboxylic acid 2,2,2-trichloro-1,1-dimethylethyl ester (R1)

Bicyclononene Q1 (948 mg, 1.13 mmol) was dissolved in $CH_2Cl_2$ (20 mL). The sol. was cooled to 0° C. and 4M HCl/dioxane (20 mL) was added. After 2.25 h the solvents were rapidly removed under reduced pressure, and the residue was immediately dried under high vacuum. The resulting foam was then dissolved in THF (55 mL) and cooled to −78° C. DIPEA (0.774 mL, 4.51 mmol) and DMAP (cat. amount) were added, followed by the addition of acetyl chloride (0.064 mL, 0.91 mmol). After 2.5 h at −78° C., MeOH (20 mL) was added, and the reaction mixture was allowed to warm to rt. The reaction mixture was diluted in EtOAc, washed with aq. 1 M HCl (1×), and the org. extract were dried over $MgSO_4$ and filtered. The solvents were removed under reduced pressure. Purification of the residue by FC (EtOAc/heptane 1:2) yielded the title compound (651 mg, 55%). LC-MS: $R_t$=5.47; ES+: 689.05.

(rac.)-(1R*,5S*)-3-Acetyl-7-[4-(3-hydroxypropyl)phenyl]-6-[2-(2-methoxyphenyl)acetoxymethyl]-3,9-diazabicyclo[3.3.1]non-6-ene-9-carboxylic acid 2,2,2-trichloro-1,1-dimethylethyl ester (R2)

To a sol. of bicyclononene Q2 (1.47 g, 1.72 mmol) in $CH_2Cl_2$ (25 mL), 4M HCl/dioxane (25 mL) was added at 0° C. After 2.25 h at 0° C. the solvents were rapidly removed under reduced pressure, and the residue was immediately dried under high vacuum. The resulting foam was then dissolved in THF (75 mL) and cooled to −78° C. DIPEA (1.18 mL, 6.88 mmol) and DMAP (cat. amount) were added, followed by slow addition of acetyl chloride (0.098 mL, 1.38 mmol). After 2.5 h at −78° C. MeOH (80 mL) was added, and the reaction mixture was allowed to warm up to rt. After dilution with EtOAc, the mixture was washed with aq. 1 M HCl (1×) and the org. extracts were dried over $MgSO_4$ and filtered. The solvents were removed under reduced pressure. Purification of the residue by FC (EtOAc/heptane 1:2) yielded the title compound (651 mg, 55%).

Compounds of Type S (rac.)-(1R*,5S*)-3-Acetyl-7-{4-[3-(2-methoxybenzyloxy)propoxy]phenyl}-3,9-diazabicyclo[3.3.1]non-6-ene-6,9-dicarboxylic acid 6-ethyl ester 9-(2,2,2-trichloro-1,1-dimethylethyl) ester (S1)

A sol. of bicyclononene H5 (5.35 g, 6.95 mmol) in $CH_2Cl_2$ (30 mL) was cooled to 0° C. 4M HCl/dioxane (30 mL) was added. The sol. was stirred at 0° C. for 3.5 h, the solvents were removed under reduced pressure and the residue dried at high vacuum. The resulting foam was dissolved in THF (100 mL) and cooled to −78° C. DIPEA (5.80 mL, 34.7 mmol) was added. A sol. of acetyl chloride (0.494 mL, 6.95 mmol) in THF (10 mL) was added slowly. The reaction mixture was stirred at −78° C. for 90 min, then allowed to warm to rt and diluted in MeOH (5 mL), then in EtOAc. The org. extracts were washed with aq. 1M HCl (2×), aq. sat. $NaHCO_3$ (1×), dried over $MgSO_4$, filtered and the solvents were removed under reduced pressure. Purification of the residue by FC (EtOAc/heptane 1:4→1:3→1:1→EtOAc) yielded the title compound (3.67 g, 74%). $R_f$=0.50 (EtOAc). LC-MS: 6.22; ES+: 711.31.

(rac.)-(1R*,5S*)-3-Acetyl-7-{4-[3-(2-chlorophenoxy)propyl]phenyl}-3,9-diazabicyclo[3.3.1]non-6-ene-6,9-dicarboxylic acid 6-ethyl ester 9-(2,2,2-trichloro-1,1-dimethylethyl) ester (S2)

As for compound S1, from H6 (10.8 g, 14.5 mmol), $CH_2Cl_2$ (110 mL), 4M HCl/dioxane (110 mL), THF (220 mL), DIPEA (12.4 mL, 72.6 mmol), DMAP (89 mg, 0.73 mmol), acetyl chloride (1.24 mL, 17.4 mmol), and MeOH (5 mL). Purification of the residue by FC (EtOAc/heptane 1:3→1:1→EtOAc) yielded the title compound (8.59 g, 86%). $R_f$=0.43 (EtOAc). LC-MS: 6.32; ES+: 684.99.

(rac.)-(1R*,5S*)-3-Acetyl-7-[4-(2-hydroxyethyl) phenyl]-3,9-diazabicyclo-[3.3.1]non-6-ene-6,9-dicarboxylic acid 6-ethyl ester 9-(2,2,2-trichloro-1,1-dimethylethyl) ester (S3)

As for compound S1, from 112 (3.00 g, 4.08 mmol), $CH_2Cl_2$ (30 mL), 4M HCl/dioxane (30 mL), THF (60 mL), DMAP (25 mg, 0.204 mmol), DIPEA (2.74 mL, 16.4 mmol), acetyl chloride (0.343 mL, 4.08 mmol), and MeOH (5 mL). Purification of the residue by FC (EtOAc/heptane 1:1→EtOAc→MeOH/EtOAc 1:9) led to the title compound (1.80 g, 79%). $R_f$=0.20 (EtOAc).

(rac.)-(1R*,5S*)-3-Acetyl-7-[4-(2-hydroxyethoxy) phenyl]-3,9-diazabicyclo-[3.3.1]non-6-ene-6,9-dicarboxylic acid 6-ethyl ester 9-(2,2,2-trichloro-1,1-dimethylethyl) ester (S4)

As for compound S1, from H7 (5.80 g, 7.73 mmol), $CH_2Cl_2$ (60 mL), 4M HCl/dioxane (60 mL), THF (50 mL), DMAP (47 mg, 0.384 mmol), DIPEA (5.29 mL, 31.7 mmol), acetyl chloride (0.604 mL, 8.08 mmol), and MeOH (5 mL). Purification of the residue by FC (EtOAc/heptane 1:1→EtOAc MeOH/EtOAc 1:9) led to the title compound (3.07 g, 69%). $R_f$=0.20 (EtOAc). LC-MS: $R_t$=4.80; ES+: 576.93.

(rac.)-(1R*,5S*)-3-Acetyl-7-[4-(3-hydroxypropyl) phenyl]-3,9-diazabicyclo-[3.3.1]non-6-ene-6,9-dicarboxylic acid 6-ethyl ester 9-(2,2,2-trichloro-1,1-dimethylethyl) ester (S5)

As for compound S1, from H3 (5.04 g, 6.74 mmol), $CH_2Cl_2$ (80 mL), 4M HCl/dioxane (80 mL), THF (80 mL), without DMAP, DIPEA (4.62 mL, 27.0 mmol), acetyl chloride (0.430 mL, 6.06 mmol), and MeOH (5 mL). Purification of the residue by FC (EtOAc/heptane 1:1→EtOAc→MeOH/EtOAc 1:9) led to the title compound (3.23 g, 83%). $R_f$=0.20 (EtOAc). LC-MS: Rt 1.00; ES+: 575.13.

Compounds of Type T

(rac.)-(1R*,5S*)-3-Acetyl-7-{4-[3-(2-methoxybenzyloxy)propoxy]phenyl}-3,9-diazabicyclo[3.3.1] non-6-ene-6,9-dicarboxylic acid 9-(2,2,2-trichloro-1,1-dimethylethyl) ester (T1)

To a sol. of bicyclononene S1 (3.67 g, 5.15 mmol) in EtOH (27 mL) was added aq. NaOH (1M, 27 mL, 27 mmol). The mixture was heated to 80° C. for 3 h and then allowed to cool to rt. After adjustment of the pH to 1-2 with aq. 1M HCl and extraction with EtOAc (2×), the combined org. extracts were dried over MgSO4, filtered, and evaporated under reduced pressure. Purification of the residue by FC (EtOAc/heptane 1:1∝3:1→EtOAc→MeOH/EtOAc 1:9) yielded the title compound (1.45 g, 41%). LC-MS: $R_t$=5.50; ES+: 683.24.

(rac.)-(1R*,5S*)-3-Acetyl-7-{4-[3-(2-chlorophenoxy)propyl]phenyl}-3,9-diazabicyclo[3.3.1]non-6-ene-4,9-dicarboxylic acid 9-(2,2,2-trichloro-1,1-dimethylethyl) ester (T2)

From bicyclononene S2 (8.59 g, 12.5 mmol) the title compound (4.29 g, 52%) was obtained after purification by FC (MeOH/$CH_2Cl_2$ 1:99→1:49→3:97→1:24) as described for T1. LC-MS: $R_t$=5.61; ES−: 655.24.

(rac.)-(1R*,5S*)-3-Acetyl-7-[4-(2-hydroxyethoxy) phenyl-3,9-diazabicyclo[3.3.1]non-6-ene-6,9-dicarboxylic acid 9-(2,2,2-trichloro-1,1-dimethylethyl) ester (T3)

From bicyclononene S4 (3.07 g, 5.73 mmol) in EtOH (119 mL) and aq. 1M NaOH (119 mL) the title compound (1.88 g, 60%) was obtained after purification by FC (MeOH/$CH_2Cl_2$ 1:99→1:49→3:97→1:24) as described for T1. LC-MS: $R_t$=4.32; ES+: 548.96.

(rac.)-(1R*,5S*)-3-Acetyl-7-{4-[3-(tert-butyldimethylsilanyloxy)propyl]-phenyl}-3,9-diazabicyclo[3.3.1] non-6-ene-6,9-dicarboxylic acid 9-(2,2,2-trichloro-1, 1-dimethylethyl) ester (T4)

A mixture of bicyclononene AZ1 (1.60 g, 2.93 mmol), imidazol (797 mg, 11.7 mmol) and TBDMS-Cl (1.1 g, 7.30 mmol) in DMF (20 mL) was stirred at rt overnight. Aq. sat $NH_4Cl$ was added and the mixture was extracted with hexane (3×). The combined org. extracts were dried over MgSO4, filtered, and the solvents were evaporated under reduced pressure. A mixture of this crude product and $K_2CO_3$ (0.2 g) in THF (30 ml), MeOH (10 ml), and $H_2O$ (10 ml) was stirred at rt for 3 h. Aq. sat. $NH_4Cl$ was added and this mixture was extracted with $Et_2O$ (3×). The combined org. extracts were dried over MgSO4, filtered, and the solvents were removed under reduced pressure. This yielded the title compound (1.85 g, 95%) that was used without further purification.

(rac.)-(1R*,5S*)-7-{4-[2-(tert-Butyldiphenylsilanyloxy)ethyl]phenyl}-3,9-diazabicyclo[3.3.1]non-6-ene-3,6,9-tricarboxylic acid 3-tert-butyl ester 9-(2,2, 2-trichloro-1,1-dimethylethyl) ester (T5)

As for compound T4, but from bicyclononene AZ2 (crude, about 5.79 mmol), imidazol (1.2 g, 17.6 mmol) and TBDPS-Cl (4.84 g, 17.6 mmol) in DMF (50 mL), then $K_2CO_3$ (0.5 g), THF (60 mL), MeOH (20 mL), and H20 (20 mL). The crude title compound (9.6 g, quantitative yield) was used further without purification. LC-MS: $R_t$=1.26.

Compounds of Type U

(rac.)-(1R*,5S*)-3-Acetyl-7-(4-hydroxyphenyl)-6-(methylphenethylcarbamoyl)-3,9-diazabicyclo[3.3.1] non-6-ene-9-carboxylic acid 2,2,2-trichloro-1,1-dimethylethyl ester (U1)

To a sol. of bicyclononene W1 (0.93 g, 1.37 mmol) in $CH_2Cl_2$ (10 mL) was added HCl/dioxane (10 mL) at 0° C. After 15 min, the ice bath was removed. The reaction mixture was stirred at rt for 1 h and the solvents were removed under reduced pressure. After drying at high vacuum for 30 min., the resulting solid or foam was dissolved in THF (10 mL). DIPEA (0.983 mL, 5.48 mmol) and DMAP (cat. amount) were added. The sol. was cooled to −78° C. and a sol. of AcCl (0.0973 mL, 1.37 mmol) in THF (5 mL) was slowly added over 2 min. After 75 min at −78° C. MeOH (10 mL) was added and the mixture was allowed to warm up. After dilution in EtOAc, the reaction mixture was washed with aq. 1M HCl (1×) and aq. sat $NaHCO_3$ (1×). The org. extracts were dried over MgSO4, filtered, and evaporated under reduced pressure. Purification of the residue by FC (EtOAc/heptane 1:3→1: 1→3:1→EtOAc→MeOH/EtOAc 1:19→1:9) yielded the title compound (253 mg, 30%). $R_f$=0.30 (EtOAc). LC-MS: $R_t$=5.12; ES+: 622.31.

(rac.)-(1R*,5S*)-3-Acetyl-7-[4-(2-hydroxyethyl) phenyl]-6-(methylphenethylcarbamoyl)-3,9-diazabicyclo[3.3.1]non-6-ene-9-carboxylic acid 2,2,2-trichloro-1,1-dimethylethyl ester (U2)

To a sol. of bicyclononene W2 (3.46 g, 4.88 mmol) in $CH_2Cl_2$ (35 mL) was added HCl (4M in dioxane, 35 mL) at 0° C. After 1 h the ice bath was removed, and stirring continued for 1 h at rt. The solvents were removed under reduced pressure and the residue dried under high vacuum. The resulting foam was dissolved in THF (50 mL). DIPEA (3.34 mL, 19.5 mmol) and DMAP (cat. amount) were added. The reaction mixture was cooled to −78° C. and AcCl (0.347 mL, 4.88 mmol) in THF (20 mL) was added dropwise. After 2 h at −78° C., AcCl (0.100 mL, 1.41 mmol) was added again, followed by a third portion of AcCl (0.050 mL, 0.71 mmol) 1.5 h later. MeOH (10 mL) was added after 30 min. and the mixture was allowed to warm up to rt. After dilution with EtOAc and washing with aq. 1M HCl (1×) and aq. sat $NaHCO_3$ (1×), the org. extracts were dried over $MgSO_4$ and filtered. The solvents were removed under reduced pressure. Purification of the residue by FC (EtOAc/heptane 1:1→EtOAc→MeOH/EtOAc 1:9) yielded the title compound as a colorless foam (2.06 g, 65%). $R_f$=0.15 (EtOAc). LC-MS: $R_t$=5.14; ES+: 650.21.

(rac.)(1R*,5S*)-3-Acetyl-7-[4-(3-hydroxypropyl) phenyl]-6-methylphenethylcarbamoyl)-3,9-diazabicyclo[3.3.1]non-4-ene-9-carboxylic acid 2,2,2-trichloro-1,1-dimethylethyl ester (U3)

To a sol. of bicyclononene W3 (3.18 g, 4.40 mmol) in $CH_2Cl_2$ (30 mL) was added HCl (4M in dioxane, 30 mL) at 0° C. After 1 h at 0 C and h at rt, the solvents were removed under reduced pressure and the residue dried under high vacuum. The residue was dissolved in THF (45 mL), and DIPEA (3.02 mL, 17.6 mmol) and DMAP (cat amount) were added. The sol. was cooled to −78° C. and a sol. of AcCl (0.313 mL, 4.40 mmol) in THF (15 mL) was added dropwise over 5 min. After 1.25 h, AcCl (0.070 mL, 0.984 mmol) was added again. After 30 min. MeOH (10 mL) was added and the mixture was allowed to warm up to rt. After dilution in EtOAc and washing with aq. 1M HCl (1×) and aq. sat $NaHCO_3$ (1×), the org. extracts were dried over $MgSO_4$ and filtered. The solvents were removed under reduced pressure. Purification of the residue by FC (EtOAc/heptane 1:1→EtOAc→MeOH/EtOAc 1:9) yielded the title compound (2.92 g, 66%) as a foam. $R_f$=0.23 (EtOAc). LC-MS: $R_t$=5.24; ES+: 664.29.

(rac.)-(1R*,5S*)-3-Acetyl-7-[4-(2-hydroxyethoxy) phenyl]-6-methylphenethylcarbamoyl)-3,9-diazabicyclo[3.3.1]non-6-ene-9-carboxylic acid 2,2,2-trichloro-1,1-dimethylethyl ester (U4)

A mixture of bicyclononene T3 (1.88 g, 3.42 mmol), methylphenethylanine (1.49 mL, 10.3 mmol), DMAP (41 mg, 0.34 mmol), DIPEA (2.33 mL, 18.0 mmol), HOBt (46 mg, 0.34 mmol) and EDC.HCl (1.64 g, 8.55 mmol) in $CHCl_3$ (40 mL) was stirred overnight at rt. The mixture was diluted in $CH_2Cl_2$ and washed with aq. 1M HCl (2×) and aq. sat $NaHCO_3$. The organic extracts were dried over $MgSO_4$, filtered, and the solvents were removed under reduced pressure. Purification of the residue by FC (EtOAc/ heptane 1:4→1:1→4:1→EtOAc) yielded the title compound (1.33 g, 58%). LC MS: $R_t$=5.25; ES+: 666.08.

Compounds of Type V

(rac.)-(1R*,5S*)-7-(4-Hydroxyphenyl)-3,9-diazabicyclo[3.3.1]non-6-ene-3,6,9-tricarboxylic acid 3-tert-butyl ester 9-(2,2,2-trichloro-1,1-dimethylethyl) ester (V1)

To a sol. of bicyclononene H1 (4.18 g, 5.79 mmol) in EtOH (55 mL) aq. NaOH (1M, 55 mL, 55 mmol) was added. The mixture was stirred at 80° C. for 28 h before it was allowed to cool to rt and acidified to pH 1 with aq. 1M HCl. After extraction with EtOAc (3×) the combined org. extracts were dried over $MgSO_4$ and filtered. The solvents were removed under reduced pressure. Purification of the residue by FC (MeOH/$CH_2Cl_2$ 1:49→3:97→1:24→1:19→1:9→1:4) yielded the title compound (1.50 g, 40%). $R_f$=0.29. LC-MS: $R_t$=4.91; ES−: 561.12.

(rac.)-(1R*,5S*)-7-[4-(2-Hydroxyethyl)phenyl]-3,9-diazabicyclo[3.3.1]non-6-ene-3,6,9-tricarboxylic acid 3-tert-butyl ester 9-(2,2,2-trichloro-1,1-dimethylethyl) ester (V2)

To a sol. of bicyclononene R2 (13.75 g, 18.7 mmol) in EtOH (180 mL) aq. NaOH (1M, 180 mL, 180 mmol) was added. The mixture was stirred at 80° C. for 8 h and then left at −5° C. overnight The mixture was acidified to pH 1 with aq. 1M HCl and extracted with EtOAc (3×). The org. extracts were dried over $MgSO_4$ and filtered. The solvents were removed under reduced pressure. Purification of the residue by FC (MeOH/$CH_2Cl_2$ 1:49→3:47→1:24→1:19→1:9→1:4) yielded the title compound, contaminated with (rac.)-(1R*,5S*)-7-[4-(2-hydroxyethyl)phenyl]-3,9-diazabicyclo[3.3.1] non-7-ene-3,6,9-tricarboxylic acid 3-tert-butyl ester 9-(2,2,2-trichloro-1,1-dimethylethyl) ester (7.09 g, 64%). $R_f$=0.40 MeOH/$CH_2Cl_2$ 1:9). $R_t$=4.90; ES−: 589.16.

(rac.)(1R*,5S*)-7-[4-(3-Hydroxypropyl)phenyl]-3,9-diazabicyclo[3.3.1]non-6ene-3,6,9-tricarboxylic acid 3-tert-butyl ester 9-(2,2,2-trichloro-1,1-dimethylethyl) ester (V3)

To a sol. of bicyclononene H3 (13.50 g, 18.0 mmol) in EtOH (180 mL) aq. NaOH (1M, 180 mL, 180 mmol) was added. The mixture was heated to 40° C. and after 1 h to 80° C. After 7 h, the mixture was left overnight at −5° C. EtOH (100 mL) and aq. NaOH (1M, 50 mL, 50 mmol) were added and the sol. was heated to 80° C. for 6 h. After cooling to rt and adjustment of the pH to 1 with aq. 1M HCl, the mixture was extracted with EtOAc (3×). The combined org. extracts were dried over $MgSO_4$ and filtered. The solvents were removed under reduced pressure. Purification of the residue by FC (MeOH/$CH_2Cl_2$ 1:49→3:97→1:24→1:19→1:9→1:4) yielded the tide compound (4.80 g, 55%). $R_f$=0.50 (MeOH/$CH_2Cl_2$ 1:9). LC-MS: $R_t$=4.99; ES−: 603.20.

Compounds of Type W

(rac.)-(1R*,5S*)-7-(4-Hydroxyphenyl)-6-(methylphenethylcarbamoyl)-3,9-diazabicyclo[3.3.1]non-6-ene-3,9-dicarboxylic acid 3-tert-butyl ester 9-(2,2,2-trichloro-1,1-dimethylethyl) ester (W1)

To a susp. of bicyclononene V1 (1.50 g, 2.66 mmol) in $CHCl_3$ (30 mL) was added methylphenethylamine (0.774 mL, 5.32 mmol). DMAP (32.5 mg, 0.266 mmol), HOBt (36 mg, 0.266 mmol), and EDC.HCl (765 mg, 3.99 mmol) were added successively. After 3 days at rt the mixture was diluted in CH$_2$Cl$_2$ and washed with aq. 1M HCl (1×) and aq. sat. NaHCO$_3$ (1×). The org. extracts were dried over MgSO$_4$ and filtered. The solvents were removed under reduced pressure. Purification of the residue by FC (EtOAc/heptane 1:9→1:4→3:7→2:3→1:1→3:2→7:3) yielded the title compound as a colorless solid (0.93 g, 51%). R$_f$=0.25 (EtOAc/heptane 1:1). LC-MS: R$_t$=5.86; ES−: 678.14.

(rac.)(1R*,5S*)-7-[4(2-Hydroxyethyl)phenyl]-6-(methylphenethylcarbamoyl)-3,9-diazabicyclo[3.3.1]non-6-ene-3,9-dicarboxylic acid 3-tert-butyl ester 9-(2,2,2-trichloro-1,1-dimethylethyl) ester (W2)

To a sol. of bicyclononene V2 (7.09 g, 11.97 mmol) in CHCl$_3$ (140 mL) were added N-methylphenethylamine (3.48 mL, 24.0 mmol), DMAP (137 mg, 1.12 mmol), HOBt (151 mg, 1.12 mmol) and EDC.HCl (3.44 g, 18.0 mmol). The mixture was stirred at rt for 3 days, before it was diluted with CH$_2$Cl$_2$ and washed with aq. 1M HCl (1×) and aq. sat. NaHCO$_3$ (1×). The org. extracts were dried over MgSO$_4$ and filtered. The solvents were removed under reduced pressure. Purification of the residue purified by FC (MeOH/CH$_2$Cl$_2$ 1:49→3:122→4:121→1:24→1:9→1:4) yielded the title compound (3.46 g, 41%). R$_f$=0.26 (MeOH/CH$_2$Cl$_2$ 1:19). LC-MS: R$_t$=5.87; ES+: 708.40.

(rac.)(1R*,R5S*)-7-[4-(3-Hydroxypropyl)phenyl]-6-(methylphenethylcarbamoyl)-3,9-diazabicyclo[3.3.1]non-6-ene-3,9-dicarboxylic acid 3-tert-butyl ester 9-(2,2,2-trichloro-1,1-dimethylethyl) ester (W3)

To a sol. of bicyclononene V3 (7.59 g, 12.5 mmol) in CHCl$_3$ (150 mL) were added methylphenethylamine (3.63 mL, 25.0 mmol), DMAP (153 mg, 1.25 mmol), HOBt (169 mg, 1.25 mmol) and EDC.HCl (3.80 g, 19.2 mmol). The mixture was stirred at rt for 3 days before it was diluted in CH$_2$Cl$_2$ and washed with aq. 1M HCl (1×) and aq. sat. NaHCO$_3$ (1×). The org. extracts were dried over MgSO$_4$ and filtered. The solvents were removed under reduced pressure. Purification of the residue by FC (MeOH/CH$_2$Cl$_2$ 1:49→3:97→1:24→1:9→1:4) yielded the title compound (3.18 g, 35%). R$_f$=0.42 (MeOH/CH$_2$Cl$_2$ 1:19). LC-MS: R$_t$=5.99; ES+: 744.50.

(rac.)-(1R*,5S*)-3-Acetyl-6-hydroxymethyl-7-{4-[3-(2-methoxybenzyloxy)-propoxy]phenyl}-3,9-diazabicyclo[3.3.1]non-6-ene-9-carboxylic acid 2,2,2-trichloro-1,1-dimethylethyl ester (X)

To a sol. of bicyclononene Si (2.29 g, 3.21 mmol) in CH$_2$Cl$_2$ (100 mL) was added BF$_3$Et$_2$O (0.460 mL, 3.66 mmol) at −78° C. The mixture was stirred at −78° C. for 30 min and DIBAL (1M in toluene, 6.42 mL, 6.42 mmol) was added. After 75 min, ice was added and the mixture was allowed to warm up to rt. CH$_2$Cl$_2$ was added and the mixture was washed with aq. 1M HCl (1×). The org. extracts were separated, dried over MgSO$_4$ and filtered. The solvents were removed under reduced pressure. Purification of the residue by FC (EtOAc/heptane 1:2→1:1→EtOAc) yielded the title compound (1.01 g, 47%).

(rac.)-(1R*,5S*)-3-Acetyl-6-formyl-7-{4-[3-(2-methoxybenzyloxy)propoxy]-phenyl}-3,9-diazabicyclo[3.3.1]non-6ene-9-carboxylic acid 2,2,2-trichloro-1,1-dimethylethyl ester (Y)

To a sol. of bicyclononene X (258 mg, 0.385 mmol) in CH$_2$Cl$_2$ (5 mL) was added to 0° C. Dess-Martin periodane (170 mg, 0.401 mmol) at 0° C. After 45 min. at 0° C. a second portion periodane was added. The sol. was stirred for 15 min before the solvents were removed under reduced pressure. Direct purification of the residue by FC (EtOAc/heptane 2:3→1:1→3:2→7:3) yielded the title compound (188 mg, 73%). R$_f$=0.49 (EtOAc). LC-MS: R$_t$=6.18; ES+: 667.21.

(rac.)-(1R*,5S*)-3-Acetyl-7-{4-[3-(2-methoxybenzyloxy)propyl]phenyl}-6-methylaminomethyl-3,9-diazabicyclo[3.3.1]non-6-ene-9-carboxylic acid 2,2,2-trichloro-1,1-dimethylethyl ester (Z)

To a sol. of bicyclononene Y (334 mg, 0.50 mmol) in MeOH (10 mL) methylamine (40% in water, 0.215 mL, 2.5 mmol) was added. The mixture was stirred at rt for 1 h and then cooled to 0° C. NaBH4 (20 mg, 0.50 mmol) was added. The mixture was stirred at rt for 4 h before K$_2$CO$_3$ (263 mg) was added. After evaporation under reduced pressure the residue was distributed between EtOAc and water. The org. extracts were separated, dried over MgSO$_4$, and filtered. The solvents were removed under reduced pressure. Purification of the residue by RP18-WPLC yielded the title compound (130 mg, 38%). LC-MS: R$_t$=1.00; ES+: 682.14.

(rac.)-(1R*,5S*)-7-{4-[3-(2-Chlorophenoxy)propyl]phenyl}-3,9-diazabicyclo-[3.3.1]non-6-ene-3,6,9-tricarboxylic acid 3-tert-butyl ester 9-(2,2,2-trichloro-1,1-dimethylethyl) ester (AA)

Bicyclononene H6 (1.71 g, 2.3 mmol) was dissolved in EtOH (50 mL). Aq. 1M NaOH (50 mL) was added and the mixture was heated to 80° C. The sol. was stiffed for 5 h at 80° C., then allowed to cool down to rt. After acidification to pH=1-2 with aq. 1M HCl the mixture was extracted with EtOAc (3×). The combined org. extracts were dried over MgSO$_4$, filtered and the solvents were removed under reduced pressure. Purification of the residue by FC (EtOAc/heptane 2:3→1:2→1:1) yielded the title compound (504 mg, 31%). R$_f$=0.30 (EtOAc/heptane 1:1). LC-MS: R$_t$=6.21; ES−: 712.34.

(rac.)-(1R*,5S*)-7-{4-[3-(2-Chlorophenoxy)propyl]phenyl}-6-([2-(2-chlorophenyl)ethyl]methylcarbamoyl}-3,9-diazabicyclo[3.3.1]non-6-ene-3,9-dicarboxylic acid 3-tert-butyl ester 9-(2,2,2-trichloro-1,1-dimethylethyl) ester (AB)

Bicyclononene AA (504 mg, 0.703 mmol) was dissolved in CHCl$_3$ (25 mL). [2-(2-chlorophenyl)ethyl]methylamine (Jaques B.; Wallace R. G., *Tetrahedron*, 1977, 33, 581; 238 mg, 1.40 mmol), DIPEA (0.240 mL, 1.40 mmol), DMAP (17 mg, 0.14 mmol), HOBt (19 mg, 0.10 mmol) and EDC.HCl (135 mg, 1.40 mmol) were added. The sol. was stirred at rt overnight. The mixture was diluted with CH$_2$Cl$_2$ and washed with water (1×). The org. extracts were dried over MgSO$_4$ and the solvents were removed under reduced pressure. Purification of the residue by filtration through silica gel yielded the title compound as a yellowish foam (336 mg, 55%).

(rac.)-(1R*,5S*)-7-{4-[3-(2-Chlorophenoxy)propyl]
phenyl}-6-{[2-(2-chlorophenyl)ethyl]methylcarbam-
oyl}-3,9-diazabicyclo[3.3.1]non-6-ene-9-carboxylic
acid 2,2,2-trichloro-1,1-dimethylethyl ester hydro-
chloride salt (AC)

Bicyclononene AB (336 mg, 0.378 mmol) was dissolved in $CH_2Cl_2$ (3 mL). 4M HCl/dioxane (13 mL) was added and the mixture was stirred at rt for 2 h. The solvents were removed under reduced pressure. Drying the residue at high vacuum yielded the title compound as a colorless foam that was used without further purification. LC-MS: $R_t$=5.26; ES+: 765.85.

9-Methyl-7-oxo-3,9-diazabicyclo[3.3.1]nonane-3-
carboxylic acid tert-butyl ester (AE)

(4Benzyl-6-ethoxycarbonylmethyl-1-methylpiperazin-2-yl)acetic acid ethyl ester (Patent WO 92/05174) (71.0 g, 0.196 mol) was dissolved in MeOH (400 mL). TFA (77.8 mL, 1.02 mol) was added and the flask was purged with nitrogen. Pd/C (10%, 50% moisture, 3.6 g) was added. The flask was closed and purged with hydrogen (3×). After 1 day, the mixture was filtered through celite and washed with MeOH. The solvent was removed under reduced pressure and the foamy residue (92.7 g) was dried under high vacuum. A sol. of tBuOK (117.2 g, 1.04 mol) in toluene (3.07 L) was heated to reflux. A sol. of the crude piperazine formerly obtained, dissolved in THF (300 mL), was added dropwise over 50 min.

The black mixture was stirred for 10 further min. and allowed to cool to rt. The mixture was cooled to 0° C. and AcOH (36.6 mL, 0.635 mol) was added. The solvents were removed under reduced pressure and the residue purified by FC (MeOH/$CH_2Cl_2$ 1:9→1:4→1:3). The fractions with an $R_f$-value close to 0.10 (MeOH/$CH_2Cl_2$ 1:9) were collected and the solvent removed under reduced pressure. The residue was dissolved in aq. 5M HCl (2 L) and the reaction mixture heated to reflux overnight. The mixture was allowed to cool to rt, then cooled to 0° C. with an ice bath. The pH was brought to 12 by adding carefully solid KOH. This mixture was extracted with $CH_2Cl_2$ (3×). The combined org. extracts were dried over $MgSO_4$ and the solvents were removed under reduced pressure. The residue was suspended in $CH_2Cl_2$ (400 mL) and cooled to 0° C. DIPEA (19.1 mL, 112 mmol) was added. A sol. of $Boc_2O$ (24.3 g, 113 mmol) in $CH_2Cl_2$ (200 mL) was added dropwise. The mixture was stirred for 1 h at 0° C., then 1 h at rt. The mixture was washed with aq. 10% $Na_2CO_3$ (2×). The org. extracts were dried over $MgSO_4$, filtered and the solvents were evaporated under reduced pressure. The residue was purified by FC (EtOAc/heptane 1:1→EtOAc). The title compound was obtained as a solid that could be recrystallized from heptane (15.6 g, 30%). $R_f$=0.45 (MeOH/$CH_2Cl_2$ 1:9). LC-MS: $R_t$=1.55; ES+: 254.16.

(1R,5S)-9-Methyl-7-oxo-3,9-diazabicyclo[3.3.1]
nonane-3,6-dicarboxylic acid 3-tert-butyl ester 6-me-
thyl ester (AF)

To a susp. of (−)-bis[(S)-1-phenylethyl]amine hydrochloride (226 mg, 0.864 mmol) in THF (3 mL) at 0° C. was added dropwise n-BuLi (1.6M in hexane, 1.136 mL, 1.808 mmol). The mixture was stirred for 1 h at 0° C., then cooled to −78° C. A sol. of bicyclononane AE (200 mg, 0.786 mmol) in THF (2 mL) was added dropwise over 3 min. The reaction mixture was stirred for 3 h at −78° C., then methylcyanoformat (0.081 mL, 1.02 mmol) was added. The reaction mixture was stirred for 30 min. at −78° C. and a sol. of $AgNO_3$ (191 mg, 1.124 mmol) in $H_2O$/THF (1:1, 2 mL) was added. After 10 min. $H_2O$ (1.5 mL) and AcOH (1.5 mL) were added and the reaction mixture was allowed to warm to rt. Ammoniac (25% in water) was added until the Ag-salt had completely dissolved. The reaction mire was extracted with EtOAc (1×) and $CH_2Cl_2$ (2×). The combined org. extracts were dried over $MgSO_4$ and the solvents were removed under reduced pressure. Purification of the residue by FC (MeOH/$CH_2Cl_2$ 1:14) yielded the title compound (167 mg, 68%). $R_f$=0.37 (MeOH/$CH_2Cl_2$ 1:9). LC-MS: $R_t$=0.76; ES+: 313.10. ee=82%.

(1R,5S)-9-Methyl-7-oxo-3,9-diazabicyclo[3.3.1]
nonane-3,6-dicarboxylic acid 6-benzyl ester3-tert-
butyl ester (AG)

To a susp. of (−)-bis[(S)-1-phenylethyl]amine hydrochloride (226 mg, 0.864 mmol) in THF (3 mL) at 0° C. was added dropwise n-BuLi (1.6M in hexane, 1.136 mL, 1.808 mmol). The mixture was stirred for 1 h at 0° C., then cooled to −78° C. A sol. of bicyclononane AE (200 mg, 0.786 mmol) in THF (2 mL) was added dropwise over 3 min. The reaction mixture was stirred for 3 h at −78° C., then methylcyanoformat (0.081 mL, 1.02 mmol) was added. The reaction mixture was stirred for 30 min. at −78° C. and a sol. of $AgNO_3$ (191 mg, 1.124 mmol) in $H_2O$/THF (1:1, 2 mL) was added. After 10 min., $H_2O$ (1.5 mL) and AcOH (1.5 mL) were added and the reaction mixture was allowed to warm to rt. Ammoniac (25% in water) was added until the Ag-salt had completely dissolved. The reaction mixture was extracted with EtOAc (1×) and $CH_2Cl_2$ (2×). The combined org. extracts were dried over $MgSO_4$ and the solvents were removed under reduced pressure. Purification of the residue by FC (MeOH/$CH_2Cl_2$ 1:14) yielded the title compound (150 mg, 49%). $R_f$=0.50 (MeOH/$CH_2Cl_2$ 1:9). LC-MS: $R_t$=0.87; ES+: 389.09. ee=84%.

(rac.)-(1R*,5S*)-3-Acetyl-7-{4-[2-(2-bromo-5-fluo-
rophenoxy)ethyl]phenyl}-3,9-diazabicyclo[3.3.1]
non-6-ene-6,9-dicarboxylic acid 6-ethyl ester 9-(2,2,
2-trichloro-1,1-dimethylethyl) ester (AH)

A sol. of bicyclononene S3 (900 mg, 1.60 mmol) in toluene (15 mL) was purged with $N_2$ (4×). 2-Bromo-5-fluorophenol (0.267 mL, 2.4 mmol), TMAD (344 mg, 2.00 mmol) and tributylphosphine (1.18 mL, 4.80 mmol) were added and the reaction mixture was heated to reflux for 1 h. The mixture was allowed to cool to rt, and the solvents were removed under reduced pressure. Purification of the residue by FC (EtOAc/heptane 1:24→1:9→2:3→7:3) yielded the title compound (1.06 g, 90%). $R_f$=0.58 (EtOAc). LC-MS: $R_t$=6.52; ES+: 733.00.

Compounds of Type AJ (rac.)-(1R*,5S*)-3-Acetyl-7-{4-[2-(2-bromo-5-fluo-
rophenoxy)ethyl]phenyl}-3,9-diazabicyclo[3.3.1]
non-6-ene-6,9-dicarboxylic acid 9-(2,2,2-trichloro-1,
1-dimethylethyl) ester (AJ1)

A mixture of bicyclononene AH (1.06 g, 1.44 mmol) in EtOH (30 mL) and aq. 1M NaOH (30 mL) was stirred efficiently at 80° C. for 2.5 h. The mixture was allowed to cool to rt, acidified with aq. 1M HCl, and extracted with EtOAc (3×). The combined org. phases were dried over $MgSO_4$, filtered, and the solvents were removed under reduced pressure. Purification of the residue by FC (EtOAc/heptane 1:1→3:1→EtOAc→MeOH/EtOAc 1:19→1:9) yielded the title compound (845 mg, 83%). $R_f$=0.10 (EtOAc). LC-MS: $R_t$=5.78; ES−: 702.81.

(rac.)-1R*,5S*)-3-Acetyl-7-{4-[3-(2,3,6-trifluorophenoxy)propyl]phenyl}-3,9-diazabicyclo[3.3.1]non-6-ene-6,9-dicarboxylic acid 9-(2,2,2-trichloro-1,1-dimethylethyl) ester (AJ2)

A sol. of bicyclononene AR1 (296 mg, 0.39 mmol) in MeOH (10 mL) at 0° C. was purged with $N_2$ (3×). Pd/C (10%, cat. amount) was added and the mixture was purged with $H_2$ (4×). The mixture was stirred under $H_2$ for 2 h at 0° C., and was filtered through Celite. The solvents were removed under reduced pressure and the residue was dried under high vacuum (200 mg, 80%). It was used without further purification. LC-MS: $R_t$=5.83.

(rac.)(1R*,5S*)-3-Acetyl-7-{4-[3-(3-fluorophenoxy)propyl]phenyl}-3,9-diazabicyclo[3.3.1]non-6-ene-6,9-dicarboxylic acid 9-(2,2,2,trichloro-1,1-dimethylethyl) ester (AJ3)

As for compound AJ2, but from AR2 (205 mg, 0.25 mmol), Pd/C (cat. amount) and MeOH (10 mL). The crude material (100 mg, 56%) was used without further purification. LC-MS: $R_t$=5.81.

(rac.)-(1R*,5S*)-3-Acetyl-7-{4-[3-(2-bromo-5-fluorophenoxy)propyl]phenyl}-3,9-diazabicyclo[3.3.1]non-6-ene-6,9dicarboxylic acid 9-(2,2,2-trichloro-1,1-dimethylethyl) ester (AJ4)

As for compound AJ1, but from bicyclononene BL (1.55 g, 2.07 mmol), EtOH (55 mL) and aq. 1M NaOH (55 mL). Purification of the residue by FC (EtOAc/heptane 1:1→EtOAc→MeOH/EtOAc 1:9) yielded the title compound (1.17 g, 78%). $R_f$=0.20 (EtOAc). $R_t$=6.02; ES+: 721.12.

Compounds of Type AK (rac.)(1R*,5S*)-7-{4-[2-(2-Bromo-5-fluorophenoxy)ethyl]phenyl}-6-(methylphenethylcarbamoyl)-3,9-diazabicyclo[3.3.1]non-6-ene-3,9dicarboxylic acid 3-tert-butyl ester 9-(2,2,2-trichloro-1,1-dimethylethyl) ester (AK1)

A sol. of bicyclononene W2 (1.68 g, 2.37 mmol) in toluene (50 mL) was purged with $N_2$ (4×). 2-Bromo-5-fluorophenol (0.403 mL, 3.56 mmol), azodicarboxylic dipiperidide (897 mg, 3.56 mmol) and tributyl phosphine (1.62 mL, 7.12 mmol) were added. The mixture was heated to reflux for 2 h. The mixture was then allowed to cool to rt and the solvents were removed under reduced pressure. Purification of the residue by FC (EtOAc/heptane 1:19→1:9→1:4→1:1→3:1) yielded the title compound (1.88 g, 90%). $R_f$=0.80 (EtOAc). LC-MS: $R_t$7.30.

(rac.)-(1R*,5S*)-6-[(2-Chlorobenzyl)cyclopropylcarbamoyl]-7-{4-[3-(2,3,6-tri-fluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK2)

A mixture of bicyclononene AY1 (12.15 g, 16 mmol), (2-chlorobenzyl)-cyclopropylamine (9.08 g, 50 mmol), DIPEA (10.9 mL, 64 mmol), DMAP (488 mg, 4 mmol), HOBt (2.43 g, 18 mmol) and EDC.HCl (4.60 g, 24 mmol) in $CH_2Cl_2$ (250 mL) was stirred overnight. The mixture was diluted with $CH_2Cl_2$, and washed with aq. 1M HCl (3×) and with aq. sat $NaHCO_3$ (1×). The org. extracts were dried over $MgSO_4$, filtered, and the solvents were removed under reduced pressure. Purification of the residue by FC (EtOAc/heptane 1:5→1:3→1:2) yielded the title compound (9.10 g, 63%). LC-MS: $R_t$=7.68.

(rac.)-(1R*,5S*)-6-(Benzylcyclopropylcarbamoyl)-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK3)

As for bicyclononene AK2, but from bicyclononene AY1 (552 mg, 0.75 mmol), benzylcyclopropylamine (Loeppky, R. N.; et al., J. Org. Chem., 2000, 65, 96; 221 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (570 mg, 88%). LC-MS: $R_t$=1.28.

(rac.)-(1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK4)

As for bicyclononene AK2, but from bicyclononene AY1 (552 mg, 0.75 mmol), (2-chlorobenzyl)ethylamine (Ishihara, Y; et al.; Chem. Pharm. Bull., 1991, 39, 3225; 255 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (543 mg, 82%). LC-MS: $R_t$=1.29.

(rac.)-(1R*,5S*)-6-[Cyclopropyl-(2-fluorobenzyl)carbamoyl]-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK5)

As for bicyclononene AK2, but from bicyclononene AY1 (552 mg, 0.75 mmol), cyclopropyl-(2-fluorobenzyl)amine (248 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (526 mg, 79%). LC-MS: $R_t$=1.28.

(rac.)-(1R*,5S*)-6-[Cyclopropyl-(3-trifluoromethylbenzyl)carbamoyl]-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK6)

As for bicyclononene AK2, but from bicyclononene AY1 (552 mg, 0.75 mmol), cyclopropyl-(3-trifluoromethylbenzyl)amine (Brabander, H. J.; et al.; J. Org. Chem., 1967, 32, 4053; 323 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (551 mg, 79%). LC-MS: $R_t$=1.25.

(rac.)-(1R*,5S*)-6-[Cyclopropyl-(2-methylbenzyl) carbamoyl]-7-{4-[3-(2,3,6-trifluorophenoxy)propyl] phenyl}-3,9-diazabicyclo[3.3.1]non-6-ene-3,9-dicarboxylic acid 3-tert-butyl ester 9-(2,2,2-trichloro-1,1-dimethylethyl) ester (AK7)

As for bicyclononene AK2, but from bicyclononene AY1 (552 mg, 0.75 mmol), cyclopropyl-(2-methylbenzyl)-amine (242 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (553 mg, 84%). LC-MS: $R_t$=1.29.

(rac.)-(1R*,5S*)-6-{Cyclopropyl-[2-(4methoxyphenoxy)ethyl]carbamoyl}-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethyl-ethyl) ester (AK8)

As for bicyclononene AK2, but from bicyclononene AY1 (552 mg, 0.75 mmol), cyclopropyl-[2-(4-methoxy-phenoxy)ethyl]amine (311 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (566 mg, 82%). LC-MS: $R_t$=1.28.

(rac.)-(1R*,5S*)-6-{Cyclopropyl-[2-(2-methoxyphenoxy)ethyl]carbamoyl}-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethyl-ethyl) ester (AK9)

As for bicyclononene AK2, but from bicyclononene AY1 (552 mg, 0.75 mmol), cyclopropyl-[2-(2-methoxy-phenoxy)ethyl]amine (311 mg, 1.56 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (570 mg, 82%). LC-MS: $R_t$=1.28.

(rac.)-(1R*,5S*)-6-[Cyclopropyl-(2-m-tolyloxyethyl)carbamoyl]-7-{4-[3-(2,3,6-trifluorophenoxy) propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK10)

As for bicyclononene AK2, but from bicyclononene AY1 (552 mg, 0.75 mmol), cyclopropyl-(2-m-tolyloxy-ethyl)amine (287 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (506 mg, 74%). LC-MS: $R_t$=1.30.

(rac.)-(1R*,5S*)-6-{Cyclopropyl-[2-(3,4-dimethylphenoxy)ethyl]carbamoyl}-7-{4-[3-(2,3,6-trifluorophenoxy)propyl]phenyl}-3,9-diazabicyclo[3.3.1] non-6-ene-3,9-dicarboxylic acid 3-tert-butyl ester 9-(2,2,2-trichloro-1,1-dimethyl-ethyl) ester (AK11)

As for bicyclononene AK2, but from bicyclononene AY1 (552 mg, 0.75 mmol), cyclopropyl-[2-(3,4-dimethyl-phenoxy)ethyl]amine (462 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (693 mg, 100%). LC-MS: $R_t$=1.28.

(rac.)-(1R*,5S*)-(Cyclopropylphenethylcarbamoyl)-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK12)

As for bicyclononene AK2, but from bicyclononene AY1 (552 mg, 0.75 mmol), cyclopropylphenethylamine (Smith, P. W.; et al.; *J. Med. Chem.*, 1998, 41, 787; 242 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (510 mg, 77%). LC-MS: $R_t$=1.28.

(rac.)-(1R*,5S*)-6-{[2-(2-Chlorophenyl)ethyl]cyclopropylcarbamoyl}-7-{4-[3-(2,3,6-trifluorophenoxy) propyl]phenyl}-3,9-diazabicyclo[3.3.1]non-6-ene-3, 9-dicarboxylic acid 3-tert-butyl ester 9-(2,2,2-trichloro-1,1-dimethylethyl) ester (AK13)

As for bicyclononene AK2, but from bicyclononene AY1 (552 mg, 0.75 mmol), [2-(2-chlorophenyl)ethyl]-cyclopropylamine (294 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (540 mg, 79%). LC-MS: $R_t$=1.28.

(rac.)-(1R*,5S*)-6-{Cyclopropyl-[2-(2,3-difluorophenyl)ethyl]carbamoyl}-7-{4-[3-(2,3,6-trifluorophenoxy)propyl]phenyl}-3,9-diazabicyclo[3.3.1] non-6-ene-3,9-dicarboxylic acid 3-tert-butyl ester 9-(2,2,2-trichloro-1,1-dimethylethyl) ester (AK14)

As for bicyclononene AK2, but from bicyclononene AY1 (552 mg, 0.75 mmol), cyclopropyl-[2-(2,3-difluoro-phenyl)ethyl]amine (296 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (572 mg, 83%). LC-MS: $R_t$=1.28.

(rac.)-(1R*,5S*)-6-{Cyclopropyl-[2-(4-fluorophenyl)ethyl]carbamoyl}-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK15)

As for bicyclononene AK2, but from bicyclononene AY1 (552 mg, 0.75 mmol), cyclopropyl-[2-(4-fluoro-phenyl) ethyl]amine (269 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (533 mg, 79%). LC-MS: $R_t$=1.28.

(rac.)-(1R*,5S*)-6-[Cyclopropyl-(2-o-tolylethyl) carbamoyl]-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK16)

As for bicyclononene AK2, but from bicyclononene AY1 (552 mg, 0.75 mmol), cyclopropyl-(2-o-tolylethyl)-amine (263 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (562 mg, 84%). LC-MS: $R_t$=1.29.

(rac.)-(1R*,5S*)-6-[Cyclopropyl-(3,5-dimethoxybenzyl)carbamoyl]-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK17)

As for bicyclononene AK2, but from bicyclononene AY1 (552 mg, 0.75 mmol), cyclopropyl-(3,5-dimethoxy-benzyl)amine (311 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (530 mg, 76%). LC-MS: $R_t$=1.28.

(rac.)-(1R*,5S*)-6-[Cyclopropyl-(2-p-tolylethyl) carbamoyl]-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK18)

As for bicyclononene AK2, but from bicyclononene AY1 (552 mg, 0.75 mmol), cyclopropyl-(2-p-tolylethyl)-amine (263 mg, 1.50 mmol), DIPEA (0.515 mL, 3.00 mmol), DMAP (23 mg, 0.19 mmol), HOBt (101 mg, 0.75 mmol) and EDC.HCl (216 mg, 1.12 mmol) in $CH_2Cl_2$ (7 mL). Purification by FC yielded the title compound (530 mg, 79%). LC-MS: $R_t$=1.30.

(rac.)-(1R*,5S*)-6-Cyclopropyl-[2-(2-hydroxyethyl)benzyl]carbamoyl}-7-{4-[3-(2,3,6-trifluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK19)

As for bicyclononene AK2, but from bicyclononene AY1 (1.30, 1.77 mmol), (2-allylbenzyl)cyclopropyl-amine (992 mg, 5.30 mmol), DIPEA (1.01 mL, 7.08 mmol), DMAP (54 mg, 0.44 mmol), HOBt (263 mg, 1.95 mmol) and EDC.HCl (509 mg, 2.66 mmol) in $CH_2Cl_2$ (25 mL). Purification by FC yielded the intermediate compound (1.49 g, 93%). LC-MS: $R_t$=7.81.

Then as for compound AT, but from the former intermediate compound (1.49 g, 1.65 mmol), NMO.$H_2O$ (245 mg, 1.82 mmol), and $OsO_4$ (2.5% in tert-BuOH, 0.207 mL, 0.017 mmol) in THF (4 mL), tert-BuOH (2 mL) and water (1 mL). Purification of the residue by FC (EtOAc/heptane 1:4→2:3→3:2→4:1→EtOAc) yielded the $2^{nd}$ intermediate compound (866 mg, 56%). $R_f$=0.50 (EtOAc). LC-MS: $R_t$=6.95.

Then as for compound AU, but from the $2^{nd}$ intermediate compound (866 mg, 0.922 mmol) and $NaIO_4$ (217 mg, 1.01 mmol) in THF (8 mL) and water (2 mL). Purification of the residue by FC (EtOAc/heptane 1:4→2:3) yielded the $3^{rd}$ intermediate compound (751 mg, 90%). $R_f$=0.75 (EtOAc).

Finally as for compound AV, but from the $3^{rd}$ intermediate compound (751 mg, 0.828 mmol) and $NaBH_4$ (35 mg, 0.9 mmol) in MeOH (10 mL). Purification of the residue by FC (EtOAc/heptane 2:3) yielded the title compound (599 mg, 80%). LC-MS: $R_t$=7.30.

(rac.)-(1R*,5S*)-7-{4-[3-(2-Bromo-5-fluorophenoxy)propyl]phenyl}-6-[(2-chlorobenzyl)cyclopropylcarbamoyl]-3,9-diazabicyclo[3.3.1]non-6-ene-3,9-dicarboxylic acid 3-tert-butyl ester 9-(2,2,2-trichloro-1,1-dimethylethyl) ester (AK20)

As for bicyclononene AK2, but from bicyclononene AY2 (7.68 g, 9.86 mmol), (2-chlorobenzyl)cyclopropylamine (5.37, 29.6 mmol), DIPEA (6.75 mL, 39.4 mmol), DMAP (301 mg, 2.47 mmol), HOBt (1.46 mg, 10.8 mmol) and EDC.HCl (2.84 g, 14.8 mmol) in $CH_2Cl_2$ (150 mL). Purification by FC (EtOAc/heptane 1:4→3:7→2:3→1:1) yielded the title compound (3.7 g, 40%). $R_f$=0.55 (EtOAc/heptane 1:1). LC-MS: $R_t$=7.97.

(rac.)-(1R*,5S*)-6-(Benzylcyclopropylcarbamoyl)-7-{4-[3-(2-bromo-5-fluoro-phenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK21)

As for bicyclononene AK2, but from bicyclononene AY2 (779 mg, 1.00 mmol), benzylcyclopropylamine (Loeppky, R. N.; et al., J. Org. Chem., 2000, 65, 96; 1.27 g, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in $CH_2Cl_2$ (10 mL). Purification by FC yielded the title compound (520 mg, 57%). LC-MS: $R_t$=7.79.

(rac.)-(1R*,5S*)-7-{4-[3-(2-Bromo-5-fluorophenoxy)propyl]phenyl}-6-[(2-chlorobenzyl)ethylcarbamoyl]-3,9-diazabicyclo[3.3.1]non-6-ene-3,9-dicarboxylic acid 3-tert-butyl ester 9-(2,2,2-trichloro-1,1-dimethylethyl) ester (AK22)

As for bicyclononene AK2, but from bicyclononene AY2 (779 mg, 1.00 mmol), (2-chlorobenzyl)ethylamine (Ishihara, Y; et al.; Chem. Pharm. Bull., 1991, 39, 3225; 254 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in $CH_2Cl_2$ (10 mL). Purification by FC yielded the title compound (475 mg, 51%). LC-MS: $R_t$=7.82.

(rac.)-(1R*,5S*)-7-{4-[3-(2-Bromo-5-fluorophenoxy)propyl]phenyl}-6-[cyclopropyl-(2-fluorobenzyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK23)

As for bicyclononene AK2, but from bicyclononene AY2 (779 mg, 1.00 mmol), cyclopropyl-(2-fluorobenzyl)amine (247 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in $CH_2Cl_2$ (10 mL). Purification by FC yielded the title compound (465 mg, 50%). LC-MS: $R_t$=7.69.

(rac.)-(1R*,5S*)-7-{4-[3-(2-Bromo-5-fluorophenoxy)propyl]phenyl}-6-[cyclopropyl-(3-trifluoromethylbenzyl)carbamoyl]-3,9-diazabicyclo[3.3.1]non-6-ene-3,9-dicarboxylic acid 3-tert-butyl ester 9-(2,2,2-trichloro-1,1-dimethyl-ethyl) ester (AK24)

As for bicyclononene AK2, but from bicyclononene AY2 (779 mg, 1.00 mmol), cyclopropyl-(3-trifluoromethylbenzyl)amine (Brabander, H. J.; et al.; *J. Org. Chem.*, 1967, 32, 4053; 323 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in CH$_2$Cl$_2$ (10 mL). Purification by FC yielded the title compound (345 mg, 35%). LC-MS: R$_t$=7.76.

(rac.)-(1R*,5S*)-7-{4-[3-(2-Bromo-5-fluorophenxy)propyl]phenyl}-6-[cyclopropyl-(2-methylbenzyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK25)

As for bicyclononene AK2, but from bicyclononene AY2 (779 mg, 1.00 mmol), cyclopropyl-(2-methylbenzyl)amine (242 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in CH$_2$Cl$_2$ (10 mL). Purification by FC yielded the title compound (722 mg, 78%). LC-MS: R$_t$=7.77.

(rac.)-(1R*,5S*)-7-{4-[3-(2-Bromo-5-fluorophenoxy)propyl]phenyl}-6-{cyclopropyl-[2-(4-methoxyphenoxy)ethyl]carbamoyl}-3,9-diazabicyclo[3.3.1]non-6-ene-3,9-dicarboxylic acid 3-tert-butyl ester 9-(2,2,2-trichloro-1,1-dimethyl-ethyl) ester (AK26)

As for bicyclononene AK2, but from bicyclononene AY2 (779 mg, 1.00 mmol), cyclopropyl-(4-methoxyphenoxymethyl)amine (311 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in CH$_2$Cl$_2$ (10 mL). Purification by FC yielded the title compound (579 mg, 60%). LC-MS: R$_t$=7.64.

(rac.)-(1R*5S*)-7-{4-[3-(2-Bromo-5-fluorophenoxy)propyl]phenyl}-6-[cyclopropyl-(2-m-tolyloxyethyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK27)

As for bicyclononene AK2, but from bicyclononene AY2 (779 mg, 1.00 mmol), cyclopropyl-m-tolyloxymethylamine (311 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in CH$_2$Cl$_2$ (10 mL). Purification by FC yielded the title compound (340 mg, 36%). LC-MS: R$_t$=7.83.

(rac.)-(1R*,5S*)-7-{4-[3-(2-Bromo-5-fluorophenoxy)propyl]phenyl}-6-{cyclopropyl-[2-(3,4-dimethylphenoxy)ethyl]carbamoyl}-3,9-diazabicyclo[3.3.1]-non-6-ene-3,9-dicarboxylic acid 3-tert-butyl ester 9-(2,2,2-trichloro-1,1-dimethylethyl) ester (AK28)

As for bicyclononene AK2, but from bicyclononene AY2 (779 mg, 1.00 mmol), cyclopropyl-(3,4-dimethylphenoxymethyl)amine (308 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in CH$_2$Cl$_2$ (10 mL). Purification by FC yielded the title compound (470 mg, 49%). LC-MS: R$_t$=7.93.

(rac.)-(1R*,5S*)-7-{4-[3-(2-Bromo-5-fluorophenoxy)propyl]phenyl}-6-(cyclo-propylphenethylcarbamoyl)-3,9-diazabicyclo[3.3.1]non-6-ene-3,9-dicarboxylic acid 3-tert-butyl ester 9-(2,2,2-trichloro-1,1-dimethylethyl) ester (AK29)

As for bicyclononene AK2, but from bicyclononene AY2 (779 mg, 1.00 mmol), cyclopropyl-phenethylamine (Smith, P. W.; et al.; *J. Med. Chem.*, 1998, 41, 787; 242 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in CH$_2$Cl$_2$ (10 mL). Purification by FC yielded the title compound (449 mg, 49%). LC-MS: R$_t$=7.72.

(rac.)-(1R*,5S*)-7-{4-[3-(2-Bromo-5-fluorophenoxy)propyl]phenyl}-6-{[2-(2-chlorophenyl)ethyl]cyclopropylcarbamoyl}-3,9-diazabicyclo[3.3.1]non-6-ene-3,9-dicarboxylic acid 3-tert-butyl ester 9-(2,2,2-trichloro-1,1-dimethylethyl) ester (AK30)

As for bicyclononene AK2, but from bicyclononene AY2 (779 mg, 1.00 mmol), [2-(2-chlorophenyl)ethyl]cyclopropylamine (294 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in CH$_2$Cl$_2$ (10 mL). Purification by FC yielded the title compound (605 mg, 63%). LC-MS: R$_t$=7.89.

(rac.)-(1R*,5S*)-7-{4-[3-(2-Bromo-5-fluorophenoxy)propyl]phenyl}-6-{cyclopropyl-[2-(2,3-difluorophenyl)ethyl]carbamoyl}-3,9-diazabicyclo[3.3.1]non-6-ene-3,9-dicarboxylic acid 3-tert-butyl ester 9-(2,2,2-trichloro-1,1-dimethyl-ethyl) ester (AK31)

As for bicyclononene AK2, but from bicyclononene AY2 (779 mg, 1.00 mmol), cyclopropyl-[2-(2,3-difluorophenyl)ethyl]amine (296 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in CH$_2$Cl$_2$ (10 mL). Purification by FC yielded the title compound (670 mg, 70%). LC-MS: R$_t$=7.70.

(rac.)-(1R*,5S*)-7-{4-[3-(2-Bromo-5-fluorophenoxy)propyl]phenyl}-6-{cyclopropyl-[2-(4-fluorophenyl)ethyl]carbamoyl}-3,9-diazabicyclo[3.3.1]non-6-ene-3,9-dicarboxylic acid 3-tert-butyl ester 9-(2,2,2-trichloro-1,1-dimethyl-ethyl) ester (AK32)

As for bicyclononene AK2, but from bicyclononene AY2 (779 mg, 1.00 mmol), cyclopropyl-[2-(4-fluorophenyl)ethyl]amine (269 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in CH$_2$Cl$_2$ (10 mL). Purification by FC yielded the title compound (638 mg, 68%). LC-MS: R$_t$=7.70.

(rac.)-(1R*,5S*)-7-{4-[3-(2-Bromo-5-fluorophenoxy)propyl]phenyl}-6-[cyclopropyl-(2-o-tolylethyl) carbamoyl]-3,9-diazabicyclo[3.3.1]non-6-ene-3,9-dicarboxylic acid 3-tert-butyl ester 9-(2,2,2-trichloro-1,1-dimethylethyl) ester (AK33)

As for bicyclononene AK2, but from bicyclononene AY2 (779 mg, 1.00 mmol), cyclopropyl-(2-o-tolylethyl)amine (263 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in $CH_2Cl_2$ (10 mL). Purification by FC yielded the title compound (659 mg, 70%). LC-MS: $R_t$=7.58.

1:1 Mixture of (rac.)-(1R*,5S*)-7-{4-[3-(2-bromo-5-fluorophenoxy)propyl]-phenyl}-6-[((2R*)-2-hydroxy-2-phenylethyl)methylcarbamoyl]-3,9-diazabicyclo[3.3.1]non-6-ene-3,9-dicarboxylic acid 3-tert-butyl ester 9-(2,2,2-trichloro-1,1-dimethylethyl) ester and (rac.)-(1R*,5S*)-7-{4-[3-(2-bromo-5-fluorophenoxy)propyl]phenyl}-6-[((2S*)-2-hydroxy-2-phenylethyl)methylcarbamoyl]-3,9-diazabicyclo[3.3.1]non-6-ene-3,9-dicarboxylic acid 3-tert-butyl ester 9-(2,2,2-trichloro-1,1-dimethylethyl) ester (AK34)

As for bicyclononene AK2, but from bicyclononene AY2 (779 mg, 1.00 mmol), (rac.)-2-methylamino-1-phenylethanol (310 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in $CH_2Cl_2$ (10 mL). Purification by FC yielded the title compounds (456 mg, 50%). LC-MS: $R_t$=7.42.

(rac.)-(1R*,5S*)-7-{4-[3-(2-Bromo-5-fluorophenoxy)propyl]phenyl}-6-[cyclopropyl-(3,5-dimethoxybenzyl)carbamoyl]-3,9-diazabicyclo[3.3.1]non-6-ene-3,9-dicarboxylic acid 3-tert-butyl ester 9-(2,2,2-trichloro-1,1-dimethyl-ethyl) ester (AK35)

As for bicyclononene AK2, but from bicyclononene AY2 (779 mg, 1.00 mmol), cyclopropyl-(3,5-dimethoxybenzyl)amine (311 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in $CH_2Cl_2$ (10 mL). Purification by FC yielded the title compound (736 mg, 76%). LC-MS: $R_t$=7.73.

(rac.)-(1R*,5S*)-7-{4-[3-(2-Bromo-5-fluorophenoxy)propyl]phenyl}-6-[cyclopropyl-(2-p-tolylethyl) carbamoyl]-3,9-diazabicyclo[3.3.1]non-6-ene-3,9-dicar-boxylic acid 3-tert-butyl ester 9-(2,2,2-trichloro-1,1-dimethylethyl) ester (AK36)

As for bicyclononene AK2, but from bicyclononene AY2 (779 mg, 1.00 mmol), cyclopropyl-(2-p-tolylethyl)amine (263 mg, 1.50 mmol), DIPEA (0.684 mL, 4.00 mmol), DMAP (30 mg, 0.25 mmol), HOBt (135 mg, 1.00 mmol) and EDC.HCl (287 mg, 1.50 mmol) in $CH_2Cl_2$ (10 mL). Purification by FC yielded the title compound (718 mg, 77%). LC-MS: $R_t$=7.73.

(rac.)-(1R*,5S*)-6-[(2-Allylbenzyl)cyclopropylcarbamoyl]-7-{4-[3-(2-bromo-5-fluorophenoxy)propyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK37)

As for bicyclononene AK2, but from bicyclononene AY2 (1.45, 2.00 mmol), (2-allylbenzyl)cyclopropylamine (1.12 g, 6.00 mmol), DIPEA (1.37 mL, 8.00 mmol), DMAP (62 mg, 0.50 mmol), HOBt (298 mg, 2.20 mmol) and EDC.HCl (576 mg, 3.00 mmol) in $CH_2Cl_2$ (20 mL). Purification by FC yielded the intermediate compound (1.77 g, 93%). LC-MS: $R_t$=7.95.

Then as for compound AT, but from the former intermediate compound (1.77 g, 1.86 mmol), NMO.H$_2$O (516 mg, 3.82 mmol), and OsO$_4$ (2.5% in tert-BuOH, 0.276 mL, 0.023 mmol) in THF (40 mL), tert-BuOH (20 mL) and water (10 mL). Purification of the residue by FC (EtOAc/heptane 1:4→2:3→3:2→4:1→EtOAc) yielded the $2^{nd}$ intermediate compound (548 mg, 27%). $R_f$=0.60 (EtOAc). LC-MS: $R_t$=7.43; ES+: 980.18.

Then as for compound AU, but from the $2^{nd}$ intermediate compound (928 mg, 0.945 mmol) and NaIO$_4$ (222 mg, 1.04 mmol) in THF (8 mL) and water (2 mL). Purification of the residue by FC (EtOAc/heptane 1:4→2:3) yielded the $3^{rd}$ intermediate compound (868 mg, 97%). $R_f$=0.80 (EtOAc).

Finally as for compound. AV, but from the $3^{rd}$ intermediate compound (868 mg, 0.914 mmol) and NaBH$_4$ (38 mg, 1.0 mmol) in MeOH (10 mL). Purification of the residue by FC (EtOAc/heptane 2:3) yielded the title compound (603 mg, 69%). LC-MS: $R_t$=1.44.

(rac.)-(1R*,5S*)-6-[(2-Chlorbenzyl)cyclopropylcarbamoyl]-7-{4-[2-(2,3,5-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK38)

As for bicyclononene AK2, but from bicyclononene AY3 (411 mg, 0.58 mmol), (2-chlorobenzyl)-cyclopropylamine (211 mg, 1.16 mmol), DIPEA (0.397 mL, 2.32 mmol), DMAP (18 mg, 0.15 mmol), HOBt (86 mg, 0.64 mmol) and EDC.HCl (167 mg, 0.87 mmol) in $CH_2Cl_2$ (8 mL). Purification by FC yielded the title compound (312 mg, 62%). LC-MS: $R_t$=7.66.

(rac.)-(1R*,5S*)(Benzylcyclopropylcarbamoyl)-7-{4-[2-(2,3,5-trimethyl-phenoxy)ethyl]phenyl}-3,9-diazabicyclo[3.3.1]non-6-ene-3,9-dicarboxylic acid 3-tert-butyl ester 9-(2,2,2-trichloro-1,1-dimethyl-ethyl) ester (AK39)

As for bicyclononene AK2, but from bicyclononene AY3 (411 mg, 0.58 mmol), benzyl-cyclopropylamine (Loeppky, R. N.; et al., *J. Org. Chem.*, 2000, 65, 96; 171 mg, 1.16 mmol), DIPEA (0.397 mL, 2.32 mmol), DMAP (18 mg, 0.15 mmol), HOBt (86 mg, 0.64 mmol) and EDC.HCl (167 mg, 0.87 mmol) in $CH_2Cl_2$ (8 mL). Purification by FC yielded the title compound (340 mg, 70%). LC-MS: $R_t$=8.12.

(rac.)-(1R*,5S*)-6-[(2-Chlorobenzyl)ethylcarbamoyl]-7-{4-[2-(2,3,5-trimethyl-phenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK40)

As for bicyclononene AK2, but from bicyclononene AY3 (411 mg, 0.58 mmol), (2-chlorobenzyl)-ethylamine (Ishihara, Y; et al.; *Chem. Pharm. Bull.*, 1991, 39, 3225; 197 mg, 1.16 mmol), DIPEA (0.397 mL, 2.32 mmol), DMAP (18 mg, 0.15 mmol), HOBt (86 mg, 0.64 mmol) and EDC.HCl (167 mg, 0.87 mmol) in $CH_2Cl_2$ (8 mL). Purification by FC yielded the title compound (374 mg, 74%). LC-MS: $R_t$=8.30.

(rac.)-(1R*,5S*)-6-[Cyclopropyl-(2-fluorobenzyl)carbamoyl]-7-{4-[2-(2,3,5-tri-methylphenoxy)ethyl]phenyl}-3,9-diazabicyclo[3.3.1non-6-ene-3,9dicarboxylic acid 3-tert-butyl ester 9-(2,2,2-trichloro-1,1-dimethylethyl) ester (AK41)

As for bicyclononene AK2, but from bicyclononene AY3 (411 mg, 0.58 mmol), cyclopropyl-(2-fluorobenzyl)amine (192 mg, 1.16 mmol), DIPEA (0.397 mL, 2.32 mmol), DMAP (18 mg, 0.15 mmol), HOBt (86 mg, 0.64 mmol) and EDC.HCl (167 mg, 0.87 mmol) in $CH_2Cl_2$ (8 mL). Purification by FC yielded the title compound (350 mg, 70%). LC-MS: $R_t$=8.13.

(rac.)-(1R*,5S*)-6-[Cyclopropyl-(3-trifluoromethyl-benzyl)carbamoyl]-7-{4-[2-(2,3,5-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK42)

As for bicyclononene AK2, but from bicyclononene AY3 (411 mg, 0.58 mmol), cyclopropyl-(3-trifluoromethylbenzyl)amine (Brabander, H. J.; et al.; *J. Org. Chem.*, 1967, 32, 4053; 250 mg, 1.16 mmol), DIPEA (0.397 mL, 2.32 mmol), DMAP (18 mg, 0.15 mmol), HOBt (86 mg, 0.64 mmol) and EDC.HCl (167 mg, 0.87 mmol) in $CH_2Cl_2$ (8 mL). Purification by FC yielded the title compound (294 mg, 56%). LC-MS: $R_t$=8.16.

(rac.)-(1R*,5S*)-6-[Cyclopropyl-(2-methylbenzyl)carbamoyl]-7-{4-[2-(2,3,5-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK43)

As for bicyclononene AK2, but from bicyclononene AY3 (411 mg, 0.58 mmol), cyclopropyl-(2-methylbenzyl)amine (187 mg, 1.16 mmol), DIPEA (0.397 mL, 2.32 mmol), DMAP (18 mg, 0.15 mmol), HOBt (86 mg, 0.64 mmol) and EDC.HCl (167 mg, 0.87 mmol) in $CH_2Cl_2$ (8 mL). Purification by FC yielded the title compound (294 mg, 56%). LC-MS: $R_t$=8.15.

(rac.)-(1R*,5S*)-6-{Cyclopropyl-[2-(4-methoxyphenoxy)ethyl]carbamoyl}-7-{4-[2-(2,3,5-trimethylphenoxy)ethyl]phenyl}-3,9-diazabicyclo[3.3.1]non-6-ene-3,9-dicarboxylic acid 3-tert-butyl ester 9-(2,2,2-trichloro-1,1dimethyl-ethyl) ester (AK44)

As for bicyclononene AK2, but from bicyclononene AY3 (411 mg, 0.58 mmol), cyclopropyl-[2-(4-methoxyphenoxy)ethyl]amine (187 mg, 1.16 mmol), DIPEA (0.397 mL, 2.32 mmol), DMAP (18 mg, 0.15 mmol), HOBt (86 mg, 0.64 mmol) and EDC.HCl (167 mg, 0.87 mmol) in $CH_2Cl_2$ (8 mL). Purification by FC yielded the title compound (159 mg, 30%). LC-MS: $R_t$=7.93.

(rac.)-(1R*,5S*)-6-{Cyclopropyl-[2-(3-methoxyphenoxy)ethyl]carbamoyl}-7-{4-[2-(2,3,5-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethyl-ethyl) ester (AK45)

As for bicyclononene AK2, but from bicyclononene AY3 (411 mg, 0.58 mmol), cyclopropyl-[2-(3-methoxyphenoxy)ethyl]amine (287 mg, 1.16 mmol), DIPEA (0.397 mL, 2.32 mmol), DMAP (18 mg, 0.15 mmol), HOBt (86 mg, 0.64 mmol) and EDC.HCl (167 mg, 0.87 mmol) in $CH_2Cl_2$ (8 mL). Purification by FC yielded the title compound (237 mg, 45%). LC-MS: $R_t$=7.69.

(rac.)-(1R*,5S*)-6-[Cyclopropyl-(2-m-tolyloxy-ethyl)carbamoyl]-7-{4-[2-(2,3,5-trimethylphenoxy)ethyl]phenyl}-3,9-diazabicyclo[3.3.1]non-6-ene-3,9-dicar-boxylic acid 3-tert-butyl ester 9-(2,2,2-trichloro-1,1-dimethylethyl) ester (AK46)

As for bicyclononene AK2, but from bicyclononene AY3 (411 mg, 0.58 mmol), cyclopropyl-(2-m-tolyloxyethyl)amine (222 mg, 1.16 mmol), DIPEA (0.397 mL, 2.32 mmol), DMAP (18 mg, 0.15 mmol), HOBt (86 mg, 0.64 mmol) and EDC.HCl (167 mg, 0.87 mmol) in $CH_2Cl_2$ (8 mL). Purification by FC yielded the title compound (185 mg, 36%). LC-MS: $R_t$=8.12.

(rac.)-(1R*,5S*)-6-Cyclopropylphenethylcarbamoyl]-7-{4-[2-(2,3,6-trimethyl-phenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK47)

As for bicyclononene AK2, but from bicyclononene AY3 (590 mg, 0.83 mmol), cyclopropyl-phenethylamine (Smith, P. W.; et al.; *J. Med. Chem.*, 1998, 41, 787; 402 mg, 2.49 mmol), DIPEA (0.568 mL, 3.32 mmol), DMAP (25 mg, 0.21 mmol), HOBt (169 mg, 1.25 mmol) and EDC.HCl (239 mg, 1.25 mmol) in $CH_2Cl_2$ (10 mL). Purification by FC yielded the title compound (309 mg, 44%). LC-MS: $R_t$=8.01.

(rac.)-(1R*,5S*)-6-{[2-(2-Chlorophenyl)ethyl]cyclopropylcarbamoyl}-7-{4-[2-(2,3,6-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK48)

As for bicyclononene AK2, but from bicyclononene AY3 (590 mg, 0.83 mmol), [2-(2-chlorophenyl)ethyl]cyclopropylamine (487 mg, 2.49 mmol), DIPEA (0.568 mL, 3.32 mmol), DMAP (25 mg, 0.21 mmol), HOBt (169 mg, 1.25 mmol) and EDC.HCl (239 mg, 1.25 mmol) in $CH_2Cl_2$ (10 mL). Purification by FC yielded the title compound (272 mg, 37%). LC-MS: $R_t$=8.20.

(rac.)-(1R*,5S*)-6-{Cyclopropyl-[2-(2,3-difluorophenyl)ethyl]carbamoyl}-7-{4-[2-(2,3,6-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK49)

As for bicyclononene AK2, but from bicyclononene AY3 (590 mg, 0.83 mmol), cyclopropyl-[2-(2,3-difluorophenyl)ethyl]amine (491 mg, 2.49 mmol), DIPEA (0.568 mL, 3.32 mmol), DMAP (25 mg, 0.21 mmol), HOBt (169 mg, 1.25 mmol) and EDC.HCl (239 mg, 1.25 mmol) in $CH_2Cl_2$ (10 mL). Purification by FC yielded the title compound (309 mg, 42%). LC-MS: $R_t$=7.98.

(rac.)-(1R*,5S*)-6-{Cyclopropyl-[2-(4-fluorophenyl)ethyl]carbamoyl}-7-{4-[2-(2,3,6-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK50)

As for bicyclononene AK2, but from bicyclononene AY3 (590 mg, 0.83 mmol), cyclopropyl-[2-(4-fluorophenyl)ethyl]amine (491 mg, 2.49 mmol), DIPEA (0.568 mL, 3.32 mmol), DMAP (25 mg, 0.21 mmol), HOBt (169 mg, 1.25 mmol) and EDC.HCl (239 mg, 1.25 mmol) in $CH_2Cl_2$ (10 mL). Purification by FC yielded the title compound (294 mg, 41%). LC-MS: $R_t$=7.93.

(rac.)-(1R*,5S*)-6-[Cyclopropyl-(2-o-tolylethyl)carbamoyl]-7-{4-[2-(2,3,6-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK51)

As for bicyclononene AK2, but from bicyclononene AY3 (590 mg, 0.83 mmol), cyclopropyl-(2-o-tolylethyl)amine (491 mg, 2.49 mmol), DIPEA (0.568 mL, 3.32 mmol), DMAP (25 mg, 0.21 mmol), HOBt (169 mg, 1.25 mmol) and EDC.HCl (239 mg, 1.25 mmol) in $CH_2Cl_2$ (10 mL). Purification by FC yielded the title compound (258 mg, 36%). LC-MS: $R_t$=8.16.

1:1—Mixture of (rac.)-1R*,5S*)-6-[((2R*)-2-hydroxy-2-phenylethyl)methylcarbamoyl]-7-{4-[2-(2,3,6-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester and (rac.)-(1R*,5S*)-6-[((2S*)-2-hydroxy-2-phenylethyl)methylcarbamoyl]-7-{4-[2-(2,3,6-trimethylphenoxy)ethyl]-phenyl}-3,9-diazabicyclo[3.3.1]non-6-ene-3,9-dicarboxylic acid 3-tert-butyl ester 9-(2,2,2-trichloro-1,1-dimethylethyl) ester (AK52)

As for bicyclononene AK2, but from bicyclononene AY3 (590 mg, 0.83 mmol), (rac.)-2-methylamino-1-phenylethanol (377 mg, 2.49 mmol), DIPEA (0.568 mL, 3.32 mmol), DMAP (25 mg, 0.21 mmol), HOBt (169 mg, 1.25 mmol) and EDC.HCl (239 mg, 1.25 mmol) in $CH_2Cl_2$ (10 mL). Purification by FC yielded the title compounds (117 mg, 17%). LC-MS: $R_t$=7.50.

(rac.)-(1R*,5S*)-6-[Cyclopropyl-(3,5-dimethoxybenzyl)carbamoyl]-7-{4-[2-(2,3,6-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK53)

As for bicyclononene AK2, but from bicyclononene AY3 (590 mg, 0.83 mmol), cyclopropyl-(3,5-dimethoxybenzyl)amine (516 mg, 2.49 mmol), DIPEA (0.568 mL, 3.32 mmol), DMAP (25 mg, 0.21 mmol), HOBt (169 mg; 1.25 mmol) and EDC.HCl (239 mg, 1.25 mmol) in $CH_2Cl_2$ (10 mL). Purification by FC yielded the title compound (258 mg, 35%). LC-MS: $R_t$=7.80.

(rac.)-(1R*,5S*)-6-[Cyclopropyl-(2-p-tolylethyl)carbamoyl]-7-{4-[2-(2,3,6-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK54)

As for bicyclononene AK2, but from bicyclononene AY3 (590 mg, 0.83 mmol), cyclopropyl-(2-p-tolylethyl)amine (426 mg, 2.49 mmol), DIPEA (0.568 mL, 3.32 mmol), DMAP (25 mg, 0.21 mmol), HOBt (169 mg, 1.25 mmol) and EDC.HCl (239 mg, 1.25 mmol) in $CH_2Cl_2$ (10 mL). Purification by FC yielded the title compound (235 mg, 32%). LC-MS: $R_t$=8.16.

(rac.)-(1R*,5S*)-6-{Cyclopropyl-[2-(2-hydroxyethyl)benzyl]carbamoyl}-7-{4-[2-(2,3,6-trimethylphenoxy)ethyl]phenyl}-3,9-diazabicyclo[3.3.1]non-6-ene-3,9-dicarboxylic acid 3-tert-butyl ester 9-(2,2,2-trichloro-1,1-dimethylethyl) ester (AK55)

As for bicyclononene AK2, but from bicyclononene AY3 (1.18 g, 1.66 mmol), (2-allylbenzyl)cyclopropylamine (932 mg, 4.98 mmol), DIPEA (1.14 mL, 6.64 mmol), DMAP (51 mg, 0.42 mmol), HOBt (338 mg, 2.50 mmol) and EDC.HCl (478 mg, 2.50 mmol) in $CH_2Cl_2$ (20 mL). Purification by FC yielded the intermediate compound (613 mg, 42%). LC-MS: $R_t$=8.16.

Then as for compound AT, but from the former intermediate compound (613 mg, 0.697 mmol), $NMO.H_2O$ (141 mg, 1.05 mmol), and $OsO_4$ (2.5% in tert-BuOH, 0.175 mL, 0.014 mmol) in THF (8 mL), tert-BuOH (4 mL) and water (2 mL). Purification of the residue by FC (EtOAc/heptane 1:1→EtOAc) yielded the $2^{nd}$ intermediate compound (348 mg, 55%). $R_f$=0.05 (EtOAc/heptane 1:1). LC-MS: $R_t$=7.31.

Then as for compound AU, but from the $2^{nd}$ intermediate compound (348 mg, 0.381 mmol) and $NaIO_4$ (122 mg, 0.571 mmol) in THF (6 mL) and water (2 mL). Drying the residue under high vacuum yielded the $3^{rd}$ intermediate compound (269 mg, 80%) that was used without further purification. LC-MS: $R_t$=7.29.

Finally as for compound AV, but from the $3^{rd}$ intermediate compound (269 mg, 0.305 mmol) and $NaBH_4$ (13 mg, 0.34 mmol) in MeOH (5 mL). Purification of the residue by FC (EtOAc/heptane 1:4→2:3→3:2→4:1) yielded the title compound (210 mg, 78%). LC-MS: $R_t$=7.55.

(rac.)-(1R*,5S*)-6-[(2-Chlorobenzyl)cyclopropylcarbamoyl]-7-{4-[2-(2-chloro-4,5-dimethylphenoxy)ethoxy]phenyl}-3,9-diazabicyclo[3.3.1]non-6-ene-3,9-dicarboxylic acid 3-tert-butyl ester 9-(2,2,2-trichloro-1,1-dimethylethyl) ester (AK56)

As for bicyclononene AK2, but from bicyclononene AY4 (596 mg, 0.80 mmol), (2-chlorobenzyl)-cyclopropylamine (290 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (451 mg, 74%). LC-MS: $R_t$=1.30.

(rac.)-(1R*,5S*)-6-[(2-Chlorobenzyl)ethylcarbamoyl]-7-{4-[2-(2-chloro-4,5-dimethylphenoxy)ethoxy]phenyl}-3,9-diazabicyclo[3.3.1]non-6-ene-3,9-dicarboxylic acid 3-tert-butyl ester 9-(2,2,2-trichloro-1,1-dimethylethyl) ester (AK57)

As for bicyclononene AK2, but from bicyclononene AY4 (596 mg, 0.80 mmol), (2-chlorobenzyl)-ethylamine (Ishihara, Y; et al.; *Chem. Pharm. Bull.*, 1991, 39, 3225; 290 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (596 mg, 83%). LC-MS: $R_t$=1.30.

(rac.)-(1R*,5S*)-7-{4-[2-(2-Chloro-4,5-dimethylphenoxy)ethoxy]phenyl}-6-[cyclopropyl-(2-fluorobenzyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK58)

As for bicyclononene AK2, but from bicyclononene AY4 (596 mg, 0.80 mmol), cyclopropyl-(2-fluorobenzyl)amine (264 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (519 mg, 73%). LC-MS: $R_t$=1.29.

(rac.)-(1R*,5S*)-7-{4-[2-(2-Chloro-4,5-dimethylphenoxy)ethoxy]phenyl}-6-[cyclopropyl-(3-trifluoromethylbenzyl)carbamoyl]-3,9-diazabicyclo[3.3.1]-non-6-ene-3,9-dicarboxylic acid 3-tert-butyl ester 9-(2,2,2-trichloro-1,1-dimethylethyl) ester (AK59)

As for bicyclononene AK2, but from bicyclononene AY4 (596 mg, 0.80 mmol), cyclopropyl-(3-trifluoromethylbenzyl)amine (Brabander, H. J.; et al; *J. Org. Chem.*, 1967, 32, 4053; 344 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (584 mg, 78%). LC-MS: $R_t$=1.30.

(rac.)-(1R*,5S*)-7-{4-[2-(2-Chloro-4,5-dimethylphenoxy)ethoxy]phenyl}-6-[cyclopropyl-(2-methylbenzyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK60)

As for bicyclononene AK2, but from bicyclononene AY4 (596 mg, 0.80 mmol), cyclopropyl-(2-methylbenzyl)amine (258 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (569 mg, 48%). LC-MS: $R_t$=1.30.

(rac.)-(1R*,5S*)-7-{4-[2-(2-Chloro-4,5-dimethylphenoxy)ethoxy]phenyl}-6-{cyclopropyl-[2-(4-methoxyphenoxy)ethyl]carbamoyl}-3,9-diazabicyclo-[3.3.1]non-6-ene-3,9-dicarboxylic acid 3-tert-butyl ester 9-(2,2,2-trichloro-1,1-dimethylethyl) ester (AK61)

As for bicyclononene AK2, but from bicyclononene AY4 (596 mg, 0.80 mmol), cyclopropyl-[2-(4-methoxyphenoxy)ethyl]amine (332 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (591 mg, 79%). LC-MS: $R_t$=1.28.

(rac.)-(1R*,5S*)-7-{4-[2-(2-Chloro-4,5-dimethylphenoxy)ethoxy]phenyl}-6-{cyclopropyl-[2-(3-methoxyphenoxy)ethyl]carbamoyl}-3,9-diazabicyclo-[3.3.1]non-6-ene-3,9-dicarboxylic acid 3-tert-butyl ester 9-(2,2,2-trichloro-1,1-dimethylethyl) ester (AK62)

As for bicyclononene AK2, but from bicyclononene AY4 (596 mg, 0.80 mmol), cyclopropyl-[2-(3-methoxyphenoxy)ethyl]amine (332 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (584 mg, 77%). LC-MS: $R_t$=1.28.

(rac.)-(1R*,5S*)-7-{4-[2-(2-Chloro-4,5-dimethylphenoxy)ethoxy]phenyl}-6-[cyclopropyl-(2-m-tolyloxyethyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK63)

As for bicyclononene AK2, but from bicyclononene AY4 (596 mg, 0.80 mmol), cyclopropyl-(2-p-tolyloxyethyl)amine (306 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (525 mg, 71%). LC-MS: $R_t$=1.30.

(rac.)-(1R*,5S*)-7-{4-[2-(2-Chloro-4,5-dimethylphenoxy)ethoxy]phenyl}-6-(cyclopropylphenethylcarbamoyl)-3,9-diazabicyclo[3.3.1]non-6-ene-3,9-dicarboxylic acid 3-tert-butyl ester 9-(2,2,2-trichloro-1,1-dimethylethyl) ester (AK64)

As for bicyclononene AK2, but from bicyclononene AY4 (596 mg, 0.80 mmol), cyclopropyl-phenethylamine (Smith, P. W.; et al.; *J. Med. Chem.*, 1998, 41, 787; 258 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (360 mg, 50%). LC-MS: $R_t$=1.30.

(rac.)-(1R*,5S*)-7-{4-[2-(2-Chloro-4,5-dimethylphenoxy)ethoxy]phenyl}-6-{[2-(2-chlorophenyl)ethyl]cyclopropylcarbamoyl}-3,9-diazabicyclo[3.3.1]non-6-ene-3,9-dicarboxylic acid 3-tert-butyl ester 9-(2,2,2-trichloro-1,1-dimethyl-ethyl) ester (AK65)

As for bicyclononene AK2, but from bicyclononene AY4 (596 mg, 0.80 mmol), [2-(2-chlorophenyl)ethyl]cyclopropylamine (313 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (572 mg, 76%). LC-MS: $R_t$=1.30.

(rac.)-(1R*,5S*)-7-{4-[2-(2-Chloro-4,5-dimethylphenoxy)ethoxy]phenyl}-6-{cyclopropyl-[2-(2,3-difluorophenyl)ethyl]carbamoyl}-3,9-diazabicyclo[3.3.1]-non-6-ene-3,9-dicarboxylic acid 3-tert-butyl ester 9-(2,2,2-trichloro-1,1-dimethylethyl) ester (AK66)

As for bicyclononene AK2, but from bicyclononene AY4 (596 mg, 0.80 mmol), cyclopropyl-[2-(2,3-difluorophenyl)ethyl]amine (316 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (584 mg, 79%). LC-MS: $R_t$=1.29.

(rac.)-(1R*,5S*)-7-{4-[2-(2-Chloro-4,5-dimethylphenoxy)ethoxy]phenyl}-6-{cyclopropyl-[2-(4-fluorophenyl)ethyl]carbamoyl}-3,9-diazabicyclo[3.3.1]non-6-ene-3,9-dicarboxylic acid 3-tert-butyl ester 9-(2,2,2-trichloro-1,1-dimethyl-ethyl) ester (AK67)

As for bicyclononene AK2, but from bicyclononene AY4 (596 mg, 0.80 mmol), cyclopropyl-[2-(4-fluorophenyl)ethyl]amine (287 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (616 mg, 84%). LC-MS: $R_t$=1.28.

(rac.)-(1R*,5S*)-7-{4-[2-(2-Chloro-4,5-dimethylphenoxy)ethoxy]phenyl}-6-[cyclopropyl-(2-o-tolylethyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK68)

As for bicyclononene AK2, but from bicyclononene AY4 (596 mg, 0.80 mmol), cyclopropyl-(2-o-tolylethyl)amine (280 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (556 mg, 76%). LC-MS: $R_t$=1.28.

1:1—Mixture of (rac.)-(1R*,5S*)-7-{4-[2-(2-chloro-4,5-dimethylphenoxy)-ethoxy]phenyl}-6-[((2R*)-2-hydroxy-2-phenylethyl)methylcarbamoyl]-3,9-diazabicyclo[3.3.1]non-6-ene-3,9-dicarboxylic acid 3-tert-butyl ester 9-(2,2,2-trichloro-1,1-dimethyl-ethyl) ester and (rac.)-(1R*,5S*)-7-{4-[2-(2-chloro-4,5-dimethylphenoxy)ethoxy]phenyl}-6-[((2S*)-2-hydroxy-2-phenylethyl)methylcarbamoyl]-3,9-diazabicyclo[3.3.1]non-6-ene-3,9-dicarboxylic acid 3-tert-butyl ester 9-(2,2,2-trichloro-1,1-dimethyl-ethyl) ester (AK69)

As for bicyclononene AK2, but from bicyclononene AY4 (596 mg, 0.80 mmol), (rac.)-2-methylamino-1-phenylethanol (242 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compounds (380 mg, 54%). LC-MS: $R_t$=1.23.

(rac.)-(1R*,5S*)-7-{4-[2-(2-Chloro-4,5-dimethylphenoxy)ethoxy]phenyl}-6-[cyclopropyl-(3,5-dimethoxybenzyl)carbamoyl]-3,9-diazabicyclo[3.3.1]non-6-ene-3,9-dicarboxylic acid 3-tert-butyl ester 9-(2,2,2-trichloro-1,1-dimethyl-ethyl) ester (AK70)

As for bicyclononene AK2, but from bicyclononene AY4 (596 mg, 0.80 mmol), cyclopropyl-(3,5-dimethoxybenzyl)amine (332 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (619 mg, 83%). LC-MS: $R_t$=1.28.

(rac.)-(1R*,5S*)-7-{4-[2-(2-Chloro-4,5-dimethylphenoxy)ethoxy]phenyl}-6-[cyclopropyl-(2-p-tolylethyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK71)

As for bicyclononene AK2, but from bicyclononene AY4 (596 mg, 0.80 mmol), cyclopropyl-(2-p-tolylethyl)amine (280 mg, 1.60 mmol), DIPEA (0.548 mL, 3.2 mmol), DMAP (25 mg, 0.21 mmol), HOBt (135 mg, 1.00 mmol) and EDC.HCl (307 mg, 1.55 mmol) in $CH_2Cl_2$ (5 mL). Purification by FC yielded the title compound (619 mg, 83%). LC-MS: $R_t$=1.28.

(rac.)-(1R*,5S*)-7-{4-[2-(2-Chloro-4,5-dimethylphenoxy)ethoxy]phenyl}-6-{cyclopropyl-[2-(2-hydroxyethyl)benzyl]carbamoyl}-3,9-diazabicyclo[3.3.1]-non-6-ene-3,9-dicarboxylic acid 3-tert-butyl ester 9-(2,2,2-trichloro-1,1-dimethyl-ethyl) ester (AK72)

As for bicyclononene AK2, but from bicyclononene AY3 (1.00 g, 1.34 mmol), (2-allylbenzyl)cyclopropylamine (752 mg, 4.02 mmol), DIPEA (0.918 mL, 5.26 mmol), DMAP (41 mg, 0.34 mmol), HOBt (199 mg, 1.47 mmol) and EDC.HCl (385 mg, 2.01 mmol) in $CH_2Cl_2$ (15 mL). Purification by FC yielded the intermediate compound (845 mg, 69%). $R_f$=0.45 (EtOAc/heptane 1:1). LC-MS: $R_t$=7.85.

Then as for compound AT, but from the former intermediate compound (845 mg, 0.926 mmol), $NMO.H_2O$ (150 mg, 1.11 mmol), and OsO$_4$ (2.5% in tert-BuOH, 0.173 mL, 0.014 mmol) in THF (8 mL), tert-BuOH (4 mL) and water (2 mL). Purification of the residue by FC (EtOAc/heptane 1:1→EtOAc→MeOH/EtOAc 1:9) yielded the 2$^{nd}$ intermediate compound (616 mg, 70%). R$_f$=0.05 (EtOAc/heptane 1:1). LC-MS: R$_t$=7.04.

Then as for compound AU, but from the 2$^{nd}$ intermediate compound (616 mg, 0.649 mmol) and NaIO$_4$ (208 mg, 0.973 mmol) in THF (6 mL) and water (2 mL). Drying the residue under high vacuum yielded the 3$^{rd}$ intermediate compound (477 mg, 80%) that was used without further purification. LC-MS: R$_t$=7.43.

Finally as for compound AV, but from the 3$^{rd}$ intermediate compound (477 mg, 0.520 mmol) and NaBH$_4$ (22 mg, 0.57 mmol) in MeOH (5 mL). Purification of the residue by FC (EtOAc/heptane 1:4→2:3→3:2→4:1) yielded the title compound (210 mg, 78%). R$_f$=0.10 (EtOAc/heptane 1:1). LC-MS: R$_t$=7.26.

(rac.)-(1R*,5S*)-7-{4-[2-(4-Bromophenoxy)ethoxy]phenyl}-6-[(2-chloro-benzyl)cyclopropylcarbamoyl]-3,9-diazabicyclo[3.3.1]non-6-ene-3,9-dicarboxylic acid 3-tert-butyl ester 9-(2,2,2-trichloro-1,1-dimethylethyl) ester (AK73)

As for bicyclononene AK2, but from bicyclononene AY5 (534 mg, 0.7 mmol), (2-chlorobenzyl)-cyclopropylamine (200 mg, 1.10 mmol), DIPEA (0.479 mL, 2.8 mmol), DMAP (21 mg, 0.18 mmol), HOBt (113 mg, 0.84 mmol) and EDC.HCl (211 mg, 1.1 mmol) in CH$_2$Cl$_2$ (7 mL). Purification by FC yielded the title compound (263 mg, 39%). LC-MS: R$_t$=1.28.

(rac.)-(1R*,5S*)-6-(Benzylcyclopropylcarbamoyl)-7-{4-[2-(4-bromophenoxy)-ethoxy]phenyl}-3,9-diazabicyclo[3.3.1]non-6-ene-3,9-dicarboxylic acid 3-tert-butyl ester 9-(2,2,2-trichloro-1,1-dimethylethyl) ester (AK74)

As for bicyclononene AK2, but from bicyclononene AY5 (534 mg, 0.7 mmol), benzylcyclopropyl-amine (Loeppky, R. N.; et al., J. Org. Chem., 2000, 65, 96; 162 mg, 1.10 mmol), DIPEA (0.479 mL, 2.8 mmol), DMAP (21 mg, 0.18 mmol), HOBt (113 mg, 0.84 mmol) and EDC.HCl (211 mg, 1.1 mmol) in CH$_2$Cl$_2$ (7 mL). Purification by FC yielded the title compound (263 mg, 39%). LC-MS: R$_t$=1.26.

(rac.)-(1R*,5S*)-7-{4-[2-(4-Bromophenoxy)ethoxy]phenyl}-6-[(2-chloro-benzyl)ethylcarbamoyl]-3,9-diazabicyclo[3.3.1]non-6-ene-3,9-dicarboxylic acid 3-tert-butyl ester 9-(2,2,2-trichloro-1,1-dimethylethyl) ester (AK75)

As for bicyclononene AK2, but from bicyclononene AY5 (534 mg, 0.7 mmol), (2-chlorobenzyl)-ethylamine (Ishihara, Y; et al.; Chem. Pharm. Bull., 1991, 39, 3225; 187 mg, 1.10 mmol), DIPEA (0.479 mL, 2.8 mmol), DMAP (21 mg, 0.18 mmol), HOBt (113 mg, 0.84 mmol) and EDC.HCl (211 mg, 1.1 mmol) in CH$_2$Cl$_2$ (7 mL). Purification by FC yielded the title compound (204 mg, 32%). LC-MS: R$_t$=1.28.

(rac.)-(1R*,5S*)-7-{4-[2-(4-Bromophenoxy)ethoxy]phenyl}-6-[cyclopropyl-(2-fluorobenzyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK76)

As for bicyclononene AK2, but from bicyclononene AY5 (534 mg, 0.7 mmol), cyclopropyl-(2-fluorobenzyl)amine (182 mg, 1.10 mmol), DIPEA (0.479 mL, 2.8 mmol), DMAP (21 mg, 0.18 mmol), HOBt (113 mg, 0.84 mmol) and EDC.HCl (211 mg, 1.1 mmol) in CH$_2$Cl$_2$ (7 mL). Purification by FC yielded the title compound (233 mg, 37%). LC-MS: R$_t$=1.27.

(rac.)-(1R*,5S*)-7-{4-[2-(4-Bromophenoxy)ethoxy]phenyl}-6-[cyclopropyl-(3-trifluoromethylbenzyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK77)

As for bicyclononene AK2, but from bicyclononene AY5 (534 mg, 0.7 mmol), cyclopropyl-(3-trifluoromethylbenzyl)amine (Brabander, H. J.; et al.; J. Org. Chem., 1967, 32, 4053; 237 mg, 1.10 mmol), DIPEA (0.479 mL, 2.8 mmol), DMAP (21 mg, 0.18 mmol), HOBt (113 mg, 0.84 mmol) and EDC.HCl (211 mg, 1.1 mmol) in CH$_2$Cl$_2$ (7 mL). Purification by FC yielded the title compound (276 mg, 41%). LC-MS: R$_t$=1.27.

(rac.)-(1R*,5S*)-7-{4-[2-(4-Bromophenoxy)ethoxy]phenyl}-6-[cyclopropyl-(2-methylbenzyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK78)

As for bicyclononene AK2, but from bicyclononene AY5 (534 mg, 0.7 mmol), cyclopropyl-(2-methylbenzyl)amine (178 mg, 1.10 mmol), DIPEA (0.479 mL, 2.8 mmol), DMAP (21 mg, 0.18 mmol), HOBt (113 mg, 0.84 mmol) and EDC.HCl (211 mg, 1.1 mmol) in CH$_2$Cl$_2$ (7 mL). Purification by FC yielded the title compound (171 mg, 27%). LC-MS: R$_t$=1.26.

(rac.)-(1R*,5S*)-7-{4-[2-(4-Bromophenoxy)ethoxy]phenyl}-6-{cyclopropyl-[2-(4-methoxyphenoxy)ethyl]carbamoyl}-3,9-diazabicyclo[3.3.1]non-6-ene-3,9-dicarboxylic acid 3-tert-butyl ester 9-(2,2,2-trichloro-1,1-dimethylethyl) ester (AK79)

As for bicyclononene AK2, but from bicyclononene AY5 (534 mg, 0.7 mmol), cyclopropyl-[2-(4-methoxyphenoxy)ethyl]amine (228 mg, 1.10 mmol), DIPEA (0.479 mL, 2.8 mmol), DMAP (21 mg, 0.18 mmol), HOBt (113 mg, 0.84 mmol) and EDC.HCl (211 mg, 1.1 mmol) in CH$_2$Cl$_2$ (7 mL). Purification by FC yielded the title compound (190 mg, 29%). LC-MS: R$_t$=1.26.

(rac.)-(1R*,5S*)-7-{4-[2-(4-Bromophenoxy)ethoxy]phenyl}-6-{cyclopropyl-[2-(3,4-dimethylphenoxy)ethyl]carbamoyl}-3,9-diazabicyclo[3.3.1]non-6-ene-3,9-dicarboxylic acid 3-tert-butyl ester 9-(2,2,2-trichloro-1,1-dimethylethyl) ester (AK80)

As for bicyclononene AK2, but from bicyclononene AY5 (700 mg, 0.918 mmol), cyclopropyl-[2-(3,4-dimethylphenoxy)ethyl]amine (565 mg, 2.75 mmol), DIPEA (0.628 mL, 3.67 mmol), DMAP (28 mg, 0.23 mmol), HOBt (136 mg, 1.01 mmol) and EDC.HCl (264 mg, 1.38 mmol) in CH$_2$Cl$_2$ (10 mL). Purification by FC yielded the title compound (199 mg, 23%). LC-MS: R$_t$=7.76.

(rac.)-(1R*,5S*)-7-{4-[2-(4-Bromophenoxy)ethoxy]phenyl}-6-{[2-(2-chlorophenyl)ethyl]cyclopropylcarbamoyl}-3,9-diazabicyclo[3.3.1]non-6-ene-3,9-dicarboxylic acid 3-tert-butyl ester 9-(2,2,2-trichloro-1,1-dimethylethyl) ester (AK81)

As for bicyclononene AK2, but from bicyclononene AY5 (700 mg, 0.918 mmol), [2-(2-chlorophenyl)ethyl]cyclopropylamine (538 mg, 2.75 mmol), DIPEA (0.628 mL, 3.67 mmol), DMAP (28 mg, 0.23 mmol), HOBt (136 mg, 1.01 mmol) and EDC.HCl (264 mg, 1.38 mmol) in CH$_2$Cl$_2$ (10 mL). Purification by FC yielded the title compound (256 mg, 30%). LC-MS: R$_t$=7.70.

(rac.)-(1R*,5S*)-7-{4-[2-(4-Bromophenoxy)ethoxy]phenyl}-6-{cyclopropyl-[2-(2,3-difluorophenyl)ethyl]carbamoyl}-3,9-diazabicyclo[3.3.1]non-6-ene-3,9-dicarboxylic acid 3-tert-butyl ester 9-(2,2,2-trichloro-1,1-dimethylethyl) ester (AK82)

As for bicyclononene AK2, but from bicyclononene AY5 (700 mg, 0.918 mmol), cyclopropyl-[2-(2,3-difluorophenyl)ethyl]amine (542 mg, 2.75 mmol), DIPEA (0.628 mL, 3.67 mmol), DMAP (28 mg, 0.23 mmol), HOBt (136 mg, 1.01 mmol) and EDC.HCl (264 mg, 1.38 mmol) in CH$_2$Cl$_2$ (10 mL). Purification by FC yielded the title compound (245 mg, 28%). LC-MS: R$_t$=7.55.

(rac.)-(1R*,5S*)-7-{4-[2-(4-Bromophenoxy)ethoxy]phenyl}-6-{cyclopropyl-[2-(4-fluorophenyl)ethyl]carbamoyl}-3,9-diazabicyclo[3.3.1]non-6-ene-3,9-dicar-boxylic acid 3-tert-butyl ester 9-(2,2,2-trichloro-1,1-dimethylethyl) ester (AK83)

As for bicyclononene AK2, but from bicyclononene AY5 (700 mg, 0.918 mmol), cyclopropyl-[2-(4-fluorophenyl)ethyl]amine (493 mg, 2.75 mmol), DIPEA (0.628 mL, 3.67 mmol), DMAP (28 mg, 0.23 mmol), HOBt (136 mg, 1.01 mmol) and EDC.HCl (264 mg, 1.38 mmol) in CH$_2$Cl$_2$ (10 mL). Purification by FC yielded the title compound (220 mg, 26%). LC-MS: R$_t$=7.51.

(rac.)-(1R*,5S*)-7-{4-[2-(4-Bromophenoxy)ethoxy]phenyl}-6-[cyclopropyl-(2-o-tolylethyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK84)

As for bicyclononene AK2, but from bicyclononene AY5 (700 mg, 0.918 mmol), cyclopropyl-(2-o-tolylethyl)amine (482 mg, 2.75 mmol), DIPEA (0.628 mL, 3.67 mmol), DMAP (28 mg, 0.23 mmol), HOBt (136 mg, 1.01 mmol) and EDC.HCl (264 mg, 1.38 mmol) in CH$_2$Cl$_2$ (10 mL). Purification by FC yielded the title compound (252 mg, 30%). LC-MS: R$_t$=7.66.

(rac.)-(1R*,5S*)-7-{4-[2-(4-Bromophenoxy)ethoxy]phenyl}-6-[cyclopropyl-(3,5-dimethoxybenzyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK85)

As for bicyclononene AK2, but from bicyclononene AY5 (700 mg, 0.918 mmol), Cyclopropyl-(3,5-dimethoxy-benzyl)-amine (570 mg, 2.75 mmol), DIPEA (0.628 mL, 3.67 mmol), DMAP (28 mg, 0.23 mmol), HOBt (136 mg, 1.01 mmol) and EDC.HCl (264 mg, 1.38 mmol) in CH$_2$Cl$_2$ (10 mL). Purification by FC yielded the title compound (242 mg, 28%). LC-MS: R$_t$=7.42.

(rac.)-(1R*,5S*)-7-{4-[2-(4-Bromophenoxy)ethoxy]phenyl}-6-[cyclopropyl-(2-p-tolylethyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (AK86)

As for bicyclononene AK2, but from bicyclononene AY5 (700 mg, 0.918 mmol), cyclopropyl-(2-p-tolylethyl)amine (482 mg, 2.75 mmol), DIPEA (0.628 mL, 3.67 mmol), DMAP (28 mg, 0.23 mmol), HOBt (136 mg, 1.01 mmol) and EDC.HCl (264 mg, 1.38 mmol) in CH$_2$Cl$_2$ (10 mL). Purification by FC yielded the title compound (246 mg, 29%). LC-MS: R$_t$=7.66.

(rac.)-(1R*,5S*)-7-{4-[2-(4-Bromophenoxy)ethoxy]phenyl}-6-{cyclopropyl-[2-(2-hydroxyethyl)benzyl]carbamoyl}-3,9diazabicyclo[3.3.1]non-6-ene-3,9-dicarboxylic acid 3-tert-butyl ester 9-(2,2,2-trichloro-1,1-dimethylethyl) ester (AK87)

As for bicyclononene AK2, but from bicyclononene AY5 (1.00 g, 1.31 mmol), (2-allylbenzyl)cyclopropylamine (752 mg, 4.02 mmol), DIPEA (0.918 mL, 5.26 mmol), DMAP (41 mg, 0.34 mmol), HOBt (199 mg, 1.47 mmol) and EDC.HCl (385 mg, 2.01 mmol) in CH$_2$Cl$_2$ (15 mL). Purification by FC yielded the intermediate compound (875 mg, 72%). R$_f$=0.45 (EtOAc/heptane 1:1). LC-MS: R$_t$=7.69.

Then as for compound AT, but from the former intermediate compound (875 mg, 0.939 mmol), NMO.H$_2$O (152 mg, 1.13 mmol), and OsO$_4$ (2.5% in tert-BuOH, 0.236 mL, 0.019 mmol) in THF (8 mL), tert-BuOH (4 mL) and water (2 mL). Purification of the residue by FC (EtOAc/heptane 1:1→EtOAc→MeOH/EtOAc 1:9) yielded the 2$^{nd}$ intermediate compound (310 mg, 34%). R$_f$=0.05 (EtOAc/heptane 1:1). LC-MS: R$_t$=6.86.

Then as for compound AU, but from the 2$^{nd}$ intermediate compound (310 mg, 0.321 mmol) and NaIO$_4$ (139 mg, 0.481 mmol) in THF (6 mL) and water (2 mL). Drying the residue under high vacuum yielded the 3$^{rd}$ intermediate compound (239 mg, 80%) that was used without further purification. LC-MS: R$_t$=7.29.

Finally as for compound AV, but from the 3$^{rd}$ intermediate compound (239 mg, 0.256 mmol) and NaBH$_4$ (11 mg, 0.28 mmol) in MeOH (5 mL). Purification of the residue by FC (EtOAc/heptane 1:4→2:3→3:2→4:1) yielded the title compound (170 mg, 71%). R$_f$=0.10 (EtOAc/heptane 1:1). LC-MS: R$_t$=7.13.

Compounds of Type AL (rac.)-(1R*,5S*)-7-{4-[2-(2-Bromo-5-fluorophenoxy)ethyl]phenyl}-6-(methyl-phenethylcarbamoyl)-3,9-diazabicyclo[3.3.1]non-6ene-9-carboxylic Acid 2,2,2-trichloro-1,1-dimethylethyl ester hydrochloride salt (AL1)

A sol. bicyclononene AK1 (540 mg, 0.61 mmol)I in CH$_2$Cl$_2$ (10 mL) was cooled to 0° C. HCl/dioxane (4M, 10 mL) was added and the ice bath was removed. After 4 h stirring at rt the solvents were removed under reduced pressure and the residue dried under high vacuum. The crude was used without further purification.

(rac.)-(1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethyl-ethyl ester hydrochloride salt (AL2)

As for compound AL1 but from bicyclononene AK2 (407 mg, 0.47 mmol) in CH$_2$Cl$_2$ (5 mL) and HCl/dioxane (4M, 5 mL). LC-MS: R$_t$=1.06; ES+: 796.34.

(rac.)-(1R*,5S*)-6-(Benzylcyclopropylcarbamoyl)-7-{4-[3-(2,3,6-trifluorophenoxy)propyl]phenyl}-3,9-diazabicyclo[3.3.1]non-6-ene-9-carboxylic acid 2,2,2-trichloro-1,1-dimethyl-ethyl ester hydrochloride salt (AL3)

As for compound AL1 but from bicyclononene AK3 (570 mg, 0.65 mmol) in CH$_2$Cl$_2$ (5 mL) and HCl/dioxane (4M, 5 mL). LC-MS: R$_t$=1.04; ES+: 766.34.

(rac.)-(1R*,5S*)-6-[(2-Chlorobenzyl)ethylcarbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL4)

As for compound AL1 but from bicyclononene AK4 (about 0.55 mmol) in CH$_2$Cl$_2$ (5 mL) and HCl/dioxane (4M, 5 mL). LC-MS: R$_t$=1.19; ES+: 786.25.

(rac.)-(1R*,5S*)-6-[Cyclopropyl-(2-fluorobenzyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL5)

As for compound AL1 but from bicyclononene AK5 (about 0.55 mmol) in CH$_2$Cl$_2$ (5 mL) and HCl/dioxane (4M, 5 mL). LC-MS: R$_t$=1.18; ES+: 782.28.

(rac.)-(1R*,5S*)-6-[Cyclopropyl-(3-trifluoromethylbenzyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL6)

As for compound AL1 but from bicyclononene AK6 (about 0.55 mmol) in CH$_2$Cl$_2$ (5 mL) and HCl/dioxane (4M, 5 mL). LC-MS: R$_t$=1.20.

(rac.)-(1R*,5S*)-6-[Cyclopropyl-(2-methylbenzyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL7)

As for compound AL1 but from bicyclononene AK7 (about 0.55 mmol) in CH$_2$Cl$_2$ (5 mL) and HCl/dioxane (4M, 5 mL). LC-MS: R$_t$=1.21; ES+: 778.30.

(rac.)-(1R*,5S*)-6-[Cyclopropyl-(4-methoxyphenoxymethyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL8)

As for compound AL1 but from bicyclononene AK8 (about 0.55 mmol) in CH$_2$Cl$_2$ (5 mL) and HCl/dioxane (4M, 5 mL). LC-MS: R$_t$=1.21.

(rac.)-(1R*,5S*)-6-[Cyclopropyl-(3-methoxyphenoxymethyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL9)

As for compound AL1 but from bicyclononene AK9 (about 0.55 mmol) in CH$_2$Cl$_2$ (5 mL) and HCl/dioxane (4M, 5 mL). LC-MS: R$_t$=1.18.

(rac.)-(1R*,5S*)-6-(Cyclopropyl-m-tolyloxymethylcarbamoyl)-7-{4-[3-(2,3,6-trifluorophenoxy)propyl]phenyl}-3,9-diazabicyclo[3.3.1]non-6-ene-9-carboxylic lic acid 2,2,2-trichloro-1,1-dimethylethyl ester hydrochloride salt (AL10)

As for compound AL1 but from bicyclononene AK10 (about 0.55 mmol) in CH$_2$Cl$_2$ (5 mL) and HCl/dioxane (4M, 5 mL). LC-MS: R$_t$=1.24.

(rac.)-(1R*,5S*)-6-[Cyclopropyl-(3,4-dimethylphenoxymethyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL11)

As for compound AL1 but from bicyclononene AK11 (about 0.55 mmol) in CH$_2$Cl$_2$ (5 mL) and HCl/dioxane (4M, 5 mL). LC-MS: R$_t$=1.28.

(rac.)-(1R*,5S*)-6-(Cyclopropylphenethylcarbamoyl)-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL12)

As for compound AL1 but from bicyclononene AK12 (about 0.55 mmol) in CH$_2$Cl$_2$ (5 mL) and HCl/dioxane (4M, 5 mL). LC-MS: R$_t$=1.18; ES+: 778.30.

(rac.)-(1R*,5S*)-6-{[2-(2-Chlorophenyl)ethyl]cyclopropylcarbamoyl}-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL13)

As for compound AL1 but from bicyclononene AK13 (about 0.55 mmol) in $CH_2Cl_2$ (5 mL) and HCl/dioxane (4M, 5 mL). LC-MS: $R_t$=1.21.

(rac.)-(1R*,5S*)-6-{Cyclopropyl-[2-(2,3-difluorophenyl)ethyl]carbamoyl}-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester (AL14)

As for compound AL1 but from bicyclononene AK14 (about 0.55 mmol) in $CH_2Cl_2$ (5 mL) and HCl/dioxane (4M, 5 mL). LC-MS: $R_t$=1.21.

(rac.)-(1R*,5S*)-6-{Cyclopropyl-[2-(4-fluorophenyl)ethyl]carbamoyl}-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL15)

As for compound AL1 but from bicyclononene AK15 (about 0.55 mmol) in $CH_2Cl_2$ (5 mL) and HCl/dioxane (4M, 5 mL). LC-MS: $R_t$=1.18; ES+: 796.28.

(rac.)-(1R*,5S*)-6-[Cyclopropyl-(2-o-tolylethyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL16)

As for compound AL1 but from bicyclononene AK16 (about 0.55 mmol) in $CH_2Cl_2$ (5 mL) and HCl/dioxane (4M, 5 mL). LC-MS: $R_t$=1.21; ES+: 794.30.

(rac.)-(1R*,5S*)-6-[Cyclopropyl-(3,5-dimethoxybenzyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL17)

As for compound AL1 but from bicyclononene AK17 (about 0.55 mmol) in $CH_2Cl_2$ (5 mL) and HCl/dioxane (4M, 5 mL). LC-MS: $R_t$=1.16.

(rac.)-(1R*,5S*)-6-[Cyclopropyl-(2-p-tolylethyl)carbamoyl]-7-{4-[3-(2,3,6-tri-fluorophenoxy)propyl]phenyl}-3,9-diazabicyclo[3.3.1]non-6-ene-9-carboxylic acid 2,2,2-trichloro-1,1-dimethylethyl ester hydrochloride salt (AL18)

As for compound AL1 but from bicyclononene AK18 (about 0.55 mmol) in $CH_2Cl_2$ (5 mL) and HCl/dioxane (4M, 5 mL). LC-MS: $R_t$=1.22; ES+: 792.30.

(rac.)-(1R*,5S*)-6-{Cyclopropyl-[2-(2-hydroxyethyl)benzyl]carbamoyl}-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt (AL19)

As for compound AL1 but from bicyclononene AK19 (about 0.55 mmol) in $CH_2Cl_2$ (5 mL) and HCl/dioxane (4M, 5 mL). LC-MS: $R_t$=1.01.

(rac.)-(1R*,5S*)-7-{4-[3-(2-Bromo-5-fluorophenoxy)propyl]phenyl}-6-[(2-chlorobenzyl)cyclopropylcarbamoyl]-3,9-diazabicyclo[3.3.1]non-6-ene-9-carboxylic acid 2,2,2-trichloro-1,1-dimethylethyl ester hydrochloride salt (AL20)

As for compound AL1 but from bicyclononene AK20 (about 0.55 mmol) in $CH_2Cl_2$ (5 mL) and HCl/dioxane (4M, 5 mL). LC-MS: $R_t$=5.26; ES+: 806.26.

(rac.)-(1R*,5S*)-6-(Benzylcyclopropylcarbamoyl)-7-{4-[3-(2-bromo-5-fluorophenoxy)propyl]phenyl}-3,9-diazabicyclo[3.3.1]non-6-ene-9-carboxylic acid 2,2,2-trichloro-1,1-dimethylethyl ester hydrochloride salt (AL21)

As for compound AL1 but from bicyclononene AK21 (519 mg, 0.54 mmol) in $CH_2Cl_2$ (5 mL) and HCl/dioxane (4M, 5 mL). LC-MS: $R_t$=1.06.

(rac.)-(1R*,5S*)-7-{4-[3-(2-Bromo-5-fluorophenoxy)propyl]phenyl}-6-[(2-chlorobenzyl)ethylcarbamoyl]-3,9-diazabicyclo[3.3.1]non-6-ene-9-carboxylic acid 2,2,2-trichloro-1,1-dimethylethyl ester hydrochloride salt (AL22)

As for compound AL1 but from bicyclononene AK22 (about 0.8 mmol) in $CH_2Cl_2$ (5 mL) and HCl/dioxane (4M, 5 mL). LC-MS: $R_t$=5.30; ES+: 828.33.

(rac.)-(1R*,5S*)-7-{4-[3-(2-Bromo-5-fluorophenoxy)propyl]phenyl}-6-[cyclopropyl-(2-fluorobenzyl)carbamoyl]-3,9-diazabicyclo[3.3.1]non-6-ene-9-carboxylic acid 2,2,2-trichloro-1,1-dimethylethyl ester hydrochloride salt (AL23)

As for compound AL1 but from bicyclononene AK23 (about 0.8 mmol) in $CH_2Cl_2$ (5 mL) and HCl/dioxane (4M, 5 mL).

(rac.)-(1R*,5S*)-7-{4-[3-(2-Bromo-5-fluorophenoxy)propyl]phenyl}-6-[cyclopropyl-(3-trifluoromethylbenzyl)carbamoyl]-3,9-diazabicyclo[3.3.1]non-6-ene-9-carboxylic acid 2,2,2-trichloro-1,1-dimethylethyl ester hydrochloride salt (AL24)

As for compound AL1 but from bicyclononene AK24 (about 0.8 mmol) in $CH_2Cl_2$ (5 mL) and HCl/dioxane (4M, 5 mL). LC-MS: $R_t$=5.33; ES+: 820.40.

(rac.)-(1R*,5S*)-7-{4-[3-(2-Bromo-5-fluorophenoxy)propyl]phenyl}-6-[cyclopropyl-(2-methylbenzyl)carbamoyl]-3,9-diazabicyclo[3.3.1]non-6-ene-9-carboxylic acid 2,2,2-trichloro-1,1-dimethylethyl ester hydrochloride salt (AL25)

As for compound AL1 but from bicyclononene AK25 (about 0.8 mmol) in $CH_2Cl_2$ (5 mL) and HCl/dioxane (4M, 5 mL). LC-MS: $R_t$=1.06.

(rac.)-(1R*,5S*)-7-{4-[3-(2-Bromo-5-fluorophenoxy)propyl]phenyl}-6-{cyclopropyl-[2-(4-methoxyphenoxy)ethyl]carbamoyl}-3,9-diazabicyclo[3.3.1]non-6-ene-9-carboxylic acid 2,2,2-trichloro-1,1-dimethylethyl ester hydrochloride salt (AL26)

As for compound AL1 but from bicyclononene AK26 (about 0.8 mmol) in $CH_2Cl_2$ (5 mL) and HCl/dioxane (4M, 5 mL). LC-MS: $R_t$=5.08; ES+: 866.40.

(rac.)-(1R*,5S*)-7-{4-[3-(2-Bromo-5-fluorophenoxy)propyl]phenyl}-6-[cyclopropyl-(2-m-tolyloxyethyl)carbamoyl]-3,9-diazabicyclo[3.3.1]non-6-ene-9-carboxylic acid 2,2,2-trichloro-1,1-dimethylethyl ester hydrochloride salt (AL27)

As for compound AL1 but from bicyclononene AK27 (about 0.8mmol) in $CH_2Cl_2$ (5 mL) and HCl/dioxane (4M, 5 mL). LC-MS: $R_t$=1.07.

(rac.)-(1R*,5S*)-7-{4-[3-(2-Bromo-5-fluorophenoxy)propyl]phenyl}-6-{cyclopropyl-[2-(3,4-dimethylphenoxy)ethyl]carbamoyl}-3,9-diazabicyclo[3.3.1]-non-6-ene-9-carboxylic acid 2,2,2-trichloro-1,1-dimethylethyl ester hydrochloride salt (AL28)

As for compound AL1 but from bicyclononene AK28 (about 0.8 mmol) in $CH_2Cl_2$ (5 mL) and HCl/dioxane (4M, 5 mL). LC-MS: $R_t$=1.08.

-(1R*,5S*)-7-{4-[3-(2-Bromo-5-fluorophenoxy)propyl]phenyl}-6-(cyclopropylphenethylcarbamoyl)-3,9-diazabicyclo[3.3.1]non-6-ene-9-carboxylic acid 2,2,2-trichloro-1,1-dimethylethyl ester hydrochloride salt (AL29)

As for compound AL1 but from bicyclononene AK29 (about 0.8 mmol) in $CH_2Cl_2$ (5 mL) and HCl/dioxane (4M, 5 mL). LC-MS: $R_t$=5.25; ES+: 820.38.

(rac*)-(1R*,5S*)-7-{4-[3-(2-Bromo-5-fluorophenoxy)propyl]phenyl}-6-{[2-(2-chlorophenyl)ethyl]cyclopropylcarbamoyl}-3,9-diazabicyclo[3.3.1]non-6-ene-9-carboxylic acid 2,2,2-trichloro-1,1-dimethylethyl ester hydrochloride salt (AL30)

As for compound AL1 but from bicyclononene AK30 (about 0.8 mmol) in $CH_2Cl_2$ (5 mL) and HCl/dioxane (4M, 5 mL). LC-MS: $R_t$=5.35; ES+: 854.30.

(rac.)-(1R*,5S*)-7-{4-[3-(2-Bromo-5-fluorophenoxy)propyl]phenyl}-6-{cyclopropyl-[2-(2,3-difluorophenyl)ethyl]carbamoyl}-3,9-diazabicyclo[3.3.1]non-6-ene-9-carboxylic acid 2,2,2-trichloro-1,1-dimethylethyl ester hydrochloride salt (AL31)

As for compound AL1 but from bicyclononene AK31 (about 0.8 mmol) in $CH_2Cl_2$ (5 mL) and HCl/dioxane (4M, 5 mL). LC-MS: $R_t$=5.40; ES+: 856.38.

(rac.)-(1R*,5S*)-7-{4-[3-(2-Bromo-5-fluorophenoxy)propyl]phenyl}-6-{cyclopropyl-[2-(4-fluorophenyl)ethyl]carbamoyl}-3,9-diazabicyclo[3.3.1]non-6-ene-9-carboxylic acid 2,2,2-trichloro-1,1-dimethylethyl ester hydrochloride salt (AL32)

As for compound AL1 but from bicyclononene AK32 (about 0.8 mmol) in $CH_2Cl_2$ (5 mL) and HCl/dioxane (4M, 5 mL). LC-MS: $R_t$=5.28; ES+: 838.40.

(rac.)-(1R*,5S*)-7-{4-[3-(2-Bromo-5-fluorophenoxy)propyl]phenyl}-6-[cyclopropyl-(2-o-tolylethyl)carbamoyl]-3,9-diazabicyclo[3.3.1]non-6-ene-9-carboxylic acid 2,2,2-trichloro-1,1-dimethylethyl ester hydrochloride salt (AL33)

As for compound AL1 but from bicyclononene AK33 (about 0.8 mmol) in $CH_2Cl_2$ (5 mL) and HCl/dioxane (4M, 5 mL). LC-MS: $R_t$=5.36; ES+: 834.42.

1:1—Mixture of (rac.)-(1R*,5S*)-7-{4-[3-(2-Bromo-5-fluorophenoxy)propyl]-phenyl}-6-[((2R*)-2-hydroxy-2-phenylethyl)methylcarbamoyl]-3,9-diazabicyclo[3.3.1]non-6-ene-9-carboxylic acid 2,2,2-trichloro-1,1-dimethylethyl ester hydrochloride salt and (rac.)-(1R*,5S*)-7-{4-[3-(2-Bromo-5-fluoro-phenoxy)propyl]phenyl}-6-[((2S*)-2-hydroxy-2-phenylethyl)methylcarbamoyl]-3,9-diazabicyclo[3.3.1]non-6-ene-9-carboxylic acid 2,2,2-trichloro-1,1-dimethylethyl ester hydrochloride salt (AL34)

As for compound AL1 but from bicyclononenes AK34 (about 0.3 mmol) in $CH_2Cl_2$ (5 mL) and HCl/dioxane (4M, 5 mL). LC-MS: $R_t$=0.99.

(rac.)-(1R*,5S*)-7-{4-[3-(2-Bromo-5-fluorophenoxy)propyl]phenyl}-6-[cyclopropyl-(3,5-dimethoxybenzyl)carbamoyl]-3,9-diazabicyclo[3.3.1]non-6-ene-9-carboxylic acid 2,2,2-trichloro-1,1-dimethylethyl ester hydrochloride salt (AL35)

As for compound AL1 but from bicyclononene AK35 (about 0.8 mmol) in $CH_2Cl_2$ (5 mL) and HCl/dioxane (4M, 5 mL). LC-MS: $R_t$=5.23; ES+: 866.40.

(rac.)-(1R*,5S*)-7-{4-[3-(2-Bromo-5-fluorophenoxy)propyl]phenyl}-6-[cyclopropyl-(2-p-tolylethyl)carbamoyl]-3,9-diazabicyclo[3.3.1]non-6-ene-9-carboxylic acid 2,2,2-trichloro-1,1-dimethylethyl ester hydrochloride salt (AL36)

As for compound AL1 but from bicyclononene AK36 (about 0.8 mmol) in $CH_2Cl_2$ (5 mL) and HCl/dioxane (4M, 5 mL). LC-MS: $R_t$=5.59; ES+: 834.42.

(rac.)-(1R*,5S*)-7-{4-[3-(2-Bromo-5-fluorophenoxy)propyl]phenyl}-6-{cyclopropyl-[2-(2-hydroxyethyl)benzyl]carbamoyl}-3,9-diazabicyclo[3.3.1]non-6-ene-9-carboxylic acid 2,2,2-trichloro-1,1-dimethylethyl ester hydrochloride salt (AL37)

As for compound AL1 but from bicyclononene AK37 (about 0.8 mmol) in CH$_2$Cl$_2$ (5 mL) and HCl/dioxane (4M, 5 mL). LC-MS: R$_t$=1.01.

(rac.)-(1R*,5S*)-6-[(2-Chlorobenzyl)cyclopropylcarbamoyl]-7-{4-[2-(2,3,6-trimethyl-phenoxy)ethyl]phenyl}-3,9-diazabicyclo[3.3.1]non-6-ene-9-carboxylic acid 2,2,2-trichloro-1,1-dimethylethyl ester hydrochloride salt (AL38)

As for compound AL1 but from bicyclononene AK38 (312 mg, 9.35 mmol) in CH$_2$Cl$_2$ (5 mL) and HCl/dioxane (4M, 5 mL). LC-MS: R$_t$=1.08; ES+: 774.33.

(rac.)-(1R*,5S*)-6-(Benzylcyclopropylcarbamoyl)-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL39)

As for compound AL1 but from bicyclononene AK39 (340 mg, 0.40 mmol) in CH$_2$Cl$_2$ (5 mL) and HCl/dioxane (4M, 5 mL). LC-MS: R$_t$=1.05; ES+: 740.42.

(rac.)-(1R*,5S*)-6-[(2-Chlorobenzyl)ethylcarbamoyl]-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL40)

As for compound AL1 but from bicyclononene AK40 (374 mg, 0.43 mmol) in CH$_2$Cl$_2$ (5 mL) and HCl/dioxane (4M, 5 mL). LC-MS: R$_t$=1.07; ES+: 762.34.

(rac.)-(1R*,5S*)-6-[Cyclopropyl-(2-fluorobenzyl)carbamoyl]-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL41)

As for compound AL1 but from bicyclononene AK41 (350 mg, 0.41 mmol) in CH$_2$Cl$_2$ (5 mL) and HCl/dioxane (4M, 5 mL). LC-MS: R$_t$=1.06; ES+: 758.38.

(rac.)-(1R*,5S*)-6-[Cyclopropyl-(3-trifluoromethylbenzyl)carbamoyl]-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL42)

As for compound AL1 but from bicyclononene AK42 (294 mg, 0.32 mmol) in CH$_2$Cl$_2$ (5 mL) and HCl/dioxane (4M, 5 mL). LC-MS: R$_t$=1.08.

(rac.)-(1R*,5S*)-6-[Cyclopropyl-(2-methylbenzyl)carbamoyl]-7-{4-[2-(2,3,6-trimethylphenoxy)ethyl]phenyl}-3,9-diazabicyclo[3.3.1]non-6ene-9-carboxylic acid 2,2,2-trichloro-1,1-dimethylethyl ester hydrochloride salt (AL43)

As for compound AL1 but from bicyclononene AK43 (322 mg, 0.38 mmol) in CH$_2$Cl$_2$ (5 mL) and HCl/dioxane (4M, 5 mL). LC-MS: R$_t$=1.08; ES+: 752.39.

(rac.)-(1R*,5S*)-6-{Cyclopropyl-[2-(4-methoxyphenoxy)ethyl]carbamoyl}-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL44)

As for compound AL1 but from bicyclononene AK44 (159 mg, 0.18 mmol) in CH$_2$Cl$_2$ (5 mL) and HCl/dioxane (4M, 5 mL). LC-MS: R$_t$=1.07.

(rac.)-(1R*,5S*)-{Cyclopropyl-[2-(3-methoxyphenoxy)ethyl]carbamoyl}-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester (AL45)

As for compound AL1 but from bicyclononene AK45 (237 mg, 0.26 mmol) in CH$_2$Cl$_2$ (5 mL) and HCl/dioxane (4M, 5 mL). LC-MS: R$_t$=1.00.

(rac.)-(1R*,5S*)-6-[Cyclopropyl-(2-m-tolyloxyethyl)carbamoyl]-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL46)

As for compound AL1 but from bicyclononene AK46 (185 mg, 0.21 mmol) in CH$_2$Cl$_2$ (5 mL) and HCl/dioxane (4M, 5 mL). LC-MS: R$_t$=1.09; ES+: 784.40.

(rac.)-(1R*,5S*)-6-(Cyclopropylphenethylcarbamoyl)-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL47)

As for compound AL1 but from bicyclononene AK47 (about 0.3 mmol) in CH$_2$Cl$_2$ (5 mL) and HCl/dioxane (4M, 5 mL). LC-MS: R$_t$=1.09; ES+: 754.44.

(rac.)-(1R*,5S*)-6-{[2-(2-Chlorophenyl)ethyl]cyclopropylcarbamoyl}-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL48)

As for compound AL1 but from bicyclononene AK48 (about 0.3 mmol) in CH$_2$Cl$_2$ (5 mL) and HCl/dioxane (4M, 5 mL). LC-MS: R$_t$=1.10; ES+: 788.41.

(rac.)-(1R*,5S*)-6-{Cyclopropyl-[2-(2,3-difluorophenyl)ethyl]carbamoyl}-7-{4-[2-(2,3,6-trimethylphenoxy)ethyl]-phenyl}-3,9-diazabicyclo[3.3.1]non-6-ene-9-carboxylic acid 2,2,2-trichloro-1,1-dimethylethyl ester hydrochloride salt (AL49)

As for compound AL1 but from bicyclononene AK49 (about 0.3 mmol) in $CH_2Cl_2$ (5 mL) and HCl/dioxane (4M, 5 mL). LC-MS: $R_t$=1.09; ES+: 788.41.

(rac.)-(1R*,5S*)-6-(Cyclopropyl-[2-(4-fluorophenyl)ethyl]carbamoyl}-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL50)

As for compound AL1 but from bicyclononene AK50 (about 0.3 mmol) in $CH_2Cl_2$ (5 mL) and HCl/dioxane (4M, 5 mL). LC-MS: $R_t$=1.09; ES+: 772.41.

(rac.)-(1R*,5S*)-6-[Cyclopropyl-(2-o-tolylethyl)carbamoyl]-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL51)

As for compound AL1 but from bicyclononene AK51 (about 0.3 mmol) in $CH_2Cl_2$ (5 mL) and HCl/dioxane (4M, 5 mL). LC-MS: $R_t$=1.10; ES+: 768.44.

1:1—Mixture of (rac.)-(1R*,5S*)-6-[((2S*)-2-hydroxy-2-phenylethyl)methylcarbamoyl]-7-{4-[2-(2,3,6-trimethylphenoxy)ethyl]phenyl}-3,9-diazabicyclo-[3.3.1]non-6-ene-9-carboxylic acid 2,2,2-trichloro-1,1-dimethylethyl ester hydrochloride salt and (rac.)-(1R*,5S*)-6-[((2S*)-2-hydroxy-2-phenylethyl)-methylcarbamoyl]-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL52)

As for compound AL1 but from bicyclononene AK52 (about 0.3 mmol) in $CH_2Cl_2$ (5 mL) and HCl/dioxane (4M, 5 mL). LC-MS: $R_t$=1.02; ES+: 744.44.

(rac.)-(1R*,5S*)-6-[Cyclopropyl-(3,5-dimethoxybenzyl)carbamoyl]-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL53)

As for compound AL1 but from bicyclononene AK53 (about 0.3 mmol) in $CH_2Cl_2$ (5 mL) and HCl/dioxane (4M, 5 mL). LC-MS: $R_t$=1.07.

(rac.)-(1R*,5S*)-6-[Cyclopropyl-(2-p-tolylethyl)carbamoyl]-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL54)

As for compound AL1 but from bicyclononene AK54 (about 0.3 mmol) in $CH_2Cl_2$ (5 mL) and HCl/dioxane (4M, 5 mL). LC-MS: $R_t$=1.10; ES+: 768.44.

(rac.)-(1R*,5S*)-6-{Cyclopropyl-[2-(2-hydroxyethyl)benzyl]carbamoyl}-7-{4-[2-(2,3,6-trimethylphenoxy)ethyl]phenyl}-3,9-diazabicyclo[3.3.1]non-6-ene-9-carboxylic acid 2,2,2-trichloro-1,1-dimethylethyl ester hydrochloride salt (AL55)

As for compound AL1 but from bicyclononene AK55 (about 0.3 mmol) in $CH_2Cl_2$ (5 mL) and HCl/dioxane (4M, 5 mL). LC-MS: $R_t$=1.03; ES+: 784.44.

(rac.)-(1R*,5S*)-6-[(2-Chlorobenzyl)cyclopropylcarbamoyl]-7-{4-[2-(2-chloro-4,5-dimethylphenoxy)ethoxy]phenyl}-3,9-diazabicyclo[3.3.1]non-6-ene-9-carboxylic acid 2,2,2-trichloro-1,1-dimethylethyl ester hydrochloride salt (AL56)

As for compound AL1 but from bicyclononene AK56 (about 0.5 mmol) in $CH_2Cl_2$ (5 mL) and HCl/dioxane (4M, 5 mL). LC-MS: $R_t$=1.08; ES+: 785.26.

(rac.)-(1R*,5S*)-6-[(2-Chlorobenzyl)ethylcarbamoyl]-7-{4-[2-(2-chloro-4,5-dimethylphenoxy)ethoxy]phenyl}-3,9-diazabicyclo[3.3.1]non-6-ene-9-carboxylic acid 2,2,2-trichloro-1,1-dimethylethyl ester hydrochloride salt (AL57)

As for compound AL1 but from bicyclononene AK57 (about 0.5 mmol) in $CH_2Cl_2$ (5 mL) and HCl/dioxane (4M, 5 mL). LC-MS: $R_t$=1.06.

(rac.)-(1R*,5S*)-7-{4-[2-(2-Chloro-4,5-dimethylphenoxy)ethoxy]phenyl}-6-[cyclopropyl-(2-fluorobenzyl)carbamoyl]-3,9-diazabicyclo[3.3.1]non-6-ene-9-carboxylic acid 2,2,2-trichloro-1,1-dimethylethyl ester hydrochloride salt (AL58)

As for compound AL1 but from bicyclononene AK58 (about 0.5 mmol) in $CH_2Cl_2$ (5 mL) and HCl/dioxane (4M, 5 mL). LC-MS: $R_t$=1.06.

(rac.)-(1R*,5S*)-7-{4-[2-(2-Chloro-4,5-dimethylphenoxy)ethoxy]phenyl}-[cyclopropyl-(3-trifluoromethylbenzyl)carbamoyl]-3,9-diazabicyclo[3.3.1]-non-6-ene-9-carboxylic acid 2,2,2-trichloro-1,1-dimethylethyl ester hydrochloride salt (AL59)

As for compound AL1 but from bicyclononene AK59 (about 0.5 mmol) in $CH_2Cl_2$ (5 mL) and HCl/dioxane (4M, 5 mL). LC-MS: $R_t$=1.08.

(rac.)-(1R*,5S*)-7-{4-[2-(2-Chloro-4,5-dimethylphenoxy)ethoxy]phenyl}-6-[cyclopropyl-(2-methylbenzyl)carbamoyl]-3,9-diazabicyclo[3.3.1]non-6-ene-9-carboxylic acid 2,2,2-trichloro-1,1-dimethylethyl ester hydrochloride salt (AL60)

As for compound AL1 but from bicyclononene AK60 (about 0.5 mmol) in $CH_2Cl_2$ (5 mL) and HCl/dioxane (4M, 5 mL). LC-MS: $R_t$=1.07; ES+: 788.40.

(rac.)-(1R*,5S*)-7-{4-[2-(2-Chloro-4,5-dimethylphenoxy)ethoxy]phenyl}-6-{cyclopropyl-[2-(4-methoxyphenoxy)ethyl]carbamoyl}-3,9-diazabicyclo-[3.3.1]non-6-ene-9-carboxylic acid 2,2,2-trichloro-1,1-dimethylethyl ester hydrochloride salt (AL61)

As for compound AL1 but from bicyclononene AK61 (about 0.5 mmol) in $CH_2Cl_2$ (5 mL) and HCl/dioxane (4M, 5 mL). LC-MS: $R_t$=1.06.

(rac.)-(1R*,5S*)-7-{4-[2-(2-Chloro-4,5-dimethylphenoxy)ethoxy]phenyl}-6-{cyclopropyl-[2-(3-methoxyphenoxy)ethyl]carbamoyl}-3,9-diazabicyclo[3.3.1]non-6-ene-9-carboxylic acid 2,2,2-trichloro-1,1-dimethylethyl ester hydrochloride salt (AL62)

As for compound AL1 but from bicyclononene AK62 (about 0.5 mmol) in $CH_2Cl_2$ (5 mL) and HCl/dioxane (4M, 5 mL). LC-MS: $R_t$=1.07.

(rac.)-(1R*,5S*)-7-{4-[2-(2-Chloro-4,5-dimethylphenoxy)ethoxy]phenyl}-6-[cyclopropyl-(2-m-tolyloxyethyl)carbamoyl]-3,9-diazabicyclo[3.3.1]non-6-ene-9-carboxylic acid 2,2,2-trichloro-1,1-dimethylethyl ester hydrochloride salt (AL63)

As for compound AL1 but from bicyclononene AK63 (about 0.5 mmol) in $CH_2Cl_2$ (5 mL) and HCl/dioxane (4M, 5 mL). LC-MS: $R_t$=1.08.

(rac.)-(1R*,5S*)-7-{4-[2-(2-Chloro-4,5-dimethylphenoxy)ethoxy]phenyl}-6-(cyclopropylphenethylcarbamoyl)-3,9-diazabicyclo[3.3.1]non-6-ene-9-carboxylic acid 2,2,2-trichloro-1,1-dimethylethyl ester hydrochloride salt (AL64)

As for compound AL1 but from bicyclononene AK64 (about 0.5 mmol) in $CH_2Cl_2$ (5 mL) and HCl/dioxane (4M, 5 mL). LC-MS: $R_t$=1.07; ES+: 788.39.

(rac.)-(1R*,5S*)-7-{4-[2-(2-Chloro-4,5-dimethylphenoxy)ethoxy]phenyl}-6-{[2-(2-chlorophenyl)ethyl]cyclopropylcarbamoyl}-3,9-diazabicyclo[3.3.1]non-6-ene-9-carboxylic acid 2,2,2-trichloro-1,1-dimethylethyl ester hydrochloride salt (AL65)

As for compound AL1 but from bicyclononene AK65 (about 0.5 mmol) in $CH_2Cl_2$ (5 mL) and HCl/dioxane (4M, 5 mL). LC-MS: $R_t$=1.08.

(rac.)-(1R*,5S*)-7-{4-[2-(2-Chloro-4,5-dimethylphenoxy)ethoxy]phenyl}-6-{cyclopropyl-[2-(2,3-difluorophenyl)ethyl]carbamoyl}-3,9-diazabicyclo-[3.3.1]non-6-ene-9-carboxylic acid 2,2,2-trichloro-1,1-dimethylethyl ester hydrochloride salt (AL66)

As for compound AL1 but from bicyclononene AK66 (about 0.5 mmol) in $CH_2Cl_2$ (5 mL) and HCl/dioxane (4M, 5 mL). LC-MS: $R_t$=1.06.

(rac.)-(1R*,5S*)-7-{4-[2-(2-Chloro-4,5-dimethylphenoxy)ethoxy]phenyl}-6-{cyclopropyl-[2-(4-fluorophenyl)ethyl]carbamoyl}-3,9-diazabicyclo[3.3.1]non-6-ene-9-carboxylic acid 2,2,2-trichloro-1,1-dimethylethyl ester hydrochloride salt (AL67)

As for compound AL1 but from bicyclononene AK67 (about 0.5 mmol) in $CH_2Cl_2$ (5 mL) and HCl/dioxane (4M, 5 mL). LC-MS: $R_t$=1.06.

(rac.)-(1R*,5S*)-7-{4-[2-(2-Chloro-4,5-dimethylphenoxy)ethoxy]phenyl}-6-[cyclopropyl-(2-o-tolylethyl)carbamoyl]-3,9-diazabicyclo[3.3.1]non-6-ene-9-carboxylic acid 2,2,2-trichloro-1,1-dimethylethyl ester (AL68)

As for compound AL1 but from bicyclononene AK68 (about 0.5 mmol) in $CH_2Cl_2$ (5 mL) and HCl/dioxane (4M, 5 mL). LC-MS: $R_t$=1.08.

1:1—Mixture of (rac.)-(1R*,5S*)-7-{4-[2-(2-chloro-4,5-dimethylphenoxy)-ethoxy]phenyl}-6-[((2R*)-2-hydroxy-2-phenylethyl)methylcarbamoyl]-3,9-diazabicyclo[3.3.1]non-6-ene-9-carboxylic acid 2,2,2-trichloro-1,1-dimethylethyl ester hydrochloride salt and (rac.)-(1R*,5S*)-7-{4-[2-(2-chloro-4,5-dimethylphenoxy)ethoxy]phenyl}-6-[((2S*)-2-hydroxy-2-phenylethyl)methylcarbamoyl]-3,9-diazabicyclo[3.3.1]non-6-ene-9-carboxylic acid 2,2,2-trichloro-1,1-dimethylethyl ester hydrochloride salt (AL69)

As for compound AL1 but from bicyclononene AK69 (about 0.5 mmol) in $CH_2Cl_2$ (5 mL) and HCl/dioxane (4M, 5 mL). LC-MS: $R_t$=0.99; ES+: 780.37.

(rac.)-(1R*,5S*)-7-{4-[2-(2-Chloro-4,5-dimethylphenoxy)ethoxy]phenyl}-6-[cyclopropyl-(3,5-dimethoxybenzyl)carbamoyl]-3,9-diazabicyclo[3.3.1]non-6-ene-9-carboxylic acid 2,2,2-trichloro-1,1-dimethylethyl ester hydrochloride salt (AL70)

As for compound AL1 but from bicyclononene AK70 (about 0.5 mmol) in $CH_2Cl_2$ (5 mL) and HCl/dioxane (4M, 5 mL). LC-MS: $R_t$=1.06.

(rac.)-(1R*,5S*)-7-{4-[2-(2-Chloro-4,5-dimethylphenoxy)ethoxy]phenyl}-6-[cyclopropyl-(2-p-tolylethyl)carbamoyl]-3,9-diazabicyclo[3.3.1]non-6-ene-9-carboxylic acid 2,2,2-trichloro-1,1-dimethylethyl ester hydrochloride salt (AL71)

As for compound AL1 but from bicyclononene AK71 (about 0.5 mmol) in $CH_2Cl_2$ (5 mL) and HCl/dioxane (4M, 5 mL). LC-MS: $R_t$=1.08.

(rac.)-(1R*,5S*)-7-{4-[2-(2-Chloro-4,5-dimethylphenoxy)ethoxy]phenyl}-6-{cyclopropyl-[2-(2-hydroxyethyl)benzyl]carbamoyl}-3,9-diazabicyclo[3.3.1]-non-6-ene-9-carboxylic acid 2,2,2-trichloro-1,1-dimethylethyl ester hydrochloride salt As for compound AL1 but from bicyclononene AK72 (about 0.5 mmol) in $CH_2Cl_2$ (5 mL) and HCl/dioxane (4M, 5 mL). LC-MS: $R_t$=1.01.

(rac.)-(1R*,5S*)-7-{4-[2-(4-Bromophenoxy)ethoxy]
phenyl}-6-[(2-chloro-benzyl)cyclopropylcarbam-
oyl]-3,9-diazabicyclo[3.3.1]non-6-ene-9-carboxylic
acid 2,2,2-trichloro-1,1-dimethyl-ethyl ester hydro-
chloride salt (AL73)

As for compound AL1 but from bicyclononene AK73 (0.28 mmol) in $CH_2Cl_2$ (5 mL) and HCl/dioxane (4M, 5 mL). LC-MS: $R_t$=4.98; ES+: 824.32.

(rac.)-(1R*,5S*)-6-(Benzylcyclopropylcarbamoyl)-
7-}4-[2-(4-bromophenoxy)-ethoxy]phenyl}-3,9-
diazabicyclo[3.3.1]non-6-ene-9-carboxylic acid 2,2,
2-trichloro-1,1-dimethylethyl ester hydrochloride
salt (AL74)

As for compound AL1 but from bicyclononene AK74 (0.27 mmol) in $CH_2Cl_2$ (5 mL) and HCl/dioxane (4M, 5 mL). LC-MS: $R_t$=1.03; ES+: 792.36.

(rac.)-(1R*,5S*)-7-{4-[2-(4-Bromophenoxy)ethoxy]
phenyl}-6-[(2-chlorobenzyl)ethylcarbamoyl]-3,9-
diazabicyclo[3.3.1]non-6-ene-9-carboxylic acid 2,2,
2-trichloro-1,1-dimethylethyl ester hydrochloride
salt (AL75)

As for compound AL1 but from bicyclononene AK75 (0.22 mmol) in $CH_2Cl_2$ (5 mL) and HCl/dioxane (4M, 5 mL). LC-MS: $R_t$=4.92; ES+: 812.35.

(rac.)-(1R*,5S*)-7-{4-[2-(4-Bromophenoxy)ethoxy]
phenyl}-6-[cyclopropyl-(2-fluorobenzyl)carbamoyl]-
3,9-diazabicyclo[3.3.1]non-6-ene-9-carboxylic acid
2,2,2-trichloro-1,1-dimethylethyl ester hydrochloride
salt (AL76)

As for compound AL1 but from bicyclononene AK76 (0.26 mmol) in $CH_2Cl_2$ (5 mL) and HCl/dioxane (4M, 5 mL). LC-MS: $R_t$=4.78; ES+: 808.40.

(rac.)-(1R*,5S*)-7-{4-[2-(4-Bromophenoxy)ethoxy]
phenyl}-6-[cyclopropyl-(3-trifluoromethylbenzyl)
carbamoyl]-3,9-diazabicyclo[3.3.1]non-6-ene-9-
carboxylic acid 2,2,2-trichloro-1,1-dimethylethyl
ester hydrochloride salt (AL77)

As for compound AL1 but from bicyclononene AK77 (0.29 mmol) in $CH_2Cl_2$ (5 mL) and HCl/dioxane (4M, 5 mL). LC-MS: $R_t$=4.97; ES+: 858.42.

(rac.)-(1R*,5S*)-7-{4-[2-(4-Bromophenoxy)ethoxy]
phenyl}-6-[cyclopropyl-(2-methylbenzyl)carbam-
oyl]-3,9-diazabicyclo[3.3.1]non-6-ene-9-carboxylic
acid 2,2,2-trichloro-1,1-dimethylethyl ester hydro-
chloride salt (AL78)

As for compound AL1 but from bicyclononene AK78 (0.28 mmol) in $CH_2Cl_2$ (5 mL) and HCl/dioxane (4M, 5 mL). LC-MS: $R_t$=5.01; ES+: 804.42.

(rac.)-(1R*,5S*)-7-{4-[2-(4-Bromophenoxy)ethoxy]
phenyl}-6-{cyclopropyl-[2-(4-methoxyphenoxy)
ethyl]carbamoyl}-3,9-diazabicyclo[3.3.1]non-6-ene-
9-carboxylic acid 2,2,2-trichloro-1,1-dimethylethyl
ester hydrochloride salt (AL79)

As for compound AL1 but from bicyclononene AK79 (0.2 mmol) in $CH_2Cl_2$ (5 mL) and HCl/dioxane (4M, 5 mL). LC-MS: $R_t$=5.03; ES+: 850.44.

(rac.)-(1R*,5S*)-7-4-[2-(4-Bromophenoxy)ethoxy]
phenyl}-6-{cyclopropyl-[2-(3,4-dimethylphenoxy)
ethyl]carbamoyl}-3,9diazabicyclo[3.3.1]non-6-ene-
9-carboxylic acid 2,2,2-trichloro-1,1-dimethylethyl
ester hydrochloride salt (AL80)

As for compound AL1 but from bicyclononene AK80 (0.21 mmol) in $CH_2Cl_2$ (5 mL) and HCl/dioxane (4M, 5 mL). LC-MS: $R_t$=5.11; ES+: 848.43.

(rac.)-(1R*,5S*)-7-{4-[2-(4-Bromophenoxy)ethoxy]
phenyl}-6-{[2-(2-chlorophenyl)ethyl]cyclopropyl-
carbamoyl}-3,9-diazabicyclo[3.3.1]non-6-ene-9-
carboxylic acid 2,2,2-trichloro-1,1-dimethylethyl
ester hydrochloride salt (AL81)

As for compound AL1 but from bicyclononene AK81 (0.27 mmol) in $CH_2Cl_2$ (5 mL) and HCl/dioxane (4M, 5 mL). LC-MS: $R_t$=5.09; ES+: 838.36.

(rac.)-(1R*,5S*)-7-{4-[2-(4-Bromophenoxy)ethoxy]
phenyl}-6-{cyclopropyl-[2-(2,3-difluorophenyl)
ethyl]carbamoyl}-3,9-diazabicyclo[3.3.1]non-6-ene-
9-carboxylic acid 2,2,2-trichloro-1,1-dimethylethyl
ester hydrochloride salt (AL82)

As for compound AL1 but from bicyclononene AK82 (0.26 mmol) in $CH_2Cl_2$ (5 mL) and HCl/dioxane (4M, 5 mL). LC-MS: $R_t$=4.44; ES+: 840.42.

(rac.)-(1R*,5S*)-7-{4-[2-(4-Bromophenoxy)ethoxy]
phenyl}-6-{cyclopropyl-[2-(4-fluorophenyl)ethyl]
carbamoyl}-3,9-diazabicyclo[3.3.1]non-6-ene-9-
carboxylic acid 2,2,2-trichloro-1,1-dimethylethyl
ester hydrochloride salt (AL83)

As for compound AL1 but from bicyclononene AK83 (0.24 mmol) in $CH_2Cl_2$ (5 mL) and HCl/dioxane (4M, 5 mL). LC-MS: $R_t$=4.89; ES+: 822.39.

(rac.)-(1R*,5S*)-7-{4-[2-(4-Bromophenoxy)ethoxy]
phenyl}-6-[cyclopropyl-(2-o-tolylethyl)carbamoyl]-
3,9-diazabicyclo[3.3.1]non-6-ene-9-carboxylic acid
2,2,2-trichloro-1,1-dimethylethyl ester hydrochloride
salt (AL84)

As for compound AL1 but from bicyclononene AK84 (0.27 mmol) in $CH_2Cl_2$ (5 mL) and HCl/dioxane (4M, 5 mL).

(rac.)-(1R*,5S*)-7-{4-[2-(4-Bromophenoxy)ethoxy] phenyl}-6-[cyclopropyl-(3,5-dimethoxybenzyl)carbamoyl]-3,9-diazabicyclo[3.3.1]non-6-ene-9-carboxylic acid 2,2,2-trichloro-1,1-dimethylethyl ester hydrochloride salt (AL85)

As for compound AL1 but from bicyclononene AK85 (0.25 mmol) in $CH_2Cl_2$ (5 mL) and HCl/dioxane (4M, 5 mL). LC-MS: $R_t$=4.76; ES+: 850.40.

(rac.)-(1R*,5S*)-7-{4-[2-(4-Bromophenoxy)ethoxy] phenyl}-6-[cyclopropyl-(2-p-tolylethyl)carbamoyl]-3,9-diazabicyclo[3.3.1]non-6-ene-9-carboxylic acid 2,2,2-trichloro-1,1-dimethylethyl ester hydrochloride salt (AL86)

As for compound AL1 but from bicyclononene AK86 (0.27 mmol) in $CH_2Cl_2$ (5 mL) and HCl/dioxane (4M, 5 mL). LC-MS: $R_t$=4.99; ES+: 820.78.

(rac.)-(1R*,5S*)-7-{4-[2-(4-Bromophenoxy)ethoxy] phenyl}-6-{cyclopropyl-[2-(2-hydroxyethyl)benzyl]carbamoyl}-3,9-diazabicyclo[3.3.1]non-6-ene-9-carboxylic acid 2,2,2-trichloro-1,1-dimethylethyl ester hydrochloride salt (AL87)

As for compound AL1 but from bicyclononene AK87 (0.18 mmol) in $CH_2Cl_2$ (5 mL) and HCl/dioxane (4M, 5 mL). LC-MS: $R_t$=4.58; ES+: 834.43.

(rac.)-(1R*,5S*)-7-Hydroxy-9-methyl-3,9-diazabicyclo[3.3.1]non-6-ene-3,6-dicarboxylic acid 6-benzyl ester 3-tert-butyl ester (AM)

Ti(OEt)$_4$ (2.92 mL, 13.9 mmol) was added to a sol. of bicyclononane A (13.0 g, 39.8 mmol) in benzyl alcohol (90 mL). The mixture was heated to 125° C. and stirred at this temperature for 28 h. The mixture was allowed to cool to rt and aq. 10% HCl (1.80 mL) was added. The mixture was extracted with Et$_2$O (3×). The combined org. extracts were washed with aq. NaHCO$_3$ (2×), with brine (1×). The org. extracts were then dried over MgSO$_4$, filtered, and the solvents were removed first under reduced pressure, then under high vacuum. Purification of the residue by FC (EtOAc/heptane 1:1→3:1→EtOAc) yielded the title compound (9.90 g, 64%). LC-MS: $R_t$=1.39; ES+: 389.25.

(rac.)-(1R*,5S*)-9-Methyl-7-trifluoromethanesulfonyloxy-3,9-diazabicyclo-[3.3.1]non-6-ene-3,6-dicarboxylic acid 6-benzyl ester 3-tert-butyl ester (AN)

NaH (55% in oil, 2.20 g, 50.5 mmol) was added to a sol. of bicyclononane AM (15.69 g, 40.4 mmol) in THF (290 mL) at 0° C. After 15 min. Tf$_2$NPh (19.2 g, 53.7 mmol) was added and the mixture was stirred overnight while warming up to rt. Ice was added and the mixture was diluted with EtOAc, and washed with aq. 10% Na$_2$CO$_3$. The org. extracts were dried over MgSO$_4$, filtered, and the solvents were removed under reduced pressure. Purification of the residue by FC (EtOAc/heptane 1:1→3:1) yielded the title compound (17.1 g, 81%). $R_f$=0.15 (EtOAc/heptane 1:1). LC-MS: $R_t$=5.62; ES+: 521.37.

Compounds of Type AO

(rac.)-(1R*,5S*)-7-{4-[3-(tert-Butyldimethylsilanyloxy)propyl]phenyl}-9-methyl-3,9-diazabicyclo[3.3.1]non-6-ene-3,6-dicarboxylic acid 6-benzyl ester 3-tert-butyl ester (AO1)

BuLi (1.5M in hexane, 3.81 mL, 5.71 mmol) was added to a sol. of [3-(4-bromophenyl)propoxy]-tert-butyldimethylsilane (Kiesewetter D. O., *Tetrahedron Asymmetry*, 1993, 4, 2183, 1.88 g, 5.71 mmol) in THF (33 mL) at −78° C. After 30 min ZnCl$_2$ (1M in ThF, 6.97 mL, 6.97 mmol, prepared as described for compound G1) was added and the mixture was allowed to warm up to rt. Bicyclononene AN (1.65 g, 3.17 mmol) and Pd(PPh$_3$)$_4$ (92 mg, 0.080 mmol) were added. The mixture was heated to 40° C. and stirred at this temperature for 30 min. The mixture was allowed to cool to rt and aq. 1M HCl (1 mL) was added. The mixture was diluted with EtOAc and washed with aq. 1M NaOH (1×). The org. extracts were dried over MgSO$_4$, filtered, and the solvents were removed under reduced pressure. Purification of the residue by FC (MeOH/CH$_2$Cl$_2$ 1:49→3:97→2:48→5:95) yielded the title compound (1.78 g, 90%). LC-MS: $R_t$=5.55; ES+: 681.30.

(rac.)-(1R*,5S*)-9-Methyl-7-{4-[2-(2,3,5-trimethylphenoxy)ethyl]phenyl}-3,9-diazabicyclo[3.3.1]non-6-ene-3,6-dicarboxylic acid 6-benzyl ester 3-tert-butyl ester (AO2)

BuLi (1.6M in hexane, 19.40 mL, 31.0 mmol) was added to a sol. of compound C2 (9.90 g, 31.0 mmol) in THF (100 mL) at −78° C. After 30 min ZnCl$_2$ (0.83M in THF, 43.8 mL, 37.2 mmol, prepared as described for compound G1) was added and the mixture was allowed to warm up to rt. Bicyclononene AN (9.90 g, 19.0 mmol) and Pd(PPh$_3$)$_4$ (550 mg, 0.475 mmol) were added. The mixture was heated to reflux for 1 h. The mixture was allowed to cool to rt and aq. 1M HCl (1 mL) was added. The mixture was diluted with EtOAc and washed with aq. 1M NaOH (1×). The org. extracts were dried over MgSO$_4$, filtered, and the solvents were removed under reduced pressure. Purification of the residue by FC (MeOH/CH$_2$Cl$_2$ 1:49→3:97→2:48→5:95) yielded the title compound (6.20 g, 54%). LC-MS: $R_t$=5.10; ES+: 611.59.

Compounds of Type AP

(rac.)-(1R*,5S*)-7-{4-[3-(tert-Butyldimethylsilanyloxy)propyl]phenyl}-3,9-diazabicyclo[3.3.1]non-6-ene-3,6,9-tricarboxylic acid 6-benzyl ester 3-tert-butyl ester 9-(2,2,2-trichloro-1,1-dimethylethyl)ester (AP1)

A sol. of bicyclononene AO1 (1.78 g, 2.87 mmol) and 2,2,2-trichloro-tert-butyl chloroformate (3.44 g, 14.4 mmol) in CH$_2$ClCH$_2$Cl (35 mL) was heated to reflux for 2 h. The mixture was allowed to cool to rt and the solvents were removed under reduced pressure. Purification of the residue by FC (EtOAc/heptane 1:8→1:1) yielded the title compound (1.88 g, 81%). LC-MS: $R_t$=8.34.

(rac.)-(1R*,5S*)-7-{4-[2-(2,3,5-Trimethylphenoxy)ethyl]phenyl}-3,9-diazabicyclo[3.3.1]non-6ene-3,6,9-tricarboxylic acid 6-benzyl ester 3-tert-butyl ester 9-(2,2,2-trichloro-1,1-dimethylethyl)ester (AP2)

As for compound AP1 but from bicyclononene AO2 (22.4 g, 36.7 mmol) and 2,2,2-trichloro-tert-butyl chloroformate (44 g, 184 mmol) in CH$_2$ClCH$_2$Cl (400 mL). Purification of the residue by FC (EtOAc/heptane 1:8→1:1) yielded the title compound (19.2 g, 65%). LC-MS: R$_t$=7.95.

(rac.)-(1R*,5S*)-3-Acetyl-7-[4-(3-hydroxypropyl)phenyl]-3,9-diazabicyclo-[3.3.1]non-6-ene-6,9-dicarboxylic acid 6-benzyl ester 9-(2,2,2-trichloro-1,1-dimethylethyl) ester (AQ) HCl/dioxane (4M, 20 mL) was added to a sol. of bicyclononene AP1 (1.88 g, 2.32 mmol) in CH$_2$Cl$_2$ (20 mL) was cooled to 0° C. The ice bath was removed and the mixture was stirred for 3 h at rt. The solvents were removed under reduced pressure and the residue was dried under high vacuum. This residue was then dissolved in THF (30 mL) and the sol. was cooled to −78 ° C. DMAP (cat. amount), DIPEA (1.60 mL, 9.28 mmol) and AcCl (0.165 mL, 2.32 mmol) were added. The mixture was stirred for 15 min at −78° C. and MeOH (10 mL) was added. The mixture was allowed to warm up to rt, was dissolved in EtOAc and washed with aq. 1M HCl (1×) and aq. sat. NaHCO$_3$ (1×). The org. Extracts were dried over MgSO$_4$, filtered, and the solvents were removed under reduced pressure. Purification of the residue by FC (EtOAc/heptane 1 . . . 4→1:1→EtOAc→MeOH/EtOAc 1:9) yielded the title compound (936 mg, 63%). LC-MS: R$_t$=5.47; ES+: 637.06.

Compounds of Type AR (rac.)-(1R*,5S*)-3-Acetyl-7-{4-[3-(2,3,6-trifluorophenoxy)propyl]phenyl}-3,9-diazabicyclo[3.3.1]non-6-ene-6,9-dicarboxylic acid 6-benzyl ester 9-(2,2,2-trichloro-1,1-dimethylethyl) ester (AR1)

A mixture of bicyclononene AQ (468 mg, 0.73 mmol), 2,3,6-trifluorophenol (216 mg, 1.46 mmol), azodicarboxylic dipiperidide (277 mg, 1.10 mmol) and tributyl phosphine (0.541 mL, 2.19 mmol) in toluene (15 mL) was heated to reflux for 20 h. The mixture was allowed to cool to rt and the solvents were removed under reduced pressure. Purification of the residue by FC (EtOAc/heptane 1:49→1:19→1:9) yielded the title compound (297 mg, 53%). LC-MS: R$_t$=6.87; ES+: 767.04.

(rac.)-(1R*,5S*)-3-Acetyl-7-{4-[3-(2-bromo-5-fluorophenoxy)propyl]phenyl}-3,9-diazabicyclo[3.3.1]non-6-ene-6,9-dicarboxylic acid 6-benzyl ester 9-(2,2,2-trichloro-1,1-dimethylethyl) ester (AR2)

As for the bicyclononene AR1, but from bicyclononene AQ1 (468 mg, 0.73 mmol), 2-bromo-5-fluorophenol (0.163 mL, 1.46 mmol), azodicarboxylic dipiperidide (277 mg, 1.10 mmol) and tributyl phosphine (0.541 mL, 2.19 mmol) in toluene (15 mL). Purification of the residue by FC (EtOAc/heptane 1:49→1:19→1:9) yielded the title compound (205 mg, 35%). LC-MS: R$_t$=7.06.

(rac.)-(1R*,5S*)-3-Acetyl-6-[(2-allylbenzyl)cyclopropylcarbamoyl]-7-{4-[3-(2-bromo-5-fluorophenoxy)propyl]phenyl}-3,9-diazabicyclo[3.3.1]non-6-ene-9-carboxylic acid 2,2,2-trichloro-1,1-dimethylethyl ester (AS)

A mixture of bicyclononene AJ4 (225 mg, 0.300 mmol), (2-allylbenzyl)-cyclopropylamine (168 mg, 0.900 mmol), DIPEA (0.300 mL, 1.80 mmol), DMAP (10 mg, 0.082 mmol), HOBt (41 mg, 0.300 mmol) and EDC.HCl (86 mg, 0.450 mmol) in CH$_2$Cl$_2$ (3 mL) was stirred for 2 days. EDC.HCl (29 mg, 0.150 mmol) was added again after 24 h and 30 h. The mixture was diluted with CH$_2$Cl$_2$ and washed with aq. 1M HCl (1×). The org. extracts were dried over MgSO$_4$, filtered, and the solvents were removed under reduced pressure. Purification of the residue by FC (EtOAc/heptane 1:4→3:7→2:3→1:1→3:2→7:3→4:1) yielded the title compound (185 mg, 67%). R$_f$=0.63 (EtOAc). LC-MS: R$_t$=7.40.

1:1—Mixture of (rac.)-(1R*,5S*)-3-acetyl-7-{4-[3-(2-bromo-5-fluorophenoxy)-propyl]phenyl}-6-{cyclopropyl-[2-((2R*)-2,3-hydroxypropyl)benzyl]-carbamoyl}-3,9-diazabicyclo[3.3.1]non-6-ene-9-carboxylic acid 2,2,2-trichloro-1,1-dimethylethyl ester and (rac.)-(1R*,5S*)-3-acetyl-7-{4-[3-(2-bromo-5-fluorophenoxy)propyl]phenyl}-6-{cyclopropyl-[2-((2S*)-2,3-dihydroxypropyl)benzyl]carbamoyl}-3,9-diazabicyclo[3.3.1]non-6-ene-9-carboxylic acid 2,2,2-trichloro-1,1-dimethylethyl ester (AT)

A mixture of bicyclononene AS (281 mg, 0.316 mmol), NMO.H$_2$O (44.8 mg, 0.332 mmol), and OsO$_4$ (2.5% in tert-BuOH, 0.0396 mL, 0.00316 mmol) in THF (4 mL), tert-BuOH (2 mL) and water (1 mL) was stirred overnight. NMO.H$_2$O (10 mg, 0.074 mmol) and OsO$_4$ (0.010 mL, 0.008 mmol) were added again and the mixture was stirred again for 3 h. The solvents were removed under reduced pressure, and the residue was diluted with EtOAc, washed with aq. 1M HCl (1×), and with aq. sat. NaHCO$_3$ (1×). The org. extracts were dried over MgSO$_4$, filtered, and the solvents were removed under reduced pressure. Purification of the residue by FC (EtOAc/heptane 1:4→2:3→3:2→4:1→EtOAc→MeOH/EtOAc 1:9) yielded the title compounds (207 mg, 71%). R$_f$=0.20 (EtOAc). LC-MS: R$_t$=6.23; ES+: 922.59.

(rac.)-(1R*,5S*)-3-Acetyl-7-{4-[3-(2-bromo-5-fluorophenoxy)propyl]phenyl}-6-{cyclopropyl-[2-(2-oxoethyl)benzyl]carbamoyl}-3,9-diazabicyclo[3.3.1]non-6-ene-9-carboxylic acid 2,2,2-trichloro-1,1-dimethylethyl ester (AU)

A mixture of bicyclononenes AT (167 mg, 0.181 mmol) and NaIO$_4$ (40 mg, 0.187 mmol) in THF (3 mL) and water (1 mL) was stirred at rt for 1 h. NaIO4 (20 mg, 0.01 mmol) was added again and the mixture was stirred for 3 h. The mixture was diluted with EtOAc and washed with aq. sat. NaHCO$_3$ (1×). The org. extracts were dried over MgSO$_4$, filtered, and the solvents were removed under reduced pressure. The residue was dried under high vacuum and the title compound (156 mg, 97%) was used without further purification. LC-MS: R$_t$=6.87; ES+: 891.78.

(rac.)-(1R*,5S*)-3-Acetyl-7-{4-[3-(2-bromo-5-fluorophenoxy)propyl]phenyl}-6-{cyclopropyl-[2-(2-hydroxyethyl)benzyl]carbamoyl}-3,9-diazabicyclo[3.3.1]-non-6-ene-9-carboxylic acid 2,2,2-trichloro-1,1-dimethylethyl ester (AV)

A mixture of bicyclononene AU (44.6 mg, 0.05 mmol) and NaBH$_4$ (about 2 mg, about 0.05 mmol) in MeOH (1 mL) was stirred at rt for 90 min. The mixture was diluted with EtOAc and washed with aq. 1M HCl (1×). The org. extracts were

Compounds of Type AW (rac.)-(1R*,5S*)-7-[4-(3-Hydroxypropyl)phenyl]-3,
9-diazabicyclo[3.3.1]non-6-ene-3,6,9-tricarboxylic
acid 3-tert-butyl ester 6-ethyl ester 9-(2,2,2-trichloro-
1,1-dimethylethyl) Ester (AW1)

TBAF (28.8 g, 91.4 mmol) was added to a sol. of bicyclononene H3 (45.6 g, 60.9 mmol) in THF (900 mL) at 0° C. After 20 min, the ice bath was removed. After stirring the mixture at rt for 5 h, it was diluted with EtOAc and washed with water (2×). The org. extracts were dried over $MgSO_4$, filtered, and the solvents were removed under reduced pressure. Purification of the residue by FC (EtOAc/heptane 1:4→1:1) yielded the title compound (27.6 g, 72%). $R_f$=0.22 (EtOAc/heptane 1:1). LC-MS: $R_t$=6.11; ES+: 655.23.

(rac.)-(1R*,5S*)-7-[4-(2-Hydroxyethoxy)phenyl]-3,
9-diazabicyclo[3.3.1]non-6-ene-3,6,9-tricarboxylic
acid 3-tert-butyl ester 6-ethyl ester 9-(2,2,2-trichloro-
1,1-dimethylethyl) ester (AW2)

As for compound AW1 but from bicyclononene H7 (44.4 g, 59.2 mmol) TBAF (28.0 g, 88.9 mmol) and THF (600 mL). Purification by FC (EtOAc/heptane 1:3→1:1→EtOAc) yielded the title compound (23.67 g, 63%). $R_f$=0.20 (EtOAc/heptane 1:1). LC-MS: $R_t$=6.02; ES+: 635.36.

Compounds of Type AX (rac.)-(1R*,5S*)-7-{4-[3-(2,3,6-Trifluorophenoxy)
propyl]phenyl}-3,9-diazabicyclo[3.3.1]non-6-ene-3,
6,9-tricarboxylic acid 3-tert-butyl ester 6-ethyl ester
9-(2,2,2-trichloro-1,1-dimethylethyl) ester (AX1)

A mixture of bicyclononene AW1 (20.22 g, 32.0 mmol), 2,3,6-trifluorophenol (9.50 g, 64.0 mmol), azodicarboxylic dipiperidide (16.15 g, 64.0 mmol) and tributyl phosphine (85%, 27.9 mL, 96.0 mmol) in toluene (800 ml) was heated to reflux for 2 h. The mixture was allowed to cool to rt and the solvent removed under reduced pressure. Purification of the residue was purified by FC (EtOAc/heptane 1:19→1:9→1:4) yielded the title compound (21.7 g, 89%). $R_f$=0.60 (EtOAc/heptane 1:1). LC-MS: $R_t$=1.25; ES+: 765.22.

(rac.)-(1R*,5S*)-7-{4-[3-(2-Bromo-5-fluorophe-
noxy)propyl]phenyl}-3,9-diazabicyclo[3.3.1]non-6-
ene-3,6,9-tricarboxylic acid 3-tert-butyl ester 6-ethyl
ester 9-(2,2,2-trichloro-1,1-dimethylethyl) ester
(AX2)

As for AX1, but from bicyclononene AW1 (27.63 g, 43.6 mmol), 2-bromo-5-fluorophenol (9.70 mL, 87.2 mmol), azodicarboxylic dipiperidide (22.0 g, 87.2 mmol), tributyl phosphine (32.2 mL, 131 mmol), and toluene (550 ml). Purification of the residue by FC (EtOAc/heptane 1:19→1:9→1:4) yielded the title compound (31.67 g, 90%). $R_f$=0.60 (EtOAc/heptane 1:1). LC-MS: $R_t$=7.63.

(rac.)-(1R*,5S*)-7-{4-[2-(2-Chloro-4,5-dimeth-
ylphenoxy)ethoxy]phenyl}-3,9-diazabicyclo[3.3.1]
non-6-ene-3,6,9-tricarboxylic acid 3-tert-butyl ester
6-ethyl ester 9-(2,2,2-trichloro-1,1-dimethylethyl)
ester (AX3)

As for AX1, but from bicyclononene AW2 (11.83 g, 18.6 mmol), 2-chloro-4,5-dimethylphenol (5.83 mL, 37.2 mmol), azodicarboxylic dipiperidide (9.39 g, 37.2 mmol), tributyl phosphine (85%, 16.2 mL, 55.8 mmol), and toluene (300 ml). Purification of the residue by FC (EtOAc/heptane 1:19→1:9→1:3→1:1) yielded the title compound (13.35 g, 93%). $R_f$=0.50 (EtOAc/heptane 1:1). LC-MS: $R_t$=7.60.

(rac.)-(1R*,5S*)-7-{4-[2-(4-Bromophenoxy)ethoxy]
phenyl}-3,9-diazabicyclo-[3.3.1]non-6-ene-6,9-di-
carboxylic acid 6-ethyl ester 9-(2,2,2-trichloro-1,1-
dimethylethyl) ester (AX4)

As for AX1, but from bicyclononene AW2 (11.83 g, 18.6 mmol), 4-bromophenol (6.43 mL, 37.2 mmol), azodicarboxylic dipiperidide (9.39 g, 37.2 mmol), tributyl phosphine (85%, 16.2 mL, 55.8 mmol), and toluene (300 ml). Purification of the residue by FC (EtOAc/heptane 1:19→1:9→1:3→1:1) yielded the title compound (13.6 g, 92%). $R_f$=0.50 (EtOAc/heptane 1:1). LC-MS: $R_t$=7.49.

Compounds of Type AY (rac.)-(1R*,5S*)-7-{4-[3-(2,3,6-Trifluorophenoxy)
propyl]phenyl}-3,9-diazabicyclo[3.3.1]non-6-ene-3,
6,9-tricarboxylic acid 3-tert-butyl ester 9-(2,2,2-
trichloro-1,1-dimethylethyl) ester (AY1)

A mixture of bicyclononene AX1 (15.76 g, 20.7 mmol) in EtOH (600 mL) and aq. 1M NaOH (600 mL) was stirred for 7 h at 80° C. The mixture was allowed to cool to rt and the solvents were partially removed under reduced pressure. The residue was diluted with EtOAc and aq. 1M HCl was added to pH 1-2. The phases were shaken, separated and the aq. phase was extracted with EtOAc (2×). The combined org. extracts were dried over $MgSO_4$, filtered, and the solvents were removed under reduced pressure. Purification of the residue by FC (EtOAc/heptane 1:4→1:2→1:1) yielded the title compound (12.15 g, 80%). LC-MS: $R_t$=1.16; ES+: 737.21.

(rac.)-(1R*,5S*)-7-{4-[3-(2-Bromo-5-fluorophe-
noxy)propyl]phenyl}-3,9-diazabicyclo[3.3.1]non-6-
ene-3,6,9-tricarboxylic acid 3-tert-butyl ester 9-(2,2,
2-trichloro-1,1-dimethylethyl) ester (AY2)

As for compound AY1, but from bicyclononene AX2 (29.67 g, 36.8 mmol), EtOH (760 mL) and aq. 1M NaOH (700 mL). Purification by FC (EtOAc/heptane 1:1→EtOAc→MeOH/EtOAc 1:9) yielded the title compound 26.67 g (94%). LC-MS: $R_t$=6.89; ES+: 749.92.

(rac.)-(1R*,5S*)-7-{4-[2-(2,3,5-Trimethylphenoxy)
ethyl]phenyl}-3,9-diazabicyclo[3.3.1]non-6-ene-3,6,
9-tricarboxylic acid 3-tert-butyl ester 9-(2,2,2-
trichloro-1,1-dimethylethyl) ester (AY3)

Under $N_2$ Pd/C (10%, 1.92 g) was added to a sol. of bicyclononene AP2 (19.2 g, 24.0 mmol) in MeOH (390 mL) cooled to 0° C. The mixture was purged with $H_2$ (4×) and stirred at 0° C. under $H_2$ for 7 h. The mixture was filtered through Celite, diluted with EtOAc and washed with aq. 1M HCl (1×). The org. extracts were dried over MgSO$_4$, filtered, and the solvents were removed under reduced pressure. Purification by FC (EtOAc/heptane 1:3→1:1→EtOAc→MeOH/EtOAc 1:9) yielded the title compound (4.26 g, 25%). LC-MS: R$_t$=7.10.

(rac.)-(1R*,5S*)-7-{4-[2-(2-Chloro-4,5-dimethylphenoxy)ethoxy]phenyl}-3,9-diazabicyclo[3.3.1]non-6-ene-3,6,9-tricarboxylic acid 3-tert-butyl ester 9-(2,2,2-trichloro-1,1-dimethylethyl) ester (AY4)

As for compound AY1, but from bicyclononene AX3 (13.35 g, 17.2 mmol), EtOH (670 mL) and aq. 1M NaOH (670 mL). Purification by FC (EtOAc/heptane 1:1→EtOAc→MeOH/EtOAc 1:9) yielded the title compound 12.3 g (96%). R$_f$=0.75 (EtOAc). LC-MS: R$_t$=6.94.

(rac.)-(1R*,5S*)-7-{4-[2-(4-Bromophenoxy)ethoxy]phenyl}-3,9-diazabicyclo-[3.3.1]non-6-ene-6,9-dicarboxylic acid 9-(2,2,2-trichloro-1,1-dimethylethyl) ester (AY5)

As for compound AY1, but from bicyclononene AX4 (13.6 g, 17.2 mmol), EtOH (680 mL) and aq. 1M NaOH (680 mL). Purification by FC (EtOAc/heptane 1:1→EtOAc→MeOH/EtOAc 1:9) yielded the title compound 12.2 g (93%). R$_f$=0.75 (EtOAc). LC-MS: R$_t$=6.75.

Compounds of Type AZ (rac.)-(1R*,5S*)-3-Acetyl-7-[4-(3-hydroxypropyl)phenyl]-3,9-diazabicyclo-[3.3.1]non-6-ene-6,9-dicarboxylic acid 9-(2,2,2-trichloro-1,1-dimethylethyl) ester (AZ1)

A mixture of bicyclononene S5 (3.23 g, 5.60 mmol) in EtOH (50 mL) and aq. 1M NaOH (50 mL) was stirred at 80° C. for 5 h. The mixture was allowed to cool to rt and diluted with EtOAc. The mixture was brought to pH 2 with aq. 1M HCl and extracted with EtOAc (3×). The combined org. extracts were dried over MgSO$_4$, filtered, and the solvents were removed under reduced pressure. Purification by FC (MeOH/CH$_2$Cl$_2$ 1:19→1:9→1:4) yielded the title compound (1.40 g, 46%). LC-MS: R$_t$=0.89; ES+: 547.28.

(rac.)-(1R*,5S*)-7-[4-(2-Hydroxyethyl)phenyl]-3,9-diazabicyclo[3.3.1]non-6-ene-3,6,9-tricarboxylic acid 3-tert-butyl ester 9-(2,2,2-trichloro-1,1-dimethyl-ethyl) ester (AZ2)

As for compound AZ1 but from bicyclononene H8 (4.96 g), EtOH (150 mL) and aq. 1M NaOH (150 mL). The crude material was used further without purification.

Compounds of Type BA (rac.)-(1R*,5S*)-3-Acetyl-7-{4-[3-(tert-butyldimethylsilanyloxy)propyl]-phenyl}-6-[(2-chlorobenzyl)cyclopropylcarbamoyl]-3,9-diazabicyclo[3.3.1]-non-6-ene-9-carboxylic acid 2,2,2-trichloro-1,1-dimethylethyl ester (BA1)

A mixture of bicyclononene T4 (1.85 g, 2.79 mmol), (2-chlorobenzyl)-cyclopropylamine (1.52 g, 8.37 mmol), DMAP (85 mg, 0.70 mmol), DIPEA (1.91 mL, 11.2 mmol), HOBt (377 mg, 2.79 mmol) and EDC.HCl (803 mg, 4.19 mmol) in CH$_2$Cl$_2$ (50 mL) was stirred at rt for 18 h. The mixture was diluted with more CH$_2$Cl$_2$ and washed with aq. 1M HCl (1×) and aq. sat. NaHCO$_3$ (1×). The org. extracts were dried over MgSO$_4$, filtered, and the solvents were removed under reduced pressure. Purification of the residue by FC (EtOAc/heptane 1:4→1:3→1:2→1:1) yielded the title compound (1.16 g, 50%). LC-MS: R$_t$=1.37.

(rac.)-(1R*,5S*)-7-{4-[2-(tert-Butyldiphenylsilanyloxy)ethyl]phenyl}-6-[(2-chlorobenzyl)cyclopropylcarbamoyl]-3,9-diazabicyclo[3.3.1]non-6-ene-3,9-dicarboxylic acid 3-tert-butyl ester 9-(2,2,2-trichloro-1,1dimethylethyl) ester (BA2)

As for compound BA1, bur from bicyclononene T5 (crude, about 5.79 mmol), (2-chlorobenzyl)cyclopropylamine (3.10 g, 17.1 mmol), DIPEA (3.9 mL, 22.8 mmol), DMAP (140 mg, 1.14 mmol), HOBt (770 mg, 5.70 mmol), and EDC.HCl (1.64 g, 8.55 mmol), in CH$_2$Cl$_2$ (50 mL). Purification of the residue by FC (EtOAc/heptane 1:8→1:4) yielded the title compound 3.35 g (58%). R$_f$=0.55 (EtOAc/heptane 2:3). LC-MS: R$_t$=1.40.

(rac.)-(1R*,5S*)-3-Acetyl-7-{4-[2-(tert-butyldiphenylsilanyloxy)ethyl]phenyl}-6-[(2-chlorobenzyl)cyclopropylcarbamoyl]-3,9-diazabicyclo[3.3.1]non-6-ene-9-carboxylic acid 2,2,2-trichloro-1,1-dimethylethyl ester (BA3)

As for compound S1, from BA2 (1.45 g, 1.45 mmol), CH$_2$Cl$_2$ (10 mL), 4M HCl/dioxane (10 mL), THF (20 mL), without DMAP, DIPEA (4.62 mL, 27.0 mmol), acetylchloride (0.903 mL, 9.55 mmol), and MeOH (5 mL). Purification of the residue by FC (ErOAc/heptane 1:1→EtOAc→MeOH/EtOAc 1:9) led to the title compound (1.34 g, 75%). Rf=0.30 (EtOAc/heptane 1:1). LC-MS: R$_t$=1.39.

Compounds of Type BB (rac.)-(1R*,5S*)-3-Acetyl-6-[(2-chlorobenzyl)cyclopropylcarbamoyl]-7-[4-(3-hydroxypropyl)phenyl]-3,9-diazabicyclo[3.3.1]non-6-ene-9-carboxylic acid 2,2,2-trichloro-1,1-dimethylethyl ester (BB1)

A mixture of bicyclononene BA1 (1.16 g, 1.40 mmol) and TBAF (884 mg, 2.80 mmol) in THF (10 mL) was stirred at rt for 90 min. The mixture was diluted with EtOAc and washed with water (2×) and brine (1×). The org. extracts were dried over MgSO$_4$, filtered, and the solvents were removed under reduced pressure. Purification by FC (MeOH/CH$_2$Cl$_2$ 1:49→1:9) yielded the title compound (990 mg, 98%). R$_f$=0.47 (MeOH/CH$_2$Cl$_2$ 1:9). LC-MS: R$_t$=1.11.

(rac.)-(1R*,5S*)-3-Acetyl-6-[(2-chlorobenzyl)cyclopropylcarbamoyl]-7-[4-(2-hydroxyethyl)phenyl]-3,9-diazabicyclo[3.3.1]non-6-ene-9-carboxylic acid 2,2,2-trichloro-1,1-dimethylethyl ester (BB2)

As for compound BB1, but from BA3 (1.99 g, 2.21 mmol), TBAF (1M in THF, 4.5 mL, 4.5 mmol) in THF (15 mL). Purification by FC (EtOAc/heptane 1:5→1:1→EtOAc) yielded the title compound (1.00 g, 68%). R$_f$=0.38 (EtOAc/heptane 1:1). LC-MS: R$_t$=1.09; ES+: 698.02.

(rac.)-(1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-ene-3-carboxylic acid tert-butyl ester (BC)

Zn (1.63 g, 24.9 mmol) was added to a sol. of bicyclononene AK2 (2.25 g, 2.50 mmol) in THF (30 mL) and AcOH (10 mL) under efficient stirring. The mixture was stirred efficiently for 2.5 h, then filtered and washed with THF. The filtrate was diluted with EtOAc and washed with aq. 1M NaHO (2×). The org. extracts were dried over $MgSO_4$, and filtered. Evaporating the solvents under reduced pressure yielded the title compound that was used without further purification.

(1R,5S)-9-Methyl-7-trifluoromethanesulfonyloxy-3,9-diazabicyclo[3.3.1]non-6-ene-3,6-dicarboxylic acid 6-benzyl ester 3-tert-butyl ester (BD)

A sol. of bicyclononene AG (1.13 g; 2.91 mmol) in THF (8 ml) was added to a suspension of NaH (ca 60%, 175 mg; 4.36 mmol) in THF (2 ml) at 0° C. After 30 min $Tf_2NPh$ (1.56 g; 4.36 mmol) was added and the mixture was stirred at rt for 12 h. Ice (5 g) was added and THF was evaporated. The aq. residue was extracted with EtOAc (3×). The combine org. extracts were dried over $MgSO_4$, filtered, and the solvents were removed under reduced pressure. Puriciation of the residue by FC (EtOAc/cyclohexane 1:1→EtOAc) yielded the title compound (1.28 g, 84%). $R_f$=0.53 (EtOAc).

(1R,5S)-7-{4-[3-(tert-Butyldimethylsilanyloxy)propyl]phenyl}-9-methyl-3,9-diazabicyclo[3.3.1]non-6ene-3,6-dicarboxylic acid 6-benzyl ester 3-tert-butyl ester (BE)

BuLi (1.6 M in hexane, 3.82 mL, 5.98 mmol) was added to a sol. of [3-(4-bromophenyl)propoxy]-tert-butyldimethylsilane (Kiesewetter D. O., *Tetrahedron Asymmetry*, 1993, 4, 2183; 1.97 g; 5.98 mmol) in THF (4 ml) at −78° C. After 30 min, $ZnCl_2$ (1M in THF, 7.2 ml; 7.2 mmol) was added and the mixture was alloed to warm up to rt. A sol. of bicyclononene BD (1.24 g: 2.39 mmol) in THF (7 ml) and $Pd(PPh_3)_4$ (69 mg; 0.060 mmol) were added after each other and the mixture was heated to 40° C. for 35 min. The reaction mixture was allowed to cool to rt, sat. solution of $NH_4Cl$ was added, and the mixture was extracted with EtOAc (3×). The combined org. extracts were dried over $MgSO_4$, filtered, and the solvents were removed under reduced pressure. Purification of the residue by FC (EtOAc/cyclohexane 1:1→EtOAc) yielded the title compound (1.22 g, 82%). $R_f$=0.27 (EtOAc). LC-MS: $R_t$=5.68; ES+=621.30.

(1R,5S)-7-{4-[3-(tert-Butyldimethylsilanyloxy)propyl]phenyl}-3,9-diazabicyclo[3.3.1]non-6-ene-3,6,9-tricarboxylic acid 6-benzyl ester 3-tert-butyl ester 9-(2,2,2-trichloro-1,1-dimethylethyl) ester (BF)

A mixture of bicyclononene BE (1.66 g, 2.67 mmol) and β,β,β-trichloro-tert-butyl chloroformate (13.4 g, 240 mmol) in 1,2-dichloroethane (10 ml) was heated to reflux for 4 h. The mixture was allowed to cool to rt and the solvents were removed under reduced pressure. Purification of the residue by FC EtOAc/cyclohexane 1:4) yielded the title compound (1.75 g, 83%). $R_f$=0.43 (EtOAc/cyclohexane 1:4). LC-MS: $R_t$=8.30.

(1R,5S)-7-[4-(3-Hydroxypropyl)phenyl]-3,9-diazabicyclo[3.3.1]non-6-ene-3,6,9-tricarboxylic acid 6-benzyl ester 3-tert-butyl ester 9-(2,2,2-trichloro-1,1-dimethylethyl) ester (BH)

A sol. of bicyclononene BF (1.59 g, 1.96 mmol) in $CH_2Cl_2$ (3 ml) was cooled to 0° C. and HCl/dioxane (4M, 10 ml) was added. The mixture was stirred for 2 h at 0° C. and subsequently for 3 h at rt. After the solvents were removed under reduced pressure the crude was dried under high vacuum. The cresidue was dissolved in TIF (5 ml). DMAP (12 mg, 0.098 mmol) and DIPEA (1.34 ml; 7.849 mmol) were added and the mixture was cooled to −78° C. AcCl (0.153 ml; 2.16 mmol) was added and reaction mixture was stirred at −78° C. for 30 min. After addition of MeOH (1 ml) and warming up to rt, aq. HCl (1M, 10 ml) was added and reaction mixture was extracted with EtOAc (3×). The combined org. extracts were washed with aq. sat. $NaHCO_3$ (1×), and the org. extracts were dried over $MgSO_4$, filtered, and the solvents were removed under reduced pressure. Purification of the residue by FC EtOAc/cyclohexane 1:3→1:1) yielded the title compound (280 mg, 22%). $R_f$=0.38 (EtOAc). LC-MS: $R_t$=5.43; ES+=637.17.

(1R,5S)-7-[4-(3-Hydroxypropyl)phenyl]-3,9-diazabicyclo[3.3.1]non-6-ene-3,9-tricarboxylic acid 3-tert-butyl ester 9-(2,2,2-trichloro-1,1-dimethyl-ethyl) ester (BI)

A mixture of bicyclononene BH (140 mg; 0.219 mmol) and Pd/C (10%, 25 mg) in MeOH (4 ml) was stitted at rt under $H_2$ for 2 h. The mixture was filtered through *Celite,* washed with MeOH, and the solvents were evaporated under reduced pressure. The crude product (110 mg) was directly used in the next reaction without purification. $R_f$=0.15 (EtOAc). LC-MS: $R_t$=4.41; ES−: 545.02.

(1R,5S)-7-[4-(3-Hydroxypropyl)phenyl]-6-(methylphenethylcarbamoyl)-3,9-diazabicyclo[3.3.1]non-6-ene-3,9-dicarboxylic acid 3-tert-butyl ester 9-(2,2,2-trichloro-1,1-dimethylethyl) ester (BJ)

A mixture of bicyclononene BI (95 mg; 0.17 mmol), phenethylmethylamine (0.48 ml; 0.34 mmol); HOBt (6.0 mg, 0.042 mmol), EDC.HCl (49 mg; 0.255 mmol) and DMAP (5.0 mg; 0.042 mmol) in $CHCl_3$ (6 ml) was stirred at rt for 14 h. Aq HCl (1M) was added and the mixture was extracted with $CH_2Cl_2$ (3×). The org. phase was washed with aq. sat $NaHCO_3$ (1×), the combined org. extracts were dried over $MgSO_4$, filtered, and the solvents were removed under reduced pressure. Purification of the residue by FC (EtOAc/cyclohexane 1:1→EtOAc) yielded the title compound (64 mg, 44%). $R_f$=0.25 (EtOAc). LC-MS: $R_t$=5.37; ES+: 664.29.

(1R,5S)-7-{4-[3-(2-Bromo-5-fluorophenoxy)propyl]phenyl}-6-(methylphenethylcarbamoyl)-3,9-diazabicyclo[3.3.1]non-6-ene-3,9-dicarboxylic acid 3-tert-butyl ester 9-(2,2,2-trichloro-1,1-dimethyl-ethyl) ester (BK)

A mixture of bicyclononene BJ (60 mg; 0.090 mmol), 2-bromo-5-fluorophenol (34 mg, 0.18 mmol), azodicarboxylic dipiperidide (34 mg; 0.135 mmol) and tributylphosphine (67 mg; 0.270 mmol) in toluene (2 ml) was heated to reflux for 20 h. The solvent was removed under reduced pressure. Purification of the residue was by FC EtOAc/cyclohexane 2:1→4:

1) yielded the title compound (58 mg, 76%). R$_f$=0.60 (EtOAc). LC-MS:R$_t$=7.01; ES+=836.07.

(rac.)-(1R*,5S*)-3-Acetyl-7-{4-[3-(2-bromo-5-fluorophenoxy)-propyl]phenyl}-3,9-diazabicyclo[3.3.1] non-6-ene-6,9-dicarboxylic acid 6-ethyl ester 9-(2,2, 2-trichloro-1,1-dimethylethyl) ester (BL)

HCl/dioxane (4M, 20 mL) was added to a sol. of bicyclononene AX2 (2.00 g, 2.47 mmol) in CH$_2$Cl$_2$ (20 mL) cooled to 0° C. The ice bath removed and the mixture was stirred at rt for 2 h. The solvents were removed under reduced pressure and the foamy residue dried under high vacuum. A mixture of this residue, DMAP (15 mg, 0.123 mmol) and DIPEA (1.69 mL, 9.88 mmol) in THF (40 mL) was cooled to −78° C., and AcCl (0.186 mL, 2.47 mmol) was added. The mixture was stirred for 20 min at −78° C. and MeOH (5 mL) was added. The mixture was allowed to warm up to rt, was diluted with EtOAc and washed with aq. 1M HCl (1×). The org. extracts were dried over MgSO$_4$, filtered, and the solvents were removed under reduced pressure. Purification of the residue by FC (EtOAc/heptane 1:4→1:1→EtOAc) yielded the title compound (1.55 g, 83%). R$_f$=0.50 (EtOAc).

Compounds of Type BM

3-Acetyl-7-{4-[2-(2-bromo-5-fluorophenoxy) ethoxy]phenyl}-3,9-diazabicyclo[3.3.1]non-6-ene-6, 9-dicarboxylic acid 6-ethyl ester 9-(2,2,2-trichloro-1, 1-dimethylethyl) ester (BM2)

Tributylphosphine (3.84 mL, 15.6 mmol) was added to a sol. of bicyclononene S4 (3.00 g, 5.19 mmol), 2-bromo-5-fluorophenol (1.15 mL, 10.4 mmol) and azodicarboxylic dipiperidide (1.97 g, 7.79 mmol) in toluene (30 mL). The mixture was heated to reflux for 2 h and allowed to cool to rt. The solvents were removed under reduced pressure. Purification by FC (EtOAc/heptane 1:1→2:1→3:1) yielded the title compound (2.70 g, 69%).

3-Acetyl-7-{4-[2-(2-chloro-4,5-dimethylphenoxy) ethoxy]phenyl}-3,9-diazabicyclo[3.3.1]non-6-ene-6, 9-dicarboxylic acid 6-ethyl ester 9-(2,2,2-trichloro-1, 1-dimethylethyl) ester BM3

As described for compound BM2, but from bicyclononene S4 (3.00 g, 5.19 mmol), 2-chloro-4,5-dimethylphenol (1.64 g, 10.5 mmol), azodicarboxylic dipiperidide (1.98 g, 7.86 mmol), tributylphosphine (3.90 mL, 15.7 mmol) and toluene (50 mL). Purification by FC yielded the title compound (2.82 g, 75%).

3-Acetyl-7-{4-[2-(2,6-dichloro-4-methylphenoxy) ethoxy]phenyl}-3,9-diazabicyclo[3.3.1]non-6-ene-6, 9-dicarboxylic acid 6-ethyl ester 9-(2,2,2-trichloro-1, 1-dimethylethyl) ester (BM4)

As described for compound BM2, but from bicyclononene S4 (3.00 g, 5.19 mmol), 2,6-dichloro-4-methylphenol (1.84 g, 10.38 mmol), azodicarboxylic dipiperidide (1.97 g, 7.79 mmol), tributylphosphine (3.84 mL, 15.6 mmol) and toluene (50 mL). Purification by FC yielded the title compound (2.76 g, 72%).

3-Acetyl-7-{4-[2-(2,3-dichlorophenoxy)ethoxy]phenyl}-3,9-diazabicyclo-[3.3.1]non-6-ene-6,9-dicarboxylic acid 6-ethyl ester 9-(2,2,2-trichloro-1,1-dimethylethyl) ester (BM5)

As described for compound BM2, but from bicyclononene S4 (3.20 g, 5.54 mmol), 2,3-dichlorophenol (1.80 g, 11.1 mmol), azodicarboxylic dipiperidide (2.10 g, 8.31 mmol), tributylphosphine (4.11 mL, 16.6 mmol) and toluene (50 mL). Purification by FC yielded the title compound (2.22 g, 55%).

3-Acetyl-7-{4-[2-(4-chloro-2-methylphenoxy) ethoxy]phenyl}-3,9-diazabicyclo[3.3.1]non-6-ene-6, 9-dicarboxylic acid 6-ethyl ester 9-(2,2,2-trichloro-1, 1-dimethylethyl) ester (BM7)

As described for compound BM2, but from bicyclononene S4 (3.00 g, 5.19 mmol), 4-chloro-2-methylphenol (1.48 g, 10.4 mmol), azodicarboxylic dipiperidide (1.97 g, 7.79 mmol), tributylphosphine (3.84 mL, 15.6 mmol) and toluene (50 mL). Purification by FC yielded the title compound (1.36 g, 37%).

3-Acetyl-7-{4-[2-(2,4,5-trichlorophenoxy)ethoxy] phenyl}-3,9-diazabicyclo-[3.3.1]non-6-ene-6,9-dicarboxylic acid 6-ethyl ester 9-(2,2,2-trichloro-1,1-dimethylethyl) ester (BM9)

As described for compound BM2, but from bicyclononene S4 (3.00 g, 5.19 mmol) 2,4,5-trichlorophenol (2.05 g, 10.4 mmol), azodicarboxylic dipiperidide (1.97 g, 7.79 mmol), tributylphosphine (3.84 mL, 15.6 mmol) and toluene (50 mL). Purification by FC yielded the title compound (2.76 g, 72%).

3-Acetyl-7-{4-[2-(2-chloro-fluorophenoxy)ethoxy] phenyl}-3,9-diazabicyclo[3.3.1]non-6-ene-6,9-dicarboxylic acid 6-ethyl ester 9-(2,2,2-trichloro-1,1-dimethylethyl) ester (BM10)

As described for compound BM2, but from bicyclononene S4 (3.18 g, 5.50 mmol) 2-chloro-5-fluorophenol (1.61 g, 11.0 mmol), azodicarboxylic dipiperidide (2.08 g, 8.25 mmol), tributylphosphine (4.10 mL, 16.6 mmol) and toluene (50 mL). Purification by FC yielded the title compound (2.67 g, 69%).

Compounds of Type BN

3-Acetyl-7-{4-[2-(2-bromo-5-fluorophenoxy) ethoxy]phenyl}-3,9-diazabicyclo[3.3.1]non-6-ene-6, 9-dicarboxylic acid 9-(2,2,2-trichloro-1,1-dimethylethyl) ester (BN2)

A mixture of bicyclononene BM2 (2.69, 3.58 mmol) in aq. 1M NaOH (30 mL) and EtOH (70 mL) was stirred for 1 h at 85° C. The mixture was allowed to cool to rt and the solvents were partially removed under reduced pressure. The residue was acidified to pH 2 with aq. 1M HCl and this mixture was extracted with EtOAc (3×). The combined org. extracts were dried over MgSO$_4$, filtered, and the solvents were removed under reduced pressure. The crude title compound (2.96 g, quantitative yield) was used further without purification.

3-Acetyl-7-{4-[2-(2-chloro-4,5-dimethylphenoxy) ethoxy]phenyl}-3,9-diazabicyclo[3.3.1]non-6-ene-6, 9-dicarboxylic acid 9-(2,2,2-trichloro-1,1-dimethylethyl) ester (BN3)

As described for compound BN2, but from bicyclononene BM3 (2.82 g, 3.94 mmol), aq. 1M NaOH (30 mL) and EtOH (70 mL). The crude title compound (2.59 g, 96%) was used further without purification.

3-Acetyl-7-{4-[2-(2,6-dichloro-4-methylphenoxy) ethoxy]phenyl}-3,9-diazabicyclo[3.3.1]non-6-ene-6, 9-dicarboxylic acid 9-(2,2,2-trichloro-1,1diethylethyl) ester (BN4)

As described for compound BN2, but from bicyclononene BM4 (2.75 g, 3.73 mmol), aq. 1M NaOH (30 mL) and EtOH (70 mL). The crude title compound (2.63 g, quantitative yield) was used further without purification.

3-Acetyl-7-{4-[2-(2,3-dichlorophenoxy)ethoxy]phenyl}-3,9-diazabicyclo-[3.3.1]non-6-ene-6,9-dicarboxylic acid 9-(2,2,2-trichloro-1,1-dimethylethyl) ester (BN5)

As described for compound BN2, but from bicyclononene BM5 (2.22 g, 3.07 mmol), aq. 1M NaOH (30 mL) and EtOH (70 mL). The crude title compound (1.59 g, 75%) was used fuirther without purification.

3-Acetyl-7-{4-[2-(4-chloro-2-methylphenoxy) ethoxy]phenyl}-3,9-diazabicyclo[3.3.1]non-6-ene-6, 9-dicarboxylic acid 9-(2,2,2-trichloro-1,1-dimethylethyl) ester (BN7)

As described for compound BN2, but from bicyclononene BM7 (1.35 g, 1.92 mmol), aq. 1M NaOH (30 mL) and EtOH (70 mL). The crude title compound (1.25 g, 97%) was used further without purification.

3-Acetyl-7-{4-[2-(2,4,5-trichlorophenoxy)ethoxy] phenyl}-3,9-diazabicyclo-[3.3.1]non-6-ene-6,9-dicarboxylic acid 9-(2,2,2-trichloro-1,1-dimethylethyl) ester (BN9)

As described for compound BN2, but from bicyclononene BM9 (2.31 g, 3.05 mmol), aq. 1M NaOH (30 mL) and EtOH (70 mL). The crude title compound (2.19 g, 99%) was used fiwdier without purification.

3-Acetyl-7-{4-[2-(2-chloro-5-fluorophenoxy)ethoxy] phenyl}-3,9-diazabicyclo-[3.3.1]non-6-ene-6,9-dicarboxylic acid 9-(2,2,2-trichloro-1,1-dimethylethyl) ester (BN10)

As described for compound BN2, but from bicyclononene BM10 (2.82 g, 3.94 mmol), aq. 1M NaOH (30 mL) and EtOH (70 mL). The crude title compound (1.90 g, 74%) was used ftther without purification.

Preparation of the Final Compounds

Typical Procedure (A) for the acylation

To a solution of bicyclononene in anhydrous EtOAc was added vacuum dried-Amberlyst 21 (1.5 g/mmole of bicyclononene) or another suitable scavenger, followed by the addition of the desired acid chloride (1.5 eq.). After shaking the suspension for 3 h, an aliquot water was added and shaking was continued for 1 h. The resin was then removed by filtration, washed with EtOAc and the filtrate was evaporated to yield the intermediate amide.

The synthesis of the sulfonamide, carbamate or urea derivatives was performed in analogy to the above-described procedure, by using the corresponding sulfonyl chloride, chloroformate or carbamoyl chloride respectively.

Typical Procedure (B) for amide Formation from acid ahlorides

To a sol. of the acid chloride (1 eq.) in $CH_2Cl_2$ (2.5 mL/mmol) at 0° C. the amine (3 eq.) was added. The mixture was stirred for 3 h while warming up slowly to rt. If necessary, more $CH_2Cl_2$ was added, then the reaction mixture was washed with aq. sat. $NaHCO_3$ (1×) and aq. 1M HCl (1×). The extracts were dried over $MgSO_4$ and the solvents were removed under reduced pressure. The obtained product was used without further purification.

Typical Procedure (C) for an amide Coupling with CDI

To a sol. of the carboxylic acid (1 eq.) in $CH_2Cl_2$ (4 mL/mmol) CDI (1 eq.) was added. The sol. or suspension was stirred for 2 h at rt, then cooled to 0° C. The amine (6 eq.) was added and the sol. or suspension was stirred for 2 h while warming up slowly to rt. The sol. or suspension was washed with water (1×). The org. extracts were evaporated under reduced pressure and the obtained residue was used further without purification.

Typical Procedure (D) for the Reduction of an amide to an amine with CDI

To a sol. of the amide (1 eq.) was dissolved in THF (3 mL/mmol) LAH (1M in THF, 3 eq.) was added carefully. The mixture was stirred at rt for 30 min, then heated to 60° C. for 3 h before it was allowed to cool down to rt, then to 0° C. For ×g of $LiAlH_4$ initially added, was added ×g of water, then ×g of aq. 15% NaOH, and finally 3×g of water again. The resulting mixture was stirred overnight, filtered, and the precipitate washed with EtOAc. The filtrate was evaporated under reduced pressure and the residue diluted in a small amount of MeOH. The sol. was passed through a pad of SCX silica gel (sulfonic acid). Elution started with MeOH, followed by $NH_3$/MeOH. The amines eluted with the second eluent. The solvents were removed under reduced pressure. The isolated amines were either used without further purification or purified by HPLC, depending on the purity.

Typical Procedure (E) for the Cleavage of the 2,2,2-trichloro-1,1-dimethylethylcarbamate Protecting Group:

The crude product from another typical procedure was dissolved in THF/AcOH (1:0.1) and treated with zinc (20 eq.). The suspension was stirred for 5 h and filtered through celite, which was washed with EtOAc. The filtrate was evaporated under reduced pressure and the residue was purified by HPLC.

Typical Procedure M for the Formation of aryl ether (Mitsunobu Reaction)

The bicyclononene (0.05 mmol) was dissolved or suspended in toluene (1.00 mL). The phenol derivative (0.075 mmol) in toluene (0.50 mL) was added. TMAD (0.075 mmol) in toluene (0.50 mL) was added, followed by tributylphosphine (0.15 mmol). The reaction mixture was stirred for 2 h at rt and then 2 h at 60 °C. Sometimes, it was necessary to add a second portion of tributylphosphine and to stir overnight. Sometimes, TIF was necessary as cosolvent to dissolve the reactants. The reaction mixture was allowed to cool to rt, then water was added. The mixture was extracted with EtOAc, and the org. extracts were evaporated under reduced pressure.

Typical Procedure (G) for an amide Coupling

To a sol. of bicyclononene (0.05 mmol) in $CHCl_3$ (2 mL) the desired carboxylic acid (0.10 mmol) was added. DIPEA (0.10 mmol), DMAP (0.01 mmol), HOBt (0.01 mmol), and EDC.HCl (0.05 mmol) were added and the reaction mixture was stirred overnight. Sometimes, it was necessary to add another portion of acid, DMAP, HOBt and EDC.HCl and to continue stirring for 24 h. $CH_2Cl_2$ was added and the mixture was washed with water. The org. extracts were separated, dried over $Na_2SO_4$ and filtered. The solvent was removed under reduced pressure.

Typical Procedure (H) for an amide Coupling

To a sol. of the bicyclononene (0.05 mmol) $CHCl_3$ or $CH_2Cl_2$ (2 mL) the desired amine (commercially available or prepared following known, standard procedures) (0.10 mmol) was added. DIPEA (0.10 mmol), DMAP (0.01 mmol), HOBt (0.01 mmol) and EDC.HCl (0.05 mmol) were added. The reaction mixture was stirred overnight. Sometimes, it was necessary to add another portion of amine, DMAP, HOBt and EDC.HCl and to continue stirring the sol. for 24 h. $CH_2Cl_2$ was added and the mixture was washed with water. The org. extracts were separated, dried over $Na_2SO_4$ and filtered. The solvents were removed under reduced pressure.

Typical Procedure (J) for Reductive Amination

To a solution of aldehyde (1 eq.) in MeOH (0.5 mL/mmol) was added an amine (1.2 eq.). The solution was stirred for 2 h. Sodium borohydride (1.2 eq.) was added portionwise at 0° C. and then string was continued, at rt, for 4 h. A solution of NaOH 1N was added and the MEOH was evaporated. The mixture was extracted with EtOAc twice and the organic layer was washed with brine, dried over $Na_2SO_4$ and filtered. The solvent was removed under reduced pressure. The isolated amines were either used without further purification or purified by flash chromatography (EtOAc/heptane: 2/8), depending on the purity.

Typical Procedure (K) for an anhydride Coupling

To a sol. of the bicyclononene (0.05 mmol) in $CH_2Cl_2$ (0.4 mL) was added DIPEA (0.1 mmol) followed by the anhydride (0.06 mmol) in $CH_2Cl_2$ (0.4 mL) at 0° C. After stirring for 3 h at rt, the solvent was evaporated under reduced pressure.

Typical Procedure (L) for Protecting Group (BOC and TBDMS) Cleavage

To a sol. of the bicyclononene (0.05 mmol) in $CH_2Cl_2$ (0.5 mL), cooled to 0° C., was added 4M HCl/dioxane(0.5 mL) The ice bath was removed and the solution was stirred for 1 h30 to 3 h, depending on the compound. The solvents were evaporated under reduced pressure without heating.

Typical Procedure (M) for Tile Saponification of esters

A mixture of the ester (1 eq.) and LiOH (2 eq.) in THF was stirred at rt for 2 h. The solvents were removed under reduced pressure and the residue was extracted on isolute sorbent (0.25 g pre-washed with 0.300 mL aq. 1M HCl, elution with 2 mL $CH_2Cl_2$). The solvent was removed under reduced pressure and the residue was used without further purification.

Preparation of Amines (2-Chlorobenzyl)cyclopropylamine

Synthesized according to typical procedures B and D from 2-chlorobenzoyl chloride and cyclopropylamine.

Benzylcyclopropylamine

See Loeppky, R. N.; et al., *J. Org. Chem.*, 2000, 65, 96.

(2-Chlorobenzyl)ethylamine

See Ishihara, Y; et al.; *Chem. Pharm Bull.*, 1991, 39, 3225.

Cyclopropyl-(3-trifluoromethylbenzyl)amine

See Brabander, H. J.; et al.; *J. Org. Chem.*, 1967, 32, 4053.

Cyclopropylphenethylamine

See Smith, P. W.; et al.; *J. Med. Chem.*, 1998, 41, 787.

Methyl(3-phenoxypropyl)amine

Synthesized according to typical procedures C and D from 3-phenoxypropionic acid and methylamine.

(2-p-Tolyloxyethyl)methylamine

Synthesized according to typical procedures C and D from 2-p-tolyloxyacetic acid and methylamine.

[2-(3-Chlorophenyl)ethyl]amine

Synthesized according to typical procedures C and D from 3-chlorophenylacetic acid and methylamine.

[2-(2-Methoxyphenyl)ethyl]amine

Synthesized according to typical procedures C and D from 2-methoxyphenylacetic acid and methylamine.

(2-Allylbenzyl)cyclopropylamine

BuLi (1.55 M in hexane, 14.7 mL, 22.7 mmol) was added to a sol. of 1-bromo-2-(dimethoxymethyl)benzene (5.00 g, 21.6 mmol) in $Et_2O$ (50 mL). The mixture was stirred for 30 min at −78 °C. and $MgBr_2.Et_2O$ (5.87 g, 22.7 mmol) was added. The mixture was allowed to warm up to 0° C. over 15 min and CuI (420 mg, 2.16 mmol) was added. The mixture was stirred at 0° C. for 5 min and allyl bromide (1.92 mL, 22.7 mmol) was added. The mixture was stirred overnight while warming up to rt. Aq. 1M HCl (1 mL) was added and the mixture was diluted with Et$_2$O, and washed with aq. 1M HCl (1×). The org. Extracts were dried over MgSO$_4$, filtered, and the solvents were removed under reduced pressure. The residue was dissolved in acetone (20 mL) and water (10 mL), and TosOH (cat. amount) was added. The mixture was stirred for 5 h at rt, and the solvents were partially removed under reduced pressure. The residue was diluted with Et$_2$O, and washed with aq. 1M HCl (1×), and aq. sat. NaHCO$_3$ (1×). The org. extracts were dried over MgSO$_4$, filtered, and the solvents were removed under reduced pressure. Purification of the residue by FC (Et$_2$O/petroleum ether 1:49→24:1) yielded 2-allylbenzaldehyde (1.06 g, 34%). This compound was transformed into the title compound following typical procedure J with cyclopropylamine.

Cyclopropyl-(2-fluorobenzyl)amine

Synthesized according to typical procedure J from 2-fluorobenzaldehyde and cyclopropylamine.

Cyclopropyl-(2-methylbenzyl)amine

Synthesized according to typical procedure J from 2-methylbenzaldehyde and cyclopropylamine.

Cyclopropyl-[2-(4methoxyphenoxy)ethyl]amine

Synthesized according to typical procedures C and D from (4-methoxyphenoxy)-acetic acid and cyclopropylamine.

Cyclopropyl-[2-(3-methoxyphenoxy)ethyl]amine

Synthesized according to typical procedures C and D from (3-methoxyphenoxy)-acetic acid and cyclopropylamine.

Cyclopropyl-(2-o-tolyloxyethyl)amine

Synthesized according to typical procedures C and D from o-tolyloxyacetic acid and cyclopropylamine.

Cyclopropyl-[2-(3,4-dimethylphenoxy)ethyl]amine

Synthesized according to typical procedures C and D from (3,4-dimethylphenoxy)acetic acid and cyclopropylamine.

[2-(2-Chlorophenyl)ethyl]cyclopropylamine

Synthesized according to typical procedures C and D from (2-chlorophenyl)-acetic acid and cyclopropylamine.

Cyclopropyl-[2-(2,3-difluorophenyl)ethyl]amine

Synthesized according to typical procedures C and D from (2,3-difluorophenyl)-acetic acid and cyclopropylamine.

Cyclopropyl-[2-(4-fluorophenyl)ethyl]amine

Synthesized according to typical procedures C and D from (4-fluorophenyl)acetic acid and cyclopropylamine.

Cyclopropyl-(2-o-tolylethyl)amine

Synthesized according to typical procedures C and D from o-tolylacetic acid and cyclopropylamine.

Cyclopropyl-(2-p-tolylethyl)amine

Synthesized according to typical procedures C and D from ptolylacetic acid and cyclopropylamine.

Cyclopropyl-(3,5-dimethoxybenzyl)amine

Synthesized according to typical procedure J from 2,5-dimethoxybenzaldehyde and cyclopropylamine.

(2-Chlorobenzyl)methylamine

See Kihara, M; et al.; *Heterocycles,* 1989, 29, 957.

(2-Chlorobenzyl)isopropylamine

Synthesized according to typical procedure J from 2-chlorobenzaldehyde and isopropylamine.

Cyclopropyl-(2-fluoro-5methoxybenzyl)amine

Synthesized according to typical procedure J from 2-fluoro-5-methoxybenzaldehyde and cyclopropylamine.

Cyclopropyl-(3-methoxybenzyl)amine

Synthesized according to typical procedure J from 3-methoxybenzaldehyde and cyclopropylamine.

Cyclopropyl-(3,4dimethoxybenzyl)amine

Synthesized according to typical procedure J from 3,4-dimethoxybenzaldehyde and cyclopropylamine.

(2-Chloro-3-trifluoromethylbenzyl)cyclopropylamine

Synthesized according to typical procedure J from 2-chloro-3-trifluoromethylbenzaldehyde and cyclopropylamine.

(6-Chlorobenzo[1,3]dioxol-5-ylmethyl)cyclopropylamine

Synthesized according to typical procedure J from 6-chlorobenzo[1,3]dioxole-5-carbaldehyde and cyclopropylamine.

Cyclopropyl-(5-fluoro-2-methoxybenzyl)amine

Synthesized according to typical procedure J from 5-fluoro-2-methoxybenzaldehyde and cyclopropylamine.

(2-Chloro-6-fluorobenzyl)cyclopropylamine

Synthesized according to typical procedure J from 2-chloro-6-fluorobenzaldehyde and cyclopropylamine.

(2-Bromobenzyl)cyclopropylamine

Synthesized according to typical procedure J from 2-bromobenzaldehyde and cyclopropylamine.

Cyclopropyl-(2,6-difluorobenzyl)amine

Synthesized according to typical procedure J from 2,6-difluorobenzaldehyde and cyclopropylamine.

Cyclopropyl-(2,3-dimethylbenzyl)amine

Synthesized according to typical procedure J from 2,3-dimethylbenzaldehyde and cyclopropylamine.

Cyclopropyl-(3-fluoro-2-methylbenzyl)amine

Synthesized according to typical procedure J from 3-fluoro-2-methylbenzaldehyde and cyclopropylamine.

Cyclopropyl-(3,5-difluorobenzyl)amine

Synthesized according to typical procedure J from 3,5difluorobenzaldehyde and cyclopropylamine.

(2-Chloro-3,6-difluorobenzyl)cyclopropylamine

Synthesized according to typical procedure J from 2-chloro-3,6-difluorobenzaldehyde and cyclopropylamine.

(2,3-Dichlorobenzyl)cyclopropylamine

Synthesized according to typical procedure J from 2,3-dichlorobenzaldehyde and cyclopropylamine.

Cyclopropyl-(3-trifluoromethoxybenzyl)amine

Synthesized according to typical procedure J from 3-trifluoromethoxy-benzaldehyde and cyclopropylamine.

Cyclopropyl-(3-methylbenzyl)amine

Synthesized according to typical procedure J from 3-methylbenzaldehyde and cyclopropylamine.

Cyclopropyl-(2,3-difluorobenzyl)amine

Synthesized according to typical procedure J from 2,3-difluorobenzaldehyde and cyclopropylamine.

(3-Chlorobenzyl)cyclopropylamine

Synthesized according to typical procedure J from 3-chlorobenzaldehyde and cyclopropylamine.

Cyclopropyl-(4-fluorobenzyl)amine

Synthesized according to typical procedure J from 4fluorobenzaldehyde and cyclopropylamine.

Preparation of Other Reagents

4Carbamoylbutyric acid

See Melnyk, O., et al.; *J. Org. Chem.*, 2001, 66, 4153.

meso-3,4-Dihydroxytartaric acid anhydride

A mixture of meso-3,4-Diydroxytartaric acid (1.00 g, 6.67 mmol) and trifluoroacetic acid anhydride (5 mL) was stirred for 2 h at rt. The solvents were removed under reduced pressure and the residue was used as crude product without further purification.

Succinamic acid

See Bellier, B., et al.; *J. Med. Chem.*, 2000, 43, 3614.

SPECIFIC EXAMPLES

Example 1

(rac.)-(2-Methoxyphenyl)acetic acid (1R*,5S*)-3-[2-(4-chlorophenyl)acetyl]-7-{4-[3-(2-methoxybenzyloxy)propoxy]phenyl}-3,9-diazabicyclo[3.3.1non-6-en-6-yl methyl ester trifluoroacetate salt Synthesized according to typical procedure A from bicyclononene N and 4-chlorophenylacetyl chloride, then according to typical procedure E. LC-MS: $R_t$=4.57; ES+: 725.35.

Example 2

(rac.)-(2-Methoxyphenyl)acetic acid (1R*,5S*)-7-{4-[3-(2-methoxybenzyloxy)propoxy[phenyl}-3-(quinoxaline-2-carbonyl)-3,9-diazabicyclo[3.3.1] non-6-en-6-yl methyl ester trifluoroacetate salt Synthesized according to typical procedure A from bicyclononene N and 2-quinoxaloyl chloride, then according to typical procedure E. LC-MS: $R_t$=4.55; ES+: 728.94.

Example 3

(rac.)-(2-Methoxyphenyl)acetic acid (1R*,5S*)-7-{4-[3-(2-methoxybenzyloxy)propoxy]phenyl}-3-phenylmethanesulfonyl-3,9-diazabicyclo[3.3.1]-non-6-en-6-yl methyl ester trifluoroacetate salt Synthesized according to typical procedure A from bicyclononene N and phenylmethanesulfonyl chloride, then according to typical procedure E. LC-MS: $R_t$=4.75; ES+: 727.74.

Example 4

(rac.)-(2-Methoxyphenyl)acetic acid (1R*,5S*)-7-{4-[3-(2-methoxybenzyloxy)propoxy]phenyl}-3-(2-thiophen-2-ylacetyl)-3,9-diazabicyclo[3.3.1]non-6-en-6-yl methyl ester trifluoroacetate salt Synthesized according to typical procedure A from bicyclononene N and thiophen-2-ylacetyl chloride, then according to typical procedure E. LC-MS: $R_t$=4.52; ES+: 696.91.

Example 5

(rac.)-(2-Methoxyphenyl)acetic acid (1R*,5S*)-3-(benzo[b]thiophene-3-carbonyl)-7-{4-[3-(2-methoxybenzyloxy)propoxy]phenyl}-3,9-diazabicyclo-[3.3.1]non-6-en-6-yl methyl ester trifluoroacetate salt Synthesized according to typical procedure A from bicyclononene N and benzothiophene-3-carbonyl chloride, then according to typical procedure E. LC-MS: $R_t$=4.76; ES+: 733.80.

Example 6

(rac.)-(1R*,5S*)-7-{4-[3-(2-Methoxybenzyloxy)propoxy]phenyl}-6-[2-(2-methoxyphenyl)acetoxymethyl]-3,9-diazabicyclo[3.3.1]non-6-ene-9-carboxylic acid 2,2,2-trichloro-1,1-dimethylethyl ester trifluoroacetate salt Prepared as compound N, but then purified by HPLC. LC-MS: $R_t$=5.30; ES+: 774.97.

Example 7

(rac.)-(1R*,5S*)-3-Acetyl-7-{4-[3-(2-methoxybenzyloxy)propoxy]phenyl}-3,9-diazabicyclo[3.3.1]non-6-ene-6-carboxylic acid [2-(2-chlorophenyl)ethyl]-methylamide trifluoroacetate salt Synthesized according to typical procedures H and E from bicyclononene T1 and [2-(2-chlorophenyl)ethyl]methylamine (Jaques B.; Wallace R. G., *Tetrahedron*, 1977, 33, 581). LC-MS: $R_t$=0.89; ES+: 632.40.

Example 8

(rac.)-(2-Methoxyphenyl)acetic acid (1R*,5S*)-3-acetyl-7-{4-[3-(2-methoxybenzyloxy)propoxy]phenyl}-3,9-diazabicyclo[3.3.1]non-6en-6-ylmethyl ester trifluoroacetate salt Synthesized according to typical procedures A and E from bicyclononene N and acetyl chloride. LC-MS: $R_t$=0.93; ES+: 615.29.

Example 9

(rac.)-(1R*5S*)-3-Acetyl-7-{4-[3-(2-methoxybenzyloxy)propoxy]phenyl}-3,9-diazabicyclo[3.3.1]non-6-ene-6-carboxylic acid [2-(4-methoxyphenyl)ethyl]-methylamide trifluoroacetate salt Synthesized according to typical procedures H and E from bicyclononene T1 and [2-(4-methoxyphenyl)ethyl]methylamine (Ho C. Y.; Kukla M. J., *Tetrahedron Let.* 1997, 38, 2799). LC-MS: $R_t$=0.83; ES+: 628.44.

Example 10

(rac.)-(2-Methoxyphenyl)acetic acid (1R*,5S*)-3-[2-(4-chlorophenyl)acetyl]-7-{6-[3-(2-methoxybenzyloxy)propoxy]pyridin-3-yl}-3,9-diazabicyclo[3.3.1]-non-6-en-6-ylmethyl ester trifluoroacetate salt Synthesized according to typical procedures A and E from bicyclononene P and 4-chlorophenylacetyl chloride. LC-MS: $R_t$=1.03; ES+: 726.44.

Example 11

(rac.)-(1R*,5S*)-3-Acetyl-7-{4-[3-(2-methoxybenzyloxy)propoxy]phenyl}-3,9-diazabicyclo[3.3.1]non-6-ene-6-carboxylic acid [2-(4-chlorophenyl)ethyl]-methylamide trifluoroacetate salt Synthesized according to typical procedures H and E from bicyclononene T1 and [2-(4-chlorophenyl)ethyl]methylamine (You Q., et al., *Chem Res. Chin. Univ.*, 1992, 8, 468). LC-MS: $R_t$=0.90; ES+: 632.40.

Example 12

(rac.)-(1R*,1S*)-3-Acetyl-7-{4-[3-(2-methoxybenzyloxy)propoxy]phenyl}-3,9-diazabicyclo[3.3.1]non-6-ene-6-carboxylic acid [2-(3-chlorophenyl)ethyl]-methylamide trifluoroacetate salt Synthesized according to typical procedures H and E from bicyclononene T1 and [2-(3-chlorophenyl)ethyl]methylamine. LC-MS: $R_t$=0.92; ES+: 632.37.

Example 13

(rac.)-(1R*,5S*)-3-Acetyl-7-{4-[3-(2-methoxybenzyloxy)propoxy]phenyl}-3,9-diazabicyclo[3.3.1]non-6-ene-6-carboxylic acid ethylphenethylamide trifluoroacetate salt Synthesized according to typical procedures H and E from bicyclononene T1 and ethylphenethylamine (Cossy J., Rakotoarisoa, H., *Tetrahedron Lett.*, 2000, 41, 2097). LC-MS: $R_t$=0.89; ES+: 612.46.

Example 14

(rac.(1R*,5S*)-3-Acetyl-7-{4-[3-(2-methoxybenzyloxy)propoxy]phenyl}-3,9-diazabicyclo[3.3.1]non-6-ene-6-carboxylic acid [2-(3-methoxyphenyl)ethyl]-methylamide trifluoroacetate salt Synthesized according to typical procedures H and E from bicyclononene T1 and [2-(3-methoxyphenyl)ethyl]methylamine. LC-MS: $R_t$=0.88; ES+: 628.41.

Example 15

(rac.)-(2-Methoxyphenyl)acetic acid (1R*,5S*)-7-{4-[3-(2-methoxybenzyloxy)propoxy]phenyl}-3-methyl-3,9-diazabicyclo[3.3.1]non-6-en-6-ylmethyl ester trifluoroacetate salt A sol. of bicyclononene N (0.05 mmol) in $CH_2Cl_2$ (2 mL) was cooled to 0° C. DIPEA (0.10 mmol) and methyl iodide (0.10 mmol) were added. The mixture was stirred at 0° C. for 2 h, then overnight at rt. Methyl iodide (0.50 mmol) and DIPEA (0.15 mmol) were added again and stirring was continued for 4 h at rt. EtOAc was added and the mixture was washed with water. The org. extracts were separated, dried over $MgSO_4$ and filtered. The solvents were removed under reduced pressure and the residue was porcessed further according to general procedure E. LC-MS: $R_t$=4.04; ES+: 587.38.

Example 16

(rac.)-(1R*5S*)-3-Acetyl-7-{4-[3-(2-methoxybenzyloxy)propoxy]phenyl}-3,9-diazabicyclo[3.3.1]non-6-ene-6-carboxylic acid [2-(3,4-dimethoxyphenyl)-ethyl]methylamide trifluoroacetate salt Synthesized according to typical procedures H and E from bicyclononene T1 and [2-(3,4-dimethoxyphenyl)ethyl]methylamine. LC-MS: $R_t$=0.89; ES+: 644.48.

Example 17

(rac.)-2-Methoxyphenyl)acetic acid (1R*,5S*)-7-{4-[3-(2-methoxybenzyloxy)propoxy]phenyl}-3,9-diazabicyclo[3.3.1]non-6-en-6-ylmethyl ester trifluoroacetate salt Synthesized according to typical procedure E from bicyclononene N. LC-MS: $R_t$=0.83; ES+: 573.29.

Example 18

(rac.)-N-((1R*,5S*)-3-Acetyl-7-{4-[3-(2-methoxybenzyloxy)propoxyphenyl}-3,9-diazabicyclo[3.3.1]non-6-en-6-ylmethyl)-2-(2-methoxyphenyl)-N-methylacetamide trifluoroacetate salt Synthesized according to typical procedures G and E from bicyclononene Z and (2-methoxyphenyl)acetic acid. LC-MS: $R_t$=3.98; ES+: 628.63.

Example 19

(rac.)-(1R*,5S*)-3-Acetyl-7-{4-[3-(2-methoxybenzyloxy)propoxy]phenyl}-3,9-diazabicyclo[3.3.1]non-6-ene-6-carboxylic acid methyl(3-phenylpropyl)amide trifluoroacetate salt Synthesized according to typical procedures H and E from bicyclononene T1 and N-methyl(3-phenylpropyl)amine (Lavastre I.; et al., *Bull. Soc. Chim. Fr.*, 1995, 132, 188). LC-MS: $R_t$=0.88; ES+: 612.45.

Example 20

(rac.)-(1R*,5S*)-3-Acetyl-7-{4-[3-(2-methoxybenzyloxy)propoxy]phenyl}-3,9-diazabicyclo[3.3.1]non-6-ene-6-carboxylic acid [2-(2-methoxyphenyl)ethyl]-methylamide trifluoroacetate Synthesized according to typical procedures H and E from bicyclononene T1 and [2-(2-methoxyphenyl]ethyl]methylamine. LC-MS: $R_t$=0.88; ES+: 628.45.

Example 21

(rac.)-(1R*,5S*)-3-Acetyl-7-{4-[3-(2-methoxybenzyloxy)propoxy]phenyl}-3,9-diazabicyclo[3.3.1]non-6-ene-6-carboxylic acid benzylmethylamide trifluoroacetate Synthesized according to typical procedures H and E from bicyclononene T1 and N-methylbenzylamine. LC-MS: $R_t$=0.84; ES+: 684.41.

Example 22

(rac.)-(2-Methoxyphenyl)acetic acid (1R*,5S*)-3-acetyl-7-{4-[3-(2-chlorophenoxy)propyl]phenyl}-3,9-diazabicyclo[3.3.1]non-6-en-6-ylmethyl ester trifluoroacetate Synthesized according to typical procedures F and E from bicyclononene R2 and 2-chlorophenol. LC-MS: $R_t$=0.89; ES+: 589.34.

Example 23

(rac.)-(2-Methoxyphenyl)acetic acid (1R*,5S*)-3-acetyl-7-{6-[3-(2-methoxybenzyloxy)propoxy]pyridin-3-yl}-3,9-diazabicyclo[3.3.1]non-6-en-6-ylmethyl ester trifluoroacetate salt Synthesized according to typical procedures A and E from bicyclononene P and acetyl chloride. LC-MS: $R_t$=0.90; ES+: 616.44.

Example 24

(rac.)-(2-Methoxyphenyl)acetic acid (1R*,5S*)-3-acetyl-7-{4-[3-(2-bromophenoxy)propyl]phenyl}-3,9-diazabicyclo[3.3.1]non-6-en-6-ylmethyl ester trifluoroacetate salt Synthesized according to typical procedures F and E from bicyclononene R2 and 2-bromophenol. LC-MS: $R_t$=0.92; ES+: 633.26.

Example 25

(rac.)-(2-Methoxyphenyl)acetic acid (1R*5S*)-3-[2-(4-chlorophenyl)ethyl]-7-{4-[3-(2-methoxybenzyloxy)propoxy]phenyl}-3,9-diazabicyclo[3.3.1]non-6-en-6-yl-methyl ester trifluoroacetate salt To a sol. of bicyclononene N (0.05 mmol) in $CH_2Cl_2$ (2 mL) $NaBH_3OAc$ (0.065 mmol) and (4-chlorophenyl)acetaldehyde (Zhuangyu Z., et al., Synthesis, 1991, 539, 0.065 mmol) were added. The mixture was stirred overnight. The solvent was removed under reduced pressure and the residue treated according to typical procedure E. LC-MS: $R_t$=4.88; ES+: 711.47.

Example 26

(rac.)-(2-Methoxyphenyl)acetic acid (1R*,5S*)-3-acetyl-7-{4-[2-(3-chlorophenoxy)ethyl]phenyl}-3,9-diazabicyclo[3.3.1]non-6-en-6-ylmethyl ester trifluoroacetate salt Synthesized according to typical procedures F and E from bicyclononene R1 and 3-chlorophenol. LC-MS: $R_t$=4.17; ES+: 575.62.

Example 27

(rac.)-(2-Methoxyphenyl)acetic acid (1R*,5S*)-3-acetyl-7-{4-[3-(3-chlorophenoxy)propyl]phenyl}-3,9-diazabicyclo[3.3.1]non-6-en-6-ylmethyl ester trifluoro-acetate salt Synthesized according to typical procedures F and E from bicyclononene R2 and 3-chlorophenol. LC-MS: $R_t$=0.90; ES+: 589.33.

Example 28

(rac.)-(2-Methoxyphenyl)acetic acid (1R*,5S*)-3-acetyl-7-{4-[2-(2-chlorophenoxy)ethyl]phenyl}-3,9-diazabicyclo[3.3.1]non-6-en-6-ylmethyl ester trifluoroacetate salt Synthesized according to typical procedures F and E from bicyclononene R1 and 2-chlorophenol. LC-MS: $R_t$=0.94; ES+: 575.34.

Example 29

(rac.)-(1R*,5S*)-3-Acetyl-7-{4-[3-(2-methoxybenzyloxy)propoxy]phenyl}-3,9-diazabicyclo[3.3.1]non-6-ene-6-carboxylic acid phenethylamide trifluoroacetate salt Synthesized according to typical procedures H and E from bicyclononene T1 and phenethylamine. LC-MS: $R_t$=0.91; ES+: 584.44.

Example 30

(rac.)-(2-Methoxyphenyl)acetic acid (1R*,5S*)-3-acetyl-7-[4-(3-phenoxypropyl)phenyl]-3,9-diazabicyclo[3.3.1]non-6-en-6-ylmethyl ester trifluoroacetate salt Synthesized according to typical procedures F and E from bicyclononene R2 and phenol. LC-MS: $R_t$=0.87; ES+: 555.31.

Example 31

1:1—Mixture of (2R)- and (2S)-N-((1R*,5S*)-3-acetyl-7-{4-[3-(2-methoxybenzyloxy)propoxy]phenyl}-3,9-diazabicyclo[3.3.1]non-6-en-6-ylmethyl)-N-methyl-2-phenylpropionamide trifluoroacetate salt Synthesized according to typical procedures G and E from bicyclononene Z and (rac.)-2-phenylpropionic acid. LC-MS: $R_t$=0.87; ES+: 612.42.

Example 32

(rac.)-(1R*,5S*)-3-Acetyl-7-{4-[3-(2-methoxybenzyloxy)propoxy]phenyl}-3,9-diazabicyclo[3.3.1]non-6-ene-6-carboxylic acid [2-(2-methoxyphenyl)ethyl]-amide trifluoroacetate salt Synthesized according to typical procedures H and E from bicyclononene T1 and 2-(2-methoxyphenyl)ethylamine. LC-MS: $R_t$=4.06; ES+: 614.35.

Example 33

(rac.)-(1R*,5S*)-3-Acetyl-7-{4-[2-(2-chlorophenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-chlorophenol. LC-MS: $R_t$=0.84; ES+: 558.24.

Example 34

(rac.)-(1R*,5S*)-3-Acetyl-7-{4-[2-(2-ethoxyphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-ethoxyphenol. LC-MS: $R_t$=0.84; ES+: 568.30.

Example 35

(rac.)-(1R*,5S*)-3-Acetyl-7-{4-[2-(2-acetylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-acetylphenol. LC-MS: $R_t$=1.13; ES+: 566.29.

Example 36

(rac.)-(1R*,5S*)-3-Acetyl-7-{4-[2-o-toluoxyethyl]phenyl}-3,9-diazabicyclo-[3.3.1]-non-6-ene-6-carboxylic acid methylphenethylamide formate salt Synthesized according to typical procedures F and E from bicyclononene U2 and 2-methylphenol. LC-MS: $R_t$=1.18; ES+: 538.27.

Example 37

(rac.)-(1R*,5S*)-3-Acetyl-7-{4-[2-(3-methoxyphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 3-methoxyphenol. LC-MS: $R_t$=1.15; ES+: 554.28.

Example 38

(rac.)-(1R*,5S*)-3-Acetyl-7-{4-[2-(3-trifluoromethoxyphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 3-trifluoromethoxyphenol. LC-MS: $R_t$=1.19; ES+: 608.28.

Example 39

(rac.)-(1R*,5S*)-3-Acetyl-7-{4-[2-m-toluoxyethyl]phenyl}-3,9-diazabicyclo-[3.3.1]-non-6-ene-6-carboxylic acid methylphenethylamide formate salt Synthesized according to typical procedures F and E from bicyclononene U2 and 3-methylphenol. LC-MS: $R_t$=1.17; ES+: 538.26.

Example 40

(rac.)-(1R*,5S*)-3-Acetyl-7-{4-[2-(3-isopropylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 3-isopropylphenol. LC-MS: $R_t$=1.19; ES+: 608.28.

Example 41

(rac.)-(1R*,5S*)-3-Acetyl-7-{4-[3-(2-chlorophenoxy)propyl]phenyl}-3,9-diazbicyclo[3.3.1]non-6-ene-6-carboxylic acid methylphenethylamide trifluoroacetate salt Synthesized according to typical procedures F and E from bicyclononene U3 and 2-chlorophenol. LC-MS: $R_t$=0.87; ES+: 572.13.

Example 42

(rac.)-(1R*,5S*)-3-Acetyl-7-{4-[3-(2-bromophenoxy)propyl]phenyl}-3,9-diazabicyclo[3.3.1]non-6-ene-6-carboxylic acid methylphenethylamide formate salt Synthesized according to typical procedures F and E from bicyclononene U3 and 2-bromophenol. LC-MS: $R_t$=0.79; ES+: 616.11.

Example 43

(rac.)-(1R*,5S*)-3-Acetyl-7-{4-[3-(2-fluorophenoxy)propyl]phenyl}-3,9-diazabicyclo[3.3.1]non-6-ene-6-carboxylic acid methylphenethylamide formate salt Synthesized according to typical procedures F and E from bicyclononene U3 and 2-fluorophenol. LC-MS: $R_t$=0.75; ES+: 556.20.

Example 44

(rac.)-(1R*,5S*)-3-Acetyl-7-{4-[3-(2-acetylphenoxy)propyl]phenyl}-3,9-diazabicyclo[3.3.1]non-6-ene-6-carboxylic acid methylphenethylamide formate salt Synthesized according to typical procedures F and E from bicyclononene U3 and 2-acetylphenol. LC-MS: $R_t$=0.71; ES+: 580.20.

Example 45

(rac.)-(1R*,5S*)-3-Acetyl-7-{4-[3-o-toluoxypropyl]phenyl}-3,9-diazabicyclo-[3.3.1]non-6-ene-6carboxylic acid methylphenethylamide trifluoroacetate salt Synthesized according to typical procedures F and E from bicyclononene U3 and 2-methylphenol. LC-MS: $R_t$=0.90; ES+: 552.20.

Example 46

(rac.)-(1R*,5S*)-3-Acetyl-7-{4-[3-(3-methoxyphenoxy)propyl]phenyl}-3,9-diazabicyclo[3.3.1]non-6-ene-6-carboxylic acid methylphenethylamide trifluoroacetate salt Synthesized according to typical procedures F and E from bicyclononene U3 and 3-methoxyphenol. LC-MS: $R_t$=0.86; ES+: 568.21.

Example 47

(rac.)-(1R*,5S*)-3-Acetyl-7-{4-[3-m-toluoxypropyl]phenyl}-3,9-diazabicyclo-[3.3.1]non-6-ene-6-carboxylic acid methylphenethylamide formate salt Synthesized according to typical procedures F and E from bicyclononene U3 and 3-methylphenol. LC-MS: $R_t$=0.79; ES+: 552.21.

Example 48

(rac.)-(1R*,5S*)-3-Acetyl-7-{4-[3-(3-chlorophenoxy)propyl]phenyl}-3,9-diazabicyclo[3.3.1]non-6-ene-6-carboxylic acid methylphenethylamide trifluoroacetate salt Synthesized according to typical procedures F and E from bicyclononene U3 and 3-chlorophenol. LC-MS: $R_t$=4.44; ES+: 572.32.

Example 49

(rac.)-(1R*,5S*)-3-Acetyl-7-{4-[2-(3-bromophenoxy)ethyl]phenyl}-3,9-diazabicyclo[3.3.1]non-6-ene-6-carboxylic acid methylphenethylamide formate salt Synthesized according to typical procedures F and E from bicyclononene U2 and 3-bromophenol. LC-MS: $R_t$=0.78; ES+: 602.10.

Example 50

(rac.)-(1R*,5S*)-3-Acetyl-7-{4-[2-(2,3-dichlorophenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2,3-dichlorophenol. LC-MS: $R_t$=0.78; ES+: 592.10.

Example 51

(rac.)-(1R*,5S*)-3-Acetyl-7-{4-[2-(2-chloro-3-trifluoromethylphenoxy)ethyl]-phenyl}-3,9-diazabicyclo[3.3.1]non-6-ene-6-carboxylic acid methylphenethylamide formate salt Synthesized according to typical procedures F and E from bicyclononene U2 and 2-chloro-3-trifluoromethylphenol. LC-MS: $R_t$=0.80; ES+: 626.11.

Example 52

(rac.)-(1R*,5S*)-3-Acetyl-7-{4-[2-(2,3-difluorophenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2,3-difluorophenol. LC-MS: $R_t$=0.74; ES+: 560.13.

Example 53

(rac.)-(1R*,5S*)-3-Acetyl-7-{4-[2-(2,3-dimethylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2,3-dimethylphenol. LC-MS: $R_t$=0.79; ES+: 559.19.

Example 54

(rac.)-(1R*,5S*)-3-Acetyl-7-{4-[2-(2-ethylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-ethylphenol. LC-MS: $R_t$=0.80; ES+: 552.19.

Example 55

(rac.)-(1R*,5S*)-3-Acetyl-7-{4-[3-(3-bromophenoxy)propyl[phenyl}-3,9-diazabicyclo[3.3.1]non-6-ene-6-carboxylic acid methylphenethylamide trifluoroacetate salt Synthesized according to typical procedures F and E from bicyclononene U3 and 3-bromophenol. LC-MS: $R_t$=0.92; ES+: 616.05.

Example 56

(rac.)-(1R*,5S*)-3-Acetyl-7-{4-[3-(2,3-dichlorophenoxy)propyl]phenyl}-3,9-diazabicyclo[3.3.1]non-6ene-6-carboxylic acid methylphenethylamide trifluoroacetate salt Synthesized according to typical procedures F and E from bicyclononene U3 and 2,3-dichlorophenol. LC-MS: $R_t$=0.93; ES+: 606.12.

Example 57

(rac.)-(1R*,5S*)-3-Acetyl-7-{4-[3-(2-chloro-3-trifluoromethylphenoxy)-propyl]phenyl}-3,9-diazabicyclo[3.3.1]non-6-ene-6-carboxylic acid methylphenethylamide trifluoroacetate salt Synthesized according to typical procedures F and E from bicyclononene U3 and 2-chloro-3-trifluoromethylphenol. LC-MS: $R_t$=0.93; ES+: 640.10.

Example 58

(rac.)-(1R*,5S*)-3Acetyl-7-{4-[3-(2,3-difluorophenoxy)propyl]phenyl}-3,9-diazabicyclo[3.3.1]non-6-ene-6-carboxylic acid methylphenethylamide trifluoroacetate salt Synthesized according to typical procedures F and E from bicyclononene U3 and 2,3-difluorophenol. LC-MS: $R_t$=0.88; ES+: 574.17.

Example 59

(rac.)-(1R*,5S*)-3-Acetyl-7-{4-[3-(2,3-dimethylphenoxy)propyl]phenyl}-3,9-diazabicyclo[3.3.1]non-6-ene-6-carboxylic acid methylphenethylamide trifluoroacetate salt Synthesized according to typical procedures F and E from bicyclononene U3 and 2,3-dimethylphenol. LC-MS: $R_t$=0.93; ES+: 566.22.

Example 60

(rac.)-(1R*,5S*)-3-Acetyl-7-{4-[3-(2-ethylphenoxy)propyl]phenyl}-3,9-diazabicyclo[3.3.1]non-6ene-6-carboxylic acid methylphenethylamide trifluoroacetate salt Synthesized according to typical procedures F and E from bicyclononene U3 and 2-ethylphenol. LC-MS: $R_t$=0.93; ES+: 566.22.

Example 61

(rac.)-(1R*,5S*)-3-Acetyl-7-{4-[3-(2-isopropylphenoxy)propyl]phenyl}-3,9-diazabicyclo[3.3.1]non-6-ene-6-carboxylic acid methylphenethylamide formate salt Synthesized according to typical procedures F and E from bicyclononene U3 and 2-isopropylphenol. LC-MS: $R_t$=0.86; ES+: 580.22.

Example 62

(rac.)-(1R*,5S*)-3-Acetyl-7-{4-[3-(2-tert-butylphenoxy)propyl]phenyl}-3,9-diazabicyclo[3.3.1]non-6-ene-6-carboxylic acid methylphenethylamide formate salt Synthesized according to typical procedures F and E from bicyclononene U3 and 2-tert-butylphenol. LC-MS: $R_t$=0.89; ES+: 594.24.

Example 63

(rac.)-(1R*,5S*)-3-Acetyl-7-{4-[3-(4chloro-2-methoxyphenoxy)propyl]phenyl}-3,9-diazabicyclo[3.3.1]non-6-ene-6-carboxylic acid methylphenethylamide formate salt Synthesized according to typical procedures F and E from bicyclononene U3 and 4-chloro-2-methoxyphenol. LC-MS: $R_t$=0.77; ES+: 602.14.

Example 64

(rac.)-(1R*,5S*)-3-Acetyl-7-{4-[3-(2,4-dichlorophenoxy)propyl]phenyl}-3,9-diazabicyclo[3.3.1]non-6-ene-6-carboxylic acid methylphenethylamide formate salt Synthesized according to typical procedures F and E from bicyclononene U3 and 2,4-dichlorophenol. LC-MS: $R_t$=0.84; ES+: 606.08.

Example 65

(rac.)-(1R*,5S*)-3-Acetyl-7-{4-[3-(4-fluorophenoxy)propyl]phenyl}-3,9-diazabicyclo[3.3.1]non-6-ene-6-carboxylic acid methylphenethylamide formate salt Synthesized according to typical procedures F and E from bicyclononene U3 and 4-fluorophenol. LC-MS: $R_t$=0.76; ES+: 556.19.

Example 66

(rac.)-(1R*,5S*)-3-Acetyl-7-{4-[3-(2-tert-butyl-4-methylphenoxy)propyl]-phenyl}-3,9-diazabicyclo[3.3.1]non-6-ene-6-carboxylic acid methylphenethylamide formate salt Synthesized according to typical procedures F and E from bicyclononene U3 and 2-tert-butyl-4-methylphenol. LC-MS: $R_t$=0.93; ES+: 608.25.

Example 67

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid methylphenethylamide formate salt Synthesized according to typical procedures F and E from bicyclononene U3 and 2-bromo-5-fluorophenol. LC-MS: $R_t$=0.80; ES+: 634.05.

Example 68

(rac.)-(1R*,5S*)-3-Acetyl-7-{4-[3-(2,5-difluorophenoxy)propyl]phenyl}-3,9-diazabicyclo[3.3.1]non-6-ene-6-carboxylic acid methylphenethylamide formate salt Synthesized according to typical procedures F and E from bicyclononene U3 and 2,5-difluorophenol. LC-MS: $R_t$=0.76; ES+: 574.14.

Example 69

(rac.)-(1R*,5S*)-3-Acetyl-7-{4-[3-(2-chloro-5-methylphenoxy)propyl]-phenyl}-3,9-diazabicyclo[3.3.1]non-6-ene-6-carboxylic acid methylphenethylamide formate salt Synthesized according to typical procedures F and E from bicyclononene U3 and 2-chloro-5-methylphenol. LC-MS: $R_t$=0.82; ES+: 586.16.

Example 70

(rac.)-(1R*,5S*)-3-Acetyl-7-{4-[3-(2,5-dimethylphenoxy)propyl]phenyl}-3,9-diazabicyclo[3.3.1]non-6-ene-6-carboxylic acid methylphenethylamide formate salt Synthesized according to typical procedures F and E from bicyclononene U3 and 2,5-dimethylphenol. LC-MS: $R_t$=0.83; ES+: 566.20.

Example 71

(rac.)-(1R*,5S*)-3-Acetyl-7-{4-[2-(2-isopropylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-isopropylphenol. LC-MS: $R_t$=0.82; ES+: 566.22.

Example 72

(rac.)-(1R*,5S*)-3-Acetyl-7-{4-[2-(2-tert-butylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-tert-butylphenol. LC-MS: $R_t$=0.85; ES+: 580.26.

Example 73

(rac.)-(1R*,5S*)-3-Acetyl-7-{4-[2-(2-propionylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-propionylphenol. LC-MS: $R_t$=0.72; ES+: 580.21.

Example 74

(rac.)-(1R*,5S*)-3-Acetyl-7-{4-[2-(2,4-dichlorophenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2,4-dichlorophenol. LC-MS: $R_t$=0.80; ES+: 592.09.

Example 75

(rac.)-(1R*,5S*)-3-Acetyl-7-{4-[2-(2-tert-butyl-4-methylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-tert-butyl-4-methylphenol. LC-MS: $R_t$=0.88; ES+: 594.27.

Example 76

(rac.)-(1R*,5S*)-3-Acetyl-7-{4-[2-(4-methoxyphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 4-methoxyphenol. LC-MS: $R_t$=0.71; ES+: 554.18.

Example 77

(rac.)-(1R*,5S*)-3Acetyl-7-{4-[2-(2-bromo-5-fluorophenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-bromo-5-fluorophenol. LC-MS: $R_t$=0.76; ES+: 620.09.

Example 78

(rac.)-(1R*,5S*)-3-Acetyl-7-{4-[2-(2,5-difluorophenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2,5-difluorophenol. LC-MS: $R_t$=0.73; ES+: 560.17.

Example 79

(rac.)-(1R*,5S*)-3-Acetyl-7-{4-[2-(2-chloro-5-methylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-chloro-5-methylphenol. LC-MS: $R_t$=0.78; ES+: 572.13.

Example 80

(rac.)-(1R*,5S*)-3-Acetyl-7-{4-[2-(2-methoxy-5-methylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-methoxy-5-methylphenol. LC-MS: $R_t$=0.72; ES+: 568.19.

Example 81

(rac.)-(1R*,5S*)-3-Acetyl-7-{4-[2-(2,5-dimethylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2,5-dimethylphenol. LC-MS: $R_t$=0.90; ES+: 552.24.

Example 82

(rac.)-(1R*,5S*)-3-Acetyl-7-{4-[2-(2-chlorophenoxy)ethoxy]phenyl}-3,9-diazabicyclo[3.3.1]non-6-ene-6-carboxylic acid methylphenethylamide formate salt Synthesized according to typical procedures F and E from bicyclononene U1 and 2-(2-chlorophenoxy)ethanol. LC-MS: $R_t$=0.75; ES+: 574.15.

Example 83

(rac.)-(1R*,5S*)-3-Acetyl-7-{4-[2-(3-methylphenoxy)ethoxy]phenyl}-3,9-diazabicyclo[3.3.1]non-6-ene-6-carboxylic acid methylphenethylamide formate salt Synthesized according to typical procedures F and E from bicyclononene U1 and 2-(3-methylphenoxy)ethanol. LC-MS: $R_t$=0.76; ES+: 554.18.

Example 84

(rac.)-(1R*,5S*)-3-Acetyl-7-{4-[2-(2-chlorophenyl)ethoxy]phenyl}-3,9-diazabicyclo[3.3.1]non-6-ene-6-carboxylic acid methylphenethylamide formate salt Synthesized according to typical procedures F and E from bicyclononene U1 and 2-(chlorophenyl)ethanol. LC-MS: $R_t$=0.77; ES+: 558.13.

Example 85

(rac.)-(1R*5S*)-3-Acetyl-7-{4-[2-(3-chlorophenyl)ethoxy]phenyl}-3,9-diazabicyclo[3.3.1]non-6-ene-6-carboxylic acid methylphenethylamide formate salt Synthesized according to typical procedures F and E from bicyclononene U1 and 2-(3-chlorophyl)ethanol. LC-MS: $R_t$=0.77; ES+: 558.14.

Example 86

(rac.)-(1R*,5S*)-3-Acetyl-7-{4-[2-(2-methoxyphenyl)ethoxy]phenyl}-3,9-diazabicyclo[3.3.1]non-6-ene-6-carboxylic acid methylphenethylamide trifluoroacetate salt Synthesized according to typical procedures F and E from bicyclononene U1 and 2-(2-methoxyphenyl)ethanol. LC-MS: $R_t$=0.85; ES+: 554.21.

Example 87

(rac.)-(1R*,5S*)-3-Acetyl-7-{4-[2-(2,5-dichlorophenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2,5-dichlorophenol. LC-MS: $R_t$=0.79; ES+: 592.07.

Example 88

(rac.)-(1R*,5S*)-3-Acetyl-7-{4-[2-(2,3,6-trifluorophenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2,3,6-trifluorophenol. LC-MS: $R_t$=0.74; ES+: 578.14.

Example 89

(rac.)-(1R*,5S*)-3-Acetyl-7-{4-[2-(3,5-dimethylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 3,5-dimethylphenol. LC-MS: $R_t$=0.80; ES+: 552.20.

Example 90

(rac.)-(1R*,5S*)-3-Acetyl-7-{4-[2-(3-chlorophenoxy)ethyl]phenyl}-3,9-diazabicyclo3.3.1]non-6-ene-6-carboxylic acid methylphenethylamide formate salt Synthesized according to typical procedures F and E from bicyclononene U2 and 3-chlorophenol. LC-MS: $R_t$=0.77; ES+: 558.15.

Example 91

(rac.)-(1R*,5S*)-3-Acetyl-7-{4-[2-(3-trifluoromethylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 3-trifluoromethylphenol. LC-MS: $R_t$=0.78; ES+: 592.17.

Example 92

(rac.)-(1R*,5S*)-3-Acetyl-7-{4-[2-(4-tert-butyl-2-methylphenoxy)ethyl]-phenyl}-3,9-diazabicyclo[3.3.1]non-6-ene-6-carboxylic acid methylphenethylamide formate salt Synthesized according to typical procedures F and E from bicyclononene U2 and 4-tert-butyl-2-methylphenol. LC-MS: $R_t$=0.88; ES+: 594.22.

Example 93

(rac.)-(1R*,5S*)-3-Acetyl-7-{4-[2-(3,4-dichlorophenoxy)ethyl]phenyl}-3,9-diazabicyclo[3.3.1]non-6-ene-6-carboxylic acid methylphenethylamide formate salt Synthesized according to typical procedures F and E from bicyclononene U2 and 3,4-dichlorophenol. LC-MS: $R_t$=0.81; ES+: 592.12.

Example 94

(rac.)-(1R*,5S*)-3-Acetyl-7-{4-[2-(4-bromo-3-methylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 4-bromo-3-methylphenol. LC-MS: $R_t$=0.81; ES+: 616.12.

Example 95

(rac.)-(1R*,5S*)-3-Acetyl-7-{4-[2-(3,4-dimethylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 3,4-dimethylphenol. LC-MS: $R_t$=0.78; ES+: 552.18.

Example 96

(rac.)-(1R*,5S)-3-Acetyl-7-{4-[2-(3,5-dichlorophenoxy)ethyl]phenyl}-3,9-diazabicyclo[3.3.1]non-6-ene-6-carboxylic acid methylphenethylamide formate salt Synthesized according to typical procedures F and E from bicyclononene U2 and 3,5-dichlorophenol. LC-MS: $R_t$=0.82; ES+: 592.10.

Example 97

(rac.)-(1R*,5S*)-3-Acetyl-7-{4-[2-(3,5-dimethylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 3,5-dimethylphenol. LC-MS: $R_t$=0.79; ES+: 552.20.

Example 98

(rac.)-(1R*,5S*)-3-Acetyl-7-{4-[2-(3,5-dimethoxyphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 3,5-dimethoxyphenol. LC-MS: $R_t$=0.72; ES+: 584.19.

Example 99

(rac.)-(1R*,5S*)-3-Acetyl-7-{4-[2-(2-chloro-4,5-dimethylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2-chloro-4,5-dimethylphenol. LC-MS: $R_t$=0.81; ES+: 586.17.

Example 100

(rac.)-(1R*,5S*)-3-Acetyl-7-{4-[2-(2,3,5-trimeth-ylphenoxy)ethyl]phenyl}-3,9-diazabicyclo[3.3.1]non-6-ene-6-carboxylic acid methylphenethylamide formate salt Synthesized according to typical procedures F and E from bicyclononene U2 and 2,3,5-trimethylphenol. LC-MS: $R_t$=0.82; ES+: 566.21.

Example 101

(rac.)-(1R*,5S*)-3-Acetyl-7-{4-[3-(2,5-dichlorophe-noxy)propyl]phenyl}-3,9-diazabicyclo[3.3.1]non-6-ene-6-carboxylic acid methylphenethylamide formate salt Synthesized according to typical procedures F and E from bicyclononene U3 and 2,5-dichlorophenol. LC-MS: $R_t$=0.83; ES+: 606.12.

Example 102

(rac.)-(1R*,5S*)-3-Acetyl-7-{4-[3-(2-acetyl-5-fluo-rophenoxy)propyl]phenyl}-3,9-diazabicyclo[3.3.1]non-6-ene-6-carboxylic acid methylphenethylamide formate salt Synthesized according to typical procedures F and E from bicyclononene U3 and 2-acetyl-5-fluorophenol. LC-MS: $R_t$=0.73; ES+: 598.18.

Example 103

(rac.)-(1R*,5S*)-3-Acetyl-7-{4-[3-(2,3,6-trifluo-rophenoxy)propyl]phenyl}-3,9-diazabicyclo[3.3.1]non-6-ene-6-carboxylic acid methylphenethylamide trifluoroacetate salt Synthesized according to typical procedures F and E from bicyclononene U3 and 2,3,6-trifluorophenol. LC-MS: $R_t$=0.88; ES+: 592.19.

Example 104

(rac.)-(1R*,5S*)-3-Acetyl-7-{4-[3-(2,4-dimethylphe-noxy)propyl]phenyl}-3,9-diazabicyclo[3.3.1]non-6-ene-6-carboxylic acid methylphenethylamide formate salt Synthesized according to typical procedures F and E from bicyclononene U3 and 2,4-dimethylphenol. LC-MS: $R_t$=0.83; ES+: 566.22.

Example 105

(rac.)-(1R*,5S*)-3-Acetyl-7-{4-[3-(2-tert-butyl-6-methylphenoxy)propyl]phenyl}-3,9-diazabicyclo[3.3.1]non-6-ene-6-carboxylic acid methylphenethy-lamide formate salt Synthesized according to typical procedures F and E from bicyclononene U3 and 2-tert-butyl-6-methylphenol. LC-MS: $R_t$=0.88; ES+: 608.27.

Example 106

(rac.)-(1R*,5S*)-3-Acetyl-7-{4-[3-(4-tert-butyl-2-methylphenoxy)propyl]phenyl}-3,9-diazabicyclo[3.3.1]non-6-ene-6-carboxylic acid methylphenethy-lamide formate salt Synthesized according to typical procedures F and E from bicyclononene U3 and 4-tert-butyl-2-methylphenol. LC-MS: $R_t$=0.93; ES+: 608.25.

Example 107

(rac.)-(1R*,5S*)-3-Acetyl-7-{4-[3-(3,4-dichlorophe-noxy)propyl]phenyl}-3,9-diazabicyclo[3.3.1]non-6-ene-6-carboxylic acid methylphenethylamide formate salt Synthesized according to typical procedures F and E from bicyclononene U3 and 3,4-dichlorophenol. LC-MS: $R_t$=0.84; ES+: 606.12.

Example 108

(rac.)-(1R*,5S*)-3-Acetyl-7-{4-[3-(4-bromo-3-me-thylphenoxy)propyl]phenyl}-3,9-diazabicyclo[3.3.1]non-6-ene-6-carboxylic acid methylphenethylamide formate salt Synthesized according to typical procedures F and E from bicyclononene U3 and 4-bromo-3-methylphenol. LC-MS: $R_t$=0.85; ES+: 630.11.

Example 109

(rac.)-(1R*,5S*)-3-Acetyl-7-{4-[3-(3,4-dimethylphe-noxy)propyl]phenyl}-3,9-diazabicyclo[3.3.1]non-6-ene-6-carboxylic acid methylphenethylamide formate salt Synthesized according to typical procedures F and E from bicyclononene U3 and 3,4-dimethylphenol. LC-MS: $R_t$=0.82; ES+: 566.20.

Example 110

(rac.)-(1R*,5S*)-3-Acetyl-7-{4-[3-(3,5-dichlorophe-noxy)propyl]phenyl}-3,9-diazabicyclo[3.3.1]non-6-ene-6-carboxylic acid methylphenethylamide formate salt Synthesized according to typical procedures F and E from bicyclononene U3 and 3,5-dichlorophenol. LC-MS: $R_t$=0.87; ES+: 606.13.

Example 111

(rac.)-(1R*,5S*)-3-Acetyl-7-{4-[3-(3,5-dimethylphe-noxy)propyl]phenyl}-3,9-diazabicyclo[3.3.1]non-6-ene-6-carboxylic acid methylphenethylamide formate salt Synthesized according to typical procedures F and E from bicyclononene U3 and 3,5-dimethylphenol. LC-MS: $R_t$=0.82; ES+: 566.21.

Example 112

(rac.)-(1R*,5S*)-3-Acetyl-7-{4-[3-(2-chloro-4,5-dimethylphenoxy)propyl]phenyl}-3,9-diazabicyclo[3.3.1]non-6-ene-6-carboxylic acid methylphenethylamide formate salt Synthesized according to typical procedures F and E from bicyclononene U3 and 2-chloro-4,5-dimethylphenol. LC-MS: $R_t$=0.85; ES+: 600.18.

Example 113

(rac.)-(1R*,5S*)-3-Acetyl-7-{4-[3-(2,3,5-trimethylphenoxy)propyl]phenyl}-3,9-diazabicyclo[3.3.1]non-6-ene-6-carboxylic acid methylphenethylamide formate salt Synthesized according to typical procedures F and E from bicyclononene U3 and 2,3,5-trimethylphenol. LC-MS: $R_t$=0.86; ES+: 580.23.

Example 114

(rac.)-Acetic acid (1R*,5S*)-2-(7-{4-[3-(2-chlorophenoxy)propyl]phenyl}-6-{[2-(2-chlorophenyl)ethyl]methylcarbamoyl}-3,9-diazabicyclo[3.3.1]non-6-en-3-yl)-2-oxoethyl ester formate salt Synthesized according to typical procedures A and E from bicyclononene AC and acetic acid chlorocarbonylmethyl ester. LC-MS: $R_t$=1.01; ES+: 664.14.

Example 115

(rac.)-(1R*,5S*)-7-{4-[3-(2-Chlorophenoxy)propyl]phenyl}-3-(2-cyanoacetyl)-3,9-diazabicyclo[3.3.1]non-6-ene-6-carboxylic acid [2-(2-chlorophenyl)ethyl]-methylamide formate salt Synthesized according to typical procedures K and E from bicyclononene AC and cyanoacetic acid. LC-MS: $R_t$=1.02; ES+: 631.13.

Example 116

(rac.)-(1R*,5S*)-3-(2-Acetylaminoacetyl)-7-{4-[3-(2-chlorophenoxy)propyl]-phenyl}-3,9-diazabicyclo[3.3.1]non-6-ene-6-carboxylic acid [2-(2-chlorophenyl)ethyl]methylamide formate salt Synthesized according to typical procedures K and E from bicyclononene AC and acetylaminoacetic acid. LC-MS: $R_t$=0.96; ES+: 663.14.

Example 117

1:1 Mixture of (1R,5S)-3-((4S)-2-acetylamino-4-methylpentanoyl)-7-{4-[3-(2-chlorophenoxy)propyl]phenyl}-3,9-diazabicyclo[3.3.1]non-6ene-6-carboxylic acid [2-(2-chlorophenyl)ethyl]methylamide formate salt and (1S,5R)-3-((4S)-2-acetyl-amino-4-methylpentanoyl)-7-{4-[3-(2-chlorophenoxy)propyl]phenyl}-3,9-diazabicyclo[3.3.1]non-6-ene-6-carboxylic acid [2-(2-chlorophenyl)-ethyl]methylamide formate salt Synthesized according to typical procedures K and E from bicyclononene AC and acetyl leucine. LC-MS: $R_t$=1.05; ES+: 719.19.

Example 118

(rac.)-(1R*,5S*)-3-Acetyl-7-{4-[3-(2-chlorophenoxy)propyl]phenyl}-3,9-diazabicyclo[3.3.1]non-6-ene-6-carboxylic acid [2-(2-chlorophenyl)ethyl]-methylamide formate salt Synthesized according to typical procedures G and E from bicyclononene T2 and [2-(2-chlorophenyl)ethyl]methylamine (Jaques B.; Wallace R. G., *Tetrahedron*, 1977, 33, 581). LC-MS: $R_t$=0.90; ES+: 606.08.

Example 119

(rac.)-(1R*,5S*)-3-Acetyl-7-{4-[3-(2-chlorophenoxy)propyl]phenyl}-3,9-diazabicyclo[3.3.1]non-6-ene-6-carboxylic acid (2-hydroxybenzyl)methylamide formate salt Synthesized according to typical procedures G and E from bicyclononene T2 and 2-methylaminomethylphenol (Ross S. D., et al.; *J. Org. Chem.*, 1966, 31, 133). LC-MS: $R_t$=0.83; ES+: 574.10.

Example 120

(rac.)-(1R*,5S*)-3-Acetyl-7-{4-[3-(2-chlorophenoxy)propyl]phenyl}-3,9-diazabicyclo[3.3.1]non-6-ene-6-carboxylic acid (2-chlorobenzyl)cyclopropylamide formate salt Synthesized according to typical procedures G and E from bicyclononene T2 and (2-chlorobenzyl)cyclopropylamine. LC-MS: $R_t$=0.92; ES+: 617.94.

Example 121

1:1 Mixture of (rac.)-(1R*,5S*)-3-acetyl-7-{4-[3-(2-chlorophenoxy)propyl]-phenyl}-3,9-diazabicyclo[3.3.1]non-6-ene-6-carboxylic acid [(3R*)-3-(2-chlorophenyl)butyl]methylamide formate salt and (rac.)-(1R*,5S*)-3-acetyl-7-{4-[3-(2-chlorophenoxy)propyl]-phenyl}-3,9-diazabicyclo[3.3.1]non-6-ene-6-carboxylic acid [(3S*)-3-(2-chlorophenyl)butyl]methylamide formate salt Synthesized according to typical procedures G and E from bicyclononene T2 and (rac.)-methyl(3-phenylbutyl)amine (Meyers A. I., et al.; *J. Am. Chem. Soc.*, 1982, 104, 877). LC-MS: $R_t$=0.91; ES+: 600.13.

Example 122

(rac.)-(1R*,5S*)-3-Acetyl-7-{4-[3-(2-chlorophenoxy)propyl]phenyl}-3,9-diazabicyclo[3.3.1]non-6-ene-6-carboxylic acid methyl-(4-phenylbutyl)amide formate salt Synthesized according to typical procedures G and E from bicyclononene T2 and methyl(4-phenylbutyl)amine (Neale R. S., et al.; *J. Org. Chem.*, 1965, 30, 3683). LC-MS: $R_t$=0.91; ES+: 600.20.

Example 123

(rac.)-(1R*,5S*)-3-Acetyl-7-{4-[3-(2-dichlorophenoxy)propyl]phenyl}-3,9-diazabicyclo[3.3.1]non-6-ene-6-carboxylic acid methyl-(3-phenoxypropyl) amide formate salt Synthesized according to typical procedures G and E from bicyclononene T2 and methyl(3-phenoxypropyl)amine. LC-MS: $R_t$=0.88; ES+: 602.09.

Example 124

(rac.)-(1R*,5S*)-3-Acetyl-7-{4-[3-(2-chlorophenoxy)propyl]phenyl}-3,9-diazabicyclo[3.3.1]non-6-ene-6-carboxylic acid methyl-(4-phenylpentyl)amide formate salt Synthesized according to typical procedures G and E from bicyclononene T2 and methyl(5-phenylpentyl)amine (Neale R. S., et al.; *J. Org. Chem.*, 1965, 30, 3683). LC-MS: $R_t$=0.95; ES+: 614.12.

Example 125

(rac.)-(1R*,5S*)-3-Acetyl-7-{4-[3-(2-chlorophenoxy)propyl]phenyl}-3,9-diazabicyclo[3.3.1]non-6-ene-6-carboxylic acid (3-benzo[1,3]dioxol-5-ylpropyl)-methylamide formate salt Synthesized according to typical procedures G and E from bicyclononene T2 and (3-benzo[1,3]dioxol-5-ylpropyl)methylamine (Dallacker, et al.; *Chem. Ber.*, 1971, 104, 2517). LC-MS: $R_t$=0.86; ES+: 630.10.

Example 126

(rac.)-(1R*,5S*)-3-Acetyl-7-{4-[3-(2-chlorophenoxy)propyl]phenyl}-3,9-diazabicyclo[3.3.1]non-6-ene-6-carboxylic acid [2-(4-methoxyphenoxy)ethyl]-methylamide formate salt Synthesized according to typical procedures G and B from bicyclononene T2 and [2-(4-methoxyphenoxy)ethyl]methylamine. LC-MS: $R_t$=0.84; ES+: 618.03.

Example 127

(rac.)-(1R*,5S*)-3-Acetyl-7-{4-[3-(2-chlorophenoxy)propyl]phenyl}-3,9-diazabicyclo[3.3.1]non-6-ene-6-carboxylic acid [2-(4-chlorophenoxy)ethyl]-methylamide formate salt Synthesized according to typical procedures G and E from bicyclononene T2 and [2-(4-chlorophenoxy)ethyl]methylamine. LC-MS: $R_t$=0.90; ES+: 622.03.

Example 128

(rac.)-(1R*,5S*)-3-Acetyl-7-{4-[3-(2-chlorophenoxy)propyl]phenyl}-3,9-diazabicyclo[3.3.1]non-6-ene-6-carboxylic acid methyl-(2-p-tolyloxyethyl)-amide formate salt Synthesized according to typical procedures G and E from bicyclononene T2 and (2-p-tolyloxyethyl)methylamine. LC-MS: $R_t$=0.89; ES+: 602.08.

Example 129

(rac.)-(1R*,5S*)-3-Acetyl-7-{4-[3-(2-chlorophenoxy)propyl]phenyl}-3,9-diazabicyclo[3.3.1]non-6-ene-6-carboxylic acid diethylamide formate salt Synthesized according to typical procedures G and E from bicyclononene T2 and diethylamine. LC-MS: $R_t$=0.79; ES+: 510.06.

Example 130

(rac.)-(1R*,5S*)-3-Acetyl-7-{4-[3-(2-chlorophenoxy)propyl]phenyl}-3,9-diazabicyclo[3.3.1]non-6-ene-6-carboxylic acid methyl-(2-pyridin-2-ylethyl)-amide formate salt Synthesized according to typical procedures G and E from bicyclononene T2 and ethyl(2-pyridin-2-ylethyl)amine. LC-MS: $R_t$=0.89; ES+: 602.08.

Example 131

(1S,5R)-3-Acetyl-7-{4-[2-(2,3,6-trifluorophenoxy)ethyl]phenyl}-3,9-diazabicyclo[3.3.]non-6-ene-6-carboxylic acid methylphenethylamide Synthesized according to typical procedures F and E from bicyclononene BJ and 2,3,6-trifluorophenol. LC-MS: $R_t$=0.94; ES+: 592.19. ee=80%.

Example 132

1:1—Mixture of (rac.)-(1R*,5S*)-3-acetyl-7-{4-[3-(2-bromo-5-fluorophenoxy)-propyl]phenyl}-3,9-diazabicyclo[3.3.1]non-6-ene-6-carboxylic acid cyclopropyl-[2-((2R*)-2,3-dihydroxypropyl)benzyl] amide trifluoroacetate salt and (rac.)-(1R*,5S*)-3-acetyl-7-{4-[3-(2-bromo-5-fluorophenoxy)-propyl] phenyl}-3,9-diazabicyclo[3.3.1]non-6-ene-6-carboxylic acid cyclopropyl-[2-((2S*)-2,3-dihydroxypropyl)benzyl]amide trifluoroacetate salt Synthesized according to typical procedure E from bicyclononene AT. LC-MS: $R_t$=3.99; ES+: 720.49.

Example 133

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid cyclopropyl-[2-(2-hydroxyethyl)benzyl]amide trifluoroacetate salt Synthesized according to typical procedure E from bicyclononene AV. LC-MS: $R_t$=3.94; ES+: 692.77.

Example 134

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid benzylcyclopropylamide formate salt Synthesized according to typical procedures H and E from bicyclononene AJ4 and benzylcyclopropylamine. LC-MS: $R_t$=0.89 ES+: 646.41.

Example 135

(rac.)-(1R*,5S*)-3-Acetyl-7-{4-[3-(2-bromo-5-fluoro-phenoxy)propyl]-phenyl}-3,9-diazabicyclo[3.3.1]non-6-ene-6-carboxylic acid (2-chlorobenzyl)-ethylamide formate salt Synthesized according to typical procedures H and E from bicyclononene AJ4 and (2-chlorobenzyl)ethylamine. LC-MS: $R_t$=0.91 ES+: 668.44.

Example 136

(rac.)-(1R*,5s*)-3-Acetyl-7-{4-[3-(2-bromo-5-fluorophenoxy)propyl]phenyl}-3,9-diazabicyclo[3.3.1]non-6-ene-6-carboxylic acid cyclopropyl-(2-fluorobenzyl)amide formate salt Synthesized according to typical procedures H and E from bicyclononene AJ4 and (2-fluorobenzyl)cyclopropylamine. LC-MS: $R_t$=0.90 ES+: 664.46.

Example 137

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid cyclopropyl-(2-methylbenzyl)amide formate salt Synthesized according to typical procedures H and E from bicyclononene AJ4 and (2-methylbenzyl)cyclopropylamine. LC-MS: $R_t$=0.92 ES+: 660.47.

Example 138

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid cyclopropyl-[2-(4-methoxyphenoxy)ethyl]amide formate salt Synthesized according to typical procedures H and E from bicyclononene AJ4 and cyclopropyl[2-(4-methoxyphenoxy)ethyl]amine. LC-MS: $R_t$=0.90 ES+: 706.44.

Example 139

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid cyclopropyl-(2-m-tolyloxyethyl)amide formate salt Synthesized according to typical procedures H and E from bicyclononene AJ4 and cyclopropyl[2-(3-methylphenoxy)ethyl]amine. LC-MS: $R_t$=0.93 ES+: 690.47.

Example 140

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid cyclopropyl-[2-(3,4-dimethylphenoxy)ethyl]amide formate salt Synthesized according to typical procedures H and E from bicyclononene AJ4 and cyclopropyl[2-(3,4-dimethylphenoxy)ethyl]amine. LC-MS: $R_t$=0.94 ES+: 704.48.

Example 141

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid cyclopropylphenethylamide formate salt Synthesized according to typical procedures H and E from bicyclononene AJ4 and cyclopropylphenethylamine. LC-MS: $R_t$=0.90 ES+: 660.50.

Example 142

(rac.)-(1R*,5S*)-3-Acetyl-7-{4-[3-(2-bromo-5-fluorophenoxy)propyl]phenyl}-3,9-diazabicyclo[3.3.1non-6-ene-6-carboxylic acid [2-(2-chlorophenyl)ethyl]-cyclopropylamide formate salt Synthesized according to typical procedures H and E from bicyclononene AJ4 and [2-(2-chlorophenyl)ethyl]cyclopropylamine. LC-MS: $R_t$=0.92 ES+: 694.44.

Example 143

(rac.)-(1R*,5S*)-3-Acetyl-7-{4-[3-(2-bromo-5-fluorophenoxy)propyl]phenyl}-3,9-diazabicyclo3.3.1]non-6-ene-6-carboxylic acid cyclopropyl-[2-(2,3-difluorophenyl)ethyl]amide formate salt Synthesized according to typical procedures H and E from bicyclononene AJ4 and [2-(2,3-difluorophenyl)ethyl]cyclopropylamine. LC-MS: $R_t$=0.91 ES+: 696.47.

Example 144

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid cyclopropyl-[2-(4-fluorophenyl)ethyl]amide formate salt Synthesized according to typical procedures H and E from bicyclononene AJ4 and [2-4-fluorophenyl)ethyl]cyclopropylamine. LC-MS: $R_t$=0.91 ES+: 678.53.

Example 145

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid cyclopropyl-(2-o-tolylethyl)amide formate salt Synthesized according to typical procedures H and E from bicyclononene AJ4 and [2-(2-methylphenyl)ethyl]cyclopropylamine. LC-MS: $R_t$=0.92 ES+: 674.55.

Example 146

1:1—Mixture of (rac.)-(1R*,5S*)-3-Acetyl-7-{4-[3-(2-bromo-5-fluorophenoxy)-propyl]phenyl}-3,9-diazabicyclo[3.3.1]non-6-ene-6-carboxylic acid ((2R*)-2-hydroxy-2-phenylethyl)methylamide formate salt and (rac.)-(1R*,5S*)-3-acetyl-7-{4-[3-(2-bromo-5-fluorophenoxy)-propyl]phenyl}-3,9-diazabicyclo[3.3.1]non-6-ene-6-carboxylic acid ((2S*)-2-hydroxy-2-phenylethyl)methylamide formate salt Synthesized according to typical procedures G and E from bicyclononene AJ4 and α-(methylaminomethyl)benzyl alcohol. LC-MS $R_t$=0.85 ES+: 650.49.

Example 147

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid cyclopropyl-(3-trifluoromethylbenzyl)amide formate salt Synthesized according to typical procedures H and E from bicyclononene AJ4 and (3-trifluoromethylbenzyl)cyclopropylamine. LC-MS: $R_t$=0.93 ES+: 714.40.

Example 148

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(2-o-tolylethyl)-amide formate salt Synthesized according to typical procedures H and E from bicyclononene AJ4 and [2-(2-methylphenyl)ethyl]cyclopropylamine. LC-MS: $R_t$=0.90 ES+: 632.51.

Example 149

(rac.)-(1R*,5S*)-7-{4-[3-(2,3,6-Trifluorophenoxy)propylphenyl}-3,9-diazabicyclo[3.3.1]non-6-ene-6-carboxylic acid (2-chlorobenzyl)cyclopropylamide Synthesized according to typical procedure E from bicyclononene AL2 and purification by FC. LC-MS: $R_t$=0.84 ES+: 596.30.

Example 150

(rac.)-5-((1R*,5S*)-6-[(2-Chlorobenzyl)cyclopropylcarbamoyl]-7-{4-[3-(2,3,6-trifluorophenoxy)propylphenyl}-3,9-diazabicyclo[3.3.1]non-6-en-3-yl)-5-oxopentanoic acid formate salt Synthesized according to typical procedures K and E from bicyclononene AL2 and glutaric anhydride. LC-MS: $R_t$=0.87 ES+: 710.42.

Example 151

(rac.)-(1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt Synthesized according to typical procedure L from bicyclononene AK2 and. LC-MS: $R_t$=1.06 ES+: 798.34.

Example 152

(rac.)-(1R*,5S*)-6-[(2-Chlorobenzyl)ethylcarbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt Synthesized according to typical procedure L from bicyclononene AK4 and. LC-MS: $R_t$=1.19 ES+: 788.25.

Example 153

(rac.)-(1R*,5S*)-6-[(2-Fluorobenzyl)cyclopropylcarbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt Synthesized according to typical procedure L from bicyclononene AK5. LC-MS: $R_t$=1.18 ES+: 784.27.

Example 154

(rac.)-(1R*,5S*)-6-[(2-Methylbenzyl)cyclopropylcarbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt Synthesized according to typical procedure L from bicyclononene AK7. LC-MS: $R_t$=1.21 ES+: 780.29.

Example 155

(rac.)-(1R*,5S*)-6-[Cyclopropyl-(2-o-tolylethyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt Synthesized according to typical procedure L from bicyclononene AK16. LC-MS: $R_t$=1.21 ES+: 794.30.

Example 156

(rac.)-(1R*,5S*)-6-[Cyclopropyl-(3,5-dimethoxybenzyl)carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt Synthesized according to typical procedure L from bicyclononene AK17. LC-MS: $R_t$=1.16.

Example 157

(rac.)-(1R*,5S*)-6-[Cyclopropyl-(2-p-tolylethyl) carbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester hydrochloride salt Synthesized according to typical procedure L from bicyclononene AK18. LC-MS: $R_t$=1.22 ES+: 794.30.

Example 158

(rac.)-5-((1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL2 and 2,2-dimethylglutaric anhydride. LC-MS: $R_t$=0.91 ES+: 738.52.

Example 159

(rac.)-5-((1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL2 and glutaric acid monomethylester chloride. LC-MS: $R_t$=0.93 ES+: 724.49.

Example 160

1:1—Mixture of (1R,5S)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid (2-chlorobenzyl) cyclopropylamide formate salt and (1S,5R)-3-(1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid (2-chlorobenzyl) cyclopropylamide formate salt Synthesized according to typical procedures G, E and L from bicyclononene AL2 and BOC-L-hydroxyproline. LC-MS: $R_t$=0.80 ES+: 709.38.

Example 161

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid (2-chlorobenzyl)cyclopropylamide formate salt Synthesized according to typical procedures G and E from bicyclononene AL2 and 4-carbamoylbutyric acid. LC-MS: $R_t$=0.86 ES+: 709.38.

Example 162

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid benzylcyclopropylamide formate salt Synthesized according to typical procedures G and E from bicyclononene AL3 and 4-carbamoylbutyric acid. LC-MS: $R_t$=0.84 ES+: 675.49.

Example 163

(rac.)-(1R*,5S*)-3-(Carbamoylbutyryl)-7-{4-[3-(2,3,6-trifluorophenoxy)-propyl]phenyl}-3,9-diazabicyclo[3.3.1]non-6-ene-6-carboxylic acid (2-chlorobenzyl)ethylamide formate salt Synthesized according to typical procedures G and E from bicyclononene AL4 and 4-carbamoylbutyric acid. LC-MS: $R_t$=0.86 ES+: 697.40.

Example 164

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(2-fluorobenzyl)amide formate salt Synthesized according to typical procedures G and E from bicyclononene AL5 and 4-carbamoylbutyric acid. LC-MS: $R_t$=0.85 ES+: 693.43.

Example 165

(rac.)-(1R*,5S*)-3-(4Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(3-trifluoromethylbenzyl)amide formate salt Synthesized according to typical procedures G and E from bicyclononene AL6 and 4-carbamoylbutyric acid. LC-MS: $R_t$=0.88 ES+: 743.41.

Example 166

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(2-methylbenzyl)amide formate salt Synthesized according to typical procedures G and E from bicyclononene AL7 and 4-carbamoylbutyric acid. LC-MS: $R_t$=0.86 ES+: 689.47.

Example 167

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-[2-(4-methoxyphenoxy)ethyl]amide formate salt Synthesized according to typical procedures G and E from bicyclononene AL8 and 4-carbamoylbutyric acid. LC-MS: $R_t$=0.85 ES+: 735.47.

Example 168

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-[2-(3-methoxyphenoxy)ethyl]amide formate salt Synthesized according to typical procedures G and E from bicyclononene AL9 and 4-carbamoylbutyric acid. LC-MS: $R_t$=0.86 ES+: 735.47.

Example 169

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(2-m-tolyloxyethyl)amide formate salt Synthesized according to typical procedures G and E from bicyclononene AL10 and 4-carbamoylbutyric acid. LC-MS: $R_t$=0.87 ES+: 719.46.

Example 170

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-[2-(3,4-dimethylphenoxy)ethyl]amide formate salt Synthesized according to typical procedures G and E from bicyclononene AL11 and carbamoylbutyric acid. LC-MS: $R_t$=0.89 ES+: 733.49.

Example 171

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropylphenethylamide formate salt Synthesized according to typical procedures G and E from bicyclononene AL12 and 4-carbamoylbutyric acid. LC-MS: $R_t$=0.85 ES+: 689.48.

Example 172

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid [2-(2-chlorophenyl)ethyl]cyclopropylamide formate salt Synthesized according to typical procedures G and E from bicyclononene AL13 and 4-carbamoylbutyric acid. LC-MS: $R_t$=0.87 ES+: 723.43.

Example 173

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-[2-(2,3-difluorophenyl)ethyl]amide formate salt Synthesized according to typical procedures G and E from bicyclononene AL14 and 4-carbamoylbutyric acid. LC-MS: $R_t$=0.86 ES+: 725.45.

Example 174

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-[2-(4-fluorophenyl)ethyl]amide Synthesized according to typical procedures G and E from bicyclononene AL15 and 4-carbamoylbutyric acid. LC-MS: $R_t$=0.86 ES+: 707.44.

Example 175

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(2-o-tolylethyl)amide formate salt Synthesized according to typical procedures G and E from bicyclononene AL16 and 4-carbamoylbutyric acid. LC-MS: $R_t$=0.87 ES+: 703.47.

Example 176

(rac.)-(1R*,5*S)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(3,5-dimethoxybenzyl)amide formate salt Synthesized according to typical procedures G and E from bicyclononene AL17 and 4-carbamoylbutyric acid. LC-MS: $R_t$=0.85 ES+: 735.47.

Example 177

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(2-p-tolylethyl)amide formate salt Synthesized according to typical procedures G and E from bicyclononene AL18 and 4-carbamoylbutyric acid. LC-MS: $R_t$=0.87 ES+: 703.46.

Example 178

1:1—Mixture of (1R,5S)-3-(1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid benzylcyclopropylamide formate salt and (1S,5R)-3-((1S,4R)-4-hydroxypyrrolidine-2-carbonyl)-7-{4-[3-(2,3,6-trifluorophenoxy)-propyl]phenyl}-3,9-diazabicyclo[3.3.1]non-6-ene-6-carboxylic acid benzylcyclopropylamide formate salt Synthesized according to typical procedures G, E and L from bicyclononene AL3 and BOC-L-hydroxyproline. LC-MS: $R_t$=0.78 ES+: 675.47.

Example 179

1:1—Mixture of (1R,5S)-3-((1S,4R)-4-hydroxypyrrolidine-2-carbonyl)-7-{4-[3-(2,3,6-trifluorophenoxy)propylphenyl}-3,9-diazabicyclo[3.3.1]non-6-ene-6-carboxylic acid (2-chlorobenzyl)ethylamide formate salt and (1S,5R)-3-((1S,4R)-4-hydroxypyrrolidine-2-carbonyl)-7-{4-[3-(2,3,6-trifluorophenoxy)-propylphenyl}-3,9-diazabicyclo[3.3.1]non-6-ene-6-carboxylic acid (2-chlorobenzyl)ethylamide formate salt Synthesized according to typical procedures G, E and L from bicyclononene AL4 and BOC-L-hydroxyproline. LC-MS: $R_t$=0.79 ES+: 697.40.

Example 180

1:1—Mixture of (1R,5S)-3-(1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-fluorobenzyl)amide formate salt and (1S,5R)-3-((1S,4R)-4-hydroxpyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-fluorobenzyl)amide formate salt Synthesized according to typical procedures G, E and L from bicyclononene AL5 and BOC-L-hydroxyproline. LC-MS: $R_t$=0.78 ES+: 693.44.

Example 181

1:1—Mixture of (1R,5S)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(3-trifluoromethylbenzyl)amide formate salt and (1S,5R)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(3-trifluoromethylbenzyl)amide formate salt Synthesized according to typical procedures G, E and L from bicyclononene AL6 and BOC-L-hydroxyproline. LC-MS: $R_t$=0.81 ES+: 743.42.

Example 182

1:1—Mixture of (1R,5S)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-methylbenzyl)amide formate salt and (1S,5R)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-methylenzyl)amide formate salt Synthesized according to typical procedures G, E and L from bicyclononene AL7 and BOC-L-hydroxyproline. LC-MS: $R_t$=0.79 ES+: 689.47.

Example 183

1:1—Mixture of (1R,5R)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-m-tolyloxyethyl)amide formate salt and (1S,5R)-3-((1R,4S-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-m-tolyloxyethyl)amide formate salt Synthesized according to typical procedures G, E and L from bicyclononene AL10 and BOC-L-hydroxyproline. LC-MS: $R_t$=0.81 ES+: 719.45.

Example 184

1:1—Mixture of (1R,5S)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(3,5-dimethoxybenzyl)amide formate salt and (1S,5R)-3-((1S,4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(3,5-dimethoxybenzyl)amide formate salt Synthesized according to typical procedures G, E and L from bicyclononene AL17 and BOC-L-hydroxyproline. LC-MS: $R_t$=0.78 ES+: 735.48.

Example 185

1:1—Mixture of (1R,5S)-3-((1S,4R)-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid cyclopropyl-(2-p-tolylethyl)amide formate salt and (1S,5R)-3-((1S,4R)-hydroxypyrrolidine-2-carbonyl)-7-{4-[3-(2,3,6-trifluorophenoxy)-propyl]phenyl}-3,9-diazabicyclo[3.3.1]non-6-ene-6-carboxylic acid cyclopropyl-(2-p-tolylethyl)-amide formate salt Synthesized according to typical procedures G, E and L from bicyclononene AL18 BOC-L-hydroxyproline. LC-MS: $R_t$=0.81 ES+: 703.48.

Example 186

1:1—Mixture of (rac.)-(3R*)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt and (rac.)-(3S*)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt Synthesized according to typical procedures K, E and L from bicyclononene AL2 and 3-(tert-butyldimethylsilyloxy) glutaric anhydride. LC-MS: $R_t$=0.86 ES+: 726.40.

Example 187

1:1—Mixture of (rac.)-(3R*)-5-((1R*,5S*)-6-(benzylcyclopropylcarbamoyl)-7-{4-[3-(2,3,6-trifluorophenoxy)propyl]phenyl}-3,9-diazabicyclo[3.3.1]non-6-en-3-yl)-3-hydroxy-5-oxopentanoic acid formate salt and (rac.)-(3S*)-5-((1R*,5S*)-6-(benzylcyclopropylcarbamoyl)-7-{4-[3-(2,3,6-trifluorophenoxy)-propyl]phenyl}-3,9-diazabicyclo[3.3.1]non-6-en-3-yl)-3-hydroxy-5-oxopentanoic acid formate salt Synthesized according to typical procedures K, E and L from bicyclononene AL3 and 3-(tert-butyldimethylsilyloxy) glutaric anhydride. LC-MS: $R_t$=0.84 ES+: 692.45

Example 188

1:1—Mixture of (rac.)-(3R*)-5-((1R*,5S*)-6-[(2-chlorobenzyl)ethylcarbamoyl]-7-{4-[3-(2,3,6-trifluorophenoxy)propyl]phenyl]-3,9-diazabicyclo-[3.3.1]non-6-en-3-yl)-3-hydroxy-5-oxopentanoic acid formate salt and (rac.)-(3S*)-5-((1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid formate salt Synthesized according to typical procedures K, E and L from bicyclononene AL4 and 3-(tert-butyldimethylsilyloxy) glutaric anhydride. LC-MS: $R_t$=0.86 ES+: 714.38

Example 189

1:1—Mixture of (rac.)-(3R*)-5-((1R*,5S*)-6-[cyclopropyl-(2-fluorobenzyl)-carbamoyl]-7-{4-[3-(2,3,6-trifluorophenoxy)propyl]phenyl}-3,9-diazbicyclo-[3.3.1]non-6-en-3-yl)-3-hydroxy-5-oxopentanoic acid formate salt and (rac.)-(3S*)-5-((1R*,5S*)-6-[cyclopropyl-(2-fluorobenzyl)carbamoyl]-7-{4-[3-(2,3,6-trifluorophenoxy)propyl]phenyl}-3,9-diazbicyclo-[3.3.1]non-6-en-3-yl)-3-hydroxy-5-oxopentanoic acid formate salt Synthesized according to typical procedures K, E and L from bicyclononene AL5 and 3-(tert-butyldimethylsilyloxy) glutaric anhydride. LC-MS: $R_t$=0.84 ES+: 710.42

Example 190

1:1—Mixture of (rac.)-(3R*)-5-((1R*,5S*)-6-[cyclopropyl-(3-trifluoromethylbenzyl)carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid formate salt and (rac.)-(3S*)-5-((1R*,5S*)-6-[cyclopropyl-(3-trifluoromethylbenzyl)-carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt Synthesized according to typical procedures K, E and L from bicyclononene AL6 and 3-(tert-butyldimethylsilyloxy) glutaric anhydride. LC-MS: $R_t$=0.88 ES+: 760.39

Example 191

1:1—Mixture of (rac.)-(3R*)-5-((1R*,5S*)-6-[cyclopropyl-(2-methylbenzyl)-carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt and (rac.)-(3S*)-5-((1R*,5S*)-6-[cyclopropyl-(2-methylbenzyl)carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt Synthesized according to typical procedures K, E and L from bicyclononene AL7 and 3-(tert-butyldimethylsilyloxy) glutaric anhydride. LC-MS: $R_t$=0.86 ES+: 706.44

Example 192

1:1—Mixture of (rac.)-(3R*)-5-((1R*,5S*)-6-{cyclopropyl-[2-(4-methoxyphenoxy)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid formate salt and (rac.)-(3S*)-5-((1R*,5S*)-6-{cyclopropyl-[2-(4-methoxyphenoxy)-ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid formate salt Synthesized according to typical procedures K, E and L from bicyclononene AL8 and 3-(tert-butyldimethylsilyloxy) glutaric anhydride. LC-MS: $R_t$=0.85 ES+: 752.43

Example 193

1:1—Mixture of (rac.)-(3R*)-5-((1R*,5S*)-6-{cyclopropyl-[2-(3-methoxyphenoxy)ethyl]carbamoyl{-7-{4-[3-(2,3,6-trifluorophenoxy)propyl]phenyl}-3,9-diazabicyclo[3.3.1]non-6-en-3-yl-)3-hydroxy-5-oxopentanoic acid formate salt and (rac.)-(3S*)-5-(1R*,5S*)-6-{cyclopropyl-[2-(3-methoxyphenoxy)-ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid formate salt Synthesized according to typical procedures K, E and L from bicyclononene AL9 and 3-(tert-butyldimethylsilyloxy) glutaric anhydride. LC-MS: $R_t$=0.85 ES+: 752.44

Example 194

1:1—Mixture of (rac.)-(3R*)-5-((1R*,5S*)-6-[cyclopropyl-(2-m-tolyloxyethyl)-carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt and (rac.)-(3S*)-5-((1R*,5S*)-6-[cyclopropyl-(2-m-tolyloxyethyl)carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt Synthesized according to typical procedures K, E and L from bicyclononene AL10 and 3-tert-butyldimethylsilyloxy) glutaric anhydride. LC-MS: $R_t$=0.87 ES+: 736.45.

Example 195

1:1—Mixture of (rac.)-(3R*)-5-((1R*,5S*)-6-{cyclopropyl-[2-(3,4-dimethylphenoxy)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid formate salt and (rac.)-(3S*)-5-((1R*,5S*)-6-{cyclopropyl-[2-(3,4-dimethylphenoxy)-ethyl]carbamoyl}-7-{4-[3-(2,3,6-trifluorophenoxy)propyl]-phenyl}-3,9-diazabicyclo[3.3.1]non-6-en-3-yl)-3-hydroxy-5-oxopentanoic acid formate salt Synthesized according to typical procedures K, E and L from bicyclononene AL11 and 3-(tert-butyldimethylsilyloxy)glutaric anhydride. LC-MS: $R_t$=0.89 ES+: 750.47

Example 196

1:1—Mixture of (rac.)-(3R*)-5-((1R*,5S*)-(6-(cyclopropylphenethylcarbamoyl)-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt and (rac.)-(3S*)-5-((1R*,5S*)-5-(6-(cyclopropylphenethylcarbamoyl)-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt Synthesized according to typical procedures K, E and L from bicyclononene AL12 and 3-(tert-butyldimethylsilyloxy)glutaric anhydride. LC-MS: $R_t$=0.85 ES+: 706.43

Example 197

1:1—Mixture of (rac.)-(3R*)-5-((1R*,5S*)-6-{[2-(2-chlorophenyl)ethyl]-cyclopropylcarbamoyl}-7-{4-[3-(2,3,6-trifuorophenoxy)propyl]phenyl}-3,9-diazabicyclo[3.3.1]non-6-en-3-yl)-3-hydroxy-5-oxopentanoic acid formate salt and (rac.)-(3S*)-5-((1R*,5S*)-6-{[2-(2-chlorophenyl)ethyl]cyclopropylcarbamoyl}-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt Synthesized according to typical procedures K, E and L from bicyclononene AL13 and 3-(tert-butyldimethylsilyloxy)glutaric anhydride. LC-MS: $R_t$=0.87 ES+: 740.40

Example 198

1:1—Mixture of (rac.)-(3R*)-5-((1R*,5S*)-6-{cyclopropyl-[2-(2,3-difluorophenyl)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid formate salt and (rac.)-(3S*)-5-((1R*,5S*)-6-{cyclopropyl-[2-(2,3-difluorophenyl)ethyl]-carbamoyl}-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt Synthesized according to typical procedures K, E and L from bicyclononene AL14 and 3-(tert-butyldimethylsilyloxy)glutaric anhydride. LC-MS: $R_t$=0.86 ES+: 742.42

Example 199

1:1—Mixture of (rac.)-(3R*)-5-(1R*,5S*)-6-{cyclopropyl-[2-(4-fluorophenyl)-ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid formate salt and (rac.)-(3S*)-5-((1R*,5S*)-6-{cyclopropyl-[2-(4-fluorophenyl)ethyl]-carbamoyl}-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt Synthesized according to typical procedures K, E and L from bicyclononene AL15 and 3-(tert-butyldimethylsilyloxy)glutaric anhydride. LC-MS: $R_t$=0.86 ES+: 724.43.

Example 200

1:1—Mixture of (rac.)-(3R*)-5-((1R*,5S*)-6-cyclopropyl-(2-o-tolylethyl)-carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt and (rac.)-(3S*)-5-((1R*,5S*)-6-[cyclopropyl-(2-o-tolylethyl)carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt Synthesized according to typical procedures K, E and L from bicyclononene AL16 and 3-(tert-butyldimethylsilyloxy)glutaric anhydride. LC-MS: $R_t$=0.87 ES+: 720.45

Example 201

1:1—Mixture of (rac.)-(3R*)-5-((1R*,5S*)-6-[cyclopropyl-(3,5-dimethoxybenzyl)carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid formate salt and (rac.)-(3S*)-5-((1R*,5S*)-6-[cyclopropyl-(3,5-dimethoxybenzyl)carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid formate salt Synthesized according to typical procedures K, E and L from bicyclononene AL17 and 3-(tert-butyldimethylsilyloxy)glutaric anhydride. LC-MS: $R_t$=0.85 ES+: 752.42

Example 202

1:1—Mixture of (rac.)-(3R*)-5-(1R*,5S*)-6-[cyclopropyl-(2-p-tolylethyl)-carbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt and (rac.)-(3R*)-5-((1R*;5S*)-6-[cyclopropyl-(2-p-tolylethyl)carbamoyl]-7-{4-13-(2,3,6-trifluorophenoxy)propyl]phenyl}-3,9-diazabicyclo-[3.3.1]non-6-en-3-yl)-3-hydroxy-5-oxopentanoic acid formate salt Synthesized according to typical procedures K, E and L from bicyclononene AL18 and 3-(tert-butyldimethylsilyloxy)glutaric anhydride. LC-MS: $R_t$=0.87 ES+: 720.43

Example 203

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid benzylcyclopropylamide formate salt Synthesized according to typical procedures A and E from bicyclononene AL3 and acetyl chloride. LC-MS: $R_t$=0.88 ES+: 604.53

Example 204

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid (2-chlorobenzyl)ethylamide formate salt Synthesized according to typical procedures A and E from bicyclononene AL4 and acetyl chloride. LC-MS: $R_t$=0.90 ES+: 626.48

Example 205

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl(2-fluorobenzyl)-amide formate salt Synthesized according to typical procedures A and E from bicyclononene AL5 and acetyl chloride. LC-MS: $R_t$=0.89 ES+: 622.53

Example 206

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(2-methylbenzyl)-amide formate salt Synthesized according to typical procedures A and E from bicyclononene AL7 and acetyl chloride. LC-MS: $R_t$=0.90 ES+: 618.54

Example 207

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl[2-(4-methoxyphenoxy)ethyl]amide formate salt Synthesized according to typical procedures A and E from bicyclononene AL8 and acetyl chloride. LC-MS: $R_t$=0.89 ES+: 664.54

Example 208

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl[2-(3-methoxyphenoxy)ethyl]amide formate salt Synthesized according to typical procedures A and E from bicyclononene AL9 and acetyl chloride. LC-MS: $R_t$=0.89 ES+: 664.53

Example 209

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl[2-(3-methylphenoxy)ethyl]amide formate salt Synthesized according to typical procedures A and E from bicyclononene AL10 and acetyl chloride. LC-MS: $R_t$=0.91 ES+: 648.53

Example 210

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropylphenethylamide formate salt Synthesized according to typical procedures A and E from bicyclononene AL12 and acetyl chloride. LC-MS: $R_t$=0.89 ES+: 618.54

Example 211

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl(3,5-dimethoxybenzyl)amide formate salt Synthesized according to typical procedures A and E from bicyclononene AL17 and acetyl chloride. LC-MS: $R_t$=0.88 ES+: 664.55

Example 212

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl(2-p-tolylethyl)amide formate salt Synthesized according to typical procedures A and E from bicyclononene AL18 and acetyl chloride. LC-MS: $R_t$=0.91 ES+: 632.54

Example 213

(rac.)-5-((1R*,5S*)-6-(Benzylcyclopropylcarbamoyl)-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL3 and glutaric anhydride. LC-MS: $R_t$=0.86 ES+: 676.54

Example 214

(rac.)-5-((1R*,5S*)-6-[(2-Chlorobenzyl)ethylcarbamoyl]-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL4 and glutaric anhydride. LC-MS: $R_t$=0.88 ES+: 698.46

Example 215

(rac.)-5-((1R*,5S*)-6-[Cyclopropyl-(2-fluorobenzyl)carbamoyl]-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL5 and glutaric anhydride. LC-MS: $R_t$=0.86 ES+: 694.51

Example 216

(rac.)-5-((1R*,5S*)-6-[Cyclopropyl(3-trifluoromethylbenzyl)carbamoyl]-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL6 and glutaric anhydride. LC-MS: $R_t$=0.89 ES+: 744.51

Example 217

(rac.)-5-((1R*,5S*)-6-[Cyclopropyl(2-methylbenzyl)carbamoyl]-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL7 and glutaric anhydride. LC-MS: $R_t$=0.88 ES+: 690.54

Example 218

(rac.)-5-((1R*,5S*)-6-{Cyclopropyl[2-(4-methoxyphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL8 and glutaric anhydride. LC-MS: $R_t$=0.87 ES+: 736.54

Example 219

(rac.)-5-(1R*,5S*)-6-{Cyclopropyl[2-(3-methoxyphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL9 and glutaric anhydride. LC-MS: $R_t$=0.87 ES+: 736.55

Example 220

(rac.)-5-((1R*,5S*)-6-{Cyclopropyl[2-(3-methylphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL10 and glutaric anhydride. LC-MS: $R_t$=0.89 ES+: 720.53

Example 221

(rac.)-5-((1R*,5S*)-6-{Cyclopropyl-[2-(3,4-dimethylphenoxy)ethyl]-carbamoyl}-7-{4-[3-(2,3,6-trifluorophenoxy)propyl]phenyl}-3,9-diazabicyclo-[3.3.1]non-6-en-3-yl)-5-oxopentanoic acid formate salt Synthesized according to typical procedures K and E from bicyclononene AL11 and glutaric anhydride. LC-MS: $R_t$=0.90 ES+: 734.57

Example 222

(rac.)-5-((1R*,5S*)-6-(Cyclopropylphenethylcarbamoyl)-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL12 and glutaric anhydride. LC-MS: $R_t$=0.87 ES+: 690.52

Example 223

(rac.)-5-(1R*,5S*)-6-{[2-(2-Chlorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL13 and glutaric anhydride. LC-MS $R_t$=0.89 ES+: 724.49

Example 224

(rac.)-5-((1R*,5S*)-6-{Cyclopropyl-[2-(2,3-difluorophenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL14 and glutaric anhydride. LC-MS: $R_t$=0.88 ES+: 726.51

Example 225

(rac.)-5-((1R*,5S*)-6-{Cyclopropyl[2-(4-fluorophenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL15 and glutaric anhydride. LC-MS: $R_t$=0.87 ES+: 708.50

Example 226

(rac.)-5-((1R*,5S*)-6-{Cyclopropyl[2-(2-methylphenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL16 and glutaric anhydride. LC-MS: $R_t$=0.88 ES+: 704.54

Example 227

(rac.)-5-((1R*,5S*)-6-[Cyclopropyl(3,5-dimethoxy-benzyl)carbamoyl]-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL17 and glutaric anhydride. LC-MS: $R_t$=0.86 ES+: 736.55

Example 228

(rac.)-5-((1R*,5S*)-6-[Cyclopropyl(2-p-tolylethyl)carbamoyl]-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL18 and glutaric anhydride. LC-MS: $R_t$=0.88 ES+: 704.54

Example 229

(rac.)-5-((1R*,5S*)-6-(Benzylcyclopropylcarbamoyl)-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL3 and glutaric acid monomethylester chloride. LC-MS: $R_t$=0.91 ES+: 690.55

Example 230

(rac.)-5-((1R*,5S*)-6-[(2-Chlorobenzyl)ethylcarbamoyl]-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL4 and glutaric acid monomethylester chloride. LC-MS: $R_t$=0.92 ES+: 712.49

Example 231

(rac.)-5-((1R*,5S*)-6-[Cyclopropyl-(2-fluorobenzyl)carbamoyl]-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL5 and glutaric acid monomethylester chloride. LC-MS: $R_t$=0.91 ES+: 708.51

Example 232

(rac.)-5-((1R*,5S*)-6-[Cyclopropyl(3-trifluoromethylbenzyl)carbamoyl]-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL6 and glutaric acid monomethylester chloride. LC-MS: $R_t$=0.94 ES+: 758.51

Example 233

(rac.)-5-((1R*,5S*)-6-[Cyclopropyl(2-methylbenzyl)carbamoyl]-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL7 and glutaric acid monomethylester chloride. LC-MS: $R_t$=0.92 ES+: 704.54

Example 234

(rac.)-5-((1R*,5S*)-6-{Cyclopropyl[2-(4-methoxyphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL8 and glutaric acid monomethylester chloride. LC-MS: $R_t$=0.92 ES+: 750.54

Example 235

(rac.)-5-((1R*,5S*)-6-{Cyclopropyl[2-(3-methoxyphenoxy)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL9 and glutaric acid monomethylester chloride. LC-MS: $R_t$=0.92 ES+: 750.56

Example 236

(rac.)-5-((1R*,5S*)-6-{Cyclopropyl[2-(3-methylphenoxy)ethyl]carbamoyl}-7-{4-[3-(2,3,6-trifluorophenoxy)propyl]phenyl-3,9-diazabicyclo[3.3.1]non-6-en-3-yl)-5-oxopentanoic acid methyl ester formate salt Synthesized according to typical procedures A and E from bicyclononene AL10 and glutaric acid monomethylester chloride. LC-MS: $R_t$=0.93 ES+: 734.58

Example 237

(rac.)-5-((1R*,5S*)-6-{Cyclopropyl[2-(3,4-dimethylphenoxy)ethyl]-carbamoyl}-7-{4-[3-(2,3,6-trifluorophenoxy)propyl]phenyl}-3,9-diazabicyclo-[3.3.1]non-6-en-3-yl)-5-oxopentanoic acid methyl ester formate salt Synthesized according to typical procedures A and E from bicyclononene AL11 and glutaric acid monomethylester chloride. LC-MS: $R_t$=0.95 ES+: 748.57

Example 238

(rac.)-5-((1R*,5S*)-6-(Cyclopropylphenethylcarbamoyl)-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL12 and glutaric acid monomethylester chloride. LC-MS: $R_t$=0.91 ES+: 704.55

Example 239

(rac.)-5-((1R*,5S*)-6-{[2-(2-Chlorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL13 and glutaric acid monomethylester chloride. LC-MS: $R_t$=0.93 ES+: 738.53

Example 240

(rac.)-5-((1R*,5S*)-6-{Cyclopropyl[2-(2,3-difluorophenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL14 and glutaric acid monomethylester chloride. LC-MS: $R_t$=0.92 ES+: 740.54

Example 241

(rac.)-5-((1R*,5S*)-6-{Cyclopropyl[2-(4-fluorophenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL15 and glutaric acid monomethylester chloride. LC-MS: $R_t$=0.92 ES+: 722.54

Example 242

(rac.)-5-(1R*,5S*)-6-{Cyclopropyl[2-(2-methylphenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL16 and glutaric acid monomethylester chloride. LC-MS: $R_t$=0.93 ES+: 718.56

Example 243

(rac.)-5-((1R*,5S*)-6-[Cyclopropyl-(3,5-dimethoxybenzyl)carbamoyl]-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL17 and glutaric acid monomethylester chloride. LC-MS: $R_t$=0.91 ES+: 750.55

Example 244

(rac.)-5-(1R*,5S*)-6-{Cyclopropyl[2-(4-methylphenyl)ethyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL18 and glutaric acid monomethylester chloride. LC-MS: $R_t$=0.93 ES+: 718.56

Example 245

(rac.)-((1R*,5S*)-6-(Benzylcyclopropylcarbamoyl)-7-}4-[3-(2,3,6-trifluorophenoxy)propyl]phenyl}-3,9-diazabicyclo[3.3.1]non-6-3-yl)-2,2-methyl-5-oxopentanoic acid methyl ester formate salt Synthesized according to typical procedures K and E from bicyclononene AL3 and 2,2-dimethylglutaric anhydride. LC-MS: $R_t$=0.90 ES+: 704.53

Example 246

(rac.)-5-(1R*,5S*)-6-[(2-Chlorobenzyl)ethylcarbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL4 and 2,2-dimethylglutaric anhydride. LC-MS: $R_t$=0.91 ES+: 726.53

Example 247

(rac.)-5-(1R*,5S*)-6-[Cyclopropyl-(2-fluorobenzyl)carbamoyl]-7-{4-[3-(2,3,6-trifluorophenoxy)propyl]phenyl}-3,9-diazabicyclo[3.3.1]non-en-3-yl)-2,2-dimethyl-5-oxopentanoic formate salt Synthesized according to typical procedures K and E from bicyclononene AL5 and 2,2-dimethylglutaric anhydride. LC-MS: $R_t$=0.90 ES+: 722.54

Example 248

(rac.)-5-(1R*,5S*)-6-[Cyclopropyl-(3-trifluoromethylbenzyl)carbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL6 and 2,2-dimethylglutaric anhydride. LC-MS: $R_t$=0.93 ES+: 772.51

Example 249

(rac.)-5-(1R*,5S*)-6-[Cyclopropyl-(2-methylbenzyl)carbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL7 and 2,2-dimethylglutaric anhydride. LC-MS: $R_t$=0.91 ES+: 718.57

Example 250

(rac.)-5-((1R*,5S*)-6-{Cyclopropyl-[2-(4-methoxyphenoxy)ethyl]carbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL8 and 2,2-dimethylglutaric anhydride. LC-MS: $R_t$=0.90 ES+: 764.55

Example 251

(rac.)-5-((1R*,5S*)-6-{Cyclopropyl-[2-(3-methoxyphenoxy)ethyl]carbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL9 and 2,2-dimethylglutaric anhydride. LC-MS: $R_t$=0.90 ES+: 764.54

Example 252

(rac.)-5-((1R*,5S*)-6-{Cyclopropyl-[2-(3-methylphenoxy)ethyl]carbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL10 and 2,2-dimethylglutaric anhydride. LC-MS: $R_t$=0.92 ES+: 748.58

Example 253

(rac.)-5-((1R*,5S*)-6-{Cyclopropyl-[2-(3,4-dimethylphenoxy)ethyl]-carbamoyl}-7-4-[3-(2,3,6-trifluorophenoxy)propyl]phenyl}-3,9-diazabicyclo-[3.3.1]non-6-en-3-yl)-2,2-dimethyl-5-oxopentanoic acid formate salt Synthesized according to typical procedures K and E from bicyclononene AL11 and 2,2-dimethylglutaric anhydride. LC-MS: $R_t$=0.93 ES+: 762.58

Example 254

(rac.)-5-(1R*,5S*)-6-(Cyclopropylphenethylcarbamoyl)-7-{4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL12 and 2,2-dimethylglutaric anhydride. LC-MS: $R_t$=0.90 ES+: 718.56

Example 255

(rac.)-5-(1R*,5S*)-6-{[2-(2-Chlorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL13 and 2,2-dimethylglutaric anhydride. LC-MS: $R_t$=0.92 ES+: 752.50

Example 256

(rac.)-5-((1R*,5S*)-6-{[2-(2,3-Difluorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL14 and 2,2-dimethylglutaric anhydride. LC-MS: $R_t$=0.91 ES+: 754.53

Example 257

(rac.)-5-((1R*,5S*)-6-{[2-(4-Fluorophenyl)ethyl]cyclopropylcarbamoyl}-7-(4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL15 and 2,2-dimethylglutaric anhydride. LC-MS: $R_t$=0.91 ES+: 736.56

Example 258

(rac.)-5-((1R*,5S*)-6-{[2-(2-Methylphenyl)ethyl]
cyclopropylcarbamoyl}-7-{4-[3-(2,3,6-trifluorophe-
noxy)propyl]phenyl}-3,9-diazabicyclo[3.3.1]non-6-
en-3-yl)-2,2-dimethyl-5-oxopentanoic acid formate
salt Synthesized according to typical procedures K and E from bicyclononene AL16 and 2,2-dimethylglutaric anhydride. LC-MS: $R_t$=0.92 ES+: 732.59

Example 259

(rac.)-5-((1R*,5S*)-6-[Cyclopropyl-(3,5-dimethoxy-
benzyl)carbamoyl]-7-{4-[3-(2,3,6-trifluorophenoxy)
propyl]phenyl}-3,9-diazabicyclo[3.3.1]non-6-en-3-
yl)-2,2-dimethyl-5-oxopentanoic acid formate salt Synthesized according to typical procedures K and E from bicyclononene AL17 and 2,2-dimethylglutaric anhydride. LC-MS: $R_t$=0.90 ES+: 764.54

Example 260

(rac.)-5-((1R*,5S*)-6-{[2-(4-Methylphenyl)ethyl]
cyclopropylcarbamoyl}-7-{4-[3-(2,3,6-trifluorophe-
noxy)propyl]phenyl}-3,9-diazabicyclo[3.3.1]non-6-
en-3-yl)-2,2-dimethyl-5-oxopentanoic acid formate
salt Synthesized according to typical procedures K and E from bicyclononene AL18 and 2,2-dimethylglutaric anhydride. LC-MS: $R_t$=0.92 ES+: 732.58

Example 261

1:1—Mixture of (rac.)-(2R*,3S*)-4-((1R*,5S*)-6-
[(2-chlorobenzyl)ethylcarbamoyl]-7-{4-[3-(2,3,6-
trifluorophenoxy)propyl]phenyl}-3,9-diazabicyclo-
[3.3.1]non-6-en-3-yl)-2,3-dihydroxy-4-oxobutyric
acid formate salt and (rac.)-(2S*,3R*)-4-((1R*,5S*)-
6-[2-chlorobenzyl)ethylcarbamoyl]-7-{4-[3-(2,3,6-
trifluorophenoxy)propyl]phenyl}-3,9-diazabicyclo-
[3.3.1]non-6-en-3-yl)-2,3-dihydroxy-4-oxobutyric
acid formate salt Synthesized according to typical procedures K and E from bicyclononene AL4 and meso-2,3-dihydroxysuccinic anhydride. LC-MS: $R_t$=0.85 ES+: 716.45

Example 262

1:1—Mixture of (rac.)-(2R*,3S*)-4-((1R*,5S*)-6-
[cyclopropyl-(2-fluorobenzyl)carbamoyl]-7-{4-[3-(2,
3,6-trifluorophenoxy)propyl]phenyl}-3,9-diazabicy-
clo[3.3.1]non-6-en-3-yl)-2,3-dihydroxy-4-oxobutyric
acid formate salt and (rac.)-(2S*,3R*)-4-((1R*,5S*)-
6-[cyclopropyl-(2-fluorobenzyl)carbamoyl]-7-{4-[3-
(2,3,6-trifluorophenoxy)propyl]phenyl}-3,9-diazabi-
cyclo-[3.3.1]non-6-en-3-yl)-2,3-dihydroxy-4-
oxobutyric acid formate salt Synthesized according to typical procedures K and E from bicyclononene AL5 and meso-2,3-dihydroxysuccinic anhydride. LC-MS: $R_t$=0.83 ES+: 712.44

Example 263

1:1—Mixture of (rac.)-(2R*,3S*)-4-((1R*,5S*)-6-
[Cyclopropyl-(3-trifluoromethylbenzyl)carbamoyl]-
7-{4-[3-(2,3,6-trifluorophenoxy)propyl]-phenyl}-3,
9-diazabicyclo-[3.3.1]non-6-en-3-yl)-2,3-dihydroxy-
4-oxobutyric acid formate salt and (rac.)-(2S*,3R*)-
4-((1R*,5S*)-6-[cyclopropyl-(3-
trifluoromethylbenzyl)carbamoyl]-7-{4-[3-(2,3,6-
trifluorophenoxy)propyl]-phenyl}-3,9-diazabicyclo-
[3.3.1]non-6-en-3-yl)-2,3-dihydroxy-4-oxobutyric
acid fromate salt Synthesized according to typical procedures K and E from bicyclononene AL6 and meso-2,3-dihydroxysuccinic anhydride. LC-MS: $R_t$=0.87 ES+: 762.42

Example 264

1:1—Mixture of (rac.)-(2R*,3S*)-4-((1R*,5S*)-6-
[cyclopropyl-(2-methylbenzyl)carbamoyl]-7-{4-[3-
(2,3,6-trifluorophenoxy)propyl]phenyl}-3,9-diazabi-
cyclo[3.3.1]non-6-en-3-yl)-2,3-dihydroxy-4-
oxobutyric acid formate salt and (rac.)-(2S*,3R*)-4-
((1R*,5S*)-6-[cyclopropyl-(2-methylbenzyl)
carbamoyl]-7-{4-[3-(2,3,6-trifluorophenoxy)propyl]
phenyl}-3,9-diazabicyclo-[3.3.1]non-6-en-3-yl)-2,3-
dihydroxy-4-oxobutyric acid formate salt Synthesized according to typical procedures K and E from bicyclononene AL7 and meso-2,3-dihydroxysuccinic anhydride. LC-MS: $R_t$=0.85 ES+: 708.46

Example 265

1:1—Mixture of (rac.)-(2R*,3S*)-4-((1R*,5S*)-6-
{cyclopropyl-[2-(2,3-difluorophenyl)ethyl]carbam-
oyl}-7-{4-[3-(2,3,6-trifluorophenoxy)propyl]phe-
nyl}-3,9-diazabicyclo[3.3.1]non-6-en-3-yl)-2,3-
dihydroxy-4-oxobutyric acid formate salt and (rac.)-
(2S*,3R*)-4-((1R*,5S*)-6-{cyclopropyl-[2-(2,3-
difluorophenyl)ethyl]carbamoyl}-7-{4-[3-(2,3,6-
trifluorophenoxy)propyl]phenyl}-3,9-diazabicyclo
[3.3.1]non-6-en-3-yl)-2,3-dihydroxy-4-oxobutyric
acid formate salt Synthesized according to typical procedures K and E from bicyclononene AL14 and meso-2,3-dihydroxysuccinic anhydride. LC-MS: $R_t$=0.85 ES+: 744.46

Example 266

1:1—Mixture of (rac.)-(2R*,3S*)-4-((1R*,5S*)-6-
{cyclopropyl-[2-(2-methyl-phenyl)ethyl]carbam-
oyl}-7-{4-[3-(2,3,6-trifluorophenoxy)propyl]phe-
nyl}-3,9-diazabicyclo[3.3.1]non-4-en-3-yl)-2,3-
dihydroxy-4-oxobutyric acid formate salt and (rac.)-
(2S*,3R*)-4-((1R*,5S*)-6-{cyclopropyl-[2-(2-
methylphenyl)-ethyl]carbamoyl}-7-{4-[3-(2,3,6-
trifluorophenoxy)propyl]phenyl}-3,9-diazabicyclo
[3.3.1]non-6-en-3-yl)-2,3-dihydroxy-4-oxobutyric
acid formate salt Synthesized according to typical procedures K and E from bicyclononene AL16 and meso-2,3-dihydroxysuccinic anhydride. LC-MS: $R_t$=0.86 ES+: 722.52

Example 267

1:1—Mixture of (rac.)-(2R*,3S*)-4-((1R*,5S*)-6-[cyclopropyl-(3,5-dimethoxy-benzyl)carbamoyl]-7-{4-[3-(2,3,6-trifluorophenoxy)propyl]phenyl}-3,9-diazabicyclo[3.3.1]non-6-en-3-yl)-2,3-dihydroxy-4-oxobutyric acid formate salt and (rac.)-(2S*,3R*)-4-((1R*,5S*)-6-[cyclopropyl-(3,5-dimethoxybenzyl)-carbamoyl]-7-{4-[3-(2,3,6-trifluorophenoxy)propyl]phenyl}-3,9-diazabicyclo-[3.3.1]non-6-en-3-yl)-2,3-dihydroxy-4-oxobutyric acid formate salt Synthesized according to typical procedures K and E from bicyclononene AL17 and meso-2,3-dihydroxysuccinic anhydride. LC-MS: $R_t$=0.84 ES+: 754.50

Example 268

1:1—Mixture of (rac.)-(2R*,3S*)-4-((1R*,5S*)-6-{cyclopropyl-[2-(4-methyl-phenyl)ethyl]carbamoyl}-7-{4-[3-(2,3,6-trifluorophenoxy)propyl]phenyl}-3,9-diazabicyclo[3.3.1]non-6-en-3-yl)-2,3-dihydroxy-4-oxobutyric acid formate salt and (rac.)-(2S*,3R*)-4-((1R*,5S*)-6-{cyclopropyl-[2-(4-methylphenyl)-ethyl]carbamoyl}-7-{4-[3-(2,3,6-trifluorophenoxy)propyl]phenyl}-3,9-diazabicyclo[3.3.1]non-6-en-3-yl)-2,3-dihydroxy-4-oxobutyric acid formate salt Synthesized according to typical procedures K and E from bicyclononene AL18 and meso-2,3-dihydroxysuccinic anhydride. LC-MS: $R_t$=0.86 ES+: 722.49

Example 269

1:1—Mixture of (rac.)-(3R*)-5-((1R*,5S*)-6-[(2-chlorobenzyl)cyclopropylcarbamoyl]-7-{4-[3-(2,3,5-trimethylphenoxy)ethyl]phenyl}-3,9-diazabicyclo-[3.3.1]non-6-en-3-yl)-3-hydroxy-5-oxopentanoic acid formate salt and (rac.)-(3S*)-5-((1R*,5S*)-6-[(2-chlorobenzyl)cyclopropylcarbamoyl]-7-{4-[3-(2,3,5-trimethylphenoxy)ethyl]phenyl}-3,9-diazabicyclo-[3.3.1]non-6-en-3-yl)-3-hydroxy-5-oxopentanoic acid formate salt Synthesized according to typical procedures K, E and L from bicyclononene AL38 and 3-(tert-butyldimethylsilyloxy)glutaric anhydride. LC-MS $R_t$=0.88 ES+: 700.52

Example 270

1:1—Mixture of (rac.)-(3R*)-5-((1R*,5S*)-6-[(2-chlorobenzyl)ethylcarbamoyl]-7-{4-[3-(2,3,5-trimethylphenoxy)ethyl]phenyl}-3,9-diazabicyclo-[3.3.1]non-6-en-3-yl)-3-hydroxy-5-oxopentanoic acid formate salt and (rac.)-(3S*)-5-(1R*,5S*)-6-[(2-chlorobenzyl)ethylcarbamoyl]-7-{4-[3-(2,3,5-trimethylphenoxy)ethyl]phenyl}-3,9-diazabicyclo[3.3.1]non-6-en-3-yl)-3-hydroxy-5-oxopentanoic acid formate salt Synthesized according to typical procedures K, E and L from bicyclononene AL40 and 3-(tert-butyldimethylsilyloxy)glutaric anhydride. LC-MS: $R_t$=0.88 ES+: 688.54

Example 271

(rac.)-5-((1R*,5S*)-7-{4-[3-(2-Bromo-5-fluorophenoxy)propyl]phenyl}-6-{cyclopropyl-[2-(2-hydroxyethyl)benzyl]carbamoyl}-3,9-diazabicyclo[3.3.1]-non-6-en-3-yl)-5-oxopentanoic acid formate salt Synthesized according to typical procedures K and E from bicyclononene AL37 and glutaric anhydride. LC-MS: $R_t$=0.86 ES+: 762.42

Example 272

(rac.)-5-((1R*,5S*)-7-{4-[3-(2-Bromo-5-fluorophenoxy)propyl]phenyl}-6-(cyclopropyl-[2-(2-hydroxyethyl)benzyl]carbamoyl}-3,9-diazabicyclo[3.3.1]-non-6-en-3-yl)-5-oxopentanoic acid methyl ester formate salt Synthesized according to typical procedures A and E from bicyclononene AL37 and glutaric acid monomethyl ester chloride. LC-MS. $R_t$=0.88 ES+: 776.43

Example 273

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid cyclopropyl-[2-(2-hydroxyethyl)benzyl]amide formate salt Synthesized according to typical procedures G and E from bicyclononene AL37 and 4-carbamoylbutyric acid. LC-MS: $R_t$=0.82 ES+: 761.45

Example 274

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-[2-(2-hydroxy-ethyl)benzyl]amide formate salt Synthesized according to typical procedures A and E from bicyclononene AL19 and acetyl chloride. LC-MS: $R_t$=0.84 ES+: 648.50

Example 275

(rac.)-5-((1R*,5S*)-6-{Cyclopropyl-[2-(2-hydroxyethyl)benzyl]carbamoyl}-7-{4-[3-(2,3,6-trifluorophenoxy)propyl]phenyl}-3,9-diazabicyclo[3.3.1]non-6-en-3-yl)-5-oxopentanoic acid formate salt Synthesized according to typical procedures K and E from bicyclononene AL19 and glutaric anhydride. LC-MS: $R_t$=0.85 ES+: 740.42

Example 276

(rac.)-5-((1R*,5S*)-6-{Cyclopropyl-[2-(2-hydroxyethyl)benzyl]carbamoyl}-7-{4-[3-(2,3,6-trifluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL19 and glutaric acid monomethylester chloride. LC-MS: $R_t$=0.87 ES+: 734.52

Example 277

(rac.)-5-(1R*,5S*)-6-{Cyclopropyl-[2-(2-hydroxyethyl)benzyl]carbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid formate salt Synthesized according to typical procedures K and E from bicyclononene AL19 and 2,2-dimethylglutaric anhydride. LC-MS: $R_t$=0.86 ES+: 748.52

Example 278

(rac.)-(1R*,5S*)-3-(4-Carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-[2-(2-hydroxyethyl)benzyl]amide formate salt Synthesized according to typical procedures G and E from bicyclononene AL19 and 4-carbamoylbutyric acid. LC-MS: $R_t$=0.81; ES+: 719.52.

Example 279

(rac.)-5-{(1R*,5S*)-7-{4-[3-(2-Bromo-5-fluorophenoxy)propyl]phenyl}-6-[(2-chlorobenzyl)ethylcarbamoyl]-3,9-diazabicyclo[3.3.1]non-6-en-3-yl}-5-oxopentanoic acid formate salt Synthesized according to typical procedures K and E from bicyclononene AL22 and glutaric anhydride. LC-MS: $R_t$=0.89; ES+: 740.38.

Example 280

(rac.)-5-{(1R*,5S*)-7-{4-[3-(2-Bromo-5-fluorophenoxy)propyl]phenyl}-6-[cyclopropyl-(2-fluorobenzyl)carbamoyl]-3,9-diazabicyclo[3.3.1]non-6-en-3-yl}-5-oxopentanoic acid formate salt Synthesized according to typical procedures K and E from bicyclononene AL23 and glutaric anhydride. LC-MS: $R_t$=0.88; ES+: 736.41.

Example 281

(rac.)-5-{(1R*,5S*)-7-{4-[3-(2-Bromo-5-fluorophenoxy)propyl]phenyl}-6-[cyclopropyl-(3-trifluoromethylbenzyl)carbamoyl]-3,9-diazabicyclo[3.3.1]-non-6-en-3-yl}-5-oxopentanoic acid formate salt Synthesized according to typical procedures K and E from bicyclononene AL24 and glutaric anhydride. LC-MS: $R_t$=0.91; ES+: 736.38.

Example 282

(rac.)-5-{(1R*,5S*)-7-{4-[3-(2-Bromo-5-fluorophenoxy)propyl]phenyl}-6-[cyclopropyl-(2-methylbenzyl)carbamoyl]-3,9-diazabicyclo[3.3.1]non-6-en-3-yl}-5-oxopentanoic acid formate salt Synthesized according to typical procedures K and E from bicyclononene AL25 and glutaric anhydride. LC-MS: $R_t$=0.89; ES+: 732.45.

Example 283

(rac.)-5-{(1R*,5S*)-7-{4-[3-(2-Bromo-5-fluorophenoxy)propyl]phenyl}-6-[cyclopropyl-[2-(4-methoxyphenoxy)ethyl]carbamoyl]-3,9-diazabicyclo-[3.3.1]non-6-en-3-yl)-5-oxopentanoic acid formate salt Synthesized according to typical procedures K and E from bicyclononene AL26 and glutaric anhydride. LC-MS: $R_t$=0.89; ES+: 778.41.

Example 284

(rac.)-5-{(1R*,5S*)-7-{4-[3-(2-Bromo-5-fluorophenoxy)propyl]phenyl}-6-[cyclopropyl-[2-(3-methylphenoxy)ethyl]carbamoyl}-3,9-diazabicyclo[3.3.1]-non-6-en-3-yl)-5-oxopentanoic acid formate salt Synthesized according to typical procedures K and E from bicyclononene AL27 and glutaric anhydride. LC-MS: $R_t$=0.91; ES+: 762.42.

Example 285

(rac.)-5-{(1R*,5S*)-7-{4-[3-(2-Bromo-5-fluorophenoxy)propyl]phenyl}-6-{cyclopropyl-[2-(3,4-dimethylphenoxy)ethyl]carbamoyl}-3,9-diazabicyclo-[3.3.1]non-6-en-3-yl)-5-oxopentanoic acid formate salt Synthesized according to typical procedures K and E from bicyclononene AL28 and glutaric anhydride. LC-MS: $R_t$=0.92; ES+: 776.45.

Example 286

(rac.)-5-[(1R*,5S*)-7-{4-[3-(2-Bromo-5-fluorophenoxy)propyl]phenyl}-6-(cyclopropylphenethylcarbamoyl)-3,9-diazabicyclo[3.3.1]non-6-en-3-yl]-5-oxopentanoic acid formate salt Synthesized according to typical procedures K and E from bicyclononene AL29 and glutaric anhydride. LC-MS: $R_t$=0.89; ES+: 732.44.

Example 287

(rac.)-5-((1R*,5S*)-7-{4-[3-(2-Bromo-5-fluorophenoxy)propyl]phenyl}-6-{[2-(2-chlorophenyl)ethyl]cyclopropylcarbamoyl}-3,9-diazabicyclo[3.3.1]non-6-en-3-yl)-5-oxopentanoic acid formate salt Synthesized according to typical procedures K and E from bicyclononene AL30 and glutaric anhydride. LC-MS: $R_t$=0.90; ES+: 766.35.

Example 288

(rac.)-5-((1R*,5S*)-7-{4-[3-(2-Bromo-5-fluorophenoxy)propyl]phenyl}-6-{[2-(2,3-difluorophenyl)ethyl]cyclopropylcarbamoyl}-3,9-diazabicyclo[3.3.1]non-6-en-3-yl)-5-oxopentanoic acid formate salt Synthesized according to typical procedures K and E from bicyclononene AL31 and glutaric anhydride. LC-MS: $R_t$=0.90; ES+: 768.35.

Example 289

(rac.)-5-(1R*,5S*)-7-{4-[3-(2-Bromo-5-fluorophenoxy)propyl]phenyl}-6-{[2-(4-fluorophenyl)ethyl] cyclopropylcarbamoyl}-3,9-diazabicyclo[3.3.1]non-6-en-3-yl)-5-oxopentanoic acid formate salt Synthesized according to typical procedures K and E from bicyclononene AL32 and glutaric anhydride. LC-MS: $R_t$=0.89; ES+: 750.40.

Example 290

(rac.)-5-((1R*,5S*)-7-{4-[3-(2-Bromo-5-fluorophenoxy)propyl]phenyl}-6-{[2-(2-methylphenyl)ethyl] cyclopropylcarbamoyl}-3,9-diazabicyclo[3.3.1]non-6-en-3-yl)-5-oxopentanoic acid formate salt Synthesized according to typical procedures K and E from bicyclononene AL33 and glutaric anhydride. LC-MS: $R_t$=0.90; ES+: 746.43.

Example 291

(rac.)-5-{(1R*,5S*)-7-{4-[3-(2-Bromo-5-fluorophenoxy)propyl]phenyl}-6-[cyclopropyl-(3,5-dimethoxybenzyl)carbamoyl]-3,9-diazabicyclo[3.3.1]non-6-en-3-yl}-5-oxopentanoic acid formate salt Synthesized according to typical procedures K and E from bicyclononene AL35 and glutaric anhydride. LC-MS: $R_t$=0.88; ES+: 778.40.

Example 292

(rac.)-5-((1R*,5S*)-7-{4-[3-(2-Bromo-5-fluorophenoxy)propyl]phenyl}-6-{[2-(4-methylphenyl)ethyl] cyclopropylcarbamoyl}-3,9-diazabicyclo[3.3.1]non-6-en-3-yl)-5-oxopentanoic acid formate salt Synthesized according to typical procedures K and E from bicyclononene AL36 and glutaric anhydride. LC-MS: $R_t$=0.90; ES+: 746.43.

Example 293

(rac.)-5-{(1R*,5S*)-7-{4-[3-(2-Bromo-5-fluorophenoxy)propyl]phenyl}-6-[(2-chlorobenzyl)ethylcarbamoyl]-3,9-diazabicyclo[3.3.1]non-6-en-3-yl}-5-oxopentanoic acid methyl ester formate salt Synthesized according to typical procedures A and E from bicyclononene AL22 and glutaric acid monomethylester chloride. LC-ES: $R_t$=0.94; ES+: 754.37.

Example 294

(rac.)-5-{(1R*,5S*)-7-{4-[3-(2-Bromo-5-fluorophenoxy)propyl]phenyl}-6-[cyclopropyl-(2-fluorobenzyl)carbamoyl]-3,9-diazabicyclo[3.3.1]non-6-en-3-yl}-5-oxopentanoic acid methyl ester formate salt Synthesized according to typical procedures A and E from bicyclononene AL23 and glutaric acid monomethylester chloride. LC-MS: $R_t$=0.93; ES+: 750.39.

Example 295

(rac.)-5-{(1R*,5S*)-7-{4-[3-(2-Bromo-5-fluorophenoxy)propyl]phenyl}-6-[cyclopropyl-(3-trifluoromethylbenzyl)carbamoyl]-3,9-diazabicyclo[3.3.1]-non-6-en-3-yl}-5-oxopentanoic acid methyl ester formate salt Synthesized according to typical procedures A and E from bicyclononene AL24 and glutaric acid monomethylester chloride. LC-MS: $R_t$=0.96; ES+: 801.40.

Example 296

(rac.)-5-{(1R*,5S*)-7-{4-[3-(2-Bromo-5-fluorophenoxy)propyl]phenyl}-6-[cyclopropyl-(2-methylbenzyl)carbamoyl]-3,9-diazabicyclo[3.3.1]non-6-en-3-yl}-5-oxopentanoic acid methyl ester formate salt Synthesized according to typical procedures A and E from bicyclononene AL25 and glutaric acid monomethylester chloride. LC-MS: $R_t$=0.94; ES+: 746.43.

Example 297

(rac.)-5-((1R*,5S*)-7-{4-[3-(2-Bromo-5-fluorophenoxy)propyl]phenyl}-6-{cyclopropyl-[2-(4-methoxyphenoxy)ethyl]carbamoyl}-3,9-diazabicyclo[3.3.1]non-6-en-3-yl)-5-oxopentanoic acid methyl ester formate salt Synthesized according to typical procedures A and E from bicyclononene AL26 and glutaric acid monomethylester chloride. LC-MS: $R_t$=0.93; ES+: 793.40.

Example 298

(rac.)-5-((1R*,5S*)-7-{4-[3-(2-Bromo-5-fluorophenoxy)propyl]phenyl}-6-{cyclopropyl-[2-(3-methylphenoxy)ethyl]carbamoyl}-3,9-diazabicyclo[3.3.1]-non-6-en-3-yl)-5-oxopentanoic acid methyl ester formate salt Synthesized according to typical procedures A and E from bicyclononene AL27 and glutaric acid monomethylester chloride. LC-MS: $R_t$=0.95; ES+: 776.41.

Example 299

(rac.)-5-((1R*,5S*)-7-{4-[3-(2-Bromo-5-fluorophenoxy)propyl]phenyl}-6-{cyclopropyl-[2-(3,4-dimethylphenoxy)ethyl]carbamoyl}-3,9-diazabicyclo-[3.3.1]non-6-en-3-yl)-5-oxopentanoic acid methyl ester formate salt Synthesized according to typical procedures A and E from bicyclononene AL28 and glutaric acid monomethylester chloride. LC-MS: $R_t$=0.97; ES+: 791.40.

Example 300

(rac.)-5-[(1R*,5S*)-7-{4-[3-(2-Bromo-5-fluorophe-noxy)propyl]phenyl}-6-(cyclopropylphenethylcar-bamoyl)-3,9-diazabicyclo[3.3.1]non-6-en-3-yl]-5-oxopentanoic acid methyl ester formate salt Synthesized according to typical procedures A and E from bicyclononene AL29 and glutaric acid monomethylester chloride. LC-MS: $R_t$=0.93; ES+: 746.43

Example 301

(rac.)-5-((1R*,5S*)-7-{4-[3-(2-Bromo-5-fluorophe-noxy)propyl]phenyl}-6-{[2-(2-chlorophenyl)ethyl]cyclopropylcarbamoyl}-3,9-diazabicyclo[3.3.1]non-6-en-3-yl)-5-oxopentanoic acid methyl ester formate salt Synthesized according to typical procedures A and E from bicyclononene AL30 and glutaric acid monomethylester chloride. LC-MS: $R_t$=0.95; ES+: 780.38.

Example 302

(rac.)-5-((1R*,5S*)-7-{4-[3-(2-Bromo-5-fluorophe-noxy)propyl]phenyl}-6-{[2-(2,3-difluorophenyl)ethyl]cyclopropylcarbamoyl}-3,9-diazabicyclo[3.3.1]non-6-en-3-yl)-5-oxopentanoic acid methyl ester formate salt Synthesized according to typical procedures A and E from bicyclononene AL31 and glutaric acid monomethylester chloride. LC-MS: $R_t$=0.94; ES+: 782.40.

Example 303

(rac.)-5-((1R*,5S*)-7-{4-[3-(2-Bromo-5-fluorophe-noxy)propyl]phenyl}-6-{[2-(4-fluorophenyl)ethyl]cyclopropylcarbamoyl}-3,9-diazabicyclo[3.3.1]non-6-en-3-yl)-5-oxopentanoic acid methyl ester formate salt Synthesized according to typical procedures A and E from bicyclononene AL32 and glutaric acid monomethylester chloride. LC-MS: $R_t$=0.94; ES+: 764.41.

Example 304

(rac.)-5-((1R*,5S*)-7-{4-[3-(2-Bromo-5-fluorophe-noxy)propyl]phenyl}-6-{[2-(2-methylphenyl)ethyl]cyclopropylcarbamoyl}-3,9-diazabicyclo[3.3.1]non-6-en-3-yl)-5-oxopentanoic acid methyl ester Synthesized according to typical procedures A and E from bicyclononene AL33 and glutaric acid monomethylester chloride. LC-MS: $R_t$=0.95; ES+: 760.43.

Example 305

(rac.)-5-{(1R*,5S*)-7-{4-[3-(2-Bromo-5-fluorophe-noxy)propyl]phenyl}-6-[cyclopropyl-(3,5-dimethoxybenzyl)carbamoyl]-3,9-diazabicyclo[3.3.1]non-6-en-3-yl}-5-oxopentanoic acid methyl ester formate salt Synthesized according to typical procedures A and E from bicyclononene AL35 and glutaric acid monomethylester chloride. LC-MS: $R_t$=0.93; ES+: 793.40.

Example 306

(rac.)-5-((1R*,5S*)-7-{4-[3-(2-Bromo-5-fluorophe-noxy)propyl]phenyl}-6-{[2-(4-methylphenyl)ethyl]cyclopropylcarbamoyl}-3,9-diazabicyclo[3.3.1]non-6-en-3-yl)-5-oxopentanoic acid methyl ester formate salt Synthesized according to typical procedures A and E from bicyclononene AL36 and glutaric acid monomethylester chloride. LC-MS: $R_t$=0.95; ES+: 760.42.

Example 307

(rac.)-5-{(1R*,5S*)-7-{4-[3-(2-Bromo-5-fluorophe-noxy)propyl]phenyl}-6-[(2-chlorobenzyl)ethylcar-bamoyl]-3,9-diazabicyclo[3.3.1]non-6-en-3-yl}-2,2-di-methyl-5-oxopentanoic acid formate salt Synthesized according to typical procedures K and E from bicyclononene AL22 and 2,2-dimethylglutaric anhydride. LC-MS: $R_t$=0.93; ES+: 768.36.

Example 308

(rac.)-5-{(1R*,5S*)-7-{4-[3-(2-Bromo-5-fluorophe-noxy)propyl]phenyl}-6-[cyclopropyl-(2-fluoroben-zyl)carbamoyl]-3,9-diazabicyclo[3.3.1]non-6-en-3-yl}-2,2-dimethyl-5-oxopentanoic acid formate salt Synthesized according to typical procedures K and E from bicyclononene AL23 and 2,2-dimethylglutaric anhydride. LC-MS: $R_t$=0.92; ES+: 764.39.

Example 309

(rac.)-5-{(1R*,5S*)-7-{4-[3-(2-Bromo-5-fluorophe-noxy)propyl]phenyl}-6-[cyclopropyl-(3-trifluorom-ethylbenzyl)carbamoyl]-3,9-diazabicyclo[3.3.1]-non-6-en-3-yl}-2,2-dimethyl-5-oxopentanoic acid formate salt Synthesized according to typical procedures K and E from bicyclononene AL24 and 2,2-dimethylglutaric anhydride. LC-MS: $R_t$=0.94; ES+: 815.40.

Example 310

(rac.)-{(1R*,5S*)-7-{4-[3-(2-Bromo-5-fluorophenoxy)propyl]phenyl}-6-[cyclopropyl-(2-methylbenzyl)carbamoyl]-3,9-diazabicyclo[3.3.1]non-6-en-3-yl}-2,2-dimethyl-5-oxopentanoic acid formate salt Synthesized according to typical procedures K and E from bicyclononene AL25 and 2,2-dimethylglutaric anhydride. LC-MS: $R_t$=0.93; ES+: 760.43.

Example 311

(rac.)-5-((1R*,5S*)-7-{4-[3-(2-Bromo-5-fluorophenoxy)propyl]phenyl}-6-{cyclopropyl-[2-(4-methoxyphenoxy)ethyl]-carbamoyl}-3,9-diazabicyclo-[3.3.1]non-6-en-3-yl)-2,2-dimethyl-5-oxopentanoic acid formate salt Synthesized according to typical procedures K and E from bicyclononene AL26 and 2,2-dimethylglutaric anhydride. LC-MS: $R_t$=0.92; ES+: >805.

Example 312

(rac.)-5-(1R*,5S*)-7-{4-[3-(2-Bromo-5-fluorophenoxy)propyl]phenyl}-6-{cyclopropyl-[2-(3-methylphenoxy)ethyl]-carbamoyl}-3,9-diazabicyclo[3.3.1]-non-6-en-3-yl)-2,2-dimethyl-5-oxopentanoic acid formate salt Synthesized according to typical procedures K and E from bicyclononene AL27 and 2,2-dimethylglutaric anhydride. LC-MS: $R_t$=0.94; ES+: 790.47.

Example 313

(rac.)-5-((1R*,5S*)-7-{4-[3-(2-Bromo-5-fluorophenoxy)propyl]phenyl}-6-{cyclopropyl-[2-(3,4-dimethylphenoxy)ethyl]-carbamoyl}-3,9-diazabicyclo-[3.3.1]non-6-en-3-yl)-2,2-dimethyl-5-oxopentanoic acid formate salt Synthesized according to typical procedures K and E from bicyclononene AL28 and 2,2-dimethylglutaric anhydride. LC-MS: $R_t$=0.95; ES+: 805.4.

Example 314

(rac.)-5-[(1R*,5S*)-7-{4-[3-(2-Bromo-5-fluorophenoxy)propyl]phenyl}-6-(cyclopropylphenethylcarbamoyl)-3,9-diazabicyclo[3.3.1]non-6-en-3-yl]-2,2-dimethyl-5-oxopentanoic acid formate salt Synthesized according to typical procedures K and E from bicyclononene AL29 and 2,2-dimethylglutaric anhydride. LC-MS: $R_t$=0.92; ES+: 760.43.

Example 315

(rac.)-5-((1R*,5S*)-7-{4-[3-(2-Bromo-5-fluorophenoxy)propyl]phenyl}-6-{[2-(2-chlorophenyl)ethyl]cyclopropylcarbamoyl}-3,9-diazabicyclo[3.3.1]non-6-en-3-yl)-2,2-dimethyl-5-oxopentanoic acid formate salt Synthesized according to typical procedures K and E from bicyclononene AL30 and 2,2-dimethylglutaric anhydride. LC-MS: $R_t$=0.94; ES+: 794.41.

Example 316

(rac.)-5-((1R*,5S*)-7-{4-[3-(2-Bromo-5-fluorophenoxy)propyl]phenyl}-6-{[2-(2,3-difluorophenyl)ethyl]cyclopropylcarbamoyl}-3,9-diazabicyclo[3.3.1]non-6-en-3-yl)-2,2-dimethyl-5-oxopentanoic acid formate salt Synthesized according to typical procedures K and E from bicyclononene AL31 and 2,2-dimethylglutaric anhydride. LC-MS: $R_t$=0.93; ES+: 796.44.

Example 317

(rac.)-5-((1R*,5S*)-7-{4-[3-(2-Bromo-5-fluorophenoxy)propyl]phenyl}-6-{[2-(4-fluorophenyl)ethyl]cyclopropylcarbamoyl}-3,9-diazabicyclo[3.3.1]non-6-en-3-yl)-2,2-dimethyl-5-oxopentanoic acid formate salt Synthesized according to typical procedures K and E from bicyclononene AL32 and 2,2-dimethylglutaric anhydride. LC-MS: $R_t$=0.93; ES+: 778.42.

Example 318

(rac.)-5-((1R*,5S*)-7-{4-[3-(2-Bromo-5-fluorophenoxy)propyl]phenyl}-6-{[2-(2-methylphenyl)ethyl]cyclopropylcarbamoyl}-3,9-diazabicyclo[3.3.1]non-6-en-3-yl)-2,2-dimethyl-5-oxopentanoic acid formate salt Synthesized according to typical procedures K and E from bicyclononene AL33 and 2,2-dimethylglutaric anhydride. LC-MS: $R_t$=0.94; ES+: 774.46.

Example 319

(rac.)-5-{(1R*,5S*)-7-{4-[3-(2-Bromo-5-fluorophenoxy)propyl]phenyl}-6-[cyclopropyl-(3,5-dimethoxybenzyl)carbamoyl]-3,9-diazabicyclo[3.3.1]non-6-en-3-yl}-2,2-dimethyl-5-oxopentanoic acid formate salt Synthesized according to typical procedures K and E from bicyclononene AL35 and 2,2-dimethylglutaric anhydride. LC-MS: $R_t$=0.92; ES+: >805.

Example 320

(rac.)-5-((1R*,5S*)-7-{4-[3-(2-Bromo-5-fluorophenoxy)propyl]phenyl}-{[2-(4-methylphenyl)ethyl]cyclopropylcarbamoyl}-3,9-diazabicyclo[3.3.1]non-6-en-3-yl)-2,2-dimethyl-5-oxopentanoic acid formate salt Synthesized according to typical procedures K and E from bicyclononene AL36 and 2,2-dimethylglutaric anhydride. LC-MS: $R_t$=0.94; ES+: 774.44.

Example 321

1:1—Mixture of (rac.)-(2R*,3S*)-4-{(1R*,5S*)-7-{4-[3-(2-bromo-5-fluorophenoxy)propyl]phenyl}-6-[(2-chlorobenzyl)ethylcarbamoyl]-3,9-diazabicyclo[3.3.1]non-6-en-3-yl}-2,3-dihydroxy-4-oxobutyric acid formate salt and (rac.)-(2S*,3R*)-4-{(1R*,5S)-7-{4-[3-(2-bromo-5-fluorophenoxy)propyl]-phenyl}-6-[(2-chlorobenzyl)ethylcarbamoyl]-3,9-diazabicyclo[3.3.1]non-6-en-3-yl}-2,3-dihydroxy-4-oxobutyric acid formate salt Synthesized according to typical procedures K and E from bicyclononene AL22 and (S,R)-2,3-dihydroxysuccinic anhydride. LC-MS: $R_t$=0.87; ES+: 758.33.

Example 322

1:1—Mixture of (rac.)-(2R*,3S*)-4-{(1R*,5S*)-7-{4-[3-(2-bromo-5-fluorophenoxy)propyl]phenyl}-6-[cyclopropyl-(2-fluorobenzyl)carbamoyl]-3,9-diazabicyclo[3.3.1]non-6-en-3-yl}-2,3-dihydroxy-4-oxobutyric acid formate salt and (rac.)-(2S*,3R*)-4-{(1R*,5S*)-7-{4-[3-(2-bromo-5-fluorophenoxy)propyl]phenyl}-6-[cyclopropyl-(2-fluorobenzyl)carbamoyl]-3,9-diazabicyclo[3.3.1]non-6-en-3-yl}-2,3-dihydroxy-4-oxobutyric acid formate salt Synthesized according to typical procedures K and E from bicyclononene AL23 and (S,R)-2,3-dihydroxysuccinic anhydride. LC-MS: $R_t$=0.85; ES+: 754.37.

Example 323

1:1—Mixture of (rac.)-(2R*,3S*)-4-{(1R*,5S*)-7-{4-[3-(2-bromo-5-fluorophenoxy)propyl]phenyl}-6-[cyclopropyl-(3-trifluoromethylbenzyl)-carbamoyl]-3,9-diazabicyclo[3.3.1]non-6-en-3-yl}-2,3-dihydroxy-4-oxobutyric acid formate salt and (rac.)-(2S*,3R*)-4-{(1R*,5S*)-7-{4-[3-(2-bromo-5-fluorophenoxy)propyl]-phenyl}-6-[cyclopropyl(3-trifluoromethylbenzyl)-carbamoyl]-3,9-diazabicyclo[3.3.1]non-6-en-3-yl}-2,3-dihydroxy-4-oxobutyric acid formate salt Synthesized according to typical procedures K and E from bicyclononene AL24 and (S,R)-2,3-dihydroxysuccinic anhydride. LC-MS: $R_t$=0.89; ES+: 805.4.

Example 324

1:1—Mixture of (rac.)-(2R*,3S*)-4-{(1R*,5S*)-7-{4-[3-(2-brom o-5-fluorophenoxy)propyl]phenyl}-6-[cyclopropyl-(2-methylbenzyl)carbamoyl]-3,9-diazabicyclo[3.3.1]non-6-en-3-yl}-2,3-dihydroxy-4-oxobutyric acid formate salt and (rac.)-(2S*,3R*)-4-{(1R*,5S*)-7-{4-[3-(2-bromo-5-fluorophenoxy)propyl]phenyl}-6-[cyclopropyl-(2-methylbenzyl)carbamoyl]-3,9-diazabicyclo-[3.3.1]non-6-en-3-yl}-2,3-dihydroxy-4-oxobutyric acid formate salt Synthesized according to typical procedures K and E from bicyclononene AL25 and (S,R)-2,3-dihydroxysuccinic anhydride. LC-MS: $R_t$=0.87; ES+: 750.39.

Example 325

1:1—Mixture of (rac.)-(2R*,3S*)-4-((1R*,5S*)-7-{4-[3-(2-bromo-5-fluorophenoxy)propyl]phenyl}-6-{cyclopropyl-[2-(4-methoxyphenoxy)ethyl]-carbamoyl}-3,9-diazabicyclo[3.3.1]non-6-en-3-yl)-2,3-dihydroxy-4-oxobutyric acid formate salt and (rac.)-(2S*,3R*)-4-((1R*,5S*)-7-{4-[3-(2-bromo-5-fluorophenoxy)propyl]phenyl}-6-{cyclopropyl-[2-(4-methoxyphenoxy)ethyl]-carbamoyl}-3,9-diazabicyclo[3.3.1]non-6-en-3-yl)-2,3-dihydroxy-4-oxobutyric acid formate salt Synthesized according to typical procedures K and E from bicyclononene AL26 and (S,R)-2,3-dihydroxysuccinic anhydride. LC-MS: $R_t$=0.86; ES+: 796.42.

Example 326

1:1—Mixture of (rac.)-(2R*,3S*)-4-((1R*,5S*)-7-{4-[3-(2-bromo-5-fluorophenoxy)propyl]phenyl}-6-{cyclopropyl-[2-(3-methylphenoxy)ethyl]-carbamoyl}-3,9-diazabicyclo[3.3.1]non-6-en-3-yl)-2,3-dihydroxy-4-oxobutyric acid formate salt and (rac.)-(2S*,3R*)-4-((1R*,5S*)-7-{4-[3-(2-bromo-5-fluorophenoxy)propyl]phenyl}-6-{cyclopropyl-[2-(3-methylphenoxy)ethyl]-carbamoyl}-3,9-diazabicyclo[3.3.1]non-6-en-3-yl)-2,3-dihydroxy-4-oxobutyric acid formate salt Synthesized according to typical procedures K and E from bicyclononene AL27 and (S,R)-2,3-dihydroxysuccinic anhydride. LC-MS: $R_t$=0.88; ES+: 780.38.

Example 327

1:1—Mixture of (rac.)-(2R*,3S*)-4-((1R*,5S*)-7-{4-[3-(2-bromo-5-fluorophenoxy)propyl]phenyl}-6-{cyclopropyl-[2-(3,4-dimethylphenoxy)ethyl]-carbamoyl}-3,9-diazabicyclo[3.3.1]non-6-en-3-yl)-2,3-dihydroxy-4-oxobutyric acid formate salt and (rac.)-(2S*,3R*)-4-((1R*,5S*)-7-{4-[3-(2-bromo-5-fluorophenoxy)-propyl]phenyl}-6-{cyclopropyl-[2-(3,4-dimethylphenoxy)-ethyl]carbamoyl}-3,9-diazabicyclo[3.3.1]non-6-en-3-yl)-2,3-dihydroxy-4-oxobutyric acid formate salt Synthesized according to typical procedures K and E from bicyclononene AL28 and (S,R)-2,3-dihydroxysuccinic anhydride. LC-MS: $R_t$=0.89; ES+: 794.44.

Example 328

1:1—Mixture of (rac.)-(2R*,3S*)-4-[(1R*,5S*)-7-{4-[3-(2-bromo-5-fluorophenoxy)propyl]phenyl}-6-(cyclopropylphenethylcarbamoyl)-3,9-diazabicyclo[3.3.1]non-6-en-3-yl]-2,3-dihydroxy-4-oxobutyric acid formate salt and (rac.)-(2S*,3R*)-4-[(1R*,5S*)-7-{4-[3-(2-bromo-5-fluorophenoxy)propyl]-phenyl}-6-(cyclopropylphenethylcarbamoyl)-3,9-diazabicyclo[3.3.1]non-6-en-3-yl]-2,3-dihydroxy-4-oxobutyric acid formate salt Synthesized according to typical procedures K and E from bicyclononene AL29 and (S,R)-2,3-dihydroxysuccinic anhydride. LC-MS: $R_t$=0.86; ES+: 750.36.

Example 329

1:1—Mixture of (rac.)-(2R*,3S*)-4-((1R*,5S*)-7-{4-[3-(2-bromo-5-fluorophenoxy)propyl]phenyl}-6-{[2-(2-chlorophenyl)ethyl]cyclopropylcarbamoyl}-3,9-diazabicyclo[3.3.1]non-6-en-3-yl)-2,3-dihydroxy-4-oxobutyric acid formate salt and (rac.)-(2S*,3R*)-4-((1R*,5S*)-7-{4-[3-(2-bromo-5-fluorophenoxy)propyl]-phenyl}-6-{[2-(2-chlorophenyl)ethyl]cyclopropylcarbamoyl}-3,9-diazabicyclo[3.3.1]non-6-en-3-yl)-2,3-dihydroxy-4-oxobutyric acid formate salt Synthesized according to typical procedures K and E from bicyclononene AL30 and (S,R)-2,3-dihydroxysuccinic anhydride. LC-MS: $R_t$=0.88; ES+: 784.34.

Example 330

1:1—Mixture of (rac.)-(2R*,3S*)-4-((1R*,5S*)-7-{4-[3-(2-bromo-5-fluorophenoxy)propyl]phenyl}-6-{[2-(4-fluorophenyl)ethyl]cyclopropylcarbamoyl}-3,9-diazabicyclo[3.3.1]non-6-en-3-yl)-2,3-dihydroxy-4-oxobutyric acid formate salt and (rac.)-(2S*,3R*)-4-((1R*,5S*)-7-{4-[3-(2-bromo-5-fluorophenoxy)propyl]-phenyl}-6-{[2-(4-fluorophenyl)ethyl]cyclopropylcarbamoyl}-3,9-diazabicyclo[3.3.1]non-6-en-3-yl)-2,3-dihydroxy-4-oxobutyric acid formate salt Synthesized according to typical procedures K and E from bicyclononene AL32 and (S,R)-2,3-dihydroxysuccinic anhydride. LC-MS: $R_t$=0.85; ES+: 768.34.

Example 331

1:1—Mixture of (rac.)-(2R*,3S*)-4-((1R*,5S*)-7-{4-[3-(2-bromo-5-fluorophenoxy)propyl]phenyl}-6-{[2-(2-methylphenyl)ethyl]cyclopropylcarbamoyl}-3,9-diazabicyclo[3.3.1]non-6-en-3-yl)-2,3-dihydroxy-4-oxobutyric acid formate salt and (rac.)-(2S*,3R*)-4-((1R*,5S*)-7-{4-[3-(2-bromo-5-fluorophenoxy)propyl]phenyl}-6-{[2-(2-methylphenyl)ethyl]cyclopropylcarbamoyl}-3,9-diazabicyclo-[3.3.1]non-6-en-3-yl)-2,3-dihydroxy-4-oxobutyric acid formate salt Synthesized according to typical procedures K and E from bicyclononene AL33 and (S,R)-2,3-dihydroxysuccinic anhydride. LC-MS: $R_t$=0.88; ES+: 764.41.

Example 332

1:1—Mixture of (rac.)-(2R*,3S*)-4-{(1R*,5S*)-7-{4-[3-(2-bromo-5-fluorophenoxy)propyl]phenyl}-6-[cyclopropyl-(3,5-dimethoxybenzyl)carbamoyl]-3,9-diazabicyclo[3.3.1]non-6-en-3-yl}-2,3-dihydroxy-4-oxobutyric acid formate salt and (rac.)-(2S*,3R*)-4-{(1R*,5S*)-7-{4-[3-(2-bromo-5-fluorophenoxy)propyl]phenyl}-6-cyclopropyl-(3,5-dimethoxybenzyl)carbamoyl]-3,9-diazabicyclo[3.3.1]non-6-en-3-yl}-2,3-dihydroxy-4-oxobutyric acid formate salt Synthesized according to typical procedures K and E from bicyclononene AL35 and (S,R)-2,3-dihydroxysuccinic anhydride. LC-MS: $R_t$=0.86; ES+: 797.38.

Example 333

1:1—Mixture of (rac.)-(2R*,3S*)-4-((1R*,5*S)-7-{4-[3-(2-bromo-5-fluorophenoxy)propyl]phenyl}-6-{[2-(4-methylphenyl)ethyl]cyclopropylcarbamoyl}-3,9-diazabicyclo[3.3.1]non-6-en-3-yl)-2,3-dihydroxy-4-oxobutyric acid formate salt and (rac.)-(2S*,3R*)-4-((1R*,5S*)-7-{4-[3-(2-bromo-5-fluorophenoxy)propyl]-phenyl}6-{[2-(4-methylphenyl)ethyl]cyclopropylcarbamoyl}-3,9-diazabicyclo-[3.3.1]non-6-en-3-yl)-2,3-dihydroxy-4-oxobutyric acid formate salt Synthesized according to typical procedures K and E from bicyclononene AL36 and (S,R)-2,3-dihydroxysuccinic anhydride. LC-MS: $R_t$=0.87; ES+: 764.38.

Example 334

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid (2-chlorobenzyl)ethylamide formate salt Synthesized according to typical procedures G and E from bicyclononene AL22 and 4-carbamoylbutyric acid. LC-MS: $R_t$=0.87; ES+: 739.49.

Example 335

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid cyclopropyl-(2-fluorobenzyl)amide formate salt Synthesized according to typical procedures G and E from bicyclononene AL23 and 4-carbamoylbutyric acid. LC-MS: $R_t$=0.86; ES+: 735.50.

Example 336

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid cyclopropyl-(2-methylbenzyl)amide formate salt Synthesized according to typical procedures G and E from bicyclononene AL25 and 4-carbamoylbutyric acid. LC-MS: $R_t$=0.88; ES+: 731.55.

Example 337

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid cyclopropyl-[2-(4-methoxyphenoxy)ethyl]amide formate salt Synthesized according to typical procedures G and E from bicyclononene AL26 and 4-carbamoylbutyric acid. LC-MS: $R_t$=0.86; ES+: 777.52.

Example 338

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid cyclopropyl-[2-(3,4-dimethylphenoxy)ethyl]amide formate salt Synthesized according to typical procedures G and E from bicyclononene AL28 and 4-carbamoylbutyric acid. LC-MS: $R_t$=0.90; ES+: 775.55.

Example 339

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid [2-(2-chlorophenyl)ethyl]cyclopropylamide formate salt Synthesized according to typical procedures G and E from bicyclononene AL30 and 4-carbamoylbutyric acid. LC-MS: $R_t$=0.89; ES+: 765.46.

Example 340

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid [2-(2,3-difluorophenyl)ethyl]cyclopropylamide formate salt Synthesized according to typical procedures G and E from bicyclononene AL31 and 4-carbamoylbutyric acid. LC-MS: $R_t$=0.88; ES+: 767.48.

Example 341

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid [2-(4-fluorophenyl)ethyl]cyclopropylamide formate salt Synthesized according to typical procedures G and E from bicyclononene AL32 and 4-carbamoylbutyric acid. LC-MS: $R_t$=0.87; ES+: 749.52.

Example 342

(rac.)-(1R*,5*S)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid [2-(2-methylphenyl)ethyl]cyclopropylamide formate salt Synthesized according to typical procedures G and E from bicyclononene AL33 and 4-carbamoylbutyric acid. LC-MS: $R_t$=0.89; ES+: 745.54.

Example 343

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid cyclopropyl-(3,5-dimethoxybenzyl)amide formate salt Synthesized according to typical procedures G and B from bicyclononene AL35 and 4-carbamoylbutyric acid. LC-MS: $R_t$=0.86; ES+: 777.53.

Example 344

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid [2-(4-methylphenyl)ethyl]cyclopropylamide formate salt Synthesized according to typical procedures G and E from bicyclononene AL36 and 4-carbamoylbutyric acid. LC-MS: $R_t$=0.88; ES+: 745.54.

Example 345

1:1—Mixture of (rac.)-(3R*)-5-{(1R*,5S*)-7-{4-[3-(2-bromo-5-fluorophenoxy)-propyl]phenyl}-6-[(2-chlorobenzyl)ethylcarbamoyl]-3,9-diazabicyclo[3.3.1]-non-6-en-3-yl}-3-hydroxy-5-oxopentanoic acid formate salt and (rac.)-(3S*)-5-{(1R*,5S*)-7-{4-[3-(2-bromo-5-fluorophenoxy)-propyl]phenyl}-6-[(2-chlorobenzyl)ethylcarbamoyl]-3,9-diazabicyclo[3.3.1]non-6-en-3-yl}-3-hydroxy-5-oxopentanoic acid formate salt Synthesized according to typical procedures K, E and L from bicyclononene AL22 and 3-(tert-butyldimethylsilyloxy)glutaric anhydride. LC-MS: $R_t$=0.87; ES+: 756.44.

Example 346

1:1—Mixture of (rac.)-(3R*)-5-{(1R*,5S*)-7-{4-[3-(2-bromo-5-fluorophenoxy)-propyl]phenyl}-6-[cyclopropyl-(2-fluorobenzyl)carbamoyl]-3,9-diazabicyclo-[3.3.1]non-6-en-3-yl}-3-hydroxy-5-oxopentanoic acid formate salt and (rac.)-(3S*)-5-{(1R*,5S*)-7-{4-[3-(2-bromo-5-fluorophenoxy)propyl]phenyl}-6-[cyclopropyl-(2-fluorobenzyl)carbamoyl]-3,9-diazabicyclo[3.3.1]non-6-en-3-yl}-3-hydroxy-5-oxopentanoic acid formate salt Synthesized according to typical procedures K, E and L from bicyclononene AL23 and 3-(tert-butyldimethylsilyloxy)glutaric anhydride. LC-MS: $R_t$=0.86; ES+: 752.46.

Example 347

1:1—Mixture of (rac.)-(3R*)-5-{(1R*,5S*)-7-{4-[3-(2-bromo-5-fluorophenoxy)-propyl]phenyl}-6-[cyclopropyl-(3-trifluoromethylbenzyl)carbamoyl]-3,9-diazabicyclo[3.3.1]non-6-en-3-yl}-3-hydroxy-5-oxopentanoic acid formate salt and (rac.)-(3S*)-5-{(1R*,5S*)-7-{4-[3-(2-bromo-5-fluorophenoxy)propyl]-phenyl}-6-[cyclopropyl-(3-trifluoromethylbenzyl)carbamoyl]-3,9-diazabicyclo[3.3.1]non-6-en-3-yl}-3-hydroxy-5-oxopentanoic acid formate salt Synthesized according to typical procedures K, E and L from bicyclononene AL24 and 3-(tert-butyldimethylsilyloxy)glutaric anhydride. LC-MS: $R_t$=0.89; ES+: 803.40.

Example 348

1:1—Mixture of (rac.)-(3R*)-5-{(1R*,5S*)-7-{4-[3-(2-bromo-5-fluorophenoxy)-propyl]phenyl}-6-[cyclopropyl-(2-methylbenzyl)carbamoyl]-3,9-diazabicyclo[3.3.1]non-6-en-3-yl}-3-hydroxy-5-oxopentanoic acid formate salt and (rac.)-(3S*)-5-{(1R*,5S*)-7-{4-[3-(2-bromo-5-fluorophenoxy)propyl]phenyl}-6-[cyclopropyl-(2-methylbenzyl)carbamoyl]-3,9-diazabicyclo-[3.3.1]non-6-en-3-yl}-3-hydroxy-5-oxopentanoic acid formate salt Synthesized according to typical procedures K, E and L from bicyclononene AL25 and 3-(tert-butyldimethylsilyloxy)glutaric anhydride. LC-MS: $R_t$=0.87; ES+: 748.52.

Example 349

1:1—Mixture of (rac.)-(3R*)-5-((1R*,5S*)-7-{4-[3-(2-bromo-5-fluorophenoxy)-propyl]phenyl}-6-{cyclopropyl-[2-(4-methoxyphenoxy)ethyl]carbamoyl}-3,9-diazabicyclo[3.3.1]non-6-en-3-yl)-3-hydroxy-5-oxopentanoic acid formate salt and (rac.)-(3S*)-5-((1R*,5S*)-7-{4-[3-(2-bromo-5-fluorophenoxy)propyl]-phenyl}-6-{cyclopropyl-[2-(4-methoxyphenoxy)ethyl]carbamoyl}-3,9-diazabicyclo[3.3.1]non-6-en-3-yl)-3-hydroxy-5-oxopentanoic acid formate salt Synthesized according to typical procedures K, E and L from bicyclononene AL26 and 3-(tert-butyldimethylsilyloxy)glutaric anhydride. LC-MS: $R_t$=0.86; ES+: 794.40.

Example 350

1:1—Mixture of (rac.)-(3R*)-5-(1R*,5S*)-7-{4-[3-(2-bromo-5-fluorophenoxy)-propyl]phenyl}-6-{cyclopropyl-[2-(3-methylphenoxy)ethyl]carbamoyl}-3,9-diazabicyclo[3.3.1]non-6-en-3-yl)-3-hydroxy-5-oxopentanoic acid formate salt and (rac.)-(3S*)-5-(1R*,5S*)-7-{4-[3-(2-bromo-5-fluorophenoxy)propyl]-phenyl}-6-{cyclopropyl-[2-(3-methylphenoxy)ethyl]carbamoyl}-3,9-diazabicyclo[3.3.1]non-6-en-3-yl)-3-hydroxy-5-oxopentanoic acid formate salt Synthesized according to typical procedures K, E and L from bicyclononene AL27 and 3-(tert-butyldimethylsilyloxy)glutaric anhydride. LC-MS: $R_t$=0.89; ES+: 778.52.

Example 351

1:1—Mixture of (rac.)-(3R*)-5-((1R*,5S*)-7-{4-[3-(2-bromo-5-fluorophenoxy)-propyl]phenyl}-6-{cyclopropyl-[2-(3,4-dimethylphenoxy)ethyl]carbamoyl}-3,9-diazabicyclo[3.3.1]non-6-en-3-yl)-3-hydroxy-5-oxopentanoic acid formate salt and (rac.)-(3S*)-5-((1R*,5S*)-7-{4-[3-(2-bromo-5-fluorophenoxy)propyl]-phenyl}-6-{cyclopropyl-[2-(3,4-dimethylphenoxy)ethyl]carbamoyl}-3,9-diazabicyclo[3.3.1]-non-6-en-3-yl)-3-hydroxy-5-oxopentanoic acid formate salt Synthesized according to typical procedures K, E and L from bicyclononene AL28 and 3-(tert-butyldimethylsilyloxy)glutaric anhydride. LC-MS: $R_t$=0.90; ES+: 792.42.

Example 352

1:1—Mixture of (rac.)-(3R*)-5-[(1R*,5S)-7-{4-[3-(2-bromo-5-fluorophenoxy)-propyl]phenyl}-6-(cyclopropylphenethylcarbamoyl)-3,9-diazabicyclo[3.3.1]-non-6-en-3-yl]-3-hydroxy-5-oxopentanoic acid formate salt and (rac.)-(3R*)-5-[(1R*,5S*)-7-{4-[3-(2-bromo-5-fluorophenoxy)propyl]phenyl}-6-(cyclo-propylphenethylcarbamoyl)-3,9-diazabicyclo[3.3.1]non-6-en-3-yl]-3-hydroxy-5-oxopentanoic acid formate salt Synthesized according to typical procedures K, E and L from bicyclononene AL29 and 3-(tert-butyldimethylsilyloxy)glutaric anhydride. LC-MS: $R_t$=0.86; ES+: 748.50.

Example 353

1:1—Mixture of (rac.)-(3R*)-5-((1R*,5S*)-7-{4-[3-(2-bromo-5-fluorophenoxy)-propyl]phenyl}-6-{[2-(2-chlorophenyl)ethyl]cyclopropylcarbamoyl}-3,9-diazabicyclo[3.3.1]non-6-en-3-yl)-3-hydroxy-5-oxopentanoic acid formate salt and (rac.)-(3R*)-5-((1R*,5S*)-7-{4-[3-(2-bromo-5-fluorophenoxy)propyl]-phenyl}-6-{[2-(2-chlorophenyl)ethyl]cyclopropylcarbamoyl}-3,9-diazabicyclo[3.3.1]non-6-en-3-yl)-3-hydroxy-5-oxopentanoic acid formate salt Synthesized according to typical procedures K, E and L from bicyclononene AL30 and 3-(tert-butyldimethylsilyloxy)glutaric anhydride. LC-MS: $R_t$=0.88; ES+: 782.49.

Example 354

1:1—Mixture of (rac.)-(3R*)-5-((1R*,5S*)-7-{4-[3-(2-bromo-5-fluorophenoxy)-propyl]phenyl}-6-{[2-(2,3-difluorophenyl)ethyl]cyclopropylcarbamoyl}-3,9-diazabicyclo[3.3.1]non-6-en-3-yl)-3-hydroxy-5-oxopentanoic acid formate salt and (rac.)-(3R*)-5-((1R*,5S*)-7-{4-[3-(2-bromo-5-fluorophenoxy)propyl]-phenyl}-6-{[2-(2,3-difluorophenyl)ethyl]cyclopropylcarbamoyl}-3,9-diazabicyclo[3.3.1]non-6-en-3-yl)-3-hydroxy-5-oxopentanoic acid formate salt Synthesized according to typical procedures K, E and L from bicyclononene AL31 and 3-(tert-butyldimethylsilyloxy)glutaric anhydride. LC-MS: $R_t$=0.88; ES+: 784.53.

Example 355

1:1—Mixture of (rac.)-(3R*)-5-((1R*,5S*)-7-{4-[3-(2-bromo-5-fluorophenoxy)-propyl]phenyl}-6-{[2-(4-fluorophenyl)ethyl]cyclopropylcarbamoyl}-3,9-diazabicyclo[3.3.1]non-6-en-3-yl)-3-hydroxy-5-oxopentanoic acid formate salt and (rac.)-(3R*)-5-((1R*,5S*)-7-{4-[3-(2-bromo-5-fluorophenoxy)propyl]phenyl}-6-{[2-(4-fluorophenyl)ethyl]cyclopropylcarbamoyl}-3,9-diazabicyclo[3.3.1]-non-6-en-3-yl)-3-hydroxy-5-oxopentanoic acid formate salt Synthesized according to typical procedures K, E and L from bicyclononene AL32 and 3-(tert-butyldimethylsilyloxy)glutaric anhydride. LC-MS: $R_t$=0.87; ES+: 766.47.

Example 356

1:1—Mixture of (rac.)-(3R*)-5-((1R*,5S*)-7-{4-[3-(2-bromo-5-fluorophenoxy)-propyl]phenyl}-6-{[2-(2-methylphenyl)ethyl]cyclopropylcarbamoyl}-3,9-diazabicyclo[3.3.1]non-6-en-3-yl)-3-hydroxy-5-oxopentanoic acid formate salt and (rac.)-(3R*)-5-((1R*,5S*)-7-{4-[3-(2-bromo-5-fluorophenoxy)propyl]-phenyl}-6-{[2-(2-methylphenyl)ethyl]cyclopropylcarbamoyl}-3,9-diazabicyclo[3.3.1]non-6-en-3-yl)-3-hydroxy-5-oxopentanoic acid formate salt Synthesized according to typical procedures K, E and L from bicyclononene AL33 and 3-(tert-butyldimethylsilyloxy)glutaric anhydride. LC-MS: $R_t$=0.88; ES+: 762.55.

Example 357

1:1—Mixture of (rac.)-(3R*)-5-{(1R*,5S*)-7-{4-[3-(2-bromo-5-fluorophenoxy)-propyl]phenyl}-6-[cyclopropyl-(3,5-dimethoxybenzyl)carbamoyl]-3,9-diazabicyclo[3.3.1]non-6-en-3-yl}-3-hydroxy-5-oxopentanoic acid formate salt and (rac.)-(3S*)-5-{(1R*,5S*)-7-4-[3-(2-bromo-5-fluorophenoxy)propyl]phenyl}-6-[cyclopropyl-(3,5-dimethoxybenzyl)carbamoyl]-3,9-diazabicyclo-[3.3.1]non-6-en-3-yl}-3-hydroxy-5-oxopentanoic acid formate salt Synthesized according to typical procedures K, E and L from bicyclononene AL35 and 3-(tert-butyldimethylsilyloxy)glutaric anhydride. LC-MS: $R_t$=0.86; ES+: 794.38.

Example 358

1:1—Mixture of (rac.)-(3R*)-5-((1R*,5S*)-7-{4-[3-(2-bromo-5-fluorophenoxy)-propyl]phenyl}-6-{[2-(4-methylphenyl)ethyl]cyclopropylcarbamoyl}-3,9-diazabicyclo[3.3.1]non-6-en-3-yl)-3-hydroxy-5-oxopentanoic acid formate salt and (rac.)-(3R*)-5-((1R*,5S*)-7-{4-[3-(2-bromo-5-fluorophenoxy)propyl]-phenyl}-6-{[2-(4-methylphenyl)ethyl]cyclopropylcarbamoyl}-3,9-diazabicyclo[3.3.1]non-6-en-3-yl)-3-hydroxy-5-oxopentanoic acid formate salt Synthesized according to typical procedures K, E and L from bicyclononene AL36 and 3-(tert-butyldimethylsilyloxy)glutaric anhydride. LC-MS: $R_t$=0.88; ES+: 762.55.

Example 359

1:1—Mixture of (rac.)-(3R*)-5-((1R*,5S*)-6-{cyclopropyl-[2-(2-hydroxyethyl)benzyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid formate salt and (rac.)-(3S*)-5-((1R*,5S)-6-{cyclopropyl-[2-(2-hydroxyethyl)benzyl]-carbamoyl}-7-{4-[3-(2,3,6-trifluorophenoxy)propyl]phenyl}-3,9-diazabicyclo-[3.3.1]non-6-en-3-yl)-3-hydroxy-5-oxopentanoic acid formate salt Synthesized according to typical procedures K, E and L from bicyclononene AL19 and 3-(tert-butyldimethylsilyloxy)glutaric anhydride. LC-MS: $R_t$=0.81; ES+: 736.54.

Example 360

(rac.)-(1R*,5S*)-3-Acetyl-7-{4-[2-(2,3,5-trimethylphenoxy)ethyl]phenyl}-3,9-diazabicyclo[3.3.1] non-6-ene-6-carboxylic acid (2-chlorobenzyl)cyclopropyl-amide formate salt Synthesized according to typical procedures A and E from bicyclononene AL38 and acetyl chloride. LC-MS: $R_t$=0.93; ES+: 612.52.

Example 361

(rac.)-(1R*,5S*)-3-Acetyl-7-{4-[2-(2,3,5-trimethylphenoxy)ethyl]phenyl}-3,9-diazabicyclo[3.3.1] non-6-ene-6-carboxylic acid (2-chlorobenzyl)ethylamide formate salt Synthesized according to typical procedures A and E from bicyclononene AL40 and acetyl chloride. LC-MS: $R_t$=0.93; ES+: 600.50.

Example 362

(rac.)(1R*,5S*)-3-Acetyl-7-{4-[2-(2,3,5-trimethylphenoxy)ethyl]phenyl}-3,9-diazabicyclo[3.3.1] non-6-ene-6-carboxylic acid (2-fluorobenzyl)cyclopropylamibe formate salt Synthesized according to typical procedures A and E from bicyclononene AL41 and acetyl chloride. LC-MS: $R_t$=0.91; ES+: 596.53.

Example 363

(rac.)-(1R*,5S*)-3-Acetyl-7-{4-[2-(2,3,5-trimethylphenoxy)ethyl]phenyl}-3,9-diazabicyclo[3.3.1] non-6-ene-6-carboxylic acid (3-trifluoromethylbenzyl)-cyclopropylamide formate salt Synthesized according to typical procedures A and E from bicyclononene AL42 and acetyl chloride. LC-MS: $R_t$=0.95; ES+: 646.54.

Example 364

(rac.)-(1R*,5S*)-3-Acetyl-7-{4-[2-(2,3,5-trimethylphenoxy)ethyl]phenyl}-3,9-diazabicyclo[3.3.1]non-6-ene-6-carboxylic acid (2-methylbenzyl)cyclopropylamibe formate salt Synthesized according to typical procedures A and E from bicyclononene AL43 and acetyl chloride. LC-MS: $R_t$=0.93; ES+: 592.56.

Example 365

(rac.)-(1R*,5S*)-3-Acetyl-7-{4-[2-(2,3,5-trimethylphenoxy)ethyl]phenyl}-3,9-diazabicyclo[3.3.1]non-6-ene-6-carboxylic acid cyclopropyl-[2-(4-methoxyphenoxy)ethyl]amide formate salt Synthesized according to typical procedures A and E from bicyclononene AL44 and acetyl chloride. LC-MS: $R_t$=0.92; ES+: 638.58.

Example 366

(rac.)-5-((1R*,5S*)-6-[(2-Chlorobenzyl)cyclopropylcarbamoyl]-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL38 and glutaric anhydride. LC-MS: $R_t$=0.91; ES+: 684.54.

Example 367

(rac.)-5-((1R*,5S*)-6-(Benzylcyclopropylcarbamoyl)-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL39 and glutaric anhydride. LC-MS: $R_t$=0.89; ES+: 650.57.

Example 368

(rac.)-5-((1R*,5S*)-6-[(2-chlorobenzyl)ethylcarbamoyl]-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL40 and glutaric anhydride. LC-MS: $R_t$=0.90; ES+: 672.55.

Example 369

(rac.)-5-(1R*,5S*)-6-[(2-Fluorobenzyl)cyclopropylcarbamoyl]-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL41 and glutaric anhydride. LC-MS: $R_t$=0.89; ES+: 668.57.

Example 370

(rac.)-5-((1R*,5S*)-6-[(3-Trifluoromethylbenzyl)cyclopropylcarbamoyl]-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL42 and glutaric anhydride. LC-MS: $R_t$=0.92; ES+: 718.52.

Example 371

(rac.)-5-((1R*,5S*)-6-[(2-Methylbenzyl)cyclopropylcarbamoyl]-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL43 and glutaric anhydride. LC-MS: $R_t$=0.90; ES+: 664.59.

Example 372

(rac.)-5-((1R*,5S*)-6-{Cyclopropyl-[2-(4-methoxyphenoxy)ethyl]carbamoyl}-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL44 and glutaric anhydride. LC-MS: $R_t$=0.89; ES+: 710.56.

Example 373

(rac.)-5-((1R*,5S*)-6-{Cyclopropyl-[2-(3-methoxyphenoxy)ethyl]carbamoyl}-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL45 and glutaric anhydride. LC-MS: $R_t$=0.90; ES+: 710.54.

Example 374

(rac.)-5-((1R*,5S*)-6-{Cyclopropyl-[2-(3-methylphenoxy)ethyl]carbamoyl}-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL46 and glutaric anhydride. LC-MS: $R_t$=0.92; ES+: 694.57.

Example 375

(rac.)-5-((1R*,5S*)-6-[(2-Chlorobenzyl)ethylcarbamoyl]-7-{4-[2-(2,3,5-trimethylphenoxy)ethyl]phenyl}-3,9-diazabicyclo[3.3.1]non-6-en-3-yl)-5-oxopentanoic acid methyl ester formate salt Synthesized according to typical procedures A and E from bicyclononene AL40 and glutaric acid monomethylester chloride. LC-MS: $R_t$=0.96; ES+: 686.54.

Example 376

(rac.)-5-((1R*,5S*)-6-[Cyclopropyl-(2-fluorobenzyl) carbamoyl]-7-{4-[2-(2,3-trimethylphenoxy)ethyl]phenyl}-3,9-diazabicyclo[3.3.1]non-6-en-3-yl)-5-oxopentanoic acid methyl ester Synthesized according to typical procedures A and E from bicyclononene AL41 and glutaric acid monomethylester chloride. LC-MS: $R_t$=0.94; ES+: 682.57.

Example 377

(rac.)-5-((1R*,5S*)-6-[Cyclopropyl-(2-methylbenzyl)carbamoyl]-7-{4-[2-(2,3,5-trimethylphenoxy)ethyl]phenyl}-3,9-diazabicyclo[3.3.1]non-6-en-3-yl)-5-oxopentanoic acid methyl ester formate salt Synthesized according to typical procedures A and E from bicyclononene AL43 and glutaric acid monomethylester chloride. LC-MS: $R_t$=0.96; ES+: 678.61.

Example 378

(rac.)-5-((1R*,5S*)-6-[(2-Chlorobenzyl)cyclopropylcarbamoyl]-7-{4-[2-(2,3,5-trimethylphenoxy)ethyl]phenyl)-3,9-diazabicyclo[3.3.1]non-6-en-3-yl)-2,2-dimethyl-5-oxopentanoic acid formate salt Synthesized according to typical procedures K and E from bicyclononene AL38 and 2,2-dimethylglutaric anhydride. LC-MS: $R_t$=0.94; ES+: 712.51.

Example 379

(rac.)-5-((1R*,5S*)-6-(Benzylcyclopropylcarbamoyl)-7-{4-[2-(2,3,5-trimethylphenoxy)ethyl]phenyl}-3,9-diazabicyclo[3.3.1]non-6-en-3-yl)-2,2-dimethyl-5-oxopentanoic acid formate salt Synthesized according to typical procedures K and E from bicyclononene AL39 and 2,2-dimethylglutaric anhydride. LC-MS: $R_t$=0.93; ES+: 678.60.

Example 380

(rac.)-5-((1R*,5S*)-6-[(2-Chlorobenzyl)ethylcarbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid formate salt Synthesized according to typical procedures K and E from bicyclononene AL40 and 2,2-dimethylglutaric anhydride. LC-MS: $R_t$=0.94; ES+: 700.52.

Example 381

(rac.)-5-((1R*,5S*)-6-[Cyclopropyl-(2-fluorobenzyl) carbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid formate salt Synthesized according to typical procedures K and E from bicyclononene AL41 and 2,2-dimethylglutaric anhydride. LC-MS: $R_t$=0.93; ES+: 696.57.

Example 382

(rac.)-5-((1R*,5S*)-6-[Cyclopropyl-(2-methylbenzyl)carbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid formate salt Synthesized according to typical procedures K and E from bicyclononene AL43 and 2,2-dimethylglutaric anhydride. LC-MS: $R_t$=0.94; ES+: 692.60.

Example 383

1:1—Mixture of (rac.)-(3R*)-4-(1R*,5S*)-6-[cyclopropyl-(2-methylbenzyl)-carbamoyl]-7-{4-[2-(2,3,5-trimethylphenoxy)ethyl]phenyl}-3,9-diazabicyclo-[3.3.1]non-6-en-3-yl)-2,3-dihydroxy-4-oxobutyric acid formate salt and (rac.)-(3S*)-4-((1R*,5S*)-6-[cyclopropyl-(2-methylbenzyl)carbamoyl]-7-{4-[2-(2,3,5-trimethylphenoxy)ethyl]phenyl}-3,9-diazabicyclo[3.3.1]non-6-en-3-yl)-2,3-dihydroxy-4-oxobutyric acid formate salt Synthesized according to typical procedures K and E from bicyclononene AL43 and (S,R)-2,3-dihydroxysuccinic anhydride. LC-MS: $R_t$=0.87; ES+: 682.57.

Example 384

(rac.)-(1R*,5S*)-3-Carbamoylbutyryl)-7-{4-[2-(2,3,5-trimethylphenoxy)-ethyl]phenyl}-3,9-diazabicyclo[3.3.1]non-6-ene-6-carboxylic acid benzylcyclopropylamide formate salt Synthesized according to typical procedures G and E from bicyclononene AL39 and 4-carbamoylbutyric acid. LC-MS: $R_t$=0.87; ES+: 649.59.

Example 385

(rac.)-(1R*,5S*)-3-(4-Carbamoylbutyryl)-7-{4-[2-(2,3,5-trimethylphenoxy)-ethyl]phenyl}-3,9-diazabicyclo[3.3.1]non-6-ene-6-carboxylic acid (2-chlorobenzyl)ethylamide formate salt Synthesized according to typical procedures G and E from bicyclononene AL40 and 4-carbamoylbutyric acid. LC-MS: $R_t$=0.88; ES+: 671.56.

Example 386

(rac.)-(1R*,5S*)-3-(4-Carbamoylbutyryl)-7-{4-[2-(2,3,5-trimethylphenoxy)-ethyl]phenyl}-3,9-diazabicyclo[3.3.1]non-6-ene-6-carboxylic acid cyclopropyl-(2-fluorobenzyl)amide formate salt Synthesized according to typical procedures G and E from bicyclononene AL41 and 4-carbamoylbutyric acid. LC-MS: $R_t$=0.87; ES+: 667.6.

Example 387

(rac.)-(1R*,5S*)-7-{4-[3-(2-Bromo-5-fluorophenoxy)propyl]phenyl}-3,9-diazabicyclo[3.3.1]non-6-ene-6-carboxylic acid (2-chlorobenzyl)ethylamide formate salt Synthesized according to typical procedure E from bicyclononene AK22. LC-MS: $R_t$=0.84; ES+: 628.36.

Example 388

7-{4-[3-(2-Bromo-5-fluorophenoxy)propyl]phenyl}-3,9-diazabicyclo[3.3.1]-non-6-ene-6-carboxylic acid cyclopropyl-(3,5-dimethoxybenzyl)amide formate salt Synthesized according to typical procedure E from bicyclononene AK35. LC-MS: $R_t$=0.84; ES+: 666.43.

Example 389

7-{4-[3-(2-Bromo-5-fluorophenoxy)propyl]phenyl}-3,9-diazabicyclo[3.3.1]-non-6-ene-6-carboxylic acid cyclopropyl-(2-methylbenzyl)amide formate salt Synthesized according to typical procedure E from bicyclononene AK25. LC-MS: $R_t$=0.85; ES+: 618.41.

Example 390

7-{4-[3-(2-Bromo-5-fluorophenoxy)propyl]phenyl}-3,9-diazabicyclo[3.3.1]-non-6-ene-6-carboxylic acid cyclopropyl-[2-(4-methoxyphenoxy)ethyl]amide formate salt Synthesized according to typical procedure E from bicyclononene AK26. LC-MS: $R_t$=0.84; ES+: 664.43.

Example 391

1:1—Mixture of (1R,5S)-7-{4-[3-(2-bromo-5-fluorophenoxy)propyl]phenyl}-3-((2S,4R)-4-hydroxypyrrolidine-2-carbonyl)-3,9-diazabicyclo[3.3.1]non-6-ene-6-carboxylic acid cyclopropyl-(3,5-dimethoxybenzyl)amide formate salt and (1S,5R)-7-{4-[3-(2-bromo-5-fluorophenoxy)propyl]phenyl}-3-((2S,4R)-4-hydroxypyrrolidine-2-carbonyl)-3,9-diazabicyclo[3.3.1]non-6-ene-6-carboxylic acid cyclopropyl-(3,5-dimethoxybenzyl)amide formate salt Synthesized according to typical procedures G, E and L from bicyclononene AL35 and BOC-L-hydroxyproline. LC-MS: $R_t$=0.80; ES+: 777.50.

Example 392

(rac.)-5-{(1R*,5S*)-7-{4-[3-(2-Bromo-5-fluorophenoxy)propyl]phenyl}-6-[(2-chlorobenzyl)cyclopropylcarbamoyl]-3,9-diazabicyclo[3.3.1]non-6-en-3-yl}-5-oxopentanoic acid formate salt Synthesized according to typical procedures K and E from bicyclononene AL20 and glutaric anhydride. LC-MS: $R_t$=0.89; ES+: 752.43.

Example 393

(rac.)-5-{(1R*,5S*)-7-{4-[3-(2-Bromo-5-fluorophenoxy)propyl]phenyl}-6-[(2-chlorobenzyl)cyclopropylcarbamoyl]-3,9-diazabicyclo[3.3.1]non-6-en-3-yl}-5-oxopentanoic acid methyl ester formate salt Synthesized according to typical procedures A and E from bicyclononene AL20 and glutaric acid monomethylester chloride. LC-MS: $R_t$=0.95; ES+: 766.42.

Example 394

(rac.)-5-{(1R*,5S*)-7-{4-[3-(2-Bromo-5-fluorophenoxy)propyl]phenyl}-6-[(2-chlorobenzyl)cyclopropylcarbamoyl]-3,9-diazabicyclo[3.3.1]non-6-en-3-yl}-2,2-dimethyl-5-oxopentanoic acid formate salt Synthesized according to typical procedures K and E from bicyclononene AL20 and 2,2-dimethylglutaric anhydride. LC-MS: $R_t$=0.93; ES+: 780.46.

Example 395

1:1—Mixture of (rac.)-(3R*)-4-{(1R*,5S*)-7-{4-[3-(2-bromo-5-fluorophenoxy)-propyl]phenyl}-6-[(2-chlorobenzyl)cyclopropylcarbamoyl]-3,9-diazabicyclo-[3.3.1]non-6-en-3-yl}-2,3-dihydroxy-4-oxobutyric acid formate salt and (rac.)-(3S*)-4-{(1R*,5S*)-7-{4-[3-(2-bromo-5-fluorophenoxy)propyl]phenyl}-6-[(2-chlorobenzyl)cyclopropylcarbamoyl]-3,9-diazabicyclo-[3.3.1]non-6-en-3-yl}-2,3-dihydroxy-4-oxobutyric acid formate salt Synthesized according to typical procedures K and E from bicyclononene AL20 and meso-dihydroxysuccinic anhydride. LC-MS: $R_t$=0.87; ES+: 770.37.

Example 396

(rac.)-5-{(1R*,5S*)-4-[3-(2-Bromo-5-fluorophenoxy)propyl]phenyl}-3-(4-carbamoylbutyryl)-3,9-diazabicyclo[3.3.1]non-6-ene-6-carboxylic acid (2-chlorobenzyl)cyclopropylamide formate salt Synthesized according to typical procedures G and E from bicyclononene AL20 and 4-carbamoylbutyric acid. LC-MS: $R_t$=0.88; ES+: 751.44.

Example 397

(rac.)-5-((1R*,5S*)-6-(Benzylcyclopropylcarbamoyl)-7-{4-[3-(2-bromo-5-fluorophenoxy)propyl]phenyl}-3,9-diazabicyclo[3.3.1]non-6-en-3-yl)-5-oxopentanoic acid formate salt Synthesized according to typical procedures K and E from bicyclononene AL21 and glutaric anhydride. LC-MS: $R_t$=0.88; ES+: 718.46.

Example 398

(rac.)-5-((1R*,5S*)-6-(Benzylcyclopropylcarbamoyl)-7-{4-[3-(2-bromo-5-fluorophenoxy)propyl]phenyl}-3,9-diazabicyclo[3.3.1]non-6-en-3-yl)-5-oxopentanoic acid methyl ester formate salt Synthesized according to typical procedures A and E from bicyclononene AL21 and glutaric acid monomethylester chloride. LC-MS: $R_t$=0.93; ES+: 732.49.

Example 399

1:1—Mixture of (rac.)-(2R*,3S*)-4-((1R*,5S*)-6-(benzylcyclopropylcarbamoyl)-7-{4-[3-(2-bromo-5-fluorophenoxy)propyl]phenyl}-3,9-diazabicyclo[3.3.1]non-6-en-3-yl)-2,3-dihydroxy-4-oxobutyric acid formate salt and (rac.)-(2S*,3R*)-4-((1R*,5S*)-6-(benzylcyclopropylcarbamoyl)-7-{4-[3-(2-bromo-5-fluorophenoxy)propyl]phenyl}-3,9-diazabicyclo[3.3.1]non-6-en-3-yl)-2,3-dihydroxy-4-oxobutyric acid formate salt Synthesized according to typical procedures K and E from bicyclononene AL21 and (S,R)-2,3-dihydroxysuccinic anhydride. LC-MS: $R_t$=0.86; ES+: 736.43.

Example 400

(rac.)-(1R*,5S*)-7-{4-[3-(2-Bromo-5-fluorophenoxy)propyl]phenyl}-3-(4-carbamoylbutyryl)-3,9-diazabicyclo[3.3.1]non-6-ene-6-carboxylic acid benzylcyclopropylamide formate salt Synthesized according to typical procedures G and E from bicyclononene AL21 and 4-carbamoylbutyric acid. LC-MS: $R_t$=0.86; ES+: 717.46.

Example 401

1:1—Mixture of (rac.)-5-{(1R*,5S*)-7-{4-[3-(2-bromo-5-fluorophenoxy)-propyl]phenyl}-6-[((2R*)-2-hydroxy-2-phenylethyl)methylcarbamoyl]-3,9-diazabicyclo[3.3.1]non-6-en-3-yl}-5-oxopentanoic acid formate salt and (rac.)-5-{(1R*,5S*)-7-{4-[3-(2-bromo-5-fluorophenoxy)propyl]phenyl}-6-[((2S*)-2-hydroxy-2-phenylethyl)methylcarbamoyl]-3,9-diazabicyclo[3.3.1]non-6-en-3-yl}-5-oxopentanoic acid formate salt Synthesized according to typical procedures K and E from bicyclononene AL34 and glutaric anhydride. LC-MS: $R_t$=0.85; ES+: 722.46

Example 402

1:1—Mixture of (rac.)-5-{(1R*,5S*)-7-{4-[3-(2-bromo-5-fluorophenoxy)-propyl]phenyl}-6-[((2R*)-2-hydroxy-2-phenylethyl)methylcarbamoyl]-3,9-diazabicyclo[3.3.1]non-6-en-3-yl}-5-oxopentanoic acid methyl ester formate salt and (rac.)-5-{(1R*,5S*)-7-{4-[3-(2-bromo-5-fluorophenoxy)propyl]phenyl}-6-[((2S*)-2-hydroxy-2-phenylethyl)methylcarbamoyl]-3,9-diazabicycl-[3.3.1]non-6-en-3-yl}-5-oxopentanoic acid methyl ester formate salt Synthesized according to typical procedures A and E from bicyclononene AL34 and glutaric acid monomethylester chloride. LC-MS: $R_t$=0.88; ES+: 736.46

Example 403

1:1—Mixture of (rac.)-5-{(1R*,5S*)-7-{4-[3-(2-bromo-5-fluorophenoxy)-propyl]phenyl}-6-[((2R*)-2-hydroxy-2-phenylethyl)methylcarbamoyl]-3,9-diazabicyclo[3.3.1]non-6-en-3-yl}-2,2-dimethyl-5-oxopentanoic acid formate salt and (rac.)-5-{(1R*,5S*)-7-{4-[3-(2-bromo-5-fluorophenoxy)propyl]phenyl}-6-[((2S*)-2-hydroxy-2-phenylethyl)methylcarbamoyl]-3,9-diazabicyclo[3.3.1]non-6-en-3-yl}-2,2-dimethyl-5-oxopentanoic acid formate salt Synthesized according to typical procedures K and E from bicyclononene AL34 and 2,2-dimethylglutaric anhydride. LC-MS: $R_t$=0.88; ES+: 750.47

Example 404

1:1—Mixture of (rac.)-(1R*,5S*)-7-{4-[3-(2-bromo-5-fluorophenoxy)propyl]-phenyl}-3-(4-carbamoylbutyryl)-3,9-diazabicyclo[3.3.1]non-6-ene-6-carboxylic acid ((2R*)-2-hydroxy-2-phenylethyl)methylamide formate salt and (rac.)-(1R*,5S*)-7-{4-[3-(2-bromo-5-fluorophenoxy)propyl]-phenyl}-3-(4-carbamoylbutyryl)-3,9-diazabicyclo[3.3.1]non-6-ene-6-carboxylic acid ((2R*)-2-hydroxy-2-phenylethyl)methylamide formate salt Synthesized according to typical procedures G and E from bicyclononene AL34 and 4-carbamoylbutyric acid. LC-MS: $R_t$=0.82; ES+: 721.46

Example 405

1:1—Mixture of (rac.)-(3R*)-5-{(1R*,5S*)-7-{4-[3-(2-bromo-5-fluorophenoxy)-propyl]phenyl}-6-[(2-chlorobenzyl)cyclopropylcarbamoyl]-3,9-diazabicyclo-[3.3.1]non-6-en-3-yl}-3-hydroxy-5-oxopentanoic acid formate salt and (rac.)-(3S*)-5-{(1R*,5S*)-7-{4-[3-(2-bromo-5-fluorophenoxy)propyl]phenyl}-6-[(2-chlorobenzyl)cyclopropylcarbamoyl]-3,9-diazabicyclo-[3.3.1]non-6-en-3-yl}-3-hydroxy-5-oxopentanoic acid formate salt Synthesized according to typical procedures K, E and L from bicyclononene AL20 and 3-(tert-butyldimethylsilyloxy)glutaric anhydride. LC-MS: $R_t$=0.88; ES+: 768.40

Example 406

1:1—Mixture of (rac.)-(3R*)-5-((1R*,5S*)-6-(benzylcyclopropylcarbamoyl)-7-{4-[3-(2-bromo-5-fluorophenoxy)propyl]phenyl}-3,9-diazabicyclo[3.3.1]non-6-en-3-yl)-3-hydroxy-5-oxopentanoic acid formate salt and (rac.)-(3S*)-5-((1R*,5S*)-6-(benzylcyclopropylcarbamoyl)-7-{4-[3-(2-bromo-5-fluorophenoxy)propyl]phenyl}-3,9-diazabicyclo[3.3.1]non-6-en-3-yl)-3-hydroxy-5-oxopentanoic acid formate salt Synthesized according to typical procedures K, E and L from bicyclononene AL21 and 3-(tert-butyldimethylsilyloxy)glutaric anhydride. LC-MS: $R_t$=0.86; ES+: 734.47

Example 407

(rac.)-(1R*,5S*)-7-{4-[2-(2-Chloro-4,5-dimethylphenoxy)ethoxy]phenyl}-3,9-diazabicyclo[3.3.1]non-6-ene-6-carboxylic acid [2-(2-chlorophenyl)ethyl]-cyclopropylamide formate salt Synthesized according to typical procedure E from bicyclononene AK65. LC-MS: $R_t$=0.84; ES+: 620.45

Example 408

(rac.)-(1R*,5S*)-7-{4-[2-(2-Chloro-4,5-dimethylphenoxy)ethoxy]phenyl}-3,9-diazabicyclo[3.3.1]non-6-ene-6-carboxylic acid cyclopropyl-(3,5-dimethoxybenzyl)amide formate salt Synthesized according to typical procedure E from bicyclononene AK70. LC-MS: $R_t$=0.84; ES+: 7632.32

Example 409

(rac.)-(1R*,5S*)-7-{4-[2-(2-Chloro-4,5-dimethylphenoxy)ethoxy]phenyl}-3,9-diazabicyclo[3.3.1]non-6-ene-6-carboxylic acid cyclopropyl-(p-toluylethyl)amide formate salt Synthesized according to typical procedure E from bicyclononene AK71. LC-MS: $R_t$=0.85; ES+: 600.29

Example 410

(rac.)-(1R*,5S*)-3-Acetyl-7-{4-[2-(4-bromophenoxy)ethoxy]phenyl}-3,9-diazabicyclo[3.3.1]non-6-ene-6-carboxylic acid (2-chlorobenzyl)cyclopropylamibe formate salt Synthesized according to typical procedures A and E from bicyclononene AL73 and acetyl chloride. LC-MS: $R_t$=0.90; ES+: 664.33

Example 411

(rac.)-(1R*,5S*)-3-Acetyl-7-{4-[2-(4-bromophenoxy)ethoxy]phenyl}-3,9-diazabicyclo[3.3.1]non-6-ene-6-carboxylic acid cyclopropyl-(3,5-dimethoxybenzyl)amide formate salt Synthesized according to typical procedures A and E from bicyclononene AL85 and acetyl chloride. LC-MS: $R_t$=0.88; ES+: 690.36

Example 412

(rac.)-5-{(1R*,5S*)-7-{4-[2-(4-Bromophenoxy)ethoxy]phenyl}-6-[(2-chlorobenzyl)cyclopropylcarbamoyl]-3,9-diazabicyclo[3.3.1]non-6-en-3-yl}-5-oxopentanoic acid formate salt Synthesized according to typical procedures K and E from bicyclononene AL73 and glutaric anhydride. LC-MS: $R_t$=0.87; ES+: 736.31

Example 413

(rac.)-5-((1R*,5S*)-6-(Benzylcyclopropylcarbamoyl)-7-{4-[2-(4-bromophenoxy)ethoxy]phenyl}-3,9-diazabicyclo[3.3.1]non-6-en-3-yl)-5-oxopentanoic acid formate salt Synthesized according to typical procedures K and E from bicyclononene AL74 and glutaric anhydride. LC-MS: $R_t$=0.85; ES+: 702.33

Example 414

(rac.)-5-{(1R*,5S*)-7-{4-[2-(4-Bromophenoxy)ethoxy]phenyl}-6-[cyclopropyl-(2-fluorobenzyl)carbamoyl]-3,9-diazabicyclo[3.3.1]non-6-en-3-yl}-5-oxopentanoic acid formate salt Synthesized according to typical procedures K and E from bicyclononene AL76 and glutaric anhydride. LC-MS: $R_t$=0.86; ES+: 720.33

Example 415

(rac.)-5-{(1R*,5S*)-7-{4-[2-(4-Bromophenoxy)ethoxy]phenyl}-6-cyclopropyl-(3-trifluoromethylbenzyl)carbamoyl]-3,9-diazabicyclo[3.3.1]non-6-en-3-yl}-5-oxopentanoic acid formate salt Synthesized according to typical procedures K and E from bicyclononene AL77 and glutaric anhydride. LC-MS: $R_t$=0.89; ES+: 770.27

Example 416

(rac.)-5-{(1R*,5S*)-7-{4-[2-(4-Bromophenoxy)ethoxy]phenyl}-6-cyclopropyl-(2-methylbenzyl)carbamoyl]-3,9-diazabicyclo[3.3.1]non-6-en-3-yl}-5-oxopentanoic acid formate salt Synthesized according to typical procedures K and E from bicyclononene AL78 and glutaric anhydride. LC-MS: $R_t$=0.87; ES+: 716.34

Example 417

(rac.)-5-{(1R*,5S*)-7-{4-[2-(4-Bromophenoxy)ethoxy]phenyl}-6-{cyclopropyl[2-(3,4-dimethylphenoxy)ethyl]carbamoyl}-3,9-diazabicyclo[3.3.1]non-6-en-3-yl}-5-oxopentanoic acid formate salt Synthesized according to typical procedures K and E from bicyclononene AL80 and glutaric anhydride. LC-MS: $R_t$=0.90; ES+: 760.37

Example 418

(rac.)-5-{(1R*,5S*)-7-{4-[2-(4-Bromophenoxy)ethoxy]phenyl}-6-{[2-(2-chlorophenyl)ethyl]cyclopropylcarbamoyl}-3,9-diazabicyclo[3.3.1]non-6-en-3-yl}-5-oxopentanoic acid formate salt Synthesized according to typical procedures K and E from bicyclononene AL81 and glutaric anhydride. LC-MS: $R_t$=0.88; ES+: 750.31

Example 419

(rac.)-5-{(1R*,5S*)-7-{4-[2-(4-Bromophenoxy)ethoxy]phenyl}-6-{cyclopropyl[2-(4-fluorophenyl)ethyl]carbamoyl}-3,9-diazabicyclo[3.3.1]non-6-en-3-yl}-5-oxopentanoic acid formate salt Synthesized according to typical procedures K and E from bicyclononene AL83 and glutaric anhydride. LC-MS: $R_f$=0.87; ES+: 734.34

Example 420

(rac.)-5-{(1R*,5S*)-7-{4-[2-(4-Bromophenoxy)ethoxy]phenyl}-6-{cyclopropyl-[2-(2-methylphenyl)ethyl]carbamoyl}-3,9-diazabicyclo[3.3.1]non-6-en-3-yl}-5-oxopentanoic acid formate salt Synthesized according to typical procedures K and E from bicyclononene AL84 and glutaric anhydride. LC-MS: $R_f$=0.88; ES+: 730.37

Example 421

(rac.)-5-{(1R*,5S*)-7-{4-[2-(4-Bromophenoxy)ethoxy]phenyl}-6-[cyclopropyl-(3,5-dimethoxybenzyl)carbamoyl]-3,9-diazabicyclo[3.3.1]non-6-en-3-yl}-5-oxopentanoic acid formate salt Synthesized according to typical procedures K and E from bicyclononene AL85 and glutaric anhydride. LC-MS: $R_f$=0.86; ES+: 762.31

Example 422

(rac.)-5-{(1R*,5S*)-7-{4-[2-(4-Bromophenoxy)ethoxy]phenyl}-6-{cyclopropyl-[2-(4-methylphenyl)ethyl]carbamoyl}-3,9-diazabicyclo[3.3.1]non-6-en-3-yl}-5-oxopentanoic acid formate salt Synthesized according to typical procedures K and E from bicyclononene AL86 and glutaric anhydride. LC-MS: $R_f$=0.88; ES+: 730.37

Example 423

(rac.)-5-{(1R*,5S*)-7-{4-[2-(4-Bromophenoxy)ethoxy]phenyl}-6-[cyclopropyl-(2-fluorobenzyl)carbamoyl]-3,9-diazabicyclo[3.3.1]non-6-en-3-yl}-2,2-dimethyl-5-oxopentanoic acid formate salt Synthesized according to typical procedures K and E from bicyclononene AL76 and 2,2-dimethylglutaric anhydride. LC-MS: $R_f$=0.89; ES+: 748.35

Example 424

(rac.)-5-((1R*,5S*)-7-{4-[2-Bromophenoxy)ethoxy]phenyl}-6-({[2-(2-chlorophenyl)ethyl]cyclopropyl-carbamoyl}-3,9-diazabicyclo[3.3.1]non-6-en-3-yl)-2,2-dimethyl-5-oxopentanoic acid formate salt Synthesized according to typical procedures K and E from bicyclononene AL81 and 2,2-dimethylglutaric anhydride. LC-MS: $R_f$=0.91; ES+: 778.33

Example 425

(rac.)-5-((1R*,5S*)-7-{4-[2-(4-Bromophenoxy)ethoxy]phenyl}-6-{cyclopropyl-[2-(2,3-difluorophenyl)ethyl]carbamoyl}-3,9-diazabicyclo[3.3.1]non-6-en-3-yl)-2,2-dimethyl-5-oxopentanoic acid formate salt Synthesized according to typical procedures K and E from bicyclononene AL82 and 2,2-dimethylglutaric anhydride. LC-MS: $R_f$=0.91; ES+: 780.36

Example 426

(rac.)-5-((1R*,5S*)-7-{4-[2-(4-Bromophenoxy)ethoxy]phenyl}-6-{cyclopropyl-[2-(2-methylphenyl)ethyl]carbamoyl}-3,9-diazabicyclo[3.3.1]non-6-en-3-yl)-2,2-dimethyl-5-oxopentanoic acid formate salt Synthesized according to typical procedures K and E from bicyclononene AL84 and 2,2-dimethylglutaric anhydride. LC-MS: $R_f$=0.92; ES+: 7758.39

Example 427

(rac.)-5-{(1R*,5S*)-7-{4-[2-(4-Bromophenoxy)ethoxy]phenyl}-6-[cyclopropyl-(3,5-dimethoxybenzyl)carbamoyl]-3,9-diazabicyclo[3.3.1]non-6-en-3-yl}-2,2-dimethyl-5-oxopentanoic acid formate salt Synthesized according to typical procedures K and E from bicyclononene AL85 and 2,2-dimethylglutaric anhydride. LC-MS: $R_f$=0.89; ES+: 790.39

Example 428

(rac.)-5((1R*,5S*)-7-{4-[2-(4-Bromophenoxy)ethoxy]phenyl}-6-{cyclopropyl-[2(4-methylphenyl)ethyl]carbamoyl}-3,9-diazabicyclo[3.3.1]non-6-en-3-yl)-2,2-dimethyl-5-oxopentanoic acid formate salt Synthesized according to typical procedures K and E from bicyclononene AL86 and 2,2-dimethylglutaric anhydride. LC-MS: $R_f$=0.91; ES+: 758.38

Example 429

(rac.)-(1R*,5S*)-7-{4-[2-(4-Bromophenoxy)ethoxy]phenyl}-3-(4-carbamoylbutyryl)-3,9-diazabicyclo[3.3.1]non-6-ene-6-carboxylic acid benzylcyclopropylamide formate salt Synthesized according to typical procedures G and E from bicyclononene AL74 and 4-carbamoylbutyric acid. LC-MS: $R_f$=0.85; ES+: 735.34

Example 430

(rac.)-(1R*,5S*)-7-{4-[2-(4-Bromophenoxy)ethoxy]phenyl}-3-(4-carbamoylbutyryl)-3,9-diazabicyclo[3.3.1]non-6-ene-6-carboxylic acid (2-chlorobenzyl)-ethylamide formate salt Synthesized according to typical procedures G and E from bicyclononene AL75 and 4-carbamoylbutyric acid. LC-MS: $R_f$=0.85; ES+: 723.32

Example 431

(rac.)-(1R*,5S*)-7-{4-[2-(4-Bromophenoxy)ethoxy]
phenyl}-3-(4-carbamoylbutyryl)-3,9-diazabicyclo
[3.3.1]non-6-ene-6-carboxylic acid cyclopropyl-(2-
fluorobenzyl)amide formate salt Synthesized according to typical procedures G and E from bicyclononene AL76 and 4-carbamoylbutyric acid. LC-MS: $R_f$=0.84; ES+: 719.33

Example 432

(rac.)-(1R*,5S*)-7-{4-[2-(4-Bromophenoxy)ethoxy]
phenyl}-3-(4-carbamoylbutyryl)-3,9-diazabicyclo
[3.3.1]non-6-ene-6-carboxylic acid cyclopropyl-[2-
(4-methoxyphenoxy)ethyl]amide formate salt Synthesized according to typical procedures G and E from bicyclononene AL79 and 4-carbamoylbutyric acid. LC:-MS: $R_f$=0.84; ES+: 761.34

Example 433

(rac.)-(1R*,5S*)-7-{4-[2-(4-Bromophenoxy)ethoxy]
phenyl}-3-(4-carbamoylbutyryl)-3,9-diazabicyclo
[3.3.1]non-6-ene-6-carboxylic acid [2-(2-chlorophe-
nyl)ethyl]cyclopropylamide formate salt Synthesized according to typical procedures G and E from bicyclononene AL81 and 4-carbamoylbutyric acid. LC-MS: $R_f$=0.86; ES+: 749.32

Example 434

(rac.)-(1R*,5S*)-7-{4-[2-(4-Bromophenoxy)ethoxy]
phenyl}-3-(4-carbamoylbutyryl)-3,9-diazabicyclo
[3.3.1]non-6-ene-6-carboxylic acid cyclopropyl-(3,5-
dimethoxybenzyl)amide formate salt Synthesized according to typical procedures G and E from bicyclononene AL85 and 4-carbamoylbutyric acid. LC-MS: $R_f$=0.84; ES+: 761.35

Example 435

(rac.)-(1R*,5S*)-7-{4-[2-(4-Bromophenoxy)ethoxy]
phenyl}-3-carbamoylbutyryl)-3,9-diazabicyclo
[3.3.1]non-6-ene-6-carboxylic acid cyclopropyl-[2-
(2-hydroxyethyl)benzyl]amide formate salt Synthesized according to typical procedures G and E from bicyclononene AL87 and 4-carbamoylbutyric acid. LC-MS: $R_f$=0.80; ES+: 745.40

Example 436

(rac.)-(1R*,5S*)-7-{4-[2-(2-Chloro-4-dimethylphe-
noxy)ethoxy]phenyl}-3-formyl-3,9-diazabicyclo
[3.3.1]non-6-ene-6-carboxylic acid (2-chlorobenzyl)-
ethylamide formate salt Synthesized according to typical procedure E from bicyclononene AK57. Obtained as side-product after purificytion by HPLC. LC-MS: $R_f$=0.91; ES+: 622.25

Example 437

(rac.)-(1R*,5S*)-7-{4-[2-(2-Chloro-4,5-dimeth-
ylphenoxy)ethoxy]phenyl}-3-formyl-3,9-diazabicy-
clo[3.3.1]non-6-ene-6-carboxylic acid cyclopropyl-
(2-o-tolylethyl)amide formate salt Synthesized according to typical procedure E from bicyclononene AK68. Obtained as side-product after purification by HPLC. LC-MS: $R_f$=0.92; ES+: 628.31

Example 438

(rac.)-(1R*,5S*)-7-{4-[2-(2-Chloro-4,5-dimeth-
ylphenoxy)ethoxy]phenyl}-3-formyl-3,9-diazabicy-
clo[3.3.1]non-6-ene-6-carboxylic acid cyclopropyl-
(3,5-dimethoxybenzyl)amide formate salt Synthesized according to typical procedure E from bicyclononene AK70. Obtained as side-product after purification by HPLC. LC-MS: $R_f$=0.90; ES+: 660.30

Example 439

(rac.)-(1R*,5S*)-3-Acetyl-7-{4-[2-(2-chloro-4,5-
dimethylphenoxy)ethoxy]-phenyl}-3,9-diazabicyclo
[3.3.1]non-6-ene-6-carboxylic acid (2-chlorobenzyl)-
cyclopropylamide formate salt Synthesized according to typical procedures A and E from bicyclononene AL56 and acetyl chloride. LC-MS: $R_f$=0.93; ES+: 648.37

Example 440

(rac.)-(1R*,5S*)-3-Acetyl-7-{4-[2-(2-Chloro-4,5-
dimethylphenoxy)ethoxy]-phenyl}-3,9-diazabicyclo
[3.3.1]non-6-ene-6-carboxylic acid (2-chlorobenzyl)-
ethylamide formate salt Synthesized according to typical procedures A and E from bicyclononene AL57 and acetyl chloride. LC-MS: $R_f$=0.92; ES+: 636.37

Example 441

(rac.)-(1R*,5S*)-3-Acetyl-7-{4-[2-(2-chloro-4,5-
dimethylphenoxy)ethoxy]-phenyl}-3,9-diazabicyclo
[3.3.1]non-6-ene-6-carboxylic acid cyclopropyl-(2-
fluorobenzyl)amide formate salt Synthesized according to typical procedures A and B from bicyclononene AL58 and acetyl chloride. LC-MS: $R_f$=0.90; ES+: 632.41

Example 442

(rac.)-(1R*,5S*)-3-Acetyl-7-{4-[2-(2-chloro-4,5-
dimethylphenoxy)ethoxy]-phenyl}-3,9-diazabicyclo
[3.3.1]non-6-ene-6-carboxylic acid cyclopropyl-(2-
methylbenzyl)amide formate salt Synthesized according to typical procedures A and B from bicyclononene AL60 and acetyl chloride. LC-MS: $R_f$=0.91; ES+: 628.43

Example 443

(rac.)-(1R*,5S)-3-Acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(3,5-dimethoxybenzyl)amide formate salt Synthesized according to typical procedures A and E from bicyclononene AL70 and acetyl chloride. LC-MS: $R_t$=0.91; ES+: 674.44

Example 444

(rac.)-(1R*,5S*)-3-Acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(2-p-tolylethyl)amide formate salt Synthesized according to typical procedures A and E from bicyclononene AL71 and acetyl chloride. LC-MS: $R_t$=0.92; ES+: 642.44

Example 445

(rac.)-5-((1R*,5S*)-6-[(2-Chlorobenzyl)cyclopropylcarbamoyl]-7-{4-[2-(2-chloro-4,5-dimethylphenoxy)ethoxy]phenyl}-3,9-diazabicyclo[3.3.1]non-6-en-3-yl)-5-oxopentanoic acid formate salt Synthesized according to typical procedures K and E from bicyclononene AL56 and glutaric anhydride. LC-MS: $R_t$=0.90; ES+: 720.36

Example 446

(rac.)-5-((1R*,5S*)-6-[(2-Chlorobenzyl)ethylcarbamoyl]-7-{4-[2-(2-chloro-4,5-dimethylphenoxy)ethoxy]phenyl}-3,9-diazabicyclo[3.3.1]non-6-en-3-yl)-5-oxopentanoic acid formate salt Synthesized according to typical procedures K and E from bicyclononene AL57 and glutaric anhydride. LC-MS: $R_t$=0.89; ES+: 708.35

Example 447

(rac.)-5-{(1R*,5S*)-7-{4-[2-(2-Chloro-4,5-dimethylphenoxy)ethoxy]phenyl}-6-[cyclopropyl-(2-fluorobenzyl)carbamoyl]-3,9-diazabicyclo[3.3.1]non-6-en-3-yl}-5-oxopentanoic acid formate salt Synthesized according to typical procedures K and E from bicyclononene AL58 and glutaric anhydride. LC-MS: $R_t$=0.88; ES+: 704.37

Example 448

(rac.)-5-{(1R*,5S*)-7-{4-[2-(2-Chloro-4,5-ethylphenoxy)ethoxy]phenyl}-6-[cyclopropyl-(3-trifluoromethylbenzyl)carbamoyl]-3,9-diazabicyclo[3.3.1]-non-6-en-3-yl}-5-oxopentanoic acid formate salt Synthesized according to typical procedures K and E from bicyclononene AL59 and glutaric anhydride. LC-MS: $R_t$=0.91; ES+: 745.38

Example 449

(rac.)-5-{(1R*,5S*)-7-{4-[2-(2-Chloro-4,5-dimethylphenoxy)ethoxy]phenyl}-6-[cyclopropyl-(2-methylbenzyl)carbamoyl]-3,9-diazabicyclo[3.3.1]non-6-en-3-yl}-5-oxopentanoic acid formate salt Synthesized according to typical procedures K and E from bicyclononene AL60 and glutaric anhydride. LC-MS: $R_t$=0.89; ES+: 700.41

Example 450

(rac.)-5-((1R*,5S*)-7-{4-[2-(2-Chloro-4,5-dimethylphenoxy)ethoxy]phenyl}-6-{cyclopropyl-[2-(4-methoxyphenoxy)ethyl]carbamoyl}-3,9-diazabicyclo-[3.3.1]non-6-en-3-yl)-5-oxopentanoic acid formate salt Synthesized according to typical procedures K and E from bicyclononene AL61 and glutaric anhydride. LC-MS: $R_t$=0.88; ES+: 746.42

Example 451

(rac.)-5-((1R*,5S*)-7-{4-[2-(2-Chloro-4,5-dimethylphenoxy)ethoxy]phenyl}-6-{cyclopropyl-[2-(3-methoxyphenoxy)ethyl]carbamoyl}-3,9-diazabicyclo-[3.3.1]non-6-en-3-yl)-5-oxopentanoic acid formate salt Synthesized according to typical procedures K and E from bicyclononene AL62 and glutaric anhydride. LC-MS: $R_t$=0.88; ES+: 746.41

Example 452

(rac.)-5-(1R*,5S*)-7-{4-[2-(2-Chloro-4,5-dimethylphenoxy)ethoxy]phenyl}-6-{cyclopropyl-[2-(3-methylphenoxy)ethyl]carbamoyl}-3,9-diazabicyclo[3.3.1]-non-6-en-3-yl)-5-oxopentanoic acid formate salt Synthesized according to typical procedures K and E from bicyclononene AL63 and glutaric anhydride. LC-MS: $R_t$=0.91; ES+: 730.44

Example 453

(rac.)-5-[(1R*,5S*)-7-{4-[2-(2-Chloro-4,5-dimethylphenoxy)ethoxy]phenyl}-6-(cyclopropylphenethylcarbamoyl)-3,9-diazabicyclo[3.3.1]non-6-en-3-yl]-5-oxopentanoic acid formate salt Synthesized according to typical procedures K and E from bicyclononene AL64 and glutaric anhydride. LC-MS: $R_t$=0.88; ES+: 700.41

Example 454

(rac.)-5-((1R*,5S*)-7-{4-[2-(2-Chloro-4,5-dimethylphenoxy)ethoxy]phenyl}-6-{[2-(2-chlorophenyl)ethyl]cyclopropylcarbamoyl}-3,9-diazabicyclo[3.3.1]-non-6-en-3-yl)-5-oxopentanoic acid formate salt Synthesized according to typical procedures K and E from bicyclononene AL65 and glutaric anhydride. LC-MS: $R_t$=0.90; ES+: 734.39

Example 455

(rac.)-5-((1R*,5S*)-7-{4-[2-(2-Chloro-4,5-dimethylphenoxy)ethoxy]phenyl}-6-{cyclopropyl-[2-(2,3-difluorophenyl)ethyl]carbamoyl}-3,9-diazabicyclo[3.3.1]-non-6-en-3-yl)-5-oxopentanoic acid formate salt Synthesized according to typical procedures K and E from bicyclononene AL66 and glutaric anhydride. LC-MS: $R_t$=0.90; ES+: 736.41

Example 456

(rac.)-5-((1R*,5S*)-7-{4-[2-(2-Chloro-4,5-dimethylphenoxy)ethoxy]phenyl}-6-{cyclopropyl-[2-(4-fluorophenyl)ethyl]carbamoyl}-3,9-diazabicyclo[3.3.1]-non-6-en-3-yl)-5-oxopentanoic acid formate salt Synthesized according to typical procedures K and E from bicyclononene AL67 and glutaric anhydride. LC-MS: $R_t$=0.89; ES+: 718.40

Example 457

(rac.)-5-(1R*,5S*)-7-{4-[2-(2-Chloro-4,5-dimethylphenoxy)ethoxy]phenyl}-6-{cyclopropyl-[2-(2-methylphenyl)ethyl]carbamoyl}-3,9-diazabicyclo[3.3.1]-non-6-en-3-yl)-5-oxopentanoic acid formate salt Synthesized according to typical procedures K and E from bicyclononene AL68 and glutaric anhydride. LC-MS: $R_t$=0.90; ES+: 714.43

Example 458

(rac.)-5-{(1R*,5S*)-7-{4-[2-(2-Chloro-4,5-dimethylphenoxy)ethoxy]phenyl}-6-[cyclopropyl-(3,5-dimethoxybenzyl)carbamoyl]-3,9-diazabicyclo[3.3.1]non-6-en-3-yl}-5-oxopentanoic acid formate salt Synthesized according to typical procedures K and E from bicyclononene AL70 and glutaric anhydride. LC-MS: $R_t$=0.89; ES+: 746.41

Example 459

(rac.)-5-((1R*,5S*)-7-{4-[2-(2-Chloro-4,5-dimethylphenoxy)ethoxy]phenyl}-6-{cyclopropyl-[2-(4-methylphenyl)ethyl]carbamoyl}-3,9-diazabicyclo[3.3.1]-non-6-en-3-yl)-5-oxopentanoic acid formate salt Synthesized according to typical procedures K and E from bicyclononene AL71 and glutaric anhydride. LC-MS: $R_t$=0.90; ES+: 714.41

Example 460

(rac.)-5-((1R*,5S*)-6-[(2-Chlorobenzyl)cyclopropylcarbamoyl]-7-{4-[2-(2-chloro-4,5-dimethylphenoxy)ethoxy]phenyl}-3,9-diazabicyclo[3.3.1]non-6-en-3-yl)-5-oxopentanoic acid methyl ester formate salt Synthesized according to typical procedures A and E from bicyclononene AL56 and glutaric acid monomethylester chloride. LC-MS: $R_t$=0.95; ES+: 734.37

Example 461

(rac.)-5-((1R*,5S*)-6-[(2-Chlorobenzyl)ethylcarbamoyl]-7-{4-[2-(2-chloro-4,5-dimethylphenoxy)ethoxy]phenyl}-3,9-diazabicyclo[3.3.1]non-6-en-3-yl)-5-oxopentanoic acid methyl ester formate salt Synthesized according to typical procedures A and E from bicyclononene AL57 and glutaric acid monomethylester chloride. LC-MS: $R_t$=0.94; ES+: 722.37

Example 462

(rac.)-5-{(1R*,5S*)-7-{4-[2-(2-Chloro-4,5-dimethylphenoxy)ethoxy]phenyl}-6-[cyclopropyl-(2-fluorobenzyl)carbamoyl]-3,9-diazabicyclo[3.3.1]non-6-en-3-yl}-5-oxopentanoic acid methyl ester formate salt Synthesized according to typical procedures A and E from bicyclononene AL58 and glutaric acid monomethylester chloride. LC-MS: $R_t$=0.93; ES+: 718.40

Example 463

(rac.)-5-{(1R*,5S*)-7-{4-[2-(2-Chloro-4,5-dimethylphenoxy)ethoxy]phenyl}-6-[cyclopropyl-(3-trifluoromethylbenzyl)carbamoyl]-3,9-diazabicyclo[3.3.1]-non-6-en-3-yl}-5-oxopentanoic acid methyl ester formate salt Synthesized according to typical procedures A and E from bicyclononene AL59 and glutaric acid monomethylester chloride. LC-MS: $R_t$=0.96; ES+: 768.38

Example 464

(rac.)-5-{(1R*,5S*)-7-{4-[2-(2-Chloro-4,5-dimethylphenoxy)ethoxy]phenyl}-6-[cyclopropyl-(2-methylbenzyl)carbamoyl]-3,9-diazabicyclo[3.3.1]non-6-en-3-yl}-5-oxopentanoic acid methyl ester formate salt Synthesized according to typical procedures A and E from bicyclononene AL60 and glutaric acid monomethylester chloride. LC-MS: $R_t$=0.94; ES+: 714.43

Example 465

(rac.)-5-[(1R*,5S*)-7-{4-[2-(2-Chloro-4,5-dimethylphenoxy)ethoxy]phenyl}-6-(cyclopropylphenethylcarbamoyl)-3,9-diazabicyclo[3.3.1]non-6-en-3-yl]-5-oxopentanoic acid methyl ester formate salt Synthesized according to typical procedures A and E from bicyclononene AL64 and glutaric acid monomethylester chloride. LC-MS: $R_t$=0.93; ES+: 714.41

Example 466

(rac.)-5-((1R*,5S*)-7-{4-[2-(2-Chloro-4,5-dimethylphenoxy)ethoxy]phenyl}-6-{[2-(2-chlorophenyl)ethyl]cyclopropylcarbamoyl}-3,9-diazabicyclo[3.3.1]non-6-en-3-yl)-5-oxopentanoic acid methyl ester formate salt Synthesized according to typical procedures A and E from bicyclononene AL65 and glutaric acid monomethylester chloride. LC-MS: $R_t$=0.93; ES+: 748.39

Example 467

(rac.)-5-((1R*,5S*)-7-{4-[2-(2-Chloro-4,5-dimethylphenoxy)ethoxy]phenyl}-6-{[2(2,3-difluorophenyl)ethyl]cyclopropylcarbamoyl}-3,9-diazabicyclo[3.3.1]-non-6-en-3-yl)-5-oxopentanoic acid methyl ester formate salt Synthesized according to typical procedures A and E from bicyclononene AL66 and glutaric acid monomethylester chloride. LC-MS: $R_t$=0.94; ES+: 750.40

Example 468

(rac.)-5-((1R*,5S*)-7-{4-[2-(2-Chloro-4,5-dimethylphenoxy)ethoxy]phenyl}-6-{[2-(4-fluorophenyl)ethyl]cyclopropylcarbamoyl}-3,9-diazabicyclo[3.3.1]non-6-en-3-yl)-5-oxopentanoic acid methyl ester formate salt Synthesized according to typical procedures A and E from bicyclononene AL67 and glutaric acid monomethylester chloride. LC-MS: $R_t$=0.93; ES+: 732.44

Example 469

(rac.)-5-((1R*,5S*)-7-{4-[2-(2-Chloro-4,5-dimethylphenoxy)ethoxy]phenyl}-6-{[2-(methylphenyl)ethyl]cyclopropylcarbamoyl}-3,9-diazabicyclo[3.3.1]non-6-en-3-yl)-5-oxopentanoic acid methyl ester formate salt Synthesized according to typical procedures A and E from bicyclononene AL68 and glutaric acid monomethylester chloride. LC-MS: $R_t$=0.95; ES+: 728.45

Example 470

(rac.)-5-{(1R*,5S*)-7-{4-[2-(2-Chloro-4,5-dimethylphenoxy)ethoxy]phenyl}-6-[cyclopropyl-(3,5-dimethoxybenzyl)carbamoyl]-3,9-diazabicyclo[3.3.1]non-6-en-3-yl}-5-oxopentanoic acid methyl ester formate salt Synthesized according to typical procedures A and E from bicyclononene AL70 and glutaric acid monomethylester chloride. LC-MS: $R_t$=0.93; ES+: 760.40

Example 471

(rac.)-5-((1R*,5S*)-7-{4-[2-(2-Chloro-4,5-dimethylphenoxy)ethoxy]phenyl}-6-{[2-(4-methylphenyl)ethyl]cyclopropylcarbamoyl}-3,9-diazabicyclo[3.3.1]non-6-en-3-yl)-5-oxopentanoic acid methyl ester formate salt Synthesized according to typical procedures A and E from bicyclononene AL71 and glutaric acid monomethylester chloride. LC-MS: $R_t$=0.95; ES+: 728.43

Example 472

(rac.)-5-((1R*,5S*)-6-[(2-Chlorobenzyl)cyclopropylcarbamoyl]-7-{4-[2-(2-chloro-4,5-dimethylphenoxy)ethoxy]phenyl}-3,9-diazabicyclo[3.3.1]non-6-en-3-yl)-2,2-dimethyl-5-oxopentanoic acid formate salt Synthesized according to typical procedures K and E from bicyclononene AL56 and 2,2-dimethylglutaric anhydride. LC-MS: $R_t$=0.93; ES+: 748.40

Example 473

(rac.)-5-((1R*,5S*)-6-[(2-Chlorobenzyl)ethylcarbamoyl]-7-{4-[2-(2-chloro-4,5-dimethylphenoxy)ethoxy]phenyl}-3,9-diazabicyclo[3.3.1]non-6-en-3-yl)-2,2-dimethyl-5-oxopentanoic acid formate salt Synthesized according to typical procedures K and E from bicyclononene AL57 and 2,2-dimethylglutaric anhydride. LC-MS: $R_t$=0.93; ES+:736.42

Example 474

(rac.)-5-{(1R*,5S*)-7-{4-[2-(2-Chloro-4,5-dimethylphenoxy)ethoxy]phenyl}-6-[cyclopropyl-(2-fluorobenzyl)carbamoyl]-3,9-diazabicyclo[3.3.1]non-6-en-3-yl}-2,2-dimethyl-5-oxopentanoic acid formate salt Synthesized according to typical procedures K and E from bicyclononene AL58 and 2,2-dimethylglutaric anhydride. LC-MS: $R_t$=0.91; ES+: 732.45

Example 475

(rac.)-5-{(1R*,5S*)-7-{4-[2-(2-Chloro-4,5-dimethylphenoxy)ethoxy]phenyl}-6-[cyclopropyl-(2-methylbenzyl)carbamoyl]-3,9-diazabicyclo[3.3.1]non-6-en-3-yl}-2,2-dimethyl-5-oxopentanoic acid formate salt Synthesized according to typical procedures K and E from bicyclononene AL60 and 2,2-dimethylglutaric anhydride. LC-MS: $R_t$=0.93; ES+: 728.48

Example 476

(rac.)-5-[(1R*,5S*)-7-{4-[2-(2-Chloro-4,5-dimethylphenoxy)ethoxy]phenyl}-6-(cyclopropylphenethylcarbamoyl)-3,9-diazabicyclo[3.3.1]non-6-en-3-yl]-2,2-dimethyl-5-oxopentanoic acid formate salt Synthesized according to typical procedures K and E from bicyclononene AL64 and 2,2-dimethylglutaric anhydride. LC-MS: $R_t$=0.92; ES+: 728.49

Example 477

(rac.)-5-((1R*,5S*)-7-{4-[2-(2-Chloro-4,5-dimethylphenoxy)ethoxy]phenyl}-6-{[2-(2-chlorophenyl)ethyl]cyclopropylcarbamoyl}-3,9-diazabicyclo[3.3.1]non-6-en-3-yl)-2,2-dimethyl-5-oxopentanoic acid formate salt Synthesized according to typical procedures K and E from bicyclononene AL65 and 2,2-dimethylglutaric anhydride. LC-MS: $R_t$=0.93; ES+: 762.42

Example 478

(rac.)-5-((1R*,5S*)-7-{4-[2-(2-Chloro-4,5-dimethylphenoxy)ethoxy]phenyl}-6-{[2-(2,3-difluorophenyl)ethyl]cyclopropylcarbamoyl}-3,9-diazabicyclo[3.3.1]-non-6-en-3-yl)-2,2-dimethyl-5-oxopentanoic acid formate salt Synthesized according to typical procedures K and E from bicyclononene AL66 and 2,2-dimethylglutaric anhydride. LC-MS: $R_t$=0.93; ES+: 764.44

Example 479

(rac.)-5-((1R*,5S*)-7-{4-[2-(2-Chloro-4,5-dimethylphenoxy)ethoxy]phenyl}-6-{[2-(4-fluorophenyl)ethyl]cyclopropylcarbamoyl}-3,9-diazabicyclo[3.3.1]non-6-en-3-yl)-2,2-dimethyl-5-oxopentanoic acid formate salt Synthesized according to typical procedures K and E from bicyclononene AL67 and 2,2-dimethylglutaric anhydride. LC-MS: $R_t$=0.92; ES+: 746.48

Example 480

(rac.)-5-((1R*,5S*)-7-{4-[2-(2-Chloro-4,5-dimethylphenoxy)ethoxy]phenyl}-6-{[2-(2-methylphenyl)ethyl]cyclopropylcarbamoyl}-3,9-diazabicyclo[3.3.1]non-6-en-3-yl)-2,2-dimethyl-5-oxopentanoic acid formate salt Synthesized according to typical procedures K and E from bicyclononene AL68 and 2,2-dimethylglutaric anhydride. LC-MS: $R_t$=0.93; ES+: 742.51

Example 481

(rac.)-5-{(1R*,5S*)-7-{4-[2-(2-Chloro-4,5-dimethylphenoxy)ethoxy]phenyl}-6-[cyclopropyl-(3,5-dimethoxybenzyl)carbamoyl]-3,9-diazabicyclo[3.3.1]non-6-en-3-yl}-2,2-dimethyl-5-oxopentanoic acid formate salt Synthesized according to typical procedures K and E from bicyclononene AL70 and 2,2-dimethylglutaric anhydride. LC-MS: $R_t$=0.92; ES+: 774.45

Example 482

(rac.)-5-((1R*,5S*)-7-{4-[2-(2-Chloro-4,5-dimethylphenoxy)ethoxy]phenyl}-6-{[2-(4-methylphenyl)ethyl]cyclopropylcarbamoyl}-3,9-diazabicyclo[3.3.1]non-6-en-3-yl)-2,2-dimethyl-5-oxopentanoic acid formate salt Synthesized according to typical procedures K and E from bicyclononene AL71 and 2,2-dimethylglutaric anhydride. LC-MS: $R_t$=0.93; ES+: 742.51

Example 483

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid (2-chlorobenzyl)cyclopropylamide formate salt Synthesized according to typical procedures G and E from bicyclononene AL56 and 4-carbamoylbutyric acid. LC-MS: $R_t$=0.88; ES+: 719.43

Example 484

(rac.)-(1R*,5S*)-3-(4-Carbamoylbutyryl-7-{4-[2-(2-chloro-4,5-dimethylphenoxy)ethoxy]phenyl}-3,9-diazabicyclo[3.3.1]non-6-ene-6-carboxylic acid (2-chlorobenzyl)ethylamide formate salt Synthesized according to typical procedures G and E from bicyclononene AL57 and 4-carbamoylbutyric acid. LC-MS: $R_t$=0.87; ES+: 707.39

Example 485

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-(2-fluorobenzyl)amide formate salt Synthesized according to typical procedures G and E from bicyclononene AL58 and 4-carbamoylbutyric acid. LC-MS: $R_t$=0.86; ES+: 703.43

Example 486

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-(3-trifluoromethylbenzyl)amide formate salt Synthesized according to typical procedures G and E from bicyclononene AL59 and 4-carbamoylbutyric acid. LC-MS: $R_t$=0.89; ES+: 753.44

Example 487

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-(2-methylbenzyl)amide formate salt Synthesized according to typical procedures G and E from bicyclononene AL60 and 4-carbamoylbutyric acid LC-MS: $R_t$=0.87; ES+: 699.47

Example 488

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-[2-(4-methoxyphenoxy)ethyl]amide formate salt Synthesized according to typical procedures G and E from bicyclononene AL61 and 4-carbamoylbutyric acid. LC-MS: $R_t$=0.86; ES+: 745.46

Example 489

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropylphenethylamide formate salt Synthesized according to typical procedures G and E from bicyclononene AL64 and 4-carbamoylbutyric acid. LC-MS: $R_t$=0.86; ES+: 699.44

Example 490

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid [2-(2-chlorophenyl)ethyl]cyclopropylamide formate salt Synthesized according to typical procedures G and E from bicyclononene AL65 and 4-carbamoylbutyric acid. LC-MS: $R_t$=0.88; ES+: 733.42

Example 491

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-[2-(2,3-difluorophenyl)ethyl]amide formate salt Synthesized according to typical procedures G and E from bicyclononene AL66 and 4-carbamoylbutyric acid. LC-MS: $R_t$=0.88; ES+: 735.43

Example 492

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6ene-6-carboxylic acid cyclopropyl-[2-(4-fluorophenyl)ethyl]amide formate salt Synthesized according to typical procedures G and E from bicyclononene AL67 and 4-carbamoylbutyric acid. LC-MS: $R_t$=0.87; ES+: 717.43

Example 493

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-(2-o-tolylethyl)amide formate salt Synthesized according to typical procedures G and E from bicyclononene AL68 and 4-carbamoylbutyric acid. LC-MS: $R_t$=0.88; ES+: 713.46

Example 494

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-(3,5-dimethoxybenzyl)amide formate salt Synthesized according to typical procedures G and E from bicyclononene AL70 and 4-carbamoylbutyric acid. LC-MS: $R_t$=0.87; ES+: 745.45

Example 495

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-(2-p-tolylethyl)amide formate salt Synthesized according to typical procedures G and E from bicyclononene AL71 and 4-carbamoylbutyric acid. LC-MS: $R_t$=0.88; ES+: 713.46

Example 496

1:1—Mixture of (rac.)-(3R*)-5-((1R*,5S*)-6-[(2-chlorobenzyl)cyclopropylcarbamoyl]-7-{4-[2-(2-chloro-4,5-dimethylphenoxy)ethoxy]phenyl}-3,9-diazabicyclo[3.3.1]non-6-en-3-yl)-3-hydroxy-5-oxopentanoic acid formate salt and (rac.)-(3S*)-5-((1R*,5S*)-6-[(2-chlorobenzyl)cyclopropylcarbamoyl]-7-{4-[2-(2-chloro-4,5-dimethylphenoxy)ethoxy]phenyl}-3,9-diazabicyclo[3.3.1]non-6-en-3-yl)-3-hydroxy-5-oxopentanoic acid formate salt Synthesized according to typical procedures K, E and L from bicyclononene AL56 and 3-(tert-butyldimethylsilyloxy)glutaric anhydride. LC-MS: $R_t$=0.88; ES+: 736.43

Example 497

1:1—Mixture of (rac.)-(3R*)-5-((1R*,5S*)-6-[(2-chlorobenzyl)ethylcarbamoyl]-7-{4-[2-(2-chloro-4,5-dimethylphenoxy)ethoxy]phenyl}-3,9-diazabicyclo[3.3.1]-non-6-en-3-yl)-3-hydroxy-5-oxopentanoic acid formate salt and (rac.)-(3S*)-5-(1R*,5S*)-6-[(2-chlorobenzyl)ethylcarbamoyl]-7-{4-[2(2-chloro-4,5-dimethylphenoxy)ethoxy]phenyl}-3,9-diazabicyclo[3.3.1]-non-6-en-3-yl)-3-hydroxy-5-oxopentanoic acid formate salt Synthesized according to typical procedures K, E and L from bicyclononene AL57 and 3-(tert-butyldimethylsilyloxy)glutaric anhydride. LC-MS: $R_t$=0.87; ES+: 724.40

Example 498

1:1—Mixture of (rac.)-(3R*)-5-{(1R*,5S*)-7-{4-[2-(2-chloro-4,5-dimethylphenoxy)ethoxy]phenyl}-6-[cyclopropyl-(2-fluorobenzyl)carbamoyl]-3,9-diazabicyclo[3.3.1]non-6-en-3-yl}-3-hydroxy-5-oxopentanoic acid formate salt and (rac.)-(3S*)-5-{(1R*,5S*)-7-{4-[2-(2-chloro-4,5-dimethylphenoxy)ethoxy]phenyl}-6-[cyclopropyl-(2-fluorobenzyl)carbamoyl]-3,9-diazabicyclo-[3.3.1]non-6-en-3-yl}-3-hydroxy-5-oxopentanoic acid formate salt Synthesized according to typical procedures K, E and L from bicyclononene AL58 and 3-(tert-butyldimethylsilyloxy)glutaric anhydride. LC-MS: $R_t$=0.86; ES+: 720.43

Example 499

1:1—Mixture of (rac.)-(3R*)-5-{(1R*,5S*)-7-{4-[2-(2-chloro-4,5-dimethylphenoxy)ethoxy]phenyl}-[cyclopropyl-(3-trifluoromethylbenzyl)-carbamoyl]-3,9-diazabicyclo[3.3.1]non-6-en-3-yl}-3-hydroxy-5-oxopentanoic acid formate salt and (rac.)-(3S*)-5-{(1R*,5S*)-7-{4-[2-(2-chloro-4,5-dimethylphenoxy)ethoxy]phenyl}-6-[cyclopropyl-(3-trifluoromethylbenzyl)-carbamoyl]-3,9-diazabicycl-o[3.3.1]non-6-en-3-yl}-3-hydroxy-5-oxopentanoic acid formate salt Synthesized according to typical procedures K, E and L from bicyclononene AL59 and 3-(tert-butyldimethylsilyloxy)glutaric anhydride. LC-MS: $R_t$=0.89; ES+: 770.40

Example 500

1:1—Mixture of (rac.)-(3R*)-5-(1R*,5S*)-7-{4-[2-(2-chloro-4,5-dimethylphenoxy)ethoxy]phenyl}-6-{cyclopropyl-[2-(4-methoxyphenoxy)ethyl]-carbamoyl}-3,9-diazabicyclo[3.3.1]non-6-en-3-yl)-3-hydroxy-5-oxopentanoic acid formate salt and (rac.)-(3S*)-5-((1R*,5S*)-7-{4-[2-(2-chloro-4,5-dimethylphenoxy)ethoxy]phenyl}-6-{cyclopropyl-[2-(4-methoxyphenoxy)-ethyl]carbamoyl}-3,9-diazabicyclo[3.3.1]non-6-en-3-yl)-3-hydroxy-5-oxopentanoic acid formate salt Synthesized according to typical procedures K, E and L from bicyclononene AL61 and 3-(tert-butyldimethylsilyloxy)glutaric anhydride. LC-MS: $R_t$=0.86; ES+: 762.46

Example 501

1:1—Mixture of (rac.)-(3R*)-5-[(1R*,5S*)-7-{4-[2-(2-chloro-4,5-dimethylphenoxy)ethoxy]phenyl}-6-(cyclopropylphenethylcarbamoyl)-3,9-diazabicyclo[3.3.1]non-6-en-3-yl]-3-hydroxy-5-oxopentanoic acid formate salt and (rac.)-(3S*)-5-[(1R*,5S*)-7-{4-[2-(2-chloro-4,5-dimethylphenoxy)ethoxy]-phenyl}-6-(cyclopropylphenethylcarbamoyl)-3,9-diazabicyclo[3.3.1]non-6-en-3-yl]-3-hydroxy-5-oxopentanoic acid formate salt Synthesized according to typical procedures K, E and L from bicyclononene AL64 and 3-(tert-butyldimethylsilyloxy)glutaric anhydride. LC-MS: $R_t$=0.86; ES+: 716.46

Example 502

1:1—Mixture of (rac.)-(3R*)-5-((1R*,5S*)-7-{4-[2-(2-chloro-4,5-dimethylphenoxy)ethoxy]phenyl}-6-{[2-(2-chlorophenyl)ethyl]cyclopropylcarbamoyl}-3,9-diazabicyclo[3.3.1]non-6-en-3-yl)-3-hydroxy-5-oxopentanoic acid formate salt and (rac.)-(3R*)-5-(1R*,5S*)-7-{4-[2-(2-chloro-4,5-dimethylphenoxy)-ethoxy]phenyl}-6-{[2-(2-chlorophenyl)ethyl]cyclopropylcarbamoyl}-3,9-diazabicyclo[3.3.1]non-6-en-3-yl)-3-hydroxy-5-oxopentanoic acid formate salt Synthesized according to typical procedures K, E and L from bicyclononene AL65 and 3-(tert-butyldimethylsilyloxy)glutaric anhydride. LC-MS: $R_t$=0.88; ES+: 750.41

Example 503

1:1—Mixture of (rac.)-(3R*)-5-((1R*,5S*)-7-{4-[2-(2-Chloro-4,5-dimethylphenoxy)ethoxy]phenyl}-6-{cyclopropyl-[2-(2,3-difluorophenyl)ethyl]-carbamoyl}-3,9-diazabicyclo[3.3.1]non-6-en-3-yl)-3-hydroxy-5-oxopentanoic acid formate salt and (rac.)-(3S*)-5-((1R*,5S*)-7-{4-[2-(2-chloro-4,5-dimethylphenoxy)ethoxy]phenyl}-6-{cyclopropyl-[2-(2,3-difluorophenyl)-ethyl]carbamoyl}-3,9-diazabicyclo[3.3.1]non-6-en-3-yl)-3-hydroxy-5-oxopentanoic acid formate salt Synthesized according to typical procedures K, E and L from bicyclononene AL66 and 3-(tert-butyldimethylsilyloxy)glutaric anhydride. LC-MS: $R_t$=0.88; ES+: 752.45

Example 504

1:1—Mixture of (rac.)-(3R*)-5-(1R*,5S*)-7-{4-[2-(2-chloro-4,5-dimethylphenoxy)ethoxy]phenyl}-6-{cyclopropyl-[2-(4fluorophenyl)ethyl]-carbamoyl}-3,9-diazabicyclo[3.3.1]non-6-en-3-yl)-3-hydroxy-5-oxopentanoic acid formate salt and (rac.)-(3S*)-5-(1R*,5S*)-7-{4-[2-(2-chloro-4,5-dimethylphenoxy)ethoxy]phenyl}-6-{cyclopropyl-[2-(4-fluorophenyl)ethyl]-carbamoyl}-3,9-diazabicyclo[3.3.1]non-6-en-3-yl)-3-hydroxy-5-oxopentanoic acid formate salt Synthesized according to typical procedures K, E and L from bicyclononene AL67 and 3-(tert-butyldimethylsilyloxy)glutaric anhydride. LC-MS: $R_t$=0.87; ES+: 734.47

Example 505

1:1—Mixture of (rac.)-(3R*)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo-[3.3.1]non-6-en-9-yl)-3-hydroxy-5-oxopentanoic acid formate salt and (rac.)-(3S*)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo-[3.3.1]non-6-en-9-yl)-3-hydroxy-5-oxopentanoic acid formate salt Synthesized according to typical procedures K, E and L from bicyclononene BC and 3-(tert-butyldimethylsilyloxy)glutaric anhydride. LC-MS: $R_t$=0.88; ES+: 726.32

Example 506

(rac.)-5-((1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-en-9-yl)-2,2-dimethyl-5-oxopentanoic acid formate salt Synthesized according to typical procedures K and E from bicyclononene BC and 2,2-dimethylglutaric anhydride. LC-MS: $R_t$=0.95; ES+: 738.37

Example 507

(rac.)-4-((1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-en-9-yl)-4-oxo-butyric acid Synthesized according to typical procedures K and E from bicyclononene BC and succinic anhydride. LC-MS: $R_t$=0.90; ES+: 696.32

Example 508

(rac.)-(1R*,5S*)-7-{4-[3-(2,3,6-Trifluorophenoxy)propyl]phenyl}-3,9-diazabicyclo[3.3.1]non-6-ene-6,9-dicarboxylic acid 6-[(2-chlorobenzyl)cyclopropylamibe]9-dimethylamide formate salt Synthesized according to typical procedures A and E from bicyclononene BC and dimethylcarbamoyl chloride. LC-MS: $R_t$=0.94; ES+: 667.38

Example 509

(rac.)-(1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-ene-9-carboxylic acid methyl ester formate salt Synthesized according to typical procedures A and E from bicyclononene BC and methyl chloroformate. LC-MS: $R_t$=0.96; ES+: 654.34

Example 510

(rac.)-(1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-ene-9-carboxylic acid ethyl ester formate salt Synthesized according to typical procedures A and E from bicyclononene BC and ethyl chloroformate. LC-MS: $R_t$=0.98; ES+: 668.37

Example 511

(rac.)-3-[(1R*,5S*)-(6-[(2-Chlorobenzyl)cyclopropylcarbamoyl]-7-{4-[3-(2,3,6-trifluorophenoxy)propyl]phenyl}-3,9-diazabicyclo[3.3.1]non-6-ene-9-carbonyl)amino]propionic acid ethyl ester formate salt Synthesized according to typical procedures A and E from bicyclononene BC and ethyl 4-isocyanatopropionate. LC-MS: $R_t$=0.95; ES+: 739.36

Example 512

1:1—Mixture of (rac.)-(3R*)-5-{(1R*,5S*)-7-{4-[2-(2-chloro-4,5-dimethylphenoxy)ethoxy]phenyl}-6-[cyclopropyl(2-o-tolylethyl)carbamoyl]-3,9-diazabicyclo[3.3.1]non-6-en-3-yl}-3-hydroxy-5-oxopentanoic acid and (rac.)-(3S*)-5-{(1R*,5S*)-7-{4-[2-(2-chloro-4,5-dimethylphenoxy)ethoxy]phenyl}-6-[cyclopropyl(2-o-tolylethyl)carbamoyl]-3,9-diazabicyclo[3.3.1]non-6-en-3-yl}-3-hydroxy-5-oxopentanoic acid Synthesized according to typical procedures K, E and L from bicyclononene AL68 and 3-(tert-butyldimethylsilyloxy) glutaric anhydride. LC-MS: $R_t$=0.88; ES+: 730.49

Example 513

1:1—Mixture of (rac.)-(3R*)-5-{(1R*,5S*)-7-{4-[2-(2-chloro-4,5-dimethylphenoxy)ethoxy]phenyl}-6-[cyclopropyl-(3,5-dimethoxybenzyl)carbamoyl]-3,9-diazabicyclo[3.3.1]non-6-en-3-yl}-3-hydroxy-5-oxopentanoic acid formate salt and (rac.)-(3S*)-{(1R*,5S*)-7-{4-[2-(2-chloro-4,5-dimethylphenoxy)ethoxy]phenyl}-6-[cyclopropyl-(3,5-dimethoxybenzyl)carbamoyl]-3,9-diazabicyclo[3.3.1]non-6-en-3-yl}-3-hydroxy-5oxopentanoic acid formate salt Synthesized according to typical procedures K, E and L from bicyclononene AL70 and 3-(tert-butyldimethylsilyloxy)glutaric anhydride. LC-MS: $R_t$=0.87; ES+: 762.47

Example 514

1:1—Mixture of (rac.)-(3R*)-5-{(1R*,5S*)-7-{4-[2-(2-chloro-4,5-dimethylphenoxy)ethoxy]phenyl}-6-[cyclopropyl(2-p-tolylethyl)carbamoyl]-3,9-diazabicyclo[3.3.1]non-6-en-3-yl}-3-hydroxy-5-oxopentanoic acid formate salt and (rac.)-(3S*)-5-{(1R*,5S*)-7-{4-[2-(2-chloro-4,5-dimethylphenoxy)ethoxy]-phenyl}-6-[cyclopropyl(2-p-tolylethyl)carbamoyl]-3,9-diazabicyclo[3.3.1]non-6-en-3-yl}-3-hydroxy-5-oxopentanoic acid formate salt Synthesized according to typical procedures K, E and L from bicyclononene AL71 and 3-(tert-butyldimethylsilyloxy)glutaric anhydride. LC-MS: $R_t$=0.88; ES+: 730.49

Example 515

1:1—Mixture of (1R,5S)-7-{4-[2-(2-chloro-4,5-dimethylphenoxy)ethoxy]-phenyl}-3-((2S,4R)-4-hydroxypyrrolidine-2-carbonyl)-3,9-diazabicyclo-[3.3.1]non-6-ene-6-carboxylic acid (2-chlorobenzyl)cyclopropylamide formate salt and (1S,5R)-7-{4-[2-(2-chloro-4,5-dimethylphenoxy)ethoxy]phenyl}-3-((2S,4R)-4-hydroxypyrrolidine-2-carbonyl)-3,9-diazabicyclo[3.3.1]non-6-ene-6-carboxylic acid (2-chlorobenzyl)cyclopropylamide formate salt Synthesized according to typical procedures G, E and L from bicyclononene AL56 and BOC-L-hydroxyproline. LC-MS: $R_t$=0.81; ES+: 791.37

Example 516

1:1—Mixture of (1R,5S)-7-{4-[2-(2-chloro-4,5-dimethylphenoxy)ethoxy]-phenyl}-3-((2S,4R)-4-hydroxypyrrolidine-2-carbonyl)-3,9-diazabicyclo-[3.3.1]non-6-ene-6-carboxylic acid cyclopropyl-(2-methylbenzyl)amide formate salt and (1S,5R)-7-{4-[2-(2-chloro-4,5-dimethylphenoxy)ethoxy]-phenyl}-3-((2S,4R)-4-hydroxypyrrolidine-2-carbonyl)-3,9-diazabicyclo-[3.3.1]non-6-ene6-carboxylic acid cyclopropyl-(2-methylbenzyl)amide formate salt Synthesized according to typical procedures G, E and L from bicyclononene AL60 and BOC-L-hydroxyproline. LC-MS: $R_t$=0.81; ES+: 699.45

Example 517

(rac.)(1R*,5S*)-3-Acetyl-7-{4-[2-(2,3,5-trimethylphenoxy)ethyl]phenyl}-3,9-diazabicyclo[3.3.1]non-6-ene-6-carboxylic acid cyclopropylphenethylamide formate salt Synthesized according to typical procedures A and E from bicyclononene AL47 and acetyl chloride. LC-MS: $R_t$=0.92; ES+: 592.52

Example 518

(rac.)(1R*,5S*)-3-Acetyl-7-{4-[2-(2,3,5-trimethylphenoxy)ethyl]phenyl}-3,9-diazabicyclo[3.3.1]non-6-ene-6-carboxylic acid [2-(2-chlorophenyl)ethyl]-cyclopropylamide formate salt Synthesized according to typical procedures A and E from bicyclononene AL48 and acetyl chloride. LC-MS: $R_t$=0.94; ES+: 626.51

Example 519

(rac.)-(1R*,5S*)-3-Acetyl-7-{4-[2-(2,3,5-trimethylphenoxy)ethyl]phenyl}-3,9-diazabicyclo[3.3.1]non-6-ene-6-carboxylic acid cyclopropyl-[2-(2,3-difluorophenyl)ethyl]amide formate salt Synthesized according to typical procedures A and E from bicyclononene AL49 and acetyl chloride. LC-MS: $R_t$=0.93; ES+: 628.54

Example 520

(rac.)-(1R*,5S*)-3-Acetyl-7-{4-[2-(2,3,5trimethylphenoxy)ethyl]phenyl}-3,9-diazabicyclo[3.3.1]non-6-ene-6-carboxylic acid cyclopropyl-(3,5dimethoxybenzyl)amide formate salt Synthesized according to typical procedures A and E from bicyclononene AL53 and acetyl chloride. LC-MS: $R_t$=0.92; ES+: 638.54

Example 521

(rac.)-(1R*,5S*)-3-acetyl-7-{4-[2-(2,3,5-Trimethylphenoxy)ethyl]phenyl}-3,9-diazabicyclo[3.3.1]non-6-ene-6-carboxylic acid cyclopropyl-(2-p-tolylethyl)-amide formate salt Synthesized according to typical procedures A and E from bicyclononene AL54 and acetyl chloride. LC-MS: $R_t$=0.94; ES+: 606.54

Example 522

(rac.)-(1R*,5S*)-3-Acetyl-7-(4-[2-(2,3,5-trimethylphenoxy)ethyl]phenyl)-3,9-diazabicyclo[3.3.1]non-6-ene-6-carboxylic acid cyclopropyl-[2-(2-hydroxyethyl)benzyl]amide formate salt Synthesized according to typical procedures A and E from bicyclononene AL55 and acetyl chloride. LC-MS: $R_t$=0.87; ES+: 622.55

Example 523

(rac.)(1R*,5S*)-3-Acetyl-7-{4-[2-(2-chloro-4,5-dimethylphenoxy)ethoxy]-phenyl}-3,9diazabicyclo[3.3.1]non-6-ene-6-carboxylic acid cyclopropyl-[2-(2-hydroxyethyl)benzyl]amide formate salt Synthesized according to typical procedures A and E from bicyclononene AL72 and acetyl chloride. LC-MS: $R_t$=0.85; ES+: 658.47

Example 524

(rac.)-5-((1R*,5S*)-(Cyclopropylphenethylcarbamoyl)-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL47 and glutaric anhydride. LC-MS: $R_t$=0.90; ES+: 664.56

Example 525

(rac.)-5-(1R*,5S*)-6-{[2-(2-Chlorophenyl)ethyl]cyclopropylcarbamoyl}-7-{4-[2(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL48 and glutaric anhydride. LC-MS: $R_t$=0.91; ES+: 698.45

Example 526

(rac.)-5-((1R*,5S*)-6-{Cyclopropyl-[2-(2,3-difluorophenyl)ethyl]carbamoyl}-7-{4-[2-(2,3,5-trimethylphenoxy)ethyl]phenyl}-3,9-diazabicyclo[3.3.1]non-6-en-3-yl)-5-oxopentanoic acid Synthesized according to typical procedures K and E from bicyclononene AL49 and glutaric anhydride. LC-MS: $R_t$=0.90; ES+: 700.50

Example 527

(rac.)-5-((1R*,5S*)-6-{Cyclopropyl-[2-(4-fluorophenyl)ethyl]carbamoyl}-7-{4-[2-(2,3,5-trimethylphenoxy)ethyl]phenyl}-3,9diazabicyclo[3.3.1]non-6-en-3-yl)-5-oxopentanoic acid formate salt Synthesized according to typical procedures K and E from bicyclononene AL50 and glutaric anhydride. LC-MS: $R_t$=0.90; ES+: 682.54

Example 528

(rac.)-5-((1R*,5S*)-6-[Cyclopropyl-(2-o-tolylethyl)carbamoyl]-7-{4-(2-(2,3,5-trimethylphenoxy)ethyl]phenyl}-3,9-diazabicyclo[3.3.1]non-6-en-3-yl)-5-oxopentanoic acid Synthesized according to typical procedures K and E from bicyclononene AL51 and glutaric anhydride. LC-MS: $R_t$=0.91; ES+: 678.55

Example 529

1:1—Mixture of (rac.)-5-((1R*,5S*)-6-[cyclopropyl-((2R*)-2-hydroxy-2-phenylethyl)carbamoyl]-7-{4-[2-(2,3,5-trimethylphenoxy)ethyl]phenyl}-3,9-diazabicyclo[3.3.1]non-6-en-3-yl)-5-oxopentanoic acid formate salt and (rac.)-5-((1R*,5S*)-6-[cyclopropyl-((2S*)-2-hydroxy-2-phenylethyl)carbamoyl]-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL52 and glutaric anhydride. LC-MS: $R_t$=0.85; ES+: 654.50

Example 530

(rac.)-5-((1R*,5S*)-6-Cyclopropyl-(3,5-dimethoxybenzyl)carbamoyl)-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL53 and glutaric anhydride. LC-MS: $R_t$=0.879; ES+: 710.50

Example 531

(rac.)-5-((1R*,5S*)-6-[Cyclopropyl-(2-p-tolylethyl)carbamoyl]-7-{4-[2-(2,3,5-trimethylphenoxy)ethyl]phenyl}-3,9-diazabicyclo[3.3.1]non-6-en-3-yl)-5-oxopentanoic acid formate salt Synthesized according to typical procedures K and E from bicyclononene AL54 and glutaric anhydride. LC-MS: $R_t$=0.91; ES+: 678.56

Example 532

(rac.)-5-((1R*,5S*)-6-{Cyclopropyl-[2-(2-hydroxyethyl)benzyl]carbamoyl}-7-{4-[2-(2,3,5-trimethylphenoxy)ethyl]phenyl}-3,9-diazabicyclo[33.1]non-6-en-3-yl)-5-oxopentanoic acid Synthesized according to typical procedures K and E from bicyclononene AL55 and glutaric anhydride. LC-MS: $R_t$=0.85; ES+: 694.53

Example 533

(rac.)-5-(1R*,5S*)-7-{4-[2-(2-Chloro-4,5-dimethylphenoxy)ethoxy]phenyl}-6-{cyclopropyl-[2-(2-hydroxyethyl)benzyl]carbamoyl}-3,9-diazabicyclo[3.3.1]-non-6-en-3-yl)-5-oxopentanoic acid formate salt Synthesized according to typical procedures K and E from bicyclononene AL72 and glutaric anhydride. LC-MS: $R_t$=0.84; ES+: 730.46

Example 534

(rac.)-5-((1R*,5S*)-(Cyclopropylphenethylcarbamoyl)-7-{4-[2-(2,3,5-trimethylphenoxy)ethyl]phenyl}-3,9-diazabicyclo[3.3.1]non-6-en-3-yl)-2,2-dimethyl-5-oxopentanoic acid formate salt Synthesized according to typical procedures K and E from bicyclononene AL47 and 2,2-dimethylglutaric anhydride. LC-MS: $R_t$=0.93; ES+: 692.55

Example 535

(rac.)-5(1R*,5S*)-6-{[2-(2Chlorophenyl)ethyl]cyclopropylcarbamoyl}-7-{4-[2(2,3,5-trimethylphenoxy)ethyl]phenyl}-3,9-diazabicyclo[3.3.1]non-6-en-3-yl)-2,2-dimethyl-5-oxopentanoic acid formate salt Synthesized according to typical procedures K and E from bicyclononene AL48 and 2,2-dimethylglutaric anhydride. LC-MS: $R_t$=0.95 ; ES+: 726.48

Example 536

(rac.)-5-((1R*,5S*)-6-{Cyclopropyl-[2-(2,3-difluorophenyl)ethyl]carbamoyl}-7-{4-[2-(2,3,trimethylphenoxy)ethyl]phenyl}-3,9-diazabicyclo[3.3.1]non-6-en-3-yl)-2,2-dimethyl-5-oxopentanoic acid formate salt Synthesized according to typical procedures K and E from bicyclononene AL49 and 2,2dimethylglutaric anhydride. LC-MS: $R_t$=0.94; ES+: 728.51

Example 537

(rac.)-5-((1R*,5S*)-6-{Cyclopropyl-[2-(4-fluorophenyl)ethyl]carbamoyl}-7-{4-[2-(2,3,5-trimethylphenoxy)ethyl]phenyl}-3,9-diazabicyclo[3.3.1]non-6-en-3-yl)-2,2-dimethyl-5-oxopentanoic acid formate salt Synthesized according to typical procedures K and E from bicyclononene AL50 and 2,2-dimethylglutaric anhydride. LC-MS: $R_t$=0.94; ES+: 710.51

Example 538

(rac.)-5-((1R*,5S*)-6-[Cyclopropyl-(2-o-tolylethyl)carbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid formate salt Synthesized according to typical procedures K and E from bicyclononene AL51 and 2,2-dimethylglutaric anhydride. LC-MS: $R_t$=0.95 ; ES+: 706.54

Example 539

(rac.)-5-(1R*,5S*)-6-[Cyclopropyl-(3,5-dimethoxybenzyl)carbamoyl]-7-{4-[2(2,3,5-trimethylphenoxy)ethyl]phenyl}-3,9-diazabicyclo[3.3.1]non-6-en-3-yl)-2,2-dimethyl-5-oxopentanoic acid formate salt Synthesized according to typical procedures K and E from bicyclononene AL53 and 2,2dimethylglutaric anhydride. LC-MS: $R_t$=0.93; ES+:758.55

Example 540

(rac.)-5-((1R*,5S*)-6-[Cyclopropyl-(2-p-tolylethyl)carbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid formate salt Synthesized according to typical procedures K and E from bicyclononene AL54 and 2,2-dimethylglutaric anhydride. LC-MS: $R_t$=0.95; ES+: 706.53

Example 541

(rac.)-5-((1R*,5S*)-7-{4-[2-(2-Chloro-4,5-dimethylphenoxy)ethoxy]phenyl}-6-{cyclopropyl-[2-(2-hydroxyethyl)benzyl]carbamoyl}-3,9-diazabicyclo[3.3.1]-non-6-en-3-yl)-2,2-dimethyl-5-oxopentanoic acid formate salt Synthesized according to typical procedures K and E from bicyclononene AL72 and 2,2-dimethylglutaric anhydride. LC-MS: $R_t$=0.87; ES+: 758.46

Example 542

(rac.)-(1R*,5S*)-3-(4-Carbamoylbutyryl)-7-{4-[2-(2,3,5-trimethylphenoxy)-ethyl]phenyl}-3,9-diazabicyclo[3.3.1]non-6-ene-6-carboxylic acid cyclopropylphenethylamide formate salt Synthesized according to typical procedures G and E from bicyclononene AL47 and 4-carbamoylbutyric acid. LC-MS: $R_t$=0.88; ES+: 663.55

Example 543

(rac.)(1R*,5S*)-3-(4-Carbamoylbutyryl)-7-{4-[2-(2,3,5-trimethylphenoxy)-ethyl]phenyl}-3,9-diazabicyclo[3.3.1]non-6-en-6-carboxylic acid [2-(2-chlorophenyl)ethyl]cyclopropylamide formate salt Synthesized according to typical procedures G and E from bicyclononene AL48 and 4-carbamoylbutyric acid. LC-MS: $R_t$=0.90; ES+: 697.49

Example 544

(rac.)-(1R*,5S*)-3-(4-Carbamoylbutyryl)-7-{4-[2-(2,3,5-trimethylphenoxy)-ethyl]phenyl}-3,9-diazabicyclo[3.3.1]non-6-ene-6-carboxylic acid cyclopropyl-[2-(2,3-difluorophenyl)ethyl]amide formate salt Synthesized according to typical procedures G and E from bicyclononene AL49 and 4carbamoylbutyric acid. LC-MS: $R_t$=0.89; ES+: 699.49

Example 545

(rac.)-(1R*,5S*)-3-(4-Carbamoylbutyryl)-7-{4-[2-(2,3,5-trimethylphenoxy)-ethyl]phenyl}-3,9-diazabicyclo[3.3.1]non-6-ene-6-carboxylic acid cyclopropyl-[2-(4-fluorophenyl)ethyl]amide formate salt Synthesized according to typical procedures G and E from bicyclononene AL50 and 4-carbamoylbutyric acid. LC-MS: $R_t$=0.88; ES+: 681.54

Example 546

(rac.)(1R*,5S*)-3-(4 Carbamoylbutyryl)-7-{4-[2-(2, 3,5-trimethylphenoxy)-ethyl]phenyl}-3,9-diazabicyclo[3.3.1]non-6-ene-6-carboxylic acid cyclopropyl-(3,5dimethoxybenzyl)amide formate salt Synthesized according to typical procedures G and E from bicyclononene AL53 and 4-carbamoylbutyric acid. LC-MS: $R_t$=0.87; ES+: 709.50

Example 547

(rac.)-(1R*,5S*)-3-(4-Carbamoylbutryl)-7-{4-[2-(2, 3,5-trimethylphenoxy)-ethyl]phenyl}-3,9-diazabicyclo[3.3.1]non-6-ene-4-carboxylic acid cyclopropyl-(2-p-tolylethyl)amide formate salt Synthesized according to typical procedures G and E from bicyclononene AL54 and 4-carbamoylbutyric acid. LC-MS: $R_t$=0.89; ES+: 677.57

Example 548

(rac.)-(1R*,5S*)-3-(4-Carbamoylbutyryl)-7-{4-[2-(2, 3,5-trimethylphenoxy)-ethyl]phenyl}-3,9-diazabicyclo[3.3.1]non-6-ene-6-carboxylic acid cyclopropyl-[2-(2-hydroxyethyl)benzyl]amide formate salt Synthesized according to typical procedures G and E from bicyclononene AL55 and 4-carbamoylbutyric acid. LC-MS: $R_t$=0.83; ES+: 693.53

Example 549

(rac.)-(1R*,5S*)-3-(4-Carbamoylbutyryl)-7-{4-[2-(2-chloro-4,5-dimethylphenoxy)ethoxy]phenyl}-3,9-diazabicyclo[3.3.1]non-6-ene-6-carboxylic acid cyclopropyl-[2-(2-hydroxyethyl)benzyl]amide formate salt Synthesized according to typical procedures G and E from bicyclononene AL72 and 4-carbamoylbutyric acid. LC-MS: $R_t$=0.82; ES+: 729.48

Example 550

(rac.)-Acetic acid (1R*,5S*)-2-(2-{[(3-acetyl-7-{4-[2-(2,3,5-trimethylphenoxy)ethyl]phenyl}-3,9-diazabicyclo[3.3.1]non-6-ene-6-carbonyl)cyclopropylamino]methyl}phenyl)ethyl ester formate salt Synthesized according to typical procedures A and E from bicyclononene AL and acetyl chloride. LC-MS: $R_t$=0.93; ES+: 664.55

Example 551

(rac.)-Acetic acid (1R*,5S*)-2-(2-{[(3-acetyl-7-{4-[2-(2-chloro-4,5-dimethylphenoxy)ethoxy]phenyl}-3,9-diazabicyclo[3.3.1]non-6-ene-6-carbonyl)cyclopropylamino]methyl}phenyl)ethyl ester formate salt Synthesized according to typical procedures A and E from bicyclononene AL72 and acetyl chloride. LC-MS: $R_t$=0.91; ES+: 700.44

Example 552

(rac.)-(1R*,5S*)-7-{4-[2-(2,3,5-Trimethylphenoxy) ethyl]phenyl}-3,9-diazabicyclo[3.3.1]non-6-ene-6-carboxylic acid cyclopropyl-[2-(4-fluorophenyl)-ethyl]amide formate salt Synthesized according to typical procedure E from bicyclononene AK50. LC-MS: $R_t$=0.86; ES+: 568.50

Example 553

(rac.)-(1R*,5S*)-7-{4-[2-(2,3,5-Trimethylphenoxy) ethyl]phenyl}-3,9-diazabicyclo[3.3.1]non-6-ene-6-carboxylic acid cyclopropyl(3,5-dimethoxybenzyl)-amide formate salt Synthesized according to typical procedure E from bicyclononene AK53. LC-MS: $R_t$=0.85; ES+: 596.53.

Example 554

(rac.)-Acetic acid (1R*,5S*)-2-(2-{[(3-acetyl-7-{4-[2-(4-bromophenoxy)-ethoxy]phenyl}-3,9-diazabicyclo[3.3.1]non-6-ene-6-carbonyl)cyclopropylamino]methyl}phenyl)ethyl ester formate salt Synthesized according to typical procedures A and E from bicyclononene AL87 and acetyl chloride. LC-MS: $R_t$=0.89; ES+: 716.35

Example 555

1:1 Mixture of (rac.)-5-{(1R*,5S*)-7-{4-[2-(2-chloro-4,5-dimethylphenoxy)-ethoxy]phenyl}-6-[((2R*)-2-hydroxy-2-phenylethyl)methylcarbamoyl]-3,9-diazabicyclo[3.3.1]non-6-en-3-yl}-2,2-dimethyl-5-oxopentanoic acid formate salt and (rac.)-5-((1R*,5S*)-7-{4-[2-(2-chloro-4,5-dimethylphenoxy)-ethoxy]phenyl}-6-[((2S*)-2-hydroxy-2-phenylethyl)methylcarbamoyl]-3,9-diazabicyclo [3.3.1]non-6-en-3-yl}-2,2-dimethyl-5-oxopentanoic acid formate salt Synthesized according to typical procedures K and E from bicyclononene AL69 and 2,2-dimethylglutaric anhydride. LC-MS: $R_t$=0.88; ES+: 718.47

Example 556

(rac.)-(1R*,5S*)-3-Acetyl-7-{4-[3-(2-bromo-5-fluorophenoxy)propyl]phenyl}-3,9-diazabicyclo[3.3.1]non-6-ene-6-carboxylic acid (2-chlorobenzyl)cyclopropylamide formate salt Synthesized according to typical procedures G and E from bicyclononene AL20 and acetyl chloride. LC-MS; $R_t$=3.63; ES+680.28.

Example 557

(rac.)-(1R*,5S*)-7-{4-[3-(2,3,6-Trifluorophenoxy) propyl]phenyl}-3,9-diazabicyclo[3.3.1]non-6-ene-6-carboxylic acid benzylcyclopropylamide formate salt Synthesized according to typical procedure E from bicyclononene AK3. LC-MS: $R_t$=0.83; ES+: 562.38

Example 558

(rac.)-(1R*,5S*)-7-{4-[3-(2,3,6-trifluorophenoxy)propyl]phenyl}-3,9-diazabicyclo[3.3.1]non-6-ene-6-carboxylic acid (2-chlorobenzyl)ethylamide formate salt Synthesized according to typical procedure E from bicyclononene AK4. LC-MS: $R_t$=0.84; ES+: 584.35

Example 559

(rac.)(1R*,5S*)-7-{4-[3-(2,3,6-Trifluorophenoxy)propyl]phenyl}-3,9-diazabicyclo[3.3.1]non-6-ene-6-carboxylic acid cyclopropyl-(2-fluorobenzyl)amide formate salt Synthesized according to typical procedure E from bicyclononene AK5. LC-MS: $R_t$=0.83; ES+: 580.38

Example 560

(rac.)-(1R*,5S*)-7-{4-[3-(2,3,6-Trifluorophenoxy)propyl]phenyl}-3,9diazabicyclo[3.3.1]non-6-ene-6-carboxylic acid cyclopropyl-(3-trifluoromethybenzyl)amide Synthesized according to typical procedure E from bicyclononene AK6. LC-MS: $R_t$=0.86; ES+: 630.43

Example 561

(rac.)-(1R*,5S*)-7-{4-[3-(2,3,6-Trifluorophenoxy)propyl]phenyl}-3,9-diazabicyclo[3.3.1]non-6-ene-6-carboxylic acid cyclopropyl-(2-methylbenzyl)amide formate salt Synthesized according to typical procedure E from bicyclononene AK7. LC-MS: $R_t$=0.84; ES+: 576.42

Example 562

(rac.)-(1R*,5S*)-7-{4-[3-(2,3,6-Trifluorophenoxy)propyl]phenyl}-3,9diazabicyclo[3.3.1]non-6-ene-6-carboxylic acid cyclopropyl-[2-(4-methoxyphenoxy)ethyl]amide formate salt Synthesized according to typical procedure E from bicyclononene AK8. LC-MS: $R_t$=0.83; ES+: 622.45

Example 563

(rac.)-(1R*,5S*)-7-{4-[3-(2,3,6-Trifluorophenoxy)propyl]phenyl}-3,9-diazabicyclo[3.3.1]non-6-ene-6-carboxylic acid [2-(2-chlorophenyl)ethyl]-cyclopropylamide formate salt Synthesized according to typical procedure E from bicyclononene AK13. LC-MS: $R_t$=0.86; ES+: 610.39

Example 564

(rac.)-(1R*,5S*)-7-{4-[3-(2,3,6-Trifluorophenoxy)propyl]phenyl}-3,9-diazabicyclo[3.3.1]non-6-ene-6-carboxylic acid cyclopropyl-[2-(2,3-difluorophenyl)ethyl]amide formate salt Synthesized according to typical procedure E from bicyclononene AK14. LC-MS: $R_t$=0.85 ; ES+: 612.44

Example 565

(rac.)-(1R*,5S*)-7-{4-[3-(2,3,6-Trifluorophenoxy)propyl]phenyl}-3,9-diazabicyclo[3.3.1]non-6-ene-6-carboxylic acid cyclopropyl-(2-o-tolylethyl)amide formate salt Synthesized according to typical procedure E from bicyclononene AK16. LC-MS: $R_t$=0.85 ; ES+: 590.42

Example 566

(rac.)-(1R*,5S*)-7-{4-[3-(2,3,6-Trifluorophenoxy)propyl]phenyl}-3,9-diazabicyclo[3.3.1]non-6-ene-6-carboxylic acid cyclopropyl-(2-p-tolylethyl)amide formate salt Synthesized according to typical procedures G and E from bicyclononene AK18. LC-MS: $R_t$=0.85 ; ES+: 590.42

Example 567

(rac.)-(1R*,5S*)-3-Acetyl-7-{4-[3-(2,5-difluorophenoxy)propyl]phenyl}-3,9-diazabicyclo[3.3.1]non-6-ene-6-carboxylic acid (2-chlorobenzyl)cyclopropylamide formate salt Synthesized according to typical procedures F and E from bicyclononene BB1 and 2,5-difluorophenol. LC-MS: $R_t$=0.89; ES+: 614.40

Example 568

(rac.)(1R*,5S*)-3-Acetyl-7-{4-[3-(2,3-dichlorophenoxy)propyl]phenyl}-3,9-diazabicyclo[3.3.1]non-6-ene-6-carboxylic acid (2-chlorobenzyl)cyclopropylamide formate salt Synthesized according to typical procedures F and E from bicyclononene BB1 and 2,3-dichorophenol. LC-MS: $R_t$=0.94; ES+: 654.32

Example 569

(rac.)-(1R*,5S*)-3-Acetyl-7-{4-[3-(2-chloro-5-fluorophenoxy)propyl]phenyl}-3,9-diazabicyclo[3.3.1]non-6-ene-6-carboxylic acid (2-chlorobenzyl)cyclopropylamide formate salt Synthesized according to typical procedures F and E from bicyclononene BB1 and 2-chloro-5-fluorophenol. LC-MS: $R_t$=0.93; ES+: 636.36

Example 570

(rac.)(1R*,5S*)-3-Acetyl-7-{4-[3-(3-cyanopyridin-2-yloxy)propyl]phenyl}-3,9diazabicyclo[3.3.1]non-6-ene-6-carboxylic acid (2-chlorobenzyl)cyclopropylamide formate salt Synthesized according to typical procedures F and E from bicyclononene BB1 and 2-hydroxynincotinonitrile. LC-MS: $R_t$=0.86; ES+: 610.42

Example 571

(rac.)-(1R*,5S*)-7-{4-[3-(2,3,6-Trifluorophenoxy)propyl]phenyl}-3,9-diazabicyclo[3.3.1]non-6-ene-3,6-dicarboxylic acid 6-[(2-chlorobenzyl)cyclopropylamide]3-dimethylamide formate salt Synthesized according to typical procedures A and E from bicyclononene AL2 and dimethylcarbamoyl chloride. LC-MS: $R_t$=0.91; ES+: 667.42

Example 572

(rac.)-(1R*,5S*)-7-{4-[3-(2,3,6-Trifluorophenoxy)propyl]phenyl}-3,9diazabicyclo[3.3.1]non-6-ene-3,6-dicarboxylic acid 6-[(2-chlorobenzyl)cyclopropylamide]3-diethylamide formate salt Synthesized according to typical procedures A and E from bicyclononene AL2 and diethylcarbamoyl chloride. LC-MS: $R_t$=0.95; ES+: 695.44

Example 573

(rac.)-(1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-ene-3-carboxylic acid methyl ester formate salt Synthesized according to typical procedures A and E from bicyclononene AL2 and methyl chloroformate. LC-MS: $R_t$=0.91; ES+: 654.37

Example 574

(rac.)-(1R*,5S*)-6-[(2Chlorobenzyl)cyclopropylcarbamoyl]-7-{4-[3-(2,3,6-trifluorophenoxy)propyl]phenyl}-3,9-diazabicyclo[3.3.1]non-6-ene-3-carboxylic acid ethyl ester formate salt Synthesized according to typical procedures A and E from bicyclononene AL2 and ethyl chloroformate. LC-MS: $R_t$=0.93; ES+: 668.40

Example 575

(rac.)-(1R*,5S*)-3-Methanesulfonyl-7-{4-[3-(2,3,6-trifluorophenoxy)propyl]-phenyl}-3,9-diazabicyclo[3.3.1]non-6-ene-4-carboxylic acid (2-chlorobenzyl)-cyclopropylamide formate salt Synthesized according to typical procedures A and E from bicyclononene AL2 and methylsulfonyl chloride. LC-MS: $R_t$=0.92 ; ES+: 674.37

Example 576

(rac.)-(1R*,5S*)-3-Ethanesulfonyl-7-{4-[3-(2,3,6-trifluorophenoxy)propyl]-phenyl}-3,9-diazabicyclo[3.3.1]non-6-ene-6-carboxylic acid (2-chlorobenzyl)-cyclopropylamide formate salt Synthesized according to typical procedures A and E from bicyclononene AL2 and ethylsulfonyl chloride. LC-MS: $R_t$=0.93; ES+: 688.36

Example 577

(rac.)-5-((1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-en-3-yl)-5-oxopentanoic acid ethyl ester formate salt Synthesized according to typical procedures A and E from bicyclononene AL2 and glutaric acid monoethylester chloride. LC-MS: $R_t$=0.94; ES+: 738.41

Example 578

(rac.)-4-(1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-4-en-3-yl)-4-oxobutyric acid formate salt Synthesized according to typical procedures K and E from bicyclononene AL2 and succinic anhydride. LC-MS: $R_t$=0.87; ES+: 696.36

Example 579

(rac.)-3-[((1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-ene-3-carbonyl)amino]propionic acid ethyl ester formate salt Synthesized according to typical procedures A and E from bicyclononene AL2 and ethyl 4-isocyanatopropionate. LC-MS: $R_t$=0.93; ES+: 739.41

Example 580

(rac.)-4-[((1R*,5S*)-6-[(2-Chlorobenzylcyclopropylcarbamoyl]-7-{4-[3-(2,3,6-trifluorophenoxy)propyl]phenyl}-3,9-diazabicyclo [3.3.1]non-6-ene-3-carbonyl)amino]butyric acid ethyl ester formate salt Synthesized according to typical procedures A and E from bicyclononene AL2 and ethyl 4-isocyanatobutyrate. LC-MS: $R_t$=0.93; ES+: 753.39

Example 581

(rac.)-(1R*,5S*)-3-(3-Carbamoylpropionyl)-7-{4-[3-(2,3,6-trifluorophenoxy)-propyl]phenyl}-3,9-diazabicyclo[3.3.1]non-6-ene-6-carboxylic acid (2-chlorobenzyl)cyclopropylamide formate salt Synthesized according to typical procedures G and E from bicyclononene AL2 and succinamic acid. LC-MS: $R_t$=0.85; ES+: 695.38

Example 582

(rac.)-(1R*,5S*)-3-(2-Hydroxyacetyl)-7-{4-[3-(2,3,6-trifluorophenoxy)-propyl]phenyl}-3,9-diazabicyclo[3.3.1]non-6-ene-6-carboxylic acid (2-chlorobenzyl)cyclopropylamide formate salt Synthesized according to typical procedures G and E from bicyclononene AL2 and glycolic acid. LC-MS: $R_t$=0.88; ES+: 654.36

Example 583

(1S,5R)-3-((3R)-3-Hydroxybutyryl)-7-{4-[3-(2,3,6-trifluorophenoxy)propyl]-phenyl}-3,9-diazabicyclo[3.3.1]non-6-ene-6-carboxylic acid (2-chlorobenzyl)-cyclopropylamide Synthesized according to typical procedures G and E from bicyclononene AL2 and (3R)-3-hydroxybutyric acid. LC-MS: $R_t$=0.88; ES+: 682.40.

Example 584

1:1—Mixture of (rac.)-(1R*,5S*)-3-((1R*,2S*)-2-hydroxycyclopentanecarbonyl)-7-{4-[3-(2,3,6-trifluorophenoxy)propyl]phenyl}-3,9-diazabicyclo-[3.3.1]non-6-ene-6-carboxylic acid (2-chlorobenzyl)cyclopropylamide formate salt and (rac.)-(1R*,5S*)-3-((1S*,2R*)-2-hydroxycyclopentanecarbonyl)-7-{4-[3-2,3,6-trifluorophenoxy)propyl]phenyl}-3,9-diazabicyclo[3.3.1]non-6-ene-6-carboxylic acid (2-chlorobenzyl)cyclopropylamide formate salt Synthesized according to typical procedures G and E from bicyclononene AL2 and cis-2-hydroxy-1-cyclopentane carboxylic acid. LC-MS: $R_t$=0.91; ES+: 708.39.

Example 585

(rac.)-(1R*,5S*)-9-Acetyl-7-{4-[3-(2,3,6-trifluorophenoxy)propyl]phenyl}-3,9-diazabicyclo[3.3.1]non-6-ene-4-carboxylic acid (2-chlorobenzyl)cyclopropylamide formate salt Synthesized according to typical procedures A and E from bicyclononene BC and acetyl chloride. LC-MS: $R_t$=0.92; ES+: 638.34.

Example 586

(rac.)-5-((1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-en-9-yl)-5-oxopentanoic acid formate salt Synthesized according to typical procedures K and E from bicyclononene BC and glutaric anhydride. LC-MS: $R_t$=0.91; ES+: 710.33.

Example 587

(rac.)-5-(1R*,5S*)-6-[(2-Chlorobenzyl)cyclopropylcarbamoyl]-7-{4-[3-(2,3,6-trifuorophenoxy)propyl]phenyl}-3,9-diazabicyclo[3.3.1]non-6-en-9-yl)-5-oxopentanoic acid methyl ester formate salt Synthesized according to typical procedures A and E from bicyclononene BC and glutaric acid monomethylester chloride. LC-MS: $R_t$=0.95; ES+: 724.33.

Example 588

(rac.)-5-(1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-en-9-yl)-5oxopentanoic acid ethyl ester formate salt Synthesized according to typical procedures A and E from bicyclononene BC and glutaric acid monoethylester chloride. LC-MS: $R_t$=0.97; ES+: 738.38.

Example 589

(rac.)-4-[((1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-ene-9-carbonyl)-amino]butyric acid ethyl ester Synthesized according to typical procedures A and E from bicyclononene BC and ethyl 4-isocyanatobutyrate. LC-MS: $R_t$=0.95; ES+: 753.37.

Example 590

(rac.)-(1R*,5S*)-3-Formyl-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide Synthesized according to typical procedure E from bicyclononene AK2. Obtained as side-product after purification by HPLC. LC-MS: $R_t$=0.89; ES+: 624.36.

Example 591

(rac.)-3-[((1R*,5S*)-6-(2-Chlorobenzyl)cyclopropylcarbamoyl]-7-{4-[3-(2,3,6-trifluorophenoxy)propyl]phenyl}-3,9-diazabicyclo[3.3.1]non-6-ene-3-carbonyl)amino]propionic acid formate salt Synthesized according to typical procedures M and E from Example 579, then typical procedure E. LC-MS: $R_t$=0.87; ES+: 711.31.

Example 592

(rac.)-3-[((1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-4-ene-9-carbonyl)amino]propionic acid formate salt Synthesized according to typical procedures G, M and E from bicyclononene BC and ethyl 4-isocyanatopropionate. LC-MS: $R_t$=0.88; ES+: 711.33.

Example 593

(rac.)-4-[((1R*,5S*)-6-[(2-Chlorobenzyl)cyclopropylcarbamoyl]-7-{4-[3-(2,3,6-trifluorophenoxy)propyl]phenyl}-3,9-diazabicyclo[3.3.1]non-6-ene-9-carbonyl)amino]butyric acid formate salt Synthesized according to typical procedures M and E from Example 580. LC-MS: $R_t$=0.89; ES+: 725.35.

Example 594

(rac.)-(1R*,5S*)-3-acetyl-7-{4-[2-(2,3,6-Trifluorophenoxy)ethyl]phenyl}-3,9-diazabicyclo[3.3.1]non-6-ene-6-carboxylic acid (2-chlorobenzyl)cyclopropylamide formate salt Synthesized according to typical procedures F and E from bicyclononene BB2 and 2,3,6-trifluorophenol. LC-MS: $R_t$=0.89; ES+: 624.37.

Example 595

(rac.)-(1R*,5S*)-3-Acetyl-7-{4-[2-(2,3-dimethylphenoxy)ethyl]phenyl}-3,9-diazabicyclo[3.3.1]non-6-ene-6-carboxylic acid (2-chlorobenzyl)cyclopropylamide formate salt Synthesized according to typical procedures F and E from bicyclononene BB2 and 2,3-dimethylphenol. LC-MS: $R_t$=0.91; ES+: 598.42.

Example 596

(rac.)-(1R*,5S*)-3-Acetyl-7-{4-[2-(2,5-dimethylphenoxy)ethyl]phenyl}-3,9-diazabicyclo[3.3.1]non-6-ene-6-carboxylic acid (2-chlorobenzyl)cyclopropylamide Synthesized according to typical procedures F and E from bicyclononene BB2 and 2,5-dimethylphenol. LC-MS: $R_t$=0.91; ES+: 598.43.

Example 597

(rac.)-(1R*,5S*)-3-Acetyl-7-{4-[2-(2-chloro-4,5-dimethylphenoxy)ethyl]-phenyl}-3,9-diazabicyclo[3.3.1]non-6-ene-6-carboxylic acid (2-chlorobenzyl)-cyclopropylamide formate salt Synthesized according to typical procedures G and E from bicyclononene BB2 and 2-chloro-4,5-dimethylphenol. LC-MS: $R_t$=0.93; ES+: 632.39.

Example 598

(rac.)-(1R*,5S*)-3-Acetyl-7-{4-[2-(2,4dichlorophenoxy)ethyl]phenyl}-3,9-diazabicyclo[3.3.1]non-6-ene-6-carboxylic acid (2-chlorobenzyl)cyclopropylamide formate salt Synthesized according to typical procedures F and E from bicyclononene BB2 and 2,4-dichlorophenol. LC-MS: $R_t$=0.91; ES+: 640.32.

Example 599

(rac.)-(1R*,5S*)-3-Acetyl-7-{4-[2-(2,3-dichlorophenoxy)ethyl]phenyl}-3,9-diazabicyclo[3.3.1]non-6-ene-6-carboxylic acid (2-chlorobenzyl)cyclopropylamide formate salt Synthesized according to typical procedures F and E from bicyclononene BB2 and 2,3-dichlorophenol. LC-MS: $R_t$=0.91; ES+: 640.34.

Example 600

(rac.)-(1R*,5S*)-3-Acetyl-7-{4-[2-(2,6-difluorophenoxy)ethyl]phenyl}-3,9-diazabicyclo[3.3.1]non-6-ene-6-carboxylic acid (2-chlorobenzyl)cyclopropylamide formate salt Synthesized according to typical procedures F and E from bicyclononene BB2 and 2,6-difluorophenol. LC-MS: $R_t$=0.88; ES+: 606.39.

Example 601

(rac.)-(1R*,5S*)-3-Acetyl-7-{4-[2-(2,5-difluorophenoxy)ethyl]phenyl}-3,9-diazabicyclo[3.3.1]non-6-ene-6-carboxylic acid (2-chlorobenzyl)cyclopropylamide fromate salt Synthesized according to typical procedures F and E from bicyclononene BB2 and 2,5-difluorophenol. LC-MS: $R_t$=0.88; ES+: 606.40.

Example 602

(rac.)-(1R*,5S*)-3-Acetyl-7-{4-[2-(3,5-dichlorophenoxy)ethyl]phenyl}-3,9-diazabicyclo[3.3.1]non-6-ene-6-carboxylic acid (2-chlorobenzyl)cyclopropylamide Synthesized according to typical procedures F and E from bicyclononene BB2 and 3,5-dichlorophenol. LC-MS: $R_t$=0.93; ES+: 638.32.

Example 603

(rac.)-(1R*,5S*)-3-Acetyl-7-{4-[2-(2-chloro-5-methylphenoxy)ethyl]phenyl}-3,9-diazabicyclo[3.3.1]non-6-ene-6-carboxylic acid (2-chlorobenzyl)-cyclopropylamide formate salt Synthesized according to typical procedures F and E from bicyclononene BB2 and 2-chloro-5-methylphenol. LC-MS: $R_t$=0.91; ES+: 618.40.

Example 604

(rac.)-(1R*,5S*)-3-Acetyl-7-{4-[2-(2-chloro-5-fluorophenoxy)ethyl]phenyl}-3,9-diazabicyclo[3.3.1]non-6-ene-6-carboxylic acid (2-chlorobenzyl)-cyclopropylamide formate salt Synthesized according to typical procedures F and E from bicyclononene BB2 and 2-chloro-5-fluorophenol. LC-MS: $R_t$=0.89; ES+: 622.33.

Example 605

(rac.)-(1R*,5S*)-3-Acetyl-7-{4-[2-(2,3,6-trichlorophenoxy)ethyl]phenyl}-3,9-diazabicyclo[3.3.1]non-6-ene-6-carboxylic acid (2-chlorobenzyl)cyclopropylamide formate salt Synthesized according to typical procedures F and E from bicyclononene BB2 and 2,5,6-trichlorophenol. LC-MS: $R_t$=0.93; ES+: 674.27.

Example 606

(rac.)-(1R*,5S*)-9-(4Carbamoylbutryl)-7-{4-[2-(2,3,6-trifluorophenoxy)-propyl]phenyl}-3,9-diazabicyclo[3.3.1]non-6-ene-6-carboxylic acid (2-chlorobenzyl)cyclopropylamide formate salt Synthesized according to typical procedures G and E from bicyclononene BC and 4-carbamoylbutyric acid. LC-MS: $R_t$=0.88; ES+: 709.39.

Example 607

(rac.)-(1R*,5S*)-9-(3-Carbamoylpropionyl)-7-{4-[2-(2,3,6-trifluorophenoxy)-propyl]phenyl}-3,9-diazabicyclo[3.3.1]non-6-ene-6-carboxylic acid (2-chlorobenzyl)cyclopropylamide formate salt Synthesized according to typical procedures G and E from bicyclononene BC and succinamic acid. LC-MS: $R_t$=0.88; ES+: 695.36.

Example 608

(rac.)-(1R*,5S*)-9-(2-Hydroxyacetyl)-7-{4-[2-(2,3,6-trifluorophenoxy)-propyl]phenyl}-3,9-diazabicyclo[3.3.1]non-6-ene-6-carboxylic acid (2-chlorobenzyl)cyclopropylamide formate salt Synthesized according to typical procedures G and E from bicyclononene BC and glycolic acid. LC-MS: $R_t$=0.90; ES+: 654.37.

Example 609

(1R,5S)-9-((3S)-3-Hydroxybutyryl)-7-{4-[2-(2,3,6-trifluorophenoxy)propyl]-phenyl}-3,9-diazabicyclo[3.3.1]non-6-ene-6-carboxylic acid (2-chlorobenzyl)-cyclopropylamide formate salt Synthesized according to typical procedures G and E from bicyclononene BC and (3R)-3-hydroxybutyric acid. LC-MS: $R_t$=0.91; ES+: 682.41.

Example 610

(rac.)-(1R*,5S*)-9-Methanesulfonyl-7-{4-[2-(2,3,6-trifluorophenoxy)propyl]-phenyl}-3,9-diazabicyclo[3.3.1]non-6-ene-6-carboxylic acid (2-chlorobenzyl)-cyclopropylamide formate salt Synthesized according to typical procedures A and E from bicyclononene BC and methylsulfonyl chloride. LC-MS: $R_t$=0.95; ES+: 674.38.

Example 611

(rac.)-(1R*,5S*)-9-Ethanesulfonyl-7-{4-[2-(2,3,6-trifluorophenoxy)propyl]-phenyl}-3,9-diazabicyclo[3.3.1]non-6-ene-6-carboxylic acid (2-chlorobenzyl)-cyclopropylamide formate salt Synthesized according to typical procedures A and E from bicyclononene BC and ethylsulfonyl chloride. LC-MS: $R_t$=0.97; ES+: 688.37.

Example 612

(rac.)-(1R*,5S*)-3-Acetyl-7-{4-[3-(2,3,6-trifluorophenoxy)propyl]phenyl}-3,9-diazabicyclo[3.3.1]non-6ene-6-carboxylic acid cyclopropyl-(2-fluoro-5-methoxybenzyl)amide formate salt Synthesized according to typical procedures H and E from bicyclononene AJ2 and cyclopropyl(2-fluoro-5-methoxybenzyl)amine. LC-MS: $R_t$=0.89; ES+: 652.31.

Example 613

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(3-methoxybenzyl)amide formate salt Synthesized according to typical procedures H and E from bicyclononene AJ2 and cyclopropyl(3-methoxybenzyl)amine. LC-MS: $R_t$=0.88; ES+: 634.34.

Example 614

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(2-methoxybenzyl)amide formate salt Synthesized according to typical procedures H and E from bicyclononene AJ2 and cyclopropyl(2-methoxybenzyl)amine. LC-MS: $R_t$=0.89; ES+: 634.32.

Example 615

(rac.)-(1R*,5S*)-3-Acetyl-7-{4-[3-(2,3,6-trifluorophenoxy)propyl]phenyl}-3,9-diazabicyclo[3.3.1]non-4-ene-6-carboxylic acid cyclopropyl-(3,4dimethoxybenzyl)amide formate salt Synthesized according to typical procedures H and E from bicyclononene AJ2 and cyclopropyl(3,4-dimethoxybenzyl)amine. LC-MS: $R_t$=0.86; ES+: 664.34.

Example 616

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid (2-chloro-3-trifluoromethylbenzyl)cyclopropylamide formate salt Synthesized according to typical procedures H and E from bicyclononene AJ2 and (2-chloro-3-trifluoromethylbenzyl)cyclopropylamine. LC-MS: $R_t$=0.94; ES+: 706.20.

Example 617

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid benzo[1,3]dioxol-5-ylmethyl-cyclopropylamide formate salt Synthesized according to typical procedures H and E from bicyclononene AJ2 and (6-chlorobenzo[1,3]dioxol-5-ylmethyl)cyclopropylamine. LC-MS: $R_t$=0.91; ES+: 682.28.

Example 618

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(5-fluoro-2-methoxybenzyl)amide formate salt Synthesized according to typical procedures H and E from bicyclononene AJ2 and cyclopropyl(2-methoxy-5-fluorobenzyl)amine. LC-MS: $R_t$=0.90; ES+: 652.32.

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid (2-chloro-6-fluorobenzyl)-cyclopropylamide formate salt Synthesized according to typical procedures H and E from bicyclononene AJ2 and cyclopropyl(2-chloro-6-fluorobenzyl)amine. LC-MS: $R_t$=0.89; ES+: 656.30.

Example 620

(rac.)-(1R*,5S*)-3-Acetyl-7-{4-[3-(2,3,6-trifluorophenoxy)propyl]phenyl}-3,9-diazabicyclo[3.3.1]non-6-ene-4-carboxylic acid (2-bromobenzyl)cyclopropylamide formate salt Synthesized according to typical procedures H and E from bicyclononene AJ2 and cyclopropyl(2-bromobenzyl)amine. LC-MS: $R_t$=0.91; ES+: 684.23.

Example 621

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(2,6-difluorobenzyl)amide formate salt Synthesized according to typical procedures H and E from bicyclononene AJ2 and cyclopropyl(2,6-difluorobenzyl)amine. LC-MS: $R_t$=0.88; ES+: 640.29.

Example 622

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(2,3-dimethylbenzyl)amide formate salt Synthesized according to typical procedures H and E from bicyclononene AJ2 and cyclopropyl(2,3-dimethylbenzyl)amine. LC-MS: $R_t$=0.92; ES+: 632.35.

Example 623

(rac.)-(1R*,5S*)-3-Acetyl-7-{4-[3-(2,3,6trifluorophenoxy)propyl]phenyl}-3,9-diazabicyclo[3.3.1]non-6-ene-6-carboxylic acid cyclopropyl-(3-fluoro-2-methylbenzyl)amide formate salt Synthesized according to typical procedures H and E from bicyclononene AJ2 and cyclopropyl(2-methyl-3-fluorobenzyl)amine. LC-MS: $R_t$=0.91; ES+: 636.31.

Example 624

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(3,5-difluorobenzyl)amide formate salt Synthesized according to typical procedures H and E from bicyclononene AJ2 and cyclopropyl(3,5-difluorobenzyl)amine. LC-MS: $R_t$=0.93; ES+: 672.23.

Example 625

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid (2-chloro-3,6difluorobenzyl)-cyclopropylamide formate salt Synthesized according to typical procedures H and E from bicyclononene AJ2 and cyclopropyl(2-chloro-3,6-difluorobenzyl)amine. LC-MS: $R_t$=0.90; ES+: 674.25.

Example 626

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(2,3-dichlorobenzyl)amide formate salt Synthesized according to typical procedures H and E from bicyclononene AJ2 and cyclopropyl(2,3-dichlorobenzyl)amine. LC-MS: $R_t$=0.93; ES+: 672.25.

Example 627

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(3-trifluoromethoxybenzyl)amide formate salt Synthesized according to typical procedures H and E from bicyclononene AJ2 and cyclopropyl(3-trifluoromethoxybenzyl)amine. LC-MS: $R_t$=0.93; ES+: 688.28.

Example 628

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(3-methylbenzyl)-amide formate salt Synthesized according to typical procedures H and E from bicyclononene AJ2 and cyclopropyl(3-methylbenzyl)amine. LC-MS: $R_t$=0.90; ES+: 618.36.

Example 629

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(2,3-difluorobenzyl)amide formate salt Synthesized according to typical procedures H and E from bicyclononene AJ2 and cyclopropyl(2,3-difluorobenzyl)amine. LC-MS: $R_t$=0.90; ES+: 640.29.

Example 630

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid (3-chlorobenzyl)cyclopropylamide formate salt Synthesized according to typical procedures H and E from bicyclononene AJ2 and cyclopropyl(3-chlorobenzyl)amine. LC-MS: $R_t$=0.91; ES+: 638.27.

Example 631

(rac.)-(1R*,5S*)-3-Acetyl-7-{4-[3-(2,3,6-trifluorophenoxy)propyl]phenyl}-3,9-diazabicyclo[3.3.1]non-6-ene-6-carboxylic acid cyclopropyl-(4-fluorobenzyl)-amide formate salt Synthesized according to typical procedures H and E from bicyclononene AJ2 and cyclopropyl(4-fluorobenzyl)amine. LC-MS: $R_t$=0.89; ES+: 622.34.

Example 632

(rac.)-(1R*,5S*)-3-Acetyl-7-{4-[3-(2-bromo-5-fluorophenoxy)ethyl]phenyl}-3,9-diazabicyclo[3.3.1]non-6-ene-6-carboxylic acid (2-chlorobenzyl)-cyclopropylamide Synthesized according to typical procedures H and E from bicyclononene AJ1 and (2-chlorobenzyl)cyclopropylamine. The title compound was purified by FC. LC-MS: $R_t$=4.17; ES+: 666.07.

Example 633

(rac.)-(1R*,5S*)-3-Acetyl-7-{4-[3-(2-chlorophenoxy)propyl]phenyl}-3,9-diazabicyclo[3.3.1]non-6-ene-6-carboxylic acid (2-chlorobenzyl)cyclopropylamide formate salt Synthesized according to typical procedures H and E from bicyclononene T2 and (2-chlorobenzyl)cyclopropylamine. LC-MS: $R_t$=0.92; ES+: 617.94.

Example 634

(rac.)-(1R*,5S*)-3-Acetyl-7-{4-[3-(2-chlorophenoxy)propyl]phenyl}-3,9-diazabicyclo[3.3.1]non-6-ene-6-carboxylic acid [2-(4-methoxyphenoxy)ethyl]-methylamide formate salt Synthesized according to typical procedures H and E from bicyclononene T2 and cyclopropyl-[2-(4-methoxyphenoxy)ethyl]amine. LC-MS: $R_t$=0.84; ES+: 618.03.

Example 635

(rac.)-(1R*,5S*)-3-Acetyl-7-{4-[3-(2-chlorophenoxy)propyl]phenyl}-3,9-diazabicyclo[3.3.1]non-6-ene-6-carboxylic acid methyl-(3-trifluoromethylbenzyl)amide formate salt Synthesized according to typical procedures H and E from bicyclononene T2 and cyclopropyl-(3-trifluoromethylbenzyl)amine. LC-MS: $R_t$=0.89; ES+: 626.06.

Example 636

(rac.)-(1R*,5S*)-3-Acetyl-7-{4-[3-(2-chlorophenoxy)propyl]phenyl}-3,9-diazabicyclo[3.3.1]non-6-ene-6-carboxylic acid [2-(3,4-dimethylphenoxy)-ethyl]methylamide formate salt Synthesized according to typical procedures H and E from bicyclononene T2 and cyclopropyl-[2-(3,4dimethylphenoxy)ethyl]amine. LC-MS: $R_t$=0.91; ES+: 616.13.

Example 637

(rac.)-(1R*,5S*)-3-Acetyl-7-{4-[3-(2-chlorophenoxy)propyl]phenyl}-3,9-diazabicyclo[3.3.1]non-6-ene-6-carboxylic acid (3,5-dimethoxybenzyl)methylamide formate salt Synthesized according to typical procedures H and E from bicyclononene T2 and cyclopropyl-(3,5-dimethoxybenzyl)amine. LC-MS: $R_t$=0.84; ES+: 618.11.

Example 638

(rac.)(1R*,5S*)-3-Acetyl-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide trifluoroacetate salt Synthesized according to typical procedures H and E from bicyclononene AJ2 and (2-chlorobenzyl)cyclopropylamine. LC-MS: $R_t$=1.00; ES+: 638.14.

Example 639

(rac.)-(1R*,5S*)-3-Acetyl-7-{4-[3-(3-fluorophenoxy)propyl]phenyl}-3,9-diazabicyclo[3.3.1]non-6-ene-6-carboxylic acid (2-chlorobenzyl)cyclopropylamide trifluoroacetate salt Synthesized according to typical procedures H and E from bicyclononene AJ3 and (2-chlorobenzyl)cyclopropylamine. LC-MS: $R_t$=0.99; ES+: 638.14.

Example 640

(rac.)-(1R*,5S*)-5-[7-{4-[2-(2-Bromo-5-fluorophenoxy)ethyl]phenyl}-6-(methylphenethylcarbamoyl)-3,9-diazabicyclo[3.3.1]non-6-en-3-yl]-2,2-dimethyl-5oxopentanoic acid trifluoroacetate salt Synthesized according to typical procedures K and E from bicyclononene AL1 and 3,3-dimethyldihydropyran-2,6-dione. LC-MS: $R_t$=0.95; ES+: 710.13.

Example 641

(rac.)-(1R*,5S*)-3-Acetyl-7-{4-[3-(2-chlorophenoxy)propyl]phenyl}-3,9-diazabicyclo[3.3.1]non-6-ene-6-carboxylic acid (2-chlorobenzyl)isopropylamide trifluoroacetate salt Synthesized according to typical procedures H and E from bicyclononene T2 and (2-chlorobenzyl)isopropylamine. LC-MS: $R_t$=1.03; ES+: 620.20.

Example 642

(rac.)-(1R*,5S*)-3-Acetyl-7-{4-[3-(2,3,6-trichlorophenoxy)ethyl]phenyl}-3,9-diazabicyclo[3.3.1]non-6-ene-6-carboxylic acid methylphenethylamide trifluoroacetate salt Synthesized according to typical procedures F and E from bicyclononene U2 and 2,3,6-trichlorophenol. LC-MS: $R_t$=1.00; ES+: 625.99.

Example 643

(rac.)-(1R*,5S*)-3-Acetyl-7-{4-[3-(2-chlorophenoxy)propyl]phenyl}-3,9-diazabicyclo[3.3.1]non-6-ene-6-carboxylic acid (2-chlorobenzyl)ethylamide formate salt Synthesized according to typical procedures H and E from bicyclononene T2 and (2-chlorobenzyl)ethylamine. LC-MS: $R_t$=0.89; ES+: 606.07.

Example 644

(rac.)-(1R*,5S*)-3-Acetyl-7-{4-[2-(3,4-dichlorophenoxy)ethoxy]phenyl}-3,9-diazabicyclo[3.3.1]non-6-ene-6-carboxylic acid methylphenethylamide formate salt Synthesized according to typical procedures F and E from bicyclononene U4 and 3,4-dichlorophenol. LC-MS: $R_t$=0.86; ES+: 608.01.

Example 645

(rac.)-(1R*,5S*)-3-Acetyl-7-{4-[2-(2-chloro-4,5-dimethylphenoxy)ethoxy]-phenyl}-3,9-diazabicyclo[3.3.1]non-6-ene-6-carboxylic acid methylphenethylamide formate salt Synthesized according to typical procedures F and E from bicyclononene U4 and 2-chloro-4,5-dimethylphenol. LC-MS: $R_t$=0.87; ES+: 602.07.

Example 646

(rac.)-(1R*,5S*)-3-Acetyl-7-{4-[3-(2-chlorophenoxy)propyl]phenyl}-3,9-diazabicyclo[3.3.1]non-6-ene-6-carboxylic acid (2-chlorobenzyl)methylamide formate salt Synthesized according to typical procedures F and E from bicyclononene T2 and (2-chlorobenzyl)methylamine. LC-MS: $R_t$=0.87; ES+: 591.99.

Example 647

(rac.)-(1R*,5S*)-3-Methyl-7-{4-[3-(2,3,6-trifluorophenoxy)propyl]phenyl}-3,9-diazabicyclo[3.3.1]non-6-ene-6-carboxylic acid (2-chlorobenzyl)-cyclopropylamide formate salt A mixture of bicyclononene AL2 (1 eq.), DIPEA (3 eq.) and methyl iodide (10 eq.) in $CH_2Cl_2$ was stirred at rt overnight. The solvents were removed under reduced pressure and the residue treated according to typical procedure E. LC-MS: $R_t$=0.89; ES+: 610.32.

Example 648

(rac.)-(1R*,5S*)-3-Ethyl-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide formate salt A mixture of bicyclononene AL2 (1 eq.), DIPEA (3 eq.) and ethyl iodide (10 eq.) in $CH_2Cl_2$ was stirred at rt overnight. The solvents were removed under reduced pressure and the residue treated according to typical procedure E. LC-MS: $R_t$=0.91; ES+: 624.33.

Example 649

(rac.)-(1R*,5S*)-3-(2-Aminoacetyl)-7-{4-[3-(2,3,6-trifluorophenoxy)propyl]-phenyl}-3,9-diazabicyclo[3.3.1]non-6-ene-6-carboxylic acid (2-chlorobenzyl)-cyclopropylamide formate salt Synthesized according to typical procedures G, L and E from bicyclononene AL2 and Boc-glycine. LC-MS: $R_t$=0.80; ES+: 653.32.

Example 650

(rac.)-(1R*,5S*)-3-(3-Aminopropionyl)-7-{4-[3-(2,3,6-trifluorophenoxy)-propyl]phenyl}-3,9-diazabicyclo[3.3.1]non-6-ene-6-carboxylic acid (2-chlorobenzyl)cyclopropylamide formate salt Synthesized according to typical procedures G, L and E from bicyclononene AL2 and Boc-β-alanine. LC-MS: $R_t$=0.80; ES+: 667.32.

Example 651

(rac.)-(1R*,5S*)-3-(5-Morpholin-4-yl-5-oxopentanoyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide formate salt Synthesized according to typical procedure H, from bicyclononene AL2 and glutaric anhydride, then according to typical procedure K and E from morpholine. LC-MS: $R_t$=0.89; ES+: 779.31.

Example 652

(rac.)-(1R*,5S*)-3-(2-Tetrazol-1-ylactyl)-7-{4-[3-(2,3,6-trifluorophenoxy)-propyl]phenyl}-3,9-diazabicyclo[3.3.1]non-6-ene-4carboxylic acid (2-chlorobenzyl)cyclopropylamide formate salt Synthesized according to typical procedures G and E from bicyclononene AL2 and (5H-tetrazol-5-yl)acetic acid. LC-MS: $R_t$=0.91; ES+: 706.23.

Example 653

(rac.)-(1R*,5S*)-3-(5-Oxo-5-piperazin-1-ylpentanoyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide formate salt Synthesized according to typical procedure H, from bicyclononene AL2 and glutaric anhydride, then according to typical procedure K, L and E from Boc-piperazine. LC-MS: $R_t$=0.78; ES+: 778.37.

Example 654

1:1—Mixture of (1R,5S)-3-((2S)-2-amino-3-hydroxypropionyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide formate salt and (1S,5R)-3-((2S)-2-amino-3-hydroxypropionyl)-7-{4-[3-(2,3,6-trifluorophenoxy)propyl]-phenyl}-3,9-diazabicyclo[3.3.1]non-6-ene-6-carboxylic acid (2-chlorobenzyl)-cyclopropylamide formate salt Synthesized according to typical procedures G, L and E from bicyclononene AL2 and Boc-serine. LC-MS: $R_t$=0.79; ES+: 683.34.

Example 655

1:1—Mixture of (1R,5S)-3-((2S)-2-aminopropionyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide formate salt and (1S,5R)-3-((2S)-2-aminopropionyl)-7-{4-[3-(2,3,6-trifluorophenoxy)propyl]phenyl}-3,9-diazabicyclo[3.3.1]non-6-ene-4carboxylic acid (2-chlorobenzyl)cyclopropylamide formate salt Synthesized according to typical procedures G, L and E from bicyclononene AL2 and Boc-alanine. LC-MS: $R_t$=0.80; ES+: 667.32.

Example 656

(rac.)-(1R*,5S*)-3-Acetyl-7-{4-[2-(2,6-dichloro-4-methylphenoxy)ethoxy]-phenyl}-3,9-diazabicyclo[3.3.1]non-6-ene-6-carboxylic acid cyclopropyl-(2,3-dichlorobenzyl)amide formate salt Synthesized according to typical procedures H and E from bicyclononene BN4 and (2,3-dichlorobenzyl)cyclopropylamine. LC-MS: $R_t$=0.96; ES+: 702.09.

Example 657

(rac.)-(1R*,5S*)-3-Acetyl-7-{4-[2-(2,6-dichloro-4-methylphenoxy)ethoxy]-phenyl}-3,9-diazabicyclo[3.3.1]non-6-ene-4-carboxylic acid cyclopropyl-(2,3-dimethylbenzyl)amide formate salt Synthesized according to typical procedures H and E from bicyclononene BN4 and cyclopropyl-(2,3-dimethylbenzyl)amine. LC-MS: $R_t$=0.94; ES+: 662.27.

Example 658

(rac.)-(1R*,5S*)-3-Acetyl-7-{4-[2-(2,6-dichloro-4-methylphenoxy)ethoxy]-phenyl}-3,9-diazabicyclo[3.3.1]non-6-ene-6-carboxylic acid (2-chloro-3-trifluoromethylbenzyl)cyclopropylamide formate salt Synthesized according to typical procedures H and E from bicyclononene BN4 and (2-chloro-3-trifluoromethylbenzyl)cyclopropylamine. LC-MS: $R_t$=0.96; ES+: 736.08.

Example 659

(rac.)-(1R*,5S*)-3-Acetyl-7-{4-[2-(2,6-dichloro-4-methylphenoxy)ethoxy]-phenyl}-3,9-diazabicyclo[3.3.1]non-6-ene-6-carboxylic acid (2-bromobenzyl)-cyclopropylamide formate salt Synthesized according to typical procedures H and E from bicyclononene BN4 and (2-bromobenzyl)cyclopropylamine. LC-MS: $R_t$=0.92; ES+: 682.20.

Example 660

(rac.)-(1R*,5S*)-3-Acetyl-7-{4-[2-(2,6-dichloro-4-methylphenoxy)ethoxy]-phenyl}-3,9-diazabicyclo[3.3.1]non-6-ene-4-carboxylic acid (2-chlorobenzyl)-cyclopropylamide formate salt Synthesized according to typical procedures H and E from bicyclononene BN4 and (2-chlorobenzyl)cyclopropylamine. LC-MS: $R_t$=0.93; ES+: 668.20.

Example 661

(rac.)-(1R*,5S*)-3-Acetyl-7-{4-[2-(2,6-dichloro-4-methylphenoxy)ethoxy]-phenyl}-3,9-diazabicyclo[3.3.1]non-6-ene-6-carboxylic acid (2-chlorobenzyl)-ethylamide formate salt Synthesized according to typical procedures H and E from bicyclononene BN4 and (2-chlorobenzyl)ethylamine. LC-MS: $R_t$=0.93; ES+: 656.20.

Example 662

(rac.)(1R*,5S*)-3-Acetyl-7-{4-[2-(2,6-dichloro-4-methylphenoxy)ethoxy]-phenyl}-3,9-diazabicyclo[3.3.1]non-6-ene-6-carboxylic acid (6-chlorobenzo[1,3]dioxol-5-ylmethyl)cyclopropylamide formate salt Synthesized according to typical procedures H and E from bicyclononene BN4 and (6-chlorobenzo[1,3]dioxol-5-ylmethyl)cyclopropylamine. LC-MS: $R_t$=0.93; ES+: 712.15.

Example 663

(rac.)-(1R*,5S*)-3-Acetyl-7-{4-[2-(2,6dichloro-4-methylphenoxy)ethoxy]-phenyl}-3,9-diazabicyclo[3.3.1]non-6-ene-6-carboxylic acid cyclopropyl-(3,5-dimethoxybenzyl)amide formate salt Synthesized according to typical procedures H and E from bicyclononene BN4 and cyclopropyl-(3,5-dimethoxybenzyl)amine. LC-MS: $R_t$=0.92; ES+: 694.20.

Example 664

(rac.)-(1R*,5S*)-3-Acetyl-7-{4-[2-(2,6-dichloro-4-methylphenoxy)ethoxy]-phenyl}-3,9-diazabicyclo[3.3.1]non-6-ene-6-carboxylic acid cyclopropyl-(3-methoxybenzyl)amide formate salt Synthesized according to typical procedures H and E from bicyclononene BN4 and cyclopropyl-(3-methoxybenzyl)amine. LC-MS: $R_t$=0.91; ES+: 664.25.

Example 665

(rac.)-(1R*,5S*)-3-Acetyl-7-{4-[2(2-chloro-5-fluorophenoxy)ethoxy]phenyl}-3,9-diazabicyclo[3.3.1]non-6-ene-6-carboxylic acid cyclopropyl-(2,3dichlorobenzyl)amide formate salt Synthesized according to typical procedures H and E from bicyclononene BN10 and cyclopropyl-(2,3-dichlorobenzyl)amine. LC-MS: $R_t$=0.92; ES+: 672.22.

Example 666

(rac.)-(1R*,5S*)-3-Acetyl-7-{4-[2-(2-chloro-5-fluorophenoxy)ethoxy]phenyl}-3,9-diazabicyclo[3.3.1]non-4-ene-4-carboxylic acid (2-chloro-3-trifluoromethylbenzyl)cyclopropylamide formate salt Synthesized according to typical procedures H and E from bicyclononene BN10 and (2-chloro-3-trifluoromethylbenzyl)cyclopropylamine. LC-MS: $R_t$=0.93; ES+: 706.09.

Example 667

(rac.)-(1R*,5S*)-3-Acetyl-7-{4-[2-(2,6-dichloro-4-methylphenoxy)ethoxy]-phenyl}-3,9-diazabicyclo[3.3.1]non-6-ene-6-carboxylic acid (3-chlorobenzyl)-cyclopropylamide formate salt Synthesized according to typical procedures H and E from bicyclononene BN4 and (3-chlorobenzyl)cyclopropylamine. LC-MS: $R_t$=0.93; ES+: 668.21.

Example 668

(rac.)-(1R*,5S*)-3-Acetyl-7-{4-[2-(2,6-dichloro-4-methylphenoxy)ethoxy]-phenyl}-3,9-diazabicyclo[3.3.1]non-6-ene-6-carboxylic acid cyclopropyl-(3-methylbenzyl)amide formate salt Synthesized according to typical procedures H and E from bicyclononene BN4 and cyclopropyl-(3-methylbenzyl)amine. LC-MS: $R_t$=0.93; ES+: 648.23.

Example 669

(rac.)-(1R*,5S*)-3-Acetyl-7-{4-[2-(2,6dichloro-4-methylphenoxy)ethoxy]-phenyl}-3,9-diazabicyclo[3.3.1]non-6-ene-6-carboxylic acid cyclopropyl-(2-fluoro-5-methoxybenzyl)amide formate salt Synthesized according to typical procedures H and E from bicyclononene BN4 and cyclopropyl-(2-fluoro-5-methoxybenzyl)amine. LC-MS: $R_t$=0.92; ES+: 682.20.

Example 670

(rac.)-(1R*,5S*)-3-Acetyl-7-{4-[2-(2-chloro-4,5dimethylphenoxy)-ethoxy]phenyl}-3,9diazabicyclo[3.3.1]non-6-ene-6-carboxylic acid cyclopropyl-(2,3-dichlorobenzyl)amide formate salt Synthesized according to typical procedures H and E from bicyclononene BN3 and cyclopropyl-(2,3-dichlorobenzyl)amine. LC-MS: $R_t$=0.95.; ES+: 684.20.

Example 671

(rac.)-(1R*,5S*)-3-Acetyl-7-{4-[3-(2-chloro-3,6-difluorophenoxy)propyl]-phenyl}-3,9-diazabicyclo[3.3.1]non-6-ene-6-carboxylic acid (2-chlorobenzyl)-cyclopropylamide formate salt Synthesized according to typical procedures F and E from bicyclononene BB1 and 2-chloro-3,6-difluorophenol. LC-MS: $R_t$=0.93; ES+: 654.28.

Example 672

(rac.)-(1R*,5S*)-3-Acetyl-7-{4-[2-(2-chloro-4,5-dimethylphenoxy)ethoxy]-phenyl}-3,9-diazabicyclo[3.3.1]non-6-ene-6-carboxylic acid (2-chloro-3-trifluoromethylbenzyl)cyclopropylamide formate salt Synthesized according to typical procedures H and B from bicyclononene BN3 and (2-chloro-3-trifluoromethylbenzyl)cyclopropylamine. LC-MS: $R_t$=0.96; ES+: 716.18.

Example 673

(rac.)-(1R*,5S*)-3-Acetyl-7-{4-[2-(2,6-dichloro-4-methylphenoxy)ethoxy]-phenyl}-3,9-diazabicyclo[3.3.1]non-6-ene-6-carboxylic acid cyclopropyl-(3,4-dimethoxybenzyl)amide formate salt Synthesized according to typical procedures H and E from bicyclononene BN4 and cyclopropyl-(3,4dimethoxybenzyl)amine. LC-MS: $R_t$=0.89; ES+: 694.23.

Example 674

(rac.)-(1R*,5S*)-3-Acetyl-7-{4-[2-(2,6-dichloro-4-methylphenoxy)ethoxy]-phenyl}-3,9-diazabicyclo[3.3.1]non-6-ene-6-carboxylic acid cyclopropyl-(3-trifluoromethoxybenzyl)amide formate salt Synthesized according to typical procedures H and E from bicyclononene BN4 and cyclopropyl-(3-trifluoromethoxybenzyl)amine. LC-MS: $R_t$=0.95; ES+: 718.13.

Example 675

(rac.)-(1R*,5S*)-3-Acetyl-7-{4-[2-(2,4,5-trichlorophenoxy)ethoxy]phenyl}-3,9-diazabicyclo[3.3.1]non-6-ene-6-carboxylic acid (2-chloro-3-trfluoromethylbenzyl)cyclopropylamide formate salt Synthesized according to typical procedures H and E from bicyclononene BN9 and (2-chloro-3-trfluoromethylbenzyl)cyclopropylamine. LC-MS: $R_f$=0.97; ES+: 758.08.

Example 676

(rac.)-(1R*,5S*)-3-Acetyl-7-{4-[2-(2,4,5-trichlorophenoxy)ethoxy]phenyl}-3,9-diazabicyclo-[3.3.1]non-6-ene-4-carboxylic acid cyclopropyl2,3-dichlorobenzyl)amide formate salt Synthesized according to typical procedures H and E from bicyclononene BN9 and cyclopropyl-(2,3dichlorobenzyl)amine. LC-MS: $R_f$=0.96; ES+: 724.02.

Example 677

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid cyclopropyl-(2,3dimethylbenzyl)amide formate salt Synthesized according to typical procedures H and E from bicyclononene BN5 and cyclopropyl-(2,3-dimethylbenzyl)amine. LC-MS: $R_t$=0.92; ES+: 648.25.

Example 678

(rac.)-(1R*,5S*)-3-Acetyl-7-{4-[2-(2,4,5-trichlorophenoxy)ethoxy]phenyl}-3,9-diazabicyclo-[3.3.1]non-6-ene-6-carboxylic acid cyclopropyl-(2,3-dimethylbenzyl)amide formate salt Synthesized according to typical procedures H and E from bicyclononene BN9 and cyclopropyl(2,3-dimethylbenzyl)amine. LC-MS: $R_f$=0.95; ES+: 684.12.

Example 679

(rac.)-(1R*,5S*)-3-Acetyl-7-{4-[2-(2-chloro-4-dimethylphenoxy)ethoxy]-phenyl}-3,9-diazabicyclo[3.3.1]non-6-ene-6-carboxylic acid cyclopropyl-(2,3-dimethylbenzyl)amide formate salt Synthesized according to typical procedures H and E from bicyclononene BN3 and cyclopropyl-(2,3-dimethylbenzyl)amine. LC-MS: $R_f$=0.94; ES+: 642.31.

Example 680

(rac.)-(1R*,5S*)-3-Acetyl-7-{4-[2-(2-bromo-5-fluorophenoxy)ethoxy]phenyl}-3,9-diazabicyclo[3.3.1]non-6-ene-6-carboxylic acid cyclopropyl-(2,3-dichlorobenzyl)amide formate salt Synthesized according to typical procedures H and E from bicyclononene BN2 and cyclopropyl-(2,3dichlorobenzyl)amine. LC-MS: $R_t$=0.92; ES+: 718.05.

Example 681

(rac.)-(1R*,5S*)-3-Acetyl-7-{4-[2-(2-chloro-4,5-dimethylphenoxy)ethoxy]-phenyl}-3,9-diazabicyclo[3.3.1]non-6-ene-6-carboxylic acid (2-bromobenzyl)-cyclopropylamide formate salt Synthesized according to typical procedures H and E from bicyclononene BN3 and (2-bromobenzyl)cyclopropylamine. LC-MS: $R_f$=0.94; ES+: 694.15.

Example 682

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid cyclopropyl-(2,3-dichlorobenzyl)amide formate salt Synthesized according to typical procedures H and E from bicyclononene BN5 and cyclopropyl-(2,3-dichlorobenzyl)amine. LC-MS: $R_f$=0.93; ES+: 690.06.

Example 683

(rac.)-(1R*,5S*)-3-Acetyl-7-{4-[2-(2-chloro-5-fluorophenoxy)ethoxy]phenyl}-3,9-diazabicyclo[3.3.1]non-6-ene-6-carboxylic acid cyclopropyl-(2,3-dimethylbenzyl)amide formate salt Synthesized according to typical procedures H and E from bicyclononene BN10 and cyclopropyl-(2,3dimethylbenzyl)amine. LC-MS: $R_f$=0.91; ES+: 632.31.

Example 684

(rac.)-(1R*,5S*)-3-Acetyl-7-{4-[2-(2,4,5-trichlorophenoxy)ethoxy]phenyl}-3,9-diazabicyclo[3.3.1]non-6-ene-6-carboxylic acid (2-chlorobenzyl)-cyclopropylamide formate salt Synthesized according to typical procedures H and E from bicyclononene BN9 and (2-chlorobenzyl)cyclopropylamine. LC-MS: $R_f$=0.94; ES+: 690.07.

Example 685

(rac.)-(1R*,5S*)-3-Acetyl-7-{4-[2-(2-bromo-5-fluorophenoxy)ethoxy]phenyl}-3,9-diazabicyclo[3.3.1]non-6-ene-6-carboxylic acid (2-chloro-3-trifluoromethylbenzyl)cyclopropylamide formate salt Synthesized according to typical procedures H and E from bicyclononene BN2 and (2-chloro-3-trifluoromethylbenzyl)cyclopropylamine. LC-MS: $R_f$=0.93; ES+: 752.06.

Example 686

(rac.)-(1R*,5S*)-3-Acetyl-7-{4-[2-(2,4,3-trichlorophenoxy)ethoxy]phenyl}-3,9diazabicyclo-[3.3.1]non-6-ene-6-carboxylic acid (2-bromobenzyl)-cyclopropylamide formate salt Synthesized according to typical procedures H and E from bicyclononene BN9 and (2-bromobenzyl)cyclopropylamine. LC-MS: $R_f$=0.95; ES+: 733.99.

Example 687

(rac.)-(1R*,5S*)-3-Acetyl-7-{4-[2-(2-bromo-5-fluorophenoxy)ethoxy]phenyl}-3,9-diazabicyclo[3.3.1]non-6-ene-6-carboxylic acid cyclopropyl-(2,3-dimethylbenzyl)amide formate salt Synthesized according to typical procedures H and E from bicyclononene BN2 and cyclopropyl-(2,3-dimethylbenzyl)amine. LC-MS: $R_t$=0.91; ES+: 678.22.

Example 688

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid (2-chloro-3-trifluoromethylbenzyl)cyclopropylamide formate salt Synthesized according to typical procedures H and E from bicyclononene BN5 and (2-chloro-3-tifluoromethylbenzyl)cyclopropylamine. LC-MS: $R_t$=0.94; ES+: 724.13.

Example 689

(rac.)-(1R*,5S*)-3-Acetyl-7-{4-[2-(2-chloro-4,5-methylphenoxy)ethoxy]-phenyl}-3,9-diazabicyclo[3.3.1]non-6-ene-6-carboxylic acid (3-chlorobenzyl)-cyclopropylamide formate salt Synthesized according to typical procedures H and E from bicyclonenene BN3 and (3-chlorobenzyl)cyclopropylamine. LC-MS: $R_t$=0.93; ES+: 648.26.

Example 690

(rac.)-(1R*,5S*)-3-Acetyl-7-{4-[2-(2,4,5-trichlorophenoxy)ethoxy]phenyl}-3,9-diazabicyclo[3.3.1]non-6-ene-6-carboxylic acid (2-chlorobenzyl)ethylamide formate salt Synthesized according to typical procedures H and E from bicyclononene BN9 and (2-chlorobenzyl)ethylamine. LC-MS: $R_t$=0.94; ES+: 678.12.

Example 691

(rac.)-(1R*,5S*)-3-Acetyl-7-{4-[2-(2-chloro-5-fluorophenoxy)ethoxy]phenyl}-3,9-diazabicyclo[3.3.1]non-6-ene-6-carboxylic acid (2-bromobenzyl)cyclopropylamide formate salt Synthesized according to typical procedures H and E from bicyclononene BN10 and (2-bromobenzyl)cyclopropylamine. LC-MS: $R_t$=0.90; ES+: 684.11.

Example 692

(rac.)-(1R*,5S*)-3-Acetyl-7-{4-[2-(4-chloro-2methylphenoxy)ethoxy]-phenyl}-3,9-diazabicyclo[3.3.1]non-6-ene-6-carboxylic acid cyclopropyl-(2,3-dichlorobenzyl)amide formate salt Synthesized according to typical procedures H and E from bicyclononene BN7 and cyclopropyl-(2,3-dichlorobenzyl)amine. LC-MS: $R_t$=0.94; ES+: 670.17

Example 693

(rac.)-(1R*,5S*)-3-Acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(3-methoxybenzyl)amide formate salt Synthesized according to typical procedures H and E from bicyclononene BN3 and cyclopropyl-(3-methoxybenzyl)amine. LC-MS: $R_t$=0.91; ES+: 644.32.

Example 694

(rac.)-(1R*,5S*)-3-Acetyl-7-{4-[2-(2-bromo-5-fluorophenoxy)ethoxy]-phenyl}-3,9-diazabicyclo[3.3.1]non-6-ene-6-carboxylic acid (2-bromobenzyl)-cyclopropylamide formate salt Synthesized according to typical procedures H and E from bicyclononene BN2 and cyclopropyl(2-bromobenzyl)amine. LC-MS: $R_t$=0.91; ES+: 728.04.

Example 695

(rac.)-(1R*,5S*)-3-Acetyl-7-{4-[2-(4-chloro-2-methylphenoxy)ethoxy]-phenyl}-3,9-diazabicyclo[3.3.1]non-6-ene-6-carboxylic acid cyclopropyl-(2,3-dimethylbenzyl)amide formate salt Synthesized according to typical procedures H and E from bicyclononene BN7 and cyclopropyl(2,3-dimethylbenzyl)amine. LC-MS: $R_t$=0.93; ES+: 628.30.

Example 696

(rac.)-(1R*,5S*)-3-Acetyl-7-{4-[2-(2,4,5-trichlorophenoxy)ethoxy]phenyl}-3,9-diazabicyclo[3.3.1]non-6-ene-6-carboxylic acid cyclopropyl-(3-methoxybenzyl)amide formate salt Synthesized according to typical procedures H and E from bicyclononene BN9 and cyclopropyl-(3-methoxybenzyl)amine. LC-MS: $R_t$=0.92; ES+: 686.14.

Example 697

(rac.)-(1R*,5S*)-3-Acetyl-7-{4-[2-(2-chloro-4,5-dimethylphenoxy)ethoxy]-phenyl}-3,9-diazabicyclo[3.3.1]non-6-nen-6-carboxylic acid cyclopropyl-(2-fluoro-5-methoxybenzyl)amide formate salt Synthesized according to typical procedures H and E from bicyclononene BN3 and cyclopropyl-(2-fluoro-5-methoxybenzyl)amine. LC-MS: $R_t$=0.91; ES+: 662.29.

Example 698

(rac.)-(1R*,5S*)-3-Acetyl-7-{4-[2-(4-chloro-2-methylphenoxy)ethoxy]-phenyl}-3,9-diazabicyclo[3.3.1]non-6-ene-6-carboxylic acid (2-bromobenzyl)-cyclopropylamide formate salt Synthesized according to typical procedures H and E from bicyclononene BN7 and (2-bromobenzyl)cyclopropylamine. LC-MS: $R_t$=0.93; ES+: 680.15.

Example 699

(rac.)-(1R*,5S*)-3-Acetyl-7-{4-[2-(2-chloro-5-fluorophenoxy)ethoxy]phenyl}-3,9-diazabicyclo[3.3.1]non-6-ene-6-carboxylic acid (2-chlorobenzyl)-cyclopropylamide formate salt Synthesized according to typical procedures H and E from bicyclononene BN10 and (2-chlorobenzyl)cyclopropylamine. LC-MS: $R_t$=0.90; ES+: 638.22.

Example 700

(rac.)-(1R*,5S*)-3-Acetyl-7-{4-[2-(2,4,5-trichlorophenoxy)ethoxy]phenyl}-3,9-diazabicyclo[3.3.1]non-6-ene-6-carboxylic acid cyclopropyl-(3,5-dimethoxybenzyl)amide formate salt Synthesized according to typical procedures H and E from bicyclononene BN9 and cyclopropyl-(3,5-dimethoxybenzyl)amine. LC-MS: $R_t$=0.93; ES+: 716.14.

Example 701

(rac.)-(1R*,5S*)-3-Acetyl-7-{4-[2-(2,3-chlorophenoxy)ethoxy]phenyl}-3,9-diazabicyclo[3.3.1]non-6-ene-6-carboxylic acid (2-bromobenzyl)cyclopropylamide formate salt Synthesized according to typical procedures H and E from bicyclononene BN5 and (2-bromobenzyl)cyclopropylamine. LC-MS: $R_t$=0.91; ES+: 700.07.

Example 702

(rac.)-(1R*,5S*)-3-Acetyl-7-{4-[2-(2-chloro-4,5-dimethylphenoxy)ethoxy]-phenyl}-3,9-diazabicyclo[3.3.1]non-6-ene-6-carboxylic acid (6-chlorobenzo[1,3]dioxol-5-ylmethyl)-cyclopropylamide formate salt Synthesized according to typical procedures H and E from bicyclononene BN3 and (6-chlorobenzo[1,3]dioxol-5-ylmethylcyclopropylamine. LC-MS: $R_t$=0.93; ES+: 694.17.

Example 703

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid (2-chlorobenzyl)cyclopropylamide formate salt Synthesized according to typical procedures H and E from bicyclononene BN5 and (2-chlorobenzyl)cyclopropylamine. LC-MS: $R_t$=0.91; ES+: 656.19.

Example 704

(rac.)-(1R*,5S*)-3-Acetyl-7-{4-[2-(4-chloro-2-methylphenoxy)ethoxy]-phenyl}-3,9-diazabicyclo[3.3.1]non-6-ene-6-carboxylic acid (2-chloro-3-trifluoromethylbenzyl)cyclopropylamide formate salt Synthesized according to typical procedures H and E from bicyclononene BN7 and (2-chloro-3-trifluoromethylbenzyl)cyclopropylamine. LC-MS: $R_t$=0.95; ES+: 702.17.

Example 705

(rac.)-(1R*,5S*)-3-Acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(3-methylbenzyl)amide formate salt Synthesized according to typical procedures H and E from bicyclononene BN3 and cyclopropyl-(3-methylbenzyl)amine. LC-MS: $R_t$=0.92; ES+: 628.32.

Example 706

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid (2-chlorobenzyl)ethylamide formate salt Synthesized according to typical procedures H and E from bicyclononene BN5 and (2-chlorobenzyl)ethylamine. LC-MS: $R_t$=0.90; ES+: 642.19.

Example 707

(rac.)-(1R*,5S*)-3-Acetyl-7-{4-[2-(2-chloro-5-fluorophenoxy)ethoxy]phenyl}-3,9-diazabicyclo[3.3.1]non-6-ene-6-carboxylic acid cyclopropyl-(2-fluoro-5-methoxybenzyl)amide formate salt Synthesized according to typical procedures H and E from bicyclononene BN10 and cyclopropyl-(2-fluoro-5-methoxybenzyl)amine. LC-MS: $R_t$=0.88; ES+: 652.26.

Example 708

(rac.)-(1R*,5S*)-3-Acetyl-7-{4-[2-(4-chloro-2-methylphenoxy)ethoxy]-phenyl}-3,9-diazabicyclo[3.3.1]non-6-ene-6-carboxylic acid (2-chlorobenzyl)-cyclopropylamide formate salt Synthesized according to typical procedures H and E from bicyclononene BN7 and cyclopropyl(2-chlorobenzyl)amine. LC-MS: $R_t$=0.92; ES+: 634.22.

Example 709

(rac.)-(1R*,5S*)-3-Acetyl-7-{4-[2-(2-bromo-5-fluorophenoxy)ethoxy]-phenyl}-3,9-diazabicyclo[3.3.1]non-6-ene-6-carboxylic acid cyclopropyl-(3,5-dimethoxybenzyl)amide formate salt Synthesized according to typical procedures H and E from bicyclononene BN2 and cyclopropyl-(3,5dimethoxybenzyl)amine. LC-MS: $R_t$=0.88; ES+: 708.14.

Example 710

(rac.)-(1R*,5S*)-3-Acetyl-7-{4-[2-(2-chloro-5-fluorophenoxy)ethoxy]-phenyl}-3,9-diazabicyclo[3.3.1]non-6-ene-6-carboxylic acid cyclopropyl-(3-methoxybenzyl)amide formate salt Synthesized according to typical procedures H and E from bicyclononene BN10 and cyclopropyl-(3-methoxybenzyl)amine. LC-MS: $R_t$=0.87; ES+: 634.27.

Example 711

(rac.)(1R*,5S*)-3-Acetyl-7-{4-[2-(2,4,5-trichlorophenoxy)ethoxy]phenyl}-3,9-diazabicyclo[3.3.1]non-6-ene-6-carboxylic acid (3-chlorobenzyl)-cyclopropylamide formate salt Synthesized according to typical procedures H and E from bicyclononene BN9 and (3-chlorobenzyl)cyclopropylamine. LC-MS: $R_t$=0.94; ES+: 690.09.

Example 712

(rac.)-(1R*,5S*)-3-Acetyl-7-{4-[2-(2,6-dichloro-4-methylphenoxy-ethoxy]-phenyl}-3,9-diazabicyclo[3.3.1]non-6-ene-6-carboxylic acid cyclopropyl-(3,5-difluorobenzyl)amide formate salt Synthesized according to typical procedures H and E from bicyclononene BN4 and cyclopropyl-(3,5-difluorobenzyl)amine. LC-MS: $R_t$=0.93; ES+: 670.22.

Example 713

(rac.)-(1R*,5S*)-3-Acetyl-7-{4-[2-(2,4,5-trichlorophenoxy)ethoxy]phenyl}-3,9-diazabicyclo[3.3.1]non-6-ene-6-carboxylic acid cyclopropyl-(2-fluoro-5-methoxybenzyl)amide formate salt Synthesized according to typical procedures H and E from bicyclononene BN9 and cyclopropyl-(2-fluoro-5-methoxybenzyl)amine. LC-MS: $R_t$=0.93; ES+: 702.40.

Example 714

(rac.)-(1R*,5S*)-3-Acetyl-7-{4-[2-(2,4,5-trichlorophenoxy)ethoxy]phenyl}-3,9-diazabicyclo[3.3.1]non-6-ene-6-carboxylic acid cyclopropyl-(3,4-dimethoxybenzyl)amide formate salt Synthesized according to typical procedures H and E from bicyclononene BN9 and cyclopropyl-(3,4-dimethoxybenzyl)amine. LC-MS: $R_t$=0.90; ES+: 716.10.

Example 715

(rac.)-(1R*,5S*)-3-Acetyl-7-{4-[2-(2-chloro-5-fluorophenoxy)ethoxy]phenyl}-3,9-diazabicyclo[3.3.1]non-6-ene-6-carboxylic acid (6-chlorobenzo[1,3]-dioxol-5-ylmethyl)cyclopropylamide formate salt Synthesized according to typical procedures H and E from bicyclononene BN10 and (6-chlorobenzo[1,3]dioxol-5-ylmethyl)cyclopropylamine. LC-MS: $R_t$=0.90; ES+: 684.19.

Example 716

(rac.)-(1R*,5S*)-3-Acetyl-7-{4-[2-(2-bromo-5-fluorophenoxy)ethoxy]phenyl}-3,9-diazabicyclo[3.3.1]non-6-ene-6-carboxylic acid (3-chlorobenzyl)-cyclopropylamide formate salt Synthesized according to typical procedures H and E from bicyclononene BN2 and (3-chlorobenzyl)cyclopropylamine. LC-MS: $R_t$=0.90; ES+: 682.16.

Example 717

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid cyclopropyl-(3,4-dimethoxybenzyl)amide formate salt Synthesized according to typical procedures H and E from bicyclononene BN5 and cyclopropyl-(3,4-dimethoxybenzyl)amine. LC-MS: $R_t$=0.97; ES+: 758.08.

Example 718

(rac.)-(1R*,5S*)-3-Acetyl-7-{4-[2-(2-chloro-5-fluorophenoxy)ethoxy]phenyl}-3,9-diazabicyclo[3.3.1]non-6-ene-6-carboxylic acid (2-chlorobenzyl)-ethylamide formate salt Synthesized according to typical procedures H and E from bicyclononene BN10 and (2-chlorobenzyl)ethylamine. LC-MS: $R_t$=0.89; ES+: 626.25.

Example 719

(rac.)-(1R*,5S*)-3-Acetyl-7-{4-[2-(4-chloro-2-methylphenoxy)ethoxy]-phenyl}-3,9-diazabicyclo[3.3.1]non-6-ene-6-carboxylic acid cyclopropyl-(3,5-dimethoxybenzyl)amide formate salt Synthesized according to typical procedures H and E from bicyclononene BN7 and cyclopropyl-(3,5-dimethoxybenzyl)amine. LC-MS: $R_t$=0.90; ES+: 660.29.

Example 720

(rac.)(1R*,5S*)-3-Acetyl-7-{4-[2-(2,4,5-trichlorophenoxy)ethoxy]phenyl}-3,9-diazabicyclo[3.3.1]non-6-ene-6-carboxylic acid cyclopropyl-(3-methylbenzyl)amide formate salt Synthesized according to typical procedures H and E from bicyclononene BN9 and cyclopropyl(3-methylbenzyl)amine. LC-MS: $R_t$=0.94; ES+: 670.22.

Example 721

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid cyclopropyl-(2-fluoro-5-methoxybenzyl)amide formate salt Synthesized according to typical procedures H and E from bicyclononene BN5 and cyclopropyl-(2-fluoro-5-methoxybenzyl)amine. LC-MS: $R_t$=0.89; ES+: 668.25.

Example 722

(rac.)-(1R*,5S*)-3-Acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(3,5-difluorobenzyl)amide formate salt Synthesized according to typical procedures H and E from bicyclononene BN3 and cyclopropyl-(3,5-difluorobenzyl)amine. LC-MS: $R_t$=0.92; ES+: 650.23.

Example 723

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid cyclopropyl-(3,5-dimethoxybenzyl)amide formate salt Synthesized according to typical procedures H and E from bicyclononene BN5 and cyclopropyl-(3,5-dimethoxybenzyl)amine. LC-MS: $R_t$=0.89; ES+: 680.22.

Example 724

(rac.)-(1R*,5S*)-3-Acetyl-7-{4-[2-(2-chloro-5-fluorophenoxy)ethoxy]-phenyl}-3,9-diazabicyclo[3.3.1]non-6-ene-6-carboxylic acid (2-chlorobenzyl)-cyclopropylamide formate salt Synthesized according to typical procedures H and E from bicyclononene BN10 and cyclopropyl(3-chlorobenzyl)amine. LC-MS: $R_t$=0.90; ES+: 638.22.

Example 725

(rac.)-(1R*,5S*)-3-Acetyl-7-{4-[2-(2-bromo-5-fluorophenoxy)ethoxy]-phenyl}-3,9-diazabicyclo[3.3.1]non-6-ene-6-carboxylic acid (2-chlorobenzyl)-cyclopropylamide formate salt Synthesized according to typical procedures H and E from bicyclononene BN2 and (2-chlorobenzyl)cyclopropylamine. LC-MS: $R_t$=0.90; ES+: 684.12.

Example 726

(rac.)-(1R*,5S*)-3-Acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(3,4-dimethoxybenzyl)amide formate salt Synthesized according to typical procedures H and E from bicyclononene BN3 and cyclopropyl-(3,4dimethoxybenzyl)amine. LC-MS: $R_t$=0.88; ES+: 674.31.

Example 727

(rac.)-(1R*,5S*)-3-Acetyl-7-{4-[2-(2-chloro-4,5-dimethylphenoxy)ethoxy]-phenyl}-3,9-diazabicyclo[3.3.1]non-6-ene-6-carboxylic acid cyclopropyl-(3-trifluoromethoxybenzyl)amide formate salt Synthesized according to typical procedures H and E from bicyclononene BN3 and cyclopropyl-(3-trifluoromethoxybenzyl)amine. LC-MS: $R_t$=0.95; ES+: 698.22.

Example 728

(rac.)-(1R*,5S*)-3-Acetyl-7-{4-[2-(2-chloro-5-fluorophenoxy)ethyl]phenyl}-3,9-diazabicyclo[3.3.1]non-6-ene-6-carboxylic acid cyclopropyl-(3-methylbenzyl)amide formate salt Synthesized according to typical procedures H and E from bicyclononene BN10 and cyclopropyl-(3-methylbenzyl)amine. LC-MS: $R_t$=0.89; ES+: 618.28.

Example 729

(rac.)-(1R*,5S*)-3-Acetyl-7-{4-[2-(2-chloro-5-fluorophenoxy)ethoxy]phenyl}-3,9-diazabicyclo[3.3.1]non-6-ene-6-carboxylic acid cyclopropyl-(3,5-dimethoxybenzyl)amide formate salt Synthesized according to typical procedures H and E from bicyclononene BN10 and cyclopropyl-(3,5-dimethoxybenzyl)amine. LC-MS: $R_t$=0.88; ES+: 664.27.

Example 730

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid cyclopropyl-(3-methylbenzyl)amide formate salt Synthesized according to typical procedures H and E from bicyclononene BN5 and cyclopropyl-(3-methylbenzyl)amine. LC-MS: $R_t$=0.90; ES+: 634.21.

Example 731

(rac.)-(1R*,5S*)-3-Acetyl-7-{4-[2-(2-bromo-5-fluorophenoxy)ethoxy]phenyl}-3,9-diazabicyclo[3.3.1]non-6-ene-6-carboxylic acid cyclopropyl-(2-fluoro-5-methoxybenzyl)amide formate salt Synthesized according to typical procedures H and E from bicyclononene BN2 and cyclopropyl-(2-fluoro-5-methoxybenzyl)amine. LC-MS: $R_t$=0.89; ES+: 696.14.

Example 732

(rac.)-(1R*,5S*)-3-Acetyl-7-{4-[2-(2-bromo-5-fluorophenoxy)ethoxy]phenyl}-3,9-diazabicyclo[3.3.1]non-6-ene-6-carboxylic acid (2-chlorobenzyl)ethylamide formate salt Synthesized according to typical procedures H and E from bicyclononene BN2 and (2-chlorobenzyl)ethylamine. LC-MS: $R_t$=0.90; ES+: 672.14.

Example 733

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid (6-chlorobenzo[1,3]dioxol-5-ylmethyl)cyclopropylamide formate salt Synthesized according to typical procedures H and E from bicyclononene BN5 and (6-chlorobenzo[1,3]dioxol-5-ylmethyl)cyclopropylamine. LC-MS: $R_t$=0.91; ES+: 700.12.

Example 734

(rac.)-(1R*,5S*)-3-Acetyl-7-{4-[2-(2,3-dichlorophenoxy)ethoxy]phenyl}-3,9-diazabicyclo[3.3.1]non-6-ene-6-carboxylic acid (3-chlorobenzyl)cyclopropylamide formate salt Synthesized according to typical procedures H and E from bicyclononene BN5 and (3-chlorobenzyl)cyclopropylamine. LC-MS: $R_t$=0.91; ES+: 656.19.

Example 735

(rac.)-(1R*,5S*)-3-Acetyl-7-{4-[2-(4-chloro-2-methylphenoxy)ethoxy]-phenyl}-3,9-diazabicyclo[3.3.1]non-6-ene-6-carboxylic acid (6-chlorobenzo[1,3]dioxol-5-ylmethyl)cyclopropylamide formate salt Synthesized according to typical procedures H and E from bicyclononene BN7 and (6-chlorobenzo[1,3]dioxol-5-ylmethyl)cyclopropylamine. LC-MS: $R_t$=0.92; ES+: 678.20.

Example 736

(rac.)-(1R*,5S*)-3-Acetyl-7-{4-[2-(2-bromo-5-fluorophenoxy)ethoxy]phenyl}-3,9-diazabicyclo[3.3.1]non-6-ene-6-carboxylic acid cyclopropyl-(3-methoxybenzyl)amide formate salt Synthesized according to typical procedures H and E from bicyclononene BN2 and cyclopropyl-(3-methoxybenzyl)amine. LC-MS: $R_t$=0.88; ES+: 678.20.

Example 737

(rac.)-(1R*,5S*)-3-Acetyl-7-{4-[2(4-chloro-2-methylphenoxy)ethoxy]-phenyl}-3,9-diazabicyclo[3.3.1]non-4-ene-4carboxylic acid (2-chlorobenzyl)-ethylamide formate salt Synthesized according to typical procedures H and E from bicyclononene BN7 and (2-chlorobenzyl)ethylamine. LC-MS: $R_t$=0.91; ES+: 622.26.

Example 738

(rac.)-(1R*,5S*)-3-Acetyl-7-{4-[2-(4-chloro-2-methylphenoxy)ethoxy]-phenyl}-3,9-diazabicyclo[3.3.1]non-6-ene-6-carboxylic acid cyclopropyl-(3-methylbenzyl)amide formate salt Synthesized according to typical procedures H and E from bicyclononene BN7 and cyclopropyl-(3-methylbenzyl)amine. LC-MS: $R_t$=0.91; ES+: 614.32.

Example 739

(rac.)-(1R*,5S*)-3-Acetyl-7-{4-[2-(2,4,5-trichlorophenoxy)ethoxy]phenyl}-3,9-diazabicyclo[3.3.1]non-6-ene-6-carboxylic acid (6-chlorobenzo[1,3]dioxol-5-ylmethyl)cyclopropylamide formate salt Synthesized according to typical procedures H and E from bicyclononene BN9 and (6-chlorobenzo[1,3]dioxol-5-ylmethyl)cyclopropylamine. LC-MS: $R_t$=0.94; ES+: 734.06.

Example 740

(rac.)-(1R,5S)-7-{4-[3-(2,3,6-Trifluorophenoxy)propylphenyl}-3,9-diazabicyclo[3.3.1]non-6-ene-6-carboxylic acid (2-chlorobenzyl)cyclopropylamide From Example 149, separated by chiral preparative HPLC.

Example 741

(rac.)-(1S,5R)-7-{4-[3-(2,3,6-Trifluorophenoxy)propylphenyl}-3,9-diazabicyclo[3.3.1]non-6-ene-6-carboxylic acid (2-chlorobenzyl)cyclopropylamide From Example 149, separated by chiral preparative HPLC.

Example 742

(rac.)-(1R*,5S*)-3-Acetyl-7-{4-[3-(2,6-dichloro-4-methylphenoxy)propyl]-phenyl}-3,9-diazabicyclo[3.3.1]non-6-ene-6-carboxylic acid (2-chlorobenzyl)-cyclopropylamide formate salt Synthesized according to typical procedures F and E from bicyclononene BB1 and 2,6-dichloro-4-methylphenol. LC-MS: $R_t$=0.96; ES+: 666.35.

Example 743

(rac.)-(1R*,5S*)-7-{4-[3-(2-Bromo-5-fluorophenoxy)propyl]phenyl}-3,9-diazabicyclo[3.3.1]non-6-ene-6-carboxylic acid (2-chlorobenzyl)cyclopropylamide Synthesized according to typical procedure E from bicyclononene AL20. LC-MS: $R_t$=0.86; ES+: 640.21.

The following assay was carried out in order to determine the activity of the compounds of general formula I and their salts.

Inhibition of Human Recombinant Renin by the Compounds of the Invention

The enzymatic in vitro assay was performed in 384-well polypropylene plates (NUNC). The assay buffer consisted of 10 mM PBS (GIBCO BRL) including 1 mM EDTA and 0.1% BSA. The incubates were composed of 50 µL per well of an enzyme mix and 2.5 µL of renin inhibitors in DMSO. The enzyme mix was premixed at 4° C. and consisted of the following components:

human recombinant renin (0.16 ng/mL);
synthetic human angiotensin(1-14) (0.5 µM); and
hydroxyquinoline sulfate (1 mM).

The mixtures were then incubated at 37° C. for 3 h.

To determine the enzymatic activity and its inhibition, the accumulated Ang I was detected by an enzyme immunoassay (EIA) in 384-well plates (NUNC). 5 µL of the incubates or standards were transferred to immuno plates which were previously coated with a covalent complex of Ang I and bovine serum albumin (Ang I-BSA). 75 µL of Ang I-antibodies in assay buffer above including 0.01% TWEEN 20 were added and a primary incubation made at 4° C. overnight. The plates were washed 3 times with PBS including 0.01% TWEEN 20, and then incubated for 2 h at room temperature with an antirabbit-peroxidase coupled antibody (WA 934, AMERSHAM). After washing the plates 3 times, the peroxidase substrate ABTS (2.2'-azino-di-(3-ethyl-benzthiazolin-sulfonate), was added and the plates incubated for 60 min at room temperature. After stopping the reaction with 0.1M citric acid pH 4.3, the plate was evaluated in a microplate reader at 405 nm. The percentage of inhibition was calculated of each concentration point and the concentration of renin inhibition was determined that inhibited the enzyme activity by 50% ($IC_{50}$). The $IC_{50}$-values of all compounds tested are below 100 nM. However selected compounds exhibit a very good bioavailability and are metabolically more stable than prior art compounds.

The invention claimed is:

1. A compound of general formula I

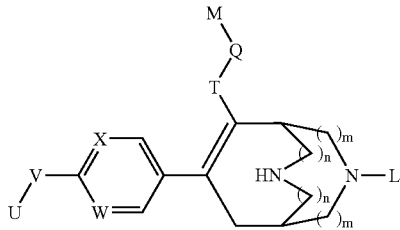

General formula I wherein

X and W represent a —CH— group;
V represents —$(CH_2)_r$—; -A-$(CH_2)_s$—; —$CH_2$-A-$(CH_2)_t$—; —$(CH_2)_s$-A-; —$(CH_2)_2$-A-$(CH_2)_u$—; -A-$(CH_2)_v$—B—; —$CH_2$—$CH_2$—$CH_2$-A-$CH_2$—; -A-$CH_2$—$CH_2$—B—$CH_2$—; —$CH_2$-A-$CH_2$-A-$CH_2$—$CH_2$—B—; —$CH_2$—$CH_2$—$CH_2$-A-$CH_2$—$CH_2$—; —$CH_2$—$CH_2$—$CH_2$—$CH_2$-A-$CH_2$—; -A-$CH_2$—$CH_2$—B—$CH_2$—$CH_2$—; —$CH_2$-A-$CH_2$—$CH_2$—B—$CH_2$—; —$CH_2$-A-$CH_2$—$CH_2$—$CH_2$—B—; or —$CH_2$—$CH_2$-A-$CH_2$—$CH_2$—B—;

A and B independently represent —O—; —S—; —SO—; or —$SO_2$—;

U represents aryl; or heteroaryl;
T represents —$CONR^1$—; —$(CH_2)_p$OCO—; —$(CH_2)_p$N$(R^1)$CO—; —$(CH_2)_p$N$(R^1)SO_2$—; or —COO—;
Q represents lower alkylene; or lower alkenylene;
M represents hydrogen; cycloalkyl; aryl; heterocyclyl; or heteroaryl;
L represents —$R^3$; —$COR^3$; —$COOR^3$; —$CONR^2R^3$; —$SO_2R^3$; —$SO_2NR^2R^3$; or —COCH(Aryl)$_2$;
$R^1$ represents hydrogen; lower alkyl; lower alkenyl; lower alkinyl; cycloalkyl; aryl; or cycloalkyl-lower alkyl;
$R^2$ and $R^{2'}$, independently represent hydrogen; lower alkyl; lower alkenyl; cycloalkyl; or cycloalkyl-lower alkyl;
$R^3$ represents hydrogen; lower alkyl; lower alkenyl; cycloalkyl; aryl; heteroaryl; heterocyclyl; cycloalkyl-lower alkyl; aryl-lower alkyl; heteroaryl-lower alkyl; heterocyclyl-lower alkyl; aryloxy-lower alkyl; or heteroaryloxy-lower alkyl; wherein these groups may be unsubstituted or mono-, di- or tri-substituted with hydroxy, —$OCOR^2$, —$COOR^2$, lower alkoxy, cyano, —$CONR^2R^{2'}$, —CO-morpholin-4-yl, —CO-((4-lower alkyl)piperazin-1-yl), —$NH(NH)NH_2$, —$NR^4R^{4'}$, or lower alkyl, with the proviso that a carbon atom is attached at the most to one heteroatom in case this carbon atom is sp3-hybridized;
$R^4$ and $R^{4'}$ independently represent hydrogen; lower alkyl; cycloalkyl; cycloalkyl-lower alkyl; hydroxyl-lower alkyl; —$COOR^2$; or —$CONH_2$;
m represents the integer 1 and n represents the integer 0;
p is the integer 1, 2, 3 or 4;
r is the integer 3, 4, 5, or 6;
s is the integer 2, 3, 4, or 5;
t is the integer 1, 2, 3, or 4;
u is the integer 1, 2, or 3; and
v is the integer 2, 3, or 4;

or optically pure enantiomers, mixtures of enantiomers, diastereomers, mixtures of diastereomers, diastereomeric racemates, mixtures of diastereomeric racemates, or the mesoform; or pharmaceutically acceptable salts, of said compound.

2. The compound of general formula I according to claim 1, wherein

L represents —$COR^{3''}$; —$COOR^{3''}$; or —$CONR^{2''}R^{3''}$; and $R^{2''}$ and $R_3''$ represent independently lower alkyl or lower cycloalkyl-lower alkyl, which lower alkyl and lower cycloalkyl-lower alkyl are unsubstituted or mono-substituted with halogen, —CN, —OH, —$OCOCH_3$, —$CONH_2$, —COOH, or —$NH_2$, with the proviso that a carbon atom is attached at the most to one heteroatom in case this carbon atom is sp3-hybridized.

3. The compound of claim 1, wherein
T represents —$CONR^1$;
Q represents methylene; and
M represents hydrogen; aryl; or heteroaryl.

4. The compound of claim 1, wherein V represents —$CH_2CH_2O$—; —$CH_2CH_2CH_2O$—; or —$OCH_2CH_2O$—.

5. The compound of claim 1, wherein
U is a mono-, di-, or tri-substituted phenyl, wherein the substituents are halogen, lower alkyl or lower alkoxy.

6. The compound according to claim 1 selected from the group consisting of:
(2-methoxyphenyl)acetic acid (1R*,5S*)-7-{4-[3-(2-methoxybenzyloxy)-propoxy]phenyl}-3-(2-thiophen-2-ylacetyl)-3,9-diazabicyclo[3.3.1]non-6-en-6-yl-methyl ester;
(2-methoxyphenyl)acetic acid (1R*,5S*)-3-[2-(4-chlorophenyl)acetyl]-7-{4-[3-(2-methoxybenzyloxy)propoxy]phenyl}-3,9-diazabicyclo[3.3.1]non-6-en-6-yl-methyl ester;
(2-methoxyphenyl)acetic acid (1R*,5S*)-7-{4-[3-(2-methoxybenzyloxy)-propoxy]phenyl}-3-(quinoxaline-2-carbonyl)-3,9-diazabicyclo[3.3.1]non-6-en-6-yl-methyl ester;
(1R*,5S*)-3-acetyl-7-{4-[3-(2-methoxybenzyloxy)propoxy]phenyl}-3,9-diazabicyclo[3.3.1]non-6-ene-6-carboxylic acid [2-(2-chlorophenyl)ethyl]methylamide;
(2-methoxyphenyl)acetic acid (1R*,5S*)-3-(benzo[b]thiophene-3-carbonyl)-7-{4-[3-(2-methoxybenzyloxy)propoxy]phenyl}-3,9-diazabicyclo-[3.3.1]non-6-en-6-yl-methyl ester;
(2-methoxyphenyl)acetic acid (1R*,5S*)-3-acetyl-7-{4-[3-(2-methoxybenzyloxy)propoxy]phenyl}-3,9-diazabicyclo[3.3.1]non-6-en-6-ylmethyl ester;
(2-methoxyphenyl)acetic acid(1R*,5S*)-7-{4-[3-(2-methoxybenzyloxy)-propoxy]phenyl}-3-phenylmethanesulfonyl-3,9-diazabicyclo[3.3.1]non-6-en-6-ylmethyl ester;

(1R*,5S*)-3-acetyl-7-{4-[3-(2-methoxybenzyloxy)propoxy]phenyl}-3,9-diazabicyclo[3.3.1]non-6-ene-6-carboxylic acid [2-(4-methoxyphenyl)ethyl]-methylamide;

(1R*,5S*)-3-acetyl-7-{4-[2-(2-chloro-5-methylphenoxy)ethyl]phenyl}-3,9-diazabicyclo[3.3.1]non-6-ene-6-carboxylic acid methylphenethylamide;

(1R*,5S*)-3-acetyl-7-{4-[2-(2-bromo-5-fluorophenoxy)ethyl]phenyl}-3,9-diazabicyclo[3.3.1]non-6-ene-6-carboxylic acid methylphenethylamide;

(2-methoxyphenyl)acetic acid (1R*,5S*)-3-[2-(4-chlorophenyl)acetyl]-7-{6-[3-(2-methoxybenzyloxy)propoxy]pyridin-3-yl}-3,9-diazabicyclo[3.3.1]non-6-en-6-ylmethyl ester;

(1R*,5S*)-3-acetyl-7-{4-[2-(2,5-dimethylphenoxy)ethyl]phenyl}-3,9-diazabicyclo[3.3.1]non-6-ene-6-carboxylic acid methylphenethylamide;

(1R*,5S*)-3-acetyl-7-{4-[3-(2-methoxybenzyloxy)propoxy]phenyl}-3,9-diazabicyclo[3.3.1]non-6-ene-6-carboxylic acid[2-(4-chlorophenyl)ethyl]methylamide;

(1R*,5S*)-3-acetyl-7-{4-[3-(2-methoxybenzyloxy)propoxy]phenyl}-3,9-diazabicyclo[3.3.1]non-6-ene-6-carboxylic acid[2-(3-chlorophenyl)ethyl]methylamide;

(1R*,5S*)-3-acetyl-7-{4-[3-(2-methoxybenzyloxy)propoxy]phenyl}-3,9-diazabicyclo[3.3.1]non-6-ene-6-carboxylic acid ethylphenethylamide;

(1R*,5S*)-3-acetyl-7-{4-[3-(2- methoxybenzyloxy)propoxy]phenyl}-3,9-diazabicyclo[3.3.1]non-6-ene-6-carboxylic acid[2-(3-methoxyphenyl)ethyl]methylamide;

(1R*,5S*)-3-acetyl-7-{4-[3-(2,3,6-trifluorophenoxy)propyl]phenyl}-3,9-diazabicyclo[3.3.1]non-6-ene-6-carboxylic acid methylphenethylamide;

(1R*,5S*)-3-acetyl-7-{4-[3-(2-methoxybenzyloxy)propoxy]phenyl}-3,9-diazabicyclo[3.3.1]non-6-ene-6-carboxylic acid methylphenethylamide;

(1R*,5S*)-3-acetyl-7-{4-[3-(2-bromo-5-fluorophenoxy)propyl]phenyl}-3,9-diazabicyclo[3.3.1]non-6-ene-6-carboxylic acid methylphenethylamide;

(2-methoxyphenyl)acetic acid(1R*,5S*)-7-{4-[3-(2-methoxybenzyloxy)-propoxy]phenyl}-3-methyl-3,9-diazabicyclo[3.3.1]non-6-en-6-ylmethyl ester;

(1R*,5S*)-3-acetyl-7-{4-[3-(2-methoxybenzyloxy)propoxy]phenyl}-3,9-diazabicyclo[3.3.1]non-6-ene-6-carboxylic acid[2-(3,4-dimethoxyphenyl)ethyl]methylamide;

(1R*,5S*)-3-acetyl-7-{4-[2-(2,3,5-trimethylphenoxy)ethyl]phenyl}-3,9-diazabicyclo[3.3.1]non-6-ene-6-carboxylic acid methylphenethylamide;

(1R*,5S*)-3-acetyl-7-{4-[3-(2,5-dichlorophenoxy)propyl]phenyl}-3,9-diazabicyclo[3.3.1]non-6-ene-6-carboxylic acid methylphenethylamide;

(1R*,5S*)-3-acetyl-7-{4-[2-(2,3-dimethylphenoxy)ethyl]phenyl}-3,9-diazabicyclo[3.3.1]non-6-ene-6-carboxylic acid methylphenethylamide;

N-(1R*,5S*)-3-acetyl-7-{4-[2-(2-chloro-4,5-dimethylphenoxy)ethyl]phenyl}-3,9-diazabicyclo[3.3.1]non-6-ene-6-carboxylic acid methylphenethylamide;

(2-methoxyphenyl)acetic acid(1R*,5S*)-7-{4-[3-(2-methoxybenzyloxy)-propoxy]phenyl}-3,9-diazabicyclo[3.3.1]non-6-en-6-ylmethyl ester;

N-((1R*,5S*)-3-acetyl-7-{4-[3-(2-methoxybenzyloxy)propoxy]phenyl}-3,9-diazabicyclo[3.3.1]non-6-en-6-ylmethyl)-2-(2-methoxyphenyl)-N-methyl-acetamide;

N-(1R*,5S*)-3-acetyl-7-{4-[2-(2-tert-butyl-4-methylphenoxy)ethyl]phenyl}-3,9-diazabicyclo[3.3.1]non-6-ene-6-carboxylic acid methylphenethylamide;

(1R*,5S*)-3-acetyl-7-{4-[2-(2,5-difluorophenoxy)ethyl]phenyl}-3,9-diazabicyclo[3.3.1]non-6-ene-6-carboxylic acid methylphenethylamide;

(1R*,5S*)-3-acetyl-7-{4-[3-(2-methoxybenzyloxy)propoxy]phenyl}-3,9-diazabicyclo[3.3.1]non-6-ene-6-carboxylic acid methyl(3-phenylpropyl)amide;

(1R*,5S*)-3-acetyl-7-{4-[3-(2,3-dichlorophenoxy)propyl]phenyl}-3,9-diazabicyclo[3.3.1]non-6-ene-6-carboxylic acid methylphenethylamide;

(1R*,5S*)-3-acetyl-7-{4-[3-(2-acetylphenoxy)propyl]phenyl}-3,9-diazabicyclo[3.3.1]non-6-ene-6-carboxylic acid methylphenethylamide;

(1R*,5S*)-3-acetyl-7-{4-[3-(2-methoxybenzyloxy)propoxy]phenyl}-3,9-diazabicyclo[3.3.1]non-6-ene-6-carboxylic acid [2-(2-methoxyphenyl)ethyl]methylamide;

(1R*,5S*)-3-acetyl-7-{4-[3-(2-methoxybenzyloxy)propoxy]phenyl}-3,9-diazabicyclo[3.3.1]non-6-ene-6-carboxylic acid benzylmethylamide;

(1R*,5S*)-3-acetyl-7-{4-[3-(2,5-difluorophenoxy)propyl]phenyl}-3,9-diazabicyclo[3.3.1]non-6-ene-6-carboxylic acid methylphenethylamide;

(1R*,5S*)-3-acetyl-7-[4-(2-o-tolyloxyethyl)phenyl]-3,9-diazabicyclo-[3.3.1]non-6-ene-6-carboxylic acid methylphenethylamide;

(1R*,5S*)-3-acetyl-7-{4-[2-(3-isopropylphenoxy)ethyl]phenyl}-3,9-diazabicyclo[3.3.1]non-6-ene-6-carboxylic acid methylphenethylamide;

(1R*,5S*)-3-acetyl-7-{4-[3-(2-chlorophenoxy)propyl]phenyl}-3,9-diazabicyclo[3.3.1]non-6-ene-6-carboxylic acid (2-chlorobenzyl)cyclopropylamide;

(1R*,5S*)-5-[7-{4-[2-(2-bromo-5-fluorophenoxy)ethyl]phenyl}-6-(methylphenethylcarbamoyl)-3,9-diazabicyclo[3.3.1]non-6-en-3-yl]-5-oxopentanoic acid;

(1R*,5S*)-3-acetyl-7-{4-[3-(2,3,6-trifluorophenoxy)propyl]phenyl}-3,9diazabicyclo[3.3.1]non-6-ene-6-carboxylic acid (2-chlorobenzyl)cyclopropylamide;

(1R*,5S*)-7-{4-[3-(2,3,6-trifluorophenoxy)propyl-phenyl}-3,9-diazabicyclo[3.3.1]non-6-ene-6-carboxylic acid (2-chlorobenzyl)cyclopropylamide;

5-((1R*,5S*)-6-[(2-chlorobenzyl)cyclopropylcarbamoyl]-7-{4-[3-(2,3,6-trifluorophenoxy)propylphenyl}-3,9-diazabicyclo[3.3.1]non-6-en-3-yl)-5-oxopentanoic acid;

5-(1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-9-carboxylic acid 2,2,2-trichloro-1,1-dimethylethyl ester;

5-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid;

5-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-3-yl)-5-oxopentanoic acid methyl ester;

(1R, 5S)-3-((1S, 4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(1S, 5R)-3-((1S, 4R)-4-hydroxypyrrolidine-2-carbonyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(1R*,5S*)-3-(4-carbamoylbutyryl)-7-{4-[3-(2,3,6-trifluorophenoxy)propyl]phenyl}-3,9-diazabicyclo[3.3.1]non-6-ene-6-carboxylic acid (2- chlorobenzyl)cyclopropylamide;

(1R*,5S*)-3-(4-carbamoylbutyryl)-7-{4-[3-(2,3,6-trifluorophenoxy)propyl]phenyl}-3,9-diazabicyclo[3.3.1]non-6-ene-6-carboxylic acid benzylcyclopropylamide;

(1R*,5S*)-3-(4-carbamoylbutyryl)-7-{4-[3-(2,3,6-trifluorophenoxy)propyl]phenyl}-3,9-diazabicyclo[3.3.1]non-6-ene-6-carboxylic acid (2-chlorobenzyl) amide;

(1R*,5S*)-3-(4-carbamoylbutyryl)-7-{4-[3-(2,3,6-trifluorophenoxy)propyl]phenyl}-3,9-diazabicyclo[3.3.1]non-6-ene-6-carboxylic acid cyclopropyl-(2-fluorobenzyl)amide;

(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(3-trifluoromethylbenzyl)amide;

(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(2-methylbenzyl)amide;

(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-phenethylamide;

(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid[2-(2-chlorophenyl)ethyl] cyclopropylamide;

(1R*,5S*)-3-(4-carbamoylbutyryl)-7-{4-[3-(2,3,6-trifluorophenoxy)-propyl]phenyl}-3,9-diazabicyclo[3.3.1]non-6-ene-6-carboxylic acid cyclopropyl-(3,5-dimethoxybenzyl)amide;

(3R*)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid;

(3S*)-5-((1R*,5S*)-6-[(2-chlorobenzyl)cyclopropylcarbamoyl]-7-{4-[3-(2,3,6-trifluorophenoxy)propyl]phenyl}-3,9-diazabicyclo-[3.3.1]non-6-en-3-yl)-3-hydroxy-5-oxopentanoic acid;

(3R*)-5-((1R*,5S*)-6-(benzylcyclopropylcarbamoyl)-7-{4-[3-(2,3,6-trifluorophenoxy)propyl]phenyl}-3,9-diazabicyclo[3.3.1]non-6-en-3-yl)-3-hydroxy-5-oxopentanoic acid;

(3S*)-5-((1R*,5S*)-6-(benzylcyclopropylcarbamoyl)-7-{4-[3-(2,3,6-trifluorophenoxy)propyl]phenyl}-3,9-diazabicyclo[3.3.1]non-6-en-3-yl)-3-hydroxy-5-oxopentanoic acid;

(3R*)-5-((1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

(3S*)-5-((1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

(3R*)-5-((1R*,5S*)-6-[cyclopropyl-(2-fluorobenzyl)-carbamoyl]-7-4-[3-(2,3,6-trifluorophenoxy)propyl]phenyl}-3,9-diazabicyclo[3.3.1]non-6-en-3-yl)-3-hydroxy-5-oxopentanoic acid;

(3S*)-5-((1R*,5S*)-6-[cyclopropyl-(2-fluorobenzyl)-carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

(3R*)-5-((1R*,5S*)-6-[cyclopropyl-(3-trifluoromethylbenzyl)carbamoyl]-7-{4-[3-(2,3,6-trifluorophenoxy)propyl]-phenyl}-3,9-diazabicyclo[3.3.1]non-6-en-3-yl)-3-hydroxy-5-oxopentanoic acid;

(3S*)-5-((1R*,5S*)-6-[cyclopropyl-(3-trifluoromethylbenzyl)carbamoyl]-7-{4-[3-(2,3,6-trifluorophenoxy)propyl]-phenyl}-3,9-diazabicyclo[3.3.1]non-6-en-3-yl)-3-hydroxy-5-oxopentanoic acid;

(3R*)-5-((1R*,5S*)-6-[cyclopropyl-(2-methylbenzyl)-carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

(3S*)-5-((1R*,5S*)-6-[cyclopropyl-(2-methylbenzyl)carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

(3R*)-5-((1R*,5S*)-6-{cyclopropyl[2-(4-methoxyphenoxy)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid;

(3S*)-5-((1R*,5S*)-6-cyclopropyl-[2-(4-methoxyphenoxy)ethyl]carbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid;

(3R*)-5-((1R*,5S*)-6-[cyclopropyl-(2-m-tolyloxyethyl)-carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

(3S*)-5-((1R*,5S*)-6-[cyclopropyl-(2-m-tolyloxyethyl)-carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

(3R*)-5-((1R*,5S*)-6-{[2-(2-chlorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid;

(3S*)-5-((1R*,5S*)-6-{[2-(2-chlorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-3-hydroxy-5-oxopentanoic acid;

(3R*)-5-((1R*,5S*)-6-[cyclopropyl-(3,5-dimethoxybenzyl)carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

(3S*)-5-((1R*,5S*)-6-[cyclopropyl-(3,5-dimethoxybenzyl)carbamoyl]-7-{4-[3-(2,3,6-trifluorophenoxy)propyl]phenyl}-3,9-diazabicyclo[3.3.1]non-6-en-3-yl)-3-hydroxy-5-oxopentanoic acid;

(1R*,5S*)-3-acetyl-7-{4-[3-(2,3,6-trifluorophenoxy)propyl]phenyl}-3,9-diazabicyclo[3.3.1]non-6-ene-6-carboxylic acid (2-chlorobenzyl)ethylamide;

(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl(3,5-dimethoxybenzyl)amide;

5-((1R*,5S*)-6-(benzylcyclopropylcarbamoyl)-7-{4-[3-(2,3,6-trifluorophenoxy)propyl]phenyl}-3,9-diazabicyclo[3.3.1]non-6-en-3-yl)-5-oxopentanoic acid;

5-((1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-en-3-yl)-5-oxopentanoic acid;

5-((1R*,5S*)-6-[cyclopropyl-(2-fluorobenzyl)carbamoyl]-7-{4-[3-(2,3,6-trifluorophenoxy)propyl]phenyl}-3,9-diazabicyclo[3.3.1]non-6-en-3-yl)-5-oxopentanoic acid;

5-((1R*,5S*)-6-[cyclopropyl(3-trifluoromethylbenzyl)carbamoyl]-7-{4-[3-(2,3,6-trifluorophenoxy)propyl]phenyl}-3,9-diazabicyclo[3.3.1]non-6-en-3-yl)-5-oxopentanoic acid;

5-((1R*,5S*)-6-[cyclopropyl(2-methylbenzyl)carbamoyl]-7-{4-[3-(2,3,6-trifluorophenoxy)propyl]phenyl}-3,9-diazabicyclo[3.3.1]non-6-en-3-yl)-5-oxopentanoic acid;

5-((1R*,5S*)-6-{[2-(2-chlorophenyl)ethyl]cyclopropylcarbamoyl}-7-{4-[3-(2,3,6-trifluorophenoxy)propyl]phenyl}-3,9-diazabicyclo[3.3.1]non-6-en-3-yl)-5-oxopentanoic acid;

5-((1R*,5S*)-6-[cyclopropyl(3,5-dimethoxybenzyl)carbamoyl]-7-{4-[3-(2,3,6-trifluorophenoxy)propyl]phenyl}-3,9-diazabicyclo[3.3.1]non-6-en-3-yl)-5-oxopentanoic acid;

5-((1R*,5S*)-6-[cyclopropyl(2-p-tolylethyl)carbamoyl]-7-{4-[3-(2,3,6-trifluorophenoxy)propyl]phenyl}-3,9-diazabicyclo[3.3.1]non-6-en-3-yl)-5-oxopentanoic acid;

5-((1R*,5S*)-6-[(2-chlorobenzyl)ethylcarbamoyl]-7-{4-[3-(2,3,6-trifluorophenoxy)propyl]phenyl}-3,9-diazabicyclo[3.3.1]non-6-en-3-yl)-5-oxopentanoic acid methyl ester;

5-((1R*,5S*)-6-[cyclopropyl-(2-fluorobenzyl)carbamoyl]-7-{4-[3-(2,3,6-trifluorophenoxy)propyl]phenyl}-3,9-diazabicyclo[3.3.1]non-6-en-3-yl)-5-oxopentanoic acid methyl ester;

5-((1R*,5S*)-6-[cyclopropyl-(3,5-dimethoxybenzyl)carbamoyl-7-{4-[3-(2,3,6-trifluorophenoxy)propyl]phenyl}-3,9-diazabicyclo[3.3.1]non-6-en-3-yl)-5-oxopentanoic acid methyl ester;

5-((1R*,5S*)-6-[(2-chlorobenzyl)ethylcarbamoyl}-7-{4-[3-(2,3,6-trifluorophenoxy)propyl]phenyl}-3,9-diazabicyclo[3.3.1]non-6-en-3-yl)-2,2-dimethyl-5-oxopentanoic acid;

5-((1R*,5S*)-6-[cyclopropyl-(2-fluorobenzyl)carbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid;

5-((1R*,5S*)-6-[cyclopropyl-(2-methylbenzyl)carbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid;

5-((1R*,5S*)-6-[cyclopropyl-(3,5-dimethoxybenzyl)carbamoyl]-7-{4-[3-(2,3,6-trifluorophenoxy)propyl]phenyl}-3,9-diazabicyclo[3.3.1]non-6-en-3-yl)-2,2-dimethyl-5-oxopentanoic acid;

(2R*,3S*)-4-((1R*,5S*)-6-[cyclopropyl-(2-methylbenzyl)-carbamoyl]-7-{4-[3-(2,3,6-trifluorophenoxy)propyl]phenyl}-3,9-diazabicyclo[3.3.1]non-6-en-3-yl)-2,3-dihydroxy-4-oxobutyric acid;

(2S*,3R*)-4-((1R*,5S*)-6-[cyclopropyl-(2-methylbenzyl)carbamoyl]-7-{4-[3-(2,3,6-trifluorophenoxy)propyl]phenyl}-3,9-diazabicyclo[3.3.1]non-6-en-3-yl)-2,3-dihydroxy-4-oxobutyric acid;

5-{1R*,5S*)-7-{4-[3-(2-bromo-5-fluorophenoxy)propyl]phenyl}-6-[cyclopropyl-(2-fluorobenzyl)carbamoyl]-3,9-diazabicyclo[3.3.1]non-6-en-3-yl}-5-oxopentanoic acid;

5-{(1R*,5S*)-7-{4-[3-(2-bromo-5-fluorophenoxy)propyl]phenyl}-6-[cyclopropyl-[2-(3-ethylphenoxy)ethyl]carbamoyl}-3,9-diazabicyclo[3.3.1]non-6-en-3-yl)-5-oxopentanoic acid;

5-[(1R*,5S*)-7-{4-[3-(2-bromo-5-fluorophenoxy)propyl]phenyl}-6-(cyclopropylphenethylcarbamoyl)-3,9-diazabicyclo[3.3.1]non-6-en-3-yl]-5-oxopentanoic acid;

5-((1R*,5S*)-7-{4-[3-(2-bromo-5-fluorophenoxy)propyl]phenyl}-6-{[2-(2-chlorophenyl)ethyl]cyclopropylcarbamoyl)-3,9-diazabicyclo[3.3.1]non-6-en-3-yl)-5-oxopentanoic acid;

5-((1R*,5S*)-7-{4-[3-(2-bromo-5-fluorophenoxy)propyl]phenyl}-6-[2-(2,3-difluorophenyl)ethyl]cyclopropylcarbamoyl}-3,9-diazabicyclo[3.3.1]non-6-en-3-yl)-5-oxopentanoic acid;

5-((1R*,5S*)-7-{4-[3-(2-bromo-5-fluorophenoxy)propyl]phenyl}-6-{[2-(2-methylphenyl)ethyl]cyclopropylcarbamoyl}-3,9-diazabicyclo[3.3.1]non-6-en-3-yl)-5-oxopentanoic acid;

5-((1R*,5S*)-7-{4-[3-(2-bromo-5-fluorophenoxy)propyl]phenyl}-6-{[2-(2-methylphenyl)ethyl]cyclopropylcarbamoyl}-3,9-diazabicyclo[3.3.1]non-6-en-3-yl)-5-oxopentanoic acid;

5-{(1R*,5S*)-7-{4-[3-(2-bromo-5-fluorophenoxy)propyl]phenyl}-6-[cyclopropyl-(3,5-dimethoxybenzyl)carbamoyl]-3,9-diazabicyclo[3.3.1]non-6-en-3-yl)-5-oxopentanoic acid;

5-{(1R*,5S*)-7-{4-[3-(2-bromo-5-fluorophenoxy)propyl]phenyl}-6-[cyclopropyl-(3,5-dimethoxybenzyl)carbamoyl]-3,9-diazabicyclo[3.3.1]non-6-en-3-yl}-5-oxopentanoic acid methyl ester;

5-{(1R*,5S*)-7-{4-[3-(2-bromo-5-fluorophenoxy)propyl]phenyl}-6-[cyclopropyl-(2-fluorobenzyl)carbamoyl]-3,9-diazabicyclo[3.3.1]non-6-en-3-yl}-2,2-dimethyl-5-oxopentanoic acid;

5-{(1R*,5S*)-7-{4-[3-(2-bromo-5-fluorophenoxy)propyl]phenyl}-6-[cyclopropyl-(2-methylbenzyl)carbamoyl]-3,9-diazabicyclo[3.3.1]non-6-en-3-yl}-2,2-dimethyl-5-oxopentanoic acid;

5-[(1R*,5S*)-7-{4-[3-(2-bromo-5-fluorophenoxy)propyl]phenyl}-6-(cyclopropylphenethylcarbamoyl)-3,9-diazabicyclo[3.3.1]non-6-en-3-yl}-2,2-dimethyl-5-oxopentanoic acid;

5-((1R*,5S*)-7-{4-[3-(2-bromo-5-fluorophenoxy)propyl]phenyl}-6-{[2-(4-methylphenyl)ethyl]cyclopropylcarbamoyl}-3,9-diazabicyclo[3.3.1]non-6-en-3-yl)-2,2-dimethyl-5-oxopentanoic acid;

5-{(1R*,5S*)-7-{4-[3-(2-bromo-5-fluorophenoxy)propyl]phenyl}-6-[cyclopropyl-(3,5-dimethoxybenzyl)carbamoyl]-3,9-diazabicyclo[3.3.1]non-6-en-3-yl}-2,2-dimethyl-5-oxopentanoic acid;

(2R*,3S*)-4-{(1R*,5S*)-7-{4-[3-(2-bromo-5-fluorophenoxy)propyl]phenyl}-6-[cyclopropyl-(3,5-dimethoxybenzyl)carbamoyl]-3,9-diazabicyclo[3.3.1]non-6-en-3-yl}-2,3-dihydroxy-4-oxobutyric acid;

(2S*,3R*)-4-{(1R*,5S*)-7-{4-[3-(2-bromo-5-fluorophenoxy)propyl]phenyl}-6-[cyclopropyl-(3,5-dimethoxybenzyl)carbamoyl]-3,9-diazabicyclo[3.3.1]non-6-en-3-yl}-2,3-dihydroxy-4-oxobutyric acid;

5-((1R*,5S*)-6-[(2-chlorobenzyl)cyclopropylcarbamoyl]-7-{4-[2-(2,3,5-trimethylphenoxy)ethyl]phenyl}-3,9-diazabicyclo[3.3.1]non-6-en-3-yl)-5-oxopentanoic acid;

5-((1R*,5S*)-6-[(3-trifluoromethylbenzyl)cyclopropylcarbamoyl]-7-{4-[2-(2,3,5-trimethylphenoxy)ethyl]phenyl}-3,9-diazabicyclo[3.3.1]non-6-en-3-yl)-5-oxopentanoic acid;

5-((1R*,5S*)-6-[(2-methylbenzyl)cyclopropylcarbamoyl]-7-{4-[2-(2,3,5-trimethylphenoxy)ethyl]phenyl}-3,9-diazabicyclo[3.3.1]non-6-en-3-yl)-5-oxopentanoic acid;

5-((1R*,5S*)-6-[(2-chlorobenzyl)ethylcarbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid;

5-((1R*,5S*)-6-[cyclopropyl-(2-fluorobenzyl)carbamoyl]-7-{4-[2-(2,3,5-trimethylphenoxy)ethyl]phenyl}-3,9-diazabicyclo[3.3.1]non-6-en-3-yl)-2,2-dimethyl-5-oxopentanoic acid;

5-{(1R*,5S*)-7-{4-[3-(2-bromo-5-fluorophenoxy)propyl]phenyl}-6-[(2-chlorobenzyl)cyclopropylcarbamoyl]-3,9-diazabicyclo[3.3.1]non-6-en-3-yl}-5-oxopentanoic acid;

5-{(1R*,5S*)-7-{4-[3-(2-bromo-5-fluorophenoxy)propyl]phenyl}-6-[(2-chlorobenzyl)cyclopropylcarbamoyl]-3,9-diazabicyclo[3.3.1]non-6-en-3-yl}-2,2-dimethyl-5-oxopentanoic acid;

5-{(1R*,5S*)-4-[3-(2-bromo-5-fluorophenoxy)propyl]phenyl}-3-(4-carbamoylbutyryl)-3,9-diazabicyclo[3.3.1]non-6-ene-6-carboxylic acid (2-chlorobenzyl)cyclopropylamide;

5-((1R*,5S*)-6-(benzylcyclopropylcarbamoyl)-7-{4-[3-(2-bromo-5-fluorophenoxy)propyl]phenyl}-3,9-diazabicyclo[3.3.1]non-6-en-3-yl)-5-oxopentanoic acid methyl ester;

(1R*,5S*)-3-acetyl-7-{4-[2-(2-chloro-4,5-dimethylphenoxy)ethoxy]-phenyl}-3,9-diazabicyclo[3.3.1]non-6-ene-6-carboxylic acid (2-chlorobenzyl)cyclopropylamide;

5-((1R*,5S*)-6-[(2-chlorobenzyl)cyclopropylcarbamoyl]-7-{4-[2-(2-chloro-4,5-dimethylphenoxy)ethoxy]phenyl}-3,9-diazabicyclo[3.3.1]non-6-en-3-yl)-5-oxopentanoic acid;

5-{(1R*,5S*)-7-{4-[2-(2-chloro-4,5-dimethylphenoxy)ethoxy]phenyl}-6-[cyclopropyl-(2-methylbenzyl)carbamoyl]-3,9-diazabicyclo[3.3.1]non-6-ene-3-yl}-5-oxopentanoic acid;

5-{(1R*,5S*)-7-{4-[2-(2-chloro-4,5-dimethylphenoxy)ethoxy]phenyl}-6-[cyclopropyl-(3,5-dimethoxybenzyl)carbamoyl]-3,9-diazabicyclo[3.3.1]non-6-en-3-yl}-5-oxopentanoic acid;

5-((1R*,5S*)-6-[(2-chlorobenzyl)cyclopropylcarbamoyl]-7-{4-[2-(2-chloro-4,5-dimethylphenoxy)ethoxy]phenyl}-3,9-diazabicyclo[3.3.1]non-6-en-3-yl)-2,2-dimethyl-5-oxopentanoic acid;

5-((1R*,5S*)-6-[(2-chlorobenzyl)ethylcarbamoyl]-7-{4-[2-(2-chloro-4,5-dimethylphenoxy)ethoxy]phenyl}-3,9-diazabicyclo[3.3.1]non-6-en-3-yl)-2,2-dimethyl-5-oxopentanoic acid;

5-{(1R*,5S*)-7-{4-[2-(2-chloro-4,5-dimethylphenoxy)ethoxy]phenyl}-6-[cyclopropyl-(2-fluorobenzyl)carbamoyl]-3,9-diazabicyclo[3.3.1]non-6-en-3-yl}-2,2-dimethyl-5-oxopentanoic acid;

5-((1R*,5S*)-6-[cyclopropyl-(3,5-dimethoxybenzyl)carbamoyl]-7-{4-[2-(2,3,5-trimethylphenoxy)ethyl]phenyl}-3,9-diazabicyclo[3.3.1]non-6-en-3-yl)-5-oxopentanoic acid;

5-((1R*,5S*)-6-[cyclopropyl-(2-p-tolylethyl)carbamoyl]-7-{4-[2-(2,3,5-trimethylphenoxy)ethyl]phenyl}-3,9-diazabicyclo[3.3.1]non-6-en-3-yl)-5-oxopentanoic acid;

5-((1R*,5S*)-7-{4-[2-(2-chloro-4,5-dimethylphenoxy)ethoxy]phenyl}-6-[cyclopropyl-[2-(2-hydroxyethyl)benzyl]carbamoyl]-3,9-diazabicyclo[3.3.1]non-6-en-3-yl)-5-oxopentanoic acid;

5-((1R*,5S*)-6-(cyclopropylphenethylcarbamoyl)-7-{4-[2-(2,3,5-trimethylphenoxy)ethyl]phenyl}-3,9-diazabicyclo[3.3.1]non-6-en-3-yl)-2,2-dimethyl-5-oxopentanoic acid;

(1R*,5S*)-7-{4-[3-(2,3,6-trifluorophenoxy)propyl]phenyl}-3,9-diazabicyclo[3.3.1]non-6-ene-6-carboxylic acid (2-chlorobenzyl) ethylamide;

(1R*,5S*)-7-{4-[3-(2,3,6-trifluorophenoxy)propyl]phenyl}-3,9-diazabicyclo[3.3.1]non-6-ene-3,6-dicarboxylic acid 6-[(2-chlorobenzyl)cyclopropylamide]3- dimethylamide;

(1R*,5S*)-7-{4-[3-(2,3,6-trifluorophenoxy)propyl]phenyl}-3,9-diazabicyclo[3.3.1]non-6-ene-3,6-dicarboxylic acid 6-[(2-chlorobenzyl)cyclopropylamide]3-diethylamide;

(1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-3-carboxylic acid methyl ester;

(1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-3-carboxylic acid ethyl ester;

(1R*,5S*)-3-methanesulfonyl-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(1R*,5S*)-3-ethanesulfonyl-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

5-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-3-yl)-5-oxopentanoic acid ethyl ester;

4-((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-en-3-yl)-4-oxobutyric acid;

3-[((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-3-carbonyl)-amino]propionic acid ethyl ester;

4-[((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-3-carbonyl)amino]butyric acid ethyl ester;

(1R*,5S*)-3-(3-carbamoylpropionyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(1R*,5S*)-3-(2-hydroxyacetyl)-7-{4-[3-(2,3,6-trifluorophenoxy)propyl]-phenyl}-3,9-diazabicyclo[3.3.1]non-6-ene-6-carboxylic acid (2-chlorobenzyl)cyclopropylamide;

(1S, 5R)-3-((3R)-3-hydroxybutyryl)-7-{4-[3-(2,3,6-trifluorophenoxy)-propyl]-phenyl}-3,9-diazabicyclo[3.3.1]non-6-ene-6-carboxylic acid (2-chlorobenzyl)cyclopropylamide;

(1R*,5S*)-3-((1R*,2S*)-2-hydroxycyclopentanecarbonyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(1R*,5S*)-3-((1S*,2R*)-2-hydroxycyclopentanecarbonyl)-7-{4-[3-(2,3,6-trifluorophenoxy)-propyl]phenyl}-3,9-diazabicyclo[3.3.1]non-6-ene-6-carboxylic acid (2-chlorobenzyl)cyclopropylamide;

(1R*,5S*)-3-formyl-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

3-[((1R*,5S*)-6-[(2-chlorobenzyl)cyclopropylcarbamoyl]-7-{4-[3-(2,3,6-trifluorophenoxy)propyl]phenyl}-3,9-diazabicyclo[3.3.1]non-6-ene-3-carbonyl)-amino]propionic acid;

(1R*,5S*)-3-acetyl-7-{4-[2-(2,3,6-trifluorophenoxy)ethyl]phenyl}-3,9-diazabicyclo[3.3.1]non-6-ene-6-carboxylic acid (2-chlorobenzyl) cyclopropylamide;

(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(2-fluoro-5-methoxybenzyl)amide;

(1R*,5S*)-3-acetyl-7-{4-[3-(2,3,6-trifluorophenoxy)propyl]phenyl}-3,9-diazabicyclo[3.3.1]non-6-ene-6-carbxoylic acid cyclopropyl-(3-methoxybenzyl)amide;

(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(3,4-dimethoxybenzyl)amide;

(1R*,5S*)-3-acetyl-7-{4-[3-(2,3,6-trifluorophenoxy)propyl]phenyl}-3,9-diazabicyclo[3.3.1]non-6-ene-6-carboxylic acid (2-chloro-3-trifluoromethylbenzyl)cyclopropylamide;

(1R*,5S*)-3-acetyl-7-{4-[3-(2,3,6-trifluorophenoxy)propyl]phenyl}-3,9-diazabicyclo[3.3.1]non-6-ene-6-carboxylic acid benzo[1,3]dioxol-5-ylmethyl-cyclopropylamide;

(1R*,5S*)-3-acetyl-7-{4-[3-(2,3,6- trifluorophenoxy)propyl]phenyl}-3,9-diazabicyclo[3.3.1]non-6-ene-6-carboxylic acid (2-chloro-6-fluorobenzyl )cyclopropylamide;

(1R*,5S*)-3-acetyl-7-{4-[3-(2,3,6-trifluorophenoxy)propyl]phenyl}-3,9-diazabicyclo[3.3.1]non-6-ene-6-carboxylic acid (2-bromobenzyl)cyclopropylamide;

(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(2,3-dimethylbenzyl)amide;

(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(3,5-difluorobenzyl)amide;

(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(2,3-dichlorobenzyl)amide;

(1R*,5S*)-3-acetyl-7-{4-[3-(2,3,6-trifluorophenoxy)propyl]phenyl}-3,9-diazabicyclo[3.3.1]non-6-ene-6-carboxylic acid cyctopropyl-(3-trifluoromethoxybenzyl)amide;

(1R*,5S*)-3-acetyl-7-{4-[3-(2,3,6-trifluorophenoxy)propyl]phenyl}-3,9-diazabicyclo[3.3.1]non-6-ene-6-carboxylic acid cyclopropyl-(3-methylbenzyl)amide;

(1R*,5S*)-3-acetyl-7-{4-[3-(2,3,6-trifluorophenoxy)propyl]phenyl}-3,9-diazabicyclo[3.3.1]non-6-ene-6-carboxylic acid (3-chlorobenzyl)cyclopropylamide;

(1R*,5S*)-7-{4-[3-(2-bromo-5-fluorophenoxy)propyl]phenyl}-3-(4-carbamoylbutryl)-3,9-diazabicyclo[3.3.1non-6-ene-6-carboxylic acid cyclopropyl-(3,5-dimethoxybenzyl)amide;

(1R*,5S*)-3-(5-morpholin-4-yl-5-oxopentanoyl)-7-{4-[3-(2,3,6-trifluorophenoxy)propyl]phenyl}-3,9-diazabicyclo[3.3.1]non-6-ene-6-carboxylic acid (2-chlorobenzyl )cyclopropylamide;

(1R*,5S*)-3-(2-tetrazol-1-ylacetyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(1R*,5S*)-3-(5-oxo-5-piperazin-1-ylpentanoyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(1R, 5S)-3-((2S)-2-amino-3-hydroxypropionyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(1S,5R)-3-((2S)-2-amino-3-hydroxypropionyl)-7-{4-[3-(2,3,6-trifluorophenoxy)propyl]phenyl}-3,9-diazabicyclo[3.3.1]non-6-ene-6-carboxylic acid (2-chlorobenzyl)cyclopropylamide;

(1R,5S)-3-((2S)-2-aminopropionyl)-7-{4-[3-(2,3,6-trifluorophenoxy)propy]phenyl}-3,9-diazabicyclo[3.3.1]non-6-ene-6-carboxylic acid (2-chlorobenzyl )cyclopropylamide;

(1S,5R)-3-((2S)-2-aminopropionyl)-7-{4-[3-2,3,6-trifluorophenoxy)propyl]phenyl}-3,9-diazabicyclo[3.3.1]non-6-ene-6-carboxylic acid (2-chlorobenzyl)cyclopropylamide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid cyclopropyl-(2,3-dichlorobenzyl)amide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid cyclopropyl-(2,3-dimethylbenzyl)amide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid (2-chloro-3-trifluoromethylbenzyl)cyclopropylamide;

(1R*,5S*)-3-acetyl-7-{4-[2-(2,6-dichloro-4-methylphenoxy)ethoxy]-phenyl}-3,9-diazabicyclo[3.3.1]non-6-ene-6-carboxylic acid (2-bromobenzyl)cyclopropylamide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid (2-chlorobenzyl )cyclopropylamide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid (2-chlorobenzyl)ethylamide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid (6-chlorobenzo-[1,3]dioxol-5-ylmethyl)cyclopropylamide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid cyclopropyl-(3,5-dimethoxybenzyl)amide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid cyclopropyl-(3-methoxybenzyl)amide;

(1R*,5S*)-3-acetyl-7-{4-[2-(2-chloro-5-fluorophenoxy)ethoxy]phenyl}-3,9-diazabicyclo[3.3.1]non-6-ene-6-carboxylic acid cyclopropyl-(2,3-dichlorobenzyl)amide;

(1R*,5S*)-3-acetyl-7-{4-[2-(2-chloro-5-fluorophenoxy)ethoxy]phenyl}-3,9-diazabicyclo[3.3.1]non-6-ene-6-carboxylic acid (2-chloro-3-trifluoromethylbenzyl)-cyclopropylamide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid (3-chlorobenzyl )cyclopropyiamide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid cyclopropyl-(3-methylbenzyl)amide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid cyclopropyl-(2-fluoro-5-methoxybenzyl)-amide;

(1R*,5S*)-3-acetyl-7-{4-[2-(2-chloro-4,5-dimethylphenoxy)ethoxy]phenyl}-3,9-diazabicyclo[3.3.1]non-6-ene-6-carboxylic acid cyclopropyl-(2,3-dichlorobenzyl)amide;

(1R*,5S*)-3-acetyl-7-{4-[3-(2-chloro-3,6-difluorophenoxy)propyl]phenyl}-3,9-diazabicyclo[3.3.1]non-6-ene-6-carboxylic acid (2-chlorobenzyl)cyclopropylamide;

(1R*,5S*)-3-acetyl-7-{4-[2-(2-chloro-4,5-dimethylphenoxy)ethoxy]phenyl}-3,9-diazabicyclo[3.3.1]non-6-ene-6-carboxylic acid (2-chloro-3-trifluoromethylbenzyl)-cyclopropylamide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid cyclopropyl-(3,4-dimethoxybenzyl)amide;

(1R*,5S*)-3-acetyl-7-{4-[2-(2,6-dichloro-4-methylphenoxy)ethoxy]phenyl}-3,9-diazabicyclo[3.3.1]non-6-ene-6-carboxylic acid cyclopropyl-(3-trifluoromethoxybenzyl)-amide;

(1R*,5S*)-3-acetyl-7-{4-[2-(2,4,5-trichlorophenoxy)ethoxy]phenyl}-3,9-diazabicyclo[3.3.1]non-6-ene-6-carboxylic acid (2-chloro-3-trifluoromethylbenzyl)-cyclopropylamide;

(1R*,5S*)-3-acetyl-7-{4-[2-(2,4,5-trichlorophenoxy)ethoxy]phenyl}-3,9-diazabicyclo[3.3.1]non-6-ene-6-carboxylic acid cyclopropyl-(2,3-dichlorobenzyl)amide;

(1R*,5S*)-3-acetyl-7-{4-[2-(2,3-dichlorophenoxy)ethoxy]phenyl}-3,9-diazabicyclo[3.3.1]non-6-ene-6-carboxylic acid cyclopropyl-(2,3-dimethylbenzyl)amide;

(1R*,5S*)-3-acetyl-7-{4-[2-(2,4,5-trichlorophenoxy)ethoxy]phenyl}-3,9-diazabicyclo[3.3.1]non-6-ene-6-carboxylic acid cyclopropyl-(2,3-dimethylbenzyl)amide;

(1R*,5S*)-3-acetyl-7-{4-[2-(2-chloro-4,5-dimethylphenoxy)ethoxy]phenyl}-3,9-diazabicyclo[3.3.1]non-6-ene-6-carboxylic acid cyclopropyl-(2,3-dimethylbenzyl)amide;

(1R*,5S*)-3-acetyl-7-{4[2-(2-bromo-5-fluorophenoxy)ethoxy]phenyl}-3,9-diazabicyclo[3.3.1]non-6-ene-6-carboxylic acid cyclopropyl-(2,3-dichlorobenzyl)amide;

(1R*,5S*)-3-acetyl-7-{4-[2-(2-chloro-4,5-dimethylphenoxy)ethoxy]phenyl}-3,9-diazabicyclo[3.3.1]non-6-ene-6-carboxylic acid (2-bromobenzyl)cyclopropylamide;

(1R*,5S*)-3-acetyl-7-{4-[2-(2,3-dichlorophenoxy)ethoxy]phenyl}-3,9-diazabicyclo[3.3.1]non-6-ene-6-carboxylic acid cyclopropyl-(2,3-dichlorobenzyl)amide;

(1R*,5S*)-3-acetyl-7-{4-[2-(2-chloro-5-fluorophenoxy)ethoxy]phenyl}-3,9-diazabicyclo[3.3.1]non-6-ene-6-carboxylic acid cyclopropyl-(2,3-dimethylbenzyl)amide;

(1R,5S)-7-{4-[3-(2,3,6-trifluorophenxoy)propyl]phenyl}-3,9-diazabicyclo[3.3.1]non-6-ene-6-carboxylic acid (2-chlorobenzyl)cyclopropylamide; and (1S,5R)-7-{4-[3-(2,3,6-trifluorophenxoy)propyl]phenyl}-3,9-diazabicyclo[3.3.1]non-6-ene-6-carboxylic acid (2-chlorobenzyl)cyclopropylamide.

7. A pharmaceutical composition comprising the compound of any one of claims 1, 2-4 or 5 and a pharmaceutically acceptable carrier with or without an adjuvant.

8. The pharmaceutical composition of claim 7, further comprising a pharmacologically active compound selected from the group consisting of ACE inhibitors, angiotensin II receptor antagonists, endothelin receptor antagonists, vasodilators, calcium antagonists, potassium activators, diuretics, sympatholitics, beta-adrenergic antagonists and alpha-adrenergic antagonists.

9. A pharmaceutical composition comprising the compound of claim 6 and a pharmaceutically acceptable carrier with or without an adjuvant.

10. The pharmaceutical composition of claim 9, further comprising a pharmacologically active compound selected from the group consisting of ACE inhibitors, angiotensin II receptor antagonists, endothelin receptor antagonists, vasodilators, calcium antagonists, potassium activators, diuretics, sympatholitics, beta-adrenergic antagonists and alpha-adrenergic antagonists.

* * * * *